US009271992B2

(12) United States Patent
Michaelis et al.

(10) Patent No.: US 9,271,992 B2
(45) Date of Patent: Mar. 1, 2016

(54) METHOD FOR ALLEVIATING PAIN USING SPHINGOSINE-1-PHOSPHATE AND RELATED COMPOUNDS, AND ASSAYS FOR IDENTIFYING SUCH COMPOUNDS

(75) Inventors: Martin Michaelis, Frankfurt (DE); Gerd Geisslinger, Bad Soden (DE); Klaus Scholich, Dreieich (DE)

(73) Assignee: FRAUNHOFER-GESELLESCHAFT ZUR FORDERUNG DER ANGEWANDTEN FORSCHUNG E.V, Munich (DE)

( * ) Notice: Subject to any disclaimer, the term of this patent is extended or adjusted under 35 U.S.C. 154(b) by 159 days.

(21) Appl. No.: 12/696,250

(22) Filed: Jan. 29, 2010

(65) Prior Publication Data

US 2010/0137257 A1 Jun. 3, 2010

Related U.S. Application Data

(62) Division of application No. 10/850,586, filed on May 20, 2004, now Pat. No. 7,691,563.

(60) Provisional application No. 60/520,780, filed on Nov. 17, 2003.

(30) Foreign Application Priority Data

May 30, 2003 (EP) .................................... 03012389

(51) Int. Cl.

| | |
|---|---|
| ***A61K 31/133*** | (2006.01) |
| ***A61K 31/661*** | (2006.01) |
| ***C07F 9/113*** | (2006.01) |
| ***G01N 33/50*** | (2006.01) |
| ***G01N 33/68*** | (2006.01) |
| ***G01N 33/92*** | (2006.01) |
| ***A61K 31/685*** | (2006.01) |

(52) U.S. Cl.

CPC ............. *A61K 31/661* (2013.01); *A61K 31/685* (2013.01); *C07F 9/113* (2013.01); *G01N 33/5008* (2013.01); *G01N 33/5023* (2013.01); *G01N 33/5058* (2013.01); *G01N 33/6896* (2013.01); *G01N 33/92* (2013.01); *G01N 2333/988* (2013.01); *G01N 2500/02* (2013.01); *G01N 2500/04* (2013.01); *G01N 2500/10* (2013.01)

(58) Field of Classification Search

None

See application file for complete search history.

(56) References Cited

U.S. PATENT DOCUMENTS

| | | | |
|---|---|---|---|
| 5,663,404 A | 9/1997 | Igarashi et al. |
| 5,712,262 A | 1/1998 | Spiegel |
| 6,004,565 A | 12/1999 | Chiba et al. |
| 2001/0041688 A1 | 11/2001 | Waeber et al. |

FOREIGN PATENT DOCUMENTS

| | | |
|---|---|---|
| CA | 2323887 | 9/1999 |
| EP | 1195165 | 4/2002 |
| WO | WO 99/12533 | 3/1999 |
| WO | WO 02/064616 | 8/2002 |

OTHER PUBLICATIONS

Budde, K., et al. 2002 J Am Soc Nephrol 13: 1073-1083.*
Zimmermann, M. 2001 European Journal of Pharmacology 429: 23-37.*
Burstein, R., et al. 2000 Brain 123: 1703-1709.*
Pietrobon, D., et al. 2003 Nature Reviews Neuroscience 4: 386-398.*
Chun, J., et al. 2002 Pharmacol Rev 54(2): 265-269.*
The Richeimer Pain Update: Understanding Nociceptive and Neuropathic Pain, Dec. 2000: 3 pages total.*
Zhen, Mei et al., Regulation of Presynaptic Terminal Organization by C. elegans RPM-1, a Putative Guanine Nucleotide Exchanger with a RING-H2 Finger Domain. Neuron, (2000), vol. 26, pp. 331-343.
Bailey, Craig H. et al., Toward a molecular definition of long-term memory storage, Proc. Natii. Acad. Sci. USA (1996), vol. 93, pp. 13445-13452.
Bek, Martin J. et al., Differential expression of adenylyl cyclases in the rat nephron, Kidney International, (2001), vol. 60, pp. 890-899.
Brandon, Eugene P. et al., PKA isoforms, neural pathways, and behaviour: making the connection, Current Opinion in Neurobiology, (1997), vol. 7, pp. 397-403.
Brinkman, Volker et al., The Immune Modulator FTY720 Targets Sphingosine 1-Phosphate Receptors, The Journal of Biochemistry, (2002), vol. 277, No. 24, pp. 21453-21457.
Caligan, Thomas B. et al., A High-Performance Liquid Chromatographic Method to Measure Sphingosine 1-Phosphate and Related Compounds from Sphingosine Kinase Assays and Other Biological Samples, Analytical Biochemistry, (2000), vol. 281, pp. 36-44.
Chang, Qiang et al., highwire, rpm-1, and futsch: Balancing Synaptic Growth and Stability, Neuron, (2000), vol. 26, pp. 287-290.
Chen, Zutang et al., Expression of Type V Adenylyl Cyclase Is Required for Epidermal Growth Factor-mediated Stimulation of cAMP Accumulation, The Journal of Biological Chemistry, (1995), vol. 270, No. 46, pp. 27525-27530.
Chomczynski, Piotr et al., Single-Step Method of RNA Isolation by Acid Guanidinium Thiocyanate-Phenol-Chloroform Extraction, Analytical Biochemistry, (1987), vol. 162, pp. 156-159.
Corina et al., Protein associated with Myc (PAM) is involved in spinal nociceptive processing, J. of Neurochemistry, vol. 88, No. 4, Feb. 2004, pp. 948-957.
Diantonio, Aaron et al., Ubiquilination-dependent mechanisms regulate synaptic growth and function, Nature (2001), vol. 412, pp. 449-452.

(Continued)

*Primary Examiner* — Marsha Tsay
(74) *Attorney, Agent, or Firm* — Daren P. Nicholson

(57) ABSTRACT

Methods for alleviating pain comprising administering to a subject sphingosine-1-phosphate, functional fragments and derivatives thereof, and other compounds, and assays for identifying such compounds.

21 Claims, 173 Drawing Sheets

(56) References Cited

OTHER PUBLICATIONS

Graziano, Michael P. et al., Purification of Recombinant G, Methods in Enzymology, (1991), vol. 195, pp. 192-203.
Grossberger, Rupert et al., Characterization of the DOC1/APC10 Subunit of the Yeast and the Human Anaphase-promoting Complex, The Journal of Biological Chemistry, (1999), vol. 274, No. 20, pp. 14500-14507.
Guo, Qingbin et al., Identification of a large Myc-binding protein that contains RCC1-like repeats, Proc. Natl. Acad. Sci. USA, (1998), vol. 95, pp. 9172-9177.
Hla, Timothy et al., Lysophospholipids—Receptor Revelations, Science, (2001), vol. 294, pp. 1875-1878.
Jin, Yishi, Synaptogenesis: insights from worm and fly, Current Opinion in Neurobiology, (2002), vol. 12, pp. 71-79.
Julius, David et al., Molecular mechanisms of nociception, Nature, (2001), vol. 413, pp. 203-210.
Kassis, Shouki et al., Different Mechanisms of Desensitization of Adenylate Cyclase by Isoproterenol and Prostaglandin E1 in Human Fibroblasts, The Journal of Biological Chemistry, (1982), vol. 257, No. 9, pp. 5312-5318.
Kind, Peter C. et al., Plasticity: downstream of glutamate, TRENDS in Neuroscience, (2001), vol. 24, No. 10, pp. 553-555.
Kluk, Michael J. et al., Signaling of sphingosine-1-phosphate via the S1P/EDG-family of G-protein-coupled receptors, Biochimica et Biophysica Acta, (2002), vol. 1582, pp. 72-80.
Mandala, Suzanne et al., Alteration of Lymphocyte Trafficking by Sphingosine-1-Phosphate Receptor Agonists, Science, (2002). vol. 296, pp. 346-349.
Meller, S. T. et al., Intraplantar zyrnosan as a reliable, quantifiable model of thermal and mechanical hyperalgesia in the rat, European Journal of Pain, (1997), vol. 1, pp. 43-52.
Nair, Bipin G. et al., Gs Alpha Mediates Epidermal Growth Factor-elicited Stimulation of Rat Cardiac Adenylate Cyclase, The Journal of Biological Chemistry, (1990), vol. 265, No. 34, pp. 21317-21322.
Nestler, Eric J., Molecular Basis of Long-Term Plasticity Underlying Addiction, Nature Reviews: Neuroscience, (2001), vol. 2, pp. 119-122.
Patel, Tarun B. et al., Functional Analyses of Type V Adenylyl Cyclase, Methods in Enzymology, (2002), vol. 345, pp. 160-187.
Payne, Shawn G. et al., Sphingosine-1-phosphate: dual messenger functions, FEBS Letters, (2002), vol. 52, pp. 54-57.
Postma, Friso R. et al., Sphingosine-1-phosphate rapidly induces Rho-dependent neurite retraction: action through a specific cell surface receptor, The EMBO Journal, (1996), vol. 15, No. 10, pp. 2388-2395.
Pyne et al., Spingosine 1-Phosphate Signalling Via The Endothelial Differentiation Gene Family of G-Protein-Coupld Receptors, Pharmacology and Therapeutics, vol. 88, 2000, pp. 115-131.
Rebecchi, Mario J. et al., Structure, Function, and Control of Phosphoinositide-Specific Phospholipase C, Physiological Reviews, (2000), vol. 80, No. 4, pp. 1291-1335.
Ruppert, Christian et al., Proto-oncogene c-myc is expressed in cerebellar neurons at different developmental stages, Embo Journal, (1986), vol. J5, pp, 1897-1901.
Sato, Koichi et al., Exogenous Sphingosine 1-Phosphate Induces Neurite Retraction Possibly through a Cell Surface Receptor in PC12 Cells, Biochemical and Biophysical Research Communications, (1997), vol. 240, pp. 329-334.
Schaefer, Anneliese M. et al., rpm-1, A Conserved Neuronal Gene that Regulates Targeting and Synaptogenesis in C. elegans, Neuron, (2000), vol. 26, pp. 345-356.
Schaible, Hans-Georg et al., How do we manage chronic pain?, Bailliee's Clinical Rheumatology, (2000), vol. 14, No. 4, pp. 797-811.
Scherr, Michaela et al., Gene Silencing Mediated by Small Interfering RNAs in Mammalian Cells, Current Medicinal Chemistry, (2003), vol. 10, pp. 245-256.
Scholich, Klaus et al., Facilitation of Signal Onset and Termination by Adenylyl Cyclase, Science, (1999), vol. 283, pp. 1328-1331.
Scholich, Klaus et al., Protein Associated with Myc (PAM) Is a Potent Inhibitor of Adenylyi Cyclases, The Journal of Biological Chemistry, (2001), vol. 276, No. 50, pp. 47583-47589.
Scholz, Joachim, et al., Can we conquer pain?, Nature Neuroscience, (2002), vol. 5, pp. 1062-1067.
Siehler, Sandra et al., Pathways of transduction engaged by sphingosine 1-phosphate through G protein-coupled receptors, Biochimica at Biophysica, (2002), vol. 1582, pp. 94-99.
Snyder, Solomon H., Adenosine as a Neuromodulator, Ann. Rev. Neursci., (1985), vol. 8, pp. 103-124.
Spiegel, Sarah et al., Functions of a new family of sphingosine-1-phosphate receptors, Biochimica et Biophysica Acta, (2000), vol. 1484, pp. 107-116.
Spiegel, Sarah et al., Sphingosine 1-Phosphate, a Key Cell Signaling Molecule, The Journal of Biological, (2002), vol. 277, No. 29, pp. 25851-25854.
Trajkovic, Vladimir et al., Muramyl dipeptide potentiates cytokine-induced activation of inducible nitric oxide synthase in rat astrocytes, Brain Research, (2000), vol. 883, pp. 157-163.
Wan, Hong I, et al., Highwire Regulates Synaptic Growth in *Drosophila*, Neuron, (2000), vol. 26, pp. 313-329.
West, Anne E. et al., Calcium regulation of neuronal gene expression, PNAS, (2001), vol. 98, No. 20, pp. 11024-11031.
Wilde, Jonathan I. et al., Regulation of phospholipase C Gamma Isoforms in Haematopoietic cells Why one, not the other?, Cellular Signalling, (2001), vol. 13, pp. 691-701.
Wood, John N., Pathobiology of Visceral Pain: Molecular Mechanisms and Therapeutic Implications II. Genetic approaches to pain therapy, Am. J. Physiol Gastrointest Liver Physiol, (2000), vol. 278. pp. G507-G512.
Woolf, Clifford J. et al., Neuronal Plasticity: Increasing the Gain in Pain, Science, (2000), vol. 288, pp. 1765-1768.
Woolf, Clifford J. et al., Neuropathic pain: aetiology, symptoms, mechanisms, and management, The Lancet, (1999), vol. 353, pp. 1959-1964.
Woolf, Clifford J. et al., Transcriptional and posttranslational plasticity and the generation of inflammatory pain, Proc. Natl. Acad. Sci. USA, (1999), vol. 96, pp. 7723-7730.
Xia, Zhengui et al., Calmodulin-regulated adenylyl cyclases and neuromodulation, Current Opinion in Neurobiology, (1997), vol. 7, pp. 391-396.
Xu, Dingbang et al., Human airway smooth muscle expresses 7 isoforms of adenylyl cyclase: a dominant role for isoform V, Am. J. Physiol. Lung Cell Mol. Physiol., (2001), vol. 281, pp. L832-L843.
Yang, Huaitao et al., Developmental expression of PAM (protein associated with MYC) in the rodent brain, Developmental Brain Research, (2002), vol. 136, pp. 35-42.
May et al. 'The Trigeminovascular System in Humans: Pathophysiologic Implications for Primary Headache Syndromes of the Neural Influences on the Cerebral Circulatio.' Journal of Cerebral Blood Flow and Metabolism. 1999, vol. 19, No. 2, pp. 115-127.
"Cranial Nerves," Wikipedia, https://en.wikipedia.org/wiki/cranial_nerves, print-out Sep. 23, 2015.
"Dorsal root ganglion," Wikipedia, https://en.wikipedia.org/wiki/Dorsal_root_ganglion, print-out Sep. 23, 2015.
Potrebic et al., "Peptidergic Nociceptors of Both Trigeminal and Dorsal Root Ganglia Express Serotonin 1D Receptors: Implications for the Selective Antimigraine Action of Triptans," J. NeuroScience 2003, 10988-10997.
Zhang et al., "Antinociceptive effects of FTY720 during trauma-induced neuropathic pain are mediated by spinal S1P receptors," Biol Chem. 2015;396:783-94.
"Trigeminal Nerve," Wikipedia, https://en.wikipedia.org/wiki/Trigeminal_nerve, print-out Sep. 23, 2015.

* cited by examiner

FIGURE 7A

```
   1 tcttggagcg ttctcagttt ctcaacagat cttcacttgc taggcagcca gaagccggcg
  61 gcagtggcgg caccgcctcc tcctcacatt cccggggtgg cggggttaga tgagcggccc
 121 cagtcgcggc gccgggggcg ctgttcatgc cggttccccga cggctccgtg gctgctgcgg
 181 ggctggggct ggggctaccc gccgcggact ccccgggtca ctaccagctg ctgctgtcag
 241 gccgggccct ggccgaccgc taccggagga tttataccgc tgcgctcaat gacagggacc
 301 agggggcgg cagcgctgga cacccagcct ccaggaataa gaaaatttta aataagaaga
 361 aattgaaaag aaaacagaag agcaaatcaa aagtgaagac aagaagcaag tctgaaaact
 421 tagagaatac agtaatcata ccagatatca aactacatag caatccttct gctttcaata
 481 tttactgtaa tgtacgccat tgcgttctgg aatggcagaa aaaggaaata tcattggcag
 541 ccgcatctaa gaactctgtg cagagtggag aatcagatag tgatgaagaa gaggaatcca
 601 aagagccccc tatcaagctt ccaaagatta ttgaggttgg cctttgtgaa gtttttgaat
 661 tgatcaaaga gacacgattt tctcatccat ccctgtgtct caggagtctc caagccctgc
 721 tcaacgtgct gcagggccag cagccagaag tgctccagtc tgagccacct gaggtcctag
 781 agtctctctt ccagcttctt ttggaaatca ccgttcgaag tactgggatg aatgacagca
 841 caggacagtc cttaacagca ctttcctgtg cttgcctctt tagtctggtg gcttcttggg
 901 gagaaacagg aaggacactt caggccatct ctgctatcct caccaacaat ggaagccatg
 961 cttgccaaac tattcaggtg ccaacaattc taaattcgct acagagaagt gtacaagcag
1021 ttttggtggg aaaaattcaa attcaggact ggtttagtaa tggcattaag aaagcagctt
1081 taatgcacaa gtggccatta aaagaaatat ctgttgatga agatgaccaa tgtctacttc
1141 agaatgatgg atttttttctt tatctattat gcaaggatgg attatataaa ataggctctg
1201 gatacagtgg aacagttagg ggccatatat acaattctac atcccgtatt agaaacagaa
1261 aagaaaaaaa gtcttggtta gggtatgctc agggttattt attatataga gatgtgaata
1321 accacagcat gacagccata aggataagcc ctgaaacact ggagcaagat ggtactgtga
1381 tgttaccaga ttgccacact gaaggtcaaa atattttatt cactgatgga gaatatatta
1441 atcagatagc tgcttcaaga gatgatggct ttgttgtcag aatatttgcc acaagcactg
1501 aacctgttct acagcaagaa ttgcaactta aactggctag aaaatgctta catgcctgtc
1561 gtatctcatt attcgatctg gaaaaggact tgcatattat aagtacagga tttgatgagg
1621 agtcagcaat tcttggtgca ggacgagagt ttgcgctaat gaaaacagca aatggaaaga
1681 tatattacac tggcaaatac cagagtcttg gaatcaaaca aggtggtcct tcagcaggaa
```

FIG. 7A (Cont.)

```
1741 aatgggttga gctaccaatt acaaaatctc caaagatagt acacttctca gttggacacg
1801 atggctctca cgccctttta gttgcagaag atgggagcat attctttaca ggatctgcta
1861 gtaaaggaga agatggagaa tcaattaaga gcagacggca atccaaacct tataaaccta
1921 aaaagataat taagatggaa ggaaagattg tggtatatac agcctgcaat aatggaagta
1981 gttctgttat ttctaaagat ggagaactct acatgtttgg aaaagatgcc atttactctg
2041 atagttcaag tttggtaact gatttgaagg gccattttgt aactcaggta gctatgggca
2101 aagctcacac ttgtgtttta atgaagaatg gagaggtgtg gacatttggt gtaaataata
2161 aaggacagtg tggacgagat actggtgcca tgaaccaagg tgggaaaggg tttggagttg
2221 aaaatatggc aacagcaatg gatgaagacc tggaagaaga actagatgaa aaagatgaga
2281 agtctatgat gtgccctcca ggcatgcaca aatggaagct ggagcagtgc atggttgca
2341 ctgtctgtgg agactgtaca ggttatggag ccagctgtgt cagtagtgga cggccagaca
2401 gagtccccgg agggatctgt ggttgtggtt ccggagaatc tggttgtgct gtgtgtggat
2461 gttgcaaggc ctgtgcaaga gagttagatg gtcaagaggc aagacaaaga ggaattcttg
2521 atgcagtgaa agaaatgata cctttagatc ttcttttagc tgtcccagtg cccggggtta
2581 acattgaaga acaccttcag ttacgacaag aagaaaaacg gcaacgtgta atcagaaggc
2641 acagattaga ggaaggaaga ggcccccttg tatttgctgg tcctattttt atgaaccatc
2701 gagaacaggc tctagccaga ctcagatccc atccagcaca cgtaaagcat aaacgggaca
2761 agcacaaaga tggaagtgga gaaagaggcg aaaaggatgc aagcaaaatc acaacatacc
2821 ctccaggctc tgtgcgattt gactgtgagc tccgggcagt ccaagtcagc tgtggatttc
2881 accattcagt ggttttaatg gaaaatggag atgtctatac atttggttat gggcagcatg
2941 ggcagctagg acatggagat gtcaactcca ggggatgtcc cactcttgtt caagcattgc
3001 caggccctag cacacaagtc actgcaggca gcaaccatac ggcagtactt ttaatggatg
3061 gacaggtctt cacatttgga agtttttcta aaggacaact gggcagacca attttggatg
3121 tgccatattg gaatgcaaag ccagctccca tgcctaacat tggatcaaaa tatggaagaa
3181 aagctacttg gataggtgca agtggggacc aaactttttt acgaattgat gaagcactta
3241 ttaattctca tgtacttgct acatcagaaa tttttgccag taaacacata ataggcttgg
3301 tacctgcttc tatatcagaa cctcctccat ttaaatgcct tctgataaat aaagtggatg
3361 ggagttgtaa aacttttaat gactcagaac aagaggatct gcaaggattt ggtgtgtgtc
3421 ttgatcctgt atatgatgta atttggaggt ttcgaccaaa tactagagag ctgtggtgtt
3481 acaatgcggt ggttgctgat gccaggcttc cctctgcagc agacatgcag tccagatgta
3541 gtatcctaag tcctgaactt gccttaccaa caggatcaag ggccctcact acccgatctc
3601 atgcagcttt gcacatttta ggttgtcttg ataccttggc agctatgcag gacttaaaaa
3661 tgggtgttgc aagtacagag gaagagactc aagcagtaat gaaggtttat tctaaagaag
3721 attatagtgt ggtaaacagg tttgaaagtc atggaggagg ctggggttat tctgcccatt
```

FIG. 7A (Cont.)

3781 cagtagaagc tatacgtttc agtgccgaca ctgatatttt acttggtggt cttggtctgt
3841 ttggaggtag aggagaatat actgctaaaa ttaagctgtt tgaattgggt cctgatggag
3901 gagatcatga aactgatggt gaccttcttg cagagactga tgtattggct tatgactgtg
3961 ctgctagaga aaaatatgca atgatgtttg atgagcctgt tctcctgcaa gctgggtggt
4021 ggtatgtggc atgggcccga gtgtcaggac ccagcagtga ctgtggatct catggacagg
4081 catctattac cacagatgat ggggttgttt tccagttcaa gagttcaaag aaatcaaata
4141 atggtacaga tgttaatgcg ggtcagatac ctcagttatt atacagactt ccaaccagtg
4201 atggcagtgc ttcaaaaggc aaacagcaaa ccagtgaacc tgtacacatt ttaaagaggt
4261 cttttgcaag aactgtctca gtggaatgtt ttgagtcatt gttgagtatt cttcactgga
4321 gctggaccac cttagtctta ggagttgaag aacttagagg attaaaagga ttccagttca
4381 cagctacact cctagattta gagagactgc gctttgtggg tacctgttgt ctgaggttat
4441 tgcgtgtcta tacctgtgaa atttacccag tgtcagctac aggaaaagca gttgtagaag
4501 aaactagcaa attagcagag tgtattggaa aaaccagaac tttgttaaga aaaattttat
4561 cagaaccact tgatcactgc atggtgaaat tggataatga tcctcaagga tatctcagtc
4621 aacccttgag tcttctagaa gctgtccttc aggaatgtca taatactttc actgcctgct
4681 ttcattcttt ctacccaact cctgccttac agtgggcttg cctttgtgat ctgctgaatt
4741 gtttggatca ggatatccaa gaagcaaact tcaagacatc aagtagccga ctccttgcag
4801 ctgttatgtc agctctgtgt cacacgtctg ttaagctgac ttccatcttc ccgattgcgt
4861 atgatggaga agtattacta cgatcaattg ttaaacaagt tagtacagag aacgactcaa
4921 cactagttca tcgttttccc cttttggtgg cacatatgga aaaactcagc cagagtgaag
4981 agaatatctc agggatgaca agcttccgtg aagttctgga gaaaatgctg gtcattgttg
5041 tgctaccagt caggaacagc ctgaggagag aaaatgaact cttctcctcc cacctcgtct
5101 ctaacacctg tggattactg gccagcattg tcagtgaact gacagcgtca gccctgggat
5161 ctgaggttga tggacttaat tctcttcact ctgtaaaagc tagtgctaac cgatttacaa
5221 aaacaagtca gggcagaagt tggaacactg ggaacgggtc ccctgatgca atctgttttt
5281 cagtagacaa acctggaata gttgtggttg gtttctctgt ctatggagga ggtggaattc
5341 atgaatatga attagaggtg ttggttgatg atagtgaaca tgcaggagat tcaactcatt
5401 cccacagatg gacatctctg gaattagtga aaggaacgta cacaacggat gactcaccca
5461 gtgatatagc tgagatcaga cttgacaaag tggttccttt aaaggaaaat gttaaatatg
5521 ctgtgcgctt gaggaactat ggaagccgta cagccaatgg agatggagga atgaccacag
5581 ttcagtgccc tgatggtgtg acattcacat tcagcacgtg cagcttgagc agtaacggca
5641 caaaccaaac cagaggacag atcccacaga tactctacta taggagtgaa tttgatggag
5701 atttacaatc ccaacttctg agtaaagcca atgaagaaga taaaaactgt agcagagcat
5761 tgtctgttgt aagcactgtc gttcgagcct ctaaggacct cctgcacaga gctcttgctg

FIG. 7A (Cont.)

```
5821 tggatgctga tgacattcca gaactgctga gttcttccag tctgttttcc atgctgctcc
5881 cccttattat agcctacata ggaccagtag ctgctgctat tcccaaggtg gctgtagaag
5941 tctttggcct tgtccaacaa ttgcttccgt cagttgccat tttgaatcag aagtatgcac
6001 cgcctgcctt caaccctaat cagtcgacag atagcaccac aggaaaccag cctgaacagg
6061 gcctctctgc ttgtacaacc tccagtcact atgctgtcat agagagtgag caccccgtata
6121 aacctgcctg tgtgatgcat tacaaggtga cattcccaga atgtgtgagg tggatgacaa
6181 tcgaatttga ccctcagtgt ggtactgcac agtcagaaga tgtccttcgt ttgttgattc
6241 ctgtcagaac tgttcagaat tcaggatatg gaccaaaatt gacatctgtt catgaaaatc
6301 ttaattcatg gatagaatta aagaaatttt caggatcctc tgggtggcct actatggttt
6361 tggtgttgcc aggaaatgag gcccttttttt cattggagac tgcatcagat tatgtgaaag
6421 atgacaaagc ttcttttctat ggttttatgt gttttgcaat tggatatgaa tttagccctg
6481 gacctgatga gggagtcatc caattggaaa aagaattagc caatcttggt ggggtttgtg
6541 cagcagctct gatgaagaag gacctagcac ttcctattgg taatgaatta gaagaagacc
6601 ttgaaattct tgaggaggct gcattgcagg tgtgcaaaac ccattctgga attcttggaa
6661 agggtctagc tctttctcat tcaccaacta tattagaagc acttgaggga aatttaccac
6721 tccaaatcca aagcaatgaa cagtcttttc tggatgattt tattgcctgt gtcccaggat
6781 caagtggtgg aaggcttgca aggtggcttc agccagattc atatgcggat cctcagaaaa
6841 catctttgat cctgaataag gatgatattc gttgtggttg gcctaccacc ataactgttc
6901 aaacaaaaga ccagtatggg gatgtggtac atgttcccaa tatgaaggtg gaagtgaaag
7021 ggattcctgg cagtcctgca gtaacagctg catcttctaa tactgacatg acttatggag
7081 ggctggcatc accaaagcta gatgtttcat atgaaccaat gatagtgaag gaagctcgat
7141 atattgccat aacaatgatg aaggtttatg aaaattattc atttgaagaa ctacgttttg
7201 catcaccaac tcctaagaga cccagtgaga atatgctgat ccgtgtcaat aatgatggga
7261 cttattgtgc aaattggact ccaggggcta ttggactcta cactcttcat gttaccattg
7321 atggcattga aatcgatgct ggtctggaag taaaagtaaa agacccacca aaagggatga
7381 taccaccagg aactcagttg gtcaaaccaa agtctgaacc tcagcctaat aaggttcgaa
7441 aatttgtggc caaggacagt gcggggcttc gcatccgtag ccacccttcc cttcagagtg
7501 agcagatagg catagtgaaa gtcaatggaa ctatcacttt tattgatgag atccataatg
7561 atgatggtgt gtggctgagg ctgaatgatg agacaataaa gaagtatgtc cctaacatga
7621 atggttacac tgaagcctgg tgcctctctt ttaatcaaca tcttggcaag agtcttctgg
7681 tccctgttga cgaatctaaa actaatactg atgacttttt caaagacata aactcctgct
7741 gcccacagga agcaacaatg caagaacaag atatgccatt cttgcgagga gggccaggca
7801 tgtacaaggt agtgaagacg ggaccttcag gtcacaacat cagaagctgc cctaacctta
7861 gaggtatccc aattggaatg ttagttctgg gaaacaaagt caaagcagtg ggagaggtaa
```

FIG. 7A (Cont.)

```
7921 ccaattctga agggacatgg gtgcaactgg atcagaacag catggtagag ttctgtgaga
7981 gtgatgaagg agaggcatgg tcccttagcta gagacagagg cggaaaccag tacctccgac
8041 atgaagatga acaagctctt ctggatcaga attctcaaac tcctcctcca agccctttct
8101 cagtgcaagc ttttaataaa ggggcaagtt gcagtgccca aggatttgat tatggactcg
8161 gaaatagcaa aggtgatcga ggaaacatct caacatcttc taaaccagcc tctacatcag
8221 gaaaatcaga gctgtcctct aaacacagca gatcgcttaa acctgatgga cgtatgagcc
8281 ggactactgc tgatcagaag aagccaaggg gcacagaaag tttatctgct agtgaatccc
8341 tcatcttaaa atctgatgct gcaaagttga ggtcagattc ccacagtagg tcattatccc
8401 ccaaccataa caccttgcag acattgaaat ctgatgggag gatgccttct agctccagag
8461 ctgaatcccc aggaccaggt tctcggttgt catctcctaa gccaaagact ctcccagcca
8521 ataggtctag cccatcgggt gctagttctc cacgctcctc ctcaccacat gataaaaatc
8581 tacctcaaaa aagtactgct cctgttaaga caaagcttga tcctcctcgg gaacgttcta
8641 aatcagactc ttacacactt gatccagata ccctccgcaa gaagaaaatg cccctcacag
8701 aacctttgag aggacggtca acgtcaccaa aaccaaaatc agtaccaaag gattctacag
8761 attcccctgg atctgaaaat agagctccct ctccccatgt ggtacaggaa aacctccaca
8821 gtgaggtggt cgaagtctgc acctcaagta ctttaaaaac aaatagtcta acagacagca
8881 cctgcgatga cagcagtgaa tttaagagtg tggatgaagg ttcaaataaa gttcatttta
8941 gcattggaaa agcaccactg aaagatgaac aggaaatgag agcatctccc aaaataagtc
9001 gaaaatgtgc taatagacac accaggccca aaaaagaaaa atcgagtttt cttttcaaag
9061 gagatggatc caagccttta gagccagcca agcaagccat gtctccttct gtggccgaat
9121 gtgccagagc tgtgtttgct tccttcctct ggcatgaagg catagtacat gatgcaatgg
9181 cttgttcttc tttcctaaag tttcatcctg aactttccaa agaacatgct cctataagga
9241 gtagtttaaa tagccaacaa cctacagaag aaaaagaaac caagttaaaa aatagacatt
9301 cattagaaat atcatctgca ctgaatatgt ttaatattgc accccatgga ccagatatat
9361 ctaagatggg tagcatcaac aaaaacaagg tattgtctat gcttaaggaa ccacctctgc
9421 atgaaaaatg tgaggatggg aaaaccgaga ccacttttga aatgtccatg cataacacaa
9481 tgaagtctaa gtctcctctt cccttaactt tacaacattt agtggctttt tgggaagaca
9541 tctctttggc tactatcaaa gctgcttccc agaatatgat tttccaagt cctggttcct
9601 gtgcagttct taaaaagaaa gagtgtgaga aaggaaggaa taagaagtcc aaaaaggaaa
9661 aaaagaaaaa agaaaaggca gaagttaggc ccaggggtaa tttgtttgga gagatggccc
9721 agctggcagt aggaggacca gagaaagata ccatctgtga actgtgtggg gagtcacatc
9781 catacccggt gacctatcac atgagacaag ctcacccagg ttgtggccga tatgctggtg
9841 gacaaggtta caatagcatt gggcattttt gtggaggatg ggctggtaac tgtggtgatg
9901 gtggcatagg aggaagcact tggtatctgg tatgtgatcg ctgtagagaa aaatacctcc
```

FIG. 7A (Cont.)

```
 9961 gcgaaaaaca ggctgctgca agggagaagg tcaaacaatc taggagaaaa ccaatgcaag
10021 tcaagacccc tcgtgccttg cccaccatgg aagctcacca ggtgattaaa gccaatgcac
10081 tcttcctgct gtccctgagc agtgcagcag aaccgagcat tctgtgttac catcctgcaa
10141 agccattcca atctcagttg cccagtgtaa aagaaggcat ttctgaggat cttcctgtga
10201 aaatgccttg tctgtacctg cagacattag ctaggcatca tcatgaaaat tttgtgggct
10261 atcaagatga caatctattc caggatgaaa tgagatatct acgttcaaca tctgtacctg
10321 ccccgtatat atcagtaact cctgatgcaa gtcctaatgt atttgaagag ccagagagca
10381 atatgaagtc tatgccacca agtttagaaa ccagtcccat aactgatact gatcttgcaa
10441 agagaactgt cttccaaaga tcatactcag ttgttgcttc cgaatatgat aaacaacact
10501 ccattttacc tgcacgagtt aaagctattc ctagaagaag agttaacagt ggagacactg
10561 aagttggttc ttcccttttg agacatccgt ctcctgagct ttctcggcta atctcagccc
10621 acagctctct ttctaaagga gaacgaaatt tccagtggcc agttttagct tttgttatac
10681 aacatcatga tctagaaggt cttgaaatag caatgaaaca ggccctaagg aaatctgctt
10741 gtcgagtttt tgctatggag gctttcaact ggcttctgtg taatgtcatc caaaccactt
10801 ctctccatga tattctgtgg cattttgtgg catcactgac tcctgcacca gtggaaccag
10861 aggaagaaga ggatgaagaa aataaaacaa gcaaagaaaa ttcagaacaa gagaaagata
10921 caagagtatg tgaacatcca ctctcagaca tagtgattgc cggggaacgt gctcatcctt
10981 taccacacac ctttcaccgc ttgctgcaga ccatctcaga ccttatgatg tctctcccca
11041 gcggcagttc attacagcaa atggccctga ggtgctggag tctcaaattc aagcaatctg
11101 atcaccagtt ccttcatcag agcaacgtct ttcatcacat taacaatatt ttgtcaaagt
11161 cagatgatgg cgatagtgaa gagagtttta gcatcagtat acagtctggc tttgaagcta
11221 tgagtcagga attatgcata gtaatgtgct taaaggactt aaccagcatt gttgacataa
11281 aaacttcaag ccgacctgcc atgattggca gtttgacaga cggctccaca gaaacctttt
11341 gggaatcagg agatgaagat aaaaacaaaa ctaagaacat caccatcaac tgtgtaaaag
11401 gaatcaatgc ccgctatgtg tctgttcacg tggacaattc ccgagatctt gggaataaag
11461 ttacctcaat gaccttctta actggcaaag cagtagaaga tttgtgcaga ataaagcagg
11521 ttgatctgga ttccaggcac attggctggg taacaagtga acttccagga ggggataatc
11581 acatcataaa aattgaatta aaaggcccag aaaatacact gagagttcga caagtcaaag
11641 tcctgggctg gaaagatggt gaaagcacaa aaatagctgg ccagatttca gccagtgtgg
11701 cccagcagag gaactgtgaa gctgagactc tgcgagtatt cagactgatt acgtctcaag
11761 tatttggaaa gctcatctct ggagatgctg aacctacacc agaacaagag gaaaaagcac
11821 tattgtcatc acctgaagga gaagaaaaag tatacaatgc aacatcagat gctgacctga
11881 aagaacatat ggttggaatc atattcagca ggagtaagct gactaactta caaaaacagg
11941 tgtgtgctca tattgtccaa gctattcgca tggaagctac cagagtccgt gaagaatggg
```

FIG. 7A (Cont.)

12001 aacatgctat atcaagcaaa gaaaatgcca attctcagcc aaatgatgaa gatgcctcct
12061 ctgatgccta ctgctttgag ctgctctcta tggttttagc actgagtggc tctaacgttg
12121 gccggcaata tctggctcaa cagctaaccc tgcttcagga tctcttctcg ctgcttcaca
12181 cagcctctcc tagagtccag agacaggtaa cctctttact aagaagagtt ttgcctgaag
12241 taacccctag tcgtctggcc agcatcatag gagtgaaatc cctcccccca gcagatatca
12301 gtgatatcat tcactcaaca gagaaaggag actggaataa gctgggtatc ttggacatgt
12361 ttctaggatg cattgccaaa gcactcactg tacagctaaa agccaaagga accaccatca
12421 ctggaacagc tggtaccact gtgggcaaag gagttacaac agttactctt ccgatgattt
12481 tcaattccag ttatctccga cgaggtgaaa gtcattggtg gatgaagggc tcaaccccta
12541 cccagatctc agagatcatc attaaactta tcaaggatat ggcagcaggt catctgtcag
12601 aagcttggtc ccgagtgaca aaaaatgcta ttgcagaaac catcattgcc ttgaccaaga
12661 tggaagaaga atttaggtct ccagtgagat gtattgcaac aactagactc tggcttgctc
12721 tcgcatccct atgtgttctt gatcaggacc acgtagatcg tctctcctcg ggagatgga
12781 tgggaaagga tggacaacaa aaacaaatgc ctatgtgtga taaccatgat gatggtgaaa
12841 ctgcagcaat cattttatgc aatgtctgtg gaaatttatg tacagactgt gacagattcc
12901 ttcaccttca tcgaagaacc aaaactcatc aaagacaggt cttcaaagaa gaagaagaag
12961 ctataaaggt tgaccttcat gaaggttgtg gtagaaccaa attgttctgg ttgatggcac
13021 tggcagattc taaaacaatg aaggcaatgg tggaattccg agaacacaca ggcaaaccca
13081 ccacgagtag ctcagaagca tgtcgcttct gtggttccag gagtggaaca gagttatctg
13141 ctgttggcag tgtttgttct gatgcagatt gccaggaata cgctaagata gcctgtagta
13201 agacgcatcc ttgtggccat ccatgcgggg gtgttaaaaa cgaagagcac tgtctgccct
13261 gtctacacgg ctgtgacaaa agtgccacaa gcctgaagca agacgccgat gacatgtgca
13321 tgatatgttt caccgaagcg ctctcggcag caccagccat tcagctggat tgtagtcaca
13381 tattccactt acagtgctgt cggcgagtat tagaaaatcg atggcttggc ccaaggataa
13441 catttggatt tatatcttgt cccatttgca agaacaaaat taatcacata gtactaaaag
13501 acctacttga tccaataaaa gaactctatg aggatgtcag aagaaagcc ttaatgagat
13561 tggaatatga aggtctgcat aagagtgaag ctatcacaac tcctggtgtg aggtttata
13621 atgacccagc tggctatgca atgaatagat atgcatatta tgtgtgctac aaatgcagaa
13681 aggcatattt tggtggtgaa gctcgctgcg atgctgaggc tggacgggga gatgattatg
13741 atcccagaga gctcatttgt ggtgcctgtt ctgatgtttc cagggctcag atgtgtccca
13801 aacatggcac agactttttg gaatataaat gtcgctactg ctgttcagtg gctgtttttt
13861 tctgttttgg aacaacacat ttttgtaatg cttgtcatga tgattttcaa agaatgacta
13921 gcattcctaa ggaagaacta ccacactgtc ctgcaggtcc caaaggcaag cagttagaag
13981 gaactgaatg tccactccat gttgttcatc cacccactgg ggaagagttt gctctgggat

FIG. 7A (Cont.)

14041 gtggagtgtg cagaaatgcc cacacttttt agaacacgca gatcctttgt ctacagagag
14101 aaaaattgcc ttcatccccc aagaggatgc ggtgaagttt aaactctgct caccataagg
14161 acgggaccat ttttacatcc atgaaaatga accattcaca gtgcaagaag gataccaaat
14221 accatgtaca taattcttgc tatgaaaagt ttccccatta ttttggttta tctttctttg
14281 aacaaatgac atcaaacttg tgaggtgttt gcatgtggcc attaccgtca ttggcctgtg
14341 aagcattgga catttataga taattgatat aaaagaatcg ccatgcccat ggactaagaa
14401 cgatgctggc tttcaagcaa aaaagaaaaa taatcattgt ttattgtata ctgccttttt
14461 gtaatcctgt acaattgcat cacgggtggg gataaaaaga ggaatattct ggtttatttc
14521 ctagactgtt atttaaaaaa aaaaaaaaca ttgtgttagg acagcatata aatgtaataa
14581 gtatcacact gtatataaac atatcaatgt ttgtcctgta taagaattac taaattacaa
14641 atgcaatttc atttaaactt ctaggttaag tttgagcctg aaattttaat gaagtgcaat
14701 actgagtgtg cctcattatc ttgcagctgt aaacatattg gaatgtacat gtcaataaaa
14761 ccactgtaca tttttataca gtgataaagt ctaaaaaaaa aaaaaaa

FIGURE 7B

```
   1 mpvpdgsvaa aglglglpaa dspghyqlll sgraladryr riytaalndr dqgggsaghp
  61 asrnkkilnk kklkrkqksk skvktrskse nlentviipd iklhsnpsaf niycnvrhcv
 121 lewqkkeisl aaasknsvqs gesdsdeeee skeppiklpk iievglcevf eliketrfsh
 181 pslclrslqa llnvlqgqqp evlqseppev leslfqllle itvrstgmnd stgqsltals
 241 caclfslvas wgetgrtlqa isailtnngs hacqtiqvpt ilnslqrsvq avlvgkiqiq
 301 dwfsngikka almhkwplke isvdeddqcl lqndgfflyl lckdglykig sgysgtvrgh
 361 iynstsrirn rkekkswlgy aqgyllyrdv nnhsmtairi spetleqdgt vmlpdchteg
 421 qnilftdgey inqiaasrdd gfvvrifats tepvlqqelq lklarkclha crislfdlek
 481 dlhiistgfd eesailgagr efalmktang kiyytgkyqs lgikqggpsa gkwvelpitk
 541 spkivhfsvg hdgshallva edgsifftgs askgedgesi ksrrqskpyk pkkiikmegk
 601 ivvytacnng sssviskdge lymfgkdaiy sdssslvtdl kghfvtqvam gkahtcvlmk
 661 ngevwtfgvn nkgqcgrdtg amnqggkgfg venmatamde dleeeldekd eksmmcppgm
 721 hkwklegcmv ctvcgdctgy gascvssgrp drvpggicgc gsgesgcavc gcckacarel
 781 dgqearqrgi ldavkemipl dlllavpvpg vnieehlqlr qeekrqrvir rhrleegrgp
 841 lvfagpifmn hreqalarlr shpahvkhkr dkhkdgsger gekdaskitt yppgsvrfdc
 901 elravqvscg fhhsvvlmen gdvytfgygq hgqlghgdvn srgcptlvqa lpgpstqvta
 961 gsnhtavllm dgqvftfgsf skgqlgrpil dvpywnakpa pmpnigskyg rkatwigasg
1021 dqtflridea linshvlats eifaskhiig lvpasisepp pfkcllinkv dgscktfnds
1081 eqedlqgfgv cldpvydviw rfrpntrelw cynavvadar lpsaadmqsr csilspelal
1141 ptgsralttr shaalhilgc ldtlaamqdl kmgvasteee tqavmkvysk edysvvnrfe
1201 shgggwgysa hsveairfsa dtdillgglg lfggrgeyta kiklfelgpd ggdhetdgdl
1261 laetdvlayd caarekyamm fdepvllqag wwyvawarvs gpssdcgshg qasittddgv
1321 vfqfksskks nngtdvnagq ipqllyrlpt sdgsaskgkq qtsepvhilk rsfartvsve
1381 cfesllsilh wswttlvlgv eelrglkgfq ftatlldler lrfvgtcclr llrvytceiy
1441 pvsatgkavv eetsklaeci gktrtllrki lsepldhcmv kldndpqgyl sqplslleav
1501 lqechntfta cfhsfyptpa lqwaclcdll ncldqdiqea nfktsssrll aavmsalcht
1561 svkltsifpi aydgevllrs ivkqvstend stlvhrfpll vahmeklsqs eenisgmtsf
1621 revlekmlvi vvlpvrnslr renelfsshl vsntcqllas ivseltasal gsevdglnsl
1681 hsvkasanrf tktsqgrswn tgngspdaic fsvdkpgivv vgfsvygggg iheyelevlv
1741 ddsehagdst hshrwtslel vkgtyttdds psdiaeirld kvvplkenvk yavrlrnygs
1801 rtangdggmt tvqcpdgvtf tfstcslssn gtnqtrgqip qilyyrsefd gdlqsqllsk
```

FIG. 7B (Cont.)

1861 aneedkncsr alsvvstvvr askdllhral avdaddipel lsssslfsml lpliiayigp
1921 vaaaipkvav evfglvqqll psvailnqky appafnpnqs tdsttgnqpe qqlsacttss
1981 hyaviesehp ykpacvmhyk vtfpecvrwm tiefdpqcgt aqsedvlrll ipvrtvqnsg
2041 ygpkltsvhe nlnswielkk fsgssgwptm vlvlpgneal fsletasdyv kddkasfygf
2101 mcfaigyefs pgpdegviql ekelanlggv caaalmkkdl alpignelee dleileeaal
2161 qvckthsgil gkglalshsp tilealegnl plqiqsneqs flddfiacvp gssggrlarw
2221 lqpdsyadpq ktslilnkdd ircgwpttit vqtkdqygdv vhvpnmkvev kavpvsqkkm
2281 slqqdqakkp qripgspavt aassntdmty gglaspkldv syepmivkea ryiaitmmkv
2341 yenysfeelr fasptpkrps enmlirvnnd gtycanwtpg aiglytlhvt idgieidagl
2401 evkvkdppkg mippgtqlvk pksepqpnkv rkfvakdsag lrirshpslq seqigivkvn
2461 gtitfideih nddgvwlrln detikkyvpn mngyteawcl sfnqhlgksl lvpvdesktn
2521 tddffkdins ccpqeatmqe qdmpflrggp gmykvvktgp sghnirscpn lrgipigmiv
2581 lgnkvkavge vtnsegtwvq ldqnsmvefc esdegeawsl ardrggnqyl rhedeqalld
2641 qnsqtpppsp fsvqafnkga scsaqgfdyg lgnskgdrgn istsskpast sgkselsskh
2701 srslkpdgrm srttadqkkp rgteslsase slilksdaak lrsdshsrsl spnhntlqtl
2761 ksdgrmpsss raespgpgsr lsspkpktlp anrsspsgas sprsssphdk nlpqkstapv
2821 ktkldpprer sksdsytldp dtlrkkkmpl teplrgrsts pkpksvpkds tdspgsenra
2881 psphvvqenl hsevvevcts stlktnsltd stcddssefk svdegsnkvh fsigkaplkd
2941 eqemraspki srkcanrhtr pkkekssflf kgdgskplep akqamspsva ecaravfasf
3001 lwhegivhda macssflkfh pelskehapi rsslnsqqpt eeketklknr hsleissaln
3061 mfniaphgpd iskmgsinkn kvlsmlkepp lhekcedgkt ettfemsmhn tmkskspipl
3121 tlqhlvafwe dislatikaa sqnmifpspg scavlkkkec ekgrnkkskk ekkkekaev
3181 rprgnlfgem aqlavggpek dticelcges hpypvtyhmr qahpgcgrya ggggynsigh
3241 fcggwagncg dggiggstwy lvcdrcreky lrekqaaare kvkqsrrkpm qvktpralpt
3301 meahqvikan alfllslssa aepsilcyhp akpfqsqlps vkegisedlp vkmpclylqt
3361 larhhhenfv gyqddnlfqd emrylrstsv papyisvtpd aspnvfeepe snmksmppsl
3421 etspitdtdl akrtvfqrsy svvaseydkq hsilparvka iprrrvnsgd tevgssllrh
3481 pspelsrlis ahsslskger nfqwpvlafv iqhhdlegle iamkqalrks acrvfameaf
3541 nwllcnviqt tslhdilwhf vasltpapve peeeedeenk tskensegek dtrvcehpls
3601 diviagerah plphtfhrll qtisdlmmsl psgsslqqma lrcwslkfkq sdhqflhqsn
3661 vfhhinnils ksddgdsees fsisiqsgfe amsqelcivm clkdltsivd iktssrpami
3721 qsltdgstet fwesgdedkn ktknitincv kginaryvsv hvdnsrdlgn kvtsmtfltg
3781 kavedlcrik qvdldsrhig wvtselpggd nhiikielkg pentlrvrqv kvlgwkdges
3841 tkiaqqisas vaqqrnceae tlrvfrlits qvfgklisgd aeptpeqeek allsspegee

FIG. 7B (Cont.)

3901 kvynatsdad lkehmvgiif srskltnlqk qvcahivqai rmeatrvree wehaissken
3961 ansqpndeda ssdaycfell smvlalsgsn vgrqylaqql tllqdlfsll htasprvgrq
4021 vtsllrrvlp evtpsrlasi igvkslppad isdiihstek gdwnklgild mflgclakal
4081 tvqlkakgtt itgtagttvg kgvttvtlpm ifnssylrrg eshwwmkgst ptqiseiiik
4141 likdmasghl seawsrvtkn aiaetiialt kmeeefrspv rciattrlwl alaslcvldq
4201 dhvdrlssgr wmgkdgqqkq mpmcdnhddg etaaiilcnv cgnlctdcdr flhlhrrtkt
4261 hqrqvfkeee eaikvdlheg cgrtklfwlm aladsktmka mvefrehtgk pttssseacr
4321 fcgsrsgtel savgsvcsda dcqeyakiac skthpcghpc ggvkneehcl pclhgcdksa
4381 tslkqdaddm cmicfteals aapaiqldcs hifhlqccrr vlenrwlgpr itfgfiscpi
4441 cknkinhivl kdlldpikel yedvrrkalm rleyeglhks eaittpgvrf yndpagyamn
4501 ryayyvcykc rkayfggear cdaeagrgdd ydprelicga csdvsraqmc pkhgtdfley
4561 kcryccsvav ffcfgtthfc nachddfqrm tsipkeelph cpagpkgkql egtecplhvv
4621 hpptgeefal gcgvcrnaht f
//

FIGURE 7C:
(SEQ ID No.3)

CTTCAGCTTGGAGTACTAAATATATTCTATGAAATATACTTTATTTTAAAGTGCAATATATTTGTCAAGA
ATGCACTATCTTATTACCCTTAAAAAGAGAAGGTCACTGAAGAGTAAAGCATGTCTTCACTCTTCAAGCC
TAAGCTTTTTCTTTTTTTTTTCCCAAATTGTTCTCAGCTACCAATTTTGTTTTTAAATTCCCCAATACAT
TGTTGTACAAATCCAGGAAACAAACGCAGACTTTACCACAGCATTTTCAGCAGTCTCGATGTACCTAATA
ATATACATACTTCCTGTGTTTGTAGTCTTGTAGCTTTAGTACAATATTAACCCTTTAAATGAAACAACAC
TAATCTGTCCTCTTATATACACGTTATGGTTCCTGCCCTGTTATTTACTACATCAGCACGGGTAGCTTCC
TTTAAAAACAAAATCGTTAAAGATGAGAGTAGGAAAAATGTAAATGTGATAAGAGTTCAAAAAACTGTGG
TCCAGGTTTGCAATGTTAAGTGGAAAAGAACGACTAAATCTGTGATCACAAGGGGAAAGATGAAGCCATA
GTCTTATTACATGGGCACAGGACAGAGAGATCTCTTTTGCGAAATGAGCATACCAACCACAAAGAATAAA
ACATACTACGCCCGTAATAAAATGGGCACAGGCAGGATTTGCCGTAGTTCAATGCTATTCTTTGAGGGCG
AATGTGTCGTGGGTGAACTGCTGTCTAGCCCATTCCGACACCCAAGCCGCCCAGGCGGCCCCCACGCCCC
CCGGCTGCAGCCCTCCCTGTACACACAAATGCACACACGCCCAGCCCGGCCGCTGGAGGAACTAAGATGG
CAGCGCAGAAAGCACGGGGGCCGAGCTCGGTGGGGTGGGGAAAGAAAAGCAAAGCCCTCTGTGTTTTTTC
ATTCTGTATAGGTCCCCCTCTTTCCCCAAACACAAGGGCTGCGTAAGGCATTCGGTAGTAGAGCTCGCAG
GAGCGGCGGGAGGGGACGCTTGCTTTGCATACTGCCAGAAACCCACGTCTCCGATCTGCAGCGACGGTTC
AGGCGACCCTCGCGACTTGTGACCACACTCTCCTTCACGTCCCCTTGACAGTAGAAGTAAGGGTGACTCC
AAATGCCTTTTTCTTTCTGGCATGCGCCCCACTCCCCCGCCATCCCAGGGGAGCCTTCCAAGTTGCCCAG
CTGCCAAGGCGGTAGCTGTGGCAGTTGCAGGGACCGGGGAGCGCGCCGTGCGGAGGCAGGAAGAGGAGGA
GGAGGAGAAAAAACGCTGCACTGGCTATCAATTTTGAGGAGAGCGACCGCTGCCGCTGCCGTGGAAGGAA
ACGCTGCCAACCGCAACAGAAATGCCACTCTCGGATACCTAAGTGAGCATGTGTGCGACTCTGCGCACGC
CTAGTTGCGCAGCTCAATGACATCGGGCTTCTTAGCAAGTTATCCAGTTTCCGGGTTTTGAGTGTACCCA
TCAGGCTCCGTAGGGGCCTGTCTGGGACTGAACAGCAGTAAAGATTGAAGCGAAATTAATGAATGGTGGG
AAGAGCCCGGAGACCAGGGCAGCCACGCGGGTCAATGTCCACTAGAAACTCTAAATGGGCAGTGACTGCA
CATTCCACCACCTGAGCCTGCGCTGTAAATGTTTTCTGTGCAAGCAACATTCATTCATTCAGCCAACATC
TATTTCCCTCCTGTTCAGGGCTAGACCCTGTGCTAGGAGCCTGTGATGGTTGAACAGACACCATTGCTAC
CCTACGGAAAACCTAGTGTTTTGTTTAGTATGTGCTACCATTTGTGAAAATTCATGTGCCAAGTTGGACA
TCCTAGATCCTTTAAGTCCTCCCTCAATCTCATGTAGTGGGTATTCTTTTGAGCATTATTCAGAGGAGAT
AATTTGCCCAAAGCCAGACAAGTATTAAGTAGCAGAGTCAGGATCCAATTCCAGGGCTGTCTGATTTCAG
AGCCTTTTAGCTACCCTGCTAGGTCTTGCAATAGTAATGGGCCCTCTCATTGCTTACCTGTCAGGCCTTA
GAATTCTTAGAATTTAGCTGCCTCTACACCATTGTCTTGGTTCTCACTCCAGGGTTAGGGGCTGCCTGGT
CAACACTGAGGTCTTTAACTGTGCTGAAGCATTAGGATAGAAATTTAGTCTAATAAATACTTACTGGATA

FIG. 7C (Cont.)

CCTACTACATGCAAAGTCCTGAAGTGGCTGAAGGAGACACAAAAGCAGCAAGCTCTGAAGGAACTTAGGT
AAGGAAACAAGACAAATACAAAAACTTAACAGGGCTAATTACAGTACTAAAATACTATGATTCCACATGT
CTTGTCCTTTGTTCCTATGTTTATCCCACTGCTAATTATCTTTAAAAAAACTAAATGAAATCCATCCATT
ATTTAAAGCTTCAGAAAAAAATGCATTGCTTTCAGCAACCTTCCACCCTAAAACTAGAATTAATTTACTT
TCCTATTCCTTGTTGTTTGCACTTCTCAAACACTAAGGAGGATTTTTTAACATTTATTTTATTTTTTTTT
AAGAGAAGGCCATCCGAAGAAGAGGCACAGATATAAGAACTAGTACATAGATGAAAGATACAGTACTGGG
ATGACAGAACTTATAAATTATTTTGTCAGGACTGTAAATTAGGAAACTCTTCAAATTGAGAGTCAAAGGA
TAAAACGTAGTAGGAATCAAAGTGCATTGGCACGTATATTTCTAGAGCATATACTTAGATGGGGTTCGTA
GGTTAGCTTGGAACAAAGGACTGAGCAAATGTTACTTTTTTATAGACAACAACAAGATATGTGATGGATC
TGACATTTTCAGACGCTATACAGTCTCCGTCACAATTATTGTTTCAGATCGCATTCAAGAATTATCTTTA
AAAATGTAAGTTTGGGCAGAAAAAAATAAACCATTAAATGACCACTGCCAAGAGATAAAAGTGCACTCTT
AGGTGAGTGAGGAGTCAATAAAAAAGAGTAATTTAAAAAATATTATTGCTCCGTTGAGAACAAGAATTTG
GGAATGACTCTGGCTTGTGAATACTAGCCTATCTGTTATACTTTCACACACAAAATACTTTCACACACAA
AAAAGAATGTGCTAGATTACTACCTGTCTTTGTAAGTAAAAGCTGTGTTAAACAAGCGTAAATCCTAATG
ACAAAAACCATATAAAATAAGATCGCTAAAGGCACTTCTAATTGGCATGGTTTTCTCTGCCTTAAACTCT
GAATTAACCAGCACAATTCACAGTAAATCTTCCTGTTGGCAGCAGAGCCTTGGAGAAGAGGTAGCAGAAG
AGCGTGCCACTCCTCCTCTGGCGATGGGCACGTTCCCCCTTGCTTTCTGGTCCTCGTTCTTCCACCTGGA
GGGAACCTGAAGTCGAACGTCAGTAGCTGACAGCCTCCCCAGCACTTTCCTTACTCTTCTTCAAGCTGCC
AGTAAAACCCGGAGAAGTGGACTACTTCAGATTCCGCACAACCCAACAGCCCCAAACCCAAAGCCCCGAG
GCGGAGGGAGTGGTGGCGGAGAGGGGGTGGGGAGGAAAAGGGGCGGCAGTTACTGAGCATGTGCGAGGAG
TGGCGCATGCTCTGTGAGGCCGGCAGCTTCCCATTGCGGGTAGCCCCGGCGGTGGTGGCGGTGGTAGCGG
TGGTGGCGGCGGCAGTGGCGGCACCGCCTCCTCCTCACATTCCCGGGGTGGCGGGGTTAGATGAGCGGCC
CCAGTAGCGGCGAGGGCGGCGCGGGGGGGAGGAGGAGAAGAAGGAGGAGGAGAAGGAGGTCGCTGTCTTT
GTAGTCTCCCTGCTGCGGGAGCCAGAGGCCGCCGCCGGAGCCGTCGTCGTTGGAAAGGGCTGTGTGTGC
GCGCGCGTGTCTGCCCGCCCGGCCCGCGGGGACGAGGCGGCGGCGGCGGCGGCGGCGAGGATGATGA
TGTGCGCAGCGACTGCCTCCCCCGCCGCCGCCTCCTCGGGGCTCGGCGGGGACGGATTCTACCCAGCCGC
CACCTTCTCTTCCTCCCCGGCGCCGGGGGCGCTGTTCATGCCGGTTCCCGACGGCTCCGTGGCTGCTGCG
GGGCTGGGGCTGGGGCTACCCGCCGCGGACTCCCGGGGTCACTACCAGCTGCTGCTGTCAGGCCGGGCCC
TGGCCGACCGCTACCGGAGGATTTATACCGCTGCGCTCAATGACAGGGACCAGGGGGGCGGCAGCGCTGG
ACACCCAGCCTCCAGGTGCGTCCCCAGGGTGCCCTTCCTTGCGCCCCATGCCGCCCTTCCTTGCGCCCCA
TGCCGCGCGTGCACCCGCGTGTGTGTGTGCTTGCGTGTGTGTACCTGCGCATTTATTGAGCTTTCAGTCC
GCTCTGGATGTCTGTTGGCAGGAGCACTTATCGAGATAGGAGGGTGCGGTGGCTGCAGTTTCTCGTGTGT
GTGTGTGTGTGTGTGTGTGTGTGTGTGTGTGTGTGTGTGTCTGCCTGCCTATGTGGGGGGATAGTGAGGGGT

FIG. 7C (Cont.)

GGTAGGGGAACCTGTGATGCTGGAAAAGGCGATGGTGCTGGTCGGCTGTGACACGTGTGTGTATCGTTGA
GGTAGGAGGTGGCATGGGTAGAGAGGGTAAGAGGATGATACACGAAGAGAATTGCAACAGTGGCAAGGGA
AGTGGCGTTTTCAGTGTCTCTGCCGCAATGTTATTTGCACGTGCCGCCTCTCCCATGACATTCCTTCCAG
CCCTTTCCACCTCCCTTCAATCTGCCTTTCACCAAGAGGAGTCATGGTATAGATTGGTTGAGTTTTGGAT
AAGCAGGCCCGAGGGATAGGCGTGAGGTTTGCTTTAAAAAGATTTATGAATAAGGGACGCAGATGGAGAT
CTGTGTGGATGCGAAAGGTGTCTGATAGAGATTTTTAGAGCTGTACTTTGATAACCGGGCCTTTTGGTCT
TCTAGAAATGAGGTTGCAGTTACTCTTGTGATCTGATGTCCCATCGGCCATTTCTCTTCATCCTCTGTTC
GATTTCCTCTGTTACTTACAGGCTTTAGAGTAGAGAGGGTTTTGTAGGGAAAAGGGGAAAACTGCAGAAC
TTCAGAATATGACAGCTGGTACAGCGTTCAACTGCCACTAGCTAGAAAATCTGAATAGCGCGTAGATTTG
TCTCTTTTACTTGGGTTGGCTACACCTTCAGCTTCCTTGATGTAGATGTTCAGTTGGTTTCATTTTCTTT
TTCTTAAAATGTGGGTGCTTTTTTTTGCTGAGGGCTCTCCTATTGTTTTCTTTTCCATGCCCTTACATGC
CGCATACCCTGAAGGTTGGTGACTGACTTGTTTCACCAGCTTTGACAGTGGTAATTGGGAGTTGGCTTCA
TCTTTTTTTTCCCACAGCTTCTTGCAGTACATGGGGAAAACATAGTAGGAAACTGTCAAAATGAGTTAAA
GAGTTTACTGTTATTTATTGAATGTGCAATTTATTAGGCAATTGTTAGGTGTCTTTTTCTCCCATTATGA
AAGGGACGAGGCTGTAAGTCAGGTATTTGTAGCTTATCACTAGGTATCATGGCTTATCTGTTGGAGACAG
TTGTAAAGCTGGAGCTTTGTTCACACTTTTTCTAGGTTAACCAGTTTTCTCATGTCTGTGATTGTTTACA
GGATTGGGCACAGCAGTAGTTTTACCATATGGATGTAAACGTGTGTAACTATTTTTTGCTATCTGAACTG
AAGGCCAGAATGGCACAAGTCTGTTTCTTGCTAATGCTTTTGAAAATAGCACAAAACTACGTGAGACAGT
TTGCCCTGATAATTAGGTATAATTTTGATCTGTAAATCTCTAAATTATGGCACCGCAGGAACATCTTTAC
AAACTCCTCTCAAAGAATTTAAATTTATTTTGTGTATGGTTTCCAGACTTATGCAATAATTTTTGACTTC
TATATTCCTGTTTTGACTTCCTACTACTAGTGTAATATGATTTCTGTGTATCTAGAACTATATTAACGGT
TTTAGACAAAATTAACATAGATTAATCATATAACATTTGTGAATGATTTTTTAGCCCTTGGTCCATTTTT
GTACAAGCCGTCAATGAAAAGTAATGAAGAATTAGTTCAAGTATTTCAAGAACTACTCATGGAAATCAGC
ATTATGTTATGATATTGCCTGCTAATGCTTGTTCAACGCAACATTATTGTTTATTTAAGTTCACATTATT
TTATTACAAAAAGTAGCCTGCAACTACTCTATTGATGATTTGATTAAGAATTAAATCACATTTCTTATTA
AAGATGTTGAGGAAAGTAGACTTGGGGTTTCGGCTCTGAATGAATGATAGAATTATTTGTATAGGGACAC
AAGTTAAAGGAGAAGATGATATCTTTTAGAGAGACTGAATGGAGCAATAATAGAGAATGAAGCTCTAGTG
AGCATCAGGTTTAAAGGTGTGAGAGAAAGGAGACAGTGAAGGAAACGGAATCAAAATTAAGAAGAAAATC
ATGAAACAGTAGCCTCTGTGGCTCTAGGAGAGTGGATTGAAAATTCTCAGAAGTGGTAAATGTTGAAGAA
AGTGAGAACCGTTTTCAGGTCATTGATAACTTTTGAGGAAGTGGTCAGAATAGAGGGATGTGGTGAGGAG
TGAATGGAATGTGTTTTTGGTAACTCAAGGGGATTTCAAAGTTGAGGGAAGGATATTCAAGTATAGGAGG
TTGGGTGGGATATGCAAATATGGGAGGCTAAATGGAGAGACACAGAGTGAAGAAGTGAGAGAGGGGATAATT

FIG. 7C (Cont.)

GATAGGAAAAGGTCAAAGGGATCTCAGGGACAGGAAGAGGTCAAAGGGATCTCAGGGATAGAGTTAAGGT
GACAGGTGGAGAGGTTAGCCATTGAAAAAAGGAGCAGTTAATATAGAAGGGGTGGAGGTGAGTACTTGTA
AATATAAAGACTGGGAGTTTATTGAGGATAGGCATCATATCCTATTCGTTTTGATAATCCCAATGTCTAG
CACATTTTTTGGCATGAATTCTGTAAACATCAAGTGCCTGCTCTGTGCCAGGCAGTATTGCAGATGCTGA
AGATGTAGCGGTGAGCAAGATAGACAAAGTCTCTGCCGTCTTGGAAAATCCACTCCAATGGGAGAAATAG
ACAACTCATAATTTCACTTAGTAATAAGTAACTGTGAAGGCAATAAAACCTATTTCATGTGATAGGGCAA
TTTGTAGTGGGGCTATTTTAGGTAACATGGTCAGGAAATGTCTCTTTGAGAGTTGGCATTTAAATTGAAT
TGCCATGATGAGGAGGCAGATGTAGAGGAAGAATGTTCTGGGAATTTATAAAGGCCTTGAAATGGGAACA
GGCTTGTGTTCAAGAAACAAAAACATGATGAGTGAGTTATCAGTCAATGTCAAATGAATTAATTACTCTT
TGCTTTAGGTGTACAGTTGAGAAGTTGAGAGTTTCAAACCTAATGGACTCAGTGACTTTGATGACAGTCT
AACAAAGTGGTTAAGAGCTTGGGCACAGAAGCTAGACTGGTTTTGCATCCTGGTTTTGTCATTTGCTAGC
TGTGTAACTTTGAGTATATTACATAACTTCTATGCCTCAGTTTTTTAAATATGTAGAATGGGGATCATAA
TACTAACATGAATTGTTTTGTAGATTAAATGAATCAATGTATGTGCTTGGCATGTTGACTGCTATGAAAT
ATTAGTTACTGTTTTTTGTCTGTTTGTTTTTGCTGAGAATGAGGGGTGTGGGGACTTGAAGAGAAGGCAA
GGATCATGTCTTACTCTTTTATTTTTGGTCTCAGTGACTGTGTAGAATGTGGGAATAACTCTTTCATTTA
TCCAGTGACTGAATAGATATATTTTTGGATGAATGAGGCCAATCAAAATCGGAACATTCTGTTGGGGAAA
GGGGTTGGACAGGAAATGTATGAAGGAATGTATGATCTGTTCTGAATGTGAATGGTGGTATAACCATGCA
CTTGGGAGGCACCATAGCACAGTGGCTAAATGTTAGAGCACTGGAGGTAGACTCCCTTAGTTCACGTCTA
CCTTTTTCTACTTGTGTTAAATTGGGCAAGTTAATTAGACTTTGTCTGTTTCTTTACTTGTAACTTTGTA
GTGTTATCAAAAGGACATTATGTCCGCACCTGGTAAGTGCCCATGAAATGTTACCTGTTGTTATTATTAA
AATCACATTTAAAATTCCAACCAGCATGGCACTGTATGTTTTTCCACACAAAATAGAAATGGAGAAAACC
TAGTTGAGTTGATTTAGGGTTAAAGAAAAAAGAAATGGAAGGTTTTGGGGACAGTGTTTGACTATATGGT
AAAAAGGAAAGTGATGCCAAGAGGGAACTGATAGACTGGAAGATAAAGAGGAGTCAGAGTATCTGGGTCC
TGAAGTCCTAGAAGAACAATGTTAGTGAAAACAATAGAGGGGATTGTGACCAAAATGGGGAATCTAAACT
TAACCCCCTTAGTTTTTTCAGCTGCTTTATCTCTTTCTTGTTAGAAATGGTATTTGAGTCCATCCTTCAG
ATGCATGGGATTTTGGTTGTAAGAGGTTAAGTAGTCATTTTAGCAAAAGTTCAGGGATTATTTTATTTTA
CTTATTTTGAGGCAGGCTGGAGTGCAATGGTGTGAACATAGCTCACTGCAGCCTCAACCTCTTGGGCTCA
AGTGATCTTCCTGCCTCAGTCTCCTCCAGTAGCTGGGACTACAGGCATGCACCACCATGCCTGGCTTGTT
TTTTATTTTTTGTAGACACAGGGTCTCACCATGTTGTCCAGGCTGGTCTTGAACTCCTGAGCTTAAGTGA
TCCTCCCACCTCCACCTCCCAAAGTGCTGGGATTATGGGTGTGAGCCACCATGCTCAGCTTGCTCAGGGA
TTATTACTTGGCACTAACCATTGGCCCTATAAAAATTTATAAGACACAAATTCTAGACTTGAGTTTACTG
TCTATCTGGAAGTGCAAGATACAAAGGCAGATACTTATAGAAGTGTTAAATGAAATGACCAAGAAAGTAT
AACCTACTATGACAAAGGCATGGCATTCTAGGCTGGCTTAAAAGCATCAGCAGAGACAGGAAAGCACAGT

FIG. 7C (Cont.)

TTGTATGTAGGTAACAGTAGGAATTCTGTTAGAGCTAGAATGCAGGTGTCATGAAGGACAGTAGTGGAAT
TCATTCTGGAAATGGAGGCTTTGGCTAGGATGGGGCATCTTGAAGACCAAGGTAAGAATTAGATTTTATT
CAGTAGACACTGATCACCCTTGATGGTTTTAAGCTATGAAGAGACGTTATTTATTGTAGGAATATGTCAG
GAAGTAATGCGGGATTGAATCTGTATGTGTACATCTGTATTTGTGCATAGGTAGTAATTTTCTTCATGTA
GCTGTTATATCAGTGGAATCCTGTATAGTGTATAAACACAAGTTAAGGCAAAAACTGCTCTATTGGTATA
CTGGTAGGTAGAAATGTGAAATGAATTAGTTTCCTAACTCAAGAGAAGAAAAAAATCTTGCCTCTGGGCT
TAAAAGGAAAATAAAAATGTCAATCTAAAAATACTTTTGTCCTTTAATATATTTGTTTAAAAAATCAACA
GAATAGTCTCACTTTTTTCTCAAAAACCAGATTAAACATTTAGGTTTTCTGAGGAGGGGTTAGGTTAATT
GAGGTTTAATTTATATACAATAAAATTCATCCTCTTTAAATGTTCATTTGAAGAGTCCTGAAACTATCAC
CACAGTCAAGTATAGACTGTTTCCATCACTTCATATAAAAAGTTCTGTCAGGCCCTCCTACCCCTGGTTA
CTGACCGCTGCAAATCAGTTTTCTGTCACTAATATTTTACCTTTTCTAGAATGTCATATAAATCTAGCTC
CTTAAGGGCAGGGCCCCCAGGTATTGTTCATCTTTCTGTCTTGTATCTGTATTTCCTGTAAGTGGAAGCT
AGACCTTAAGGGTTTATTAGGTGTTCATTAGAAAATTTTTTAGCAAGAATATTGTATATGGCGCTGGGTA
CTGCATGTTGCATCCCATCCAGAGGTTGTGAGGTTGTCTCACTATTTAATATGTTAAATCTGATTACTTG
GGTAAGACGGTACCTACTAGATTTCATCTCTGTAAATGTATGCTTTTTCCATTTGTAAAGAACAAGTAAT
CACAGGGTAAAAATTTGAGCACATTGTGAATGCCTTTTACCTAATGCTTTTAGCATTCTTTGATAATCCT
TGTCTGAGTCAATAATTTCATTAGGGGTTGCAAAATGATGAATTAAAAAATAATTCTGTTATTTCTTCTA
TGTTTATTAGCTGGTACTCTTCTGCAAAGAAGAGTTGGCCTTCACTGACTGTCAGTGAAATGTAGTTTCT
CCTAATCCAGCAGCATAAATGCTTAATTCTCTTCCCTCATTAGCCAAATTGGTGTAATAGTCCAGTGGTG
GTGTGGCAGGTGCTGTGGTTAGGCTTTCAGATCCCGCTTTCAGGCACATGTTCCCCTAGCTCTTGGCAAT
ATTGGCAGCTAAAACTGATTGCAGCTGAGTCCCACTCCACGCATTGCCCTGAGCCAAGAGTTGCCTCCCC
CAGAGTCATGCCTCCTCTTCAGGGGCAGTTTACATCTAATATCTATACAGTGTAGGGATATAAATGCCTA
GCGCTTTTGCTATAAGACAAGCCAACCTTGAAGTCTATCCCAACACCAGAGAGCTCTCCCATGGGTCTGG
CTGAGGGCTTCCTGGGACTGCATTGCAGATCAACTCCTTCCTCTGTTCAGTCTTACGTCTTTCACTGCCC
CACAGTTGTTGGTTCGGAGGGCACTCCGCAATAAACTTCCGGTGTGCACATCTGCATTTGAGAGTCTGTT
TCCTGGGAACCCTCCTACCCAAAGCAGTTGGTGCCAGGAGTGGTCTCAGAAAGTAGACTTTACAGTGAGG
TTTTGAAGCTGGATTATTGGCTGGCTGGCTGGCAATGAGAATCGATTCTGGTGCTAGATGGAGCACTAAT
ACTGATAACGCTTGGCATGCACTGTAGCTATGCAACTTAAAACTTTCACTGGTGGTGAGTTGGAATGCTA
TTCCTGTTGAAGGGAATGCACTGGTGAGTGCACTAGGCTTTTGAGAAGTTCAGAGAAATTAATTATGAGG
ACAATCATCAGATGGCTTTTGGTAAATAACATTGATAGATTGGAGAAAGATGATGCAAGGTGGAAGATAA
TTGGGGGCAAAATGTAAAAGGAAATTTATTTAGCATCATGTAAAGAAACACATATACAGTAAGAGGAAAA
ATCTAAGGCTTCAACCCAAAACTTAATTTTAAGGGTAGCAGAGCACCAAGGTAGGTAGAATTCTCTCTCA
GCTATGCTAAGGTCAGTGTTCTGGTTGGGCAGGAATCCTGACCCTTAGGATGGGGCATCTGAGTGCACTT
GAAAACCCTGAAACCCCAAATTCCTCTTAACCCTCTGGGCCTGCAGAAGTGGCCTTCTTCTACTAGCTAG

FIG. 7C (Cont.)

AGGGGTTGCTTGCAGACTGTGCTGTCCCTCTTACCCCCAGCTCCTCCTCTCTCGCCTACTGACTATCACC
AAACCAACAACTAGGGTTAAGTCACAAGAACACCTAGTTCGGGGTGCTGGATCTGCGAAGGGAGGAAGGG
ACTGTACACACAAACACACACACACACACGTTCCCAAACTGCACCAAGGCACCCCAAAGCACCACCACAG
ACACAAAAGAATACCATGGGATATTTCAGAATTTTAAAGGAAACACAGCAATATCTGTCACAAATTACTA
GCTTGAGGTAGTTCACGGTTTTGACATTAGCTCATGCCACATTTCTTTTGATGATGTCATATTTTTGCAG
GGTTGGATTTTTACTAGTTGTGATACAGATCAAGCACTGTGCAAAAATCAGTGTGGAACAGGAAAGGAGG
GTGGCATGTTCAGTCTGATTCCAAGTTTGAGAAGTTGTTCTGTGTCTAACAGGCACACATGTCATATTAT
CAAGTAATTGAAGTTTTTGTTTGTTTGTTTGTTTTGAGGCAGAGTCTCGCTCTGTCACCCAGGCCAGAGT
GCAGTGGTGCGATCTCGGCTCACTGCAACCTCCGCCTGCCAGGTTCAAGTGATTCTTCTGCCTCAGCCTC
CTGAGTAGTTGGGATTACAGGCGTGTCCCACCACACTCGGCTGATTTTTGTATTTTTACTAGAGGTGGGG
TTTCACCATATTGGTCAGGCTGGTCTCGAACTCCTCACCTCGTGATCCGCCTGCCTCGTTCTCCCAAAGT
GCTGGGATTACAGGCGTGAGCCACTGCGCCTGGCCCAGTATTTGTAGTTTTTAAGAAGGAAATAAAAATA
TTTTTCTTCCAATTTATGTGTTATTTTTTCAAATGTCTACTCATTTGTTAGGACATGAATTCTTGTTATT
TGGATCTAACTACTTAATAAACACTACTGTTTGGTATTTCTTTTGGCCTATGAGTGCATGGAAAAATTAC
CGATGATGGCTGTGCATGGGCCCAATAAAAGGGTTTTCATTCACCAGTGCTGATCTAGCAACTGCTGCTG
CTGAATATCCAGCCTGACAGCAGCAGAGATCAATCATCCTTCAAGCAGGCCAACCAGTCCTTATACAGTG
GAAAGGACCATGATTCATTTTGATTGGATTTGAGACATATTCTGGGTCTGAATTTGTCTTTCCAGCAGGG
TCTCACCCAGGACTACTGTTTGAGGGCTTGCAGGATGTTTGATCCTCTACTACAGGGATCATTTCAGAAT
AAGGGACCCACTGTTATGTTATGTTATGTTATGTTATGTTATGTTATGTTATGTTATGTTATGTTATGTT
ATGTTATGTTTTGAGACGGAGTCTTGCTCTGTTGCCCAAGCTGGAGTGCAATGGCGTGATCTCAGCTGAC
TGCAACCTCCGCCTCCCGGGTTCAAGCAGTTCTCCTACCTCAGCCTCCTGAGTTGCTGGGACTACAGGTG
CACATCACCACGCCCAGCTAATTTTTGTGTTTTTAGTAGAGACGGGGTTTCACCATGTGGACCAGGATGG
TCTCGAACTCCTGACCTCGTGATCCGGCCACGTCAGCCTCCCAAAGTGCTGGGATTACAGGCGTGAGCCA
CCGCGCCCGGCCGGGACCCACTTTTATAGAATAGGAGAATCATTTGTCCCATCTTGCACCACACCGTCCA
GAAGCTGATGACTTGATAGAGCAGTAAAACAGTCCTTTGATGGCACAGCTGATGATGAGATCCTGCAGCT
TGGGCATGATGCCCTGCAAGGGTGAGGCGCCCATTCTCCAGTGTTCCCAGTAGGAAGATCACATGAAATT
AGGAGTGGCTCCGCATAGCATCACTCTGTGAATCACCTGGGCAGTTTCTGCTTCCCATCTCCATAGCTCT
GATGGCAAGGGGTTAAAAGATCCTGGTTCTCAGAAGAGAAACATTTCCAACAGAGGGCGCTATGAGAATC
CTGTTATACTTTAAAGTACAGCTGCCACTAGGATTTGGGGCTCCTTTTCTAAATAAAGAAGTCACCAGGC
TGGGCACGATGGCTCACGCCTGTAATCCCAGCACTTTGGGAGGCCGAGATGAGTGGATCACGTGAAGTCA
GGAGTTCGAAACCAGCTCAGCCAACATGGTGAGACCCTGTTTGTACTACAAATACAAAACAATTAGCCGG
GCATGTTGGCGCGTGCTTGTAATCCCAGCTAATTGGGAGGCTGAGTCAGGAGAACTGCTTGAACCTGGGA
TGTGGAGGTTGCAGTGAGCCGAGATTGCGCCACTGCACTCCAGCCTGGGCAATAGAGCAAGACTCCATCT
CAAAACAAAAAAAAAACAACAAAAAAAGAAGTCACCATTTGGACAGGGTTAATGTCCTTGTTCATGTGGA

FIG. 7C (Cont.)

GGAGGTAGGGCTGTGTTCCACAGTGGAGCATGGAGGTTTGGCACACAGGTGATCTATAAGGTGTCTCTTG
GTACTTCCTTGTCCAGTGTTTGTGGTAAATGGACACGAGAAAGGCCCAGTGACCACCCCATGAAGTCAGC
CACCTGGACCAACAGAAATACTAGCCATAGATTAAAGGAATCTAGAATGGCTAGTAGAGAAGAGTTGTTG
ATATCAATTTTACCGTCTGTAGTGGCTGGGGCTGTGGTTTGACCCACTTTCCTTCCTCTGGAAAGTTTCT
CCAGGAAATGACACTCACCAGAATTCTGGAGGAACTTTTTCCATGCCTTATTTGAAGCAAGTGAATCCTA
ATTGTATAATAGGCGAAATATAGTGAATCCTGTATTGTGGAACCCAGAGCCCCTGCCCAGCACTGATGTG
CTCAAAATTCCCCCACGACTGCTGGGAACATTGGTTGGCTACAGACTCTTCCCTAGTTCCAATATGGGCA
TTGCCTTTGGCAATAGGTGATGGCCCTAGGTGATGGATCATTCTTGGGGGCAGCCTGAATGAACTGGTTG
ATCGGGGCATTTTATGGTTTTTAGTGCTACTGTAACTAGTTTAGTTTTTCCTATTTTTCAGTTGTTTGAT
ATGAATATATAACAATACAGTTGCTTTTGAATGTTAACCTTGTATCTCTGATCTTGTTAAGCTCATTTAT
TAACTTTAATAGTTTTGTAAATTCCCTGGGATGTTCTGTGTAAATAATCATATTGTCTTTCTTTCTGATC
TCTAGATTCTCCTACCCCTCAGCCCCTACTTTATTCCAATTACTTAATTCTCCCTTGTTTTTAATCTGAG
AGAAAAACAACTACAAATTAATCTTACAGTTTTTTAAATCATTAAGTATGATATTAGCTGTAGGTGTTTC
AATGGCCTCTATCAATTTGAAGATATTCCCTAGTATTCCTACTTTGCTGATAGTTTTTATTTTTTATATT
TTAATTTTTTTTTTTTTTTTTTTGAGACAGAGCCTTGCTCTGTTGCCCAGGCTGGAGTGCAGTGGCATA
ATCTCGGCTCACTGAAGCCTCTGCCTCCCGGGATCCAGCAAGTCTCCTGCCTCAGCTTCCTGAGTAGCTG
GGATTACAGGCACACGCCACTATGCCTGACTAATTTTTGTATTTTTAGTAGAGATGAGATTTCACCACGT
TGGCCACTCTGGTCTTGAACTGCTGACCTCAGGTGATCCACCTGCCTCAGACTCTGAAAGTGCTGGGATT
ACAGGCGTGAGCCATCGCACCCGGCTTGCTGATAGTTTTTAATTATAAATGTGTATTGAGTTTTGTCAAA
TGCTTTTCCTCTACCTGTTAAAATGATCATATAGTAAGAGAACAAAAGGAAAATTGAATTACATTAATTA
ATTTTTGAATGTTAAATTAACTTTGCATTCCTGGGATAAAACCATCATATTTGGAATGTATTGCTGAATT
TGATTTGCTGGTATTATGCTAAGAATTTTCAGGTTTATATTCATGAGGGATATTGGTCTGTAATCGGTTT
TTTTTCTTTTCTTTTCTTGCTAATCCTGTCAGGCTTTAGAATTAGTTATCCTCGTCTCATAAAGTGAGTT
ACATAGTAATCCTACCCTACCCAGTCCTACCCAATTTTTAAAATGTTTGCGTAAGATTGTTGTTATTTCT
TCTTGAATGTTTGACAGAATTCACCAGTGGCACCATCTGGTCCTGGAATTTTATTTTGGGGAAGCTTTTG
ACAAATTCACGTTCTTTAATAGTTAGAGCGTTATTCAGATTTTCTGTTATTATTCATGTCAATTTTGGTA
ACTTGTATTTTTTTGGAGAAGTTCATTCATTTCATACTTCTAAGTTGTTGAAGTTTTTAGCATGAAGTTA
TCCATAGCATTCTTTCATTATCCTTTAAGGTCTATGGGATCTCTGATAATAACTCCCTCCTTTTTTAAAA
AAAATATTTTTTTAAGAGCAGTTTTAAGTTCATAGCAAAATTGAGAAGAGGGTACAGAGATTTTCCATCT
ATCCCTTTCCCCCACTCACGCATAGCCTCATCCATATCAACATCCCCCACCAGAGTGGCATTTTTGTGGC
CATTGTTTAACCTCCACTGACACATCATAATCACTCTCAAGTCCAGAGTTTACATTAGGGTTCACTCTTG
GGGTTATACATTTTTTGGTTCAGAAAAATGTATAATGACATGTATTTATCACTGTAGTATCATACAGAAT
ATTTTCACTGCCCTCAATATCATCTGTGCTCCACCTATTCCTGTTTCTCTGCCACTCAACCCCAGGTAAT
CACTTACTGTCTCCATAGTTTTGCCTTTTCCAGAATGTGCTATAGTTGAAATCATACAGTATGTGGCCTT

FIG. 7C (Cont.)

TTCAGATTGGTTTCCTTCACTTAGTAATGTGCATTTAGGTTCATTCTTTTTTTGTGTATGAGACTTGATA
GCTCATTTCTTACCACTGAATAATCCACCATGTAGATGTACCAGAATTTGTCTGTTCACCTACAATTTGG
TGAGTTTGGAGGACAATTGGGTTGCTTCCAAGTTTTGGCAATTATGGATAAAGCTGCTCTAAACATCTGT
GTGCAGGTTTTTGTGTGGACATACATTTTCTTTTTTAGAAATTGACAAATGACATTGTATGTTTTTATAA
TGTACAGCATGATGTTTTGAAGTACATATACATTGGGGAATGGTTAAATCTAGTGGACATGTTTTCAGCT
CCTTTGGGTTAATACCAGAAACAGTGATTGTGGGATCACGTGCTAAGAGTAGGTTTAGTTTTTGTAGGAA
ATCACCAAACTGTCTTACAAAGTGGCTGTTTCATTTTTCATTTCCACCAGCAATAAATGAGAGTTCCTCT
TGCATTAAAGCCTCGCCAACATTTGATGTTGTCTATGTTCTGGATTTTGGCCATTCTGATAGGTGTGTAG
TAGAATCTCGTTTTTTTTTTTCATTTCTCTGATGACATATGATGTAGAACATCTTTTCATAACGCTTATT
TGCCATCTATATATCTTGTTCGGTGAGGTGTCTGTTAAGGTCTTTGCCCCATCTTTAATTGAGTTGTTTG
TTTTCTTATTGTTAGAGTTTTGAGAGTTCTTGGTATTCTGTGAGGGTGTAACTGAGGAGATGGGGAAAAA
AGTTCTTGGTATTTTGGATAACAGTCCTTTATCAGATGTGTCTTTTGCAAATATTTTCTTTCAATCTGTG
CCTTGTCTTCTCGTTCTCTTGGCATTGTCTTTTGCAGAGCAGAGGTTTTTAATTTTAGTATTCAGCTTAT
TAATTATTTCTTTAATGGATTGTACCTTGGTGTTGTAGCTAAAAAGTTATCTAGGTTTTCTCCTGTGTTA
TTTTCTAAGAGTTTTATAGTTTTGCATTTTACATATAAAGTCCGTTTTCCATTTTGAGTTAATTTTTGTG
AAGGGTGTAAGGTTTGTTTCTAGATTCATTTCTTTGTATGTGATCCAAAGAACCAACTTTTGGCTTTCTT
AATTTTCTCTATTATTGATCTGTTTTCTATTTCATTGGCTTTTCCATCATCATTGTAATTTATTTCTTTC
TACTTTCTTTAAGTTTACTTTGCTGTTCTAATTTCTTAAGGTGGAATCCTAGGCCATTGATTTTAAATTT
TTCTTCCAATATAAGTATTTAAAGCTATGAATTTTTATCTGGGCTGTGCTTTAGTTACATCCCACAAATT
TTGACTGCTATATATTTGTCATTTAGTTCAAATTATTTTCCAATTTATTGTTTAAAATTATTACAACTTT
CAGATATGGTGTTTTCTTACATATTAATATATTATTGTTATTACTTTCTAATATAAACCTTGTATGATTT
TGATCTTTAACATTTATTGAGATTTGTTTTATTGCCCAGGATATGTTCTGTCTTGGTGATTGTATTATAC
ACACTTGAGAAGAATGTGTTCGGTCATCTTTGGACATGAAGTTCTATAAATGTCAGTTAAAGTTGGATGA
TAAGTGTTGTTTGGATGTTTATGTTTTTATATTTAAAGTTTCTCCTCTTAGGCAACTAGTATAGAACCTT
GCCCTTAAAAAAAGAAATCCACTGTCAATCTTTGCCTTTCAATTGGAGTGTTTAGATTATTAATATTTAA
TATGATTAATTATTGACATATTTACCATATCAACAGTGATAGGTCTGCCACTTTATTGTCTTCTGTTTCT
CTTTTTTTGTTCCTTTCTTCCTCCTTTTCTGCTTCTTTGGGATTATATTTTGGGATTATTGGGAGTATTT
CATTTTAGTTGCTCTATTGGTCTTTTCAGCAATATCTCTTTGTATTTACTTTTTTTATGCCCTAGGGATT
ACAGTATGCATACCTAACTTTTTACAGGCTACTTAGGGTTATTATTATACTAATTCACTTAAAACACAGA
AACCTTGCAACCCTACAGATCCTTTTATTCTCCCCTCCCCCAGAGACCTTTATGTTATAGTTGTCATGCA
TACTATACTTGGCAAACATCACCAAACAATGTTATAGTTTTTGTTGTCGACAGTCATGTGTACTTTATAG
AACTTAGAGGAAAAATCTAGTATTTTGTGTTTTCCTATATATTTATTGTTTCTATTGCTCTTTCTTCATT
CCTGAAGATGCAGCATTTCCTTTCAGCCTAATGTTGACCTTAGCTTTTCTAGCAGATCAGTCTGCTGGGG

FIG. 7C (Cont.)

ATACATTCTCTTTGTTTTTCTTTGAGAATGTATTTATTTTACTTTCATTCCTAAAGGATATTTTAGGTGG
ATATATAATTCCGAGTAGATGCTTGCTTCCTTGAGCACCTCAATGATGCCATTTAGCTGTCTTTTCACTT
CTCTGATTTCTGGTGAAAAATCTTTGTAATGTAAACCTTATTCCCCTCTGTGTGGTGTGTAATTTTTTTC
TAGCTGCTTTCAAAAATTTTTTCTTTGTTTTTGGTTTTCAGCAGCTTAATTTGATGTGTATCTAGTCATT
TTCTTTAAGTTTATCCTCTTTGAAGAGTACTGAGCTTCTCAAATCGGTAAATTTTTGGCTTTCACTAAGT
TTAGAATGTTTTCTACCATTGTGTCTTTCTTCTGACCTTACAAAATTCTAGTGGCAATTATGATAAAACT
TTTGAGATTGTTTCACAGGCCTCTAACTGTTCAGTCTCCTATCAATTTTTTTTCTCTGTTTTTCAGATGA
GGTTATTTTTATTGATACACGTTCAGGTTCACAGACTCTTTTCTCCCATCTCCATTTTCTTATTGAGTCC
AACCAGTGAACTTTTTATGTATTGTTTATTTCACTTTTAACATTTACATTTGGTTCTTTAAAAAAAAAAC
AAAAAAAAAAAAACAAAAAAAAAACTTCTCTTTCCCTGCCGAGAACCTCTTTCCATTCCATTCAGTTGTCC
TTGTCTTTCCTCAATGTAGCATATTTATAGTGGTTGCCTTCCAGTCATTGTTGGATAATTACAACATGTG
CATCGTCTTAGGGTTGGCATCTTTTGATTGTCTCTTCCCTTGAAGTTGTTCACATTTTTCTTGTGTTTTG
CATTGTGAGAATTTGGGATTGTATCTTGGACATGGTTAATGTTATGTTTTGTAAACTCTAGGGTTTATTA
TAATTCTCTGGAGGATGTTGTGTTTTTTTGTTGTTTAGGGGATCCCTTTCTGTGTCTTACTCTTTTTCAGG
ACTTCTTACCCATTTTCCATCATATCAGTTTCTTTTCTCAGTTCCTCTGGCCAGAAAGAGTTTTAACTTG
GAATTTTAACTTTTGGGTTGTAGCCCTGTAATGCAGTGATCTCTTCCTGGCCTTCAGGCAAAGCTGTTAG
TGAAAGGAGAAAAACAACCAAACTGGGAAATTTACTCTTCTGTGAATCACTTTTCCAAGTTTTGACTCCC
CTCCAGAATTTGCTTTTATTTGTTTTTCAGAGTCCTGAAGTACTTTTTTTGTCTTTTTAAAAATTTTGCC
CAAAGTAGTTGTAAACAGTGGGGAAAATAGGCTGTTTTGGGGTTTATGCCAATGTACTGGAACCAGAACT
CTCTTATCTGGCTTTAAAAAAAGATTTTCCCTTTTATTGATTTTTAGCAGCTTGACTGTATTGTACCTAA
ATATGGTGTGTGTGTGTGTGTGCATGCGCACGCACACACGTCTGTGTCTCTGTGTGTGTGTATCCTGCTT
GGTATCCTTTCAGTTTGTTAGATCTGTGTGATGTCAATTTTTATTTAACTTGCAAATTTTGGCCTTTATT
TCCTCAAATATTATTTCAGACTCAATTTCTTATTTCCTTCTGGGAATCCAATTATATATATATGATACTG
TTTGATATCATATGTGTCTATAATCATATATATGACATATTTATATGACCAGATAGTAAATAACTTAGAC
TTTATGGGCCATAGAGTCTCTGTTGCAACCATGCAGCTCTGTTCTTTAGTTTGAAAGCAACCACAGACAA
TATATATAAATGGATAAGCATGGCTGTGTTCCAATATAACTTTATTTACAAAGATAGACAGGAAGCTGTT
TTTGGCATGTAGACTATAGTTTGCTGACCCCTGAGTAGGTGGTAATCGTTGCTGGAGCTACATTGTGAAT
TCAGGGAATCAAAGAAGTGCAAAACAGAAATGTTGGAAATAACTACAATGTAGGTAGCGGGGTGCATAAA
AATGAGGAGGTAGCAGATATGGCTAGAAAGATATGTTAGGACTAGGTTATTATGTTCCCTGTATTGCTTT
ATTTGAAAATAGTATGGAACAATCATAGGGTATTTTTTGTTTGTTTTCTTTTTTTTGTCTGTTTTTCTGA
GACGGAGTCTCACTCCGTTGCCAGGCTGGAGTGCAGTGGGGCGATCTTGGCTTACTGCAACCTCCGCCTC
CTGAGTTCAAGAGATTCTTCTGCCTCAGCCTTCTACATAGCAGGGACTACAGGCACCCACCACCACGCCC
AGCTAATTTTTGTATTTTTAGTAGAGATGGGATTTCACCATCTTGGCCAGGATGGTCTTCATCTCTTGAC
CTCGTGATTTGCCCGCCTCGACCTCCCAAAGTACTGAGATTACAGGCGTGAGCCACTGCGCCCAGCCAAT

FIG. 7C (Cont.)

CATAGGTTTTTAAGCAATGTAATGGTAGAGTTAAACTTTCAATTTATAAAGATAATCTCTAGTAGTGTTA
TAGAGGATGAATGAAAAGGAGCAGATCTGCAAAGCAGGGCTACCTTTAAAGAGACAGTTGCAGTAACTCT
GACAAGTGAAAATACTGAGAAAAGATAATGGGAATAGATGGAATAAAGTGGATTTAATGATATATTTAGC
AGGTGACTAGATCTCAAGTGCAAATATAATAATGATTTTCATCTAGATAGAAAGGGAGGAAGAGCTAGTT
TCTCAAGAGTCCATTCTTGGGATTCTTCTCTCTGAATTTTCTTCTTTGGTTGTCTCAGGCTTATGATTTC
AGATATGCATTTGACTTCCTGGTCTGTGGTTTTTAGGTAAAACCTCTTTTCTTAAGTTCTAGCCTGTATT
TTGAAAAGTCTACTGCTAGGATTCTCTCAGTCCTGTTCAGATACATTATGTTCAGTATATTCAAAGTCTC
CTCGTGAACATACTGTCACTCACAAACTGCCTCTTTTCCCTTAGGCCAGTGAAACCGAAGTCTGAGATAG
GTTCTTGAGGTTGGCAATAAGAAATTATAATGAGCCAACACCCACTCACTTCACCTCCTTTTTTCAGGAG
GCAGGGAAAAGTGGGAAAGTGAGGCTGGACATGGGAGTATTTAGAAATAGTGTTTAATAATGTTTAAAGG
GCAAGAAGGAAGGCAGTAGCTTAAGGAAGGAGACAAATAATTAATCTTTTGGATTAGATAACCTGTAGGA
GATGTTCTTAGTGTCCTAGCCATATCCCTTTGGCATCCATTTGCATACTGTCTTCTGCAAACATCTATGA
CTATCTGCCTGAAAAGAAACACACTTGGCCTGTGTGCAGGGCAACTCACATGCGCCAGAGAGTTAATGCC
TTCAGAAAAACTTTCCACCAGTGATGGATGGGGAGTTGGTAGATAAATACCTTTGTCTCACCTGCATTTA
GGATAACTGAGCCATGTTTTCTGCTGTCTACCAGAGTTCTCCACTGGTTCAGGCCCTAGTTCCCCATCAG
GGTAACTGGCTTCATAATATGTCCTTTCTTGACTTCCTTCTTTTCCCTGTTTTACTTTTGTTTTCCCTAC
TGGTGTTTTTCCTGGGATCACCTCTCAAAATAACTACTGCACTTGAATTCTTGAATTGACGTCTGCTTCT
GGGGAAACCCAAACCAAGGTAGACATTTGAATTTGGCATGGGAATAATAATAAAAATGTGTTTAGCACTT
ACTAAATACCAGGCATAATTCTAAGTGTGACATCATCCAGTGGGAGAGGTACTGTTTTCACCCTATTGTA
TGGATGAGAGAACTGAGGCACAGAGAGATTAAAGTAATACCAAGATCACAGTGCTGGTAAATGACAGAGC
TTGTATTTGAACCCAAGTCATTTGTTTCTAAATTCTGTACTCTTAACCTATCTTGACATAGCAGGCTGAA
GGAAAAGGGCAAGGATAGTAAAAAAGAGAGAGAGAATGGGAATAATTAATAGAGTAAGGCCCTGGGTTAG
AGATCATTTCAAGGTGGGTGGAAGAAAAGCAAAGGGAGTACATTTGTAATGGTGTCTCTATTTTATTGGT
TAAATAGATGGTTAGATTCTCTGCTCTGAGTTGATGGGTAGGGGAGGGATTTTGAAGTAGCTGGAAAGGT
TCTAGATTTTTATGGTAGATGTACCTTGATAGAGAACTTAACTGGCTCTAGACCAGCAGTCTAATGATGT
TCAGTAACTCCAATAGCTATTATTGTTTAGGGTTGTTATAGCTTATTGAACAAGGTTTGTAACTAACCAG
TATAGAAGTGAATATAGAACATGAGCAGATAGCTCACATTAGAAGTGATATATGTAGTAAAGACTTAAGG
GACAGGAAGAGGAAGAAAAAGGAGCCAGTAAAGAAGACTGAGAAGGAACCACCATCAGAGGTAGAAGGAA
CACTAAAGTAGAGGTTCTAGAAGCTGGCGGGACAGGGGGCAGGGATGTAAAGAAGTAGGCACTGTTTGGT
AGTTATCGTATGTAGGAGAATGTGAAGGATAAAGACTGAAGATGGGCAGTTGAATTGGCTACTAGAAAGT
TTGTGGTATTGAGAAGTCTCATAGACTTGCATGAGTTTGATAGTAAGGTGTTAAAAAACTTCAATACAAT
GAAGTTTTTTTTTTTTTTTTTTTTTTTTTTTTTGAGACAGGGTCTCACTTTGTCATCCAGGCTGGGGTGC
AGTGGCATGACCATAGCTCAGTGCAGCCTCTAACTCCTGGACCAAAGCGATCTTCCCACCTCAGCCATCT
GAGTAGCTGGGACTACAGGCACATGCCACCGTGCCTGGCTAATTTTTTTTTTTTTAATAGAGACGGGGTC

FIG. 7C (Cont.)

TTGCTATGTTGCCCAGGCCAGGACCATTTTTTTCTTCAAGAAATTTAGTGATGAAGAGGGATAGAGGATT
ACTTAAACTTTTTTCCCCTTTTGAATTGGAGAATGACAGTAGGCCTCTAAGGTTAGAAACCACAGAAAAA
AAGCATAAAGGGTAAACAAAGAGAGGGATGTATGGTTGAGCAAAATCTCAAGGATGGTGAATGAAATGGG
ATCTGGTGTATGAGAGGAAGTGCATACTTGGATAGAGTAAGAGCTGTCTCTTTTGGGATGGGGGAAGGAG
GAAGTTTCAGATTTGAAAAGGTCTCAGGGACATATTTTTAGCCTTTTTATGTTTCTGTGAAGAATTCCAG
ATTCTTTTTCTGATCTGTTTTCTAGATCTTAAATTTTCTATTCAGCTGTGTCCTGTACACTTAAATCCAC
CTATGGAGTCTGTAGTGTCAGTTATTTTTCATGTCTAGTTTGATTTTTTTTCAAATGTGCTTGGTTGTTC
CCCATTCCCTGCAGATATTTTAATGATAGTCTTTTATTTCTTTAAATTTGATACACATGTTCTTGTTGCA
ATCTTTCCGAAAATCCCACCATCTGAAGTCTATATAGGTGTCTTTCTGTTGCCTAGTTCTGCTGTTCTCA
CTCAGAGTGCCTTGTATCTCTGTGTTCTTAGTTATTTGCTTGCTCTCATTCCTCTTGTTGTTCTCTGAGG
CCTGGGATGAATAGATTGTATTCATGATATCATTAGAAAGTGTTACAGTTTTACAATTGCTTCAAGGCTT
GAGTTTCCCTGGCCTACCTAGCCTATGTTTACTTAAGAGTACAAATATGCATGAGGCAGGGTCTATAGCC
AAAGCTTTTCAGAGAGTTCTCTTCCCCTCACTTATGCTCCCTTCCATATTCCCCTACCCTCTTTTCTTTT
TCCTTCTGCTGCTCTGCCCATTGCCAAGGTAGCTTTATTTATAGTCCTCCCCCCATGTGAAGACTTCCAA
ATAAGATCAAGAGACTGAAGCTATATATAAGAAATCTGTTTTCATCTCTCCCCTAAATCAAGTTGAACTG
TTAAAATCTCTTTCTTATTACTAATTAGCCGGCTAGGTTAAGTAAATAAAAGTTTTCTACTTAGTAATGA
GATAACTATTCCTCCCTAATTTATTCATTGATGCTTGAACATGATAGGAGTATCATTACATTAATTACAC
AGAATGAATCTGGCTTCTATGGAAAAGCTTCAGTTTACATAAGGTGCTTCATAGATTGATTTTTAAAAGT
TGGTCTTGTATCCAGTGACCTTGATAATTCCCTTGTTAATTCTTTATTTGTGGATTATTTTGTATTTTCT
ATAAATATAATTATCTACAAATAAAAAATGCTTTACTTTTAATTTTTAACCATTATGACTTTTATTTCAT
TTGCATCACTTACTGACCTTCAATATTGTGTTAACAGAAGTGGTGATAGTACAAATCCTTGCATTTTCCT
CCTATGCCTAAGTGGAAATACTTAATTTTTCAACATTCAGTATAGTTGAATACACTGTTAAAAGTAGGTT
TTTTATAGATAATCTGTATTAGATTAAGTAAAATCTGTTCCTGGTTCACCAAGGAGTTTCATCACTAGTG
GTTGTTGAGTTTTAAAAAATACTTTTTCTGTTTCTATTGAAGTGATCATATGTTTTGTTTCTTTTGTTCTG
TTATTATATTGAATTATGTTGATTATGTATTTATTCTTTCCACATGTTGTTAGACAAAATTATTTGTAGG
TAAATGGCTCTCTCTTTTTTTAAAAATAAAAGGGGTAATACACATACCATAAATTCACCCTTTTATACAA
CTTATTGGTTTCCAGTATATTCACAAAGTCATACAACTAAACATTTTTGTCTCTCCATAAATCCCAAAGC
TATTAGCAGTCAGTTTCTATTCTCCTTTCTATCAGTTTTTGGCAACTACTACTTCCTGTTTTTATGAATT
TGCCTACCTAGACATTACATATAAATGGAATTATACAATTTATGACCTTTTGTTGCCATTGTTTCTTTCA
CTTAGCATAATGTTTTCAAGGTTCATCCATGTTGTAGCATGAGTCAGTACTTCATTCTTTTTTTATGGGT
AAACAACATTCTCTTATATGGAAGTGCTACACTTTATACATTCATTAGTTGGTGAGCATTTGGGTTGTTG
CTATTTTTTGGCTGTGCAGTATTTTTGCTTCTATGTTCATAGGAGATATTGGTCTGAAATTTTTGTATTT
TGAAATGTTCTCTTCAAATTTTGATATCAGAGTTATGCTTGTCTTATGAGTTGGGAAATGTTTCTTCTTT
TTATATTGTCTAAAAGAGTCTAACATTGATAATGTTTGAAAGAACTACCAGTGAATTTTTAAAGTATTTG

FIG. 7C (Cont.)

GAAGAATTCACCAACAAAGCCATCCGAGTCTAGAGTTTTCTTTGTGGATAGATTTTGATTAGGGATCCAG
TTTTTTTTCAATATATAGAAGACTATTCAGATATTACATTTTTTTCCCTTGTTTAATGTTGAGAAGTTA
CATTTTTTCAAGGAATTTATCCATTTTATTTGTCAAATTTATGGGCAGCATCTGTAGTGATGTCTCCTTT
CTTATTTCTCATATTGGTAATTTGTGCTTTTACTTTTTTCCTGACCATTTTTGCTCTAGGTTTATTATAT
TTATTTCATTTTATTTTAAAATATTTGCTATATATTTAATTCACAAATAATTGTACTTATACATGGGGTA
TAATATGATATTTTGATACATGTTTACAATGTGTAATGATCAAATCAGGATAATTAGCATATTTATCACC
TCCGACATTTATCATTTTATCATTTCTTTGTCATGAGACCATTCAAAATCCTCTCTTCTAGCTGTTTGAA
GTTGTATAATACATTGTTGTTTATGATAGTCACCCTGTGGTGCTATATAACACTCAAACTTACTCCTACT
TTCTAGCTCTGATTTTGCATCCATTAGCCAACCCCTGGCTACTCTTCAACAACTCTTCTACTTTCTACTT
TTATGAGATCAACTTTTTTAGCTTCCACATATGAGTAAAAACATGCCATATTCATCTTTCTTTGCCTGGC
TTCTTTAACTTAAGATAATGTCCTCCAGGCTCATCCACGGTGCTGCAAATGACAGAATTTTACTCTTTTT
TAATCACTAAATGGTATTTCATTGTGTATATATATCACATTTTCTTTATCCATTCATCTGCTCATGGAAA
CGTAGGTTGATTCCACATCTTGGCTATTGTGAATAGTGTAGCAGTGAACATGGGAGTTCTGAATCTTTTC
AACATACGGATTTTTTTCCTTTGGATATACACCCAGTAGTGGAATTGCTGGATCATATGGTAGTTCTGTT
TTTAGTTTTTTCAGGAGCCTCCATTCTATTTTCCACAATGGTTGTACTAATTCACATTCCCATCAACAGT
GTAGTTCTACTTTCTCCACATCTTCAATAGCATTTATTTTTTGTCTTTTTGTTATGTATACTAATCTTTT
CAGAGAACCAATTTTTGGCTCCCTGATAACCTCTATTGAATGTCTGCTTTCCATTTCATTGGTATCTACT
CTTATTTTTATTTCCTTTCTACTACATATTTTGCATTTAATTTGTGGTTTTCTTTCTAGCTTCTTGAGTT
GTAAGTCTAGATAATTTACTTTCAGTGTTTTTTTTTTCAGTATATGCATTTATGTGTATGCAAAAGGAGA
TGCATTTTGTGGAAGTACTGCGTTAGCAGCATTCTACCGATTTTGTTATGTCAAATTTCATTTTCATTTT
ATGGAAAATATTTTCTGATTTCCATTGTGACTAGTTCTTTGACCCATAGTTTATTTAGAAGTCTTGTTTT
TTTGATTGCCAAACATTTGGGAATTTCTTAGTTGTTTGTTTTTTTTTAATTTCTCGTTTAATTTTTCCAT
GACCAGAGAATTACCTTATCATTCAGTCCTTGGAAATTTGTTTAGACTTGGTCTGTGGTCCAGCATATTA
TCTATTTTGGTAAATGTTCTATATGCACTTGAAAAGAATATGTATTCTATTGTTGTTGGATATGTTTCTG
TATGTATGCCAATTAGGTCAGGTTGATTAATCATGGTTTGTTTGTTTGTTTGTTTTGAGACGGAGTCTCG
CTCTGTCGCCCAGGCTGGAGGACAGTGGTGTGATCTACGCACACTGCAACCGCCACCTCTCGGGTTCAAG
CGATTCTCCTGCCTCAGCCTCCTGAGTAGCTGGGATTACAGGTGCGTGCCACCACGCCCGGCTAATTTTT
GTATTTTTAGTAGAGACGGTATTTCACCATGTTGGTGAGGCTGGTCTCGAACACCTGACCTCATGATCCA
CCTGCCTTGGCCTCCCAAAGTGCTGGGATTACAGGCATGAGCCACCGCGCCTGGCCGATTAATCATGTTT
TCAAGTTTTTCTATGTCAGTGCTGTTTTGGTCTCTACTTGTTCTATCAGTTACAGAGAGGTATGTTAGAA
CTTACTCTTTCAATTGTGGATTTGTATTTTCCCATTTAACTTCTGTCAATTTTACTTTATATATTTTGAA
GCTGTGTTACTGGATGCATTCAAATTTAGGAGTGTTATGATTTCCTAATGATTTGACCCTTTTGCCATTT
AGAAATGCTCTTTTCATTTCTTTTAATACTGTTGCCTTAAAAATTACTTTGTCAAATATTAAAATAGCCA
CTCCAACTTTTTTTGGGACACTGGAGAGTGTGCTTGAGATACATCTTTTTCTGTCCTTTTAGCATGTATC

FIG. 7C (Cont.)

CTTTCATTTAAAATTATGATATTACAGTTATTAAAGGAAGACTTTCCTTCAGTATTTCTTGTAATATTGG
TCTCTTGACAGTGAATTATGTCAGCTTTCATGGATCTAAAAACATCTTTATTTTTGTCTTCATTCTTACA
GGATACTTTTAGAATCCTTTATGTGAATTATATCAGCTTTCATGGATCTAAAAACATCTTTATTTTTGTC
TTCATTCTTAAAAGATACATTCTTAAAGGTTACATGATTCCAGGTTACTTTCCCCCACCTCTAACCCCCA
TCCCTCCACTCTACCACCTCCCCCTCCCCACCCCCCAGCCCTTTTCAACACAAAGAATGGAAACTATCAA
TTTTATTGTTCCTTTAAGCATATCTCTTCTCTGGCTGCTTTAAAGATTTTCTCTTTATGCTTTGCTTTTA
GCAATATGACCATGCTGTGCCTAGGTATGCTTTTCTTTGGATTTTCCTGCTTAAAGTTCCCTGAGTTTCT
TGAATCTCTCAGTTGATTTCTTTCTTCACTTTTGGGAAATTGTCAGTAATTATCTTGTCATATATTGCTT
TTGTTCCATTCTTTTTTCTCTCTTTCTGGGATTCCAATTATATGAATATGAGACCATCTGACTTTGTCCC
ACATGTCTCGTTCTCTGTTTGGTTCATCCCATTTTTGTTTCCGTGATTGAATTCTGTTATTTATTTATTT
ATTTATTTTTGGCCTGTTTGCAAGTCTGTGAAACCTGTTTTTCTGTAACTTACTCTGCTTTTAAAATCAT
ATGAGAAGTTCTTAATTTCAGATGTTTATTTTTCAGTTTCAGAATGTCCACTTGGTTCTTTTTTTATAAA
TTATGTTGAAAATTGCCAATTGCATTATTTTACACATATTGTTAATCTCTGCATCTCAGGTACTTGCCTC
CTAACGTTAATATCTGGGTTTTCTGTGAGTCTGACTAATTTTCTGGTTTTCTCTTGATTATGTGTCTGCC
ACATATTTTGCTTCTTTTGATGTCCCTTAATGTGTTTACTTAGTGTCCCCGAACTAGACTAACACTGTGT
ATGAATGAACATGATTTTCTTTCAGATCATGTGTTTTCTCCTAGAGAGGTGTGCTCTTTGCTGTGTCAGA
CAGATAGAATGAGGAGTTTGATTATCTCAATCCAGTGAGGGATTACATAGACCGCTCCCTCCCTCTACTA
GGATTCTGTCTTCTTACGGAAGTTTTCTCTTCCCTTTTGACCCAGCCTCTTTTTTTTTTTTTTTTTTTTT
TTTTTTGAGATGGAGTCTTGCTCTGTAGCCCAGGCTGGAGTGCAGTGGCGCGATCTTGGCTCTTGGCTCG
TCACAACCTCTGCCTTCCAGGTTCAAGCGATTCTCCTGCCTCCGCCTCCCTAGTTGCTGGGATTGCAGGC
GTGCACCACCATACCCAGCTAATTTTTTTGCATTTTTAGTAGAGACGGGGTTTCACCATGTTGGCCAAGCT
GGTCTCGAACTCCTGACCTCAAGTAATCTGCCCGCCTCAGCTTCCCAAAGTGCTGGTATTACAGGTGTGA
GCCACCGCGCCCAGCCTTGACCCAGCCTCTCTATCATCCTTCAGTGTTCCAGTTACATTTCTGAGGAGAT
ATACCACTGGGAAAGCTGTCTATGTATCTAGAGCTTTTCTAGATTCCAGTCTGTCATTTCAGCCCACATG
GGCATCTAAAGCACTACTAGTCTCTTGTTTCCTTTATTAGAGTTCCTCTGCTTAAGCCAAGCTCAGTCCT
TACTCATGCCCAAGCTCTGCAGTTACCCCCATGGAAGAACAAGCCAGTGGTCTCAGCTGCCTTGGAAGTG
CTCTTCCACCTCTGGATTTTTTGTTCTTTTAGTCCTCATTGCTTCCACAGCTTTCTTACGTTGGTTAGTC
TGGTCTTTGAAGCAGGCGCATTGGCCTGCCTCCTATCTAATCACTTACTTTAGGGAAGTGGAAGTCAGAA
GTTTATCTTTATAAAAAGAAAAGGCAGATAATTTTAGGAGTGCTTATTTTTATAAGCATAGTGATGTTTT
GAATAGTTTTATCTGTGTTGCATACTCATAGCTATAAAGCATTTTTTTCCTTTCTGATATGGGCCTGTTT
ATCAAAATATGCCCCAGATCTGGGGCGAGCAAACAAAGACCCACAGACCAATGAGGCCCAATTCTTGTTT
TTATGTAGCCTGTGAACTAAAAGTGGTTTTTACATTTTTAAAAGGTTGAAAAGAAAATAAAAAAGGAAGA
GAATGTTTTGTGAGCATTATGTGAAATTTGGAAGTTTTATTGTAATATATGCACACTCCTCTCTTTATGT
GCTGCCGATGGCTGCTTTCGTGCTGTAACCATTGAGTAGTTGCAACAGAGATCTTGTGACTCACAAAGTG

FIG. 7C (Cont.)

TAAAATATTTGCTGTGTGGCCCTTTGCAGAAAAAATTTCCCTATTCCTGCTTTACATCACAGGCTCAGGA
ATTTTTTATTTCTTATTACTAAGAGAAATTAAGCAAAAGATTGAAACCATTTTATTCCAGAAGTTCTGTA
AATTTGGATTTATTAAAATCTTAGCATTTTAGAGGATTTACAAGGAACCTCAGTCTCCTTCATCTCTTTA
TTTTGCAAATGAAGCAGATTTGAGTGAAAGAGGTTTTAAAATTATGACTACATTTTTGGTATAAAGTATA
CTCAGTAATAAGCTGATAGAGAAACTATTGATCTATATCACTGAATAATTTGCAAAATTGATTTGTTCTT
ATATTGCAGAAGTATTTGATTTTTCTTAAGCAGTGTAGCTCTTAAGAAAATATTTTTGGAATTTTTAAAG
TAAATATTTTAAGATAAATATTTAAGGCATGTTAATAGCCTTTTCCTTTTATTGTCAACCACAATTCTTT
CAAATCTGATGGATATGAAGTTATTTTTGTGAGAAGACTGAAAGTCTTACAGGACCAATTCCAGACATTC
TTCATTAAGCTTCGATTGATTTAGAATATAAAGCCCTAAATCATCAGAAATTCCAAGTTAAATTGTTAAT
GTGTAAGACTGGTTTTTAGAGTTTCTCTTTTATATTCCCATCCTCAGATATTGTGAAAGGTTTAAGCTTA
GTTCTCAAATATAGAGATATAATGGTGTGTTATATTACTAGCAAATGGCATTTTTAAATTTTCCAATGTT
GAATACAAATTTTGTTTATATAATTTTCAACTTATTACTGGCTCTTTTAGAAAACTTCTACCTCTTCCTC
TGCAAACCAAATCAACAACAACAACAAAAAACACAGTAAAAGTAATTTATAATTAATTTGGGAATAGCTA
GTTCTTGGATGGCCTGTACTTAAGAATTGATGGGTTCAGATTCATAAGAATTGTTACAACCAATTAAATG
CCATCATGCATAGAAAGAAGTATTTTAGAAATGTACGTAAAGTCATTTGAACTTTAAAGAAGTTCCATTA
GATAAAACAGACACAAACATTGGTCTCTAATTGGGAAAATTTGAGTCAGTTATAACTTGTCTTTAGGAAA
TCTATCTGAATTTGGATTTATATATTCTACTTCTCTGAAAATTGGTTTGGAATAAATTTTGATGCTTTTA
TAAGTTATATAGAAGGGGCTAACCTCTTAGTAGTTATGTATTCCTGTTGCTCAAATACCTGATTTCACTC
AGGTAATCTTTAATATAAAGGAAAGTTGGTTTCCTAAATAGTATGAAGAATACGTATTGTGTTTTATTTA
TTTATTTGTTCATCTGATATTTATTGACCATCCCTGATGCTTCACATTGATGCAGGTGCTGAAAGTACAC
AGTTGAAATAGACATTCATCATGCCCTCACAATGCTAGTAGTTGAGTAGATTCTATAAGCAGGTATATGT
ATTTATGTTTAGCATTTGGCACTGTTAATCTTTCTCTTTCTCTTTACTTTTATGGCATACTATCTTGTGG
AAATCTCATCCACATACATAGTTTCCATGACCTCCTTTGTACTAAAGTCTGTGCAAAATAATCCCAAGGA
TAACTCCTTAGTGGGCCTTTCTGGCTAGAGATGCTTTAAATGCACTCATGTCGATACCATAGATGTAGAT
ACCTTATTTTAATCTCTGAGTAAGGCATGTAGCTGTAGCTCTCAACTTCCTCATTTCTCCCCTTCCTCAC
TCTTTCTCTTATACTTTCTCTTTCTCTTAAAATACTCGTTGAGTACTATATCCCAGGAACTTTTCTGGAC
AGAGGCTAGAGTAGTGAACAAGAAAGACAGGGCCCCTGCACTATTGGAGCTTTTAGCTTGGCGAGGAAGC
AATACATTAAACAGTTCCATACATAATTACAGTTATTGGCTGTACAATGAAACATAAATATACGATGAAT
GAGAGTGTATATTAGGGAAACTCATCCAGTGTGGGGAGTTAGACTTAAGTGACACTTATGCTGAGACCTC
GAAGATAAGTAGTGGTTAGCAGGAGAAGACGTGGTAGAGAATTTCAGGAAGAGGGAAAACCTTTGTGAAA
GTTGTGATGAAGCTTAACAGGTTCAGACAACTGAAAGAATATCCTTCTTGCTGGAGTATGATGAATCAGG
TGGAAAAGAATGCAAAATGAGGCAGGAGAGATTGATGGAGGTCAGTTATTGGAAGAGGATCTTTTAAACG
ATGTCGGTGCTTTTGGACTTTATCTTAAGAGAATTGAGAAGATACTGATTTTTAAGCTGGGGAATTATCC
ACTCAGGTTTGTGTCTTTAAAAGTTGAGTTAGGTTCCTATGTGAAGAATGGATTGAAGGGTATGGATGTG

FIG. 7C (Cont.)

CAGAAATGAGTTAAGCTTTTGCAGTGGTCCAGGTAAGAGGTGGTGGTAACCTAGCTTATTAGCATTGCAG
CAGTAAAGATGGTGTGGACAGATTCAATAACTGTTTATGAGATATAATTGACCAGATTTTGTGATTATTT
TGATTTCAAGAGTGAAACTGAAGGCAATGTCAAGGATAACATTTTCATCTGCTTGTTACTCTTGTCTATT
TGTTGACATTTTGGTATTTTGAAGTTACACATCTTCAAAATCAAACCCATTACTTTTTTTCCAGCAGGCT
AACTCTTCCTTCTAACTTCTCTATTTTTAAGAGTGACATTGTCTACCTCCAAGTGACCTAGGCTTAAAAT
TTTTCTCTTTTGTCACTGCTGTTACTAAATTAGTTACCAAATCTTAAGGACTTGACCCCTTCAGCATCTG
GAACAACCTCCTCCCCTTCGTTCTCCCTGCATTCCCTCTTCCCCCCGACTTCATCCTTTTTTCTTTATTA
CAGCAGTAGTATCCTCTTGTTAGATCACTAAACTGTGCTTTCCATTCAAGTCTCTGAGCTCCTTGGGGAC
AAGAACTGTCTTTTTCATTTTGTGTCTTTACTACTTTGCATCTCAGCATGGTGAACATAAAACATATTAA
GTGAAATGAAAATAAAATGTTTTCCTTGCTTCTTGTTTCTTGCACCATAATTCTTATTCTTTATCACATA
TTTTTTTCTGTTTCTCAAAAGTTATTCAGGGGCTTCCTTTTGCTTAAAGAATAATTTGGTCTTAGGACTA
TGTGATAATGAAGTATCCAGACTGGCTGCTGGAGACATAAAGTATATGAGCTGGGGATTTTCCTATAGTA
GTTTAGTAAAAAGTGGCTCTTAAGTCCCTTTGCACCGTAGCCCTCACTACCAAAAAGAGCAGATTTTTTT
TCTTGGAAACATCACTGACATTTGTAAACATCCCACTATGGATAAAGTATAAAACACTTCATTTGATGCC
TTTTTAATGTTTTAAGTTTATGTTTTTGCAGAATTCAAATTTGTATTATCATTTAATATATATTGTATAT
TGCTTAGCTGCCCCATGTTATCTTCTCAATAGCTACTTTATATGTTAGTATCTTATATGTGTATGTAAAG
TATATTGTTTCACATAAAGAAATTTTGCAAGAAAAAGATCCAAATGTCTACTTTGGAAATACCCATTTTT
GATAGCTTTGTATGTCCTAATATGAACATTCATATTTTTTTCCCATTTTTCTTTTAATATTTAGGAATAA
GAAAATTTTAAATAAGAAGAAATTGAAAAGAAAACAGAAGAGCAAATCAAAAGTGAAGACAAGAAGCAAG
GTAAAGCTGCTGGTAATTGATAAGGAATAGGACTTTTTCATATGGTGATTTGAATAAAAATGCCAAGATT
AAAAAATATAATTAAACCATTTTATTAGTATGTGCTGAAGTAATTTTGTAAAAGCCCTTTATGATTTGGT
TCCTCTTTTAGTTTCATCTTTCTTTTGGGTGTTTCTTTTCTTTCTTGCCTTTTTTTTTTTCTTTTTTGAAA
CAGGGTCTTGTTTTGTCACCCAGGCTGGAGTCCAGTAGTTTCCTGGGCTCAAGTGATCCTTCCACCTCAG
CCTCCTGAGTAGCTGGGACTACAAGTAAATGCCACCACAACCAGCTAATTGTTAAATTTTTTGTAGAGAC
AGGGTCTCACGGTATTGGCCAGGCTTGTCTCGAACTCGTGGGCTCAAGCAATCCTCTCACCTCGGCCTCC
CAAAGTACTGACATTGCAGACATGAGCCACTGTGCCCAGCCTATTTCTGGGATTTTCTTGACCAGTAGCC
TGGAAGTTAATATCTGGATGTTGAAAATTATTTGCTATTTATTCTTATTATCTTTGATCAGTCCTTTGGG
GAACATATCCATTTCTGTTCTCTTTTTTCAATCTGACTACAGGTACTAGAAACTTGAGTAAAATTAGCTT
GTAAACTGGGACTTGGATTTGGGTTCATCATATGCCTTTCTTGACAGGAATTAGGGAAACTTGGTGTGTC
CATATTGTTCTGAGCCTCTTTTGACTGTTGGTAGCTCTGCAAAAGAAAAGGCAATATGGAATATTTGAAT
TAGGTGAGACCTTAGAAACCAAGAATCTATTTTCACCTAATGCAGAGATCTCTATAAAATCCATCTTTTT
TATACTGAACATTTTCAGTGACCAGAGCACTTGATATAACAGTCTCTTTTCTATTGAACATCTAGACAGA
AGGAAGAGAGGAGTCGTAACTATGATTCCTGAATAGCTTCACTTTGAGTTAAAGAAACAATAGATTTGCT
GGGCCTGTATAGCAACTATAGAGGCAATTGTTTCCTACACTTTTAAGTTAGTGTTTTTACTATTGTAACT

FIG. 7C (Cont.)

GAGAGAAATCTACTTCAAAGTAGCAAACCTAAAATAAAATGAAAGGTTGGGGGATGGCATTTATTTGGTG
GCTCTATCTTGAGACACAGATGGATCCGGGGATGAAATGATATCATTGGCTGGGTGCAGTGGCTCACGCC
TGTAATCCCCGCACTTTGGGAGGCCGAGGCTGGCAGATCACGAGGTCAAGAGGTCGAGACCATCCTGGCC
AACATGGTGAAACCCTGTCTCTACGAAAAATACAAAAATTAGCTGGGCGTGGTGGTGGGTGCCTGTAGTC
CCAGCTACTCAGGAGGCTGAGGCAGGAGATTGCTTGAACCCGGGAGGAGCAGGTTGCAGTGAGCTGAGAT
CGCACCACTGCACTCCAGCCTGGCGACAGAGTAAGACTCCGTCTCAAAAATAAATAAATAAATAAAAATA
ATCAAACCCATATTTTCAGCTCTTGCTTCTGCCTTCCTCTGTGTGTGGACTTATTACCTGTGACTGAGGC
TGAGGCTGCCAGTAGCTCCAACTCCATTTGCTCTGAGCAAGAGGCAATCTCTTATACTAGTCATAGCAGA
AAGTCTTGGGTAGGATTTTCGGTTTACCTGCATCATTTGCTTTGACCACGGAGATACGGGATACTTTGGT
TAGACTGAGTTATATTTTTAACCCTGAGATGGGCAGTGGGTGAGCACCCTGGTGAATAGGCCACATGAAA
TGAGGGAGGAATAGTTACCCTAAGGAAAGTGTTGCCGGGTAGGCAGAAAAATAATCTGTTCACTGTATCC
CTTCTCATTACTTCTGCTTCTGGGATAGAGGAGGGAAGTGGAGCGCATTGTCAATATACAGAAAACCTCT
AACAAATACAGTCATTCCAACCTCTATCCCTTTTCAACTTTTTGGTGCTATGTGCAAATCGGAGTATGGG
AATCTTGAATATCTTTTAAGTTTTTTTAAGGTTTCATTTGGTGATTTTCCTGAAGTGGTGGCATATGATA
TCCAGGAAGAGGTGAGGAGAAGTCAAGGTCTTTTGTCCCCTTCAATTCGGCCTCCAACTAGCTTTGTGCC
CTTAGTAATTCAGTTTTTTTCCTCTTGCTCTCAGTATTTCTATATCTTCTTTTTAAGAGTAGTTTGAGAT
AACAGTGATGTAAGTAAGTTCATTCATTTATTCCTCAAACATTAATTGCATGCTGAGTATGTGCAGGCAT
TATGCTGGATGTTTGGGATACAAAGATGAGTAAGAGGCATTTTTTGCTCATGGAAAGCATATAAAGTAGT
AAAATGGTGTTGTTAGTCTCCTTGACCTGTATTACTTTTTCCAGATTATTTTTCATCTACCCTCTTTCTG
AAAGTTATTTTTAAAATGCCATTTAGCTGGCATTTTATCTACTTTATATCTACTTTATATATATTTTATA
TATATGTATATATATATGTATATATATATATATATATATATAGCCATTATATCTACTTTATGGCTATC
ATCAACCCCTCTATTTCTCCTCATCCATCAGTCATCTCCTTTATTTAATTTCCATCTTACCCAGGTTAGA
TACCAGTCTTTCTTTTTAGAAAAACTCTTATTTAATCTGTAACAAATTACAAAAACTTGATGGTTTAAAT
TAACACTCGTTATCTTACAGTTCTGGAAATCTGAAGTCCAAAATGGATCTCACTGAGCTAAAATCAAGGT
GTCAGCAAGGCTTTATTCCTTCTGGAGGCTCTAGGAGGGAATCTGTTTTTTTGCCTTTCCAGTTTCTATA
GTAGAGGCTGCTCAGATGTCTTGGGTTGTGGCCCCCTTCCATCTTCAAAGCCAGTGGCGGTTGGTTGAGT
TTTCTCATGCGGCATCACTGATAGTTTTCTGTTGTTTTATCTCCTCCTCTTACTGTCCAGCCTCCCTCTT
TCACTTGTAAGGACCCTTGTGATTACATTGGCCCATCCAGATAATCTGTGCATTTCAAAATCCTTAGTTT
AATCACATATACAGAGTCCCTTTTGCCATGTAAGGTAATATTCACCTGGGTTCTGGGGAATTAGGGTATA
GAAGTTTTTGGAGGCTATTATTTACCTACCATATCTCCCTTGTATATTTGTTGCATTAATCTGACAAAAC
TCAATCTTGTGTGAATCCAGTTATTTTGTCCCTCCCTTAAGGTGAGTTCCATGTGCTGCCAAAGAGAGTT
ACACAAGAGTTAACTGATAATGATACACATTCATGATCATCAATCTCAAGTATACCATAGCCAGACTATC
TTATTATTTTTTCTGGTCAAATAGTTCTCTTTTCTTCTGTGATTATTTCAGACCTTTGCCATGCTCCTCA
AACCTCTGATAAATTCTACCTTCCAGCACATGACTTCACTTTCTTACAGGAGAAATCAAATTCATTACTC

FIG. 7C (Cont.)

AGAAAAGTTCCTCAACTTCCTAATCCCAAATGCGTCTGTCTTCAGGCTTCTCAGTAGCTGAGCCTGACAT
AGAGATTTGAAGTTTGCAGTTCAGTAAGTTTTGAAAGTTAACATTCATGCATAGAAGCACTACTGCAGTC
AAAGTTCAGAACATTTCTATCATCTCCAGGGGTTTTCTTTTTTTTTCTTTCTTTTTTTTTTTTTTTTTT
GAGACGGAGTCTTGCTCTGTCTCCCAGGCTGGAGTGCAGTGGTGTGCGATCTCAGCTCACTGCAGCTTCT
ACCTCCTGGGTTCAAGCAATTCCCTGCCTCAGCCTCCTGAGTAGCTGGGATTACAGGCACCAGCCACCAC
GTCCAGCTAATTTTTGTATTTTTAGTAGAGACAAGATTTCACCATGTTGGCCAGGCTGTCTCAAACTCCT
GACCTCAGGTGAACCACCCGCCTTGGCCTCCCAAAGTGCTGGGATTACAGGCACAAGCCACCGTGCCTGG
CCGGTTTTCTTACCCTCTGCTGATTCCATCCCTCCCTATAACCCTGGCTGTAGACAACCACAGATATATT
TTCTGTCACTGTAGATTAGTTTTCATTTTCTAGAACTTCATATAAATGTGATCATATTGTGAGTGCTCTT
TTTTTTTTAAATCTGGTGTCTTTCCCTCAGCATAATGATTTGTGTTAATGTTGTTGTATATCAATAGTTC
ATTCCATTTTTTTGCTGATTTTATATACATATATATGCACTTGTGTGTGTATGTGTGTGTGTTCAGTTTT
CTTGGGTGCATACTGAGGAGTGGAATGTTTAGGTGGTTTTTCCTTTGATTTGCCAGAAGGACTCATAAAT
CTCACAAGCAATTTATACTCATGGCTAAGATTTATTACAACAAAGGATACAGAGCAAGCAGCAGGAAAAA
GGTATGTGTTTGTGATGTATAGGAAGTTATGGCATAGGCTTCCTAGTTCTTCATTGACTGAGCTTTCATG
TCAGAAAGAAAGACATGCTTTCTCTCTGGCAGTGAACTACAGAGAAATGTGTATATTGTTTTTGCTCAGG
TGAGTTTTAGAATTCAAGACTTTGTGGGTTTGGTCACACAGACATATCTTGTTAGTCAATCAGACATGGT
AAGTGAAACTCAGGTACACATTGTAAAGCTTGATGTTCGTACATGCAGAGCAGTCTGACAGGCCAGGAGG
CATGGTCCATTGCTCTGTGTGTTCATAACACAATCATCAATCACTACCACAAAGAAAACTCTAAACATCC
ACATTCCCAAAGGTTAGCCAAGGGTCAATCATGGTTTCCTTGGGGAAATACAAGGAGTAAGCAATCATGC
CTGCAGCGTTAACTTTTTCCTCAGAGTGGGCACGGTAAATGTACGTTTAGTTTAGCTTTTTTTTTTTTTT
TGAGACAGAGTTTCGCTCTTGTTCCGCAGGTTAGAGTGCAATGGCACGATCTCGGCTCATTGCAACCTCC
GCCTCCCAGGTTCAAGCAATTCTCCTGCCTCAGGCTCCCGAGGAGCTGGGATTACAGGCATGCACCGCCA
CGCCCGGCTAATTTTGTATTTTTAGTAGAGACGGGGTTTCTCCATGTGGAGGCTGGTCTCGAACTCCTGA
CCTCAGGTGATCTGCCCGCCTTGGCCTCCCAAAGTGCTGGGATTACAGGCGTGAGTCACTGCACCCGGCC
TGTACATTTAGCTTTTTAAGAAACTAGAAAACTCTTTTCCAAAGTGGTTGTTCCAATCTGTAGTCCCACC
AGTGGTATATGACCAATCTAGTTGCTTCATATCTTTGCAAACATATGGTATTCGCTTTTTAAATTTTAGT
CAGCCTACTAAGTAGGGGTTTCCCATTGTGGTTTTAGCTTGCTTTTCTCTAATGACTAATGATGTGAAAT
CTTTTCATGTACCTTTTGCCATTCTTATTTTTTTGATGTGAAATGTCTGTTCAGATCTTGCCTCTTATTT
TTGTAATTGTCTTCTTCTTATTGAATTGCCAGAGTTTCTCATATATTCTAAATACAAGTCTTTTGTCAGA
TATCTGCATTCCAAATACATTTCTCCTGTTCTGTGGCTTGCTTTTGGGGGAAGAATTGCCATTTTAATGA
TATTGAATTTTCCAATCCATGAACATGGTATATGTCTCCATTTATTTAAGTCTTTAAATTTCACTCAGCA
ACACTTTTTTGTTTTCAGTGTGTAGGGCTTACACATATTTTATTACTTTTATTTACAATTATTATATATT
TTTGATGTTACTGTAAATGCAGTTATTTTTGAAAATTTATTTTGCTTTGAGATGATTTCAGTATGAATGC
AGTGTGTATGTGTTTGTGTGCACCTAAGTCTGTGTAATTTTATCACATGTGTAGGTCCATGTGACTCTTA

FIG. 7C (Cont.)

CCACAGTCTGGATATACAGCAGTTCCATCACAAGGATTCTCTGTGATATCCTTTATAGCCACAGGTATCT
TCCTTCCTCACCCTCTCCTTAGCTTCTGGCAACCACTGATCTGTTCAGCATTTATAATTTTGCCATTTTA
AGAATGTTGTCCAGTGAAATTGTACAGTATGTAATCATTTAAGATTGGTGCTTTTTTTCCCCACTTGGCA
AAATGTCTTTGAGATTCACACACATTGTTGCATATTGTTTGTTCCTTGATGAGTAAGCATTTCATGGTAT
GGATGTACTATAGTTTGTTTAACCATTTACCCATTAAAAGATATCTGAGTTGTTTCTAGCTTTTGACTAT
TTTAAAAGAATGCTATTACGAACATTCGTGTACTGGTTTTTGTGTGAACATAAGTTTTTATTTCTCTGGT
GTAAATGTCCAAGAACATAATTGCTGGATTATATGGTAAGCACATATTTAGTTTTGTAGGAAATTGCTGT
ACTTTCTTCCAGAGTGGCTGTACCATTTTACATGACCATCAGCAATGTATAAGTTTCTCCTCATCCCCAC
CAGCATTTGGTGTTGTCACTATTTATTTTAGCCATTCTGATAGGTGTGTACTATATCTCATTTTAATTTG
CATTTTCCTAGTAGCTAATGATGTTGAAATTCTTTTCATGTGCTTATTCACCCTTTGTGTAAATATCTTC
TATATTGATGTGTTTATTCCTATCTTTTGCCCATTTGTTAATTGGATTCCTTGTTTGTTTTTACTGTTGA
CTTTTGAGAATTCTTTATATATTCTGAATACTCATCCTTTGTTGGATATGTGGTTTGCAAATATTTTCTC
CCAGTCTGTGACTTCAATGCTATTATTTTTGAAATTACATTTTTTCAGTTGTTCATTCCTAGTATGTGGA
TATACTACTCATTTTTATATAGTAATTTTATATCCTGTGATTTTGTTAAATCTGCATACTATTTCTGGTA
ACTTTTTTGCAGATTCCTTAAGATTCTCTACATGTTTTTTTACAAGTAAAAACATTTCTTTTTTAGAAAA
TACTTCTTGCCTTTTTCCCTTGGCTGGATAGGATATTTTCCTTGCACTAGATAGGATATCCAGTACAATG
TTGATGAGTTGCTGAGAGTAGACCAATTTGCCTGGATCACAATCTTAGAGGGAAAGCATTCAGTCTATTA
CCATGTTAGCTGTGGTTATTTTGTAGATACCCTTTATCAAGTTGAGAAAATTCCCTTCTATTCCTAACTT
AGACTTTTTTTTTTTCTATCATGAATCGATACTGGATTTTTGTCAAGTGATCTTTCTGTGTTTATTTGAA
GTATAATATATTTTTTCTCTGTTACAACAGTGGTTGCTTTTCCAGTGTTGTGCCAGCATTGTCCCTGGGT
TAAACCTCAGTTGGTCATAATGTATTACTTTTTTATATATTGTTGGATTTGAATAGCTAATACTTGTAAT
ATCTCTGGATATTTGGATGAGATATTTGTAATATCTCTTATACATATATTCATAAGTTATATGCCATGCC
AATTTAACTTTTTGATGTATTTCTTATTTAACAAGTGTATTTTTTTTTTCCAATTCTTTATGGAAGAAGA
GTCGAATATTTGGGACCAAGTGTTTTTGGTACTTGAGGTATCATTTTGTTTATCTTAGATACTTCCTGGA
CATACTCTAATTATTGGAAGTTGAATTTCTAAAATATTTTAAAACAGCTTTTTATATTTATAATATAAAT
GTTGATCTTGAAATTGTAGTTGCTGTCTGATGAATAAAATATTGGGCATAAAAGAGAAACTGTTTAGTCT
TAACAAATTACCAATCACATGATTTTTAGCCTTTATCAATACTGATAGGTGAGAGAGAGCTTAGGGAAGC
ATCTACAGTTTACTTGGCATTACTGTTACTTGAATGAGAATGAAATGAGCTGATGAAAATTAAGTGTTTT
TTTGGGAGGCCCTCATTTCTGTGTAAACTTCTATATCTACTTTTAAAAGCATTCAAAATGCAATCTAATG
TTTGTAGTAGGTCATTGAGACTCTACAGTGTGTCTAGAGTCTCTTAGGAAGTCGTAAAATGAATTTCCTT
TGATACAGAACTCTAAGAGTTAAGCTTTGTTGAGTCTATTCCTGTCATGGCGATACAAGAATATTTCTAA
GTTTTTTGCCCATCCTTTTCCAGCCCTTGTCAGATTGGTTGGTTATTGCTGCATTGCTCAAAAAATAGTG
AGGTATAGAAAAGGGGACTAGAAGTTGGGTCCATAGACTTAGACTGTCTCTGCTGTGTCACATAATGTGT
CTTCTGCAAGTCAGTTAGTGTGTCTAATCTTTACTTTTATGTAAAATGGGACTTGATGATAGAAAAGAGT

FIG. 7C (Cont.)

GTGAAATGGAAATATTCTGTTTTGTATTTCAGTCTGAAAACTTAGAGAATACAGTAATCATACCAGATAT
CAAACTACATAGCAATCCTTCTGCTTTCAATATTTACTGTAATGTACGCCATTGCGTTCTGGAATGGCAG
AAAAAGGAAATATCATTGGCAGCCGCATCTAAGAACTCTGTGCAGAGTGGAGAATCAGATAGTGATGAAG
AAGAGGAATCCAAAGAGCCCCCTATCAAGCTTCCAAAGGTAAGCCACTGAGTTCTATTAATATTTAGATG
TGTAACCTGCAGGTGTTCTGGCTATAATGCATATATACGCATTGCTAAAATACTTTGCTTTATGTAAAAT
TGCACACTAAAAATAACACGGCTTATGGGCAAAAATAGATTTGGAGCAGAAAAGGAAAACTCTGCAACTT
TATAACTAAGGTGCTAACAAAGTCAATAATTGATAATTCACTGGAAAGCGCAGGAAGGGAGATCAGTGGG
TTGGAGTCTGTTATAGGGGCAATTAAAAAATGTACAAAAGCAGTAGGGTGGAAATGCTAGTATAGAGGCA
TTGAGCCATGGCAGATGGAAGTAGAGCTCTGAGCCAGTGAGCCGAGAGTAAGGTGGGCACAAGAGAAAGC
CAAGAGCCCTGGAAAGCTGGGAGGTGCTCCTCACCTGGGATGCAGGTATGCGTTTTTATTTTTCTTGAAA
TAGAACTACAAAGCCTCTCAGCTGTGTAGTAGCAGGGCTGAGAGCCTTTTCCTTTCTGCCTAAGCTTATA
ATTGTACTCTTGATATTGTGGTTTCCCTTGATTAGGAAAAAAAAAAATCACCTATGAACCAACTGAACTT
CTGCATTATTCTGATATTACTCCCTTATTTACCAGGAGCATATAAACTAGTTGGTATTTCTATAATAGAA
GCATGTATTGTAGGCCGGGCGCAGTGGCTCTCACACCTGTAATCCCAGCACTTTGGGAGGCCAAGGCGGG
TGGATCACCTGAGGTCAGGAGTTTGAGAACAGCCTGGCCAACATGGTGAAACCCTGTCTCTACTAAAAAT
ACAAAAATTAGCCCGGCATTGTGGCAGTCGCCTATAATCCCAGCTACTCAGAGGCTGAGGCAGGAAAATT
GCTTGAACCCAGGAGGCGGAGGTTGCAGTGAGCCGAGATCATGCCATTGCACTCCGGCCTGGGTGACAGA
GTGAGACTGTCTCAAAAAAAAAAAAAGAAACTGGCTGGGCGTAATGGCTCACGCCTGTAATCCCAGCTCT
TTGGGAGGCCAAGGCGGGCGGATCACGAGGTCAGGAGATCGAGACCATCCTGGCTAACACGGTGAAACCC
CGTCTGTACTAAAAACACAAAAAAAACTTAGCCCGTCACGGTGGCGGGCGCCTGTAGTCCCAGCTACTCG
GGAGGCTGAGGCAGGAGAATGGCGTGAACCCGGGAGGCGGAGCTTGCAGTGAGCCGAGATGGCGCCACTG
CACTCCAGCCTGGACAACAGAGCTAGACTCCATTTACCAAAACAAAAAACCTGTATTATAGAACTACTCT
CAGTTTACTCTGTTCTGTTTAAGTATTGGTATATTTAAGACTGGAAGGTCTATATATATATATATATATA
TATATATATTTTTTTTTTTTTTTTTTTTTTTTTTTTTTTTGAGACGGAGTCTAGCTCTGTTGCCCAG
GCTGGAGTGCAGTGGTGCCATCTCGGCTCACTGCAAGCTCCGCCTCCCAGGTTCAGGCCATTCTCCTGCC
TCAGCCTCCCAAGTAGCTGGGACTACAGGCACCTGCCACCGCGCCCGGCTAATTTTTTTTGTATTTTTA
GTAGAGACGGGGTTTCACCGTGTTAGCCGGGATGGTCTCGATCTCCTGACCTCGTGATCCGCCTGCCTCG
GCCTCCCAACGTGCTGGGATTACAGGCGTGAGCCACTGCACCCAGCCTGTTATATATATATTTTTTCTATAT
AGTAGATATAGTTAATATTTACAACAAAAGAATAGGTGAAAATATAGACATTTTTAAATGGTGCCTTTAT
ATGACTTATGCATATTGCTTTTTTCTAAACAGAGCTATTCAAAATGATTTTATAATTATAAATGATTTAT
GACTATTGCCTTTTTACTAAACTGATACCTTAAAATTATGCCTTGAAAGCTTATACATATCCACAAGGGA
TTGTGTAAATATTTTTTACTACTTGGAAATAGCAGCATAAATGGAACCTGGTCTGAGTTCTTTTGCACAT
TTTATGGTGGCTGTTCCTAAGTACACCACCATCCTTAATCATATTGTCAGGTTCTTCTCACCTTATTCTC
GGCAGATGGCTTGCTTCATATTTCATAGAGTAATACAAGTTTTGTGAACTTACTCAGCTTCTTGATCAGC

FIG. 7C (Cont.)

CATCTTCACATGTCCTTTTTGCCTCCTGTTTTAGAGTGGGACCCTTTTCTTTTTCTTATTTCCTTTGTCT
GCAATGTCCTAACTGTACCTACTCTAATAGCTCCTTCCTTCCTTCCTTTGCTTTCCTTTGCTTTCCTTTC
CTTTCCTTTCCTTTCCTTTCCTTTCCTTTCCCTTCCTTTCTCCTTTTTTCTTTTCCCTTTCCTTTTCCCT
TTTCCTTTGCCTTTCCCTTTCCTTTCCTTTCTTTCACGGAGTTTTGCTCTTGCTGTCCAGGCTGGAGTGC
AATGGCATGATCTTGGCTTACTGAAACCTGTGCCTCCTGGGTTCAAGCAATTCTCCTGCCTCAGCCTCCT
GAGTAGCTGGGATTACAGGCATGTGCCACCGCGCCTGGCTAATTTTGTATTTTTATTAGAGATGGGGTTT
CTCCATGTTGGTAAAGCTGGTCTCAAACTCTGGACCTCAGGTGATCTACCCACCTTGGCCTCCCAAAGTG
CTGGGATTACAGGTGTGAGTCACCGTGCCTGGCCAATAGCTTCTTTCTTTAACCTAAAACAAACATGTTT
ATCTTTAATATGGGAGCTGCTCTACATAGAAATTATGGTCTCTAATTGTAATTTCTTATGCTTAACTAGG
AGAGATTGAGATAAAAAACATAGTTGAGTTAGGACGTAGGGCTGGAGGACTTGTATAATTTACTTTTTAG
TTAGAATACCAATTCTGTGTATGTGTGAGTCACACTGTATTATAGTAATTGTGCTACTTAAGTTCAATAT
TGTGAGAGAAAACAAAAGCCTGGGTAAATTTTTTACACAGGTATGCAGATTTTGAATAGTAAACTGTAGT
TCAAATTAAATTGCATAAACAAGAACAATGGATTCCTAGGGTGTTTAAAAACATCAGGATTAGTGAGTAT
TAAATGAAATATCAGGCATTCTTAAGATAACCTTTTGCAGCATAATTAACAGAGTCAAAGGGGTATCTTT
CAAAGAAAATTAAAGAAGATCAGATAGCCCAAGTGATTAATACTGAATTTTCTACCAAGTACTGACCTGT
CTGCAAACAGGGTTAGCATGGGTTATGGAGCCAAACTGCTGGGGTTCAAACACCATTAAAATTACTAGCT
ATGTGACACTGGAAGTTATTTGACACATCCGTGCCTCAGTTTTGTCATCTATAGATTGGGGGTTGCATCT
ACCTCATAGGGTTGTAGTGACAATTTAAATGAATTAATGGATGTTGAGTGCTTGAGAGAACAGTACCTGG
CAGAAAGAAGTGCTCGGTAAATGATATATATAGTTGTAAGTGTCAGTTTAGGTGCAAACAAGAAAATGTG
TAGGTGCAAATGAATTTGAGTTACTTGTCAAGGAACTCTTCAGTTTATTAAAAAAATTATGCAAGCAAAT
GAAACTTCTAGAGAATCAGTGCAATCACCTGATGAATGAGAGGTAAAGAGAGGAAGAAGTGATGAGATGC
CTCTATGCAGAGGCAAGCAGATACTATGGGTGGGGAGTGAAACTTTCAGGTGATATTTTTTGGCAGCCAT
TTCCATGACATGAAGGATTGACACTGAGGACGAAATTAGTCTCTTAAGGTTTGAGGTGATGGGATTTGAA
GGCAAGTGGGAAATGTTGGCATTTTTCTTTTCCCTTTGACCTTCTCTGTGCCTCAGCCCCAAATGCTGCT
ATTATCCTAGTTTGCTCCTTTTCTTTGTTCCTCTGTTGCTCCTCCTAAGTGTGTGGCTGTCCCATTCCTT
CTTGCCTGAGGTTTCTGTTTCTTGTACTCTTTTTTTTTTTCCTTAACATGATTAAGACAGTTTTTAATC
TGTTGTTGAAGTGTTGTTGTAATACAGTTTTATTTTTCCCATTCTTGAGTTTTAAATTATTATTTAGTTA
CTAATAAATTGAGTTTGACTGTTATATAGACCTTGATTGTCACCCTTTTGCTTTTTGCTTTTGTTTTTGT
GTTTTGCGGATCAGTAATCATTGATGTATTTAAACGAGCTTTCTATTCCCTGAATGCTTCTACATTAAGT
TTTTTAACCAGCTCAAACTGTCACTAAAATCTACATCCTCTAAAACTTTACAGATTTTATAGCTACATAA
TTTTTATTATTTTTGTTTTTATTTTCATTTTGAGACAGGGTCTGGCTCTGTCACTGGGGCTGGAGTGCAG
TGGCGTGATCTCAGCTCACCGTTAACTTCCGCCTCCTGGGCTCAAGTGATCATCCCACATTAGCCTCCCA
TGTAGCTGGGACTACAGGTGTTTGCCACCACCCCAGGATACTTTTTGTATTTTTAGTAGAGATGGGGTTT
TGCCAGATTGCCCAGGCTGGTCTCGAACTCTTGAGCTCAAGCAGTCTGACCGCCTCAGCCTTCCAAAGTA

FIG. 7C (Cont.)

CTGGGATTACAGGCAGGAGTCACCGTGCCTGGTGCATAATTTTTAAATAGTAACGCTTAGAAGTCATATT
TCCCATCTGAACCCATTTGAAGCCAGTCATGCCACATTATTAAAAGATTTAGACTTACCTAGGATCATTT
CTTTCTTAATTCAGTATATTCTTTTTGAATTTGTAGCCAGCATTATATTAGGTCCTGAGAACAAAAGGAT
GAGACATAATTCCTGCCCTCAAGAAAGCATTGTCTTGTAGGGATAAGAACCAGGTCAATAAATATTCTCT
AGTGCCTTAAGGATTGATAGGGAGTGCTAGATATAGTGGAACACGTTAGAGAAAGGACTCAACACTGGCT
GAGATAGAGCAAGAGAGAGAGAGCAGGAAGCTAAATCATGAAGGGCCTTATGTGCCATGTAATTGATTCA
GATGTTATCTCATAATTAGTAAATATTGAAGATTTTAAGCAAAAGAATATCATCAGACTTGCATGATTGC
ATCAGACTCACCACCCTGTAGTTATGAATATGCCTTACTAACACTGGAGTAACTTTGTACTCCAGTAAGT
AAGTAACTTTGTACTCCAGTTAGTAAGTAACTTTGTACTCCGGTTAGTAAGGCATATCCATAACTACAGG
GTGGTGAGTGAGACTGGAGACAGAGGAACCATTTAGGCAGTTATTGCAGTTGTCTAGAGAGTGTTAATGA
GGGTTGGAATTATGGTAGTGACAGTGTTTTGAATATAGGAAATGTTAAGCAGAATTGACAGGAATTAGTA
ATAAATTGGCTATAACGACTGAAAAAGAAGGCAGAATCTAAAGATATTCTTAAAGGTTTTGTGTGGTGAG
GGCCTTTACTGAAAGAGGGAATACTGGATGAGGAACAGTGCTTGGCTGAAATGATGATCAAGTTTAGTTC
ACATGCTGATTCTGAGGTAAATGTGAAGTATCCAGTGTGTGCTATGTAGGGCTGAAGTTCAAAAAATAAG
TGTCAGCTAGAAAAATAGATTTGGGAGTTATCACTATGTAGGCACAAGTTGAAACAAATTTCTGTGAGAG
ATCGGAGGGGGTGGGATCAAGAACATTGTTTGAAAAAATAGCTTTGAAAAGTTGAAAAGTTTTGAAAAGT
TCTCTTCCTCTGAGTGTGAAGAGAAGGGAAGAAGATGGTAGTAGTCATAGATAAATTTGTTAGGCAAGGA
ACTCAGAAACTTCACACTCATACTTTCTTTCTTTTTTTTTTTTTTTTCAAGATGGAGTTTCACTCTGCTT
GCCCAGGCTGAAGTGCAGTGGCACGATCTTGGCTCACTGCAGCCTCCACCTCCTGGGTTCAAGTGATTCT
CCTGCCTCAGCCTCCCAAGTAGCTGGGATTACAGGCATGCGCCACCATGCCTGGCTAATTTTGTATTTTT
AGTAGAGATGGGGTTTCACCATGTTGGCTAGGCTGGTTTGCAACTCCTGACCTCAGGTGATCTCCCAACC
TTGGCCTCCCAAAGTGCTGGGATTATAGGTGTGAGCTACCACACCCGGCCTCACATTCAGAATTCTCCAT
CTTAGCCTTCTCCTCCTCTCTTTCTGCTGCTGCCTCTTCCCCCTCCTTTTTTCTCTGTCTCTAGATTTTT
AAATTTTTTATTATTTGTAGATATTATCTCTGTACCAAATATTTGCTTTATACAAACAATTTTAAAAGAC
AGTATACTTCACTCTATGGTAATATGTAAATATAATTTTGATTTCCTTTTGAGCTTTTTCAAATATAAAA
GTATAGGAAGTGATTTTAGGACCTTTTAACTAAACAAGATACAATTTTTAAGGGTAAAGAATTAATTATT
AAATCCAAATGTGATGTAACTAAACTTTTATGATCACACTTAGTCATGAAATAATAAAGTCACGTTTGGA
AATATATGATTTGAGAAGGGCAAAATAAAACCTTGAAAGACTCTTTATATATCATTTTTCTTTGGCCAAA
TATATTTTTATCTCACTTTCCTAGCATATTAGACTGGCTGTATCAGGTAATTATTTGGGCTTCATGTTTC
TTTATCTTTCAAATATGATAGATAACCTTCAAAATTTAATTATTTGAGAGCAGCAGTAAAGGTAAAATTC
AGTAAATTTACAAAGACTATTTTCTGAAGAGAAGTGCGAAAGCATGTGTTGGGTAATTAGTTATAGTTC
GTTATGGAAAGTATTGAAGCTTCTTGTGTTCTTTTATTGTTATAATTATTATTTTTATTAAATATCACAT
TTATTTATTTTGCTAATTATACATATTTATTGTAGATGATTTGAAAAATCAGAACATTTTTCTAAAGAGG
TATTAAAAATCGGAAGTAATATTTGAAATACCATTAACCAAAATATACCCCAATATAAACATTTTTATTT

FIG. 7C (Cont.)

CTTTTGTCATTTTTTCTATGTACACATTAAAATGTTTTTTACACACAAATGAAATAATACTATATTGGCA
GGACTATATTTTTTCTCCTTACACTCTTCCTTCCTGATACTGAAGGAGGGAGAAATATGTGTTTTCATTG
ACTATAAGACTTCAAACTGTTTTAAAGTCTACTTTCAAAGTTCAAACTTTTGGTAAAATACTTTATACTT
AGCCAAACAGCAGAAAAAGACTTATTTAAGAACATGTCTGTTACCTCTGTGCAATAATCCATAGCTAAAT
ATTAAAAATTCTTTAATAGTTGCAGAACTTGAGGTTGATTTTTGTTGTGTATTGAATATATATTACTATT
CTGAAAATGAATGTTTTCCCATTTGTTAAACAAAAAGTCTACAATGAACCAAGATGTGGATAATTAGTGA
GACTCTCACAGTGTTTAACCCAGACAGATGAAGAGTTCCCTATCATCATTGTGACCAAAGTTTTATGGGC
CAGTCTCACTAAAACCGGCTAGCTCTGTTTCTAGGCAGCCCACCTGAGTTGCCTATTGCCATTCACTTGT
TATTACACCTTAAACTTACCAGAGAGATCAAGAACCTGTTCATTAGGCAGTCTTACTGTTTCTGGCAAGG
TTCAATAATTCCGTTGTCACCGTAGGAAACTGTATCTATAATAAATGAACCTTAGCCAAAAATGTCATCT
GTGAAAAATCCTCTTGGATTTATGAAAAATCATGGTTGGTAGCAGAGTAAGCAATCTGAAAGAATAACAG
AATATAGTAGTCTTCCATTGGCTTGAGAATAGAGCCCCATATTTTGTACTCTGGAGATCTTTGACTTCAC
ATTTCTCTTTCCTGTAAGTACATAAGCAGATGGAAATCTTGGACAGCATGTTCTTGTTTTCTAGTCCATT
CCAGGAAAAGAAACTATATCAAATGTGAAAGTTTAATCACTTAATGTGTTTAATCAATTGAAACTCTATG
CAGACTCTTCTGTAATATTAGCTATAATCAAGTCTGTTAGCATTTTAGATAACTTCTCCAAAGACAGTCC
TCCTAGTTATTTGACTTCTTAGCTATATCTGTTGTTTCCAGAAAACTTGTAAATGTTAATCAGAACTACA
ATTGACTTACCTTCAGCCGACTTGCTTCTGGTTTAGAAAATGTATTTCTGAGATGCAGTGGTTTTTTAGC
AAACAATTTAGTGAATAAATTAAACAAATATTTAATGTGTGCCTACCATATGCTAGGTAATTGGCTAGGC
ATGGGAGGTATTAAGCCGTTTAAGACATGTTCCTTGTATATTGGAAGATAATACAAGCCGTTTAAGACAT
GTTCCTTGTATATTGGAAGATCCCAACATGGTTGGGAAAATGAAAACAAAAATAGTTATACTGTAATGTA
ATAAATGCTATAACAGAGGTCTGTATTGAGTATGAATTATATAGCATGACTAATTTACCCTATTAGATTA
TAAACTCTTAGAGGACAGGGTCTAGTATACCTTCATATTTCCTAAAGTGAGTTTGCACAATATGAGTGCT
TAGGAGGTATTTATGTAATATATGAATTAATGCAAAAATATCAGCAGAGAGAATATTCTTCCACTGTTGT
GTTCAATAGAATTAATGGTTTTGGGAGTTTCTACTAATTAGTCTTATTTCAATTTTTCTGTTACTTCTCC
AAACAATTTAATTAATACTTCTTGAACTGGTTCTCAGAATGTTGACATTGCCTGAGAAATGGAATTTGTC
TTTTGTTTTATCAGTCTTATGAAGGTATATCCTTAAACTCATTCATTGCAATTTGCTCTCTCAATCTTTA
GTAACAAATTTATCTCTTTTGCTGGATATAGAGTCTGATTTTTCTTGCACCTGATGAGGAATAGTAAGAT
AATTAAAGGAAAAGTACCAGTGATATTTTTAGCTAAGCAGTTTTAAATTGTTTTGTGATCATCCTACAAG
AAGGGATACCAACTATAAATAATAATATAGTGATTGTACCATTATAGAAAAGGCTAAGACGAAAAGCTCC
TTGTAAAATCTTTTTACTATATGTGCTGTGTTGACTTTATTTCTGGTTATAGGTAACAATTAACATGACT
TTTGACAAAAAGAGTACTGAATTTTCCTTGAGTACAATCAAATGAACTTTGCAAATTAATATAGTTTATT
TCTTCTGAGTGAATGCAATCTAGTCTCTAGTTCATTGTTATAAGCCATTTTCATGATGTTTTATTATGGC
TCCATTATACATATACATTATCATTTGCTGTGGAAGTAACTTGTACCAACTAAACTGCTTAGAAAGTGTT
ACTAGCTTACATGTCATAAAGTATATATATTTTTTCCTTTTAAATAGATTATTGAGGTTGGCCTTTGTGA

FIG. 7C (Cont.)

AGTTTTTGAATTGATCAAAGAGACACGATTTTCTCATCCATCCCTGTGTCTCAGGAGTCTCCAAGCCCTG
CTCAACGTGCTGCAGGGCCAGCAGCCAGAAGGCCTCCAGTCTGAGCCACCTGAGGTCCTAGGTAAGAGCC
AAGGCTCATTCAGTGAAGCATTTAAAAGTGAATATAATTAATAATAGAGTATTGTACACTTCAAAATTGT
TAAGAGAATATTTCTAAAGTTCTCACTACAGAAAATGTTAAGTACTTGAGGTGATAGATGTTAATTAGTC
CACATTTTATTCATGAATCATAACATCACTTTATACCCCATAAATTTATATAATTATAAATTGTCAATTT
GCAGTTTTTAAAAAGTGAAGAGCTTCTCTTATGAAGCACACACAATAGCCTGTAATGCAGTCTTTATTTA
ATTGTGGTACGGAAACAGCAGGGGTATAAGTTCTAGAGTATTTTTTTCTGTGTTCCACTGAAGTTATGGT
TTAAGAGTTGAAGTTCGTGCACACACATTTCTCAATTAGTATGATGAAGCGGGGGGCAAACAAAACATAA
ATCCCTGGAATCCAGAAATAATCCTCAAACCTTAAGGTCACTATTAACTGAAATCGTTCTTATTAAACTT
TTGGCCAAAATAGCTAACATTCACTTTCTCTAACTTGTTACTCTCAATAGTTTTAAAAAACAGGGGAAAA
GGAAATAAATGCCACAAAGCCAAAACAGTACAATTAGTTTCTAAATTGAGGGGACTTTTTTTTGTATTCA
TCATAAATAAAAATCTATTTGTGTTATGGATTAAACTTCTGACTTAGCAACTTTCATTAAGTAAATAAAG
TGTTCGCTTTTCTTAAAGTATGTTCCGATTCTTGCCTTTCATATCAGTGACCCAGACTCAACATGTAATC
CTTTAAATAAGATAGGAGCTTTTACTTAAAAGGTACTAAGGAATAGAAATATAGATGGAAGCATAATTTT
TAACTGGTTAATTGCTTTTTTTCTCCGATGCTAACTATGGGTCTTTAAACTATCTAAAGTTTTCTAGATC
CTTCTATTATTATAGGAAAATTCTCAGAAGTACTAGAGCTGTGGTTCTCATTATGTGGTTCTCAATTCTC
ATTAGCATGTATCAGAGTTATCGGGGACTTCCCTATGGTGTTTCTGATTCCATAGACTTGGGGTGGGGCC
CAAAAGTTTGTATTTGGAATTAGTTTCTTGGTGATACAGATGCTGGTTTGAGGAGTACACTGCTGGTTTA
GACTAAAACTTGGTCCTTTTTTTTCCGACTTGGCTATTTAGATTTTGTAGGACCCACCTGTGAGAACCAAA
CTGCATGAACCTAACTACATGTCAGATTTTTCTTTTTTTGGTCGCATGTGGGGACTCAGTTATTGTGTTTG
ACTTTTGTTTGTTTTAATGAGAGGGAGGATGCTGGTCATTGAATCAAGCTGAGGATTTTTTAAAACCACC
CCCCTCACATACACAGTTATTAAAAGCTATTACCAAATAGAAGCTGTCATGTTGGCAGGCAAGCACCGTG
TTGGTTATTGTTATGATAGCACCAGTGATCATATTAATATTGTGAAGTGCTGCTTGGCTTGACAGCATTT
TACTGAAGATTTGATTTATTTTATTTAACAATATTTTGCTCGGTTTTCTTGGATTTGGTTTGTTAGTTAG
CAAATAATTGGAATGTTGAAATACCCGCGAAGACTTGGATGTCGTATTTCCTACTTTGAACATGTTATTT
CTTTCCTCCTAAGTCTTCTACCATTCTCATGTCTCATGTCAGTTGTTATATACTTTCCTTTGTATCCATT
CTGTACATACTTTCTTTCCTTTATTCTTTTAAAACTAGAACTTGTTCTTAATACTGGCTTTGGCATATAA
TATGTGCTTTAGTCTTATCTTCCATCAAAACTTTCACATTATTGGCTGGGTGTGGTGGCTTATGCCTGTA
ATCCCAGCACTTTGGGAGGCTGAGGCAGGAGGATAGCTTAAGGCTGGGAGTTTGGGACCAGTCTGGGCAA
CTTAGACCCCTATCTCTCCAAAAAAAAAAAAAAAAAAAAAAACTGGGCATGGAAATGAGTGCTACTCAAG
AGGCTAAGGTGGGAGGACCGCTCGAGCCCAGGAGTCTGAGGCTACAGTCGGCTGTGATCATGCCACTGCG
CTGCACTCTAGCTGGGTGACAGAATGAGACCTCATCTCTACCAAAAAAAAAACCCCCAAAAAATCCCACA
AAACCCAAAAATATTTCACCTTATTAATCTGTTCATTTTTATTTTCTTGTTTAAAGTTTCAAATTCTGCT
GTACTGCCTTTCGTCTGTCTTCCATCCTTTCAGTGTTTACTGCTGATCTCGTCACTGCTTTGGCTTATTT

FIG. 7C (Cont.)

TTCTATGTAAGGGATTTATTATCACTTCATGTTTTCTATTTTGTTAAATTAGCTCAAAGATAAAAGCACT
GATTTGGTTCTTTTATACTAAATTTCTTTTGAAACTTGCCTCTCCTCCTTTTTTTAATCTAATATCACAA
TCTTATTGGTTATCCTTTTTTTCCCATTCGGTTGTTTTCGTGTTATTCATGAAAATATGTGTATATTTAT
ATAACTCTTACTGTGGAACATCTTGATGATTAGTATACACCAAGCTTCTTCTCTTTGCAAATAGATTTTG
ATTTTTAAATTATCTATTTAAAAATATATTTCCTTATATCCATATATTCTGTTCAATTAGATTATATTCT
CGAGTACTCACTGAAATGTAATAGCACCCCCTTTGTTATGTGCTAAGAATGTGCGATACTATTGCTGTTA
TTATGGAACTTAGCATCAGAGAGTTGGATATGTGTATAATTACAAATGTGGATAAATCGTATGGAGGAAA
GTAGAAGGAGTTCTGAGAGTCCTTTTTTGTTTTTTGAGACGGAGTCTCGCTCTGTTGCCCAGGCTGGAAT
GCAGTGGTGCGATCTTGGCTCACTGCAACTTCCACCTCCTGGGTTCAAGCTATTCTCCTGCCTCAGCTTC
CTGAGTAGCTTGGACTACAGGCGCGTTCCACAATGCCCGGCTAATTTTTGTATTTTTAGTAGAGACAGGG
TTTCACTATGTTGGCCAGGCTGGTCTCAAACTCCTGACCTCAGGTGATTTGCCCACCTCAGCCTCCCAAA
ATGCTAGGATTACAGGCATGAGCCACTGCGCCTGGCCAAGATTCCTTTTTTTAACTTAAAAATTTTTTATT
TATTTATCTTTAGGGACAGGATCTTACTATATTGCCCAGGGTAGCCTCAAACCCTGGACTCAAGTGATCC
TCCTGCCTCCACCTCCCAAGTAGCTGTGACTATAGGTACACACTGCTGCACCCAGCTCCTTCTGAGAGTC
TTTAACAGGCTCCCTGAAGATGTGACATATGAGATTTAGAGGGTGAATAGGAGGGAGTGAATTCGATTAT
AAGTGCTCTAGGCAGAAATAACAGCATTTAGTAAGGCTCTGAGACAGAAAGGAGAATGAATGAAAAGAAG
AGCAATATGGCTAGAATGTGGAGAGTGAAGGAAACAGTCTTGTGACAGGTGAGGAAGGAGGCAGGGACAT
GCAGAGCTTTACATGCCATGTTAAAGAATTTGATTAGTGGGCTAGGAGGAATGGAAAGTCATTCTCTATT
TCATTACATGAAGAATATTGTTTTTTAAATAGCCTTATTTTCTTAAATTATTTGTTTAAACTATTGACTA
TTTTCTTTCCCTGGATTCTTAACCTTTTTGAAAGGGTAGAGACATTCTTTGTCATGTTTGCCAATACCCT
AGTGTAGAATAGTTGCCAGTGTGTGAGAGTTCGGTATATATTTGCTGAATAATCAACAGATGTACTCACT
GAAGGATAATAATTGGAGGAAGGATGGGTAGATGGAAATATGGACAAACAGGGATAGATGAAAGGATGGA
GGGAAGGAAGGATAGCTGGAGGAAAAGGTAGAGGAAAGGATAAATGGAAAAAAATGGAAGTATAGGATGT
GTACAGACAAGTGAAGAGAGGAAGGGGGAAAGAAAAGAAGACAGAAGGGAGGAAGAAATTAACAAAGGAG
TGAAAGAATTTTAAGTAGACAATCAGATTTTTGGTTTGAAATTCTCCCTGGCTATTGGGGCAAAAGCGAA
TGGTAAGAGATAATTTCTTAACACTTTTTATCAAAGAGATGATGATAGCATGGATTGGAAAGATGATGAT
GAGATAGGGAAAAGTGGAGTTATCCATTAGGAAGTAAAATAAACAGGACTTAATTTGGGATTAGCTATGG
AAGATGAGGGATTGGTAGGGGCTGCCTGGGTTTCTGTAAGTTACCAGATAACCCACAGGTGGCATTTTAG
TTTTTAGAGAATTGCAGTACATTACTCCTCTTTCTCTTGTTCTCCTCCTTCTCTCCCTTCCCTTTCCCTC
TCTTCATGTTTCTCAGTTTTTCTTTTTCTAACTCTCTTTTTCCCTCTCCATCTGATTATTCACTCTATAA
GGATTTTCAAGTCTCCGTTCTATGGAAGAAATACCCAGATGTCTGTTGATTGAATCTTAGATGGAGGTGT
TCAGGGAATTTTGTGCAGAGACCTCTGCTGGTTGTAAAACATTTGTGTGTGTGTGTGTTTCATCTTCACC
ACTAAATGACTTTATGATTTAGGAAAAATCTTTTGATACCACATATCTCAATTTCATTATTAAAGGGGGA
GAATATCTGTCCTATTGACTTGGAGGTTTTTCTAGGGTATAAATGAATTACATCCTAAGTGTGAATTGCT

FIG. 7C (Cont.)

ATTATGTTAATGATATAGCCAATTTTATATTAAAGCACATTATTGCATATGTTTTATGTTTCTATTACTT
TGAAAATATATACATAATTTCCTGGACACTTAACATTTTAAGAAGCCTCCTAATCTAAAAGGTAAAATAA
GTATGACAAGTAGTCTATTACTTGATAGGATGAGTTTCTTGAATATGTGAATGCCTCTAGGCAAGCTTGT
TTTAAAAGACCTTAGATTGTCTTTTTTTACTAAGAAAAATAAGGAGTTGAACTGAATGTTCTTTAAGACC
CTTGTTACATAAATATTTTAACTTTTGGGGAAGAGAGTAACTAGAAAGAAACTAAAGCAAAGTAATTGTT
CTAGATTCCTTAAATTTCGTTTATAATGAGACAAAGTAAAAATAAATAAATATACGCATATAATGTTCCG
TATGTTGGATGAATATAATTGAATTCTATTTTATCCACAGAGTCTCTCTTCCAGCTTCTTTTGGAAATCA
CCGTTCGAAGTACTGGGATGAATGACAGCACAGGACAGTCCTTAACAGCACTTTCCTGTGCTTGCCTCTT
TAGTCTGGTGGCTTCTTGGGGAGAAACAGGAAGGACACTTCAGGCCATCTCTGCTATCCTCACCAACAAT
GGAAGCCATGCTTGCCAAACTATTCAGGTATTTCATATTTATATCTGCTTAGAAGTTTATAAGATGACAA
GTTACAGTTTCGTCTCAATTTCTGTCAATAGGAATTCTGCTTTTTCTCACTCATTACAGTAGCTTAATCT
GTCCAAGATTGATACATAAATAATCTACAGTATTTCAATTAAGTGATATGTATGTTTAACTCTGAAGCTT
TAAATATAATAAAATGAATTTTGGCCAGACCTCTTAAATCTTTAAGCTGGTCTTTGCCTTAACACCATAG
CCTTCTCTTTCCTTGCTGTTTTCTTGCTGTCTGCGTTCTCCCTTCTTCCCATCTTTCCCTGAGTTTTTTA
GTATGGAATTCATTCATGGTTTTAAATATCTTTTCTCTATTGAAAGAAAAAGATATGGTATCAATCTGAT
ATATTTTTGATTGGTTGATTATGATTTTTTTATGAATTGATTCGTTTCTGAGTTACTTCAGCTGTGTATA
AAACATTTTAGGCTTTTAATATTCAGTTGTGGAACAAACAAGCTCATCACCATTTTAGTGGTGGGAAAAA
TAATCCTTATAGGCAAACTTGACTTAATTATTTGGGAAGGCTCTGGAAATTGAGAAAGAAGTTATGATCT
TAAGACCTGACTGTCTACTCTTCTCTGGCCCCTTGGGCAACCCTAGGGCAGGTGGAAGGGATGCCTCAAT
CCTGTTATTAGCAGACCAAAGATAGCAAAAGGAGTATATTGGTCATTTTCTGTCTTATTCAGTGATTTTG
AACTCTCCTGGTCAAACAAGACCCATTCCCTTACTCAAGATTTCTGCTCTTTTCTTCCTTTCTGCCTTGC
TTGGAATCCTTTTGTCCCTTTTTATGGTCCTTAATTATTTTGAAGTTGCTCTAATACAGTGGTTTTCAAG
CTGTGTTCTGTAGACATGCTTTCAGGGTTTGGCAAATGTTTAATTTAAATATATGTTTAAAATATGCAAA
TATTTTAAAAATTGTAATAAAGTAACACAAACATTCAGATACCATATACCAGATTTTAATAGGATAGTGA
CCACCAACATATGAGCTTATGAATTTTGATATGATTTGCTTTTATATAGAGACTTAGGAATGCCATTAGA
GCTCATAGCAGGAGTATAAGAACTACGTTCATGGAAAGCCTCCCAGAGGATATGAGGTGAGATCTAAACT
AATGAGTTGAAATCAGCCAGGAGAAATTTTTGGTGTTGGTGGTGTAGAGAGAGAATGTTCTAGGTATCCA
CATGCTAAGGCATGGAGGTGAGAGTAAGAGTGAAATATTTGAAAGCTGAAAGAAGTTTAGTATAGCTATA
GCATAGAGAGCTGTCAAATAGCGTAGCCACAGCATACAGAGCTGGCAAATAACAGAGACAGGACTCGAGG
GCTTATCTGTCTCCAATATTTATGCTCAATCACTAGACAACACAAAACTACTTGATCCTCTGAATCAATA
GCTGCAGTTCTCTACAGACCTGCCACATCACCACATCCCCAACTCTAGCCTAAACTCCATATTAAAGCCC
ATTACCTTAACATGGCTTGCAGTGCTCTTCATGATTTGGCCTTTTATCTACCAACTTCATTTCCCAAAAC
TCTCCTGGCCTGACTGTTGGTAGAGGGAGAAAAGCTTTCCCTGAGAATGTGTGCATTAAGTCCGTTTTCA
CGCTGCTGATAGAGATGTACCCGAGACTGGGCAATTTACAAAAGAAAGAGGTTTAATGGATTTATAGTTC

FIG. 7C (Cont.)

CACATGGCTGGAGAAACCTCACAATCATGGTGGAAGGCAAGGAGGAGCAAGTCATGTCTTACGTGGATGG
CAGCAGGCAAAGAGAGCTTGTTCAGGGAAATTCCTCTTTATAAAACCATCAGATCTCGTGAGGCTTATTC
GCTATCATGAGAACAGCACAGGAAAGACTTGCCCCCATGATCCAGTTACCTCCCACTGGGTCCCTTCCAC
AACACGTGGGAATTCAAGATGAGATTTGAGTGGGAACACAACCAAACCATATGAGTATGTGTAACTCTTC
ACATCTCAGATTTGTTTTGGCACCCAAATGCATACTACTTGTCCATTTCATAAAGCTTAACAGAGAGTTT
AAAGCAGGGTAGACATGGTAGTACTGCAAGATGCTGTATTGAAAGACACTGAAATCCTTTCTGGAGGGTT
GAACTCTTGACTTCAAAGGCTTTCTGCAAATAAAACACTATTTATTGCATTTGAGCTCAGAAACAAATTA
ATAAAAAAAGCACATGGAAAAAGGCACCATTATTGAGAATTAGCAGAAACAAATATGGTAGAATCAATCC
TGCCAAGTCCTTAGATATTGAAATTATTTGATATAGAATGTGTATGTGTATGAATATATAAAGTATGGTT
AAAGTAATAAAAGAAAATATCAAAAGTATGATTAAGTAGTGAGAATATAAAAAGTAGTCAGACATTAGGA
AAAAAAACAAATCGAACTCCTAGAAATGAAAAACCAAATAATTACAATTAGAAACTTAAAATGGGTTAAC
TATTGTATAATATGGTTGAAGATGGAAATGGTGAACTGAAAGATAAAGAGGAAGAAATTATCTAGAATGC
AACAGAGAGACAAGGAGAGAAATATGGAAGATAAAATAAGAAACATGGATCGAGAATGACAAAATCTAAT
GTAATACAATCTGAGTTCCACAAGGCAATAATAGATTTGTGGAGATAGAGTACTTGAAATAATGGCTAAG
ATTTTACAGAATTGGTGAATGACATGGAATCCCAAGAGTAAGGAAGTCTACCTTGCTTGAGATTTGCTTC
TTATAGATGAACTTTTAGTTGGTACTTTTTGCTGGCATGCGAAATATCATTCTGAACAATTTATTGTCTT
ATGAATGATGATGTATTACCAAAGTATCTTTGTTCTGTGTTTGTAACATTTAAAAATGTTTTTTCATTAT
TTTTCTTCTCTTTTGATTAGGTGCCAACAATTCTAAATTCGCTACAGAGAAGTGTACAAGCAGTTTTGGT
GGGAAAAATTCAAATTCAGGACTGGTTTAGTAATGGCATTAAGAAAGCAGCTTTAATGCACAAGTGGCCA
TTAAAAGAAATATCTGTTGATGAAGATGACCAATGTCTACTTCAGAATGATGGATTTTTTCTTTATCTAT
TATGCAAGGATGGATTATATAAAATAGGCTCTGGATACAGTGGAACAGTTAGGGTAATGTGATTCCTTAC
AGTTCCTTAATTATACAGAGTTATAACCATAATGAATTGTGTTCTGTGTGTTTCTAGTTTCATTTCTAGA
ATATGATCTAATTTTAGTGTAATAATATTTATTTGAAAACCATAATTGAAATACATGCATTAAATGTCAT
TCACCCATTTGTATTTATTTTTCATTGATTATTAATTATGAAACCACTGATATACTAACTTTTGTTTTTTT
TGCAGGGCCATATATACAATTCTACATCCCGTATTAGAAACAGAAAAGAAAAAAAGTCTTGGTTAGGGTA
TGCTCAGGTAAGAAACTATCCACAATAAACCAAAATTTTCTTATCTTTTACAACATGTGATTTGTCCTTG
TTTAATCAGTAATATCACTTCTATTTAAACAGAAATGATAATATATTTTTACTAATATGGCCATAATAAC
TGAATAGTGTAGCGTAAAGAACACTGTCTCAGAACTCATAAGAGGTTCAATTTTAGTTCTGGCCCTGCTT
CCTACTAGCTGTATGACTGGACAACTCAGTTAACTTATTGGGTCCTCTGTTATTTAGCTTTAATATGGGA
TTAAACATACCTTCTTTAGAGTTCTTGTGTAAGTGAGCCTCTAGATAAGAATTGAAGACCACCTTTATCA
TTAGCACATTTTTTTTTTTAATTGAGACAGAATCTCGCTGTGTCACCCAGGTTAGAGTGGAGTGGCACAG
TCTCGGCTCACTGCAACCTCTGCCTCCTGAGTTCAAGTGATTCTTGTGCCTCAGCTTCCTGAGAAGGCCC
ATGCCACCATGCCTAGCTAATTTTTTTGTATTTTTAGTAGAGACAGGGTTTTGTCATTTTGGCCAGGTTG
GTCTCAAACCCCTGACCTGAAGTGAGCCACCCGCCTGGGCCTCCCAGAGTGCTGGGATTACAGGCCTGAG

FIG. 7C (Cont.)

CCACCCCACCCAGCCTCATTAGCACATTTAAATTGGAAATGTATACATGTCCTGAGGCCAAATTAGGGTT
TCTTACCACAGACTCTTTCATTTTAGTCTAGATTCAGTACTTTCTAGGAAACAGTGTTTGGCCTACTCAG
TAGACAGCTACCTGCATGAAGAATATGCAAAGAATCACAAGAGAGAAAGAAAAGCCCTGGGTTTTTGTGT
CTTAATGCTGTGATCTTATCTCCTGACCAACATAGTCAGATAGGTGTTAGCCTTTTACAAGGTCAGCAGC
CAGATGGATACATTACTCCTCTTATGGAGAAAAGCAAATGAAGGATGGACAAGAGGGACTAGAAATATTT
TTTTCCATACAGTACCTACCTGAACAGTGAAGCCCAAGTTCCTTTGTATAAGGATAAAGAATAAAGATTT
CCCTGCATGCCTGCCTTGCTGAGCTTGTGAGATTTGTTGTCAGGATCAAATGATAAAAGATATTTGAAAG
TCTTTTGAAAACTATGGAAATTACTATTGTTACATGAAGAATAATTCTACTGTATCACCTATTGGGGAGA
ATTTGAAATTAAATTTTTTTTTTTTTTTGGAGTTGTAGTTTTGCTCTTGTCGCTGAGGCTGGAATGCAGT
GGCGTGATCTCAGCTCACTGCAACCTCCGCCTCCCAGGTTCAGGCGATTCTCTTGCCTCAGCCTCCCGAG
TAGCTGGGATTACAGGTGCCCACCACCACGTCCAGCTAATTTTTGTATTTTTAGTAGAGACGGGTTTAAC
CATGCCGGCCAGGCTTGTCTCGAACTCTTAATCCCAGGTGATCCACCTGCCTCAGCCTCCCAAAGTGCTG
GGATTACAGGCGTGAGCCACCGCCCCCAGCCTGAAATTAAATTTTAGATAACAAATTAGTTTCTCAGTAA
TTGTCTCTTAAAAATTGAACTTAGTTTAAAATATCTCATCAGATTTTTATTTGCCACTCTATTGTGTTTT
ATCTAAGAAATAATGCCGTGGAAAGTATATTATTATAGCAGTGTGTTCAATGGCATACCACACCTTCTGA
AACCACTATGCTATTCATTTTCAAATAGCAAACTCAATACTTGTTATTTTTCTTAAAGTACTTGTTAAAG
TAACAGTGATCATTCATATTATTTACTTGGCAAGTGGTATGGTCATTTTGAACAAAATGTTTGTAACTGT
ACTGTCCTGTTTAGTATACCTAATTATGTTTCTGGGAATATGTTACATCAATTTTCAATAATGTATGACT
TTTCCTCTAATTGAGAGGAATGTTCTTATATTTTTAATCATTAATATCTTTTAGACATCAATATTGATGT
ATTATTGTACCTCAAAAACCTGTAATATGGAGCTGTATGGCTGCTGTTTCTGCTGAATTAGTAATAAATA
TTTTAACAGGAAAATTTTTTGCTGTTATCAGGGTTATTTATTATATAGAGATGTGAATAACCACAGCATG
ACAGCCATAAGGATAAGCCCTGAAACACTGGAGCAAGATGGTACTGTGATGTTACCAGGTATGTTTCAAG
TAGTCATTTTTTCTCCACAAGCAATTTTAAGAAATGTGCATGTTAAGCTATTTAGACACATAAAGAATGA
TTAGCAAGGGATAGTGCTTGCTTATAAAAGGGTTTTAAAAATCTTGACATACAAAGCATTTTATAGTCTA
CGTGAAGTTAATACATATCAAGAGAATAGACATAGAAATATAACAAGTTTTAATATTTGTTTTCAAACTT
GGCCGTCTATGGCCTAATCTCTGACCTCACCCCACCACTGCTGAATTAGTGGGGTGATGTAACTGTGTTG
CTCTTAATAAAAATCAGAACTCTGGCTCTCATGTGACTCAGTATAAAGAACCTTCTGTTTATTTTTACTT
TAACAACAGTGCAGTTGGGTTTTCCTCCTTATTTAATTTAATTTAATTTTATTTAATTTAATTTAATTTT
ATTTTATTTTATTTTATGTTAAAGGGGTTTCAGAGACAGAGAGTTTAGGGTAGGTCAGGAATTTTTTTTT
TTAATTTCATCATTTATGCTTCTTATGCTTCTTAATACTTTGATAAAGGTCTTTGGACACAGTTTATTTT
GCTTTAATTTTGAGGCTTTTATATATTCACTTAAATCACTGCTAAATTATCAGGCAGTAGGTCTCCAATT
TTGATGAATGCTGGAAAAATGCATATTCTTTATTGTAAGATCTTTGAATTTGTTTATAATGTTGATACTT
TCTGAGGCTGTTTATATTAAAATCTTGAGTGTCTAATGTGTCTGTCAATAATTTCATAGTAGCAATATTA
CTTGTAAGCGTTTGACCATCTGAAAGTGAGAGCTACTTCTGAAGAGTGCATTGAGAAGAATAATTGCTCC

FIG. 7C (Cont.)

TGGGCTGCATGTTTATTTTTAAATATAATCTTAATAATTTCATCAAACATTTATTTGAACCTTACTACAT
ATACATAGATACATATTAGTGTACATGACACTATGTTAAAGTAAATATGACATTTCATGTCCATTTCAGA
AATAGAGGAGCTTTGGAAAGCGGATGACTTAATAAAATCATTTTGAAAATAACCATCTATTTTCAGATAT
GTCTACAGGGTTTTTTTTTTTTTTTTTTTTTTCATTACAAGTCCTGGACCATGTCTTTGGTCATAATAAT
AATAATAATAATGACAATAATATTAAAAAATACTTTTAATAACATGCACACTCCCCCCACATATTTATAC
ATATATTGAAAGTAATCATGTTTGTTGTATAAAAATCATATGAACAAAAAAGAATGAATTGAAATAATTA
TAATCCCACTTCCCATATATAAACACTATGAACATATTGGTAAATATCCTTCTCGTATTTTTCCTTTGTG
TATATGTCCATACTTGTAAAAAAGTGTGATCATATGCTACATATTGCTTTTTTAATCTATCTCTTTCACT
TAATATTCTGAAAATATTTCTAGGTCATTAAATAGTCTTCTACAATGTCACTTAAATGTTACAAAATATA
TTCCATTGATTAATGTTTGAGAATGAAAGCCTTCCAGGGTTTTGCTATATAAATTACACTGTAATGAGCG
TTCCTATCGTGCTGTCTTTGTGCCAGTCATTTTAGGATAATGACATAGAAGAAAAATTCTAAATTGACAC
ATCCCATCCGCTATAACACATGGGTACTAATATCAAGGATTTACTTCTGAGAAACCCTGCACATTTAATA
GAGACTGTGACTTATTGATAAGACAATTTGAAAATATGTGCCTACAGCTGTTTTATTTATTCTGCCTTGA
TAAAAAAATTACTCGTTAATGTCTTTATTCAGTTTAAATCTCGTTGCTTTGTTTAACTTGTGAAATGCAA
CTTTGAACAATACAAGTGTGGCTTTCTGTGTTTCATAAGTGTGTGCTGTATTAGTGGTGAAGAATGAACC
AAACTTCAGGAAGATAGTCCCATATTTGTCTTCAGAACTGGCAGATGTTGCTTGATATATTCCTGAAGAT
ACAAGCTTAAAATATTACATGATGGATAAAGAAAGGATAAAGAGAAAATCTTGAAATCACGTGGCAGAAG
ACTCCTCCCTCAAGCCTGAAGAAGCCTTTTGTAATTTTCTTGTTTCTTTGACCTGGACTGAATTTTCATC
CAATAGCACTTTTTGTTTTTCGTGGGTAGGAATAGCTCTGCTCTGTAGCCTTCCAATCAAGGAGCAGAAG
TAAATTGTCAGGTTTATAGATGGTAATGAATACCATGTTTCAAGTTGACATAAATCAGGTAATTCCTTGA
GCTTCATGTTCCAGCTTGTCTTACAGTATAGTTTATTTAAAAAGTATTTCAACCTTGTTTTGATGAACTT
AAAACATACTTTTTTTATCTGATAATTGTCATTTTATTCTTTAAACCTCGGCTTATCTTACAGATTGTAT
CTTTATGTCATTTTCTCTCCATGTCTGGTGACAGGTTGCCTCAGTTCATGAGGCTTTTTGCTACTCTTCT
TGCGCCGCTTCACTCCTCACCCCTGCGTTTATCTGAAATTATAATGAGTTTTTCTTCTTTGCTTTTTAGT
TTAAAATCTTACTGCTTAGAGCTTGAGAAGCATCTTTCTTGCGCCTCTTTGTGTTCTGTACAGTGGACTA
GGAACTCTTTCTTTTGATTTCTCCTCTCTTTGATTACCAAGTCTCTTGGGCTACCAGTGGGCCTTGTCTC
CCAGTTTCTATTTCCAGTTTGTGATCCCTGAATTCTCTATTTGGTAAGGGTCTGCCTGTGTTTTGCATAT
TTATGATAAGGAAGTATGCTAGTATGAAGCTCCTGGGCAAAGATAAAGAATAATCCAGCTTATTCGGGTG
GGCTCCATTACTGCATTTCAAAATCAGAATTTTATGTTTTGTTGATTCAGGTGCAACTAGAAATGAAATG
TTATTTTTTGTTTTGGTATTGTGATTAATGGAGAGATTCATCCTAGTTTTCTGCAGTTATTTTGGGAAGT
ATGTGTGTGTGTGTGTGTGTGCTTTTAACTTGCTTGCTGAAAATTTGTTTTTCCAAAAGGACAGAATTTA
TCCTTGATGTTGATTTTGCTTGTAGTTTTGTGTTATTTAGTAGCAATCACTAACACGTGTTCCTGTGGTC
CTTCTGTAATACTGGTATCCCTTGTTACAATTGAGCTTGTGCATTATTTTGATCAAAGTATATGGTGTAC
TATTCTATGGAGATACATGCAGTATTGATGAAATATGGTATTCTAGCCAAGATACATGACTGCTTTGAGA

FIG. 7C (Cont.)

TAAAAATAAAAGCATAAGCATATATTTGTCTGCTCTTGTTGGACAAACATTTAAAAGTTTAGAGCACAC
TAAATGCTAAAAATGCTGTGAATAAACATTGAATTTTTAAGTGGGAAATGTACAACTGGTTTTGAATATC
CATTTTACAAAGCAAGGGATATCTGTAGTTGGACACAATAGATGTCAAATACAGAAGCTTTAGGTCGTAT
TTTTCTGTGACACTAATGACTGTGATGTATGTCTGAGAGTAGAGTGTTGCCTCCATTGCATGTGATTGTA
TTGAAATGATTGTAACCAACATTATAGTTTGTTCATCGTGGTGCATGTTTACTGTCAGACTATATCTAAT
ACTAATTCATTTTGAAATTAGGTGGGATCTCAGGTCCTTGGTTATGGAAGATTTATAAATATAAGCAAAA
ATGTAATAAGTATGATTAGTTGAATTAGTTTCTGCTAATTTATAATTCTTTATTAAAAGCACAGTCTCC
TTTTGAGTTTATCCTTATTGCGTGGAGAACTCTCATTTTGACTTCAACAGAGGAGTAAATTCATTTTGCA
AGGTGTTTGCTTGTATTGTAATATAAATACTTTTTCTTTTGCACAGATTGCCACACTGAAGGTCAAAATA
TTTTATTCACTGATGGAGAATATATTAATCAGATAGCTGCTTCAAGAGATGTAAGTATCCTGAATCTTAA
GTAGCTAGTGTAAATGGAATTCCTTTTCCTTAAATTATTTAGCTTTTATTAGATAGACTGTAGAGCCTTG
AACGACCTCTTTATGTAATGTAATGCTGTGGATGTTTTATTTTTCTTAGGATGGCTTTGTTGTCAGAATA
TTTGCCACAAGCACTGAACCTGTTCTACAGCAAGAATTGCAACTTAAACTGGCTAGAAAATGCTTACATG
CCTGTGGTATCTCACTATTCGATCTGGAAAAGGACTTGCATATTATAAGTAAGATAGCAAATTAAGTGTT
TTCCCTATATTTTAATTTTCAATTTTTCATACTCTTAAAAATGAACATTGTGTTTTCACCAGTTCAGCTT
ATGTTGTAGCAGCTATTTTGTGTCTGTTACTATTAATATAAAGGATAATTTTGAATTAATATGAATAAAT
AACTGGGAAACACAGTCTTTAAACAAAGTATGATATTTGAAGACCATTCTAAGGAATTGACTAATAATTT
CTCTTTTTTGCTTTGAATAGAGCAAAAGAAAATAAAATTTAATGAGAATTATGGATGGATATTGGTGAAT
GTCATTAGTTTATATGCTGCATCATTTTTCAACTATTTAAAAATTTGAAAACTTACGTTGTAAATGTTAT
TACAACAATATACATAGTTCTCTCGTTGAAATTTTTAAAGTTTTTACTTGAATAGATTTTCAAGGTAACT
ATAGAATGATCTCATAGATTGTCAAAATGGTAATTGGCCTTACACACGGATCAGTAATCTTTCACTTGGA
TAGAGAAATACAGATAACCACAGAGTATTTCTTGGGCTTAGATTATTTACTTTTGTAATGTTGTAAAAGT
AATTAGGATCATGAGTTCTCCTGAGAGTTTTAGTTTTGGCTTGCCATGCCACTCCAGGTTTAATAGTGAC
CTTCCGTAACTTGTAGGGTTCTTTGCAAGATCCATCTTTTTTGACTGTTATCTCATTACATTTCATAAAC
TTGGCATTAGTGCTTTACTTTCTATATTCTAATTATGTAGTATTTTTATAATTCTTCCCTAGAAAAATCT
TGAATTGAAATTACAGATTTAAAATTTTTAAAGCCCATAAACTAGTTAGTAGTTTGTATAGCTGGACAAA
GTCATAAAATGTACCATATGTAAAGCTACAATTACTCATAGTTTTACAATTTGAAAATATGCATAAGGAT
CTGTGTGTGTATATGCATATTTACATATATATATATTTGAATTGATGGAGTAGCTATATAAGATGTCTTT
CTGTAGAAAAAGACATAGGCAGAGAATCTGAAATACTTTAATTCAAATATCTGCATGGCATTGTTCCAAG
CTTGAATGACTCTGTGTCTGGACTAACCTCTCCAACCTTTATATATGCTTATTTGTAAACCAAGTGGTAT
AGTTGTGAGAATCAAATGAGATAAATTTTGTGAATTGTATAATGCCTGGTACCTAATAAACGCTCAATAA
AACTTTGAGCATTTATACATTAATTCAAGGAATATTGCTGACATTGAATTTTTAAATTTTTTTGTCGTAT
ATTTAAAAAATTAATTTGGTACTGGTTTGGAACAAGAGAAACAGATTATGATAACTTTATCTTTCCTTGG
AGTACTATACCTATGGTTAATATTTTTAAAAATTTGAGCACATGACATTTTGTCATCCTTGTTTTTTAGT

FIG. 7C (Cont.)

GATTTTGAATTGACATTGCAATCACTTAAAATAGTGCATGTTGTATTTAGAATTCTTCATATTAGAAATG
CAATAGTATTTATTAGTCTCGTATTTCAGGTACAGGATTTGATGAGGAGTCAGCAATTCTTGGTGCAGGA
CGAGAGTTTGCGCTAATGAAAACAGCAAATGGAAAGGTAAATTATTCTCTTTGGATTAAAAATGAGCATT
CTCTGATTTAAGAGATTAAAATACAATCTGTTGATTAGTTTATATAGTTTGCATGTTTAAGAAGAATCAT
CTTTTAAATTTTGATTTAAAATTATTTTTTATAAGATAAAATTTTATTCATGTAGGGAACAGTACAGGCA
TGCCTCATTTTATTGTGCTTAGTTTTGTTACACTTCACAAATAATTGCTCTTTTTACAAATTGAAGGTTT
GTGACAACCCTGAGTTGAGCAAGTCTGTTGGCATCATTTTTCTAACCGCCTGTGCTCACTTTGTGTCTCT
GTGTCACACTTTGGTAATTCTCGAAATATTTCAGACTTCTTTATTATTATTATATCTGTTATGGTGATCT
GTTATCTTTGATGTTACTATTGTAATTATTTTAGGGTGCTGTGAATTGTGCCTATAGAAGACAGGAAACT
TAATGGATAAAAGATATGAAAAAGCTATTATGAACTGTGTCTTCTTGGCAAAATATGTGTATTTCTTGCT
CAACTCCCAGAAGCTGAATAGTGTAAAAAAGAGTTTGTTTTTATGTGAATTTTATTTTTCAATAAAATAT
TGATGTCCTTTTTTTTCCTCATGTGAAACCTGATGCACTATTCCAAAAAGTACCATAATTCCTTTTTTTT
TTTAATACATAAGATATATTACACTGGCAAATACCAGAGTCTTGGAATCAAACAAGGTGGTCCTTCAGCA
GGAAAATGGGTTGAGCTACCAATTACAAAATCTCCAAAGATAGTACACTTCTCAGTTGGACACGATGGCT
CTCACGCCCTTTTAGTTGCAGAAGATGGGAGCATATTCTTTACAGGATCTGCTAGTAAAGGAGAAGATGG
AGAATCAAGTAAGTTGAGTGATCAACTATGCATTTAATAAAAATAAATGCTTTATTTTAGTAAAAATAAA
ACTTTATTAAGATAAAGTTTATGAATTTCAATAACACCACACCAACTTTATATATATATCATTGACTTGA
TGTAACTGCTTAATAAATACATATTGAATGAATGAGGAACTTATTTTACTTTCCAGGATCTAACAAGAAT
ACATGTGAATTACAACTTGGGAAAAAAAGGAGATTTTAGATATGTGTTAGTAGAATGGTATTAATAATGC
AATAGCTAATTTAGAGATTGGGCCCTCCAGGAGTTTGGTAGAAAACTAATATTACTCACTGAGAATTTGA
ATGTACTTCAGGGAATGAGGATCTAGCAATGATAGCGTAAATATTAATTGACCAGATGAGGCTAGCAGGT
TCACTGATTTTAAATGACATGTTGGGAAGCCCAGGCCTTTGTGAAAATAAACAAATAGTGTCATAAATGC
AAATAATATGGGTTTTTTTTTTAGCTTTATATACAAACCATTATTATTATTATTTGTACATAGAGGTCTT
GATTTAATCTAATTTCTTTTTTAAAGCTAAGAGCAGACGGCAATCCAAACCTTATAAACCTAAAAAGATA
ATTAAGATGGAAGGAAAGATTGTGGTATATACAGCCTGCAATAATGGAAGTAGTTCTGTTATTTCTAAAG
ATGGAGAACTCTACATGTTTGGAAAAGATGCCATTTACTCTGATAGTTCAAGTAAGTTAATAAAAAGTTT
TACTTTTATGCAAAGAAGTTTCAATACTAGTTATGTATGACAAAGACATATCTAGAAAATTTATGTTGGT
GGCATGCTTTCTCTACATTTTTTACATTTCCTTCCAAATGTGAAATATTTCGAAAGAGAAATTTTCTGTC
ATATCTTGTCACTAGGAGCACTGTCCCTAGTTTCATGCAAAGCTAATCATAGAGCTTGGCAAGGGAAGCT
TCGCTGTAGCTGTGACTTCTGTGGATGTTTTCCCTAGACTCAGGTGCTTATGGGACATGTCCCTGGGACA
GTGGTAGTATCCTGAAGAAGTGATTTTCATGACATAGCTAGTTTATAATTGTTGAAGTATTTTATCTCCC
CCATTAGGGTGTTTGGCTGGGATGATCTGTCTTATTTACTATTCTATCCCCAGTGCCCAGCACAGTGTCT
GGCACATTGTAGGGTCTCAAGAATTATTTTCTAGTGCCTGGGTGACTGATAAACCAAAAGTTTGAGAAGT
GGATATGAGGGGTAGAACTAGCTAAATGGTTTTATATTTATAAATGCTAATCTCAAAAACTTGTCATATT

FIG. 7C (Cont.)

TGGTTACTAGATTTTCTTTCTAGCAGCTAGAAATGAATATAATGAGTGAAGCATCCCACTTGGAAGGATT
TTATGTGTCATAAATATGTAAAGCCTTTGAGTTTCTTTGTAAAAAAGGAAACTAGAATTAATGAAGTTTA
TGATTAGAAATATATGTAATTGTCCCATGCTGGGGAAATTACACCTGTAGAACATTTATAGCAATTAATT
ATTAAGTGGAGGTGTACCCAGATGATAAGTGAACTGGCTTAATGTTGTAATATTTAGATTCTCAATTGGC
TGCAGCTATCAGAGTAAATCAAAATTTGGGAGTGGGTTCTTGTACAGTTTAAAAAATAATATTCAATATAA
TTGTTGCTTGCTAACATCCACTGGGTAGAGCTGATGGAAACTTGTATATTTCTTCAACATATATTTATTG
AGCATGGGTGATACATTAGTGATTGATGGACCTGACAGACCTGGATACTGCCTTTTTGAGGATCCGAGAG
ACAGTTGGGTATTACAGAACTTAAATATTGGGGAAGTGGTATTGAATGGTTATGGACATAGACTGAGATC
CTAGCACCAACACTTTTTTTTTTTGAGAGGGAGTCTCACTCTGTCTCCCAGGCTGGAGTGCAGTGGCACA
ATCTCAGCTTACTGCAACCTCTGCCTCCTAGGTTCCAGCGATTGTCCCACCTCAGCCTCCCAAGTAGCTG
AGATTATAGGCACGTGCCACAACACCCAGCTAATTTTTTGTATTTTTTGTATTTTTAGTAGAGACGAGGT
TTCACTGTGTTGGCCAGGCTGGTCTCGAACTCCTGACCTCAAGTGATACACTCGCCTCAGCCTCCTCAAG
TGCTGGGAATACAGGCGTGAGCCACCGCGCATGGCCCTTGGCACCAACGCTTTTAATTGGGTAACAGTTT
ACTTAATCTTTAACTGGGTAACAGTTTACTAAACATTTAAGAGTTTTCTTTTTGTTTTTTTCTACCTGCA
AAAAATAGATAATGATAGCACCTGCTTCATATAGTTGTTATGAAGATTATAGGAGGTAGAACTTAAGAAA
TGCTTAGCACATCATGTAAGGTCTCAAAGCATGTCAGCTAGTACTGTTAATAATAATAATAAATAACTAC
TGTTTTATATATATACACACACCCTTACCTTTTTCAAATGTGCTAAATATTAAAAGTGGAAATTTTTGAG
GTATAATTAACAAAAAGACCTAAACTAGTGAAAGGTGAAAGTGAAGGCCACCTTAAGGTAGTGATATCTG
AGCTAATAATGTAGAACAGTTTTCCCAAAGCATAATATGAGATTGATACTATTTGTAATTTAAATAAAAC
AAATACTTGATAACATGTTTTTATTTTAATGTATATTGGAAAAATAATAATCTTTGATTGTTAATGTTAA
AGATGCTTCAATCAATTTAGAGTTGATACAAAACATATTAAATAGATAATATGAGTGGCACTTGGATATG
ACAAATATAATGAAAGTAATACATGAATAAGTGAAGTTTAGAAAATAACTGTGTATTGGATTGTGGAAGA
AAGCATTGTAGGTTGAAAAGGATTAAAAAATACTGTTTTGAAAAGTCTCACTGGTTTCTACATAAACAAT
TTCATGTCAATATACTATGGCAAGTATTTTACTTTGTTTTGCTGAGGCAGGTCAAAGCAGGTAAAATAAA
TTATTTATGGACTCCTTTGTGCTTAGACCAGAAAAGTTTGAAAGTACTGTGGAGAGGTATTACCATTTGG
AGGAAGCATTCAGGAGAAGTAAGCTTGAGAGAAAGCTACAGTAAAGATATGTCCCAAGTCTGGATGATAA
TGTTTTAGGATTCACTGAAGCTACGTTACAAAGTTACAAAGTTAATTCAGTGATACTCTGCCAGTCTTTT
GGCTACTTATTTCTCATTTTGTTGAGTTATTTTGCCCCAGAAATAAACGGTTCTGCATTGAGGTAGTTCT
TTTACTAGGCTCAGAAGGGCCTTTTTGTTGTTTTTACTAAATTTGTTTCTTTCCTATAGGTTTGGTAACT
GATTTGAAGGGCCATTTTGTAACTCAGGTAGCTATGGGCAAAGCTCACACTTGTGTTTTAATGAAGAATG
GAGAGGTGTGGACATTTGGTGTAAATAATAAAGGACAGTGTGGACGAGATACTGGTGCCATGAACCAAGG
TGGGAAAGGTAGGTCTTTAATTCTTAGATATTAAAATTTGTGTTGTCTTTTCATTAGTTTTTCAGAACAA
CATAGTGAAAAGTCTTGTTCTTTTCAAAATGAGTGGCTCTTCTTTTTCTTTTTGTTCCTATTTAAATTTT
TTTTAAAAATTTTATGGGTAGATAGTAGGTATATGTATGGGGTACATGAGTTGTTTTGATACAGGCCTAC

FIG. 7C (Cont.)

AATGTGTAATAATAATCACAGGGTAAATGGGGTCTCCATCATCTCAAGCATGTATCCTTTCTTTGTGTTA
TGAGCACTCCAGTTATACTCCCTCAGTTGTTAAAGTATACAAAAAATTATCGCCAACTGTAGCCACCCTG
TTGTGCTATCAAATAGTAGATCTCTTGTATCTAATTATATTTTTGTGCCAACTAACCATCCCATTTCCCA
CCCACTCTCCCTGACTACCCTTCCCAGTCTCTAGTAACCAGCATTGTACTCTCTATCTTCATGAGTTCAA
TTGTTTTAATTTTTTAGCTCCCACAAATGAGTGACAACATGTGAAGTTGGTCTTTCGGTGCCTGGCTTCTT
TCACTTAACATAATATCCTCCAGTTACATCCTTGTTGTTGCAAATGATAGGATCTCAGTGTTTTTTATGG
TTAAATAGTACTACCTTGTGTTTATATGCCACATTTTCTTTATCCACTCATCTGTTGATGGACACTTAGG
TTGCTTCCAAATCTTGGCTATTGTCAATAGTGCTGCAATAAACATGAGAGTGCAGATATCTCTTTGATGT
ACTAATTTCCTTTCTTTTGGGTATATCCATAGCAGTGGGATTGTTGGATCATATTGAGTTCTAGTTTCAG
TTTTTTGGGGAAGCTCCATACTGTTCTCTCCAGAGTGGCTGTACTAAATTTACATTCTCACTAACAGTGT
ACAAGTGTTCCCTTTTCTCCACATCCTCTCCAACATTTGTTATTGCCTGTCTTTTGGATAAAAGCCACGT
TAACTGGGGAGAGATGGTATCTCAGTGTAGTTTTGATTTGCATTTCTCTGATGATCCATGATGTTGAGCA
CCTTTTCATATACCTGTTTGCTATTCATATGTCTACTTTTGAAAAATGTCTATTCAGAACTTTTTCACAT
TTTTTAATTGGATTTGAGTGGCTCTTTGACGTTATATTTGTGAATTAGGAAAACCACTGAATTTCTTATT
TATTTGATAATATTTACTGATAAAATATCACTGGAAAAACAAATACACTTTAGATTTTTTATTTTTGAGC
AAATGTGCTGGCTTACTCCAATCATCTTCTAAATTCTACATAAAATAGTGCTTCTTTGGCTTAGCATCTT
TGATGACTGCATTACTCCAGAAAAGTCTTTTCCAAACATTTTTTTATTAGCTGCTGTTACACGACATGTT
TTAAATTTTAACCATTTTTGGCAGCAATCTTTCTGGCGTATATTATCTTCCCATTTAACAGCACATGCTA
CCTGTAATTTAACCTGTTCTTGACAACTAAGAGTGATCCTTATGAATATCTGACACTTTACCAAGAAAAG
ACTAAATTGTAGACACACCTTCTTCACAATATCCTTTGCTCCAACCCTCAGGCCATTGAAGAGAACAAAG
GGCTTTCTCCTTTGATTGCCCTGTTTGCTGTGGTCTTGTTTTGTTGTTGTGGTTGTAAATAGCATGTCTA
CTTCTTGCCCTCAATTTTTATATCTAGCTGCTATCGTTATGTTTATAACTTTCACTCCAATTTCTGATTT
TGGTCAAGAGATTAAACCATACATATATATTATTAGAACTAAGCGTTGAACTTTGGTTAAAGTACCAATA
ATTTCGAGGATTAATGCTGTATAAATTAACAAAACCTGGTTTTTCTGTTTTGAGGCTTTGATGTCAGACT
CATCTGGATCTCAGAAACCCACCATTCTTTGTCTTTGCCTTATTCGTGTGTCTGTGTGTGTATTTAAAAT
GCATCACTTTAAAAATGAGCAAGTTACTAGAATATATTGGCAAATGAAGAAGGAACAAAAGAAAGAAAAG
AAATGGATTACTTCACAATGGAAATACTTTGATTTATTACTAAATTAGTGAACTTGTTTTGGATAATAAC
TGCTAGGACAAAGGGGAGAATCGGGTTTTTTTAATATATAATATGAATATATATTCAGATTATGTTTTAT
AAGAAGTCTGAACTAAACAACATTGTTTCCTTATTCTGAAACTCTTGTGAAAATTGAGCGTACATTTACA
CCTATGTTCTAGATTCTTCAGTGACATTTTGTAATAATCAAAGTAAAATTGTTAAAAGATTTTTTTAATA
AGAATCATACCTACCCTGCTGGTAAGTAATGAATTAGAAAGCAGATGAGTAAAGTAAGACACATACAGTG
CATACTGATTGCAGAGTCATAACAGATGCTGGGGAGAATGTGGAGAAAGGGGAATGCTCATACTTGGCTA
GTGGAAATGTAAATTAGTACAGCAACTATGGAAAACATAGATTTTTCATTCGTATGAAGGTGACTCAAAA
AACTGAAAATGGAGCTGCCACATGATCTAGCAATTCCACTTCTGGGTATATGTATCAAAAAGAAAGGAAA

FIG. 7C (Cont.)

TCTGTATGTCAGAGAGATGCCTGCATTCTCAGGTTTATCATAGCCATATCCACAACACCAAGATATGGAA
TCAACTTAAGTATCCATCAACAGATGAATGAGTAAAGAAAATGTGGTACATACACAATAGAATATTATTC
ATCCCTAAAAAAGAATGAAATATTGTTATTTGCAGAAACATGGATAGAACTGAAGGACATGATGTTAACT
GCAATAAAATAAACCAGGGACAGAGACAAATATCACTCATATATGGGAACTAAAAAATTGATTTCATGGA
GATAGTAAATAGAATAGTGATTACCAGAGACTTGTAAGGATAGTGGGAGGGGGAGAGGAAGAGTGGTTGG
TTAATAGGTACAAAAATACAGTTAGAGAGAAGGAATAAGTTCTAATGTTCAGGAGCAGAGTAGGGTGAAT
GTCGTTAACAACAATATATTGTGTATTTCAAAATAGCTAGAAGAGAGAATTTAGAATATCCCAGTTATCT
TGACTTGATCCCAGTTACCCAGATTTGATCATTAGACATTATATGCATGTATGAAAACTCACATATATGC
CATAAATAGGTATAACAGTTATGTATCAATTTAAAACGAACGTAAAGGAATATTTTAAAAGTTTATTTAA
ACCAGGAAAGTACAGAACATATTGAAATATTAAAAAATTGTGTCTCTACCATGTCTTGTCATTTTTTTTC
AGTTAAAAAAAAATCACAGATAAGATTCAAGTGCCCCATATCCCCCTTCCAAGGCTTATTATCATATTCC
ATTTCTCCCCAGAGCTAACCGCGATCATGACTTTGATAAGCATACGTTCAATCATGTTCTTATATATTTT
TACATGTTCTTTTATATTTTATGTGTAAAATAATATTGCATAATGATGTCTGTTTTACACATAAAATATA
CTACTGTTTTATGTGTTTTTATAAGTGTTAATCTGTTATTTACATTTTTCTACAAATTTTTTTTTCTCAT
CATTCTGTTAGAAATATGTCCATGTTGGTACATATAAATCTAAATGATTCATGTTAACTAATGTGTAATA
TACCACACAGTGAACATGCTATAGTGTATCCATTCTCCTGTTGATGGATGGGCTTATTTCCAATTTTTCA
TTGTTATAAATGAGTTTAAAACCTCCTTTATAAATGTTTCCTGGAAAACCTGTGAGACTTTCTCTGATGT
AATTGCTCTATTGTGGATTTCAGTTTTACTGGATTTTTCTTGAAAGAGATTGTAACAATTTATACTCTCA
CCAGTAGAGTTGGATTTTCCACATCACATCTGATATTGACAGACTGATTTTTGTCAGTTTGGTGGCTATG
AAATGATACTGTAATTTTTTATTTGTTACATTGAAGTATAATATGCATGCAGGAAAATATACATAGTATC
TTGATGAATTTTCTCAAATTGATTGTATTCATGTAATCAGCACCCAGATTAAGAAACCACATATTACCAG
CAGCCCAGAAAGCCCCACTGTATGTTCCTCTCTGCCCTTCAGTTAATTACCATAAATTAGTTTTCTTTTT
ATACTTGATATAAGTGAAATCATGCAGTATGAACTCTTTTGTGTCCAGTTTCTTTTTATTGTTTTATGTT
TATGAAGTTCATACATATTGTTACAAGTAGTTATAGATTGTTCATTTTTGTTCTATTAAATTATATATAG
ATACTACAGTTTTAAAATTGTTTCTAGTATTTGGGCATTTGGATGGTTTCCAGTTTTGGTTATTATGAAT
AATGTTGCTGTGAACATTCTAGTAAATGTCTTTTGGTGAAAGTGTTTATTCATGGCTTTTGGGTATATAC
CTAGGAGTAGAATTGCTGGTTCTCTCACTTTTCTTTTAATTTTCATTCCCTTGATTATTAATACTGAGTT
TGAACATCTCTTCAAACTTTATTTTACTTACTAAAAATTGATTTGTAGGAGCTTTTTTACGTATTATGTT
TTATATATCTTTGACTAACCTGTGGTTTACAGTTTCATTTGTTATGTATAATTTTAAAATTTTGATGTCA
AAATTTTCAACCTTTTTCTTTATAAATTTTTGATGAATGTAGCCTGGTGAGAGATTTTATTTTCCATATA
AATTAGAACCAGCTTTATTTGCTTGGCATTGTGATTGAGATTCCATTGACTGTAAAGATTAATTTGAGGA
TAATAGTTCCAGTATTGGAATGATTAAATGAGTAATGCTTATAGAGCTAGTTACAAATAGTGCTCAGTAC
ATTTTAGCTATGATTATTGAAAATAGTCACTGAGGCTTCCTTCAGGATCACTTTATTCTAATCCTAGATA
TAGCTAGCTGATGCTTGGTTATCTAATTTTTCTGCTTGCCCATAGATTAGAAGTGGCAAAACCCCAAAAG

FIG. 7C (Cont.)

GCTATATATGCTATGAGTTTATTTCTTGGTTAGATAGACCTGTATTGAGTGATAGCTGTATGTTAAATGG
ATGTGATAGGTGTGAGAGAATAAGATTGACTAAGAATAAGAGATATTATGAGCAAGACTTAACCTCATAA
CTTAGATCCTTTAGGAAAGTCAAATATAAAAAATAATTACTTGACTCCCACAGATTTGTTCTCCTGTCAT
AGGGTCTTATAACACTGTGTTCCTTCAAAACCCTACCAGTTGTAGTTTACATTTTTATTTGGTTATTTGA
TTAATGTCTGTCTTTCTTACTACATTATAAGCTTCATAACAGCTCAGTATTACCGTCTTCAGTTTCTAGA
GCAGAGGTCTGCAGAGTATAACCTGATGTCATTTTTTTATATAGCCCTCTAAGCTAAAAATTGATTTTAC
ATTGTAAGGATTGTAAAAAATGTGACAAAGATTTGTATGGGCCACAGAGCCTAAATTATTTACTGGCTCT
TTATAAAAGGTTTGCTGATTTCTTGCCGTGAAGGAATCCCTGGAGTATAGTAGGTGTTCAATTTAGAAAA
AAAGATGAATGAATTGTATTGTAACACCATTTTAAAAAGTTGTTAGGTGAGGTATAAACAGGCACTGAGG
AGGTAGTGACTGACTGCCTGGAAAAGGTAGCAAGTGCTTTAATAGGGAATGACTTCTGAGCTGAATTTTT
GAAGGCTGAAGTTTCTCTACTAGATGAGATAGGCAGAGACATCTTGTAAATGAGGAAGGAAGAGGCAGAG
GGAGCAAGAATGAACAAAGGCCCTGAGCATATGGAAGGACACAGGGTGTTTGGAGAGCAGAGGGAAAAGA
AATGAGATTGGAGAAAATTAGGAGCCATCTTGTGCCTACTGCCTCTTGCTGAGTTTTGTTCTTCTGAAGA
CCTTGGAAGGTCACTGGAGGTTTGTAAATTATGAAGTTGTCATGTGCTTTGGGAGGGTGATTGGTGGCAG
TAGGAGGATGATCTAGAGTGGGGAACTCTTGGCTTGGAGCATGGTTGGGAGGCTTTCTTTGGTCTGTTGA
ATGAAAGTGTTGGTAGTGAGGATGGAAAACAGGAAAAGATTTAAAAGTATGATTGACAGAAGGTAACAGC
CAAGAGACATTTGACAATAGCCTTCCTTGCCTTCTTTTGCAGAAATGAAATGGGGAGAGTGTTTATTAGT
GGTCCCTAAATTAAAATTTATTTTTGTTACTCAAATTTAAGCATTTCTTTGTATAATTGCTTGGATTAGC
ATGCTGTCATTTTTTTAAACTGGGAAATATAGTCATCCATCTTTTATACATGAAAGTAACCTGTATAAAA
TTACAAATTGATCTGTCAAATAGGGTTTGGAGTTGAAAATATGGCAACAGCAATGGATGAAGACCTGGAA
GAAGAACTAGATGAAAAAGATGAGAAGTCTATGATGTGCCCTCCAGGCATGCACAAATGGAAGCTGGAGC
AGTGCATGGTTTGCACTGTCTGTGGAGACTGTACAGGTTATGGAGCCAGCTGTGTCAGTAGTGGACGGCC
AGACAGAGTCCCCGGAGGGTAAGAGACAATGATTCCTACTAAAGAACATGTGCAGAACACATTTCTTTGC
AAAATCATTCCGGAGTATACTCTACTATTAATATTTTTTTCTTAAAGACCAGTGGCATCTTCACTTGATC
TTAGCCAAAAGGCCAAGAAAGTATTATAATTCTTATAATTGTTTTCTGTTATAATAATTTATAATTTAAT
GTCATCTCTAAGGTTGCCTTTCTTTCATTTGATTCATTTAAACCATTATTTAAAAACAGACCATAAGTTT
TTCAAGACTTGGGGCTGTACTTTTATTTGTATTATTTTTCAAAGCCTATTTAATGCTAGATATCTATTAT
ATTTCTTTCTGTTGAACATGAATCTTTTCTAAATAAAATTATCGATATCATAAAGAGTACTTGATTAGAT
ATATAGTTTTGTTTTAAATTAAATGTACCATTTATAAATTTAGAAACGTTGTATGCTTGCTTCTAAAGTT
ACATCATACCTGCTATATTTATCCTTGTTCTCAATGGACCACATTTTTCAGGGTTCTATATTATTGTCAA
TTTACAGTTAATATGTAAGTTTGGCAGAATAAGAATGCAGGTTTTCTGCTAGGATGTTAGGAAGAATTTT
GAATCTATTTTCTACATTGCTAGTTATAGCCACTATAACATGATGGGATATTCTTTGTGTGATCAGCTTT
GTAATAATTGGCTGATTTGGGGGAGTAGAGAAAATTTTGTGAAGAGAAGCCCAGAAGGAAGACAGCCATC
CCTGCCTCTTGACCTTCCTCTTTGTCAACTCTGTAATAGTTGCTTCTTCCCAAATATTGTCTGGATCTAA

FIG. 7C (Cont.)

TAGGAGTTTATTTCTAAGTTTATATTTGGCCTTTCATAGTTAAATAGGTCATATATAACAGGCCTTTTCT
TTAAGGCTGCTGAGATATGATTTTTTTTTTTTTTTGAGACGGAGTCTCGCTCTGTCGCCCAGGCTGGAG
TGCAGTGGCGGGATCTCGGCTCACTGCAAGCTCCGCCTCCCGGGTTCACGCCATTCTCCTGCCTCGACCT
CCCAAGTAGCTGGGACTACAGGCGCCCGCCACTACGCCCGGCTAATTTTTTGTATTTTTAGTAGAGACGG
GGTTTCACCGTTTTAGCCGGGATGGTCTCGATCTCCTGACCTCGTGATCCGCCCGCCTCGGCCTCCCAAA
GTGCTGGGATTACAGGCGTGAGCCACCGCGCCCGGCCATGAACTTTTAAAAACAAATTTTCTTTACATTA
TTAGTATAAGCAATAAAGTCGTCTTTATCAAAGGATAATATTTATTCTGTAGTGCTTTATGTTTGGCTCT
GTTTTCTGTTTTTTAAGCACCTAACTTCTTTATTTTTAAATTTAATTTGGATGCAGAAAGACTCTGATTA
TTTTTTAACAATGTTGGAATTGAAATTTATTCTCCTGGATCTCTCCAACGCTATTTCCATTAAAATTCAG
TGTTAGCTGGGTGTAGTGGCCCATGTCTGTAATCCCAGCACTTTGGGAGGCTGAGGCCAGAGGATCACTT
GAGGCCAGGAGTTTGAAACCAGCTTCAGCAGCATAGCAACACCCCTAACTCAAAAAATATATAATAAAAA
TAAAATTTAATATCCCCACTCTCTGAGCTTAAGCAGCCAGTATATATCGTGAACAAAATCTATAAATTAT
CTGGTCCCTTTTGAAATTAATTATTCTTCGTTTTTTCCTCCAGAGACTTACATAATTTATAATAATTATT
CATAGACTTACATGGACAATACTAACCAAGTATAATAATTGCTTTATGAATGAAGCAAACTGAATATATC
AGAATATTAAGGACTATTAAGCTGACTTCAATTATTATAAAATTGTGACTACATATCTTATTATGATAAA
GTACATATAAAATTGACCAGCTTAACCATTTTTAAGTAGACAGTTCTGTGGTATTAAATCCATTCATAAT
GTTGTGCAACTATTACCACCATGCATCTCCATAACTTTTCATCTTGTAAAACTGAGACTCTGTAACTGTT
AAACAATGACTCCTCATTCTTCCCTCTCCCCTGCCTCTGGCATCCACTATTCTTGTTTTCTTTCTGTGTC
TGATTGACTACTCTAGGTACCTCTCATATAAAGAGAATCAGAGTATTTGTCTTTTTTGTGACTGGCTTAT
TTCACTTAGCATAATATCCTCAGTTCATCCAGGTTGTCACATATGTCGGAACATCTTTGCTTTTTGAGGC
TGAATAATATTCTATTGTATGTATATTACCACATTTTGCTTATCCATTCACTCACTGATGAACACTTTGG
TTGCTTCCACATTGTAACTATTGTGAGTAATGCGCTGTGAAGATGAGTGTACAAGGAGCTCTTTGAGACC
CTGTTTTCAGTTCTTTTGGGCATATACCCAGAAGTGGAATTGTTGGACTATATGGTAATTTTATTTTTAA
TCTTTTGAGGAACTGCCATACTATTTTTCACAGCGGCCAACCATTTTACATTCCCACCAATAGTGTACAG
ATGTTCCAGTTTCTCCACATCCTTCTTAACACTTATGATCTGTTATTTTGGTAGTGGCATCCTAATGGGT
GTGAGATAGTATCTCATTATAGTTTTGATTTGAATTTCTCCAGTGATTAGTGATGTTCAGCATCTTTCCA
TATACTTTTTGGCCATTTGTAGATCTTTGGAGAAATGCTATTCAAGTCCTTTGCTCACTTTTGAATCAGG
TTGTCAGTTTCTTTTGTTGTTGTTGATGAGTTTTAGGAATTCTCTATATAGTTTGAATATTAATTCCTTA
TCAGATATATGATTTGAAAATAAAAAGTTCTGTCTGTGGGTTGTGTTTTTACTCTGTTGATGTTGTCTTT
TCAAGCAGAAAATTTTTAAAATTTTCATGAAGTCCAGTTGTCTATTGTTTTTTGGTTATTGTCGCCTGTG
CCTTTGGTATCATATCCAAGAAATTATTTCCCAATCTAGTGTTGTGAAGGGTTACTGTTATCTTTTCTTC
TTCTTTTTTTTTTTTTGATTATACTTTAAGTTTTAGGGTACATGTGCGCAACGTGCAGGTTAGTTACATA
TGTATACATGTGCCATGTTGGTGTGCTGCACCCATTAACTCGTTATTTAACATTAGGTATATCTCCTAAT
GCTATCCCTCCCCGCTTCCCCCACCCCACAACAGGCCCCGGTGTGTGATGTTCCTTTTCTTCTAAGAGTT

FIG. 7C (Cont.)

TTTTGTTTTTTTTTGTAATAGTTTTAGGTCTTACATTTAGGTCTTTGATTCATTTTGAGTTAATTTTTGT
ATATGCTGCTAGAGAAGTGTCCAGATCAAGTTTTCCCAGCAATGTTTATTGAAATGATTATCCTTTCTCT
ATTGAACCATCTTGGCTCCTTTGTCAAAAATCATCTGACCATATATGTGAAGGAAGATTTCTCAGCTGTC
TATTCTATCCCATTGGTCTGTATGACTGTCTTTATGCCACACCACATTGTTTTGATTACTGTAGATTTGT
AGTAAGTTTTGAAGTCAAAACCGAGTACTTTGTTCTTCTTTTTCAAGATTGTTTGGCTATTTGAGGTCCC
TAGAGATTTTCTATGAATTTTAGGATAGGTTTTTCTATTTTGTAAAAACCATCATTGGGATTTTGATAGG
GATTACAATGAATCTGTAGATTGCTTTGGGTAGTATGAACATCTTAAAAACATTAAGTCTTCTAATCCAT
GAACATAGATGTGTTTCTACTTATGTCATCTTTAATTTCTTTCAGCAATGTTTTGTAGTTCTCATTTCAC
CTCATTGGTTAATTACTAAGTGTATTCTTTTTGATGCTATGGAATTGTTTCTGTAATTTCCTTTTCATAT
TGTTCATTGTTAGTGTCTAGAAATACAACTGATTTTTGTGTGTTGACTTTGTATCTTCCTACTTTGCTGA
ATTCATTTTCTCTATTGGTTTTTTTGAGTGCAATCTTTAGGGTTTTCTACTTATGAGATTGTATTATCTG
TGAACATAGATAATTTTACTTCTTCCTTTCTGCTTTGGATGACCTTTATTTCTTTTCCTGTCCAATTGCC
CTGGCTAGAACTTCTAGTGCTGTTTAGGATTGGTCAAAGTGAGCATCCTTGTCTTCTTCCTGATATTACG
AGGAAAAGCTTTCAGTCTCTCACCATTATGATGTTCACTGTGTGTTTTTCATATGTGGTTTTTATGTTGA
GATCATTTCCTTCTATTCCTAGTTTGTCTACTGTTTTTATTATGAAAGGGCATTGAATTTTGTCAAATGC
TTTTTGTACATCAATTGAGATGATCATGTGTTTCTTTTCTTTCATTCTGTTAATGTGTTACATTACATGG
ATTGATTTTCATTTGTTGCATTCCAGGAGTAAATCCCACTTCGTTATGGTGTATAATTCTTTTAATATCC
TGCTGAATTTGTTTTGTTAGTATTTTGTTGAGGATTTTCACATCATTATTCATAAGGGATATTGGTCTGT
AGGGGTTTTTTTTTTTTGCCTCCCCCTGCCCCTCTCCCTCCTCCCTTTCTTCTCTTTCTCCTTCTCCTTCT
TCTTTCTTCTCCTCCTCCTCTTCCTCCTTCTCCTTCTTTTCCTCCTTCTCCTTCTCCTCCTGCTCCTCCT
CCTCCTCCTTCTCCTTCTTTTCCTCCTTCTCCTCCTTCTCCTTCTTTTCCTTCTTCCTTCTTCTTCTTTC
TTCTCTTCTTTCTTCTTCTTTTTCTTCATCTTTTGTCTGACATTGGTATTGGGGTAATCCTGACCTCAAA
GAATGAATTCTTGTTCTCTCCTCTTCAGTTTTTTGGAAAATTTTGAGAATTGGTGTCATAAACACTATTT
TAAAAATAGTGTCAGTCAGGCATATTACTGTGTCACAGTTTTTACTGTGTAGTAAGTGATCTTCCAAATT
GTTTATAATGCTTGCTTTTAAAAGTGACACATTTCACAGGGTGTCTAGCTATGTCTTTTAAACTGCTGCC
AGATATGTTCTTCCTTTTGTACCTTCTGAAATCTGTATAACCTGGGGTTCAACAAGGCTGTCAAAAGTTT
CAAGAACTGATCTGATGAACTACATTAAAGCTATACCTTCTACAAAATATGTGACTAAGAAGTTACTTTC
CCTGACCCCAAGTCAGTTTCTGGGAGTGTCTTTGTCAACATATACCCCATATGGTTCACAATCGATATGA
AAGGGCTGAAGGAGAAAAAGAACAGGTAATTGGACTCTGTGAAAGGAGAGAATGGGAGGTGAAGGCATGT
AAAGAAGAGAGGGGGAAGGAGACATATATGTGTTTGTGTGTGTGTATATATATGTGTGTGTGTGTGTATA
CATATATATATACATATATATGTATTATTTTTTCCTTTCCAATGTGTGAATGTTTTTATTTCCTTTGTGT
GTGTGTGTGTGTGTGTGTGTGTGTGTGTGTGTGTTACTTTACGTTCTGGGATACATGTGCAGAACGTGCA
GGTTTGTTACATAGGTATACACATGCCATGGTGGTTTGCTGTACCTGTCAACCGGTCATTAGGTATTTCT
CCTAATGCTATCCCTCCCCTAGCCCCCACCCCCCAACAGGCCCCAGTATGTGATGTTCCCTTTCCTGTGT

FIG. 7C (Cont.)

CCATGTGTTCTCATTGTTCAACTCCCACTTATGAGTGAGAACATGCAGTGTTTGGTTTTCTGTTCCTGGG
TTAGTTTGCTGAGAATGATGGTTTCCAGCCTTCATTCATGTCCCTGCAAAGAACACGAACTCATTCTTTT
TTATGGCTGCATAGTATTCCATAGTGAATATGTGCCACATTTTCTTTATCCAACCTATCATTGATGAGCA
TTTGGGTTGGTTCCAAGTCTTTGCTATTGTGAATAATGATGAAATAAACGTACATGTACATGTGTCTTTG
TAGTAGGATGATTTATAATCCTCTGGGTATATACCTAGTAATGGGACTGCTGGGTCAAATGGTATTTCTG
ATTCTAGATCCTTGAGGAATTACCACACTGCCTTCCACAATGGTTGAACTAATTTACACTCCCACCAACA
GTGTAAAAGCGTTCCTATTTCTCCACATCCTCTCCAGAATCTGTTGTGTCCTGACTTTTTAATGATCACC
ATTGTAACTGGCGTGACATGTTTTCTCATTGTGGTTTTGATTTGCATTTCTCTAATGACCAGTGATGGTG
AGCTTTTTTTCGTTTGTTGGCTGCATAAATGTCTTCGTTTGAGAAGTGTCTGTTCTTATCCTTCGCCCAC
TTTTTGATGGGGTGGTTTGTTTTCTTGTAAATTTAAGTTCTGCTGCATAAATAAATGTCTTCTTGTAAGA
AGTGTCTGTTCATATCCTTTGCCCACTTTTTGATGGGGTTGTTTGTTTTCTTGTAAATGTGTTTAAGTTC
TTTGTAGATTCTGGATATTAGCCCTTTGTCAGATGAGTAAATTGCAAAAATTTTCTCCCATTCTGTAGGT
TGCCTGTTCACTCTGATGATACTTTCTTTTGCTGTGCAGAAGCTCTTTAGTTTAATTAGATCCCATTTGT
CAATTTTGGCTTTTGTTGCCATTGCTTTTGGTGTTTTAGTCATGAAGTCTTTGCCCATGCCTGTGTCCTA
AATGGTATTACCTAGGTTTTCTTCCAGGGTTTTTATAGTCTTAGGTCTTATGTTTAAATCTTTAATCCAT
CTTGAATTAATTTTTGTATAAGGTGTAAGGAAGGGGTCCAGTTTCAGTTTTCTGCATATGTCTAGCCAGT
TTTCCCAGCACCATTTATTAAATAGGGAATGGGAAGGAGACATATTACATGAAGCTGGCAAGCTTAGGCT
CTGTTGCTGAAGGCTACCAACACCTGCCTTCACTTATCTGCTGGACAGCAACATTGTTTGATTGTTTTA
GCCAACCAACCCATCTGGGTCACTTAATCCTAAAGCTTCTGGTGCTTCACTAACTGCAAAAAGACTTTTA
AAGGATTGTTTTTAAAGTAGTGACTTTGATGATAGTCGAATCTGTGTGTATTTTCTGTAGAAATATACCA
ATTATGCCTATTGGGAGTTTAATCAGTCTTGTTTTTAATTATTCTGCTATTTATATCTTTTCTTTAAAAT
GAACAATCGTGATCTAAAGAGGTGATTTCATTGCTTACTCATTTAACAATTTCAAAAATGTGGAAAATAA
GTTATAGAAAAGAGTTTTAAAGACAAATTAGGAATATCTCAGTTGTCTTTTTTTTTTTTTTTTTGTATTTC
CCCCTAGGATCTGTGGTTGTGGTTCCGGAGAATCTGGTTGTGCTGTGTGTGGATGTTGCAAGGCCTGTGC
AAGAGAGTTAGATGGTCAAGAGGCAAGACAAAGAGGAATTCTTGATGCAGTGAAAGAAATGATACCTTTA
GATCTTCTTTTAGGTAATTTTGATTGATTATACTATGCTACACTGAGTTGTCCTCAACTCAGTAAGTCTG
ACAGTTTAAACAATTTCTTTTAGATATATGTTAATAAATTAGGATAATAATTAATGTATGCAATACTGCT
TTTACGGTAACTGACAATATGACATTGTTTAAGGGATGAGATTCTTTTTTTTTTTTTTTCTTTTTTTGAGA
TGGAGTCTTGCTCTGTTGCCAAGGCTGGAGTACAGTAGCTCAATCTCAGCTCACTGCAACCTCCGCCTTC
TAGGTTCAAGTGATTGTCCCATCTCGGCCTCCCGAGTAGCTGGAATTACAGGTGCCCGCTACCACACCTG
GCTAATTTTTGTATTTTTAGTAGAGACGGGGTTTCACCATGTTGGCCAGGCTGGTCTTGAACTCCTGACC
TCAGGTGATCTGCCCACCTTGGCCTCCCAAAGTGCTGGGATTACAGGTGTGGGCCACCATGCCTAGCCAG
AATGAGATTCTTTTTCCCTTTTTGGCTAAGAATTATTAAAGTAAAAATATTGTGTGTTTTAGACAATGTT
TTTGCTAGCTTTTACTTTCTTGAATTTTATGTAGTTCTGTCATAGCTATTATATAACATATATGTTGTTG

FIG. 7C (Cont.)

TTGTTGTTGTTTTTGGCCAATCATCTAGCTGTCCCAGTGCCCGGGGTTAACATTGAAGAACACCTTCAGT
TACGACAAGAAGAAAAACGGCAACGTGTAATCAGAAGGCACAGATTAGAGGAAGGAAGAGGTAAGATGTA
GCTACAGAGAAAAAGTACATGAAAATCCACTTTCCTACCCTATCCTGAAACCACTGAAAAGTTCACACAA
TAAACTAATTTGGTAAGAAATCATCAAAATTAAAATTAGCAATATTCTGATAACTCATATAATGGGAAAA
TATTCAGGGTATTCATGCTTCTTCTAATAACATACGTTTAGGTATTTATAATTGTGCTAATAACATACTT
TTAATTCAGCAGGGTGTTTATGGCATAAGTCAGCCATATTAAGAACTGTGCCATCTGCCTACTATCAATA
ACTATTAGAAATGGCAACTTTTTAAAAATAGATATTCTCACAACTTGTCCTTCACCCGGACTTTGGACTC
ATCTATTTGACCGTGGAACAAAATTCAATTTAGTCTTTTTCATTTCTATTTTCTTACTCATTTATGCTCA
TTATCATTTGGACATAGTCCTGCTATGCTGCCCTCCAGTTCAGCACATAACTATGCTTTCATGTGTCCTT
TTTTGGAAAAACCTCATTCTAGTTATTTACAGGAAGAGTAAGATGGCAGGTCTGCAGGTTTCATTTGCAA
AGATAGGTCTATTGTTTATCTTTTCCTCATTGTTTATGAGCTTAAAAGTTTCTTAGCTTAAAAATACATT
TAACTGGCCAGGCACGGTGGCTCACGCCTGTAATCCCAGCACTTTGGGAAGCTGAGGCAGGCAGATCACA
AGATCAAGAGATCAAGACCATCCTGGCCAACATGGTGAAACCCCATCACTACTAAAAGTACAAAAAAATT
AGCTGGGCGTGGTGGTGTGCGCCTGTAGTCCCAGCTACTCAGGAGACTGAGGCAGGAGAATCACTTGAAC
CTGGCAGGTGGAGCTTGCAGTGAGCCATGATCGCACCACTGCACTCCAGCCTGGCGACAGAGTGAGACTC
CATCTCAAAAGAAAACAAACAAAAAAAATTTAACTGTGGTTATAATTGGTATTTGAATACGCAAAGATAA
ATATATGTATTACTAAAGATTTCCTTGCTCAGTAAATTTTTTTTTTGTAGGATTAAGACAAATTGTTATG
GAAGTCTATGATTTTATTCCTCCAATAGGCAAAATTTTGATTAGAAATGTTTACTGATATTGCATATTTT
AAATGCTTATTAGAAATGGCATGATATTTGATGCATGAAATAAACCTTTTACCCATTTAACCATCATTAT
ATTTTTTTCTAGCTATTCTTTTTGTTAATATATGGAATAAGTAGTAAAATGTATAATACACATGGTGAAT
TCTAGTTTTACTAAACTTAAATTGTAAAACATATACTTGGCACATGAAGAGTGTTCTTCATAGCATCTGA
TAAGTGATGTTGATTGATAAGGTGAATATTTACTATTGTTTGGCTTTGCTTGCATAATGTCCTTTAAAGG
ATATTTTAATGAGATTAATATAGATACTGTCAGTATTTACATTATATAAGTATATGGGAAAATTGCATGT
TAAATATTTCTTACAAAACAGGATAGAATTAAGTTTCTGATGTGGTAATTAATAATTTTTTATGTTGATA
TAATTTTTTCAGATTAGTTACCATTCTATCTGTTTGCTACCTGTTTCTTCTTTCTTTAGAAATATTAGGT
TGAGCGACATGAATGAACCTACAAAATGCAGCTATTTCTTACATTTAAACTACAGTATAGCACATCCTTA
CACTTAATTATTCACATTTAATTACTTGCCTAATGCGGTGTATCTTGTTACTCTTTTTCTCTTCCCTCTA
AAAAAGCTATTCTTCTCTAGGTATAGTATATTTGTGCATATAGGAAATAAAGGAACATTGAATCGTGCAT
TGATAACTTGACATAACTTGGTGATTGCAGAATATTCTTTTGCCATTTATTTTTAAATTTGACATAAACC
TGTGAAACATAATTGTAAACATTAACCCTTTAAAGTTAAAAAAAAAATCCTCCACTAGCTAAATATTTAA
AGAAATTATGTTGTTGTATCTGACTTTCCAAAGATAGATTGAGGTTCTAGGCACTTAGTGTATATTTTGT
GACAAATAGGTTTCATCTGCAGTCCTAAATATATAGAACATCAGTAGAAACACTTTGTTCAGATTATTGG
TGTACATAAATTTTATCTTGTCCTTATTTTTTGGTAGAACTCTTTCTTAGATCACCCTCCTTCATGTTTG
GTAAAACAATATATAGTGAATATCTTTTCTTGAGTGGAATCTTCAGTATGAACCTCAATTATCACAGTCC

FIG. 7C (Cont.)

TTGCTTTCCATGGCACTAAAATTAACAGAAATGTGTGCACATTGGAACCATGTCCTCCCCTTTCACAGTC
ACCACAGTTACCTAGAATCATGCGAAAGGAGGACAGAGTTCCCGTATTTCTGTGTTTCAGTTAACACAGC
ACTATGCAAAGTGATGCCTGCTTGTATGTTTTGTTTGTTTGTTTATTTATTTATTTATTTTGAGATGAAG
TCTCACTCTGTTGCCCAGGCTGGAGTGCAGCTGCACAATCTTGGCCCACTGCAACCTCTCCCTCCCAGGT
TCAAGCGATTCTCCTACATCAGCCTCTTGAGTAGCTGGGACTACAGGTGCCCGCCACCACGCCTGGCTAA
TTTTTGTATTTTTAGTAGAGGCGAGGTTTCACCATGTTGGCCAGGCTGGTTTCAAACTCCTGACGTCAAA
TGATCCACCTGCCTCAGCCTCCCAAAGTGTTGGGATTATAGGTGTGAGGCACTGTGCCCAACCTATTTTA
TTTTAAATGAATATTTTTGCATTTGGACAAGAATTCTAACTATGTATTCATTTTTTAAAAAATCAAACTT
CAGAGTCATTCAGTGACTTTGGAAATCCTTATACTGTATTAAGTAATTAAAAATCTATTCTGATATGACA
CTTTTATGATTTTATCTTTATATTATTCTTAGCACTCCATTAAGCAATTTTTATTTAAAAACAAATTTTT
ATAAGAAAACAAAATTAGATGAATATGATATACTTACACTTCCATAGAGATAAAACAAGAAAGATAAATA
CCAAAATATTAACAATGCTTTTTCCTGACAGGTGAGTTTATAGATATTTTTTATTTTCTTCTTTACAATT
TGTTTCCTAAATATTCTCCAATAAGCATATTAGTGTATAAATAGAGTAAAAGTTATGTTTTACAACTGAA
GCCATTTTAAAAAAATACTGATTAGGTTTAAGGCATCCATACTTTGCTTACCTTTGCTTTTTAAAAAATA
TTTTTATTTTAATTGGATGGAGGACTCTCTTTCAGGTGCTGTGCTTTTCATTACTTTCTGGCCATGGTTC
TCAAGGTGGTCTCAAAGGGACCAGCATCACTTGGGCACTTGTTAGAAGTACCAGTTCTCAGGCCCCACTT
CAGATCTCTACTGAAACAAAAAACTGGGGGAGTACAGCCAGTAAACTGTGCTTTAATAGCGTTCCAGGTG
ATTCTGATGGTCCCAAAGTGTGAGACTTAGTGTGCTAGGTCAGTTGTTTGCACTTTGCGGTTTGATCCAA
TGACCTTCTGCATCAGAATCACCTGGGCCTAATGAATCAGAATTTATGGGTCAAGGGTCTTGGAAATAGA
TCTGAGTCACTTGCACAGTGTTCTAAGGCTCTTCTCTGGCACTGTGCTAGAAAAGATTGTAGTGGCTTTG
CTCCCATGAGGAATAGAAACATCAAATAAAATGTTAGTGTTCCGGCTGCCATACATACAGATCTTTTATT
TCTTTGGCCTGTTGATACTTTTTAGAAACTAAAAATTTAGTAGTATGTTAATAATTATACTTACTAGTAA
TTGGCTTTTACCTGTGTTAACATTTCAGAATTTAAGAATTAGGTTATGTTAGATTATTTTACTTGACTTT
TCTGTCTCATCTTATTTACCAAGTCTGAACTAAGTTTTTCATAGATGATCAGAACTCTGGGCTCTAGTTC
TTTTTTTTTGAGTCACAGTCCCACTCTGTTACCCAGGCTGGAGTGCAGTGGTGCGATCTCGGCTCACTGC
AACCTCCGCCTCTCGGTTTCAAGCGATTCTCCTGCCTCGGCCTCCCGAGTAGCTGGGATTATAGGCATGC
ACCACCACACCTGGCTAATTTTGCATTTTTGTTAGAGATGGGGTTTCACCATGTTGGCCAGGCTGGTCTC
AAACTTCTGACCTCAGGTGATCAGCCTCCCAAAGTGCTGGGAGTACAGGTGTGAGCCACTGCGCTCGGCC
TGGGCCCTAGTTCTTGTACTAAAGCCTTGCTCAGACAGCTTCAGGCCTATTGACGTAATTTAGTTACTGT
TTTATGACACCAGGTCTCTTATAATGGAATGTGTTATTGAAACCCAAGAAAGCAATGATATTACTGCTTC
TTCATACATTTGGAACTTTTTAATTTTAAATCTTTGTGTTATTAATAGTCTAGTTAATTTTTTTAATTTA
TCTTTTTAGGTATTAATAGTATTCATTTATAGATTTTAGTTCAATGGTTTGTGATAACTTGTCTTTTTTA
GATTATATTGGGTTGATTGATGTATTAATTTAACTGTGCAAGTGAAGTGCTTATTCAGTGAAATTCTTAA
GTAGGGCTCTTGAAGTCATCAGAAGAACTAGTGGATGATCATATCAATGATTTTATCCTTATATTCCTTT

FIG. 7C (Cont.)

TCAGCACTCTGTTTCGTAAGGAAAATTAAACTTCAATAATGTTAGCTTTTTCTTCTTTCTTCTAAGTATC
CAAGTTTCATAATTGTGAGCTGTAGATGGGCTAAACCCATGTCCTGGCTTACATGGGAGAGTCCCATTTT
ATAGGTGTCCAGGCATATTTCTTTTTTTTTTTTTTTTTTTTTTTTTGAGACGGAGTCTCGCTCTGTCGCC
CAGGCTGGAGTGCAGTGGTGCTATCTCGGCTCACTGCAAGCTCCGCCTCCTGGGTTCACACCACTCTTCT
GCCTCAGCCTCCCGAGTAGCTGGGACTGCAGGCGTTCACCACCACACCGGGCTAATTTTTTGTATTTTTA
CTAGAGATGGGGTTTCACTTTGTTAGCCAGGATAGCCTCAATCTCCTGACCTTGTAATCCGCCTGCCTTG
GCCTCCCAAAGTGCTGGGATTACAGGCGTGAGCCACCGCGTCCGGCATGTTGCTATTACTTTTTAAGCCC
TTAAAACCATTATGGTTTTCTTGATTTGACGCATCAAATCCAATATTAGCTGATATTCCAGTGACACATA
AAAGTCTCTTTTTAAATTAAAGTATTATATGAAGAATTTAGAGAGTATAAGTAAGAAAAAATAGATCAGC
ATAACCCTTTATACAAAGAGAACCATTAGTAGAATTTTGGTGTAACTTCTCACACTTTTTTACTTATTTC
ATATAATTTCATACTGTGATAGATATTGGTGTCCTGTTTGTATTCCCTTTAATATTATATCATGAAATTT
TTTTGTGCTTTATTGCAAATACCATATTAAAGTAATATAGGAATTTAGGTCAAGGTTTTGCATAAACCTA
TTCCTTAATTCAATTATTGTTTTTATTTCGTTGTCATCTTCTAATCAAGTTTTACTTATTTCTAGTTATA
TCATTGACTGAATTTTGTTTTACATTTTTGCTTAGTGTTATAATACATATATTTTTATGTTTTGCTTGTA
TTGTACCCCTACCTTCCCATTTCCATCCCCCCCTCAAAGTAAATGTTAATAGTCTAATATCTTACTCTAT
TAAAATATAATCATGTACAGAGACTTACACATATGTGAAAGTGTAGACATATGTTTATTTACAAAAGTAG
TATTCTGTATATACATTTGCAACATCTTTTTCTCATTTTACAATACAAGAAGAACACACTGTAGGTCAGT
AAATGTGGATCTACCACATTCTATACAGTAACTACCTAATATCATAATATGGCTATACCATAGTTTATAT
AACCATTATTTATTGATGGGCATTCAGGTTATTGTAAGTTTTTGTGGGTTTTACTGTAATAAATATTCTT
AAACTTAGAGCTACATATTAGTGTTTGTATAGTAGAGCTTTCCCAAAATAGAATGTGTGGGGCAGAGAGT
ATATATCTGTCTTAAATTTTAACAGATAATTCACATTGTTTTAAAAATGTTATAGGAATTTGTTTATACT
CCCTAGACTAATGTATAAGAGTAGTGTTTTCCTCTAGCATCACCTGTATTCATTATTCTTTTATTTATTT
ATTTATTTATTTATTTTTTGTAGAGGCAGGATCTTGCTATGTTGCCCAGGCTGGCCTCGAACAACTGGGC
CCAAGTGACCCTCCTGCCTCAGCCTCCCGAGTAGCTAGGACTGTACAGGCATGTGCCACCACACCTGGGT
TTAGTTATTCTTTTTAATTCTTGGAAAACAGTGGTGAACAATGTTATCTCATTGTTAATTTAAATAACAC
AAAATCATATTCTGTGTAAAATTATTTCATAAATCTCATTTTAATGGCTGCGTATTATTCCATTTAGTAG
ATGTATTATAGTTTTTAATTACTTTCATTTGGGTATTTTTAAAATGTTGCTATAATGAATAAAGTTGTAG
TAAACACCTTTGAGGTGAAATCCTTTAAAAATATTTTAGAGTTTTCTTTAGGATAGATTCCTAGGGTGCA
GTTACTAGATCAAAGGATAATAATTTTTATGATCTTGAAATATATCACCAAGAGCTTTCTGAAAGGCTTG
TACTATTTAACACTGCCACTTATTCCATGCTTTTTCTGCCTACCTGCCTACAGATGAACTCTGAATTACC
CATTGTCTACACATGAGTGTAGCTTCTATCTAAACCTGGTTATCTCATACCCCTATTTTACTCACTCCTC
TCCCAATGAAAGAAATAAATCACCAAGTTCTATTTATACAGCCTTCTTAATTCTTTAATAGCTTTTTAAT
ATCTACTTTTCAGAATCTTACTGTTTCCTTAGCTGAGGCTTCTTTTCTTTGCCTATCTGACAGCAAAAAG
CCTTTTAACTGGCCTTACCTCCAGTCTTATCTTCTAAGCCATTAGCCACCTTCTTTCCAGAATATTCATT

FIG. 7C (Cont.)

CTGCAATACAGATCAGATCAGTAGCACTTCTCTGTTTAAAACCAAAAGGCTATTCATAGTCCTTAGGATG
AAGGATATACTTTTATCTCTACAGCCTCATCTCTCTCTATTCTCATTTCTTTTCCCTTGCCCTTCCTTTT
TTTCCCCTACCTCTGAACCTTTATGCTACTTGTTACCTCCTTTATTTGACCTCATCTTATGTGGTGGTTT
CTTTTATCTCTACACTGTCTACCTTCCCACCCTCAAGTTTTGTTAGCTTCTCCTCTAGTTTGTGTGCCTC
CTTTTGTTATAGCATACTGTCATAATTTCTTGTTTAGTTGTGTGTAAACCCTCCCTCCCCTCATTAGAAT
GTGAGCTTCTTGAAGCAGAGATTGTATCTTGTTTATCAAGGGTTCCCAGAACTTCACATGGTACCTGTTA
GTACCATGATTTGTAGTATATTTTTGTTGACTAATTGAAAGCAGGTTAGGGACTTATCATCTCTAGAATG
AAGTTTTGTGGTATAAAAAGGTTTTAATTATCTGTTTTTTTGCATACCTCTCCAAGCAAATTTCCCAAGA
CTTTTGCTCCATCACATATACTCTGTAAAAGTCAGCTACATGTATTTTTAATGACTATACAATATTGTTT
AATATCTTTATGCTTTTATAAAATCCTAATTTATATCCTATTCCTTTTAACTGGAATGCCCTCTCTTCCT
TTCCTTTTCTCTTGTTAAACTTTTTGTCATTCTTTGAAACCTTGCTGATTGTCCTGAGTTTATTTAGTAT
CTTTTCTTACTTCAGGACATAATGTGTATAGATTTCTTTTATAGCATTTATTGTAATATTTCATAGTTTG
TGTTTTTATTTCTGTTTTTTTCCCTAGTGGACTGAATTCCAGTGAGACCTGTATCTTTGTCATTATATTC
ATTTCACCTAGTGTCTGCTAAATAAAAGATAATCAGAAAATTTGGTGAATAAATTAGTGACTCAACTATA
TTTAAAGAAACATTATTTTAGCCCATGGGATACAATAGTATTTTCGAGCCCAATTGCTTTAATTTTTAGA
CATGATTGCCCCCGTGCCTTCTTGATTTATAAATCAAAAGATTCTAAAAAGATTGAATTTAGCAAGACAT
TAAACGGGTGTGGGTGTGATGTATTTTCATGAGGAGAAACAATATTGTAGGCAGACCATAGAAATCAGAA
AATGGTAATATAACAATATTATTACCTTAATATCTATAACTTTTTTATATAGTTGGAAAATACTTTTTAT
AGTAATTTATATATCTGCTTTGTAACAATTGAGAAATCATGCATGTTAAGAAAATAAGGCATTTTGTTCA
TATTTGTTCATATTTGAAATATCAATTTTATTACATTTTAGAAATGGAACTCAGTTTACATAACCTTAGC
CTGAGAAAATAATTGGTACTGCATTATTGAGAACTTATTCTTCTGTTAACATTAAATTAGCATGTTTCTA
TCTGTAGTAGTCATAGAATATGTTATTCATGGTTTTTCATACAATTTGAGGTATTTGCATTTTTGTTTAT
ATCTAGAAACATAATTGAAATATGGTTCCTTTACCCACTTGTACATTTAATGAAGGGTACTTTGATATTT
AATTTGACATTTATGAAATTTTATTAGAGGGCAGTAGGCTCAATTTGTCCCATCATTAGAAAAATTAAAC
TGAAGATCAATAGAGAATCATGAAAAAACTTGTTTTAAATAAAAATGTTCAGTGCTTATATAGTGTCATA
ATTCCTGTTTCAGTTAATGGTAACCTGTCAAATTTAGAGTGTTTTCAAATTTGAAGACATTTTTGATGTT
GTTAAAACTCAAGGAAACTATAGTTCTGCTGTATAAGAAAAAAACCTAAAATTTTAAGTTGTAACTAAAA
TTTATTTTTCTTTTCAAGGTAAATAAATGTTAATGGAAAAATGATTTATTTTATTTTATTAAAATAAAT
TTGGCTGTATATTTTTTTCCTTAAATACCATATAAGTGGAAAGAGCTATAATCTGTGTGGGTATGTATTTA
TATATGTATATATATATGTACATAGTGGCACTTTAGAAGAAATGATTTAATGAAAGATGTTTCCAAAATG
TTATTTGGGTTAGGTGCCCCCTTTACCATCAATATAAAGCCCAAGCTCCTTTCTCTCTCTCTCTCTCTCT
CGTTCTCTCTCTCTCTCTGTGTGTATACATATATCTATATGCAGAATATAGACATTTTTGTTTTGTTTTT
GATCATCTGGTTTTCTTAACCTCTATTTATGATTTGTAGTAAACTCGGTAACATTTTTATTTTGGTTTTG
TAGCAAGATTAATACAAATATTAAACCTGGAAGAGCTTGTTAAAACTTAATGGTTAATTTAAAAATTAGT

FIG. 7C (Cont.)

TTTTATGTTTCAATGGAAAAGATATCTGTCTTCAACGAATACATGGTTTACTGACTTTGAATATATATGA
TATTAAAAAAGTATTTGTAAGATAATTTGATTGATTTAAATTGAACTTCTTGATTATCTATTTGAGACTA
TTAGTAACTACACAATAATTTTATGAGTATACAAGACGGGTTTTGTACTTTATAAATTATATTTAAGATA
TTAACTTTTATGTGAAATGGTGATTAGGTTATGGGTGGGGGTGGGGGGCTGGAGTGGGGAAATTGGAAGA
AAAGTATAATGTCCAAAACCGTTAAGAATAAATTTTTATGCTTTTTAGTTTGAATTATTTTTTGTTCATT
ATAGTGTTTTCATTTTGTGAGTTTTTCTATGCACATACAAAATGTTTCTCCTCAGGCCCCCTTGTATTTG
CTGGTCCTATTTTTATGAACCATCGAGAACAGGCTCTAGCCAGACTCAGATCCCATCCAGCACAGCTAAA
GCATAAACGGGACAAGCACAAAGGTATTTGGTCTTCCTTATCACCTAGGTGGGATACTTTCCCAATTTCT
TCCACTCATTTGAATTTTGTCTCTGGGAAAATGCACAAACCTGATTCTTCTACTTTGCTTCTATCATGAT
GTAGCCTGAGGAGAAAGAACATTCTGAAAGTGATACCGTTTGTCAGTGACTGTCATGCTTCTTGTTTTTT
TGTTGTCGTTAGCTTTCATAAAGGAGATATTTTACAATATATCTTTTCCTTGTCCATTTCTTTTCAAATT
TCAAAAAGTTAAGGGAAGGTGGAAAAAATAATTATTGCTTTCTGTCTTACATCCTTTATTATTTGCTCTT
TAATGACTGTGATCTGGCCTTTTACAATTCTTTTTTGAATGCTGTTTATATGCTTTAGGATAAACAATAT
TACTAAATTCAGTATATTAAATGATGATAATAAGACTGCCATTACACTTTTCCACTGTTTATTAATTAAG
TTTATATAAACAACAAATGAATATACAAATATTTGATGGTTGTGGGTTAAGTAGAGATAAGTGCAAGCAA
AGCACGAATCATGAAGACTTTCTCTAGTCCCTGGTGATGGTCAGAGGGCTATCCTAGTCTGTGAGGAAGT
AGGAATCTAGCTCGGTGTTGTCCTTTGAGATCTCAGAGTTCTGGGTTAATTAAATATATTCTTAAAGCAT
GCTTATTTTCTTGTAAACCACAAATTATGGGTCAGCTAAGATCAGGAAAGAATTTAATACAAGGAATTTA
TAAATTTATATAAAATTTTTGCCTTGTATCCTGGCCTTTGAACCAGTGTTCTTCCTTAGCTAGCACAACT
TAAAACTCCCATTTTCTTAAATGCCTAAGATAGGTCCTGCAAAATAGAATAGGAAGTTTTAAAAACATGC
TTTCCATGTAGACAAATTAATCTAATTAATGTTTGGATCCTTTTCTTTTTTTTGCTGCAAAATTGTCATA
GTCTAATTTAAAAAAATTTCATAGGCAATATAGTATAATCCACTTTATTTTTATTTGCCTCTTTCAGTCT
GTCAGTTTGCCACTCAAAACAAAAACATAAACAAAATAGACAAAACTCATCTTTAGTAAAGGTGTAAATA
GAGCACAACTTAAGATATACTCTGCAGAAATAAAAATAGTGTTTTAAATCTAATGCAATTAACCACAGTA
AAATTTGTGATTACTTTATTTACTGAGTGCTCTAACAATGCCATAAATATTTAAGGAATTTTCAACCTAA
GACAGCTGATTCCAAAAAGAAAAGATACATATATAAGGAATAATATTTGGGGTATGCAATGAAATTGTTA
TTTGCCAGAATGTCTGATCTTTTATGATTTCTACTATGTCACAATTAGAACAGATTTTTTCAGTTTCTTT
CTTCCCCCAAATATATGAAAGTGAAGTTTTCCCAATAGTTTAACTGAGGTTAAATATTCACATTTCATGA
AACAGTTTAAAACCTTTTCAGCTCCATGTTAGTATCTCATGGACAAGTATCTTTACCCTTTCCAGATTTT
TAAATGAAACGTTAAATGAAAACCAAGGTTACATATTTAAAGCAAACTTTTCCCAATGTCACATAATGAT
TGGCTATAGAAATTATTCAGTGAGGCTGGGCGCAGTGGCACATGCCTGTAATTGCAGCACTTTGGAAGGC
TGAGGGGGTGGATCACTTGAGGTCAGGAGTTCGAGGCCAGCCTGGCTAACATGGCGAAACCTCATCTCTA
CTAAAAATACAAATAATAATGATAACAATAATAAGCCCAGTGTGGTGGCACATGCCTGTAATCCCAGGTA
CTCAGGAAGCTGAGGCATGAGAACAATAATCACTTGAGCCTGGGAGGCAGAGGTTGCAGTGAAAAAACAA

FIG. 7C (Cont.)

GTTATTCAATGATAGCTAGTCTTCAAGTTTGCTTGTCATGGGGTTACTTTATAACAAGTTTCTTTGTATA
CTTGTAACCACTCTGTAAGGACCTACTTTGTAATATCACAGTGTAGGACCAGTTTTATTGGATTTTAGGG
TTTTATAGAGTGAGATAGTTTTATCTTTTTACTCCCCAAATACATTTACAATGCAAATAATAATTTATCA
ATTGGTACCCTATTTTTTTGTGAAGAGTATTAATTTACTGCTCACTAATTTCCCTCCAGCCACTAACCAT
TTACACTCACTGTCTTGTCATTTAATTATCTCTCCATTCACTGCTTTTACTTTTACGACATGTTGAACAT
CCCTAATTTGAAAATTCGAAATGCTCCAAGATCTCAAACTTTTTGAGCACCAACATGAAGCCCCCAAGTG
GGAAATTCCACACCTGACCTCCTGTGACAGGTTGCAGTCCCAGCACACAGCTTATTCAGTGTCCTAAAGT
GAAAGCAATCCTCTCAGCCCTCTTCAGCTATGATAAAGCTTTTCCATGCACAGCATGATGGTGACGCCAA
TCACAGTTTGTCTACGTGGGTGGCTGGGTGGCTGAGGTACCTTTGCTTTCTGATAGTGCAGGGATACAAA
TTTTCATGCACCAAATTATTTAAAATATTGCATAAAATTATCTTTCGGCTATGTGAGTAATTTGTATATG
AAATATCAATGAATTTCATGTTTAGACTTGGGTCCCATCCCCAAGATATCTCATAATGTATATGCAAATA
TTCCAAAATTTGAACAAACTCCAAAATCCAAAACACTTCTGGTCCCAAGCATTTCAAATAAGGGATGCTC
AACCTGTACATATTTTCAGTCTTTTAATAAGTATTTTTTCTACATATATTTTTCTCTTCACCTTACCCAG
TTTATCTTCTAGTTTATCTACTGAGAAGTTTATGGTATTGATTGCTATGTTCTATCCTACATTTAATTAT
GTTGGTACAAATTATAGGATGGTAATAGTTAAAATTTTTTAGACTGTGACTTTTTTGTGAGGGTGTAAGG
AGAGTAAGAACTGTGGATTTATTGTTAACAGGACTAAGTTCTAAGATGGAAAGTTGGAGAACTTCTGGGT
GATTGGAGAAAATTCAGAGAAGGTCAGAATTCATCCTATACAGGCAGATATTGACTAAAGGCAAAGCAGA
GTATATAGACTGAATCAATAAGTAAAATTCCATATAAAATACAGTAAATTATTCTAAAATGTGCCTATAA
ACTATATTCGAAACAGAATTAACATTTGTTTCAGCTATTCAGTACCTTACACAGAAAAATGTGTTAATAG
TGTACATAGTTAGGAACATCTGAATTGTTCTAGAGATAGTCCTAAAATCTATTTTAAAATGACTGATTTG
AAAATCTGAAGGCACACTGATAAACATCTGAGTCTATTTTACTCTTACTTTCTGTTTGGAAATGGTGCAG
TGTGATGAAAATATTATAGCCTTTGGAATTAGGCTTCAATTTTATTTCTGAATTTGTCATTTACTAGAAC
TACATGGCTGTGCAAAATGTCTTAATCTCTTTGGCTTCAGTTTTCTTATTTTAAAAACAAGAATAGTAAT
TCTTAACTGATTGTGTTGCTATGAAGATTAAAATATATGTGTGTAGTCTTTGCACACCCACATATGTAGT
CTTTGCACATATAAATCCTCCATGAATACTAGCTTTAATATTTTGAATTGAATTATTTGTTTTCTCTTTC
AGAATTATCTTAAAGGTACAATATTTGAGATTTATTAAATGCATAGTTTATTTTTACAAAGGATTTAAGG
TTTCAACCATTTGGTGGTGGTAAAATGCATGAGCCTTATTTATGATTAAACTCTAAATTTGTCCTACCAT
TTATGATTTTGGGCTGGTTACTTAACCCCTTAACCCTTCAAGCCTTAGTTTTTTCATCTGTAAGATGGAC
AAAGAATACCTATATTATCAGATTGCTTTATTCATTAAAGAAAGTAACAATAGTAAATATTGATTGAGCA
CTTTTCATATTTTATTTAATTCTCATAGGAACCTGATGAGTTACATATCATTGTTGCTATATTATAGATA
GGAAAGCTAGGACCAGAAGGTCCAGTGTCCAGTTGTCATACAACTAGCAAATGAGAAGAGCCAAGATTCC
AGTCCAAGTTCTTAAGTTCCAGTACTCCCAAGCACTCATCCACTGTGGTATTTAATTGTTTACAGTGTTC
AGTTAGCACACAGCAAGTGCTTAGTAAATTGCAACTACTTTTGTCCTTGCTGATTTGTTTTAATGATTTT
GCTCCAAGTACTCACTGTGTTCTGTGGTAGTTTCTGTTATATGCATGACTGTAGGATTACCCTCCAAAAG

FIG. 7C (Cont.)

TATAGATTTTAGTAAAAATTAAAATTAGAAGTTAGAGTCCCTTAGATACTGAACCCTCTTTTTTCTCTGT
GTATACAAATATGTGTATATAATTATATATAATGTGTACATACATATAATATTTTAGTTACATAGTTGCC
AAGGCTTTGTAGCTACTGTAGTTTCAGTGTTACATGGTATACACACACACACACACACACACACACACAC
ACACACAACATATTCATCTTAGGGAAAATACAGATGTGCTCATACTTAAATGGCCAATTATAAGATTATT
CACATCTGTCAATTTTTTATTGACAATGTTTAATTTTTTATATAGATCTAAGCTTTGGTCTTATTGCTGC
TCATTAACACTTTACTGAATAATGAGCTTGAACAGATTTTTTTTTTTTTTTTGAGACAGGGTCTCACTCT
ATCACCTAGGCTGGAGTGCAATGGCATGATCACGGCTCACTGCAGCCTTGACCTCCCGGGCTCAGGTGAT
TCTCCCACCTCAGCCACCCAAGTAGCTGGGACTGCAGGTATTCACCACCACACCCAGCTAGTTTTTTGTA
TTTTTAGTAGAGACAGGGTTTTACCATGTTGCCCAGGCTGGTCTTGAGCTCCTAGGCTCAAGTAATCTGC
CTTTCTCAGCCTCCCAAAGCCCTGAGATTACAGGTGTGAACCACCATGCCCAGCTTGAGCAGAATTAATC
TTGCTGAATTCACTTGCTGGTTCTTGAATTTGGACTAAATTTTTGGCCACTTATTAAGTGCCTTTTTTCT
TTGATAAACTTTGGTTAATGTCTGAGTTATAGGAATTATACTCAATTTTTTGATATCAAATACCATATAC
AGATATATATATAAAATATATATTTTAATTCTGCCACTGCTGCTGATAAAGATTAAGACCCTCATCTCAA
TTTTTTTACTTGTAAGATTTTCACTGTCTATAATAATTGAGAAGTTGTTTTGTACAGTTACAGTTTGTTT
CAATGAACAAAATGTTTCTAGTATTATTTTGACCTCTAAATAACAGCTGCTACTTTTTTAGTCATTGTGG
TTGTATTCACTAAATTACCAACCTTTAAAAATAATCTCCTTCCTTGATGCTATGTCTCTATTGTGGGATT
TATGCCTATATTTAATCTCCTACTCAAGGGAGGAGACAAAATGCTAAATTCAAAGGTAAAACCTTATAAC
TAGGCATCAATACATTTATATAAAGTGGAATGATACTTGAAATGTTTAATTAAGTCTGGCAGAATCATAT
GAACACAATGTATTTTCTATGTTAAATCTCATTTGGTTTTAATAATTAGACATTTTTACCAATTGAGATA
AAGCCGTAAAATTTCTTTACATCTGGCGTCTTATTAAATAGCCTTTGGAAGATATGTATTTGTGTGTGTG
TGTGTGTGTGTGTGTGTGTGTGTGTATGTGTGTGTGTGTGTAGGCTTTTGCATATATTTTACCATT
CCACTATCTTTCCAACATGAGGAGGCTTTGAACTGAGTATATTTTATTTTGGATGGAGTGAAACTAAATG
TTGTTGGTTTTTTTTTTTTTTTTTTTAGTCCATCCATTCTTTGATTTAATTTGGCAAACCCACATTAGATA
ATTTAGCAGAAGAGGAATTATATCTTCATCCTATTATAGTAAAACCTCTCACTAATTCTGAATTTATGAT
ATTTGAGATGCAGTATTTGTGATCTTTTTTGAGTAAAAAATTCAAAATAATTTCTTCCTCTGAATTTTCA
GGGTCATACTTATAAGGGGAAACCTGTCTAAAATCACTAGCTTTTCAAACCAAGGGCTCAAGAAATGAAG
GATTCCTTCAACGTGCCTTCAGCCTCTGGGTCCAGCAGTTAATTCTTGTATGTTAAAGGACTTTTATGTT
TATGGTACATTTTAAATGTAATATTGGCCTATTTTGAAATATAATGTAGGTAACCACACTCTATTTATTG
TAGCATTTAGTTTAATCTGTAATCTGTACTGCTTGAAGGTAACAAAACTGAATTTTTACTTCAGTGTTCT
GTATGATTAAGACGTTTCCAGTAAGCCACACAGGCCTACCTGTTCTATGTTATTCCGAATTAGTGAGGTT
TTACTGTCCTAGTGTCGTAAAGAGTTTCAGTCTTCTTGAAATTATAGGCATTTAGTTACGGAAAGGAAAG
TAATAATGTAGGTAGATTTTGTCTCACCTGGATGTTACTAAAGGTTAGGTAAAAAAAGAATAAACACAAA
ATGATTTAATATTATTCTGTTTAACATTCTAAAATGCACAATGAAAATACAGGATAGAAAGTGTGTGTCT
GTAGATTCACATATGTATCTTCATATAATACACACTTGTTTAGAGTTGCTATACCACTTGAGAGTGGTTT

FIG. 7C (Cont.)

AGACTAGTTGAACTTGTGAAATTCCTTCCAGATTTACATTTATTCTGTGTACAAGGAATTTGAATCTTGA
TGATATAAAGGTCATATGTTAGTGATGTATAGAAGTACATTGTGATTAGAAAAAGTAAGTTGTTGTTATT
TACACATTCCAAACAAAAATTTTTATATTCTGGAATGTGGTTTTTGATGCTATGGTTAGATTGTTGGAAA
ATTCAAAGTTGGATTGCAAAAGCCAAGGGTAAAGAAAAGGCTTAAAGCAAGCTCAATGAAGGAAATTGTG
AGAAGGGAGGAGGAAAGAAGGAGTGAAAGCAGAAAAAAGGTTTGGTTGAGGGTAGTGATTGGGGACAGGG
AGAAAACCACAAAGCAATATGGCTGAAGGTGATGGTGGCACAGGAAACATGAATAAGAATAGGCCATTGA
ACTGCAATATATTGAATAAAGCTCTTTGGTCTTTATACATTTTGAAAAGTTCAGTTGAGTTTCAAAATAC
TTATGGGCAGTGTAGCCTTTCTAAGATCTATTTAGGAAATCTAAGTCACTTGTGAATCCATTAGCAATTT
TTTAAAAATGGCTAGTACTAACAATATCACTAAGTTTAAAATAATTGTTAAATGACTTTGCATGCAGTAA
TTTTTTATGGAAACTAAATTTTCCCATATAAACTGTTACATTTTAAATTTTGTTATTTCTATAACTTAAT
GACCCGTTTATTACATAAGGTTTTATCCATAACCAGATCTTATCTCTGTTTTTATTAATTTAGTGATATT
TGCAAATGGAAGTATATAGTCTATCTTTTCAAAATTCCTTCTTTGCAGGTAGATTCTTGATCTATCACTT
CTAACAGCTACAGATTCTTCTTGCTTGTTCCTTTTAACATTTTTCTCTTGTTCTTCCATAATAAACTGAT
TTAAATTTTTATTTTGAAGATGAATAATGGCTTAATCATAATTCACAAATTATAACACTTGCAGATGGAA
GTGGAGAAAGAGGCGAAAAGGATGCAAGCAAAATCACAACATACCCTCCAGGCTCTGTGCGATTTGACTG
TGAGCTCCGGGCAGTCCAAGTCAGCTGTGGATTTCACCATTCAGGTAGCGGCTGGAACTTTAGGGTATAA
CTGCGTTTTTACAATTGTGCTCAGTAACTTATTTCTTCAGATTTGATGAACATAGCCTGTTAACTGTGTG
TTAAAAGCTGTAGCGTGGCAGTCTCTCAAATCTGTAAGACCTTTGTATTTATTACAGAATCTCTTTAAAC
AACTATGGCATGATGGAACAGGTACTTGTCTAGAGATCTAACTTCTAGTCTGTCTTCCTGTGGACTTCTT
TTATAATTCAAGACAGTCTGGAAGATGAAATAATCCTTTAAATCTCTTTCAGTTCTAGAATGCTGTGGTT
TTTGTAACATGTTCCCATATTTTGTTAATGTTCAGTGATAAATGTATGTCAACAAATTTACTTTCTTAAA
ATGTAGAAAATAATTAAATTCTTAGTAAATTATTGGCATTTGGGTTAGCTTTTGCTGTACTGTTCAACCT
TTATAAAAACAAAAATGTTAAATTCCTTCCTTGAAGATTATTTGATAAGGTATTAACAGACATTAAAGTT
CTGCTGTTTCATTGATGTTGTACGTAATTGTGCAGACCTCCTATCCTAGATAGGAGAGAACAATATTTTA
TATGTAGTTACTCATTATTAAGAAGATTTTACAGTTGACCTGAACCAGTGTGTTAATAAGAATTAATGTT
ATTAAATGGCATTTATACGAATTTTTAAGTGTGTATTATGAAAAAATTATACATTTATATGACCTACAAA
AATATTTTTCAGAACTAAAATTAATTTCTCATTAAATACAAATTTGTCCTTCAGTTACCTATTTTTAATG
GTTCTATAAATCTTAAATAGTGAAAATTACACTGCTTTTAGTATAGTTGTGATAGAAATGTAAAATGCAT
ATAATGAAAAAATAAAGCTGTGTGTTTTGGTTGCAGTGGTTTTAATGGAAAATGGAGATGTCTATACATT
TGGTTATGGGCAGCATGGGCAGCTAGGACATGGAGATGTCAACTCCAGGTACTTGCTAACTTTTCATTTG
AAGATCCAGAGTTATTTTTTCTTCTGTTTTCTTTTCCTTCTTTTTTCTTTCTTTTCTCTTTTTAAGTATA
TATTTCTAGAATTAAAATAATATTATACCACTGCTTTGCAAAGTGTGGCCCATGAATTATTGGTGGTTTC
TGATCTTATGGTTGAGTGCTTTTGTAGAGATAAAGGATTTTGTAGTTTCAGGAGAAAAGCTGATATATAT
TTTAAATAGGAGAGTGATTATGATTGTCACAAAATATCACTATATTCTTAGCAATTATCTTTTTAAAGGC

FIG. 7C (Cont.)

TGTGCATGGCAATAGAAAAATAGTGAATTGTATTTTTAAAAAATGTCAGCAATGGATTCAAACATATTCC
TGATGTCTGTTTTGAAATTTTGGTCTAATAACATGCAGTCATTGAAGCTTTTGAATAATTTTTGGACAGA
ACCTATTGGTCTCTCTGATTAACTCTTTTGACTTATTGCAAATAGTAGTAGAGAGACTGGTGGTAATTTC
CTAATATCCCTACTTCATTTGTTTTAGTTTTAGTTTTAGTTCGTGACATGATCGTGCAGCTAAAGATTCC
CTTTCTCAGCTTCCATTGCAGCAGGATGTGGCCATGTGAACTTAAGTGATAGGTGCCACTTTGGAATCTT
GCTGTTAAAGGGAAAGGGTGTACCTTTCCATTTGTCCTTCTCTCTTCCCAGCTTGCTGGCTGGAATGAAT
ATGTGGAAGCAGAAACTAAAGAAGTCATCACAGAGATAAGTTGGAGACTGTGTACTGAGAATGGCAGAAT
CATAAGATGGGAATAGGCTGGGTCTCTGACACCATGAACTGCCTCATCAGCTTCTTAAATTGCATGCTTC
TTGCGTGAGAAATAAACTTGTATCTTGAAGTCCCTCTTACTTGTCTTTCATTACAGCAGCCGAGTTTGTA
TTCTACGTAATGCAGTCAGAATACTTTTGGTCAAAAGTAATAGAAAATCCATCTTTATTAGTTCAGGTCT
TCCAGAAAGCAGATGCCAAGACAGGATTAGATATGCAAAGAATTTATTAGATACATGTAGTTTTGACCCT
ATGAAAGGAGAAAGAGAAGGAAGAATCGGGTAGGAGTCTAGGTTCCAGCATAACATTAAGAGAGTTTTAG
CCAGGCCAGTGATGTGTCCCCAAGCTGAGGATACCTTTGGAAGGGTCCTGCATTGGGCAGGAATAGACCA
ACATTCATACCTTCACCATGTTCAGTCACAGCTGGTAGCACCCCAGGGGACGAATGTCCTCGTGCATCCA
AAGGGACAGCACCTGAGGCTGTTATAATAGTTAACTCTGCTCTCTGTAGCAGATTGTCTTGAAGGAGATC
TGAGTGGTCTGTGTCTGTGGTTGTCTCACCATGGAAACAGGAGTATTTATGAAGTCTGGAAAGATAGAGA
GCAGCTTCAAGCCAGACTTCACTCAGCAATTCACTTAGCTGCAAAAACTTACCTTTTGACCTTCTACTCT
GCCTTATTCTTCCTCGCAGTCACAGTGTATATGCCAGAATCAAGGGGACTTCTATGGTTTCTCCTTTACA
TACAGTGAAAGAAAGAGAACTTACCTTCACATAGTCATTAAATAAAATTCAAGGTTGTCACTGTGTCTTG
AACTCACTCTACTATTGTGGCAGGGATGGAATTCTGCCATTTACATGGTAAAGATTAGTGATTCTTAACC
CTGGCTGTATATTAGAATTACTTAGGGAATTTGAAAAAATATCATATGTGGATTCTACATCCAGCATTTC
TGACAGATGTGTGTGTTGAAAGGCTTGTGGGTGGGACAGGGGTGGGGAGTGGTCCTTGATAGGATGCCAG
CATCAGAGTTTTTTCTAAAAGGTCCCCAGATTCTATATGTATCCAGGATGAGAACCACTCTCTACCCTTC
GAGCTGAGGCAGGGTCAGATCTGTGGGCACTGCATAAAAAATGGCAACAAAAGGGAATGTCCTGAGTTAT
GTTTATGAATGTTGTTGCTAATGATAAGAGACGATTGAGATATCATTGAGTTGAACTTCTTATTAAAAAC
ACAACTGAAACATAAAATTGATACTACTATCAAGAGGTTTGTAAAACTATCACAATCATAAATATTTAAT
GACTAATATCATACTTGCAAAGAGCAAAAGATGTGTTTGGCAGAATTACTTTATCAGATGTGTCTGCTGG
ATATGACATAATACCAACAGTGTTGAGCAATTACTGTCACAGGTGTTAGATGCCAACTGATATTTTGCTT
TGCAATTGAGTAACATTACTGAAATGCAGAGGCTGAATCTGGGTAGTAATTACAGTTGGCCCTCTGTACC
TGTGGGTTCTGCATCTGTGGATTCAATCAATCTTGACAGAAAACATAGTTAGGCCTACGATAATTGCATC
TGTACTGCACATGTACAGATGTTTTTGTCTTGTTATTATTTCCTAAACAACAGAGTATAACAACTATTAA
CATGGTGTTTACATTGTATTAGGTATTATAAGTAATCTAGAGATGTTTTAAAGTATACAGGAGGATGTGT
AGTTTATGTACAAATACTATGCCAATTTATATAAGGGATTTGAGCATCCCTAGAGTTTGGTAGCTGCAGG
GGATCCTGGAACCAATTCCCCATGGATGCTGAGGGATGACTATAACCTGTGTGGGGAAGAACGTGGCAAC

FIG. 7C (Cont.)

TTTTTGTTCTGTTTCTCATTTGAGAGTTGGGACACAGAAGAAGAGGGTTTATTTGTATCATCGTGGCTAT
TGTTGTTGTTATTTAGCTGGTGGTTATTTTGTGAGCCATAGAAACTGGGAAAGGTGCATTGCAGTTAGAT
AAGATGGGGTCTCAGTCATGTATGCAGCAAAGAGGGCACTTCACAGAAAATAATTGGCAAATAGTATTTC
ATGGTCTTGCCAGAGTGGAAAGGGAAGTAGTGAAAAGCATGGCCATGTTATAGTCAGGTTATGTTATCTT
ACTGTGCACTTGGCACTCAGAAGAATGAGCAGCATGAGCACAACATCCTTCCACACCACACTGAGGTGTG
TTGGCCGCTGAGAGGGAAGGTGTTCATGTCAGCTTTTAAAATGAAGAGATTACCTAAAAACATTACTTCG
TGGTCCTGATTATACCAGTGAACACCATTCTTCGATTCCCAAGTCTGAAGAGATATAGGGCAGTTTCAGG
CCAGACTTCCTCAGGTAATAATATTGTAGCAATATGCTCAATATTTTAAATTGCTTGAATTTATCGTCTT
CATGAAATACGATAGCATTTAATGTTGAAACAAAATATCAGGGTTTCTTATGAAGATTAAACATTGGTAG
GATCTACACAGTGGTATAGTAACTGGTAGATGCTACATAGTCATCGAACCTGGAACTGTAGAGGCAAGGT
TCAGCTCTTCACTTCTTACCAACCATATGACTATAATTTCTTAAGATTAAACACTGGTGGGATTTGTTTT
AACTGCCCAAAGTTGTTCTTTTCCAGCATGGAATGTTTTGGTCCTTGTTCCATTGAGTGGTAACTGAAAG
ACTGATTACATGAAGTGTGGGCAGAGCTACAACGGATAATGCAGTAGTCATACCTATATACTGTGCCTAG
TGGATTAGATATTCATCAAGACCGCTTCAGTCTTAAGCACTCAGTTACCCTGTCTGTCTGGACTTTTGTG
GAACTTGGAAAGTAGCAACCAAGAACTCTGTTATTAATTCAGAAAGGAGTTGATTATGTCTATAGAGGAA
CAATCTTGGGAGGAACAAAGCTTCTATAGCATATGTATTAACTACAACAAAGCAAAACATTTACAGATAG
TTGAAATAAAGGGTTACAGTTGGAGAATATGTTTGAAAAGTCTCTAGTAATCAAGAGCTGTTAACTGGAA
TTTACTATATAGCACACATTAATAATGTGTTGTTTAAGATCAATATTGTGGTATGCATGATAATGAAGAT
GGAAAAGTGTTATTGATATTCTCTTTATTTAATGTGTTATATTGCCAGAATGACTGAGTTCAGTCTCTAG
GTTGGGTCCTGATTCTGTCACTTGGTAGCTATATGATCTTGGCCAGGTTACTTAATCTTCTTGTGTCTCA
GTTTCTCAAGTTTAAATATCCATAATCTGATGATACTTTCTTCTTCTGTGATGCAGCCCTACTTTATTTC
CCTTTGACTTTATGCCCCACAGCCCTCTACTTTTTTACTCTTTTTTCACCCTTTTTTTAACTTTATTTCC
TACTCAAGTTAAAGACTGTTGCTTAATTTCTTCACCTATACTCTTACCAGTTTCTTCAGTTTTCCCACTC
TCTTGGTCGTGGTGCTAGGACATGATAAAACCGCAAACATGAATCAATCTTAATATTTCCTATGCCTATA
CTTAGGCTTCTGGAAGGTAAGAAATCACCATACCTATGCAGATTGATACTTAATTTCCAGATTCAACCAG
TTCCTGTACAATGGTCATTAATCCTCCTGTTGTGTAGTATTGAACTATTTGACTTAATACCTTTTGAGAG
TTTGATGAAAGACATGGGGTCTCTATGAAAAATACAAGAATATACACTTAAAAATTTGCTTGCAAATTTA
GGAGATCTTTTGAAGCTCACTCATGGACTTCCTAGAAGTCCTTTATATCTGAGTTGAAAACTCCTGCTCT
CGGTATGTATCTATTCCATCTACCACCACACCTTTTCTCGAATCTTCAAACTCTCCACTCACCTGTTTCC
TCCTTTTAGCATAGGATCTCCATGTACATTGCAACAGATGTAAGAAATTATTCAGCCCACCAACCCTGCA
AACCTACTTCCATCCATACCACTTCTCTGCTTCTTTCCTCATGTTACAGTTAAAGAGGAACCTGTTGTGT
CCTTGCTATGAAACCTAGCTGTCTTTTCCTTAGAGATCTATTTCTGTTTCCTGTCTTCTCTCTAACCTTT
GTCTTTAGCGTCTTTATTTTGAGTCACCTTTTAAACTTCCTCAAATCTCTTATCATTAAAAAAAAAAAAT
CCTCTCCTTCAGCTTCATTTTTCCTTTAGCTGCTGGCTCTCCTTTCTTTTTCCCTTTAGTGCTGGGATAC

FIG. 7C (Cont.)

TTAGAGCTACTTTGTGTATTCTCTGACTCCTTATCTGCTGCATTGTGGTGCCTGCTTCCACCAAAGAGAC
CTCCTTCTGCTAAATCGAGTGGTTAGGTGTATGTCTCCTTAGAGCATTTGGCATGTACTTTATTTTCCAC
GCTTGAAACCTACTCCTCCAATGAGTCTCCTTGAGTTCTTTCTTTCTGTGTGGTTTATTCTAGATGTCTG
TGAGCTGTTCTTCCTCGGTCTGTATCTAAAATGTTAGAAGAGACTCATAAGGGAAATTAGGATCTCTTCT
TTTCTCTCTCAAAGAGTCTTCCTAGATCTCATTCATTCTCATAGCTTAAGTGAATATTACCACTATCTAC
TCTGTTGCTTAAGCAAAAAAAATCTTCCTTGCCCCATATCGATCATCTGCCAAGTTTCATCAATTCTGTT
CCTTACATAGCTATCAAAGTCACCATCTCTTTCACTCTGCACTGCTCCTAGTTAAGGCCTTCATCATAAA
TTACCCAAACTACTATATAATTTTTAAAATTTAAAGTGTCATAATTACATTTCTCAAAAGCAGAGCTCTC
CTGCTATGTGTGGACTATTTCTATAATGGTTGTGTTTCTAATTACAGATAATGGTTACTAAAAATGGCTG
TTAAAAGTAGGAAAGGATACTAGGATGTCATTTATCATAATAGTTACTGTTCATTAAGTGTTAACTGTGT
GCCAGACGCTGATCCAAGTACTTGACACGTATGGGCCTCTTTACTGTTCACAGGAACTCTGTGGGGGTAG
ACACCGTTTGTTAGTATTCTCCATGTGATAAAGAGGAAACTGAAATACAAAAAGAATGAAAAACTTGTTC
GAAGTCTGGTCGCATTATTATTAAGTTGGGGAGCCAGGATTCACAACCAGCCAGTCTAGCTTTAAAGCCT
GAGCTTGTAGTCACTGCTCTAATGCCTCTCATGATACTGTGTTTTGACTCATTAACTGTGATTCTAAGAT
CTAAACTTATAGCTTAGTGATAAAAGTTAGAAAAGATGATCATAAAATTATTTCATCTAGTTCCTGGATT
GAATTTCTGTTAAGGCATTACATGATTTTTATTTCATCCAATAATTATTTATAAAGATCTCTAACAGGCC
AGTCAGTATACAGAGTACCAGATTAAAAATAAATGTAGCACCAGTTTTTCAGAAATTATTATGTGTCTAT
AATTAGGGTAATTACATTTAGAAGATCTTTTTGATGATCTCCTTAAAGTCAGCAACTGTCTTTTTCATCT
TTGTTTACCTAGTACCTGGAATGGAGATAGGCGTTTAGCACTTAAATGTTTACTGAATATTCTTATGAGT
GCCTTTTATCTTTCCTACTCCTTGTTGCATTGCTTACTTATTGTTTTTATTTTAGTTGAGTTTTGTAAGA
AATTGACTTACTTTTTTTTTTTTTTAACCTAGGGGATGTCCCACTCTTGTTCAAGCATTGCCAGGCCCTAG
CACACAAGTCACTGCAGGCAGCAACCATACGGCAGTACTTTTAATGGATGGACAGGTCTTCACATTTGGA
AGTTTTTCTGTAAGGAATTTTTAAAACATTAATAATATTGCATTATACCATTGCCTTATAATTTGTCTAT
ATTAGCTCTTTTTTTCTGTTTCCAGAATATAATATAACAATTATATTATAATTGTTACATATGCATATTTC
ATGCCTTCATCCCCAACACACACTAAACCTGAATGATATTCTTTGAAGTAATTTTCCTCTCTAGCTCAGC
ATTAGAATTTATTGAATTTAACAGCTTTGTTAGAATTGGACATGTTTATTTCAGATTAAAGTCTTTTAAG
CATTCAATAGAGCTAATTCTGTCATAGGAAAGGTTATTTCTCATCTAACTTGTAGAGATGAATTTTTCTT
AACACATAGAACTATGCTATTTTGTAACCTTTTAAAAGCCTAGTTTTTTTTATTTGATTTGTTTAAAATT
ATACTTTCTTTTTTCCTTTTCCACCCTCTGAGTCTATCCGCCTGTCTGTTACATAGGCGCTTGTGCACAT
TCTCTCCCTCTCTCTGCACCAAAGCTTAAAGAGTGAAAATGCTCTAAGAATTTTGTGTAGTTTGGGCATA
GTAGATATCAAGAAAAATCTTTGCGAGACTGTGCTAATACTCTTGTACCATTTCAGATGTGGATAATTAC
TAAGAACTCTTGAACCTAAGTGTCTGAGATGACATTTACAGCTTTTGATTTTTTAAAAACTGTAAATGTG
TACTTAAAATATTTTATTTGAAAATGGTTTCAAACTTACAGAAAGATTGCACAACTAAGAACAGTGTGTA
GAATATCTGGTTAGTGTCTTTAACCAGATTCACCTATTGTTAACATTTTGATCCAGCATTTGCTTTATTA

FIG. 7C (Cont.)

TTGCACATGTGGCTGTTCTCTTTCTCACACACGCAGTGTGTGTGTATGCACAAATGTGTGTGTGTACGTA
TGTATATAAAATATTTTTTTTCTCAAATCCTTTGACAATGTCTTGTGTACATTATGGCCCGTTACCTCC
TACATACTTTAGTTTGTATTTTGTGAATTGACCTAATAATTATTTTTTGGCATTTCTTTCCCCTCCAATC
TAGGATCAGGCATTACATTTGCCTGTTGTGTGTCTTTAGTCTCCTTTAATCTGTAACATTTCTACAGCTA
TGTATTGTCTATTATAACATTGACATTTTTGAAGAGTATATAGTACTGTTTTGAAAAATAGAATCCTCTT
CATTTTTGTTTCTTTGATAATGTCCTCATGTTTAGATGCAGGTTGTGCACCCAGGCCAAGATACTCTGTA
AGTTATGTTGTGTTTGCCCTCACTGCATCACATCTGAAGGCTCAGAATGTCCATCTGCTCTTCATTGATT
ATGGACATTTTGATCACCTGATCAAATGTCTGATTTCTGTACTGTTTCTCCTTTGAAACTATAAGCAACC
TGTAGGTTGACACTTTTAAGATGCCTGCTTCTCATCAAAATTTCCCCCTAGATTTAGCATCCATTGATCA
TTCTTTCCTGAGCTAGTCTTTACTATAATGTTTAAAAAAATGGTGATTTTTTTCAACTCCAGTAGGCACTT
GGCCTTTTACTCTAAGCAAGAGCCCTCCTTTCCTGTTTACTTGTTTTTCTACTTATTATTGGTATAGACT
CAGGTATTTGTATTTTCTTCATTATCATCTTTAATTATTTGGGTGCCTAGATTATCTCCGATTTGGCCAG
CAGTAGCCCCTTCAAGTTGGCTCCTGTATTCTTGTGACATGCCCCTTCATTTTTTGGAGTGCTTCCTTTC
TTTCCAGCATAACAAGTTGTTCAGGGTTTATCTTGTACAGGCCCTGTATGACTGTCCTAGAATCAGCCAT
TTCTCCAAGAACCCTGATTCTTTTTAGTGGGGAATAGTATTAGACACTAACTGGGCACTAGAAGTGTTCA
TTGCTACAGGACGTCTTTGGATCTCTGGTATGCATATATTTATATGTCCACATATATGTATGTATTTTAG
AAATCATAGGCCAGGTGTGGTGGCTCATACCTATAATCCCAGCACTTTGGCAGGCCAGTGTAGGAGGATC
ACTCAAGCCCAGGAGTTTGAGACCAGCCTGGACAACATAGTGAGACCCCATCTCTATTAAAAAAATTAGC
TGGGTGCCGTGGCACATGCCAGTGGTCCTAGCTGCTCAGGAGGTTGAGGTAGGAGGATCACTTGAGCCCT
GGAGGTCGAGGCTGTAGTGAGAGCTGTGATTCCATCATTGCCCTCTGGCCTGGACAGCAGAGCAAGATCC
TGTCTCAAAAAGAAAGAAAAAGAACCCCACTGTGACTTCTACTTCCAATCCATTCCCACAAGGTTCTTTC
TTACCTGTCCTGTTCTATATTTATGTACTTTCTTCCTCAGTAAGAATCTTTCCTCTCAACAATATCAATA
TATTTATTTCTCACTTAGTCCCCAGATATGTCTAAAATAGTTTTATATTTGCTTTGCCTGTACAAGTTCA
AAAAAACAAACTCACTGAAAGGTCATTCTTGCTCTTTCCCCTCCCACCTGCTCCCCACCCCAAGTCTGAA
GGTGTATAGTCAAGCACTGTCCATGAGTGGCCTGGATTCTCTCTCTCACTCCTTTCAGTGGAAATTGTGA
TTCCTTTGGAATAGAGTGGGGCTCATTTGTTTCAGTTTAAGATTCCCCTCACCCTATCCTTTGATTAAGT
TTTATTTCATTTTTAAAATATATAGAACATTTACATGTTGCTAAAAATTAAGTTATACAAAAATTGTATA
CTCAAGAGGTGTCACTTCCTCCCATATCCTTGACATTCCTGCCTCCCCACACCTTTCATTCCATACTTGG
AGGTAATGAATGTCATTGTTTTACAGTTTATTCTTCTTGTGTTTCTTCTTGTGAAGATATATAAGCATGC
AGACACACTATTTTATATATATATACCTATATATGTATGTATGTGTATACACAGTTATGCACTGTATAAC
AGTATTTTGGTCAGTGATGGACTGCGTATGCTAAGGTGTTCCCATAAGATTATAATAAGTACTTTGACTA
TAACTTTTCTATGTTTACATGCAGAAATACTTACTAATGGGTTACAGTTGCCTACAGTATTCAGTACACC
AGCATGCTGTACAGGTTGGTAGCCTAGGAGCAATAGGCTACACCATATCACCTAAGTATGTAGTAGATAT
ACCGTCTAGGTTTGTATAAGTCCACTCTGATGTTCGCAGCATCACAGAATCACCTAATGACACATATTTC

FIG. 7C (Cont.)

AGAACATATCCCTGTCATTAAGTGACATGTGACTGTACATAAATATATATATTTCCCCTTTCCCGTTTTT
TAAAGGTAATAGCCTATATATGCTCTTTTGCACTTTGCTCTTTTCGCTTCAGCATCTCTCCTAGAAATCA
CTCCATATCAATTCATAAAGCTCTTCATTTTTTTTTTTTACCTCCATGTAATACCCCATTGTGTGTATATA
TGATAGTTTATTCATTCAGTTTCTCATGTTTATATATTTACGTGGTTTCCAATACTTTGTAATGGTAGTA
GTGAATATTGTTAGAGGTGTATCTTTGAGATAAATTCCTAGAAGTGAGATTACTGTGTTGAAGGTTAATG
CCTATGTAGTTTTGTGAGATATTAACAATTCTCCTGTATTTTGCTTTCACACTAACGGTGTATGAGATTG
CCTGTTTCCACAGAATTGCCAACAGAATGTGTTGTGGTACCTTTAATTTGTGCCAGTCTGATGGGTGAGG
AATGGTCCTGCTTACTTCCAAGTTCCTTTGCCTTTAGTTGGTGCTCTGATCCTCAAAGTTCGGATCCATA
TTTAGTATTTTGGCATTGAAGGTTAACTTTCTTTTTGGGGGCATGTGTTTCCCTGTGCTTTTTCTAACTT
CTTCACACGCCTCTGTCCTCCTTCTTAAGAACTTCCCTGTTCGTGCTTTGCACATGCTCAGGTTTGCAGT
AGCCGGTGGGTGGAGAGAACTCTTGGAATTTGGCTCTTCTGCTTACAGGAAACATAGAGATCATGACACC
CGCTGTCTCCTTCCACTGCTGAAGGTTTGAGTCACATATAGATTTGTTTGCACAGCATATTTTTGTGTCT
TTTGAGGTGGTTATGTGAGTGATAAGATTTGACGTCAGACAGTCATTGTCCTCCAGTCCCAGCAGTCCTA
GTTGTGAACTTTTATGAATTTAAATGTGGCTTATTTATAACCACATTCTGGTCCTTATGGGGTTGTCCAG
GTATCTAACACATTTTTGGACTGCTTTTCTTCATATTAGTTGGTAGTAAGGGAATACATATTTATTTCAA
TAGTCAATGAAAAAGATAACTAATTTATTTTTCCTCCAAAAGCAGAATATATCCCTGAATATGATATATT
TTGCTCACTATTTACTTTTTTTTTTTCTTTTTGAGACAGAGCCTCACTCTGTCATCCAGGCTAGAATGTAG
TGGCATGATGATCTCAGCTCACTGAAACCTCCGGCTCCCAGATTCAAGCAATTCTTATGCCTCAGCCTCC
TGAGTAGCTGGGATTACAGGCCCATGCCACCACACCCAGCTAATTTTCGTATTTTTAGTAGAGACGAGGT
TTCACCATGTTGGCCAGGCTGGTCTCAAACACCTGACCTCAGGTGATCCTCCCATCTCGGCCTCCCAAAG
TGCTGGGATTACAGGCGTGAGCTACTGCACCTGGCCCCTGTTTACATTTTTGTGCTCTCTTATTTTTGTC
AAAAAATAAGGACAGATCTTAAAAGAGTATGAGAAATAAATGTTGAGTGTTTTGGCTGCTTCTCTAATCA
TGTGCTTGCCATGTTTCCTTCCCTGGTTCTGTCCAGGGATTGAAGCTCAGTTGCTTCCACAGTTAGTTTG
TGGCTGTGTTTTCTTGCTGTGCTACCTGGTGGTTGGATGAGAACGTGACCAGAGTGTTCGCAGTGCTCCA
GGCTCCCTTGTTCCAGAATGCTGTGAGGGGAGAGAGGTCCCGAGCCAGGGGTGGAAGAATATCTATTGAG
TCAATGTCAGCATTCTTTTATTCTTTTTCAGCTACAGGCTTACTAGTGAGAAACTTCCTATTACTTTTTA
AATTAAACTCTTACCTGACCAGGTCCCTATAGAGAGCCATACTTTTAAACTGGTTAATAGTTATTTACTT
AAAATATCATATCTTACCATTGATTGTGCTGTTTATTTTAAAACATAAATGAAATAATTTAGGGACATAT
CATGTGAAAACAACATTACATATTTTTCTAATTGTATTCACAGTTTCAGTATTTATTTTGGTCTTTTTAC
ATGGATATTCTCAGATTATATGAGTTCAATAGTGACTTTCTTTTATACTATCAACTTACTATGTCAAAGT
GACTTTTTAAATGAACAATTTGGAATACTAATATTTTAACATATTGTGTGTATTTGTCGTACTTTTCATT
TAAATGTAGGTGAAGACAAAGTATTTTGGAGATACTTCTTGCGTGGAAAATATTTCAAACTTTTTTTTAA
AAAATAATGCACTTTTTAAGACTTTCCAGGAATAATAGAAATTATTTTATTACTTTATAAATATTTGGTC
CAAATTCTTACATATTGTATTTATTTTAAAAACCCAAACTAACAATTGGTGAAAAATAAGGTTTCATAGA

FIG. 7C (Cont.)

TTGATTTTTATCTACTGCCTCCTTAACTTTATGAAAATTAGATTGTTTACACAGCAATATTGCTAATATG
GTTTATTTAATCTTTTAGAAAGGACAACTGGGCAGACCAATTTTGGATGTGCCATATTGGAATGCAAAGC
CAGCTCCCATGCCTAACATTGGATCAAAATATGGAAGAAAAGCTACTTGGATAGGTGCAAGTGGGGACCA
AACTTTTTTACGAATTGATGAAGCACTTATTAATTCTCATGTACTTGCTACATCAGAAATTTTTGCCAGT
AAACACATAATAGGTAATACCAGAAATAAACAAATGCCCCTTCCAAACTCTTGTCTTGATTGATAGTAAA
TGGTTTATCTTTCCCTTTAATGAAATGTACTTTTGTAGCTTTTTGTTTTCTTTCTGCTCAAAGAAATTTA
AACAAAGCCTGTAAATGTCTCCGTTTATATGTGTCTCTATGCTGAAAGAATGGAATAATTGGGAGATCTG
GAAACCACAGTATTTGTGAGCTAGACAGTGGTAGAACTATAAACTAAATTCTAGTAGGATAAAATCCATA
TTAGAGTAAGAGAGTTTTATGCATTGTTTATTGCTAAATAAATGTTAGAAATTAATTTTTATGGGAGGTT
ATATAAATCCAACTTTGAAATTTCACGAAGACCAAGTTATCAATCTGTACTGTGTCCATGATACTGTGAA
TAATTATATAATAGAGTGGTATAGCAAGAGATTAGGAGCATGTGTTGTGGATTTAGACATCTTGAGGTTT
TATTCCTAATTCTCCCACTTAAAGATTTTTTAATTACTTAGCCTCTTTTATTCTCTGCTTATTCACCTGA
GAAATGGAGATAATACTACTTTATGGGTTTTGGAGAATTTAAAAGGGTAATATATATTAAAATTATATAT
AAATATTTTTTTCTTAAGGCTTGGTACCTGCTTCTATATCAGAACCTCCTCCATTTAAATGCCTTCTGAT
AAATAAAGTGGATGGGAGTTGTAAAACTTTTAATGACTCAGAACAAGAGGATCTGCAAGGATTTGGTGTG
TGTCTTGATCCTGTATATGATGTAATTTGGAGGTAAGCATCTCAGTTTATAAAATAGTCAATAAGTTTTG
ATGCAGTTATACTCTTATGGTAATATAAACTTTATTTACAGGTGGACTTTTCACATGTGAGTACTCTCCT
GTTTATCTAATAACTGCAATTCTGTCTCAGTGATTCACAGGGACCTTTATACTGTAGCATAGTGGTTAAG
AGCATGCATTTTAAGCAACACTACCTAGGTTTATCCCAGCTCCACAACTTGCTTTCTGTGTCACCCTGGA
GAAGTTACTTTGACTGTGTGCCTCAGTTTTCTCATTTATGAAATGGGGATGCTAATACTACAGAGGTGCA
TACTAGGTGCCATATAAGTGTTTGCTATTATCATTATAATTATTAATTTTACTGTTGAGAGTTCTGTTGT
TATTTTTAGTCTGTCATCAATCCTGTTTATATTGTATAGAATTCATTCTATTTTTTGTTCTCATAATTAT
TATTAACTATGAGGAGGAAATTATGCCAAAGACAATAAAGAATAAAGAAGATAATTGAGCTTGCCCTTTA
AGAATGTGCATTAAAAAATACTCTTACTGGTAGAGAAATATACAGGATTATATGCATTCTGGAAATTATA
AAAACATAGAGATAAATAAGGCACAAAAGAGACTCAAGAAATTATGTTGCATTTGTTTGAAATTTATTGT
GGTGCTGGGCCGGGTGCGGTGGCTCACGCCTGTAATCCCAGCACTTTGGGAGGCCAAGGCGGGCAGATCA
CGAGGTCAGGAGATCGAGACCATCCTGGCTAACACAGTGAAACCCTGTCTCTACTAAAAATACGAAAAAT
TAGCCGGGCGTGGTGGCGGGCACCTGTAATCCCAGCTACTCGGGAGGCTGAGGCAGGAGAATGGCGTGAA
CCTGGGAGGCGGAATTTGCAGTGAGCCGAGATCGCACCACTGCACTCCAGCCTGGGCGAGACTCTGTCTC
AAAAAAAAAAAAAAAGAAAAAAAAAATTATTGTGGTGCTTTATATACAAAATGAATAAATAAGTTACCCTT
CTTAGTGTTTCTAGCTTTGGATACTAATAGGAGGTGTACCCTGCCATCACCACAGTGGCTCATCACAGGG
CTGAGCACTTCTTTCCTTTTGCGGCCGGCCTTAGTAGGCAAGATTCCAGTAAGTTGAAAGGTTGAAGTAG
TGTGAGTGAGGAGACTTTTTCTCTGTCTTCCTTCTTCTACCCATGCCTGCTTGCATTCTCATCAGACAGC
CAAGTTCTAAGAGGCCATGTGGTAGCAATGGGATAGATGATCTCAAATGTCTTGCCAACTCCTTGGTAAT

FIG. 7C (Cont.)

TTTCTTCCGTGTTCCAAAATAGAGATTAATAACGAGGCTTGCATTCAGAGTGAAGAGACTGCTGCACTTC
CCAGGTTGCTGGCCAGCTTCCTCTCTTATTTGGGCATTTTATGAGAAGGCGTAGTGGCCAGTATTGAGTT
GAGTACATCTCAAATCAATTACATCTCCCTGGCAGCATTGTGCAGGGTAGATGAAATAACAAGAGACTAT
GGGTGAGTGGTCTTTTGTGATCATTCTTATGAAGACATGAGGTATTAAGAACCAAAGTTAGAATGGTCAC
AGTGGGATAGAATGGAGGGGATAGAGAGGAGAAAAGATGTAAAGATAGAATTGGCTGCAGTTACTTACCG
ATTAGAAGTCAATGTTCAAGAGACTTAGTTACCAAAGAGCAGGCTCTGGTTTGGACTTAGGTGTAAATTG
ATGTTTTACTGTTTTGTAGTTCTTACATGTTTTATTTTTAAATGAAGTAAATTTGCATTAGCAAAACAAA
AATAAAAATTGGCAGTGTGGAATCTGTTTCTGGATGCATTCACTAAGTTAGCAATAACAGTATAACTAAG
CGTAACAGTAAAAACTTACTTGAACTAGAACCATTTCCGTGGGGTCTTAACAGAACTCTCAAGTATGATG
TTCAGCTGGTTGAACCTTGTCTTTTCCATTTATGGTAGTAGCAATGGGACAGATGATCTCAAATGCCCTG
CCAGCTCCTTGATCAATTTCTCCATTGTTGGAAAACAGAGATTAAGAGATGTTTTGGTAAAACAGCTGAG
AGGTATTTTTCTTTAAATCAGGATCAGAATTTCTGTTATCCTGACTTCTGGCTGCTTTGTGTCTTTTGTG
TTTTTCAATGGGGCACTTAAATTTTATAATTATCATATGCATTGCACATCCAATATTAGCTTACTTTGAC
TTTCCTTCTGGCCTGCATCTGCTTCATTTTATATTCTTTAGGAGCCAACTTTGCCTGAGTAATTAGAAAC
AACATCTATAAAGAGCAGATAAATGTTAAGAACACCTGTTTTATTTCCCACATACAAATTTACACAAATA
ATATGTGAATTTGTGTTATTTTTTAAAAAACAAAGCAAAAATACATACAGGAAAAAGGATGGTCATACTC
TGTATCTGTTTCTTTTCCCATACCGAATTCCACTAGCCTTCTCTGTGGATCACAAGTATGAAGTTTGATT
TATATCATCTGACACCTTTTAAAATGCATGTATTTTTCTTTTTATGTAAATAAAAACATACCTACTCTAA
AAGTTAGATTTTTTGCTCAAAAATAATTTAGAGATCTTTCCAAGTCAGTATTTAAAGAACAGCTTCATTA
TTAAAATTGTGGAATTCTGTAGTCTGGGTATACCAAATATACTTAACTGTTTGCCCATCAGTGAACATTT
TAGATTTTTTTTAATATTACGATACTACCTACAATGCTACAGTGAACAAATACACAGGTATCTACACACA
GAGTTTTACACACATGTGGAAGTATTTCTGCAAGCTAGCTTTTAAAATGTAGAATTGCTGAGTTAAAAGA
TAGGCTCACAGAATTGTAAAATGACTGAGGTAAGTCTGAATCACTTTAGAAGTTTATTTTTCCAAGGTTG
AGGAGATGCCTGGGAAGAAAAGACAAGCCACAGCAGGATCTGTGCCCTGTACTTTTTCTGAAGAGGTTTG
AGGCCTTCAGCATTTAAAGAGGAAAAGAGAGCAGGAGGAGAAAAGGAAAAGAAAAAATGAGAGGATGTGG
TCACATTCTTGTAAGGTTTTGATTAGGCTTACTGAATCCACATGTTGCACATGAAAAGGAAGGGGTAGAG
GGAACAGTGAATTTTGTATTTGGAGTTAAAGTAAACATAGAGTAGAGGAAGCAGTCAAATACTCATTCAT
CTGGGGCTGGGGCGGGTGGGGCTTGGTGGGGGGATGGGCAGATAATTTCTAGTATCTTCTTGTCTCTTAC
CATGAATTTTCCAGAACCAAAAAGAGATTTGAATCCATGGATATTAGAAACTATGTGTTTCTATTATTTA
CCATCAAGAGAGTTAGTGAAACTGTTGAACACTAAAGACCAAGGGGAAATCTTAAAAGCAACCAGAGAGA
AAAGAATGATTACCTAAACAATGAGATCAACAGAACTTCCCAAAAGCAATAATGCAATAATATTAATGCT
ACTAGTTATAGAAGCTACCATAATATATTTTCTCCCAAATGCTATTTTAAGTGCTTTTTAAAAATAATTT
AAAATTTTTTAATTGTGGTAAAAAAACAGTATAAAATTTACCATCTTAATCATTTTGAAAGTCTGCAGTC
AGTGGTGTTTAGTGTATTTATGTTATTGTGAAATAGATCATCAGAACTTTTTTTTCTTGGAAAACTGAGA

FIG. 7C (Cont.)

CTCTATAGTTATTAAACAATAGCTTGCATCCCTCACTTCCCGACCCCTAAAAGAGGTAAAGAAGTGGAGA
TAGTTTTTTGAAGTTTTTGTTACAAAAGAGATCAGAGAAATGGGATGATGAAGACGTTGTGGGTTCCTAA
TAGTTTTTAATTGGTTTTTACTGTTTATTCATATGGTTGAACATCCACATCCATTCTATCTGTGCTTCCT
TTCTATGGATAGCATTCCATGTCCTTGCCAATTTTTGCTATGGATTGATTGTTTCTAGCTCTTATACATT
GAGGATATTGTAGCTGTGTCTCACAGGTACACTTCACATTTTTCTTCAACTTGTCCTTTGTCTTTAAACT
TTTTTAATGGGGTATTTGTTGAGTTTCATATTTATATGTATGTATCAAAACTTTATACAGTCAAGTATTA
TAATCTACATTACTATTTTCTGTATTAAGTATTATAATCTACGTTACTATTTTCAAATTATTTCACTTTT
AGTGATATAGTTTTTTTATATGTTTAGCTTAGATCCAGAAGATAATGAGCTACATTTGTCCTCTTTAAGC
TGACTATATTATTTATTCTCTTTGTATCATCAGTTATGTTTTAGGAATTTTTTTTAAAAACAAAACCACA
TTGAGGTGCTGTAATTATTCTTTTTCTTTAAAGGTTTCGACCAAATACTAGAGAGCTGTGGTGTTACAAT
GCGGTGGTTGCTGATGCCAGGCTTCCCTCTGCAGCAGACATGCAGTCCAGATGTAGTATCCTAAGTCCTG
AACTTGCCTTACCAACAGGATCAAGGGCCCTCACTACCCGATCTCATGCAGCTTTGCACATTTTAGGTAG
GGTTGCGATTTGATGTACCATTAATTCACATTAATGTGTGCTGTCCAGGGTTTTTTTTTAGAGTATTTAA
ATTTATATGTAATTCTGTCTTGTTTGTTAAATAATAATAATGTACAAAATAAGTTAAATCCTCTAAGAGG
CTAATTCCACAGAAAACAATACATGAGACCTGTACTAACACTATCAAAGATTTATGTATGCCCAATTATT
TAATTTTCACAGAGGTAGACCCTTAAAAATAATGTTTTTGCTCAACTTGAATGTATAAACTTTTAAAGAT
ATGATAAAATTTTCAAGTATATAATATTTAATTTATGTATATTATGTTAAATAAATTCTATAAAATGTAA
TGAATTTTATATACATCTTCTGTTTCTTCTTATATAACACAGTTTTCCACAGCATATCAACTTCATTCTT
ATTTAATTACTTTGAGATGTAGTACTTATTTAATTACTTTGAGATGTAGTGCAATATATTATTTTGTAAC
TGGAAATTTTATATCACTCTATGTAACTATGTATTTTGTTGCTTTTAAAAATGATCCTTAAAAAGACTCA
TTTTCAGACTCTAGCACTTGCAGGTGTGAAATCATATTCCTAAATATAATTACCATATCATAAATATAAC
TCTTTGTTTCTTTTTTCTCAAATTTCATTTTGGTTTCTATTGTAGACATCCAAAACTAGTGTTGATTAAG
TTTGTGTGACACTAATGTGTCTTCCTCAAATAGCACTTTAAGAATCAAACTAATTTGGAGTTTCATAAAA
GGAAGAACCTTGTAAGAATTCAAAGGTTAAGTGATTTCAACTTTTCAGAGATCCAGTTTTGTGTAAAAGC
TTGTCGTATGGCAAGTTTAAATATGATCATTAATCAGACAAGGGATAATTTGTATTGGTTTTAAGCATTC
TTCCATGAAATGATGTTTAAAGCTTGGAGTAACATTCTGAGTTTATTTATTTTAATTTATCCCCTATAGC
ATTTAATGTCATCAATACCATAGGACATTTTAATTTCAAGCAGTTAAATTTTGTTTCTTTGTTGTTTTAG
GTTGTCTTGATACCTTGGCAGCTATGCAGGACTTAAAAATGGGTGTTGCAAGTACAGAGGAAGAGACTCA
AGCAGTAATGAAGGTTTATTCTAAAGAAGATTATAGTGTGGTAAACAGGTTTGAAAGTATGTATACTTCG
GTTTAGGAAATGTTGTCTTACAACTGAAATATATATGGATCTTTTAAAACATAGATTATGATTTATATAT
TCTAGGTCATGGAGGAGGCTGGGGTTATTCTGCCCATTCAGTAGAAGCTATACGTTTCAGTGCCGACACT
GATATTTTACTTGGTGGTCTTGGTCTGTTTGGAGGTAGAGGAGAATATACTGCTAAAATTAAGGTAAAGT
TCATCAACAATGTTGTCCTTTTTTGTTTGAACATACTGATTTTGACTTAATTTATTATTTTATTATTTAA
TGTCTAATTTTTTTCCTTTTTAACTGGGTTTATTTTGTTTTTAATGCTTCTTTTTAAAAAGCGATAGAGA

FIG. 7C (Cont.)

AAACATTGCTAAAATCGAATACAGTAATACTAAATTTTTTAAATTTATTTATTTATTATTATTATACTTT
AAGTTTTAGGGTACATGTGCACAATGTGCAGGTTAGTTACATATGTATACATGTGCCATGCTGATGCGCT
GCACCCACGAACTTGTCATCTAGCATTAGGTATATCTCCCAATGCTATCCCTCCCCCCTCCCCCCACCCC
ACAACAGTCTCCAGAGTGTGATGTTCCCCTTCCTGTGTCCATGTGTTCTCATTGTTCAATTCCCACCTAT
GAGTGAGAATATGCGGTGTTTGGTTTTTTGTTCTTGCGATAGTTTACTGAGAATGATGATTTCCAATTTC
ATCCATGTCCCTACAAAGGACATGAACTCATCATTTTTTATGGCTGCATAGTATTCCATGGTGTATATGT
GCCACATTTTCTTAATCCAGTCTATCATTGTTGGACATTTGGGTTGGTTTCAAGTCTTTGCTATTGTGAA
TAATGCCGCAATAAACATACGTGTGCATGTGTCTTTATAGCAGCATGATTTATAGTCCTTTGGGTATATA
CCCAGTAATGGGATGGCTGGGTCAAATGGTATTTCTAGTTCTAGATCCCTGAGGAATCGCCACACTGACT
TCCACAATGGTTGAACTAGTTTACAGTCCCACCAACAGTGTAAAAGTGTTCCTATTTCTCCACATCCTCT
CCAGCACCTGTTGTTTCCTGACTTTTTAATGATTGCCATTCTAACTGGTGTGAGATGGTATCTCATTGTG
GTTTTGATTTGCATTTCTCTGATGGCCAGTGATGGTGAGCATTTTTTCAAGTGTTTTTTGGCTGCATAAA
TGTCTTCTTTTGAGAAGTGTCTGTTCATGTCCTTCACCCACTTTTTGATGGGGTTGTTTGTTTTTTTTCT
TGTAAATTGGTTTGAGTTCATTGTAGATTCTGGATATTAGCCCTTTGTCAGATGAGTAGGTTGCAAAAAT
TTTCTCCCATTTTGTAGGTTGCCTGTTCACTCTGATGGTAGTTTCTTTTGCTGTGCAGAAGCTCTTTAGT
TTAATTAGATCCCATTTGTCAATTTTGTCTTTTGTTGCCATTGCTTTTGGTGTTTTAGACAAGAAGTCCT
TGCCCATGCCTATGTCCTGAATGGTAATGCCTAGGTTTTCTTCTAGGGTTTTTATGGTTTTAGGTCTAAC
GTTTAAGTCTTTAATCCATCTTGAATTGATTTTTGTGTAAGGTGTAAGGAAGGGATCCAGTTTCAGCTTT
CTACATATGGCTAGCCAGTTTTCCCAGCACCATTTATTAAATAGGGAATCCTTTCCCCATTTCTTGTTTT
TCTCAGGTTTGTCAAAGATCAGATAGTTGTAGATATGTGGCATTATTTCTGAGGGCTCTGTTCCGTTCCA
TTGATCTATATCTCTGTTTTGGTACCAATACCATGCTGTTTTGGTTACTGTAGCCTTGTAGTATAGTTTG
AAGTCAGGTAGTGTGATGCCTCCAGCTTTGTTCTTTTGGCTTAGGATTGACTTGGTCTTGCGGGCTCTTT
TTTGGTTCCATATGAACTTTAAAGTAGTTTTTTCCAATTCTGTGAAGAAAGTCATTGGTAGCTTGATGGG
GATGGCATTGAATCTGTAAATTACCTTGGGCAGTATGGCCATTTTCACGATATTGATTCTTCCTACCCAT
GAGCATGGGATGTTCTTCCATTTGTTTGTATCCTCTTTTATTTCCTTGAGCAGTGGTTTGTAGTTCTCCT
TGAAGAGGTCCTTCCCATCCCTTGTAAGTTGGATTCCTAGGTATTTTATTTTCTTTGAAGCAATTGTGAA
TGGGAGTTCACTCATGATTTGGCTCTCTGTTTGTCTGTTGTTGGTGTATAAGAATGCTTATGATTTTTGT
ACATTGATTTTGTATCCTGAGACTTTGCTGAAGTTGTTTATCAGCTTAAGGAGGTTTTGGGCTGAGATGA
TGGGGTTTTCTAGATATACAATCATGTCGTCTGCAAACAGGGACAATTTGACTTCCTCTTTTCCTAATTG
AATACCCTTTATTTCCTTCTCCTGCCTAATTGCCCTGGCCAGAACTTCCAACACTATGTTGAATAGGAGT
GGTGAGAGAGGGCATCCCTGTCTTGTGCCAGTTTTCAAAGGGAATGCTTCCAGTTTTTGCCCATTCAGTA
TGATACTGGCTGTGGGTTTGTCATAGATAGCTCTTATTATTTTGAAATATGTCCCATGAATACCTAATTT
ATTGAGAGTTTTTAGCATGAAGGGTTGTTGAATTTTGTCAAAGGCCTTTTCTGCATCTGTTGAGATAATC
CTGTGGTTTTTGTCTTTGGTTCTGTTTATATGCTGGATTACATTTATTGATTTGCATATATTGAACCATC

FIG. 7C (Cont.)

CTTGCATCCCAGGGATGAAGCCCACTTGATCATGGTGGATAAGCTTTTTGATGTGCTGCTGGATTCGTTT
TGCCAGTATTTTATTGAGGATTTTTGCATCAATGTTCATCAAGGATATTGGTCTAAAATTCTCTTTTTTG
GTTGTGTCTCTGCCCGGCTTTGGTATCAGGATGATGCTGGCCTCATAAAATGAGTTAGGGAGGATTCCCT
CTTTTTCTATTGATTGGAATAGTTTCAGAAGGAATGGTACCAGTTCCTCCTTGTATCTCTGGTAGAATTC
GGCTGTGAATCCATCTGGTCCTGGACTCTTTTTGGTTGGTAAGCTGTTGATTATTGCCACAATTTCAGAT
CCTGTTATTGGTCTATTCAGAGATTCAACTTCTTCCTGGTTTAGTCTTGGGAGAGTGTATGTGTCCAGGA
ATCCCTTATCCATTTCTTCTAGATTTTCTAGTTTATTTGCGTAGAGGATTTTGTAGTATTCTCTGATGGT
AGTTTGTATTTCTGTGGGATCGGTGATGATATCCCCTTTATCATTTTTTATTGCGTCTATTTGATTCTTC
TCTCTTTTTTTCTTTATTAGTCTTGTTAGCGGTCTATCAATTTTGTTGATCCTTTCAAAAAACCAGCTCC
TGGATTCATTAATTTTTTGAAGGGTTTTTTGTGTCTCTATTTCCTTCAGTTCTCTGATTTTAGTTATTTC
TTGCCTTCTGCTAGCTTTTGAATGTGTTTGCTCTTGCTTTTCTAGTTCCTTTAATTATGATGTTAGGGTG
TCAATTTTGGATCTTTCCTGCTTCCTCTTGTGGGCATTTAGTGCTATAAATTTCCCTCTACACACTGCTT
TGAATGTGTCCCAGAGATTCTGGTATGTTGCGTCTTTGTTCTCGTTGGTTTCAAAGAACATCTTTATTTC
TGCCTTCATTTCATTGTGTACCCAGTAGTCATTCAGGAGCAGGTTGTTCAGTTTCCATGTAGTTGAGTGG
TTTTGAGTGAGATTCTTAATCCTGAGTTCTAGTTTGATTGCACTGTGGTCTGAGAGACAGTTTGTTATAA
TTTCTGTTCTTTTACATTTGCTGAGGAGAGCTTTACTTCCAAGTATGTGGTCAATTTTGGAATAGGTGTG
GTGTGGTGCTGAAAAAAATGTATATTCTGTTGATTTGGGGTGGAGAGTTCTGTAGATGTCTATTAGGTCC
GCTTGGTGCAGAGCTGAGTTCAATTCCTGGATATCCTTGTTGACTTTCTGTCTTGTTGATCTGTCTGATG
TTGACAGTGGGGTGTTAAAGTCTCCCTTTATTAATGTGTGGGAGTCTAAGTCTCTTTGTAGGTCACTCAG
GACTTGCTTTATGAATCTGGGTGCTCCTGTATTGGGTGCATATATATTTAGGATAGTTAGCTCTTCTTGT
TGAATTGATCCCTTTACCATTATGTAATGGCCTTCTTTGTCTCTTTTGATCTTTGTTGGTTTAAAGTCTG
TTTTATCAGAGACTAGGATTGCAACCCCTGCCTTTTTTTGTTTTCCATTTGCTTGGTAGATCTTCCTCCA
TCCTTTTATTTTGAGCCTATATGCGTCTCTGCACGTGAGATGGGTTTCCTGAACACAGCACACTGATGGG
TCTTGACTCTTTACCCAATGTGCCAGTCTGTGTCTTTTAATTGGAGCATTTAGTCCATTTACATTTAAAG
TTAATATTGTTATGTGTGAATTTGGTCCTGTCATTATGATGTTAGCTGGTTATTTTGCTCGTTAATTGAT
GCAGTTTCTTCCTAGTCTCGATGGTCTTTACATTTTGGCATGATTTTGCAGTGGCTGGTACCGGTTGTTC
CTTTCCATGTTTAGCACTTCCTTCAGGAGCTCTTTTAGGTCAGGCCTGGTGGTGACAAAATCTCTCAGCA
TTTGCTTGTCTGTAAAGTATTTTATTTCTCCTTCACTTATGAAGCTTAGTTTGGCTGGATATGAAATTCT
GGGTTGGAAATTCTTTTCTTAAAGAATGTTGAATATTGGCCCCCACTCTCTTCTGGCTTGTAGAGTTTCT
GCTGAGAGATCCGCTGTTAGTCTGATGGGCTTCCCTTTGAGGGTAACCCGACCTTTCTCTCTGGCTGCCC
TTAACATTTTTTTCCTTCATTTCAACTTTGGTAAATCTGACAATTATGTGCCTTGGAGTTGCTCTTCTCAA
GGAGTATCTTTGTGGCGTTCTCTGTATTTCCTGAATCTGAATGTTGGCCTGCCTTGCTAGATTGGGGAAG
TTCTCCTGGATAATATCCTGCAGAGTGTTTTCCAACTTGGTTCCATTCTCCCCATCACTTTCAGGTACAC
CAATCAGACGTAGATTTGGTCTTTTCACATAGTCCCATATTTCTTGGAGGCTTTGTTCGTTTCTTTTTAT

FIG. 7C (Cont.)

TCTTTTTTCTCTAAACTTCCCTTCTCGCTTCACTTCATTTATTTCATCTTCCATCGCTGATACCCTTTCT
TCCAGTTGATCTCATCGGCTCCTGAGGCTTCTGCATTCTTCACGTAGTTCTCGAGCCTTGGTTTTCATCT
CCATCAGCTCCTTTAAGCACTTCTCTGTATTGGTTATTCTAGTTATACATTCTTCTAAATTTTTTTCAAA
GTTTTCAACTTCTTTGCCTTTGGTTTGAATGTCCTCCCGTAGCTCAGAGTAATTTGATCATCTGAAGCCT
TCTTCTCTCAGCTCGTCAAAGTCATTCTCCATCCAGCTTTGTTCCGTTGCTGGTGAGGAACTGTGTTTCT
TTGGAGGAGGAGAGTTGCTCTGCTTTTTAGAGTTTCCAGTTTTTCTGCTCTGTTTTTTCCCCATCTTTGT
GGTTTTATCGACTTTTGGTCTTTGATGATGGTGATGTACAGATGGGTTTTTGGTGTGGATGTCCTTTCTG
TTTGTTAGTTTTCCTTTTAACAGACAGGACCCTCAGCTGCAGGTCTGTTGGAGTACCAGGCAGTGTGAGG
TGTCAGTCTGCCCCTGCTGTGGGGTGCCTCCCAGTTAGGCTGCTGGAGGGTCAGGGGTCAGGGACCCACT
TGAGGAGGCAGTCTGCCCTTTCTCAGATCTCCAGCTGTGTGCTGGGAGAACCACTGCTCTCTTCAAAGCT
GTCAGACAGGGACATTTAAGTCTGCAGAGGTTACTGCTGTCTTTTTGTTTGTCTGTGCCCTGCCCCCAGA
GGTGGAGCCTACAGAGGCAGGCAGGCCTCCTTGAGCTGTGGTGGGCTCCACCCAGTTGGAGCTTCTTGGC
TGCTTTGTTTACCTAAGCAAGCCTGGGCAATGGCGGGCGCCCCTCCCCCAGCCTCGCTGCCGCCTTGCAG
TTTGATCTCAGACTGCTGTGCTAGCAATCAGCGAGACTCCATGAGCGTAGGACCCTCCGAGTCAGGTGCA
GGATATAATCTCCTGGTGTGCCGTTTTTTAAGCCCGTCAGAAAAGTGCAGTATTCAGGTGGGAGTGACCC
GATTTTCCAGGTGCCGTCTGTCACCCCTTTCTTTGACTAGGAAAGGGAACTCCCTGACCCCTTGCGCTTC
CCGAGTGAGGCAATGCCTCGCCCTGCTTCAGCTCGCGCATGGTGCGCACACCCACTGTCCTGCTCCCACT
GTCTGGCACTCCCTAGTGAGATGAACCCGGTACCTCAGATGGAAATGCAGAAATCACCCGTCTTCTGTGT
TGCTCACGCTGGGAGCTGTAGACCGGAGCTGTTCCTATTCAGCCATCTTGCCTCCTCCCCCCCTACAGTA
ATACTAAATTAATAACTCATTAAAAAAATCAAAATTCTGTAAGAAGGGAAGAAATGAAAGGAAAATTATT
TTCAACAATTTACCACTGAAGAAAGACTATATCTCAGTCCTTTCTGTGGAACTTCTGGTGGCCTAGCAAT
ACCAGTGCCTTTTTATGTGGCTACTTTCTTATAGCCATTTTAATGACAGAGGAGGCACAACTGTTTAGGG
ACATTTTGATGTAGTATGTAAACAGACATCTTCACCCCAGGAGTGGAGACCGGGAGGAGTGAGAGATAGT
GTTAGGGGAGGATTCCATCTGGTAGGCCAACTAAAAATCATTGAGAGTCATATGTTACCACACCTATTCG
TATCCAAAAGGGCCAACAAATTATCCTAAACAAAGTATATGTTCATTCTTTGAATATTCACTAATAGCTT
GAATGTTCTGCTTCTCAAATTACCTGATTTTGCTCTAAAAGTGAAAGAGAAAACTATAGTTTCTGCCTGA
ATTTCAATAGCAGGCTTCACAAAAAAATCTCGATTAAATGTCATCTGTTCAGGAGGTATTTTCTTAGTTC
TCTCAATAATATCTAAAAATGATATCAATATGTTAACACTCTTCTTCATAATGCTGGTTTCCAAGGACAT
TCCCCATGGAGGCCCAACCAGAACTGACAAACTTAAAGAAATATTTGCTTATTTCTGGTTATAGTTGGAA
TACATGCTAAAAAAGCAGATAATGTAAGAATGAATAAAGTAAAAATTTAAAGCTCCTATAGTTATATGGA
GTATAGTGATAGAATAATGATTAGGACTCTTGTAGCACATATATTTTGATAATAAGAAAAATAGTAGTTT
GGCTCATTTCAGTGCAACTGCTTTAAAATGGTTATTTTAGGATGTCTTGATTCATCCTCACGTTAGAGAA
GCAACCTCAATGTGTTATGTAGTTCTATTTGACAATGTCTAATAAGCTCATCAGGAGGATATTTTTTTTT
CTAGCTCTAAGAGATTTTTTCTTTTCGGAATAGTGAACAACGTAGTGGACCTTATCTTCAAACACTGTAG

FIG. 7C (Cont.)

TATATAGAATTATGGAGGCCTTCCATATATGTTGTTTTTATATTGGCCCTATTTTTCTTTTTCAAACTCA
AATTTTACCTCACTCCTCCTATTGTCTGGAAATGATCTTGCCTTTTGTATTCAATTATCCAGTGAGTGGG
CTAAGGCCTTTCAACAGTAGTCAGTCTTTTTTTTTCCTTCCCTTCACCTCTCTGTAATGTATGCATTTGT
TAAGCCCTTCTGTATTTTTTTGTTTTGTTTTGTTTTCATACCTGTAGTTTTTTCTTCTATCTCTTTGTAG
GTTCATCCCCTTCCACCTGGCCACTGAATGTAGGAGTTCCTCAAAGACCCAGCCCTAGGCCCTCTTTCTT
CACATATTCGTATATGCATTCTCTTTTGAGCCCAGAGTTTTAATAGCCATCAGCATACCATAATCCCCAA
ATTTGTATCTCCAACTCAGACTTCTTTGATGCATTTTCATGTAAATATGTTAAAGGCACATCAGTTATCA
GTCATAATATCTCAACTGAATTCATGCTCTTCCACTGATCTCTCTCTCTCATGATTAGTACCATCCACCA
TATGCTTGATACATAGGCCGGAAATCTAGACATTTTTCTTGATAGGCCTCCTATATCTCTTTCTTCTCCA
CAAAAAAGACTTTTCTACCACTACCCTAGGCAAAGGTATTTGTCTTGGACTAGCCACCTAGATAGTCTCT
GTACATATTCTTTCTATACTTTCTGTCTCCATTCTCTCTCTTACCATTCCTACTTGAGCCTACTCCAGTC
AGATTTTTGCCCCCACCACTGACATTGCTCTTGTCAAGGACACTGATGACTTTCATATTGCTAAATTCAA
TAGTCAAGCCTCAGCTCTCATCTTCCTTAACCAGTCAGCTGAATTTAACCCAATTGAGCTCTTCTTTGAA
ATACTTTCTTCTCTTGTCCCCCACGACACTACACTTCATTTTTCTTTTGTCCCACTGACTGTTCTTCTTA
GTCTCCTGCTGGTTGCTCATCATCTTCCTGACTTCTAAATGTTGGAGTGCCAAGAACTCAGTTTTTGACA
TCTTTTAAAAGTATTCTCTTCCTCATAGTGGTCCAGCCTCATGGACATTTATCTCTGATGACTTTTAAAT
TTATAAACCTCTTCTCTGACCTTTAAACCAATATGTACAACAGCCTACGCTGTGTCTCCACGTGACTCTC
TGATAGGCATTTTGGAGGTAACATATTCAATACTATGCTTCTGATGATCTGCCTAAACCTGCTATCCTCA
TGTTCTTCCCCATCCCAGTTAACTGACTCAGCATGGAGTTAACTTCATTCTTCTGTTTCCTCAGGCCAAA
AATCTTGGAGTCATCCTTGATTCTACTCTTTCTTTTACACACATCCACTTCGGGAGCAAATATTATCGTT
TCCACTTTCAAAATAAATCCCGTATCTAACCACTTCTGAAAACTGCCACTGCTATCAGGTTGGGTCATGC
CACAGCCATTCTCATTTGTATTATTACAGTAGCCTCCCAACTTGTGTTCTACGTCTGTCCTCACCCCATT
TGTTCTGTTCTGAGTGTGGCAGTGATTCTCTTAAAATGTACAACAGATTGCATCATTGTCTCTTCAGAAT
CCTGTAGTGTCTTCCTATGTGAGAATGAGAACCAAAAGCCTTAGAAGGACCTACAAAGTCCCCATCAGAA
CTGGCTGTCATCACCTCTCTGACCTTTTGTTCTACTAGTTGTTTCACTCTAATCCAGTGACACTGGCCTG
CTTATTGTTCCTCAGACATTCCAGGCACAGTCAAATCTCAGTACCTCTTCACTTGCTGTTTCCTCATAAC
TACAGCTCTCTTCACTTCAGCACCTACATAGCCCACTTCCCCATCACCTTCAGAGCTTCATTCCCTGGTA
AGCCTACTTAAAACTGTAAATTCAATTCCCAACCATAGACTTACTCCCAATAGCCCCCAATTCTTTGATT
GTATTGTTTGCCCCTTTATGCCCAATTTCTAGAACTGTGCTTGGCATACAGTATGTGTTCAAAAATATTG
GTTGAATGTAAATACAGGAGTCAGATTGGGGACAAATTATTAAGAACCTTCATATCATGCTGTGGAGGAG
ATGAGAAACCAAGGAATAATTTTAGATTAAGAAAGTATTCTGATAAGATATTTTTATAAGGGTACTAAGG
GTCATGAAACAAATACAAAAATCCTCAACTTTGTGGAATATGGGTTAGAAGAAGGAGAGAATGGAGATAA
GACTAATTAGTTGTTGAAATATTCCAGCCAGCAATAGGGAATATGGTTGAATTGACAAGCTTTGGTACCA
GTAAGAGAATAGATACAGTAATGGCAGAGAAATATGGAAAAATGATTATTTCGGACTATTTTTTTTTAAG

FIG. 7C (Cont.)

AGTCTCTTTGGTAGCCCACACTGGAGTGCAGTGATGCCATCTTGGCTCTCTGCAGCCTCTGCCTCCTGGG
TTCAAGCAATTCTTCTGCCTCAGCTTCCCGAGTAGCTGGGACTACAGGCATGTGCCACCACGCCCAGCTA
ATTTTTGTATTTTTAGTAGAGACGGGGTTTCACCATGTTGACCAGGCTGGTGTCAAACTCGTGACCTCAT
ATGATCTGCCTGCCTCAGCCTCCCAAAGTGCTAGGATTACAGGTGTGAGCCACCAGGCCTGGCCTATTTC
AGACTTTTTATCTAAGAGATTAGGTGAATGAAAGACCATTAACCAGAACAGAGAAGGCAGGAAGAAGGTA
TAGAACTAGTAGGACAAAGGGAATCCAATGACTGTTGAGAATAAGAGCTGAGCTGGAGAAAGATTTCTAA
GTCATTAGCATATAATTTAAAAATTTAGACACCTAGCACAGTACTTGTCCAGTAAATTTTAATGCATTTT
AATCTTTATCTGCCTCTCTTGCAATTCACCTTCCATAATTATCCAGAGGAAAAAGGTTTTCTTAAAAAAA
AAAAGGACATTTTTTAAAAAGACCTCTTCTTCATAATTCTTATTTTCACTTAATTTCATAACCTTTTTGT
ATTGGATATCTTTTCTGTTTTTTTCTTACCCAGAGGATCTTCCCCTCTTTTTTAAGAGCCATTTGTTTCA
TGCTTTTCATCTATCTTTTTCTCATGCCATATTACTTTGAACTATATTTTGTTACCTATTGTTTTTAAGG
ATTCTTATGTTGCTCTTCTCTCTCTGTAGCTAATATTTCTCTACCCTTTTTTATTGTTTGTTTTTTTAAG
AATTCTACAGTATTCACTTACTTTTTAAAAGTACTGTGAGATGGGAACTGTTAGTATCCACCCACCTTTT
ATGGATGAGGAAACTAGGTCCCAGGATCTCAGTTAGTAAGTGATGAAGCAACATTCTACCTCATTTAGAA
TGAGGTAGAATCTCACTTAGTGAGAGACTCACTTAGTTAAAATTTTTTGTTGGAGTTCTCTCACCTTTTT
CAGATGCACATATTAGGTACAAAACTTGTATAGAACTATTTAGAGCATTTGATGTAAATAGATGAATATA
TAAATTAGGAAAACAGAGATTAATGTAGACCATAAAACCTTGTTTCCTAATTTAAATACATATGTTTGTG
TATTTCACATAGTAATGTTAAAAAAGCAGGTACTCTGATTTTTTACATTTGGTATGGTCCAGCATACATT
CATCATGCACAAAATTATGAACACATTGTTCATCAGATATGTATAGCTGATTTATATAAATGATTGTCTT
TCTCCTTTCCTTAGCTGTTTGAATTGGGTCCTGATGGAGGAGATCATGAAACTGATGGTGACCTTCTTGC
AGAGACTGATGTATTGGCTTATGACTGTGCTGCTAGGTAAATAATTTGTGCATTATTCATTGTAACTCTT
GCATACTTAATATTAAAAATTTATTATAAATGAATAAACATACTTTAAAAGGAAGTTTTAAATCTGCTAT
GAATATCAAATACTTGAGAAATTAAATTATATATTAAGCAATATAAGTATTGCTTTCAAAAATGCTGAAT
TAAAACTAATATACTTCATAAATTTATTTCATAAGTCAACTGTTTCAATATTGAAGATAAAAATGGAAAT
ATGCATATATTTTATACACCTTTACTTTCATGCATCTCTTACGGAATACCTAGTTTGCTGGTGTTCTAGT
AATAATACAGTTATTTATTACTCCTAGCATTACAGGTAATAAATAATTAGCGTCAAGTGGTCATGTTTGA
CCATAATTCAGATTACCCATGTACTCTGACATCATGCTGCTAGAATATATTTGATAATAACACACTTGGG
GAGGTGACTAGCTTTACTGAAACCTTTTGGGAGTTTATAAAAATTAGTATGTTTATTTATGAAGGTTCAT
TAAGTAAGAGGATACTTACACTTTATCAGTCCTCTCTACGTAATCCTAAGAATTATCTCAATATTGTGTT
ATGATCAGTGTTCCCTGGTTTGAAGCAGGGAATATTATTATAAGAAAAATTATAAACTGAGCTTCATAGT
AGTAATAGTGTGCTATGTTTCCCAACAATAACTATGTTAGGAAAACCTTGTAGGTTTTCTTGCTAGTGAA
AATGTATATTTTCAGAAACAAGGATGATCGTAAGATACTGACTTTGCTTGTACAAGATATAAATACTTTT
GAAAACAAAAGAGTAAATCTAAAGAAAATTTTGACTATTTCTTAGGCATTAACTAATATCGCAAGATTTT
TTTAGTAACCTTTAGTGTTTTATACAAATGAATATTAGGGAAAATTTTAAGAAAGCTAATTGATTAATTT

FIG. 7C (Cont.)

TCAGCAAAGCCTTAAGGTGCCATTGTCATTTGCCGTATTTATTTATTTCTTTATTTATTCATTTATTAAT
TTTTATTTTTGAGACAGAGTCTCACTCCATCACCTAGGCTGGAGTGCAGTGGTGTGATCTCAACTCACTG
CAACCTCTGCCTCCCGGATTTAAGCGATTCTCATGCCTCAGCCTCCTGAGTAGTTGGGACTACAGTCGCA
TGCCACCAGGCCCGGCTAATGTTTGTATTTTTAGTAGAGATGGGGTTTTACCATGCTGACCAGGCTGGCC
TTGAACTCCTGACCTCAAGTGATCCTCCTGCCTTGGCCTCTGAAAGTGCTGGGATTACAGGAATGAGCCA
CTGTGCCTGGCTGCCATTTGTTTTTGACCATATGAGTTTGAGTCGAAAATATAAAGCACAGTTTCATTTA
TAGAGAATCGTCTAGGATTTCTTCATTAGCTTATATACAAAGCCCAGACTCCTAAGGCATTGGGAGCATT
GAAGGATTTCCATAACATCCAGCATCTTTTTTGACTTTCTACCACTACTCTTCTACAGCTGTCTTAATGC
ATTAATGAAATTAATAATGAACACCTTGTCATTTCCTGACCTCTTTTGTACTTCCATACCTCTACAGATT
TTTTCATGACATTCTCCTGCTTCTTTAAATGCCCTTTATTCTTCTTTCAATTCCAGCTACAACCAATAAA
CATTCCTTCCACTCTGTTACCTAGTACTTTGTAACTTGTTTATATCCTTTAGAAGATGCCCTTATTTATT
GTCTTTTTTCTTCTTCTAAATTAATAATGTTTGTATAGATATTATGTGACAGACTCCAAACACCTATCTG
ACTTAATTCATTCTAAAGGACAACTCTATGAGCAGGATATTATTTTCACCACAGTTTTCAGGTGAAGAAG
CTAAGGTACTGAGAGGATAGAGTAACTTGCCCTGCGTTGCCCTGCTAGCAGGTCACAGAGCTGGGCCTTG
AACCCAGGCTGCCTGACTCCAGGGCCATTTTCTTAATATGCTGCCTTTCAAAACTATTTAGCTGAATGAA
TGAGCTTTAAAACTAAAGTTCAGATTTTTATTTTCCAGCAAAATTTGAATGTTTTTTAATATCAGTTTAA
AACATTCTAATTTTAATATGAAAGTTTTATAACATTTAAGGATATTGTAGAATTCAAGAAGAGGAGGAAG
AAATGTAATTCTATCACCATAACATAAATAACTATATTTGCTTGCATTCTTGTCCAGACTTCTTAGAGTG
TTTTTAATGTTGTTTGATAAGAATTTTATAATACAGTTAGTTTCATGTTTTTGTTCACAAGGGATTTTGA
AAAAATAAATATATGTGACAGAGAAGTAAGAAAATATTGTTTTTGACTCACTAATTTTTTCTCAGAGAAA
AATATGCAATGATGTTTGATGAGCCTGTTCTCCTGCAAGCTGGGTGGTGGTATGTGGCATGGGCCCGAGT
GTCAGGACCCAGCAGTGACTGTGGATCTCATGGACAGGCATCTATTACCACAGATGATGGGTAAGTAAAT
GCCCAAGTGTTACTTAAGCAATACTTATTTTTGTTAGAGGAATATTGTTTTGAAAATTCAGAGTACTTTC
AGCAGGATTCAAAAGCTTAGGAAGACTAGAGCATAATATAACTGCTAAAAATTAAATTCATGTAACCTCA
TGCCAAATTGAGGTCTAGACAGAACAAGGAGATAATAAGACCACTGTACTTTGCTCCTGTCAGATGGTAT
TTGTATATATTTCTGGGTATTACATTGTTTACGAGCTTGATTACCAAATTAGAAATTATATAGAGGAAGG
TGACAAGGAAAATGAGGAGTTTGGAACCATAAAAAAGAAGTAGATATGTGATATTAAATTTGATAGTGCA
TGAGAAAACAGTTTAAAATTTCAAAGCTTCAGCAATGTGTGTTATTTTAATAAAATATAGGGAAAATTTT
GCTGTTTTAAAATAACTTTCACGTATAGAGTACTTTTCAGTTCATATTCTTATATTTTATCTGATTTGAT
GCCCTCAATAGCTTTGTGAAGCAGTTATTAGCCCCATTTTATACTCCAGGGACTAGAGAAATAAAAAGGT
GAAATTATTTGCTATTTCCTGAGAGTCATGTGGTTAAAACCAAGGTCAGACCTGTAACCTGTTGACTCTA
AATCCAACATTTCAATATTCTATTACTATGATTTATGTATTCTAAAGGACTATCATTTGTAAGATAAATT
CAGTTTATTCTTGATTACTCCTGAGCATAAACTATTTGAAATCAGTTGAAGTTATATAACAGTATATATT
CCAGTGCAGGTCAATTCATAACAAAGCTGACCAAAAAAAGAAATAGACTTATTTGTGAGGTGAATTTCCT

FIG. 7C (Cont.)

GTTGCTGAATATTCAAGGAGACTACTGTAGAAAAATCACATCTGTTGTTATGTGCATCAACTTAAGAATG
TCTTTAGAACTAAGTGACTACTTTGACCCTGGACTGTATGATTTTCATAGACAGTTCATTCAGACTTGGA
ATGTCATGGCACACTGAGGCTAAAGCTTATCATGCAGCTAGTCAAGCAGATATTATACTACTTAGTTGTA
AGTAGAAATTTTAGAAGTTTACTGCTGTGGTTAAAGCTGAGTTGGAGAGCTAGGAGGGACAGGACAGCTA
CTCATTTAGGAGTCCTAATCACGTTCAGTTCTTTCATTTTACTGACTAACCCATTCAGAGCTAGAATGAA
AATCTAGAAAATACCTTTTTGCTTTTCTTTATGTAAAAGAGTGAATCATTTTCATTGACATAAGATTTGA
AAACATGTTTCTTAAATTTCTTATTTCCTGTAATGATCATGTTGTTTTTGGTATCATTGTTTTCTCTTCT
TAGGGTTGTTTTCCAGTTCAAGAGTTCAAAGAAATCAAATAATGGTACAGATGTTAATGCGGGTCAGATA
CCTCAGTTATTATACAGGTATTTAGCATATTTATACTGAATTAGTATGGTTTATTATTTTGCTATAATGA
AGTAGAATCATTACAAAACGTGGCATAATAGGGAGAAATTATTTGAAGCATTCAGCAAATTATAATATGC
TGGTAGAACTATAAATATATTTAACAAAAACAGTTAATATTTTGTATATTTTTAAACATTTTCCATACAG
GCTTAACTTTAAACTTTGCCTGATTACTCAGATTATCTGTATTATACCAATAACAATATTTTACTGACTT
TAAAAAAAATCTATCCATTGATTTTCTTACTAATTTCAAATGTTGTAAAAGAATAAAATTTGTCTTGGAG
AAGTGAGATTGCAGGGAAGATGGGGAGGACTATAGATGCAGGCCTGGTTCATATATTGTAGTCTCATAAG
ACTGATAAAATGAGTTGGAAAATTCCCTACTGTTGGTAAATTTTCACCTTTAGCTAAAATACCAAATAAT
AACTTGCTCATATAATATTTACTATATTTTTAACATTATTGAAAAATTTTAACTTACAATAATTTAAGCA
TGTATAAAGGCATATGCCTGTGTTTACCTTATTTATTTCTAGACTACTGCAATACTTTTAGAATAAAGAA
TTCAAATGGATATAAACCGTTACTGAAAAATGTTGTCATTCGTTAAGCAGTAAAAAATCAAAGGAAATGG
TCTAGAACTGTGATTCTATCTCCCTATCTTTCTTTCTGGTAATCACTTTGTGGTTACAAACATTATTTTT
CCCCAAAAGGTTTTTTCGTTTGTTTGGTTTTTATGCACCGTGCAATCTGTTATAGTTACTGTTTGTAATA
TGTAGCTCTACAAACATAACGTGTTGCATTGGACTACTCCCAGGTACTCACTGGTTGAATAACTTTTAAA
TAACAGCATTAATAGTAGCATTACTAGAGAATATAAGTTATATGTTATATACATTATATATGTTCTCTAA
GAAGAGGAAAAAGCCTCTACTACTCGGTCTTGCGAAGGTAGGATTTAAAGGAAGTGCCCATATGCTAAAA
ACTTTGTTTAGCTTGGAAAAATGTTTCAAAAAAGCCCTGTATTGGCATTACCTGGCAAAAAAATTTAAAT
ATATAATTTATTTTCCCATTCAAAAATGTATAATATACTTTAAAAAGAAAAAATGACATTGGACTTTCTA
ACATAATTTTATATGTGTCTACTGCCTTTAGACTTCCAACCAGTGATGGCAGTGCTTCAAAAGGCAAACA
GCAAACCAGTGAACCTGTACACATTTTAAAGAGGTCTTTTGCAAGAACTGTCTCAGTGGTAAGCCATGTT
TTAAAAAATTTCAGCTTTTCTCTTCAGTCCTCAGATACATTTTGATGTTTAGAGTTTAGCTGCTCTTGTA
AGTTTATCTTAGCCTAGATTTATAAACTCAGATTTGGTTTTGTATTCACATTTATATTCTAGACCACAGA
TAAAGTATACTTTAAATCATAGAAAAATGGAGGTGTTGGCCTATGATTTTAACATGACCAGATGAATTGG
CCTTGCTGTTTTTGAAACAAATAACGATTTGCTTTTCTAGTAAATCATATATGAATGCATATGCTGAATG
AATTAGAAAATGAAGGAAAAGTTAAGGATGGTGCTGGCCCAAAAAAGCGTGATTACTACTTGAGGAACTA
GGTGGAAGAGTTGCATATCTAACTAGGAAGTTTGTTGAACCACTTGCCATCCCCATTGTACACATGAAGA
AGCACAGTGCCATTGAGGTTAACAGTGCAGAATGGAAAGTCAACATGATGTAAATAAATGAAGTATAAA

FIG. 7C (Cont.)

TTAAGGTCTTGATCTCTCATGTATTAATTGAGGATTCTTACGTATGTTACCTAAGTAAATTACATCATAG
CATTTTGAATTTCTAATGAGATAAGGGGTGTAAGATGTTTTTGGAACTGTAAGGCACCATCTGAATGTGA
TTTATTAATATAGCTAGTAGTCTTTCATATTAGTAAAATGCATAGGAAGAATGTTTCTTTCCCTTTTAAA
TTTATTTTTCAACCCACCAAGTGAATATATATTCCTGGTAGGAATGAGATAAAAGTATCCTAAAAGTATA
TGAAAGATTTTTCTCCCATTCTCATGATCACCATATATACCTACTATTTACATTTTGGTGTGTATCTTCC
CAGACCTTTTTTTTTTTTTTTTTTTGGTGAGGCAGAGTCTCGCTCTGTCGCCCAGGCTGGAGTGCAGTGG
CACGATCTTGGCTCACTGCAACCTCCGCGTCCTGAGTTCAAGCAATTCTCCTGCCTCAGCCTCCTGAGTA
GCTGGGATTACAGGCGCCTGCCACCACGCCCAGCTAATTTTTGTATTTTTAGTAGAGAGGGGGTTTCACC
ATGTTGGTGGTGGTCTCGAACCCCTGACCTCGAACAGGCTGGTCTCGAACCCCTGACCTCATGACCCACC
CGCCTCGGCCTCCCAAAGTGCTGGGATTACAGGTGTGAGCCACCGCACCCGGCCTTCCCAGACCATTTTT
ATATGCAAAAAAACTTATTAGTACGTATCAAATACAGGATGCTCTACAACATGCTTGCTTGTTTCTTACG
ATACTTACAGTTTTCATCTTTTTTAGAAAATTTCGTATTATATATCATGGACATCCTTCCCTGGCAGTAC
ATTTGGCTCTGTCAGTCTTCTCCGTTTGCGTACCATTATTCTAATTTATTCAATCTGATATCTATCAAAG
AACCACTTTGATTCTCATTTTTTGTTATTTCATCTTGCTTCATGAGCATCTATACACATACATCTTTAAA
TACTTGTGTACTTATGTGCATACTTCTACTGGAAATATGCCCATTTAAAGTTTGGTATATCCTCTCAAAG
TTGACCTTCCAAAAGAGCCATGGCAGTTTGTAGAGCTTGTGCTTTGAATAAAAGACTATGAGAACTTTGG
CTTCTTGGTAACTTTGCATCCTATTAGTCTTAAGTTGAGTTTGGTATCTTTTGATTCAAATAAGGATCTT
TGACTCTGTTATGCTTTCTTTAGTGATCTCACTTTTCTGTGCTTGGTAACCCCTTTGTATTTATGTTTAA
GTGGTTTTGTGGCCATTAGGTAATTGTAGACTTTATATACAAAACTTATTCAGTCATTTCTTTAAAAGGT
AAACTATAGGGCTTAGCACATTGGCTCACGCCTATAATCCCAGCACTTTTGGAGGCCGAGGCAGGAGGAT
TGCTTGAGCTCAGGAGTTCAAGACCAGCCAGGGCAATATAGTGAAACCCCCATCTAAAAAAACTTAAAAA
TTAGCTGGGTATGGTGGTGCGCACTTGTAGTCCCAGCTGCTTGGGAGGCTGAGGGGGTGGTGAGAGGATA
GCTTGAGTCCAGGAGGTTGAGGTTGCAGTGACCCGTGATCACACCATTGCATTCCAGTCTGGGTGATAGA
GGAAGACTCTATCTCAAAAAAAAAAAAAAAAAAAAATTGAATCTATAAACTCGTTTTCAGGAGCTCTGGG
ATTTGGTGGGAATGGGGCAGTAAGTGCTCTGCTTTGAGATTCAGGTGGTATCTGTTGTCATTTAACCATG
ATAAAACCAGAAGACTAGAACTGCAAAGAAAATCTACCATCTTAAACTCATATGCTAGAATTTTAAATAA
TCAAAATAGGAATTTTTTAGTATTTTCTAGTCAATTTTTATCTTCTATTAATGTATTTATCAAAAATTGA
CTGTAGTTTGTATTGCAAATTTTAATATATAGACATAAAATAAGTTATTTGATACTGTTACTGATATCTA
ACACTAAAACTCTATTTTATTTTTTACTACAGTGACTGTAAAAAGCTTTATTTTTCTTTCAAGTAAACAT
GCATTGTTTTATAAGTGCTTCTCATTTTTCCCTTGTTTATATGATAAGCTAGATAGCTGGGTAGCAGGAA
CACTGAAAAATTTATTTTTAAATAGGTAAATATTGAAGAATGTTGTTTTTAGAAATGCTTAACTACTTTA
CCTTTTTTGTAACAAACTTCAAAGTTACTGTTGAGGGTAATTTAATAAATGAACTATAAAAGTGTCTTGG
GCTCAGTAAAAAAAATTCAATTAAAAAACTCAGTAAAAAAATTCAAAAGAAAGTTTTGAAGTTGTCTACC
ATTGCCTTTCCATTTGATTCCGTTTATGGTATCATTTGAATTAATTGTTGTCTGTTTTTTCATATTCTGG

FIG. 7C (Cont.)

ATTAGGAATGTTTTGAGTCATTGTTGAGTATTCTTCACTGGAGCTGGACCACCTTAGTCTTAGGAGTTGA
AGAACTTAGAGGATTAAAAGGATTCCAGTTCACAGCTACACTCCTAGATTTAGAGAGACTGCGCTTTGTG
GGTACCTGTTGTCTGAGGTTATTGCGTGTCTATACCTGTGAAATTTACCCAGTGTCAGGTATGATGCATT
TTTTTTAAATGACTATAGGGAGAAAATATTAGAGACATTGAGAAGATTTACTTTGAGATAACTGAGAGTT
TATGCCCCCCAGCTGCATTTAAGCTGCTTCTAAAATGAGGGGAGAAAGTCAGCTTGCTATGATGCTTATG
TATTTGCTTATAAAGAGTAAAATAGATTACATGTCATTCTGATACAAAAAGTAATAGTGGGCCAAAGTTA
AATAATCTAATAAAGTTTAATTTTAAACAAATTCTGTCAAATAGAAATATTTTGAACAAGCAATTTGGAC
TTAAATGCTGAAACTAGGTTTTTATTCCCCCTTCCATTTAGATTAAAAATTGGGACTACACTTAATCTCT
AAGTTGTTTCATTTCTAAGATATTAGTACTTGTGATACTTAGCTGTATAGGGAATTACTGAATTATATTG
ATTGTTTTCATGCATATTTAATATTTTGCTTAATTACCAATCTGCTTTTTCCCCCTCAAAGCTACAGGAA
AAGCAGTTGTAGAAGAAACTAGCAAATTAGCAGAGTGTATTGGAAAAACCAGAACTTTGTTAAGAAAAAT
TTTATCAGAAGGAGTTGATCACTGCATGGTGAAATTGGATAATGATCCTCAAGGATATCTCAGTCAACCC
TTGAGTCTTCTAGAAGCTGTCCTTCAGGAATGTCATAATACTTTCACTGCCTGCTTTCATTCTTTCTACC
CAACTCCTGCCTTACAGTGGGCTTGCCTTTGTGATCTGCTGAATTGTTTGGATCAGGTAATTTAAGTTTG
TAAAATGTTAGTTGAAAATCTGATATATTGCTTAATACTCTTCAAGAAAATAAATTGCAGTTGCCATATC
TTCTTAACTTGTATAAAAGATAAATTAGGAAATCATTCGGTGTACATGACTTATATAAGCAAAGTTTAAA
ATTTTTTAAATCTGCTTCATCATCTTTTAGTTACAAAATTGGTAGGCACATTGTGCAGTTGCTGATTGGT
TTTTGAATTGGAGTGAGTGATTCTGAGAGAGGGAGAGAGGAAAAGAACCATAGTGACCAGGGGAGAGCAG
GGATAGCACCAGGAGGCCCCCGCCACCCTCATCTGTGAGAACAGGAAGGAGAGAGAGCTGAGAGAACAGT
CATACTAGCATTGTTCATTCATTCATGAGGAAGCCACAACCTTTGTAAACCTTTATGCACCAAGTCACAG
AGTTTCACAACACCTGAGGCAAAACACTGACAGAACTACAGGGAGAAATAGATTCACATTGACAGCTGGG
GACTTTAACACTCCTCTTTCAGTAATTAATAGAGGAACTAGGCCAAAAACATCAGCGATGCAGATTTGAA
CAGTACTGTCAACCATCTTGATCTGACATTTACAAAACAGGATATGAAACTGCAAAATACATATTCTTTT
CAAGTACACATGATTTTTAAAAGAAATATTTGGGACCATTCACTAAGGTAGATCATATGCTAGACCATAA
AATGTCTTAATAAATTTCAAAAGATTAAAATGTGAAAGAATATATTTTCAGACCACAGTAGAATTACAGT
AAAAATCAATAGCAAAGGATATCCAGAAAAAGCACCAAACATTTGGAAAATGACAGCACTTCTAAGTAAG
CAGTTGATCAAAGAAGAAGTTATAAAGGAAATTTTAAAATGTTTCACATAGAAAGATAAAAACATAATAT
CAGAATTTGTGGGATTTAGCTAAAGCATTGCTTAAAAGAGCTCTTTATACCCTTAAATGCTTATATGAAG
AAGAAAGGTTTAAAATCAGTGACCTAAGCTGCTATGTTAAGAATCTAGAAGGAAAAGCAAATCTAACCCA
AAGTTAGAAGGAAGGAAGGAAATAATAAAGATAAGAGCAGAAATCAATGAAATAGAAAGTAGAGAAAATT
AACACAGCTAAAAGTTGGTTTTTTGAAGAAAAAAAGTTGGTAAACTCCTAGCAAACCTGACTGGGAGAGA
AGAGAGAAAGAAAAAAACATGAAATACCATAATCAAAAGTGAAATAGGGGTTCACCGGGCACGGTGGCTCA
TGCCTGTAATCCCAGCACTTTGGGAGGCTGAGGTGGGTGGATCACTTGAGGTCAGGAGTTCGAGACCAGC
CTAACATGGCAAAACTCAGTCTCTACCAAAAATACAAAAATTAGCCAGGCATGGTGGTGCACAGCTGTAA

FIG. 7C (Cont.)

TCTCAGCTACTCGGGAGGCTGAGGCACGAGAATTGCTTGAAGGCGGGAGGTGAAGGTTGCATTGAGGCAA
GATTGTGCCACTGCACTCCAGCCTGGTGACAGAATGATACTCCATCTCAAAAAAAAAAAAAAAAAAAAAA
AAAAAAAGAAATAGGGACTATCACTATAAACAACTTTATACTGGTGAATTTTTCAGCCTTAGAGGAAGTT
GACAAATTCCTTGAAAAATATAATTTTATCAAAACTAACACATTAAGAAATAGAAAAATCTGAATTGCCT
CATATCCATTTAAAAATTATCAAAAACTTTCCCACAAAGAAAATTTCAAGTCCAAATATTGTCATTTATG
AATTCTGTTAAACATTTAAGAAAGAAATAATGTCAACCTTTTACAAAGTCTTTTGGAAAATACAGGAGGC
AACACTTCCCAACTAATTTTATGAGTTTAGCTTTATCCTATACCAAAACCTAACTAAGATACTACAAGGA
AAAATTACAGATGAATATCACTCAGAAACATAGATGCTCTTAAAAATATTATCAAACCAAATTGAACATG
TAAACAATATATCATAACCAAGTGGGATTTATCTTAGAAATACTTAGTTAAATAATTGAAAATCGATGTA
ATTTACCATGTTAACTGAAAAAAGAAGGCAAATTGATGATTTCCTCCATATAGCTACAGGAACAGTGGTT
GATGAAACTAGCAGTTACTCAATGATGAAAACCTCTCAGGAAAGTAGGATATAAGGAAACTCCTAAATCT
GATAAAAAGATATTTACAAAAAAATCTTCACTAACAACATCCCACTTACTGGTGAAATCTGAATATGCCC
CTAAGTTTGGAAACAAGACACGTGGTATCTACACTCACCACTTATATTCAGCAGTGCACTGGAAGTCCTA
GGCCTCCCCGCCCTCCTTCGTGAAAAAAATCATTGTCATCACTAATGCATCCCAGGCAACTTTGCATCCA
TGTAGCAGAGTAGTATGTTTTACCACTCAATTTCCAGGGGCAAGATTATTGCCTGGACTAGTGCACAACT
TAATTACTCTCTCACTCTGAACCTTCCCAGTCTGATATGGTTCTTTTCTTCTTTGCTACAGAACAGGCTA
GATTTAGCAAATGTTGGTTTAACATATGGAATGTTACTCTGCTTTTATGCTTAACTTTGTAACACAGATG
TTTGAAGGACTAGGTAATGTGTACACAATTTTGTGAATTAGGATATCATGTGTTGGCTTTAATGCTTTTT
TATGAAATTTTGTAAGTATGCTACTAATTTTTCTTGGTAAATTATGGAATGTGATAATATAATTTTGTGA
CCTTAGTGAAATGTGCTTGTAATAGCACAGATTTATAATTTGCATCATTTATTATTTGAGAAAAATAGTC
TCAGTCCTTATTGAAAATACCTTAGATACATTCTAATTGGGGCCTTTTTGGCATCTCCCTTTGAAACAGT
GCTAGAGAGTACTGTGATTGTGAGGATATGAAAATATAAAAATGCTCATTTACTAGAGGACAGGAGCCTG
ATTTTTCTTGACCAGACTTAATTTTTCATCTTCATTGAATAGAAACTTAAACAATTTTTTAAATATATAG
ATGTAGTATTATTCTATAACAAGACAATTTAAATGACAGAGTGACAGAAAATTTTGGTATAATTTAAAAG
ATGGTTTACCTTTTATGTATTCAGAAACTTAGATTATACTGATGCTATATTTTTTGGTTGGGGGGCCATA
TTTTTGTTTTTAAAAGGATATCCAAGAAGCAAACTTCAAGACATCAAGTAGCCGACTCCTTGCAGCTGTT
ATGTCAGCTCTGTGTCACACGTCTGTTAAGCTGACTTCCATCTTCCCGATTGCGTATGATGGAGAAGTAT
TACTACGATCAATTGTTAAACAAGTTAGTACAGAGAACGACTCAACACTAGTTCATCGTTTTCCCCTTTT
GGTGGCACATATGGAAAAACTCAGCCAGGTAGGTCTGTCTCTGAAATCTTTTATACAGAGGCACTAAAAC
TCTAAATGGTTTTATTTATTGCCTCTTTTATACAGAGGCAATAAAACTATAAACACACCAAGCTAAGCGT
ATTTAGCTTGGTGCTTATTCTTCTCTATTTTTAAGTATATTTACAAAATGATTATTTTAAATATTTTTGA
AAAATGTTCATATTTACCTATAAAATGAAGTTTTTTTGCTCTAACGGTTTAATCACACACCTTTAAAAAA
ATTTGAGAGTTATACAATGAATACCTACATATTTGTTTTTCCTGAACCATTTGAAGGTAAGTTGCAGATA
CTTTACATTCTAATATAATATTTTAGATTTCTAAGATAGAACAATAAGAAAATAAAGGATTTTTAAAATA

FIG. 7C (Cont.)

TCTACTTAATAACACTTTGGTATATTAAAATAAGCACTGTAAATAATAGGTATAGGAAACATTCACATAA
ATCATTTTCATGCTGGAAATCAGCTAAATTAATCATCTTTTCCCTTTTTTCTGAAAAATAAAGTATTTTT
CCTTTATTGAGACTCTGTGACTTCTTGAAATTTTTCTACCGGTAGGGGTTGGAATTTTCTTATCTCCACT
TAGGAAAACAAATACAGTAGAAATTATAAAACTACATAGGAATCATATGTGTGTACAAAAAGAATTTTGT
TAAAAAAGTGATTTACACAGACTACAGTTGCATTACAGCTAAATATACTAGAATTTATTATCTCAGATTA
AGACCTTGTCCTATAGAAAAAGCTTTTTATTTTTGTTTTTTAAGACTAGCTCATTCTGTCACCCAGTCTA
CAGTGCAGTTGTGCCATCGCAGTTTACTGCAACCTCAACCTCCTGGACTCAAACGATCTTCCCACCTCAG
CCTCCCAAGTAGCTGGGGCTGTAGGCACATACCACCACACCCAGCTAACTTTTTAAAAAAACATTTTGTA
GAGACAAAGTCTTACTATGTTGCCCAAGCTGGTCTCAAACTCCTGGCCTCAAGTGATCCTCCCATCTCAG
CCTCCCAAAGTGCTGGTATTGCTGACACCACGCCCAGCCAAAAAAGCTTTTTAAATGGAAAGAAGTTTTC
TGTCTGTCATATAGAATTGTAAATTGAAAGTTAAATAAGAGAATAAAATAGGACTCAAAGCTAATAAAAA
CATTTCGTAAATGTATGGTACTTTGATACGCAGAGACAGATAATTCAAAAAAGAACTTCTAAGTGAAAAG
TGGCTCCACATATAACCAGAAAGATTTGTAGAAATTGACCCTGATTCAAGTCTGAATTTTAAGAGTATCA
GAAAGACAAGGTTTTCAAATTGAGTACTCCTATGAAGGAAAATAAAACAATACCTTAGAACTTTTTCTTA
TGTATCGCAGAGTGAAGAGAATATCTCAGGGATGACAAGCTTCCGTGAAGTTCTGGAGAAAATGCTGGTC
ATTGTTGTGCTACCAGTCAGGAACAGCCTGAGGAGAGAAAATGAACTCTTCTCCTCCCACCTCGTCTCTA
ACACCTGTGGATTACTGGCCAGCATTGTCAGTGAACTGACAGCGTCAGCCCTGGGATCTGAGGTAATACA
TTATATTTTGACACTGGATAAAAAGCACATGTGTAAGTTTTTTACACAGTTTCTTTTTTCAACTATTTTG
GCTTTGTGGAAGCTAATTTCAGATTGGATTAGCAACCCCAATGCATTGTTTTTCTTTTTTGCCTTTCTCT
CCACCTCCTACTTTCTCTGATTTGTTACTTCTCTCTCACCAGTTTACCCAGCATCCACAGGAATATAAAG
TATACATTTTCCTCATAGAGCAGGTCGTCATCTGCCCCATTGCACAAGCCCACCACCATGCCCCGTGAAA
AGCAAAGATAGTTCTCACTGCTGGAAGATGAGTAACATTGCTGAAGTCAGGCCCTACTCATAGTGCACAC
ATAGTGTGGGAAAGGTAATGAGGTTTAGACTTCAGCTCTGCCCACTCAACCGACCCTAGAGAAATACATA
CTTAAAATTGGAATAATAATTTTTATTTCACCTCTATCACAGGTTTTTTGAAATTATAGTAAAATATACA
TAATATAAAATTTGCCATTCTAATCATTTTTACGTGTACAGTTCAGTGGCATTAAATGCATTCACTTTGT
TGTACTTAGTTGTACATTATCACAAAGTTTTCAAAGTCTCAAATATTATGTTTGAGAAAATCACTTTGAA
AGTGCCTTTACATTTTGTAAAGTAACATTATTCCATTTCACTGCCTTACTCTTTCTTATAACTTAACTGA
ATGTTTTGACTGAATTTGGGGAATGTTTCTGTTTTTTCCTCCTAAAAAACAGACAGTAGATTGGTTTGGA
AAATCATGTCCTAATATGAAATATCTTACATCATTCAAATGAATGTTTAATAATCAGCATATATTCAGTG
GCCCTAGCTCCCAAGTTCTTGTCAAGGAACTTCTTTTCTCTATTTTACTTTTATAATTCCTAATCTTTGC
TTTTTTTAAAAAATTTATTTTAACACCTATTCTGAATTAACCCATCCAATATATACACATTATTGATTAA
TTGTGACAGTTTAGCCTTTAGAATTTCATTGTATGAAATTCATACGTAAGAAATTCGCATACATATGGTT
CATCGCATACACTTGAGCTAATTTTAGTCTCTCATCCTGGGAAGCACTTTCTAAGTTTCTTGGTTAACTT
TGAGTTTGGCCTCAGAGACGATTGAAGCCCTTGTCAGAAATTTTTTAACTTTTTACATTTACTCATTTAG

FIG. 7C (Cont.)

TCTATAATACCTTCCTTTGATAGTATACTCTGCAGGATGCAGGAAAGTCTATAATGTGTAGATCCCCTTC
CAAAGTTTACTAAAGAGTTCTCCCCTTTAAACTTACCTTTCCAATGAAAAGGAATACCAAAAGTTACAGG
GTGCCTGGTATACAACTTTGGGAGTTCCCACAGGTCCTGGCTTAGAGATGAATATTTCTTTCTCAGAGAA
GTTTGCAATTTTTGTTAGAATCATAAACTTCCATTTTTGTATCTATTTAGTCTCCCAAAATTCTGTAGCC
AAGTTAGATTAGAAGTAGGCTTTGTAAATAAAAAGAGCGATTTCAACCCAAAGTAAGTTCTCTAATTCTC
TCTAGTGAAAGTCTATAATTAGTATAGTTGCACATGTGTATGTGTACGTATTCAAATACTGAATGCTGTT
ACAAAAATATCACTGTATATATTCGTAGTATTCAATCTTAGGGTATAGACCATTTTCTTCAAATGAAGTT
TTACTTGCAAATTCACAGGTAAGAGGAGAGAGGACATAGTCTGGTTGAAGAGGGGAACCATAAATTTACC
TCTTCCTTGCACACCTATCTCTGCAGAATTTCTAGAGCTCTGTGTTGCATAGTTTGAAAACTGTTGATCT
ATAGAATTTCGATGAAATTTTTAGCATCTCTTTTCAAAGTCTGATGATTTATTCATACATTATGACTGAT
AAGACAAGCTTGTACTTCTGACATTATAAATTAAGTGGAAAGTATAGTTTCATATGGCTAAAGGAAGAAA
ATACTGTCAAGTGACATTGATTTGTGAATTTAGAATGATAAAATCTGGTTTTATTGTGAGTTAATCTCTC
AGTAGAACATACCTTTAGGAATGTTTATATCCACTTATTAAATAAAGGTTATTTTATTAGACTTCTTAGA
AACCTTTGGATGGTTTTGTTAAAGGTATACCAACTACTGATACAATTGCTTTTATTGTTCACAGGTTGAT
GGACTTAATTCTCTTCACTCTGTAAAAGCTAGTGCTAACCGATTTACAAAAACAAGTCAGGGCAGAAGTT
GGAACACTGGGAACGGGTCCCCTGATGCAATCTGTTTTTCAGTAGACAAACCTGGAATAGTTGTGGTTGG
TTTCTCTGTCTATGGAGGAGGTGGAATTCATGAATATGAATTAGAGGTGTTGGTTGATGATGTAAGTATC
ACCCTTTTAGTATTTATCCTGATTAGTGGGTTGTGTATCAGGATTTACCATTGTCATAGTATGTTCAGGG
GTTTACTAGATCAATCACTGATGAATGACACTAAAGAAATTGAAAAAGACTGGCCACAGTGGCTCACACC
TGTAATCTCAGCTCTTTGAGAGGCTGAGGCAGTTGGATGACTTGAGCACAGGAGTTCAAGGCCAGCCTAG
GCAATATGGCAAAACCCTATCTCTACGAAAAATACAACGCACGCCTGTAATCCCAGCTACTCTGGAGGCT
GGGGTGGGAGGATCACTTGAGCCCGGGAGGTTGAGGCTGCAGTGAGCCATAATCATGCCACTGCACTCAA
GCCTGGGCAGCAGAGTGAGACCCGACCCTGTCTCAAAAAAAAAAAAAAAAAAAAGAAAGAAAAGAAATTG
AAAAATAATGATTTTACCTGATTGTTTGTGTTCCATCTTTCCACCTTGGGTCACTACTGCTTCATATTTT
TTGTACTTTCAGAAAGAGAAAGATTTAAAGTAGAATTAAAGACTAAAAGTGTTTAGCTAAGTCCCTGATG
ACAAGTCTTGAGTAGTTTTTTTTTTTTTTTATATTGTCATTTTTCAAGAAACACAATGTTGAGATGGACT
ATGTCATAGAGTACTAATGGGTGATTCTTAGTGAAGACACTATTTGTTGACTGATTGAGCTATATCTTTC
TATATTCTCTAAAATTAAAGTACCTGAGTTTTATTAAAATGGGACAGATGGGGTAGCATGTAAATCATTG
CCTATTAAATAGCAAGTCTATCTCTATCTCTAACTTGATTCCTTTCACTAGTTAATTTGAATTTATTCCC
TACTTCATTAGGCTTTATAAATGTGAAGAAGTAGAAATAGTTTAAGTCATCAGATGAGAAAAGCTTATTT
ATGTTGTAGTCTTCTCAAGAAATCACATAAAAATGTATATAGTACCCCCAACTTTTTCTTTCATATGTAT
GGGAAAATACTAATGGCTAATTTTATATTCAAGAAAATAAATTTTAAAAATAATAATTATAAATCAAAAT
TGTTCATACAATAAAATTAAGAGTCTGTTGGAATTTTTGTGTTTCATTTTTTTTTTTTTAGAGTGAACATG
CAGGAGATTCAACTCATTCCCACAGATGGACATCTCTGGAATTAGTGAAAGGAACGTACACAACGGATGA

FIG. 7C (Cont.)

CTCACCCAGTGATATAGCTGAGATCAGACTTGACAAAGTGGTTCCTTTAAAGGTAGTTTCAACTGAATGT
TTCTATTGTGAATAAGAGGTATTATTATGTAGTTAAAATAGTGAAGAGTATTCCATGAATTTTGTTTGTT
ACCTATAGCTATTTGTAAGTTATCCTTTATATGGTACTTAAATATTTATGGAGTACCTACTACGTACCTA
ATGTTGTACCACATTATATTATATTTTTGCATAATGTTTCTTAAAGTCAGGAGTAGTAGGAAGTTTTGTA
GTCAAACAGACTTAGCTTTGGATACCTGCTGTTCCACATGCTGACTTTAAGACACTGGCAGATCATTATT
TAACCACTTTGAGACTTATCTGTAGATTGGGAAGAATAATACCTGCATTGTAGTAGTATTGAGATTAAAT
AATGGAAATAAAACACCTGCCTTAGTGTCTAGCACAATATGAAAAATAAATATTAGCTCCTGTCTTTTCT
TCTCTTATTGTGCCCTAACTCATTTAAAAAAAAAAAAAAGTGTTTTTGTTTTGTTTTGTTTTGTTTCTTT
ATTTTTTTTTAATTATTATTATTATTTTTTTTTAGATGGAGTCTCACTCTGTCGCCCAGGCTGGAGTGCA
GTGGTGTGATCTTGGCTCACTGCAACCTCTGCCTCCCGGGTTTAAATGATTCTCCTGTGTCAGCCTCCCG
AGTAGCTGGAATTACAGCCACGTGCCACTATGCCCAGCTAATTTTGTATTTTTAGTAGAGGGGTTTCACT
GTGTTGACCAGGCTGGTCTCGAACTCCTGCCCTCAAGTGATCCACTCCGCTTGGCCTCCCAAAGTTCTGG
GATTACAAGCGTGAGCCACCGCGCCCAGCCTATTTCCTAACAATATTTGGCAAAATAGAGAAATTTTACC
ACATCAAAGTAATTATAGATGTTAAAATAAAATTAAAGTATTTCTGAATTCAACTGAAATAAATTTCATT
ATAGAGCAGAATTTTGGATAAGATCGGTACACGAGAGGTTTCATCAGGAAGAATTTAGATACTGAAAAAC
CAAAAAGCTTTTATTGTGAAATTTATATCATGGGTCATAAAGCATTAGTTTCTATAGCTCACATTTTAAA
AGTACAGTGCATTATATTTTGGACAGCTTTTTTCCTATGGGTTTTTTTTCTCATGTCTGTTTGCCTATAT
ATTTCTATCTCTGAGTTTTTCTTAAAAATATAATAGACTCACCATTTTTTTCCTCACATCTAAAATTATT
TTAAAAGTTAAACTAGTCAAGGAAAAGTATCAGCTTATGCAATTAAAATCCCTTATTGCCGGGCACAGTA
GCGCACACCTGTAATTCCAGTACTTTTGAGACACCAGGGAGGGAGGATCACTTGAGCTTGGGAGTTTGAG
GCTAGGCTGGGCAATATAGTCAGACCTTATCTCTACAGAAACACCCTAAAAAATTAACTGAGTGTGATGG
AACACACCGGTGGGAGGATTGCTTGAGCCCAGGAAGAGGAGGCCACATTGAACCAAAATTGCACCACTGC
ACTCCAGGCTGGGTGACAGAGCAAGATCCTGTCTCAGAAAAAAATATATATATATAATATATAAAATATA
TATATATTATATATATATAATATATATTATATATATATAGTATGGCTAATATTCTAGCAGTAAAATTAAG
AGCAGGCACTAGTTACATTGGTTGTGTTCAGACCTAGTTCCATCACTTACTAGCTGCGTGACTTTGAACA
AGTTACTTAACTTCTCTGAACCTCAGATTCCTCATCTGTAAAATAGGGATAGTAATGATACTTACCTTAT
GAGGTCATTTTAAGGATTAATTAAATTCCATAAAGTAGTTAGGACAGTTGCTTTTATGCAACAGGTGTTC
AGTAAATGTTAGCCGTCATCGTGTTTGATTCATTAAAAACTTATTTAATTATATCATCTGTAAATATGAC
AAAGAATTTCAGTATATTTGCCTATTTTACTGCTAGAGTTCTTTTTATATATCCTCTGTACATTGTGAAT
AAAAGATGTTTTACATCTTTATAATGAAGGAAAATGTTAAATATGCTGTGCGCTTGAGGAACTATGGAAG
CCGTACAGCCAATGGAGATGGAGGAATGACCACAGTTCAGTGCCCTGATGGTGTGACATTCACATTCAGC
ACGTGCAGCTTGAGCAGTAACGGCACAAACCAAACCAGAGGACAGATCCCACAGATACTCTACTATAGGT
GGGTGAATGTATAGAGATAACGGAAATACTTTACAGTGGTAGAACATACACAGTCTACTACCAGGTAAAA
TTGCTAACTGGATACTTATAATTAAATTGTACAGTGTATCTTCTTAGCACATACTTGTACAAATTCATAT

FIG. 7C (Cont.)

AAAGAAATCTCTTTTTAATATATAAATTCAATGTTTGCTACAAAAGTTAATGCTTTAAAATATTTTTGCT
GTTATTTCTTCAATATCATTGAAATGTTTGTGTACTGGGCATATGTGCTGTTGCTGTCACTCTATAATTT
CTGGTCTGCAATTTCAAATTTAAAGGATATTCATTTCTTTTTATAAAATACCTCAAACTAATGATCAGAT
AGACTGTACTCAGATAGTGGTGTTGCCTTGATCTTGTTATCTAGTCACAGAATATTTTGATGTCTGTGAA
TCTTGGACCTGCCCCCTGGGGCCCTAGAATATATAATAGTGTGTTTCTTATAATGTTTTTAACAAAAACC
ATTCCTTATGTAAACCTTGGAAAATAAAAGAATGATAACAACCCTTGGGTTAAAAAAATCTTTTAAATAA
ACATTTCTCACTGAGTCTGAATTTTTCTTGTAGCGGCAAAGCTGGCGTCTTAGGTAGTCATGAGTACCAT
TTACCACATTTGTCCTCAGCCTGACTTGGCATTAAATCACTGAATTTCCATGTCACTTTCAGAGGCTTGC
TGCTTCCTCTCTTTCCTTCATGAAGAGTCTAGGGATGGTGCCTACGTAGATAGTATAAAATAATTTCCCT
AGATATAGATTTTCTGCTTCCTCTTTCCATCAGAAATAGAATAGAAATAGCAGGCAGCAAATAGCTATGT
AGTTCATTGTTGCTGCTGAAATACAAAAGCTGTCTAGTCTTTTGCCCCAGTCAAGAAAAGCTTTCTGTTA
CATAAGCACTACAATAAATAGTACATTATTCTCTTTCTTAAACTATGGATTAAAAACTCTGTTATGCGTA
AGAGTTACGTGTTTCAGAAAGCTGGAGAGCCACTAAGAGCATCTGCCATCCAAACTTTATATCTTATACA
AAATACAGTGTTTTGAGTATTTTCATGTTTTCTATTAAGCTTTAAATACCCTTAGCTTTACATTTTTTAT
AAATGAAAAAATGTTAAAGTCCTTTAGTTTTAAATACCATCCTGCTCTGATAGCTCCCAAGTTTACATCCC
TAGCCTTCATGACCTCTGAGCCCTGGACTCCGGGTCTCTCTTCTGACATCTTCATTTGGATGACACTAGT
GGAGATGGTGTTAGTTACTGTGTGCCAGGACATGCTTTGAGTATGTTACCTGTGTTATTTCACCTTGTCC
TCACAGTAACCCCAGGAGGTAGGTACTTTCCTTATCCCTGTTTCACAGATGATGGAACTGAGACGCTGAA
TTGTCTAGAGTCACACCTCTGTTAAGTTACGCTACTGCGACTTGTAGGCAGGAAGTCAGATTTCAGGTGA
TACACCCTTAACCAGAATGCTGCACTTTCTCTTTAAGGATGTTCGTTATAGTTGGCTAGTAGACATCTGA
GGTTTCATGTGGCTAGAATATTCATCTCCCTTCCACAGTTACAGCCAGACACCTTGGAGTCATTCTGGAC
TTCTCTTTCCCTCATACTTTACACCTAGTTCATCAAGAAGTCCTGTCAGCTGTACTTCTAAAATGTCCTA
AATGTGACCTTTTCTTCTACTTCCATATTTAATAGTCTAGACCAAGCCACTGCAACCTCTACCTGCTAAC
TGTAATAAGCCTCTAAACTAGTCTCCCTCCTTTCACTATTGGTCTCCTACAATCAGTTCTCTACAGCACA
GCCAGAGTGATCTGATAAAAATATAAATCATACCAAGTTCCACCCTTGCTCCAAACCCAGCTTCCCATTC
TCATACCAGTATAAAATGTAAAGTCATTATGTGGCCTACAAACCTTACACAATTTGACTCTTGTTTCCCT
TCCCACCCATCACGCTTCACTCTTTCTCCTTTTCTTCCAGCCATACATGTCTTCATTCTGTTCCTTTAAT
TCACCAGTATGTTCCTTTTGCCCTGACAGTTTTCCCTCAGCTCTTCGCGTGGGTCTTTAAAAAAAAAAAA
AAATTCAGGTCAGCTGGGTGCGCGGCTCACTCCTATAATCCCAGCACTTTGGGAGTCCAAGATGGGTGGA
TCACGAGGTCAGGAGTTTGAGACCAGCCTGGCCAACGTGGTGAAACCCCATCTCTACTAAAAACAGAAAA
ATTAGCTGGGCGTGGTGGTGCATGCCTATAATCCCAGCTATTTGGGAGGCCGAGGGAGGAGAATCGCTTG
AACCTGGGAGGCGGAGGTTGCAGTGAGCCGAGATCATGCCACTGCACTCCAGCCTGGGCGACAGAGCAAG
ACTCTGTCTCAAATAAGTAAATAATTTAATTAATTAATTCAGGTCTTTGTTAAATATGAGTTCCTCGGAG
AACTGATCTTATTTAAAATAACACCCTTCACTTTATGCCCTATGCTGCTTTGTTTTTCTTCAAAGCCCTT

FIG. 7C (Cont.)

ATCATTCCCTATTATTGTATAGTTGCATGTTTACTTTTTTAACTTTTAAAAAGCTATAAATTAAATGAGG
ATCTCAGATCTAGATATGATTTCTGGCACTGGATCATGTTTTACTTACCATTGTAAAATAATCTCATGTT
TGCTCATGCTACAGGAGTGAATTTGATGGAGATTTACAATCCCAACTTCTGAGTAAAGCCAATGAAGAAG
ATAAAAACTGTAGCAGAGCATTGTCTGTTGTAAGCACTGTCGTTCGAGCCTCTAAGGACCTCCTGCACAG
AGCTCTTGCTGTGGATGGTAATATTTTTTCTTTCTCAGTAGTCATATTTTAGATTCTTTATTCACTAAAT
TTTTGCATAGAATTATTGAAGAGGAGCCTTCTATTATACAATTTTATAGAATCTAAGTGTTATTTATAGA
TCCACCCATGGATTAATTTTGGATAGGTCACACTCTCCATACTGTAATGCAGAATTATTTAGAATGCTCA
AAAGGAGTTACCATATATTCTTATTTTCTTAGTTAATTTAGTAAAAGAAAAATTGTATTTGAGTTAAACT
GGGTCTTTATTCTTCTTTTAGTAATCAAAAAGCTTTTTCTTCCTCTCTGTTCTTTTTCCAGTAATGTATC
GCTATCCACCCAAAACTCTGGGGTACCCTAACCATCTCCTCAGAGGCACTTGTCTAAATTCAGCTCTATG
AGTTTTTCCATTGGAATCTCTCTAGTTTGTATTCTCCTCTCTTTCACTTCTTCTCCTGCTGTCATTTAGA
CTGCCATGGTGCAAGTACATTTCATTTTTTAATATAGGGTTAATATCCCGATAATCTCACTGCTGCCTTT
CCCCCATTCTCCATCTAGTTGTTTAGTTATTCTTCACACTGGCAGCAGAGTTATCATTATGAAAACATGG
TTATGGCCGGACATGGTGGCTCATGCCTGTAATCCCAGCACTTTGGGAGGCCGAGGAAGGCAGATCATGA
GGTCAGGAGTTTGAGACGAGCCTGAGCAACATGGTGAAAGCCCATCTCTACTAAAAATAAAAAAATTAGC
CAGGCGTGGTGGCAGGTGCCTGTAATCCTAGCTACTCAGAAGGCTGAGGCAGGAGAATCGCTTGAACCCA
GGAGGCGGAGGCTGCAGTGAGCCGAGATCGCACCACTGCACTCCAGCCTGGATGTCAGAGTGACACTCCA
TCTCAAAAAAAAAAAAAAAAAGTTACCTCCACCTCCTTATTGTATAACATTAATTCCTAAACCTAGTTTA
ACATCAGAACCACCTGGAAAGCTTGCTGAAAATAAAGACTATTAGATTTATCCCCAGGTCCTGAAGCTAG
GCTAAAAAACTATTTTTTAAATAAGTGTGCAGCCTGTTTTGATATAACAGCAGACCTAGGAATCAGTATT
TGGGAGAATAATTGGCTTATAAAATAAAGGTCTTCACAGTATAGGCTCAGCTTATCTTTCCAGCACCATG
TTCATGGATAACTGACTAAAATGTTAATCAGCAAAGTGCTTTTCTTGGAAAAACAGAAAGCAATGTAGCT
TAATAACAGTAAACATTTTTGGAGTGCTGAATATGTGTAGGTGTTGTTCTAAGTGTTTTACATATATTAC
CTCGTTTAATCTTCCCAACATCCAAATGAGAGGAATACTGTTGTGAACCTAAGTTACAGAGTAAGTAATT
TGCCTAATGTCACTGATACAGCCATGTTTGGTGCCAGAATGGTAATTTAAAATAAAGACTCCATTACCCT
AGGTTCTGATTCCAGCTCTATTATTTTACAGGTACATGTACTTATGTATTAAGTATTTTGGGTAAGATAC
TTAAACCCTATGTGCCATGGTTTTCCTTTCTGAAAATTGGGGATAATAAAAGTATCTTATTGTGAGTATT
AGTTGAGATAAGGCATGTATTCTCAAAAGCCTTTAGAATAGTACCAGGCCCTTGACAAGCACCCAATTGG
TGTCAACTATAGTTTCGCTCAAAAGAGCAGAATATAGATTTAGTACAGCATGTATGCAGTACAATGAAAT
TACCTTCTGACTATAGTTTTAATGCCTTTTATGCCTTTTTTTAGCTGATGACATTCCAGAACTGCTGAGT
TCTTCCAGTCTGTTTTCCATGCTGCTCCCCCTTATTATAGCCTACATAGGACCAGTAGCTGCTGCTATTC
CCAAGGTGTGTAATTTAATTCTATAACTTTGAATGTTTTTTTTAAATATCTTTTTTAAAAAAAGACTTTG
TGTCTTGTCTTTACAAAAACTTGCATCTTTGAGGCATCTGGGATATAGGTAACAAGCAGAGATAGATCTG
CTAATTATTAAACTTCTCTCTTCTTAGTATTGTTTACTGGATTGCTGTGCTTATTTGTTGGCTTTTTTTT

FIG. 7C (Cont.)

TTTTTTTTTTTTTGAGACGGAGTCTTGTTCTGTCACCCAGGCGGGAGTGCTGTGGCGCGATCTCCGCTCA
CTGCAAGCTCCGCCTTCCGGGTTCACGCCATTCTCCTGCCTCAGCCTCCCGAGTTGCTGGGACTACAGGC
GCCCGCCACTGCGCCCGGCTAATTTTTTGTATTTTTAGTAGAGACGGGGTTTCACCGTGGTCTCGATCTC
CTGACCTCGTGATCCGCCCGCCTCGCCCTCCCAAAGTGCTGGGATTACAGGCGTGAGCCACCGCGCCCGG
CCTGTTGGCTTTACATTTGAAGAATCTGTGAATGGGAAATAGATTTTAGCAATTTTAGGAATATGATATG
TAAGGAAAGATTATGTTAACTGAGGTTTTTCACATTTATGAGGTTGATGCCAAATGGTCTTCATTAATAA
CAATAGCAATGTTAAAGGATAAGAGTGTTTTAAAATAGTGACATATTCAAGAGATGGAAGAAATGATAAA
CTATTGATTCTTTGGCATAATTAAGTAAAACCTGATTTACTTCAGATCATGAAAAAACAAGTTTTTAAAA
ATATAGATTTAGATATTGTCATGTAACATCTAAGATAAATCTTTTTTTAATCAATTGAAAGATTTCTCTT
TGGACAAAAACTTAACTAGTGGAAAATTTAGATGGAAATTGTTATTAGAGTAACCAACAATTATTGTAAT
GCATAATTTTAGAACCACTTTCACGTGTATCTCATTTAACCATATTTTTATATGTGTACTAGGTGGCTGT
AGAAGTCTTTGGCCTTGTCCAACAATTGCTTCCGTCAGTTGCCATTTTGAATCAGAAGTATGCACCGCCT
GCCTTCAACCCTAATCAGTCGACAGATAGCACCACAGGAAACCAGCCTGAACAGGGCCTCTCTGCTTGTA
CAACCTCCAGTCACTATGCTGTCATAGAGAGTGAGCACCCGTATAAACCTGCCTGTGTGATGCATTACAA
GGTAGGCACCGGTTCTTAGTGTGATTCGAATGTAAAACTTGGCATGAGGTTCTCTGATGATATCTTAAAG
AATGCCTGGCCTGTATTTACAAGTGTATTTTCTTTTATAGTATTTACATATAGAGAATCAGCAGGTGATT
AGGCACTGTTGGATATATAAAATAATTTAAGATGGAATTTTTATCTCAAAGATGATAAAATTTTATTGGT
TTATGAGAGTTGTTCTTAAATCTTCCTACAAGTATAGTGTGGTATATAATGCTAAACTTCATGCTGTGAT
TTGCAATAGTAGTAGATATAAGCATTAACAATTTTAAATTGTATTTTTTGAACTAACATTATTTGTACCA
CAGCCTGAGCTCTGAAAATTTACAACCCCAATGTAAGATTTAAAGTAGTCTATACATAATGTTAAAAAAA
CTATGTATAAAATGTTTATAAATTTAATGTTATTAGAGAGTATTCAAAATCCGTATTCTTTGTTTTTTCA
TTGTATCATGCAAATTAAGGAAGAGAAGGATAAACTTGTATTTTGTGTGCTTGTAAAATATTCCACTTTT
CATGGTAGAAACTATTAAGCATATAGAAGTAAACAAGCTAGTACAGTGCACTTGTTTATCCATCATCCCA
GATTCAGCAGTTTCAACTGTTAGTCAGACCTGTCTTATTTATTCCCAACCTACTTCCTAACCTCCTATAT
TGTTTTAAAGCACATTTATGATATTTATTGATACAATGTCTCCAAAATATAAAGACCCTTAAATATAACC
ATAGTATTATCACATTGAAGAAAACAATTTAATGTCTGCAAACATCATGTAAATTTTTAATAATTTGAGT
TAGAATCCATATAAAATCCATATATTGTGATTAGTATGTCTCTTAAGTCCCCTTTAATCTTAAGTCCCTT
TAAATCTATAAGTCTCCCTCTGTCTCTCTCTCTTTTTGTTCCCTTGAGTTCTATTTGTTGAAGAAACTGG
ATCCTATGTATTTGTTAGATGGGAGCCTCTTCAGCTTACCTGCTGGTTCTTTCAGACACCCCTCTTGCAG
TCATTCCTAGCTTCCTTGCTTTCTGGTAGGATAAGATGTTCCAGGCTCCCTTTATATGTTTGATGCCTCA
GACTTGGAACTAACCATTTTTTCAAAGTGTCCTGATTTCTGTTATACATACACACACATGTTATATTTAT
ATATGTATATACATAAATGTATATATGTTTATGTACAGATAGATTTATGTGTATAGTTTTTTAAAGATAA
AATACCTCATGAGTTTATACTGTTGATACTAATTCAAACAAGGACCACAGACACACCTCAGTCTCCTTTC
TCTTATATCTAAAATTCCTATTAGTGACACTGGGAATATCAGAATTAGAAAATCATTAAATTATTTCATT

FIG. 7C (Cont.)

TGGTGTGTGTGTGTGTGTGTGTGTGTGTGTGTGTGTGTGTGTGTGTGTGTGTATGTGTGTTTTGTCTT
TGAAGTATATCCCATCTAAGTGTATGTCAAATTACTGTGTTTAAAGTAAGTTGGAATGCTCCCTCTGCAT
GATTATGCATTCATTGGATATACACTTAGAGAGTCATTTATTTTATCTTAGATTTTAGGAATTGCTTTTT
AAATTTGGATTTTGTTTTATAATTCTTTACATAATTACATACTTTGAAGTCAAATTTATGAAACAAATCT
AGCTTTTATCTCTGTCCTCTTTACTCTGTTCCTCCTTCTCTGTCATAGGTAACATTTTATTCTATTTTAA
TTTTGTACTTTATCCTGTTGTGTCATTTAATAAAAGCATAGACACACACACACATACAGATGCAGATGTG
TATGTTTGTGTATATATATATCTGTATTCATGTCACTTTGCCTGTTGACCTCAGGTGACATTCCCAGAAT
GTGTGAGGTGGATGACAATCGAATTTGACCCTCAGTGTGGTACTGCACAGTCAGAAGATGTCCTTCGTTT
GTTGATTCCTGTCAGAACTGTTCAGAATTCAGGATATGGACCAAAATTGACATCTGTTCATGAAAATCTT
AATTCATGGATAGAATTAAAGAAATTTTCAGGATCCTCTGGGTGGCCTACTATGGTTTTGGTGTTGCCAG
GTAAGTTTTTTTTTTCTTCTGTTTTATGTGGTAAAATAAGTGCATTTATGTATATTTAGTAAGGGTGTAT
CATTGAAAATGTTTATCTAATTTTTAGAGAAATTTATTAAAGACCTACTATGTATCTGGATTGCATTCGA
GGAATAAATAAGGTACCCTGGGCAAGGGGCACAGCCTGATCTGAGTTTTGGAGAAGACAATGTTTTAAGG
ATTTTGTGAAAAAAAGATTAGCTTGAGCAAAGCAGAGTGTTAACGTTGAGGAGTAGCTAGCTGTCTGTGT
AGTTGGGTCCAAATTATAGAAAACAATGGATTAGATCTTTTATTTTCCCAGGAAGTGCTAAATTTTCAGA
ACTTACCTAAGGACTGAAGTCCTTCATTGTAAGAGAATTCGTAAACCACTTTCTTGTGTGAAGAGAAACT
ATGTTTTAAAACTTATGGTTTGTTGCATTCTTAACCAGTTAACCAGGACTACTCTTGTGATCCTTCAAAC
TAATAGGCAATTTCATTTCAGAAACTTCTTCTTTCCACTCTGACCTGCCTATTTGTTTGTTTGTTTGGGA
AAAGATCAGAAAAAGCCACACTCCAGGGTAGAGGATTGCCCACTTTGAAAAATAAAAAGGCTAACCTCAG
TATTTGACAAATAATTGAAAAATGATTGCCCATGTAACTGAAGTACTTTATTAAGCAGGGGAGTTTGATT
ATGAAAAAAAGTAACAATTCATTTGCGATAGACCTGTTGTTTCTAGTGTTATTTTTGGTACAGTTTCCTC
AAGTAGATATAGGAACGCTCCCCGCCGCAAGTCTATTTAAGTTATGTAGTATATGATTTGTGTTTTTACC
TATCTTGTGATAAAAGAGAAAGTCCATTGGATAAAAGACAGGGAAATTTTTATAAAATTGTTTTAGAGTT
TGAACTCAATTCTGGCATTTTTATTAGGAAATGAGGCCCTTTTTTCATTGGAGACTGCATCAGATTATGT
GAAAGATGACAAAGCTTCTTTCTATGGTTTTAAGTGTTTTGCAATTGGATATGAATTTAGCCCTGGACCT
GATGAGGTAAGAATGAATTATCTTTTCATTCTTTTAAGGAAGATTGTGTTTCTAAGGGCTAGTGAGTTGT
GCTTCTAACTGACTTAAATTGTACTGTTGCCTCTATTCGAAAAATTGGGGCCTGGTGCAGTGGCTCACAC
CTGTAATTGCAGCACTTTGAGAGGTGAGAGAATCCCTTGAGACAGTTTGAGACCAGCCTAGGCAATATAT
CGAAATCCTTTCTCTACAAAAAAAATAAAAAGAAATTAATTTTAACCTAGGGGTGTGCAATTCTAAATTT
TTGTAGTTTATGTGCAGTGGTCTGTTTTGCTACTTTTAATACATGAAGAGGATGGAGTTTGTGCAACATG
ACCCAGCCTTTGAAGTATAGTTATACCTGCCCTGAACCTGCTCAGTTGGCTATACCTTTCTGAGTAAACA
GTAGAACCTGTTTTCAAAAAGGGGCTATCATCTTGTCTAAATGTTTTAAATCATACAATAAGATAAAACC
AAGGACAAAGTGGGCCAAAGTCATGAATGAACAGTTATTTGAACAATGAACCTTTAAACCTGAACCTTAT
AACCAGCCTGAGCCACAACATTGAGTACTGAATCTCATCTACTCTCAATTTAACCATTAGCTTCACGTGC

FIG. 7C (Cont.)

TTCCTTCTCATTTCAAAAGTAATGCTTGAATTCAAATCACATTTTGTTGATAATCCGTATTATCATTCAA
ACATTTTTAAAGCAGCAAATTTTATGCAATTCCATAGGGAGTCATCCAATTGGAAAAAGAATTAGCCAAT
CTTGGTGGGGTTTGTGCAGCAGCTCTGATGAAGAAGGACCTAGCACTTCCTATTGGTAAGTGTGGCCAAT
ACTGGATGTTTTTTGATAGGGTTTTGTTTTGTTTTGTATGTATTATAAAAGGGCCAAAAATAGATTTGCA
AAATGAATTTTGTAATCTCATATATTCATGAGCAATAACTGCTTCATGTACTGGTAATTTGAGTTTGTTT
AGAGACTGAAGGGTATCCTCTGACCTTTTTTAATTTACACACGCACATGGACACCCTTTTTATGCATATA
CATGCTTTGAGCCAGGCAGTGGGTATAGTGTGTATATTCAGCCAAGCACTGAATATATAGTATTAAACCA
AAAGTTCTAGATATTTCTTAAATATTCTAGTGGAAATATCAAGTAGACAACTGAATACTCATTGTCTAGA
TCAGAGAACAGGTCGATAGAAATGTAATTGAATATGATCGTTATTTAAAGACATGGGACTGTATGAAAGA
TATTCTACAGCAAGTAGATAAGAAAGAGAAGATAGCTTAGGATTAAAGCTGTGACTTATCAAAATTTCAA
AGATGCACAGAACAGGAAGAGGAGGCTGCAGATGAGACTGTGAAGGAACAGTCAGTGAAGAGGAGAGAAA
CCAGGAGAGGGGATGCTCCTGGGATTTTTGCATGCTCTGAGAAGTGAATTAAAATCTATCATTGGACTTG
AAGACTTGTTGGTTGCTTGTATATGCAATAAGAAATATGTTAGCAAAATGAGAGAACTGTAAGTACTTTC
AGAGTAGAGAGGGAGAATGGAAAGTAAGGAAGGGCGGTCCATTTGAATATAGGTAGCTCTTTAGAAGAAT
TTTTCATTGAAGCAGAACAGAGATGAGGCAGTGGCAGAAATGGTACTTTTTTATATGGAGCAAATTTGTA
TGATATATAGATTAATCTATAATCAAGGGAGTAAAGTTGAAAGTAAAAATGCTTACTGATTCTCTAATAT
TTATACATGGTTTAAAGTTTTATTTTCTTACCCCCCCAAAATCCATCTTTACTCCTTCATTGAAGATTAC
TCTTCCCACTGTTATTTTTTTCCTCCCTTTTCTTCCTCTGCCTTTCCTTCTTTATTCCCTTTTCTCTTCC
TGGTCCCTTTTATTCTTCTCCATCCCTTTTCTCCCACTTAATATTGGTATATATGTATGGAAATGAGACC
TTGTATTCTAGCCACATGAGGAAAATTGCTAGCAACCTATTTTTGTCAATAGCTGTTAAATTTTACATTA
TATATACTTTTTGACATAGAAAATTTTTATACATACTTGCACAAATACTCAAAAAGTGTATGTTGAAGGG
TGGATTAATATAGCAGTGCTTGTGATTGTAAAACCTAGAAACAACCAAAATGTCTTTCAGTTGGGAACTG
GTTAAATAAGTAATGGCATAGCCATTCAATGGTAGTATATGCAGCTCTTTGAAAAAGTAGACCTATACAG
CCTAACAAGGAAAGCTGTCCAAATTATATTGAGAAAAGCAAGTTGCAGAAGAAGGTCCCATTTTTGCATA
CATTACTCTGTATATTACAAAAAAGTATGATCATGCCTGTAATCCCAGCACTTTGTGAGGCCAAGGTGGG
TGGATCACAAGGTCAGGAAATTGAGACCATCCTGGCTAACACAGTGAAACCCCGTCTCTACTAAAAATAC
AAAAATTAGCCGGGCATGGTGGCACATGCCTGTAGTCCCAGCTACTCGGGAGGCTGGGGCAGGAGAATCA
CTTAAACCCATGAGGTGGAGGTTGCAGTGAGCCGAGATCGCACCACTGCACTCCAGCCTGGGCAACACAG
TGAGACTCCATCTCAAAAGAAAAAAAAAGAGTATGTTTATGTGTGGTTGAAACACATATACCTTTTTGGT
TTGTTTGCACACCAAGTTTCTAGAACAACACATAGGCTGTTGACACTGGATAGTTTTAAGGGAGCACGGC
ACTGGTTAGAGGTTTAGAATTTTTTGTTCTACACTCCTATACAATTTGAGTATTTCCCATTGAACAAGTA
TTACTTTATTAGTAACATTTAATAATTAAACTATCAAAGAAAGATCAATAAATAAAATATGTTCTATATT
AACTAATAAAGGAGAAAATGGCTAGGGGATGCAGTCACTGCCTTATATTTTTCTGTGAGTCCCTGTTGTT
TACTAAAGTCATAGCTCTTCTGTAAGGCAACCAAAATATAAAGGCCCAGATCTGAAATAATTTGTTCCCT

FIG. 7C (Cont.)

CTTTTTTTAGACAAAACGAATACACTAAGTTCAGAAAGTATACATTTATATTCATAAATGTAGGATATAT
CTTTGGCAAATCACCCATGGATGCTTCTTGAGTATTGCCTTGAGAATTGTAGTATATTCCCACTGGAAGT
ATCTTATATATTAAACTGTATGCCACTAGGATTTTTTCCAGAATCACAAATCTTTTCAATCTGGAATAGC
AGAATTATTTTTTTAAAAAAAGTGTAATGAATGCAAAGGACTAGAAAATTAAACTAAACTAAATATTGAC
ATATTTTAGTAAAACTCTTTATTTACACAACAGGTAATGAATTAGAAGAAGACCTTGAAATTCTTGAGGA
GGCTGCATTGCAGGTATTGTCCCAAATGTTTTAAGGATAAACTTTGTACATTAATTTAAAAAGTATTGTC
ACTCAGATCAGCCTATTTGTCTTGACCATTGGGTTCATTCATTAAGTACTTCACTTTATTCATTGGCATT
ATAGAGATAAATAACTTATCATTGCTCCCTTTGGTGGGAGAAACCCATGTGAGCCCTATGTATTTGGTGG
GTAATTGACTCTGGAGTTAGACAAAAATCCTTCGGGAGAAAAAAACAAATCAAGTGCCAAGGGTGCGGAG
GATGGCTTGCAGAACTGTGGCCATTTAAATTGCATCTTGAAAGAATTTGTTTTTCTTTTTTTGCCTGCTA
GAGAAAGGGGAAAGACATTTCACAAAGGATGTATAGTTGTGTTATAAGAAGCAGCAAAAGGTGAGGTTGG
TACAGTTGGTGAGCTCAGTCTGTGACAAACCAGTATGTCATATTAAGTGGTTAGGGCTAGTTGCCTGTAG
ACAATTGGGAGCCATCATTTGTTGTTTTTATTATTGTTTGCTTTACCTTTTTTGCTCGTTTAGGCATTAA
CTAGCACATTTGGCACTGAATGGAAATACATGAGTACTATATTTCAGTGCAATACCCCCTTTGGATCTGT
TACGTCAACCTAATATTTCTCAAAATTGCCTAGAGATGACTACATTGTTTTCTTACTTCATTAGTCTGAC
TTCAGCTAGCTAGTAATCTGTAATAGGATGGAAATATCAGAATCTGTAGACAGCATTTGTCAAATTGTAA
TACCTACTTAGGCCAAACCAGAGTTTCTGATGTACTGCTAAGTGAGCCCCATTGGATACCACACACTGAG
AACATCAGTGATGGGGAAAATTTTGCATCTAGCAATGGTGTGAAGATAGAAGAAAAGTTGAGAGTCTCTC
AACTGGATCAGTGTTACTCAGACCCTAGGATGTGATAGATTTGTAAAATTTTCCAAAAATATTTTTCCTG
AGAACTTATTAAGTAAAAACACTCTTTAAAAATGTACTACTTTTTATCAGCAATGTCTTATAAAATAAAA
GACATTTTAATAGCCCCAGATGGAAAGGTCTTAGAATGGAAGACTCTGTTATAGCCTTAGTTTTTCTAAT
TCTGCCATGGATCAGAGAACTTTGGGCCCACATTTGGAAAACACCAATTTAGATCATACTTATTTTCTAT
ACTAGGTATATGTAGTTAGTAATAGTGATTTAAATAATATCTGTAGAGCACTTCATAGGTTTCAGCATCT
TTAATATTATCTCTCTGTTTTTATAATTACACTTCGAAATCAGTATTAGGTCTTGCATCTTACAATTATA
ATAACTGAAGTTCAAAGAAGTTTTGTGACTTCTTGAAGACTCAGAAGGGAAACAAAGGCTGGTACCCAGA
CCTTGTAATTGTGAAGGCTAGTGCTTTACATTTTACTTATTTCCTGAGGTGAATTAATCAAAGCGGTAAT
AATGAAAACATTTATTTCATCTTTGTCAAGCACTATTTTAAACATTTTGTGCATTTTTAACTCCCCACAG
CAACCCAATGAATTAAAAAGTTTTATCTCCATTTACAAATGAGGCATAGAGCATTTAGGCAGTTCGCCCA
CGATCATACAGCTAGTGAGCAACTGCACTGGGATTTGTTCGCTGGCAGTTTGGTGACAAAAGAAACCCCG
TCTCATTAGCTGGGCGTGGTGGCGCATGCCTGTAATCCCAGCTACTCAGGAGGCTGAGGCAGGAGAATCG
CTTGAACCCGGGAGTCGGAGGTTGAGGTGAGCCAAGATCATGCCATTGTACTCCAGCCCAGGCAACAAGA
GTGAAACGCCGTCTCAAAAAAAAAAAAAAAAAAAGTTTGTGATTTTGAACACTGTCTTCTGATCATAGGGA
GCTGTAGTGTTGTCAATAATGTTAAGAAACGTCTGAGTTTTAAAAAGCCATTGGCATCTTATGTGTATTC
CTTTTTTAAAGTTAAATCTTTGTACCTTAAGATTCAAAATAAAAATAAATTCAACAGATATATAATAAAC

FIG. 7C (Cont.)

AATATGTGTCAGGCAACATTCTAGGTGAAGGAGAACTATCAAAGAGTTTCTATTAGTCCATTTTCACACT
GCTATAAAGAACTACCTGAGGCTGGGTAATTTATAAAGAAAAGAGGTTTAATTGACTCACAGTTCCCTAC
ATGGCTGAGGAGGCCTCAGGAAACTTACAATCATGGCAGAAGGCAAAAGGGAAGCAAGGCAAGTCTTACA
TGGCAGCAGGAGAGAGAGAAGGGGAAAGGCCTACACACTTATCAAACAACCAGATATTGTAAGGAAAACA
GCAAGGGGGAAGTCTGCCCCCATGATTCAGTCACCTCCCGCCAGGTCACTCCCCCAACATGTGGAGATTT
ATAATTCGAGTTGAGATTTGGGTGGGACACAGAGCCAAACCATATCAGAGTTCATATATGGTTTATAAT
TTCAGGGATTATTATGGTATATAAGGTGTCATCTAGACCAGATATGGAGAGATCTTTATTATGTTATTGT
TCAAGAAAAAAAAAAATGGTGTCCCAAATTGCCTCTTTTTGGCATGTAAGGTAGTTATTCTGATAATCTA
ACATGTATTAAACACTTACTATTTGTTAGGCAATGTATTATATACTTTATATGCATTATTTAGTTTGAAT
TTTTTAACTGTGTAAGAGAGATTATTTGATGACCAGTTTATACATTTTACAGATTCAGGGATGGTAACTT
TTTAGCTTAAGAGCACACAGCAAATAATTTGTCCAAAGCCAGGATTTGAATTTAAGTCTATTTGATTCCA
AAGATGATTATTTTTGAAACTGTATAATTTCAAATTTGATAGTACTAGAAATGTAATTATTTTCTATGAA
AAAATCTTACTGGAATTTATTTTATAGTCAGTAAAAAGTTTTCAGAGTTCCAGCATTTAAAACAAGTCTC
TCCAAAAACATAAGACTTGCTTGTCAGATAGGTGAAACCTAAAATTTGTTTTATCTGCCTCTTCTTCTTA
ACTTTAGTAAGGCTTAGGCAGGCTAATGAGATGTGTGTGCTGCCACAATCAGGCTTCCACCCACTTTTTA
CCCAAGTCAAGACCTTGGTGCCCACCCACCCAAGAGAACAGACACACCTTACTCATGATAGCTGCCTGTA
AGGGGGACTGAAAAAGAGGGAAGCCGGATGCAGTGGCTCAGGCTTATAATCCCAGCATTTTGATAGGGCA
AGGTGGGAGGATTACTTGAGGCCAGGAGTTCAAGACCAGCCTGGGCAACATAGCAAGACCCCATCTCTAC
AAAAAGTTTTAAAAAAAATTAGCCAGCCATGGTGGCATACGCCTGTAAGTCCCAGCTACTTGGGAGGCTG
AGGCAGAAGGATCGCTTSAGCCCAGGAGGTTGAGGCTACAATGAGCTATGATGGCACCACTGTACTCCTG
GGTGGCAGAGTAAGGCCCTGTCTCAAAAAGAAAAAAGGGGGAGACATCCACAGTTGCTGACAGAAGGGAG
CTCTGGCCCTGAAAAATGAGGACATAACATATAGAGGACTGGCATGGAAGGAGATACACCATTTTATCCA
GCATGCAGATCTCTGACAAGGCATTTATTTTTGAGGGAGGAAAGAGACTGGAAATATTGTCTCATATTTT
TCTCTCCTAGGAATTTCCTATTCTGTGGGTTAAAAGAAGGAACAGTGGGGTACGTGGAGAAAATGATTTC
TCCGTAAAGGCCTATCTGAAAGTATCTGCATGTTGAAAAATTTTATGTAATTAAAGTTTTATTTTTAAGA
ATATATAAATATTCTTTTTTACTTAACAGGTGTGCAAAACCCATTCTGGAATTCTTGGAAAGGGTCTAGC
TCTTTCTCATTCACCAACTATATTAGAAGCACTTGAGGGAAATTTACCACTCCAAATCCAAAGCAATGAA
CAGTCTTTTCTGGATGATTTTATTGCCTGTGTCCCAGGATCAAGTGGTGGAAGGCTTGCAAGGTAAATGT
ACTTTAAGTTACTTACTTTATTTTAGGGCTTTCATCTTTCTTCATTTCTGAAAGAGGGGAGTCATTAGAA
TATTAAAATACTACTTTAAAAAAGTCTGGTTTATGTATGTTTAACTTGCTCAAATATAAAATGATAGTTA
ATATTTTTGTTTGGCGGTTGTTTGTTTGTTTGTTTTTGAGAGAGAGGGTCTCACTGTGTTGCCCAGGCTG
GAGTGCAGTGGCATGATCTCAGCTCACTGCAACCTCCACTTCCTGGACTCAAGCGATTCTTGTGCCTCAG
CCTCCCAGGTAGCTGGGATTACAGATATGCCACCACACCCGGCTATTTTTCTTTTTTGTATTTTTTGTAG
AAACAGAGTTTCCCCATGTTGCCCAGGCTGGAATAGTTATGATAGTATATGATAAGACCAGGTGCAATGG

FIG. 7C (Cont.)

CTCATGCCTGTAATCCCAGCACTTTAGGAGGCTGAGGTAAGTGGATTGCTAGAGCATAGGAGTTGAAGAC
AAGTCTGGCCAACATGGTGAAATCCTGTGTCTACAAAAAATACAAAAATTAGCCAGGCATGGTGGCACAC
TCCTGTAGTCCCAGCTACTTGGAGGCTGAGGTGGAAGGATTGCTCAAACCCTGGAGGCAGAGGTTGCTTT
GATTGTGCCAGTGCAATCCATGGTGAAACCCTGTCTCTGCAAAAAATACAAAAATTAGCCAAGCATGGTG
GCACACACCTGTAGTCCCAGCTTCTTGGAGGCTGAGGTGGGAGGATTGCTCAAACCCTAGAGGCGGAGGT
TGCTGTGATTGTGCCACTGCAACCAGCTTGGGCAACAGAGCAAGACCCTATCTCAAAAAAAAATTAACTA
ATTAAATTAAATTTATTATAGTTGTTAATTGATTATTTTTGTTGCTTTTTGTTTTTAGGATGAAAAGGGA
AAAAAATATGCTGGCCTGCATGATTTTACTAGTAAAAAAAAAATCCCAACTTTTTTCTGGTTTTAATTTT
AAAATTGCAGAGATTACTCTTTAGTTTTTAAAAATCACAAAATAGTGATTGGAGAGGAATGTCAAATCAC
TTAAGTCAGCCTCACTACTATACTATGCAGACGTTTTTATGTAATGCATGGTAGAATTACTTATTACTCA
GCTCACAGGACAACTTGAATGTGTAGATCACAGAATGAATTCAGGAATGAACATCACAAATTACACAACA
TTGATGCATTTTAGGTGGAAAGCAAGGTAATGAGGAAGATAGTTGAGAAACTGTGAAAAAAAGATGGGCA
GTACACCTTGAACCTGGCTGCTGTCAGGCAAGTAGAGGGCCATTTCTACCCCTGCTTTTACAGAGACACT
GCTTTTTCCAGGCTTGCAGGATGGCAGAGTAAGGTGGAGCTCCTTCAGAGAGAATGAGCCTGCTCAGGAC
TTCAAATTATGCACAACCTACATTCGTGTTCTTGGTGATTTTAAATTAGCCATAGTTAAAATTTCAAGTT
TCCTGGTTTTAAAAAGTATTTTTATACTGTATTTAAATATCAGAAATCTCCTGTGCTTAGGCATGTTTTT
TAAATGAATTTGTCCTTAACAGTTTCTGAGGGAGACACTCATGATTATCACTGAGTTGGAAATGAAGATA
ATGTTTTAGCATTTTGTTTGATACAAGTTTTGTTCATTTGGCTTAATTTTATATTAATTGTTGAAGATGC
TGATCAGTGTTTGGGGTTTTGTTTATTTGTTTTTCATTACTGTTAGGTGGCTTCAGCCAGATTCATATGC
GGATCCTCAGAAAACATCTTTGATCCTGAATAAGGATGATATTCGTTGTGGTTGGCCTACCACCATAACT
GTTCAAACAAAAGACCAGTATGGGGATGTGGTACATGTTCCCAATATGAAGGTAATTATAACTGGATTAA
ATTAGCAGACATCTATATACTGGCTGCAATGACTGATAAAATTTTAGAAATGCCAAGTGCTGAGAGTCCA
TTTGTTCTACCCTCTTTATATAAAGGGTGATGCTGAAAGTTTGTTTAAATGACTTGTTTATATTAATTAG
TCCCCAAGTGTCCAAGTTACACCTGTTTTTTTTGTGAGTTTGTTCTTTACATTTTGCTACCTGTTACGGG
GACTCAAAGGAGGGATAAGAAAGTATCCATCTAAAGAGTGCTAGACACATACAGTGAAGCCCCTCAATAT
GTATTGATTGAATAAATGCATGAAAGAATACATTTTTAAATTTTGTGTATAGTTTTGAAAGACTCAAGTA
CGTTCTGTGTTTGGTATTACTGAAACCACATTTTAAAAATAACACTCATTAAGTTAGAAATATATGAGTT
TAGATTGTAAAAGAATGAGGAATTGAAATAGTTGTATACCATATTGATGAATATAGAGTTTTTAGGATAC
CTCTTACCTGAAATATTAATAATAATGTTTCAGAGCATATTATACATAATTATTTGTGATTTAATCTGTT
AATATGAATATCTCATTTAAAACTTTTATTTCTGAAAAAATTATATTGAATAAAATTTTATATAGGCAGT
CCCCAGCCCTTTCCTCCTTCAAAGTTGTCTTATAGAGTGATTGGTTGTTTGAAGCTTAGAGCTGATTAAG
CCACAAAATCCTTTTTGCTCATTGGGTAGCTAATTTTGCCTCAATATTATTTTCAGTAGAACTATTTCAA
CTACTTCATGCATTCTTTCATTTATAGCGTGAAGAAGTACAATGCCAATGTAGCATCTTACCTAAGTAAA
AAATAAGAACACATTGCTTACATGACTTAAGACCAGTAAATAAAACTGTATGGAAAAGGTTTCAACCCTG

FIG. 7C (Cont.)

ATACTAAATCAAAATCAGTCTTTTAGCAGTATCTTTCAAATATTTGGCCATGATCCATAGTCAGAATTTT
TATTATAACCCAAAGATATAAATATAATATATGATGGAATAGTGTCTATGTAATAGCATATGTTAAGTAC
ATATAATATACTTTATATATACATACACACATACATACATAATATGCTATACTCTGATGCTTTCTCTATC
TTATTTTTTAAGGCAAGTCATACCCTTCACAAACTGAGTTCATGCCTACTTGGAATTATTCTATACAATG
CAAAAAGCATCACAAATTATAAGAAAAAAAGATTTAAAAATAAAGTTATCCTGATAGTGATATGAAAAAA
ATTACTACTCAAGGACAGATTTTTGATCACAGTACAATACACGTTAAGATGTTGAAGGGCTTGTATATTG
TGTATTCACTGATGAATTTCTCAATGTAGTGAGTTGTTAAATCCAATCTTTGAACCCTCAAGATTAAGTT
TTTTATTCATGTGACAACATTCTAATACCATGTTCATACTGTTACGCTTCTGATATTTCTTTAGTTGTAT
TTTCTTTCTTGTGTTTTCTCCTTTGCACCTTTTATTATCTCTTTTGATATCTGGTATGTTTATATCTTGC
ATTTGAAAGTCAGACTTCATCTTTTTTTCTTTTCATCTTAGAGTTCTTTTTTTAACCATATGATGGATCT
GCTTTTTTTTTTCCTCTCTTCTTCCCTCTCCTCTTTCCCTTTCACCTCCTTCTCCTTTTTCCTTCTTTTC
TTCCTCTTCTTTCTCCTCCATATATTTGCTTCTCCTACTATCTTTCCTTGACTTAAACCTCTTACTCAGT
GTGCTCTAAATTCATGTCAGATTTATCCAATTTAGAAACTTTCTAGAAAACCACTCTAAATACTATCTAG
AAGAAGTGATTTGTGCTCCTACTGATGTTTAATGTATTAATATCATATTATATTAGCTGGAAACAAAATT
AATTTAACCTATTTTACTTTCAGCCTATTAGTATATGAAGTCTTAGGAGCACTTTAGACTGTTCATAAAT
TGTTAAAATCTTTATGCAGTAATAGCTAATTATTTGAAGCATAAAAGTTGATTTGCAGCTAATATTTCAA
TGAGTTCCAAAATGCTTTCAAAAGCAACAAGTGTTATTGTTATAATTTTTTACTTATAAAATGACTGTTC
CCTACCTGTGATAAAATGAGTTAGAACTAAACACACATATTGTACCAATGTCAATTTCCTGGTTTTGGTT
CAGTACCATCAGTGTCTGACAGTGTTGGATAAAATGTAGCCATTGGGGGAACCTGAGTGAAGGGTACATA
GGACATTTCATCTATTTTTGAAACTTCCTGTGAATTAAAAAAAAAAGTTTATTTTAAGGAAATCTTATTT
ATTGACAAGAGAAAGTCACATAGGAAATACAAGAATAACTTTTTTTTTAAGTAACACAGTTTGTAAAAGA
AAGCAGAATGGTTATTCTATAATGTCTCAGTTTTCTTAAAGTATAAAATTATTCAGTGATTTACTTCAAG
GTTCATGGTGCATACACACATAGACTCTAATGATAATTTATTAAATACTTAGGGTAAATATAGTTGCTTA
CAGAAAGGTTAAATTGAAATAGTATGTATAAAAATAGTGTCTGTAATTTAATATCAAATATGTTTGAGAC
AGGAGAGTTCCCTTGACCCCTTTGTGGGACTTGGGACGTGGGTGTCGTGTGGCTCATTTACTTGACTGCT
GCACTCAAACCCCTTGCAGGATGGCGAGCACTGAGGCAAGCAGGTGCCAGGGCCCAGGCAAGCACCTCTG
GGCTCCAGCCCCACAGCAGCATCTAGGAGTGTGTCACAATTAATGCTTTTTTAGCTTTGTTGTCTGTGGA
TGGCTAAGTGTTAAACAGCTCAGTGAAGAATCAGCATGACAGCCTTTTTGGGTTCCTGCACCCAGTGTGT
CCTGAATTCTTGTCTGGCATTCAGGAAGAATCAGGTCATATGAATGGTTTGAAACGCGATGAATGCGTGA
ATACAGCAGATTTTTTTTTTTTTTTTTTTTTTTTGAGACAGAGTCTCGCTCTGTCGCCCAGGCTGGAGTA
CAGTGGCACGATTTCAGCTCACTGCAAGCTCCGCTTCCTGGGTTCACTCCATTCTCCTGCCTCAGCCTCC
CGAGTAGCTGAGACTACAGGCACCCGCCACCACGCCTGGCTAATTTTTTGTATTTTTAGTAGAGACGGGG
TTTCACCGTGTTAGCCAGGATGGTCTCGATCTCCTGACCTTGTGATTCGCCCGCCTCAGACTCCAAAAGT
GCTGGGATTACAGGCGTGAGCCACCGCGCCCAGCCACGGCGGATTTTATCAAACGGTGGAAGTGGCTCTC

FIG. 7C (Cont.)

AGCAGAAGGGGAGCTAGAAAGGGCATGGTGTGAGAAGAAGGTGATATTTCCCTGAAGCCCAGCCGTCTCC
AGCCATGCTCCTCTCCTAAGTGGTGCCATCTGAGGTTAAGCCGCGCGTCTCATCAGTTGCTGCTTCTCCT
CTTGGTATTCGCCACTTGTCTCTTTGCTAGCTGAAGTCTGGGATTTATAGGGGCATAGGGTAGGGGGGCA
GGGCTGGCCAAAAAGGCAACATTTAGGCGGAATACAAGGATAAACTGTTCTCATTTAGGGTCATGGTTTC
CAGGCTTGAGAGTGGGGCCTTTGCCAGGGAACCACCTTCTCCTATCCAGTATATCCCTGACTCCTGTCTG
TATCATCTTCAGATTTTTTAATTGTTTAAAGTTTAAAGCTTTTTATGCTGGCACATGTGTTTGAGTTGAA
ATTTTAACCATATACCTGTAAACTGCCATTTTTTAAATATAAGAATGGGTTTTTAATATTTCCAGGGGTT
TGTGTCAGTCCAAATACTGATCTCTTGTAACCTCACCTGAAGATAGTGGTCACTTAATGGAACATATTTG
TCACCTGTGCCTAACATTATATAAATAGCGAAAGTCTCAAACTACTGATTCCATAGAATCGCGTTGTTAA
GAACAATAAACATAAAGACAGTCTGTAGTTCTGAGGTAGCTCTCAATTACTTAAAAATACTATCACTTTT
ATCTCTGCACTTTTTCTATTTCTGTGACAATTCTGTTGAATTACCTGTTCTTGCCAACCACAAAACTATT
GTCTGTAGGGAGCAGCAGAAACTTTGAGTAAAGCTCAGAATGGTGATACCTGCTGAAGAACTAAAGTGGT
ATTCAAATTGTGTGTACATTTGTGGTTGCCTAGGGGTCAAGTGTTTTTCTGCCAATGCATAAACAAATAA
AAACAATGTTTTCTTATAATTTCTGGGAAATATTTCTAAAAAGTATTTTTCAGAAATAGTAGTTAGTAGA
TGAAATAGTAGAGTTAGTAGATCAAAGATAGTCCCGTTTTGTTGAAGAAATTGAGTTGCAAAGTTATAAT
TCCTGGAAAATATATCTAAAAGGTATTTTTATAAGACAATTTGTATTTTCAGTATATTAACATCCATTAA
CGAATCTGTTTTTTGCATCTATACTGTAGAGTTAGTGGACGAAAGATAGTCCCATTTTATTCTTAAAGAA
AGTGAGTTGCAAAGTTTAATTATTTAATAGATTGCTTAAATCAAATGTTGATGTTGGTGATAGGGCTGTC
TAATAATATTCTTTCTTCACCCGAGTAAAGAAACATATTTGGGCTTTAGGTATAAGATTTGTTTTATTAA
GTGTTAATTTTTGAAACTTCTATAAATAGAGTACATTTTCTTCTGTAGAACAGTGCAGCTCAAACTGACA
TTAGTGCTTTAAAATGTGCTGAGATTGTGGAAAGCATTTACACTTGCATTACCTGATAAAATAATTTGT
TAGTCCCTGCAATAACTTAATGTAGATTCATTCCACTATCTTTTCCTGTACTTTATTAGTGGTGCATTTG
TTTTTATGTTTTGATATCTCTGATTATGTATTCCAAAACTATGAGGCCTTGTTTTTACACCGTGTTCATG
GTTCATATTGTCAACCCATCTTGAGGTCATTTGAACTCTTTTCAATAAGCCTTTGAAGGGAATGCCAGAG
ACAGACCAATGCTAACATAAAGTATACATAATTATGAGTTTATAATAGTAAGTTGCTTATTTTGATGTCA
GTGACAATTAAATAATAATGGTATTTGGTTTCTATAATACCATGTTTAGGTGGAAGTGAAAGCTGTCCCT
GTTTCTCAGAAAAAAATGTCTTTACAACAAGATCAAGCAAAGAAACCTCAAAGGATTCCTGGCAGTCCTG
CAGTAACAGCTGCATCTTCTAATACTGACATGACTTATGGAGGGCTGGCATCACCAAAGCTAGATGTTTC
ATATGAACCAATGATAGTGAAGGAAGCTCGATATATTGCCATAACAATGATGAAGGTAATTTATTTTACT
TATCAGAAAAATTTTAGTTTTCAGCATTTGTTTATTTAACCAACATTTCAGTGATTCAGATGCAGACATG
AAATTGTAAGTCCAAAGAGCATTTGATGGATATTAAATTTGCAGCAACACTTATTAAGATGATGTTATCC
TGTCTTCAGAGAGGATTTTCATTGGTTTTTGGCAGATGTCCAGAGGGGATCACCAATTACAGATCAAGTT
AATCGAATCAGAGATACAGATGGATTAGGCTGAGTTTCAGTTCCTGTGAAAGTACTTGTCTACTTCTGAC
CAGGAACAGTGGCCCACACCTATAATCCCAGGGCTTTGGGAGGCCAAGCAGGGAACATCACTTGAGGCCA

FIG. 7C (Cont.)

AGAGTTCGAGACCAGCCTCAGTAATGTAGTGAGACCCCATCTCTACAAAAAAATAAAAATAAAATAAAAT
TTCTAAGTACTTGTCTATTTGCAGTTTACTATTCTTGCTAGAATGTATCTCTTCAGGGTTTTGGGGTTTA
CCTATGCCCCCTTCAATTTTGGGTTCTCTCAAATGCCAGATGTATCTCCTAGAACTCTTTGGGATTTTTA
GCTCTCTAATACCTTTAGACATTTAAAAAATATATATTTTGGATGTTTTAGTTATCTTCAGAGGCAATGT
TAATCCGAATTATCAAGGTAGTCATTATTTGAAGCTGAAGTTTGTAATTTTGGCATTTTCAGAGAGCAGT
GGTGAGCCATTGAAGGCTTTTGGGTAGAGGAATGGCTTGATTAGATTTGTGTTTTGTAACGATTGTGGTG
GAATATGGACAGTGTAATTGGGCAGATGATCAAGAAACATGACTTGGTTTTAGTCTCTTTAGGGGACTAT
TGACTTAATTTGGTGAGATATGCTGATCAGTTGGACTAGTGAGTTGTCAATGAGGATAGATTCAATAGAA
TCAGTAGAACCTGGTAGCTAGTGGAGGTGGAGTAAAGAAGAAAGGTAGGAAATAAAAGATGAAATTCACA
TATTGAGCTTGTGTCCAATTGATAATGGAAGAGGGGCAGGTTTTGGTTGAGAAAGATAGCAGATTCAGTT
TTGGATGAGGTGAGTTTTAGATACTTCTGAAATACCTACGTGAAGATGTATAAAACAAAGTTAGATGTAC
AGACCTGAGTGATCACAGTCTGACCTCAAGAAAAGGATTCAGGAATCATTAGCACTTACATTACTTATGA
AGTCATGGGAATAGATGATACCTTCTATGGTGAATGAAGACAGAAGTTCCAGGATAGGATCCTAAGAAAC
ACCAATATCACTGAGTCTCAGACTCTTCTCTACATCAGAAGCATCTGGAGCACTTACTTAAAAAAAAAAA
AAGATTTCCAAGCACCCAGAGATTTAGATTCAGTGGGTTTGGAGAGAGGTTCAGGAATTTACCTGAAACA
AATATGCAGTGATTCAAATTCAAAACCTAAACTTTGAGAAATACTGATTTACAAGGTAGATAAGAGAAAA
AGAAAGGAAAAGGAAAAACGATTCACATTGGTAAGAATACTAGCCAAAGAAGCAACACATAATTAAGGGA
ATGGCTGAAGTGAGTGTAGATAAGCCTTTCAAGATGTTTGACTATAGAAAGAACCAGAGGAAATGGAATT
GAGTGAAGGCTTTGGAGTATGGGGTCTTATTAATAGAGATAGAGTTACATATTTGAGTGCTGATTAGGAG
GTAATTGAGAGAAAAAACAATAAAGATACTCCGAATATAAAAATAGAATCTAGAGCTCAAGTGGTAGCAT
TGGCCTTAAATAGGAGGAGGAGTAGTGCTTGTTTCATTCTACCAGAAGAAGGAAAAGAAAGCTTAATACA
GATGCTAGTAAATTTGTAGGTTTTGCAGCCAAAGGAATTATTTAAAACAGTAATTATGTGTTTTGGGATG
GAAATGGAAGTGATGAATCTTAGGGTCAAGGTTTTGAAACAAAGCGGATAAAATGAAATTGTTATTCTAG
AGATTAAAAGAAAGCACCGATCAGAAAAGATTTATTAGATGCCTTTGAATAATCAGTTGAAATTGAAGAT
TATTTGTGAATAACAGTGTGAGTCATATGAGCATGGATAAAACAATCATTTGGATGGATCTAGCATTAAA
ATTTTGCTAGACCAGCAAAAGAACAGTGGAACAAGGAAGTTAAGTATATGGTAGCTAAAGAGAGGACAGT
GGAACCTAATTTAGTTTGGAAGGGAAGAAATTTCAGAGTCAAGGAAGTAAGAGGGACTAGACGTCAAAGT
AGATATAAGAATAGTTATTGAGGTAAAAAACTGAACAGGCCATTTTATTTTGATTTCAGAGACAGAACAA
TTCTGAGTAATGTCACAGGTCTGTGACTTTTGGTGTGAGTGGCTGGAAAAAAAGTTGAAGTTATTGAGGT
TAAAGAAATCAGGGAATGAGAAACTAGAGTTCTAGGTGAATTGTCCACTGGCTGTTAAAGAATTCCTGGA
AAAAAAGTTGAAGTTATTGAGGTTAAAGAAATCAGGGAATGAGAAACTAGAGTTCTAGGTGAATTGTCCA
CTGGCTGTTAAAGAATTCTCTTCTCTCACTTTTTACTCACCAAATTAATAATCTCATTATGAATTCTATA
TCCGAAATAAATATTTGTCTCATTTTTTAAAAAATCCATCTTACACATTTGGCTATTTTAGTATCAAATT
TTAAAATTATTTCTACTATTAAAAAAAAAAAGCAAGGCTAAAAATTCTTCTCTATTCCAACACTTGCTTAA

FIG. 7C (Cont.)

GGAATTTAGTTTCTAGTCTCCTTACCTCCCTAATCTTTTAGTTTCCTATGAACATGCTTCAGTTTGTATA
ATTTCTTTTGCAAATTTTGTTACCACAACGGAATGCAATATTTCAAACATGTTCTGAGTAGCCTAGGTTT
AGAGCAGGTATGGAATACCATTCCCAAACAGTATCTGTGAAATGTTAATTCAGGTCCCAGGAAAGGAAAT
TTTCCTTATCAACCATTCACAGATACTATGTATTCACTCAGTAGTGAGCCAAGTATTGTAGAGGATGGAA
AGATGAAATATGGTCTCTTCTTTCATTACTAAGTGTGTTAATAATATGAATTTGAGGGAGAGTGATGAAA
TAGAAAATACATTGTACTGAAAGTCTAGAAACATGGATTTCCTTTTCTCACCTTTGTATGGCTAAAGACT
CAGCCTTAACTTGCGTTTTTCTCATGTGTAACTTTTGAGTAGGTAAAGTCAGCTAGATCATTTCTAATTC
ATTTTTATGAAAACAAAAAGGGTAGAGAGAAGGAAGGGGGCTTTGAGTTTGCTTCCTTTTACTGTAAGTA
CAGGAGGAGTTAGAAGTAGATGAGCAGTTGGACATCTTGACCTGAACCTTGAAAGATAATGATTTCTTTG
CTAATGTTGCAGGCATACAGAAGTATTCAGAATAATGTGCCAAGTTTCATGTACCTACAGCCCATTTTTG
TCTTTACATTTTACCATAATTGTTTCAGGTCATTTTGTTATTTTTTTATTAAGAAACAGATTGCTACAGG
TACAATTGAAGCCTGCCTAAACCCTTCCTCAGACCCATTACCACCCCTTCCTTAGAGGTAACCACTGCCC
TGAGTGTAGTGATTCTCATTCCTGTATATATTTTTAGGCTCTTACTGAATACAAATTTATTCATAAGCAG
TATATTTTGGGTTGTTCAATACGTTTTCCAGAAGTTTATAAAATAATATCGTATTGTATGTATCATTTTG
CCAGATTTTTGCTTAATGTTGTTTTTGAGGTTCAGCCGTGTAGCTATAGGTCATTCATTTTAACTGCTTT
AAAGCATTCCATTGGGGATCTATTCCATAATCTGTCCATTCTCCCATTGATGGACGCTTATTATAAACTG
TACTGAAATAAACATTCTGTATTTGTCTCCTTTTGTACATGAGCAAGAGTTTCTGTAAGATACATACTTA
GAAGTGGAATTGTTAAGTTGTAGGGCATGCACAACTACAACTACATTAAGTATTGCCAAAACTCACACTC
CCACGAGCAATGTATGAAAGTAGCAGGTGCTGCATGTTCTCCTCTGCGCTTGGTTCTTACCAACACAATT
TGATGACCATGATGTGATTTATTTTAGTTTTGTTTTAATTCGTATTTTCCTCCAAGTTTAGTTAAATAAC
TTTTCTAGTCTTTATTGACCTTTCAGATTTCTTCTTCAGAGAATTGTCTTGACTGTCTTTTTTTGTTGTT
GTTTATCTCTTTTGTATGGATTTATTCTCTATATGTTATGGATGCATATCACCTTTGGGTTATACGAGTT
ACAAATCTCCTTCTCCAAGGTGGAAGCTTTTCCTTTCTGTATAGTATTTGTTTTGGAAAACTTTAAAATT
TTAATGTACTCAAAAGATGTTATCTGTTTTTTTCTTTTGCTTTTTTTTTTTAAGTTTTGGTGTTTACTTT
TGGATCTTCAAACCTTGTAGAATTTATCTTTAATAAATGGTCTAAAGTAGGTAATTTTTTTTCTTTTTCT
CCTATATGTATAACCAGTTGTCTCACAACCATTTATTGAATAATATATTACTCTGTTAATTGAGAATGTT
TTTAAATGATTTTACGATTGTTCAGACTGGTCTCTTTCTTAAAGGTTTATGAAAATTATTCATTTGAAGA
ACTACGTTTTGCATCACCAACTCCTAAGAGGTAAGGATCGTTTTCTCAAAGTATAACCAAAACATGTGTT
GTCAGCTGCTTGCAACTAAAATCATCCTGCATTTCAACTTTATTTTCTATAAATAAATACTTTATAGCAT
TTTTCTAGGTTGCCGATAGAGATGTCATATAATAATGTATAGATTTGCAGAAAGAATGTGTTTACATTCA
ACTGTAATACTGCCAATATATTACATAATACTACCTACTAGTGAAAATAGGTATGTAAAGTAGATATCTA
GTATGTAAAAATGTTTAAATTGACTTGTTTAGGGTTGATTAGTTTGTTTTTTGTTTGTTTGCTATTTAAA
AATTGTTCCTTTTCTCCTTCCAATGAATTGTGGAGAGATTTCAGCATGTGGTATACTTGTATTTGATTGT
ACTGTCTTAATTTTTCAGCCCGTAAGTAATTCTGTTAACTTCAGATTTAAGGACTTTTTTTGAGTTAATA

FIG. 7C (Cont.)

TTTTATTTGTTAGGAACAGTACTACTTAAAATAGAAACTTGGAAAAAATAATTAGATGCATTATACTTTG
GAGAGATCACCTCCATAGAATTTAGAAAAATCTCTGAAGTGAATCTGAGATAGCAGAATTATGTATAGGC
TGGAAATACCAGTTTGAAACTCATGGGGAAAATAAATTTGGGAATCATCTATATTGAGATGGCATTTAAA
ACTGAGGAATGGTTGTCACCTAGATAGATGGCATAGGTAGAAAAAAGATGACCCAGACCCAAATCCTGGG
GCATTCCTTAAATTAAACGGTAGTCAGAAAAGGGAAAGCAACAAAACACTGACAAAGAATGGCCAGTGAG
ATAAGAAAAAAGCCAGGAAAATGTCACAGAAGCAAAAAGAAGGAAGTATTTCAAGATAGGAAGAGTTGTC
AGCTATCAGATGCTACTGAGAGATTGCTGAGGATGAAGTGACCATTGAACTTGGGGACGTGGTGGTCATT
GGTGACTTTGACATCAGCAGTTGTAAGGAAATGTTGGAAACAAAAGCCTAATAAGGATAAATTGTGGAAA
GGAAGTAGAAGTGAGAGAATGGAGTTTGATATAAATCGGAGAAGAGATGTAAGACCTTATTAGAGGGGGT
TGTAATACCAAAGGGAGGTGTTAGTGAAGATTCTAAAGTTTGTGTGCTAATCGAAATGATTCACTAAATT
GAGAGTAATTGATGATGCATGAGAGAGAACAAGGTGATTGCAGCATAAAAATGTTGAGGGAATAAGATTC
ACAGCACAAGGGGAGGGACTAGCTTTGGATCAGATCCAGGACACTTCCTCCATTCTACCATGAGAGAAGG
CAGGGGAAAGTAGGTTTATTAATCACATTGCAACTTTGAGGTTGTATCTGATTGCTTATTGTCTCACAGA
AGAAAGAGGTGAGGTCATGATCACCTGAGAGTTAGGAAGAGAGGTGATGCAGGTTTGAGGTAAGAAAGAA
GTGAAATTCAAGCATTTTGGAGAGTAGGCAAGCGTACTATGGCAGGGTGGTAGGATTGCCAGGAGGTATG
CAAACAAATTAAATGTTTGCTGAACTATCGTAATGATGTTGACTGCTTAACCAAAAGTAAAATTTCCAAT
ATCCATCTTATTTCTTTTCAGACCCAGTGAGAATATGCTGATCCGTGTCAATAATGATGGGACTTATTGT
GCAAATTGGACTCCAGGGGCTATTGGACTCTACACTCTTCATGTTACCATTGATGGCATTGAAATCGGTA
TTTTCTTTAAAGCCATGAGCTACTACTTACTTCAAATAACTAGAGTCAAAATTATTTTTATCTTCTAGTT
TTGCCCATTAACTTGCACTAGACATATGGATAGGTTTCATAACTTATTTGAGGCCTTGTTTTCTCTTTCA
TAATGAGTATTTAATTAGTGCATTAACATTTTGTAATAATTTCTGGTGTCCGCCCAGGCACTGTAGCCCT
CATGACTCTCTCCCTCCATTTCCTGATGTTACTAGTCAGGTGTGCTCTCTTCCACGCTGCTGTTACCCTG
TCTCTCCCCTGTGGGTGTGTCTGTGCCTCTCCTGACTGTGAGCAGAAAGCATTCATGTTTGGATCTTCCA
GTGTAGCTCAGTGCCTGGCACATAATGACAGCAAATATGGATGAATGAATGCATTTTTAAATCGATCATT
GTGTTAATCTGGGTTCTCCAGAGAGACAGAACCAATAGGATATCTATACAGTCATGTACCTCATAGCATT
TTGGTCAGTGACGAACAGCGTATATAATGGTGGTCCTATAAGATTTTCCTGTACCTTTTCTATGCTTAGA
TATGTTTAGATATGCAAATCCTTACCATTGTGTTACAGTTACCTGCAGTATTCAGTAGGGTAACATGCTG
TACAGGATTGTAGCCTAAGACCAATAGGCTGTACCATATAACCCAGGTAATCTGTACCATCTAGGTTTGC
TTAAGTCCACTCTGATGTTTGCACAATGATGAAATTGCCTGGTGATTCATTTCTCAGAACATTTCCCCAT
CCTTAAGCAATGCATGTCTATATTAGATATATGAGAGGATTTATTAGGGAAATTGGCTCGCACAATTATG
GAGTCTGAAAAGTCCCATTATGGGCCACACCTGCAAGCTGGAGATCCTGAGATGCAGGTAGCCTCAGAAC
CAGGGAAGCAGATGATGTAACTCTCAGTCTGAGGCCAAAGGTCTGAGAATCCAGGAGGGCCACTAATAAT
AAGTCCTGGAGTCTAAATGCTGGGGACCCTGGAGTTCAAATGTCAAGGGACAGTAGAGGAAGTGTTTATC
CAAGCTCCAAAAAATAGAAATACATTCACCTCTCCTCTGTTTTTGTTTGCTCTGTGTCCCCAGCTGATTG

FIG. 7C (Cont.)

GACAGCGCCTGTCCACATTGAAAGCAGATCTTCTCCACCTACTCCACTCACACTCACACGCCAGTCTTGT
CTGGAAACACCCTCACAGACGCAAAAGTAATGCCTTACCAGGTTTCTAGGTATTCTTTAATCCAGTCAAG
TGGACACCTAGAAGTAATCATCACAACCATTAACTTTGAAAAACATATTTCTTTTGTTTTAGGCATTAAT
CTTTTCTTTACTTTTAAACTGTCTGTATAATAGGATAACAAGGAGAAAACTCTAGTACTTATCAGTGTGA
ATTTCTTGTAACATTATTTTTCCTGATGCTCCTCAAGGAAAGGGGTTTCTGTGATCAGATAAATTTCGAA
AACCTGGTTTGGGATGAGTATCTTTTATCTGAAATGCTTGGCACCAGAAGTATTCTAGATTTTGGACTTT
TTCTGATTTTGGAATAGTTGTATTACAGTTACCAGTTGAGCATCCCTAATTCAAAATTTCAAAATTCAGA
ATGCTCCAGTGAGCACTTTTTTTGAGCATCATGTCAGCACCCAAAGGTTTTAGATTTTAGATCATTTTGG
ATTTGGGGTTTTCAGATTAGAGATGCTCAACTTGTATATGGTAGTCTCACTTGAGACATTCACACAATCT
ACATTAACATATTAGGGATTCTGAGAAGTTCTGAAATCAAGAAACTTGTCTGACTATGTTTAATCCTTAT
CGTGGGACCCCTTGCAAGTGGAGAAGAGAGAAACAGGGTGGAGATAGTAATAATACCAATTAATATTTCA
CCAAAATATTTGGGAAACCCTGCTTTAAGTAGTTTGCTTTGGCAGTGGAGGTAAAGAGGTACTTTACATT
GATGTAATTGTATGTTCTCATACATTAATGTAACTATATAGACTCAGATATATCCAGTTCATCTGTACCA
TTCTAGAGACCTTCACCAGCAGCCTTTGCTGCACTCTTCTTTATTTCAATATATTCATAAAGCCTTTAGT
TCAGCAAATGTTTTTTGGTTCTGAGCATACATTTTCCTGGGTAAGACAATTCCTGTCAAGTGTTAACACT
TTAATGAGGATTGTGAAAATAAAACACGCAAACAAAAATCTTATGAAGTAGAATATAAGTAGTGACACAC
AAGACATACAAATTACAGTAGGAATTCGAAAGTAGAAATAGCCAAGAATGACATTGTGAAAATTTTCTTT
TCTCTAAAAATTCTGGTAAAATTTCAGTAGATAGAGTTTTTTTCATCATCTTATCTAATAGTGGGGATGA
AGAAAACTGATACAAATTAGATAAGAAAAATCCACTTATATTTGTTTTTTGGAATGAAGCTGAACAAAAA
TACTTGCTTACTTAGAATCATCCATTTTCTTCCATACTCAACTTCCCTGCTCTTCTTCCTAAGTTTTCTC
CGATGCCATCAATGGGCTGCGACCTTGCTTGACCATAGACAAGCAGAGATAATAATTCACTAGAATAGTT
ATAATAATAATAGCTAGCATTTATTGTGCATTTAATATATATCTAAATTTTCTCTATGTATACTTTTTTT
TTTTTTTTTTTGAGACAGAGTCTCACTCTGTTGCACAGGCTGGAATGCAGTGGCGCGATCCCTGCCCACT
GCAACCTCCACCTCACAGGTTCAAGCAATTCTCATGCTTCAGCTTCCTGAGTACCTAGAATTACAGGTGC
GCGCCACCAGGCCCGGCTAATTTTTGTATTTTTAGTAGAGATGGGGTTTCACTATGGTGGCCAGGCTGAT
CTTGAACTCCCGACCTCAGGTGATCCGCCTGCCCCGGCCTCCCAAAGTGCTGGGATTACAATTGTGAACC
ACTGCGCCTGGCCCCTTGTACATTTTACGTCATTTATTTCCTACAACAGCTCGGTGAGTTAGATACTGTT
ATTTTTCCCATTTTATAGATGAAGAAATTGAGGCACAGAGAGTCAAACAGTTAGTGCGAGATATTGGAGT
AACCAAAGCAGTCTAACATGAGAACCTCAGCTTCTCACAACCATGCTACATTGTCATAGAGAGGACTGGT
AGAGATGATGAGTGGTATTCTGATTGGATATTGTCAGATAAGATTTAATTCTCAAGGGTTCTTTTTTTTA
TTATTTTCCATTTTTTTCTGTATCATTTCATATGTTCTAGTTAAAGATAGGGAGCCCCTTCTTTTCCTTGA
CATCCTGAGACATTCCTTTAGAATCTCAGGGCCATTTTTAAAATATTTCTCTTGTTTAGCCTATTAAATA
TCCATCACCTTAAAAGGACAGAAATCAGATATTTGTGTTAATTTTTAAAAATAGCCTGTGGATGTTTATA
AGATTAGGTTTAAGGATCTTCCTTCTCTTTTTTTCTCAAATGTTACAGTTCTCTGATTTTTCTGACAGAT

FIG. 7C (Cont.)

GCTGGTCTGGAAGTAAAAGTAAAAGACCCACCAAAAGGGATGATACCACCAGGAACTCAGTTGGTCAAAC
CAAAGTCTGAACCTCAGCCTAATAAGGTTAGGGCAGAATGAATTGAGAGCCGGAATCATTCAATTTTTAC
GTTTGTCACTGATGCTTCAAAATGGCCAGTAAACATCTAACATTTTACTTGATTTCAGGACTTGAATTCT
AAATATCCCTAAATAAATTTAGAGAGTAGTTCATGGTAATATTTCTAAGTTGTAGCATGTGTACTTCTTT
ATTTGGTACATATTGTATTCTTCCTGCTGTGGAACATTTACAATGAACAAAGTCTACTGAAATTAAGTG
TAAAGTTTGCAAGGTGAAAATGTCCTCTACTGTCAAAAGAAAAGTTAATTTCTGAAATCTAAAGAGTAAG
TACAGGCATTTTGGTAAACTGCATGTTAAAAAAATGAAATATTGGTAATTGAATTTATTTTTCTAACAGA
AAGAAATGGTTTTTATCCTTCTTAACACGTATCTTCAGTATTTAGAAATGAGTTAAAATATATATAATTG
TCTAAGCTTTATTTTCAGTAATACACATTTCAGTGCTTAAAAGTTCTGTTGTTAGTGTTGTTATACTGTT
ATTTGCAGAGGGAGCCTCTCTACAAATAATTCTGGAACCTTATTAAGAATTACGATACTTTCAAACCTGC
TTAATTTTACTTCTTGCTACTTGTAAGATCTCTATTCTATGTTCTTCCTACCTCACTGTTTATCTTTGCC
TTTCTCAGGTTCGAAAATTTGTGGCCAAGGACAGTGCGGGGCTTCGCATCCGTAGCCACCCTTCCCTTCA
GAGTGAGCAGATAGGCATAGTGAAAGTCAATGGAACTATCACTTTTATTGATGAGGTAATTGATAAAGGA
GCTTTTGGTAGTAAATTTTGGACAGAAAGTTTTTGCATTGTTTGCATAATAATAAGGTTACTGAGTTTTT
TGTCAGAATATGTTTTAAGCAGTTTGGGAAATATTTTAAAACTATTTTATAGAATGTGTTCATTGAGTTT
CAAACATTTCATTTATTTTATCATTAAAAAATGACTAAAATTATATTTTGAACATGAAAAGAACAATGTT
CGACATAGTATTCAGAACCTGTACATGTATTCACTGAAAATGGGTATAGTTCTTCATGACATTTTAAAAT
GTTGTTTGTTTTGAAATGTGTTTCTTACTGCTTTAACTTTGGACAGTATATTTTTCTGGTAATATAACCA
AGTAACTTCTGTTTCTTAAAATATAAATATAAGGGAAGGAAGACTCATATTCCTTTGGGAAACATCTGAT
TTTACTGTTTATGTATCTTAAAGTGTGGTTTCCTTGTGTTTTTATTCCTAAGTGAAATTGTTTTTACAGT
CTTGCCACATGAATTACCATATTGTGTTGGCACTCTTTGCTGCTTTTTTTTTCCCTGGAGGGTCTCTCAG
ACTTACTTTCTGCAAAAACTAGATGCTTAATCTGCACATGCACCATCATTTTTCTGCTTTGCAGACTTTC
AGACCTTGCTAGCCTCATAGGACTTACAGGAAGGCCTGGCTTGTTTCTGTTGCTTTTTTCTATAGATCCA
TAATGATGATGGTGTGTGGCTGAGGCTGAATGATGAGACAATAAAGAAGTATGTCCCTAACATGAATGGT
TACACTGAAGCCTGGTGCCTCTCTTTTAATCAACATCTTGGCAAGAGTCTTCTGGTCCCTGTTGACGTAA
GTAAAAGGTGGTTTTAAAAAGCATTATAGATACACGCTGTTTGTTTTACAGAGCTTTCTTTAATTAAGGC
TTTTCAGTTCTGAGGTAACCCACAACTAAGTAACCTTTACTTTACAATTTCTTGAATTCTTAAGGGCTTC
TGTGTAATGAAAGTGAAGTTTGGCAAGGTTAAGGCCCTTAGTGCAGATTATGATCCATCACAGATAGGCA
GGAAGTAGTAAATTTAATTAATTGCTACTTAATTAAAACTACTGAATTCCTTTCAAAGAGGTAGAAAATG
AGAGTGGTTACATTTTTTTCTTTCTTATTTATACAGCTGTGTGGAATGAATTCCAAACTAAAGTTTATGA
ACTCAGAATTATACATTCAAAAACATGTATAAATGTATGTTATGTTCACATTTTGCAGATAGTTCTGTGT
GTTCTGTCTAATTTTGACTCTCTTCCTTCTCGGCTTATAATACTATTATTTAGATTTGTGGTGCTCCGTT
GTATTCTAGTTGAAGTTAAATCCTAGTCTTTGAGAGAATTCATTGTACCTCCTTGTTGAGTATAGTAGAA
TAGAGCCAGTGTTCACAAGATTGCTACTTCATGAAGTATAATAATAACCCACACTTCGTTTTATATATTA

FIG. 7C (Cont.)

ACCAGGAAAGAATGATTTTTCCTTTTTTCATTACCATCAAATGTGTGTGCTCTTTAGGATAGAGCTAATA
AATAGCACGGGTAAAATTTTATTTAAAAACTTAGTATTTTAAACAGTTGAATTTCTTAAAAATCCGTTTA
TAAAGTTAGCTTATTGTATCAAACCATTCAGTATATTCCATTTGACTTTCTCCTTGATTGTCCATAATAA
TGTTCTCCAAAGCAGTAGTTTATATAATACAAGACAATTCTTTGGTGAAGAAAACATTGCAATTTCTATT
TCTATTTATTGATCTCATTCTTTTTTATATGCTTTTGTGTATGTTTTATAATAGCACAGTGGAGACTGTA
TATAGACAGAGAGCAAGAAAGAGAAGGAAGATATGTGATCAAGAAGATTTAGAGTGTTGGCTTACTGCTT
TACGGAGGTTAAGTTGAACAATGATACATCTATAAGTAAAATACTAAATTTTAAATTAAAAAATTACATC
AATTACGTCTTATTAAATTTTCCTCAGATTTATACCTGCAGTTAAAAATAAAAAGGATTTTGACCCTCTA
TGAAAGTGTATTTTAAAGAGATAATTATAGCAACCACTTTTGTACAGTTTTTTTTTCCAATATAGACTTT
TTTGTTGGGCAAGGGGGAGTTGGTTTTTGTTTTTTATACAGATGGGAGAGCCAGGCGAGGTGGCTCACGC
CTGTAATCCCAGCACTTTTGGAAGCCAAGGCCAGTGGATCACCTGAGGTCAGGAGACCAGCCTGGCCAAC
ATGGTGAAACCCCGTCTCTACTAAAAATGCAAAAAATTAGCCAGGTGTGGTGGCGGGCACCTGTAATCCT
AGCTACTCTGGAGGCTGAAGCGGGAGAATCGCTGGAACTCAGGAGGTGGAGGTTGCAGTGATTCAAGATC
ACGCCACTGCACTCCAGCCTGGGAGACAGAGCGAATCTCTGTCTCAAAAAAAACACAAAAATATAGAGAT
GGGGTCTCACTATGTTGCCCAGGCTGGTCTCAAACTCCTGAGCTCAAGCGATCATCTTACCTTGGCCTCA
CAAAGTGCTCATATTACAGGCATGAGCTACCACACCTGGCCATTGTGTGTTTTATTTAAGAAAATTTTCT
TAAGTCCCTAATAAAATGTTATTCCAGATTATATTATCTTTTCTACCTTCCTAGTCCAAATTTTCTCTGA
TTTCTTTGCTCATTTGAGGAGCTGCTTTTGGGAGAGAAAGATACTCACACAGATAAAGCAAGTCAATAAA
CAAAAGTAGAAAGGAAGAGCAAGAAGTACCATCTGTCACAATTCTGAATCCCACGATTTTATTTTAAAGC
ATTGTGTTCTGTTACTTGATGCTTTTGAACCCCATCCAAGAGACAATCTGTAGTAGACAGTCTCCTTAAG
GTCAGGGAAAGAAGGGAGTAACAAAGGTTAGAGGAGCGGTAAGGAGTGGAGTGAGGCATACAGATACTTG
TGGGTGGTTTTCACTGGAATGTGAGTGCGGAGGTTGTTAATGTAAACAGCTCAAGAGTGTCTGGTATTGT
TAGGAAGCTAGGGTTTTTTTGGTTTCTTCATTTTAAGAGTAGTAGTGACTTGAGAGTTTTATAAGTTAAA
AGAAAGATACTAGTAGAAAAAGGGAGAAATTAAAGATATAGATGACAAGACTGAAGACTGAGAAACAGGA
GGAGGAAATGGAATTAAGGGCACCTTAGAGAGCTTGCTTCTGTAAAAGAGAGGGGAATATGCATGGCAGT
AGTTATGTTTTAGAGGAGGGAGGGACGAAGGGAAGAGGTTGAGGGAGACTACAAGTTCCCTTAAAATAGA
AGATAGGAAAACGATCAGTTCAGAATCAAAAGAATGAGTTAAGTTAGGGGGTTGAGAAATGCAATGAATA
TTTGAAATATTGTTTGAAGGATTACTGGGCCACTAAAGACTCAATGAGACCACTGTATAGACCCAACTGG
AATCCCCTGCCTAGTCCTTTATTGCCCTAAGTGTCTGGAATTAAAAGAGCCAAGAAAGAGCCAAGAAAGC
AAATTATAGTACTAGTTGCTGAGCTGCTGTGACAGAAATAGCAATTAAGATTATCAGTTCTGGGAATGTG
GACTCAGACCTAAGTTAGAAATGTGAAAGGACAAATGGAAGGTCCAAGGGATTTAGAAGATTTAATAAAA
TCCTAGAACAATATAGTGAATGCACTATAGTTAAAGAGTTGGAAAAATGCAGGCAATAAAGTAGAATATT
TGTATTTGATATCATAGGTAGGGCACTTTAACAAATGAGATACTCTATTACATTGCCATGGGAGGGTGGC
TGAAGTGCAGTGCACGTGGAAGTCACTACAAGTGCCTAAGTCTAGGAACTAAGAAGTTAGGCAGGTGGAA

FIG. 7C (Cont.)

GATCATCTGCATGGACTTGAAGACACACAGATGATGTGACTCACAAAGTTAAAGATAAAAACAGGCTGGG
CACGGTGGCTCACGCCTATTATGCCAGCACTTTGGGAGGCCAAGACGGGTGGATCACAAGGTTAGCAGTT
CAAGATGGTGAAATCCTGTCTCTACTAAAAATACAAAAATTAGCCAGGCGTGGTGGTGGACGCCTATAGT
CCCAGCTACTCAGGAGGCTGAGGCAGAGAATTGCTTGAACCCAGGAGGCAGAGGTTGCAGTGAGCTGAGA
TCACACCACTGCACTCCAGCCTGGGTGACAGAGTGAGACTCCGTCTCAAAAAAAAAAAAGAAAAAAAAGA
TAAAAACAATGTGTTTACCATTGGAGGAAGGGGTCCATAAGACACAATTTAAAGTCATGGGGGGATGGGA
ATAGTTTGGATCAGGAAGAAACAGAGCAGTTTGGTATAAAAATGAAAGAACAGGTAGATGACATAAGGAT
TTATGTTTTGGGTGGTGATCAAAGATGACAGATGGGGTACAGTATGGCAAAATTAATTGGCATAGGGCTC
TAAACAGATCTGGGATAAAGTTACTTCAGTACAGGTATTAACTGAGGACTCATACAGAGTCAGAGGCCTG
GCATAGGCAGGGACAGGTATGATTTTCTGTAGGGACTAGGGCAGACCCCTTACGCAGTCAGTACATTTTT
TTTATGAGTATCTGACTGTGCAGGGCTAAACATGGTAGGACATAGAATAATGATTCCCTCTCATCTTCTC
AAGGAAATAACACACCTAAATAGTTGCATCTTGCTGCCTCTTCTTTTGTATGTCTTATACATTTACTGCT
GGAAAAACTATCTTTCTCCCTTCTTACTTCAGTTCGTTTAAAGTAAATGAACTTTAATCATGGCTGTTAA
TTGTAAAACATGACTCAATAAAAAAATGAAAGCTGGGAGATATGAAATCAAATTAGAAGTATTCAAACAC
CAATGCTGCTAACTTAAAAAGAAGTGAAAGTACTGAAAAGTTGCCTTCAGCACTGTTTGTGTCTATCTCT
TCAACCTTTTCTAGTTAAAACAATTTTGTATTGACATCAATGTGTGCACGTTATTTGGATCCCAACTCAA
ACAAACTATAGAGAGAGGAATGGGGGCAGAGATTGGAAGTTTGAACACTGACTGAATGTTGGATGAATTA
TTTTTAAAAATAAGATTACTATAATTACCCATTTTAGATAATCCTTAAAGTGATCTTGTCATGCTGTCTT
GTTTACTCATGTTTTAGAATTCGTGTATTCATCGTTAAGTATGAACTTTAGCTCAATTTGGATCTATCAG
TCTTTCTATTTAAACACCATATTTGACTGAAAAATATTCATATCCTAATTTAGTTCAAAGTGACTTTAAC
TGTTTTTAGTAATGCTCTAGTTGAGAGACAAAATAACATTAGACATTCATATTATGACTGTATCGTTTCC
AAAATAATTTTTAAGTCAATGGGAAAGATAGAGCTAAATAGATGAAGGGTTCAGATCCTCTGTGAGGCAT
TCATTATCAATTATGTAGAACTTTTTGCCCTTTTTAGAACACTTTTCCTTTTTTTTTTTGTTATTTTTGT
TGTTGTTTTTTGTTTTGTTTTTTGTTTGTTTGTTTGTTTTTACAGCACCTTGCCCTGCCACCCAAGCTGG
AGTTCAGTGGCACGATCTTGGCTCACTGCAACCTCCACCTCCCAGGTTCAAGCGATTCTTATGTCTCAGC
CTCCCAAGTAGCTGGTATTACAGGCATACACCACCACACCCAGCTAATTTTTGTATTTTTAGTAGAGACG
GGCAGGGTTTTACCATGTTGGCCAGGCTGCTCTCGAACTCCTGGCCTCAAGTGATCCACCTACCTTGGCT
TCCCACAGTGCTGGGATTACAGACTGGGATTAAAGACGTGAGCCACTGCACCCGGCTGAGAACATGCTTT
CCAGTTTTATGTCTTAAGAGTCTTTGTTTTGTTGTCTAATTTATCTAGAATGGTTTCACTTCCATTTTTT
TCTAATCTTAAGTTGTCCAGACTCAAAAATTGGTTGGTGATCTTCTCTTTATTTTCCATTTTTGCTATAG
TCATTAATTCATTAATTGCTCATTTAGTAAATATTTGAGTTCTTATTCGTAGAATTCTTATTTGCATTCT
TGTTAGTAATAAATACTAAGCTGGAAAGTAGGCATTGGGTGGAGATGCAGAGGGGAGGGATACAGAGTAA
ATAACATGGGGTGAAGTTCTGATCCTTGGAGTACTCACCATGTAATGTGGTAGACATACCATATTCACAT
AATTAAATTGCATTGTGATAAGTTGTGGAATGGCTTCACTTAAGTGACATTTGAGGAGGACTTGAAGAAA

FIG. 7C (Cont.)

AGTTGCCAGGAAACAGTAAAGGAATTTCTAGACAGAGAATCAAATGTTCAGAGTTATGGGGACATGCTAT
GTATGTGAACTAATGAATAGTTGATATAGGTAAAGCAGAGAATTGAGGGTGGAAAACAGATATGTACTGG
GGAGAATAGCTTTCTCTCTTCCTTCTCAGGCAGCACTTAATCTGTAGAAGTAGAGAAGGCTTACTTCTTT
CTCCAGCTACCCATAATATTTGTTTTTCTTGCCTTCAGCCCATTTGTGTTTATGTACCTCTTATTTCTGT
TTTTAAGCTACTTAAGGATAAGGACTCATTCAGGATCCCTTCTCACTCACATTTGTTTCTTCCTAAGCAT
TAAAAATTACACTTTGCTCATAGTAGGTTTTCACAGTTTGTTGATGCTTTACACATTTGTGGATGCTTAA
TTTTAGTTCTTTGCATTTGATATGATCATTCTGTTTAAAATAATTTCTAACATATATATGCTCCTTGCCT
TAATTATCTCATTTAATCCTCATTGTGACCCTGTGATGTTAAGCATATTATAATTCTCATTTTTGCAATG
AGTAAAGATAGCCACTCACCCAGGATCACAAGTAGAAAGTAGTGGAGCTGGTATTGGAACACCAGTTGAT
ATGATTCCAAAGCCCATGCATTTATGTTCCGTATGCATTAATCTAGTGGAGAGATAAGGATAAATATAGT
TATAAAAGGATGAAGCAACTATAGCTGTAATAATCCTGTTACTTTGACTAGAACTGCCAAACTACAGAAA
GATAAATACTTATAACCTTAATGGTTGAATGAGGATGAATACCATATGTATTGAAGATGACATGAGTTAT
TCTTTGATTGCATACCTGGGGAACATTGATTGATTTTAAATTAAAATTCTGAAGATGTGGAATCTGCAAA
ATGTGAGCTAGTAGAATGTTTCAAATATCAGGGACAATGCAAGTAAAAAGATGAAGAGAGAATTTATTAT
GCACCTACCAAGGAAGACATTAGACTCTGGAATCACAAGCTTAATTTTTTGGAAAACAAGTGTACTTCTA
TGATAGGAGATGTTAATGGTTTCAAACTTACACACCCAATTCTTTGGGTACTCTGTCAAAAATGAGATCT
TTTAACATTGTGAGGGGGGTTGAGTGGAAGAGAAAGTTTATATCAAGGGAAGTAGATGATAGACAAATGG
AAGTATTCTGAGGTATCTTTATAGTTCCCATATAATCTGAATTCTTACAGAATTGAGTTTCTGTATATCT
CCATGCATTTATACAGATTACTTCTTATTTTAGGCTGATGGGTGTTCACATATAGAAAGTATACTGATTT
TCCAAATTTTGGAACCTGAAAGATTTGAAGTAGAGTTGAAGAGAAAGTATCATTTGTTAATCTTGTTTGT
ATAGCTTCACCTGGGTTAATTGATAAAATTGGCAAATGTTTCTTGCATTTTAAATCCAATTTCATTCCTT
TTTACCTAATAACATTAAATCCAATTTCATTCCTTTTTGCCTAATAACACTTAGCAGTCACAGCTTTAAC
ATACCCCAGATTTCCTGATTTTGTTAATAGCTTTGTGTGTATGTGTATACATAACCCGTGTTTTAATCTC
AATAATATTAACTTAATACAACATTAGTAAATGTGCTGTTCTTATATGGTTAAGAACAGCTTTATTTCAT
TCTTTAGCTTAGTGTTAAAGTTTCGTAAACAGAATGAGATTAAAACAGTTAAATTAAGATTGTAATAATA
TATATACGCTATTCTTAATTTTCCTGAGTCATTTCATCATTTTGCTTTAACAATGGCAATTCTTAGCTTT
GTGCTTATCTAACACAAGGAAAGATTTTTTTCTTTTATTTGCATGAGCATTTGGCATGGTTGGTCACTTA
TTTTCACTGTGATAATTATTCACTTGTTGGTCTCTTTTCTACGCCATGAAAGATTATCAGCTTAGAGTTG
CAATTTGGTGTTCATTAATTTAGTTAGATTCCCAGTATGCTTTAATTTTCTAATTTTCTTGACAGAACTT
TTCTGCCTTTAAAATAGTATTTGAGAATGAAATGTTATTTTATATATATGTGTGTTCGTATATACACATG
CACACACAAGCTGTGCTTATAATAATCTGTGAAATTATACTATATGAAAGCTAACATATTTTAATAGTGA
GAAATTGGGGCTTTGGAAAAATTAACATTTTCCTGAATGTTCATATCTTTAGACTAAAACATTTCTAAAT
TTCCAAAGAACACTATTCAAGTGTGTGTGTGTGTGTGTGTGTTTGTTTGTGTGTGTGTGTGTGTGTGT
GTGTTTGAGATGAAGTCTTGTTGTTGCCCAAGCTGGACTTGAACTTCTGGGCTCAAGGAGTCCTGCCTTC

FIG. 7C (Cont.)

TCAGCTTCCCACGTAGCTGTGACTACAGGCATGTACTACCATGCCGAGCTATATTTTTAAATTATTTTGT
AGAGACGAGGTCTCTCTGTCTTATCCAGGCTGGTCTCGAACTCCTGGATTCAAGCAATCCTCCTGTCTCA
GCCTTCTGAATAGCTACGAGTATAGGCATGCACTACTCACCCAGCTATTCAAGTATATTTTATTTTTAAA
CTCCAGCTTTCTGTTAGTCAAATTTCTGCTTCTTGATAAATGCAGTTTTATTAGGACATTGCATTTTGAA
AATAATCTTAGGGTAAACCAGTGTGAATTAAGAATTTTCTACAACTGCAGAACAAAAGCAAAAAAGTATA
AAGTTTCAATTTACATGGAAGCATATACAGAATTGATTTTATTGGCAATTTATTACCACAGTTAGCAGTT
AACATCATTTTAAAATATCATTGTACATGTTGTTGACTGAGAAAGCACTTATGTTTGCACATTGACTTAA
AAGAGAGACATAAGCTTTAAATATTGTCAACCAGTCATCACATTGCTTCTTTATCACTAACTTTACCTGC
ATTACTTTTAACAATTGCCTTTCATGTTACTTTAATACTAGAATAATTTATGCTAAAAAATAGAATACGC
TAAAAAAAAGTGATATTGTTTTATGTCAAAAAGTCTGTCCCACTATGCTTTGTAAGGGAGAAAAACCCAT
TGACCAAGTACTCTACAAATTCTTATATACGTGGATGAACCAGTATAGACATTTTTCCCCTAAAACATAG
CACTTCAAAATGCTCTGCAATATGTTTTTCACTTTACCTAAAGAGAAAGGACGTATTCCCTATCCACTTT
TAATTAGGGGGCAGTTGGCTTTGGTTTTGGTTTACATTTATTTGTAGGCATATTATTAGACACTTTGTTT
AGAGTTTTATATGTCTTATATTTATGAATTAGTATATATTTATGTAGATGGGTGTGTACCCACATTCATC
TGTACATATATATGTATATATCCATATATATATATGGATATGGAAAATATAGAACTAGAAAACAGTAAAT
AAAGTCTCATTATCTAAAATGAGATAATGAGAAAAGTTTCATTATCTAAAATGAGATAATGAGAAAAGTT
TCATTATCTAAAATGACTTATAATTGATAAGGAATTTTGATGTTTCTTTTTTTGTTGAAGTCTTAGTTGAT
CTTTTTTATTAATATTTTGAATGTCCTCTTTTTTGGTTCAAAATAACCGTTTATCATAATATTTACATAA
GCAATAAAATTGTGCAATTGCTACTCACTAGAAAGATTTTAATTTCAAATCAGATAAATATAGATTGATA
GCATGAGATAACTACGAAAATGTATATCATTTAAATTATCAGTAAAACATTTTGTGAAGATGTTAATTTT
TCTAGGATAACGTTTCTGTGAATTAATTGTTCCTTAACAAAACATTTTTAGACTTAAACTTAGAGATCCT
AAATGCTCTGCATTTCCTAAACTTTGAGATAGAGAAAAGTAGGCCTGTCTTTTGATAAAATTGATTACAT
TTTTATCTTTTGATAAAAAATTGATTGTATGTATTATGTTTTTCTTATCAAATTTGTTAGTAGCATTCAG
AAACATTTCCAAATGAATTTTTTTCCTACTTATAAAGGGAAGGAAAATTGAAAAAAATGACTCAGACTTTT
TATTTTTTACTTTTTTAGTTTTTATTTTTATTTTTGTACTTCAAAAAGTGATAAGTTCACGTAAACTACA
TGCCATTATTATTCATAATGATAATTGCATTTTCTATACAATCGATATCATTTCCATTTTTATTATAAAA
CAGCAGACTGGTTTCTGTCATAAAACAAATCTGGCTTGTATTAGAACAAATACATCCTCATTTAAAGAAT
TTTAAGGTTTCTTTCTTGCATTGAGTATCTTAAGCTTTATAACAACGTCTGGCTCTTAATTTTAGTAAAT
GGCATGACACACTATATCCATGGAGAGCTTCTGACAAAAACTTACTTATCAGACAGAATTTCTTCGGTGT
GTTGTTTACTCAGATGGCTTCAGTTTCTCTTTAGTAAAATAATATTTCCATGTTGGTGCTAGAGTACAGA
AAAATGTTGTTACTGTGCACGCATCTTCTGCAGATGATATCCTGTTCCCTTTCTTTGTTGATATTTTTCT
TTCTTAAACTTTGTTGCTCAGAATATCTTTAATGCTAGCCAAGGAGTCAGGGATTTGGACGTATTTTCAT
GGACTTCCAAAGCTTTTTTCCCCCAGGTGAGTTAACTGTAAGGAACAATAATATTTTATTCAGGTATTTC
AGCATGTATAACAAATTTTGTGTCTTTAAAACCTTTGCTTAAGATTAATAAAACCTTTTAACCAAAAAAA

FIG. 7C (Cont.)

GATCTATATGAAGTGCTGCAATTGAGTTTTCTCACTCCTGCCAAAAAGAATGTATTATTAGTTTAAGTGA
TACTTCCACATGACTTCAAATTTGCTATATTTAGTTTTATGAGTAGCTTTTCCAATGACTATATCTAAGA
TTAGTGTTTTCACAACTAACTTATTTAGGTGACAGTGTCCTGGCCTTATGGCTCTTTTATTTTTTCTGCT
GCCAACACTTTCACATTCCCTCTTTGAATGTTCATCTGAGAATGGGATGGGAATGGAGGGAGAAAATAAT
AATATTGAAATTCATGAATTTAATATGCTGGTACCTGGGTCTTACATTTCTGTATTGAATAAAGCATGTA
TTTTACTATTGCTTGAGCATGATAGGCACAGTTCTATGACTTTATGTCTGTCAGTGTTTTATACTGTTTA
GCACAAGAATTGGATAAACTTTGTTTTATACTTATTAATATAGTTTTATTACCTTTTCAATAAAATATTA
TTTTAAATTTTTAACAAGTTTTCATAATTGCCTTTCAGTGACTAGTTTGCAATTATAATTAGTTGTGCCA
AGGCTTAACTCCCAGTGTTACCCTGAATGATCAAAAGTTAGAATTATTGTTATAATTAATTAAATGCACT
AGGAATATTATTAAATACCAGTGAAGTTGGGTTTTTTTGCTAAATCTATGGATATTTGCTTTTTTATGTT
GCCATGTAATTTTTAAGAATCAGTTGTGAGTGGGATTAAAACTTGCCCCTTCCAACTATGAAATGGCATG
ATGTATTTATTTATTAACCATTTACAAACAGACATTTTAAAATGTTTACAGAAAATCTTGTGAGTGTAAT
AGCAAGTACTATGTAAAGTTTAGACCTGTGTTACTCTCAATTTTTATCTTGAGTGCTCTCTGTGTATTCA
TGTAGGTTTGCATATATATAAATTCTTACAAATATATATGATGAGTATATAAAATGCGTATTTTACATTT
ATTTTCGGTTGTAAATCTAAGTTTTTTGAGTGTTTAAAATTCTCATTTCCGTTAAATTTCCAATATGTAA
CCAAAGAATATTGGTAAATAAAATATAATTACAGTAAATGTAAATTAATTTTTCTTAGTACATATTTGTA
TAAGTAAAAATTGGTTATTCATCACTATAGTGAGATTCACAAAATATTATGTGAAAGTTAATGGTGACTT
TAACATTTTCCCTGACCAGTCATGTATGGAATTAACAAAGTAGCAGGTATACAGAATTCTTGAATCTACA
TATTTTTAAACCTGAGGATTCTATTTTTAATATTCTACTGTGTTACTGTGTGTATGAACATGTATACATA
TCTCTTCATTATGAGGCTACTGGTAGGGATAGAACTATTTAATACAATTCTATCTTGCATAATGTTAGTT
GTTAAATTTTTATTCTATTTATAACATTATTAAATATCAGTTTTAACCTAATGTTTGCATGTGTGTCTCT
TTATGGTTATCTATTACTCTATCTGAATATGAAATAAATTATAGAGTTCATATTACTGTATTTAAAAATG
CAGTTTTAAATCTCTTTTAAAGGAGTAATGATGACAATGAGAACACCCAGTGTGGACCCTTTATTTACAT
TTAGTTGGGAAAAAGAGAAAATATGGAAAGGTTATTATTTCTCTTTATTACATTCACATAGGAAACAATT
TTATCACAGCATTACAATTTAACAGAAAATTTAGGGAAGGTTCTTTCATTTTAGAAGTGACTCTTTTCAA
TAATAAATTTACGTTATATTTACTTAAATCCATGTTTAATTTCTCCTTTCTACTAAAAATATAGTCTGTT
TTTCTGTTACTAGCATTAATGTATCACTGCATAGTAATGGCTTAACAAATCTAGCAAGACGTTTTTATTT
GTACAATATTAGAGAGTATAAGTTGTTAAAATATTGTAAGCATCAATATTTCATTCATAACTAACAAATA
GCAAGATATAGCTATATTTTTAATGCATATTTTTCATCATCTCTGCTTATGGATCAGTTTTCAGATTCTT
CATACCTGTTTTCTCTATTTATAAATAATTATTTCAACATGGGAAGAAATGAATATTTAGACTTTTTTTT
ACCCATAACAATATACAGTAATGCAGTAATAATGATTCAAAATTATTCCCTTGTGGTTCACATAGTATAG
TATTTTTATTTTTCCAACTTTAAATATTGCATTAAAGATAAAAGTAAAATCAAGGATGATTATATTTCTC
AAATTATGGTGGGCAGAAGCCAGAGGTTGACTGGTTTCCTGCTATATTTTCTTGCCTTCAACTTTATTTT
AAATAGCATTGTTGAAAAACTGAGATTCTTTAATTAGTGCTAATGACTAATTCTTCAGTTATCTTTAGTT

FIG. 7C (Cont.)

ATGTGTTTTTTTTATATTGACAGTACTGTAGACTTGCTATAAAAGCTATTAATAGGAAGGCTTTGAAAGT
GATAATAGATTGTATTTTGTTTATTTTTCTTTCCTATTCAAATTTTCAGGAATCTAAAACTAATACTGAT
GACTTTTTCAAAGACATAAACTCCTGCTGCCCACAGGAAGCAACAATGCAAGAACAAGATATGCCATTCT
TGCGAGGAGGGCCAGGCATGTACAAGGTAGTGAAGACGGGACCTTCAGGTCACAACATCAGAAGCTGCCC
TAACCTTAGAGGTATCCCAATTGGAATGTTAGTTCTGGGAAACAAAGTCAAAGCAGTGGGAGAGGTATGG
ATTCTTGTAGCTTCATGACTTCTAAGATACTCATTTTTAATGTAATACAACCAAAGCATCTCTTCTAAAG
GTTGCCATTTCTACCACAGGTTTTTCAATGTTAATGTATTTTATCTTTACTTGTATTGCAAATACATAAT
TTTTCTGTGCTTCTGTCTAATGATTTGCATAATTATCCTTGTGTAAACAATATATTAACAAATGATTTGT
ATTGTATATATAAATGTTTGGTATTTGCACATATTTTTTCATTATTACAAATGTACTATACCATCATGGA
TTATCATCACTTAAAATATTCTATGTGATCGGTATGGAGATGTGGTCATATGCAAAAGGTTTCATTTCTT
TGTTCCCATTCATAGGTCTCACTGAAGTCCTGAGCAAATAAAATTACTCTTTAGGCTACTGTGGCATTTG
CCTCAGCTGATAAGCTTGAAGATGTAGTGTGTCATGCTATTTCTCAGTAAGGGTCATTTTCAAGTTACAC
TATGGATACTCTCAACCTAAATAATAGCAAGTCGGCTGTGTTAGGACATTTTAGATGCAGAAAAAAGAAA
ATGAGCCATGTGTTCTTGGGTAATTCTTAAAATTATTTAGGTGTTATCTTTGTGCTTTGAAAGTTATTAT
TTTAACCAAATTCATAAATAAGCAGTATTTTACAGAACTTTTTATTGACTTCTGTCTTACCTCAGGCTGT
GGCCTTAATTTCAGAAACTAATTTCTTAGTAGAAATGTATTGGAATGATTACACTATTCAGACACGTAAG
ATTTTTACTGGTTTTCAGACTGAGTTCCCTGAAAGAATCAAGCCAATCAATCATGCTTTTTGTTATGTAC
CAGGTAACCAATTCTGAAGGGACATGGGTGCAACTGGATCAGAACAGCATGGTAGAGTTCTGTGAGAGTG
ATGAAGGAGAGGCATGGTCCTTAGCTAGAGACAGAGGCGGAAACCAGTACCTCCGACATGAAGATGCCAA
GTTGGCTTAAATTTGTGATTTATTCCAATTAAGCTTTCAAATACAGAAGTTTAATGCCTATTGTATTGCT
TTTGTTTTAAAGAGTTTTTTGTGTGTTTGCTTTTTAACAAGCAAAACTAAAAGTTAAAAAATCTTGCAAC
TGTTAAAATTGGTTTGTAAAATACGTGAGTACTTAATGCACATTAAAGAAGAAAATTAAAAGAAAATTCG
AAACATATAGACTCATCTTTATAAAACAGGCTTTTAATTTCATTAATATAAATTTATATACCTCTTTCTT
CTGTACCAGTCCAGGACTGAACGTTCTATCCCTTCTATAATAAAATGAAACTTCGGTATTCCAACTACCA
ATCTCAGTACTTCTCCCAGGCAACTTCATTTGATTGCATTTTGTCTTAGGGAAAGAGCATTGAATAAATG
CATAGTGTCTTTAGGGTTTCCTGTTGTTAGATTTTCAACTTTAAATTTTATTTTACCTTTTTCAACATGG
CTATCACTTAATAAAATATATTCCTTTTTGTCCCCCTCTCTTTGATATCTTGGTGGCAAAAATTTGTTCT
TCGAAGTTGAGACCACATTATCACTTGTGTGATGCTTTAACTGATCACAACAGAGCAAAGAATTTCTTGT
GTTCCTAAAGAATTGTGCTCACCACTAGAACAATAGTGTCATAGTGAAGTTCATGTTTATTTCTTCATAC
CCAGTTATGAGTCCCTTGTGGACAGGCACATGGTTTTTATCTTTCCATTCCTAGTACTGAAACAGTTTTG
ACACATACTAGTTGCTCATGAAGTTTTGTAATACAACTTGAATTATAAAAATAATAGCACATCAAAATAA
GTATGTAAGCAAACATGGACTTGTCTGCCAAATCCCAAAATTTATAGGATGAAGTTAGGTAAATAAGAGA
ACATGCATCTTTATTCAAAAGATAATAAATTTATAATACTTATTATTCCAAGAGGCAATTTGGCCATAAA
TATGGATTCAGAAAAGGTTTGAAATTTGCAATAATGATGGAGTATCTTTGGAGATATCTCCCTTTTTCCC

FIG. 7C (Cont.)

CCCACAACACACCTTTGAGGTAGGTGATATAATCTTAAATTTATAGGTAGGAAACTCAAGCTCTAGAATT
TAAACTAACGTGTCTATGGTTGTACAGCTGGTGACATAGCAGATGTAAGACTTCAGCCAGAATCTTCATT
CGTGTTTTAAATGCTGTACTCATTACACCATGCTGTACACATTGAGCACAACTTGAGAACCTACCTCCTC
TCCTTGTTTTTCCCAGATAGACTTTTTTTAGTCTAAGATGATATGGTCATAAAATAATGTCCTGAAACAG
TAGAACTGTTCATTTGAAAAAGATAAGGGTTCCGCTTGATGTAAATCAGACATTTACTAAATGACTTTTT
CACTTACTATGTGCTTATTATATATTGCTGTATATTTACTTCATATTCATAAATTTTTAAACATTTTTCT
TTATATAGGAATATTCAGATATAAATGAAAATACCTAAGGGGAGATCAGCTTTATTTAAGATAAGTTAAA
TATGAGAACAGCTTAGGTGACTTCTAAAGGACTTTTCTAGCTTAATCCTTAATAATTTTTTAACTGGCAG
TACAAAAAATATGTAAGAGTGGATTCTGAAGCAGGACTGCCAGGGTACTGATCCCAGCTGTGCAACTTTT
TACTCATGTGACCTTGACCAAGTTAACCTAATATCTCTGTGCCTCAGTTTTCCCATTTATAAAATGACCT
TATAGGTCATAACCACATAAATTTGATATGAAGACTAAATGAGCAAATAACAGATAAAGCTAATGGATGG
TAAGTTAGGTCTTATTGTTAAAATGCAAAATGCCTTCCATGCTAAGGATCAAGTTTTAACCTGGGAAATT
TTATTCTTATAAACTTAGAAGATAGAAGCTTCTTTCAAGATAAAATGCCTCTTAAATTAGAGTATCATTT
AAGAAAAGTTTAAATTTTTCTCTGTAATTAGTTAATCATCTTTTACTCTTGATGTATAGATACAGACATA
AATATGGATATTTGGTGATCATGTGAATCTTACTATTTTAATATAAAACCTGGAGTGATAAGGAAAGAAA
TGATATGAAGTTAGTGCCTTTAAATCACTAAGATTAGTTGATGTGCTGCCCAAATAGTCTGTTCATTGGT
GATAATATTTAATATGGAAGTACAAAGATTTGGCACTATGGTAATTTATATGAAGTCATGTGAGTAAAAC
AAAAGCTTTCCTCTTTGTAAAAATTCTCTATTGGTCTTTGAAATCTGTAGTAGGCAAAGTTACTGCTGTG
GTAAAAACAGACTTCACTCTGGGTGCTAGACCATTCTTAGTCTAGAGAGGAAGCAGTGCTATCTTTTCCG
TTCAGTTTACTGTTCATGGGTGTTTTTCTGAAGAAACATTCTACTGCTGAAATATTGCATGCTGAAGAGT
ATTGCCTAAGGGAAGTGCTAAGATTGGTTTTTTAAATCAAGTCTACAAATGCTGGTAAAGGGATAGATTA
TACAGTACCACTGGTTTAGCAGAATTGCAATTTACAGGTAGGAAGGAAACACTCTACCACACCCTGTCTG
TAGTTCCCTGTTCTGTTTAAAGGACTATTGACTTTTTTTTTTTTTTTTTTTGAGATGGAGTCTCGCTCT
GTCACCCAGGCTGGGGTGCAGTGGCGCGATCTCGGCTCACTGCAAGCTCCGCCTCCCAGGTTCATGCCAT
TCTCCTGCCTCAGCCTCTCTGAGTAGCTGGGACTACAGGCGCCGGCCACCACGCCCGGCTAATTTTTTGT
ATTTTTAGTACAGAAGGGGTTTCACCGTGGTCTCGATCTCCTGACCTCGTGATCCGCCTGCCTTGGCCTC
CCAAAGTGCTGGGATTACAAGCGTAAGCCACCGCGACCGGCCAAGGACTATTGACTTTTAAAAAAGATAT
TTAAGATACTTAAAGATATTTTAAAAATAAGATATTTAAAAATATACTTGAGATATTTTATTTTTCATAA
GGTTATTTTAATGGAATAAATACCTTTTCCCCCCAATTTTACTTGACAGACTTTATTTTGCCTTTTTTGG
CTGGCATTAATATGGATATTTAACTAAGGTATTGTTTTATATCAGACAGAGTCTTGGAGCCAGTTGATTG
TTCATAGGGGATTAATTTAGTTTGCATATTTTATAGGTCACATCTTGCCATTTGTAAATGGATAAAACAT
TTGCCATTTTCTGCTTGAAATAAGAATTCTGATACATTTATAGACTCTGATTATGTAACATGGTTTATTA
TTATCCTTCTATTTGGGAAAAATATCTTTATGTGATAAAATAAGTTAAAAGTTAAGTTTTCCATAATTTT
CACATTCATAACTTAGAACAGTTAACAAATGAAAATTCCTTTTGGTACTAGATACTTAGTTTTTTTCTCT

FIG. 7C (Cont.)

ATTCTAATACTAATATGCAAAATACTTTTATTTCTGGTTTATAGGTTATCCATTTTGTTTTGCAAAATAC
TCTTGTATAAATTTGTTGCAAATACAAAGAGTTCCTGGTCCAGAAATATTAGTATGCATTCAGTAATGTA
TCCTGCCACAATAAAAGTAAATTGGCTTCATAAGAGCCTATCTCATTTCTAAATTTCACTGTGTATTTGA
TAAATAAAAACAAAGATTTGTCAGGTGCTTTGTTAATGTTAAGATGACCTGACTGGTATTTAAATTGATC
AAATCTAGATGTGAGCTTATTTTAAAATCTAACCATCATAAAATCTTTTGCAATTTTCTCTCTTTGTTGT
ATGAATAGGGAATAGCACGTAAGAAACTAATGTTACAGCTATGGCTTTTATTGTAGAACAAGCTCTTCTG
GATCAGAATTCTCAAACTCCTCCTCCAAGCCCTTTCTCAGTGCAAGCTTTTAATAAAGGGGCAAGTTGCA
GTGCCCAAGGATTTGATTATGGACTCGGAAATAGCAAAGGTAGGTATTTAAAAGTAAGTCTTTTACTTAC
CTAACTTCAATATTTTTTATTACCTTCTCTTTTATACACTTTTTATTTGTGTTCACCCAGAAATCTTTAT
TAAATTAAAATTTGTTCATGGAAAGCTAATAAAAAATGTTTACAAAGGTGTTCTTTTCATAGTATTGTTT
TTTGCTGTTGTTTTTTGTTTTTAACCAGTTTTGGCTTAAGTTTATGAGAGTGCTTGCTTATTTTTTTTCT
ATTTAAAAAACACTCATTTTGATTTCATATCCTAAAGATTCTATTTCACTAAATCTAGTAAAATTTGATT
TTTATCATCCACTTATTAGGATGGTAATGTTAATGAGAAACAGAGAACTTGCTCAAATGATCCATTTAAA
ATCAAACTATTACTTCTAAATAATATTTTTAAGTAATATTACACATGAGCTTTATAAAATTTATGTGGTT
TTGAATTTCTAACCCAGTAATCTTAGTTAATTTAGAATTATGTGAAATGATCTGTTTGGTTTTAATATCT
ATAATAAAACCAGAAAGTTGTAAAAAGAAGAAAACCCTAAGTCATATGAATATAATATATATACAGCTGT
TTTGGCTGCATTAATGGAAGAGACCAGCATCATGGACTGTCCAAACAATAGTTAATTTTGAAACAATTTA
TGCTGGAGGTTCATCAGAAATTGCATTTTTATGTGAATTCACACACTCTTGTTCTTTCCTATGTACCTGA
TCTAGACTCCTTCAAAATCAGCCCTATTGTCCACAGGTAACATACAGCTGGGTCATGAGTAAAAGGGAGC
AGATAGCTTACGTGGAAATAATTTTACTTTAATTTTATTTAAATTAATTCACAGGACTTGATTCCAAGGG
ACAAATACAGTGTCATTATACCTGACTTGAAGAACAAGTGAAAAAATAAAACAGTGAACAAAATGTATAA
GGAATATTCTGTTTAAAATAAAACTACTTCTATTGAATAGCTTCATTACTTTCCACAAAGTATTTTTATG
AAGGAAACCTAGCCACAAGATTTTTTTTTACTCCCTTGGACTAGCCTATCTCATAGGATTGGGTATCATC
TGCTCGCTTACTTCGGGTACCTGATTTCCATTAACTTAAGCTAGATCTTTGTACTTACATAGTGTAAATG
CTTGGTGGTGTTTTCTTTATGTCCCTTTCTCTTTACCTTTGTCAACTCTTAAAATCTCAGCATTTGCTTA
CCGCTACTATATCTCTATATAGTAATGTTTTAAAGCCTTGTTTAACACAAATTGTATGCTTTCAGTCTTT
AAACTGTCTGTCATTGTACTAATAGCTATCACAGTAAATCAGTCATTATAATTTATTAAAATATCATTAA
AATAAATATAAATGTTTGAGACACAAACATTGCCGAGAAAATTTGTTATTATGTACAAATAATAAAGTAT
TACTTTTTAAACATGAGATTTTGTGAATATCGTTCAAAAATAGCATGCACCATGCCAGGCATAGTGGCTC
ATGCCTATAGTCCCAGCTACCTGGGAAGCTGAGGCAACAGGATCACTTGAGGCCAGGAGTTTAAGGATGT
AGTCTGCTATAGTCGTGCCTGTGAATAGCCACACGCTCCATCCTGGGCAACAGAGCAGGATCCTGTTTCC
TTAAAAAAATATTAATAATAAGCCTACTCTTGTTAACAAGCTTTTAAAATATTTAGAAGGAGCAAAGAAA
TAATAAGAAACTTAAACTTGATGAAATATATCTAACTTTATTATCTGTAACAGTAGTTCCCATTTTAACT
CTTAATACTGTCCAAGATCGAAGAGCTGTTTTTTGTAAGTTTTTTTTTCTTAAAACAGTATTTTAGAAAA

FIG. 7C (Cont.)

TTCTTCATGATCTCTAAATTTTTTCCTATAATCTACAGCATTTATTTATTATTTCAAAAAAGATATATG
GCTCGTGTACACAGTTCTTTCCACATAAATCTATCCCGTGTAGGTACTTCAGTTGAAATTTTCACATATG
AAACTTTATTATATTTCAGAAATATGACTAGAAAGATACTATTTTCCAGTTTCTGCATCACCTAGTCTGG
ATGTAGTTCCCTCTCCCCACCTCCAGCATCATTTAAACTATTTAATGTATACTCACAAATAAGGAGTTAT
TATCCATCACATAATTTCATTATCTTAAAAAAAATTTTTGTAAAACCTTTTGGTACAAGGAAAAATGTTA
GAATCGATATTTTAGATACTATTCAAATTAGGTAGCTCATAATCCTTTTTGTCATATAGGACTTACAGAT
TTTTAAATTATTCATCTAAGCAAAATATTTCATGCTTTTAAACTAGAATTTCTTTGGCAGTAACAACTTA
AAAAAGAAAGTATTAATTTATAACTATAATGTAAACACATTGCTATGTTAATAACATACTTTGCCCCATT
CTGCTTTTTGAAGAAAAACTGTTAATTGCTTATTTTCTGCATGAAATATACTGCCGATGAGGCAGGGTGG
TATTAGTCATTGTTGGGAACTATGGAAAAGGCATCATTTACTTAAATCTTCATTTATATATGTTCAATAT
TGAAGCAATTTATCACTGATTCTTCATAGAGTCTTCGTTCTCCCATACATAATGAGAGATGTTATATATG
AATTTAAATGGATTTGTTTTTATAGGTGGGCTTCTATATAAGATTTGGTGGGGCGCTTCCATTAAAAAAA
AAAGCTTGCAAAATTCGGTCCCTAATCTGAGGATGATTAACAGTCACCAATTTTCACTCATTTCTGAATT
GGCATGGTTTTATTTAGTGTTCAACTCTATCTGAATGTCATAAAGCACCATTTACTTTGCCATTTTGGAT
GTTAATGAATAACGAGTTGTAGTTTTGACTGTTTTACCCACTGCAGGTGACCAACTGAGTGCCATATTGA
ATTCCATTCAGTCACGACCCAATCTCCCAGCTCCTTCCATCTTTGATCAAGCTGCAAAACCTCCCTCTTC
CCTAGTACACAGCCCATTTGTGTTCGGACAGCCCCTTTCCTTCCAGCAGCCTCAGCTTCAGAGTAAGTCT
GTCAGCCTTACCTGCCTCATCAAGCATTTCTGAAGCTTTGTTCTGAGTTGCTTATCAGTTACTAATTAGT
TATCAACTCACCTGACTGGTTTTTTTTAATTAGGATGTTATCCCCTCCCACATTTTTGAAATATCTAAGC
TATTCTGAGCTAAGACATTCTGCAGCTAAGACATTTAAAGTTGATTTAAAGTTCATATGCATGACTATGG
TAAGCATCACATACAGGGACAACTTTCAGTGGATTTTTCTTACTTCAAGATGTCCCAAAAGGATAAAGCC
ATTTCACTCTTATCAGTGGGTAGAAGAGAGACTGTACTTGTTTGGACAGGTTTGTTTGTTTTTTCTAAGT
GAATTTGGTATCTATGAAATGTATGACAATTTAGTTTTCCCGGTTTTCTCAAATTGTTGTTTCCTGTCTT
TATTTTTATTTTTTTGTTGTTGTTCCTAATATGTTAAATTGATCATTTGATTCCAGTTCTGTCTTTTAGG
ATTGCTCTAGTCCTTCATTCATGATAGTAATTCACATTGGTTTGGAAAAGATACCCAAAAAAATTATACT
TAACTGAGTGTTCTTTTTTCTTAATAACCTCCTGAACCTTCCACCTAAACTTTTCAAAGCTCTGTCCAGT
ATGACAACAGTGTGTTCTTCTTGGCATTCAGTTCTCATGTTGGCTATACAATATATAAACACATTAATTG
AATGAGCTAGTTTATGAAAGTTTCAGCTTGTATACCATTTTTCGGATTCAAATGCACAACCTCTTTGCTT
TGGTAAAGTACATTCACACTTAGGTCTAAGTTATTTGTTTACAAAAATACTTTAATAACTGTTATTAGGG
TCATGTAAAAGAATGCTAGCTGGTTTAGTTTTTATTAAAAACTAGGTTAGTATGTAGCTAGCAAATGATA
TTATTCATTACTTTATCCACCTTAGGTAAAGGGTACACAAGAGTATAAACTTTTCTGGGTTTCCACTATC
CATTAGGAAAGTTTAATTGATGAAATTAATTAGTTTGGAAATATAAGTACTATCAATTTCTAGCTTATCA
TGTTCGTTCATGTATAATATTAATTTGAATGTCTATTAAGAGAAGAATTTCAAAGAAACAAAATAGTGTC
ACATGTGCGAAATAGTTTTTTCCTTCTATGATAAATATTATTTTAGAAGAATGAAACAGAAGTGAGGAGT

FIG. 7C (Cont.)

TAGTTTATTAATTTTGTGTTGCATCAGACTTTTTACATTTAGAAGTACTACTTAGGTTTCAAGAAGTTTT
AAAGGTAAGGACAAAGGGAAAAACAAAGGAAAAATATCAGGATCAGTCAGGTAGAAAATTTATACTAGAA
AATTTAAATTCATTCATATTCAAATTCAGTTTTAAATGAAAAATTGCCTGTGTCATAGCAGTAGCAGACA
AAAGAACTAAGGAGAAAGGAGAACCTTTTTGTTCTAGCTAAAGAATCATTGCAAGTCTTTACAAAAACAA
GCATAATTACCATTTTAATTTTACCAAATTTAATTAATAAAATATTTCAAAACAATAAACAGTAATAAAA
GTTGATTTGTCTCTTCCAGGGAATAACAGTTTCTAGGTGACATTGTGTCAATATAATTTTATGCATATGT
GTTATCAGTACCACCACTTTATTTACCACTATCTTGAAGCAAATTTGAAATCATGGCTTAGCTATGTTTC
AATTAGCAATTTTCTGAATCATTACTTGCCTATAGTCCAGCAATGGAAATTACTTAGGTCTTGTTTTAAA
CTTCTTATTCGCAACAGGACGTCTCTAAATTTTGACTTCCAAATTCCAGAAAATGGAAGTCTTAATCTTT
AGCATCACAAAAAAAAGTATGGAATCTGAAAATAGTTTTAATTTTTTAAAATAATTCAGAATTGTATTTT
TTATACCGTGTTGGGAAAGGTAAATGTGGCAAAGTGCCAACATTTAAGACTCCCCAAGCAAGGTATTCTT
CCCTGAACCTCACTACCATGTATCCCACTAGTATATCACCTATGCTTTAGAAGATGGCTTATTCTTAGTG
AACTTCCCTATGCTATTTAGTAAAATGAGATTTATTTTTGTTTTATACCTTTGTGATACTAAATAAATCA
TTATGTAGAAGACCATATTTACTCAACTTTGTTTATACTGATAGTCGCCACTATGTAGTAAACACTGTAC
TTAAGCACTTTGATACAGCCTCATTTGAGATACTGTCTCTTATGTCTGTTTTACAGAGAAGGAAACATAG
GCTTAGAGAGGATAAATGATTTGCCCCAGAAACATACATAGTAAAATGGTAGAGCCAGAACTTGAGGTCA
ATTCTGTTGACTACAAAGGCTATTTTAAATATTCAGCCTTACCTCGGTAAATAATGCAAAATCTACTTTA
ATATATATATATTTTTAATTTATATTTAAACTAGGTCTGGCATCTAGAGTATTAGCTTTGTTCAGATTGA
TTATTTTTCTTTTTATAGTTTGACTTTTTTTAATGTAACAGTAGTTTGAATGGAAAAAAAGATTTCCTGA
ATGTCATAACTCAAGATCCTGGTTAACTAGAAAAATTCTACAAAGACACACATCAACCGGTGCATGGTTT
AACTTCATCTAGCATTTCTATGAGCATTATTATCTGTAATTCTTTGGTTTTTTTTTTCCGAATCATAGTT
TTTACACCTATCTTTGGAAATTTGAAAATAATCTGGCACATTAAGTTAATTTTTGATACCTTTTCTTTAG
AATCAGGCAACATTTTATTCCATAAAATAGAATATTTGGTAATTTTTAAATTAGCAAAATTATTTGATTT
TATATACGTAGAAATTATTTCAAGTGTTATTCTAGTGAAGTAGAATGTTATAGAAGTAAAAGTTAACAAA
TTTCCCTTGTCTTATGTGTGTGCACACAGAGACATGAAAAAGAAAAGTATGTATATAGAATTTTCTTTAC
TGTTCTACAATTTACTTTTTAATTTAAAAACTAATTATATAGTTTTTAGAATTGGTAAGCAATTTGGCAA
AAAAATTTTAGTGAACCAAAGTGGAGAATGATATCTGTATCTGCTTTCTTTAAGAATATTACATTCCTTA
TTTTCATTATCACCATTTCTCTTGAAAGCTTCATTTTATGTCCTGTACCTTCTGACAGTGTCTTACACAT
CACAGGCATTCAAGGAGTGTTTATTGACTGTAGGTATTTAAGATTACCATTTCATCAATTTAAGATCTTG
TGTTTTCTATTATGATATTCCATTGTTTACTCAGAGAACATCTTCAAAGAAGAGAATTTATTTCTTTCTC
TTAGTAATTAAAGCCAACTATACTGTGACAATATGATGTATGATAATTGTGGGTTTATACTGATTGAATT
CTAAGCAAGATTATCCAACTGAAAAACTATATTGCAAATGGCTTCATTTAACATAGCATTTTATCACTTT
CTACCTACTGTTCCAGAGGCTGAATAGTTCATTTTTCAACTTTTATTTATTTGTTTGTGGTAGAAAAATG
GCAAATAAAACTGAAGACAATTTGCTTTTCTCCCAGAAACTTTTTAATACTTTTTTTATTTTATAATGTT

FIG. 7C (Cont.)

TTATTTTTAATTTTGATGGGTACATAGTAGACATCTTCCAGCAATTTCAAACATGAAATATATGATATAT
GTCAAAAGACAGTACTTTCAAGCACAGATATCATAGCTCTAGGTTACCTTGCAACAAGAGTTTTTCTATT
ATACTCATAAGTCACATTCTTATGTGGGACAAAAAAAATTAAATGTGACCCCAAAATTCATTTGGATATC
TGCATGACTATTTATTTACATTTGAGAATATGAACACACTAAAGTACTATGTTTACTTAGCTTGTAGAAA
CATAGTCATGGAAAGACTTTCAGCTCAGATTTCCCTTCCAGCTACTTACTAGCTCTCTAAGTTATCTGAC
AGGTCTGAATTTTTGTTACCTCATTATAAAATGGGATTCCCAATAAATGTTATCTTTTGATGTTATTATT
GCCTTTTGATGCAAATACTTAATACCTCTCATGCTTTGAGGAAAATATAGAAAAAGTCCTTCTCTAAAAG
AGAGCAATCTATTCTTGGTGTGGAATGAGTTGCAGGAAGGAATTTAGAAAGGGACAAATGAGCTTTCCTA
GTTCCTTTTGGGTCTATTTTTGCAATGTAATTCAGTTACCTATTTTAAGATTCTTAATGTATTTAGACTG
CATTCAGATGTTAGTGTGAATGTTAGCATAAAAGCCAGGTTTGTTTGTAAGGCTTAGACTGAGTCATTTC
TACCCCGGATTATAATCTCAGCACTGTATTTGTCAGTTTGTTGTTTGCCTGCTTTGAAGGTATGTGGATG
AAGCACTTGATTTAGGAATGAGGACCTGTGGGATTTAATCCCTGTTTTAGAAGATTAGAGTCAGCATTGG
TTCACATATCAAAGTTTAATAAAACTTTTCCACTTGACTTTATAACATCTGTCACAACAACCAACATATT
TATTTTAGTTTTGGGGCTAACATCTCCAGCATCCCTACAAATACAAATCATTTTAGGCATGGGCTTGAAT
TTATCTTCACTGAGCTGAGCCATCTTCTCAGTGACCTAAAAGCTTTGACCCAGGTATTTTGTTTTGCTGC
TTCATCAGTGATTTATTCATCCACCCTTTACTTCATCCTAGGAATTCAAACCACAAAGAATGCTGATGTT
GCTTACAAGACATTTTGTCCCAGTGCATTTGTTTGCTTTCTCCTGGCTTGATTTGACCTTTTATCTCTCC
CTCTTCCCCCACCTCTTTGTTTGCTACTGTGTTTATTTCACCCTTCATTACCATCTTTCTTTAGATGACT
TATTCATTCTTCCATTTATTCACCTGCTTTTGTTAAGTATCTACTCTGTGCTAGGTTATGGTGATGAGCA
AGGTTAAAAAAAAAACAAAAAACCATGATCACTGATCTTGAAGGCTTCTAGAATATTTTAAGAGATACAA
CCTAGTTAAAGAAAAAATAATGGCATGTTTTAAGTGCAACAAGAGCAGTAGTCACAGGATGCAATGGAAA
CATAGGAAAGCTTCTGGCTCAGCTAGGAGAGGTTAGAGAAACATTCAAAAAAGAGGCAGGTCCTACTCAG
AGTGTTGAAGGACTTGTGAGAATTTATCAGGCAAGGAGGAGTGGAGATGAGGAAGGAGGTTAATGGAGCA
TTCCAACTATAAGGATAACATGAGTTACATTACAGAGATCCAATGAATCACAAAGTATTTTATTGAGTCC
ACCTACGTGTCAGGCAGTGTACTAAGCACTGTTCATGCAGAGGGCCAGTTTGGAGTAATGAAACTCCAAA
GTTTGATTAGAATAGGCTTAGGAGAAAACGGGGAAGGAGAAATTGGAGACAATGAGTATAGAGAAGTGTG
TCAAGATTTGATCTAAAGAGAAGATACTAAGAGAGAAGATACAAGATCTGGAGAGGTTTTTGTTCTATTT
TGTTTGTTAATGGAAAAAAAAGTATATCAAGGTTGTTTTCTAATGAGAGTAATTCAGTTGAAAGAAATAT
TAATAATGCAGGAGGGTGAGGAGAATTACTGGCACAATATTCTTTTATAGAAGAGGGGATGCAGACCAGG
CGTAGTGGCTCACACCTATATTCCCAGCATTTGGCAAGGCCAAGGTAGAAGGATGGCTTGAGGCCAGGAG
TTTGAGACCAGCCAAGACAACATAGCAAGTCCTTGTTTCTATAAAAATTAAGAAAAATTTTTTTAAAGAT
CAGCTGGGCATAGTGATGCACACCTGTAATCCTAGCTACTTGAGAGGCTGAAGCAGGCAAATCACTTAAG
CCCAGGAGTTCGAGGCTGCAGTCAGCCATAATTGCATGCCACCCCACTCTAGCCTGAGCAACAGAGTGAG
ACCTTGTCTCTAATATGTATATATACAGATATAATATATAATATATAAAATACATTCTATATAAAATATA

FIG. 7C (Cont.)

TATTATATATTATATAAATAAAATATTATATATAAAATATATATTATATAAATAAAACATTATATATAAA
ATATATATTTTATATATATATAATATAAAGAAGAGGGGATACAGTCCAGTGCAAAGTGGAAAGGTTGGCT
AAGTGGGATCATAAATAGTTATCCATCATAACAAGCAAGAAAGAAGTATGTATATTATTGGGAGCTCTTT
TTTCTAAGTAAAATAGGAAGCACTTATCAGCTCGGAGTTACCATGGAGAGACTGCATTGATAGTTTGAGG
AAAGAGAAGATATGAGATTTTAAAAGCTAACATATGTCAAATATTTATCACATGCCAGGCACCATTCATG
GGAATCAACTTTTATCCCTGTCCAAGAACATGGTTCACTTGAGAAACTTCATGCATGTGCAGCTTTAAGT
GACCTAGTGTCAGTGTCTTAGACTAGAGAGGTTGGGGCTGGATCATGAAGGGTCTTGTAAGCCATACTTA
GTTTAGACTTTATGTGCAGTGAATAAATGGAGGGAGCACATGGAGGAAATTGTTCTGCAGAATTTTAAAT
AAAAAGAGTGATATGATCAGTTTTACATTTGGGACAGATAACTGAAAATATTATGAAAAAGGTCCTGGAG
AAAGGGAGAATGTTGGAGGCAAAGAATCCAGAGAAAAGCTGAGTAGGGTTTAAGCTAAGGTTAATTGCAG
GGAGAATGTAGAAGAAATATTTAGGCAGTAAAATGCTTAGGACCAGTCTGGACAACAAAGCGAGACCCTG
TCTCTACTTAAAAGAAAAAAAAAAAAAATTAGCCAAGCATTGAGGGCTGCACCTATATTCCTGGCTACTT
GGGAGGCTGAAGCAGGAGGATTCCTTGAGCCCAGGAGTTTGAGGCTGCAGTGAGCAGCCTGGGCGAAAAG
AGCAAGACCCTGCCTCTTAAAAAAAAAAAAAAAAAAGGAAGTGACATGCTGATTAAAGTTAGGAGCCAGTC
TCAAATGACATCTACTTTTATGCTCTGTTTTGAAAGGTAATATCTTATCTAGTACCAAGAATAAAACACA
AAACCACCTTTTAAGGAAAAATGAGTTCGGTTGGATGACTTAGCTCCAGTTGGCTATAATATAACTTGAA
ATTGAGAAATATATTTAGCATTCTCATAATTAAAGATGGCATTGTTGACTGACAAGTTGAAAATAGAAAA
TTATTCATATATTACATTTTATTAAAAAATATTATTAAAGCATTCTCATGATTTTGCACTCAATTTAGGA
AGGATTAGGTCTGCTATATCTCCCACTTTGTTATTCTCTCAAACTTCTGTACCTGTAGTATATCTCATTA
CTTAAGCTGAACAAAACGTTCATTTTTTGTAATCAGACTTCTCATCCTTATCATCAGATTGTCTTTCCTC
CTTTGGTTTATTTAAGAAGTGTGCATCAGCAGCAGCCGTTATGTCTTATGATGGCATAATTTCAAGTGTT
CTAGGGGCCTAAGAAGTTATCCAGCTCTCATTTTGAGATGAGAGAATTCTTGCTGACTTGCCCAAAGTCA
TAGCTGGCAAATCTAGGACTTGAACATGAGAGTCTGTATTGGGGGAACCCGCCCCCAATATTTCAACGTA
GGTTCTTTCTATTTTCCCTAAGCATTGGCCAGTCTGAGAAAAAAAGAGAAAGAGTACAAAGAGGAATTTT
ACAGCTGGGCCTCTGGCGGTGACATCACATATTGGTAGGACCGTGATGTCCTCTGAGCCACAAAACCAGC
AGGTTTTTATTAAGCAGGTTTTTATCAAAAAGGGAGGGGATGCAAGAACAGGGAGTAGGTCACAAAGATC
ACATGCCTTAAAGGGCAAAAAGATCACAAGGCAAAGGGCAAAGCAAAGATCACAAGGCAGAGGGCAAAAT
TAAAATTACTGATGAGGGTCTATGTTCAGCTGTGCACGTATTGTCTTGATAAACATCTTAACAGAAAACA
GGGTTCAAGAGCAGAGAACCGATCTGACCTCAATTTCACCAGGGTGGGGTTTTTTCCCCGCCTTCTGAGC
CTGAGGGTACTGCAGGAGACCAGGGCGTATTTCAGTCCTTATCTCAACCGAATAAGACAGACACTCCCAG
AGCAGCCGTTTATAGACCTCCCCCCAGGAATGCAATTCTTTTCTTAGGGTCTTAATATTTAATATTCCTT
GCTAGGAGAAGAATTTAGTGATATCTCTCCTACTTGCACATCTGTTTATAGGCTCTCTGTAAGAAGAAAA
ATGTGGCTCTATTCTGCCTAACCCCGCAGGCAGTCAGACCTTATGGTTGTCTTCCCTTGTTCCTTGAAAA
TCGCTGTTGTTCTGTTCATTTTCAAGGTGCACTGATTTCATGTTGTTCAAACACACATGTTTTACAATCA

FIG. 7C (Cont.)

ATTTGTACAATAATGGTCCTGAGGTGACGTACATTCTCAGCTTACAAAGATAACAGGATTAAGAGATTAA
AGTAAAGACAGGCATAAGAAACTGTAAGAGTATTATTTGGGAACTGATAAATGTCCATGAAATCTTCACA
ATTTATGTTCAGAGATTGCAGTAAAAACAGGTGTAAGAAATTATAAAAGTATTAATTTGGGGAACTGATA
AATGTCCATGAAATCTTCACAATTTATGTTCCTCTGCCACGGTTCCAGCCAGTCCCTCCATTCAGGATCT
CTGACTTTCCGCAACAAGTCTGCTAACTCATTCCAGTGGTTTTTTCCAACTGCATCTCAGTTATCTTACA
TAGACTGCAAGAAGTGAGAAAGACAAGAGGTTATCTAGTCCAGCCTTGCTATTTTATAGTTTAAATCCCT
CAACCACATCCCTGATGAACTTTTGCCAGGCCGGTAATTAACAATATCACAAGGCTGTTCTGATTGTCTG
TATTTCTCAGTGTTTGTTAGAGCAGGGATGTCCAACCCCCAGGCCACAGACCAATACTGGTCCAAGGCCT
GTTAGGAACCCAGCTGTACAGCAGGAGGAGAGCATTACTGTCTCAGCTCTACTTCCTGTCAGATCAGCTG
CGGCATTAGATTCTCATAAGAGTGCAAACCCTAGTATGAACTGTGCATGCAAGGGATCTAGGTTGAGAGC
TCCTCATGAGAATCTAATGCCTGATGATCTGAGGTGGAGCAGTTCCATCTTGAGACTATTTCCCCAACCC
CCCATCATATGGAAAAATTGTCTCCCAAGAAACCAGTCCCTGGTCCCAGAAAGTTAGGGGACCATTGTGT
TAGAGAACTAAGGAAACCGTCCTCTACCTGCCACATAAGAATAAAGGAAACAATGGAACAGTTTCCCTAC
TTTCCCTAATTAACACGTATTCCCATTTTGAGGCAGTGAGTTGCTGGTACCTGCTTTCTCCTTCTTTCTC
CAAATAGTACTTTAAAAGTATCTTATCCTGGCTGGGCACAGTGGCTCATGCCTGTAATCCCAGCACTTTG
GGAGGATGAGGCGGGTGAATCACGAGGTCGACCATCCTGGCTAACACAGTGAAACCCCGTCTCTACTAAA
AATACAAAAAATTAGCTGGGTGTGGTGGCAGGCACCTGTAGTCCCAGCTACTCAGGAAGCTGAGGCGGGA
GAATGGTGTAAACCTGGGAGGCAGAGCTTGCAGTGAGCTGAGATCGTGCCTCTGCACTTTAGCCTGGGCA
ACAGAGCAAGACTCCATCTCAAAAAAAAAAAAAAAAATAAAGTATCTTATCCTAAAAGCACTTCTGTTTTT
GGTTTAGGTTTTAGCTGTCTTTGTGCTGCGTAAGCGTTGTCTCTTTCTCAGGATGTCACTTCTGGAGGCA
GGAAAGGGTTATGGTTAATGCTAATCACTTTATCAAAATGTCTGATTTCTCTGATGTATAATTAATATTT
TTCCCTTGCAACTAATAAGCAACTTGTGGGAGTAAGATTTTTACTTTTAAAAGCATATCCAACCTTCTTG
TGTCTCAAGTTAATGCTCGGGAAGCAATACCTGTCTCTTATATTTTGAAGTTATTCTTTCTAAGGCCTAA
GATATATACCCATCAAATTATGCTCAGAATTTTTGTCTCAGCCATCACAAACCCTGAAATGATACGCTTT
TCCTAAGTGTTATTTTCCTTAACCATATTTACTAGAGATTTGGAATATATTCAATAATATGCTATGAGTA
TGTTTTCTTCAAGTTCAATTATGTGTAGATGTCATTTAGAGAAACAGTATATTTTGGGGGGAATCCACTT
TATGTGTCCCATCTTCTTTCCACATTCAGATCATGTGGATTAATGTCATAGTCTAGTAAAAAGCTTGTTT
CTATTTTATCCTTAAGTTTAAAATGTTGTTCTTTCATTCTATTAGCATGATTCTTTTAGTATACTAACAT
TTATGTAAATAAGTCTTACATAAATACAGTTATATAAACAAATCTTTAGTCTAATTCTTTTAGTATACCA
ACATTTATGTAAATAAATCTTAGTTTCTGTTCCACGTCCTAAGCTGCTTTACCATTCACATAATTCCATA
TTCCTCCTAAGTTTACTACAAAGAAGAATATTAGATGTATTGATTATGCAGTGATACTGCATCTAAAGCT
GTCAGTCAAGAATGGCTGCCATAGCTAAGAGTATATACAAATCATCACTGTTACTTTATTTTATTTTTTT
AATTTTATGTATTTATTTATTTTTTTGAGACAATTTCACTCTGTCGCCCACACTGGAGTACAGTGGTGCA
ATCTAGGCTCACTGCAACCTCCCTCTCCCAGGCTCTAGTGATCCTCCCACCTCTGCCTCCTGAGTAGTGA

FIG. 7C (Cont.)

GGACTGGAGGCGAGTGTCCCCACACCTGCCTAATTTTTGTATTTTTTTGTGGAAATGGGGTTTCACCATG
TTGCCTAAGCTGGTCTCAAACTCCTGGGCTCAAGCAATTTGATTGCCTTGGCCTACCAAAGTGCTAGGAT
AACGGACTTGAGCCACTGTGCCTAGTCCTGTCACTTTCTGAAAAATCCTATGAAGCATTAATAGAAGTAA
AATCACACTTAATTATGCCTGTTTTTAAATCTGCATATTGTTTGATTAATCACATCTTTTGGCCAAGTTG
AAGGCATAATTTATATATTGTCTATAAGAATCAATAAACTAGTTTCTAAATATGTTTTAAATAAATAATT
TAAAAATTAATTTCTCAAATATCCTCAACTATAAAGTTAGACCTATTTACTGTTTCTTGTAGGAGCCTAT
TGCTGTCAAAAATATCTGAAGTTCTATTCAGAGAAAAATAGAAATGCACAATGACTGGGACTTAAGCTGA
GGAAAGTCAGCAACACTGTTCCCATCATTCTACCATAAATGTGGCAAAATCTTATTGTTTGTGACAGATC
TATAGAATTAGATTTTCTTATATCTAAAGAAATATATATAAATACATAAACGTAGGTATGTATAGCATGA
ACAGAATACAGTGCTATTTGACCATTGTCACAAGACTTATTTATAAAACCTCCTCAAGCTCTTGCCAATA
TCTTAGTTAAGATTGCATCTAAGGTGGGAGGAGGATGAAGATTGAAGAACTGTCAGGTAATGCTTGATTA
CCTGGGTGACAAAATTATGTTTACACCAAACCCCCATGACACACAGTTTACCCATGTAACAAACCTACAC
ATGTCCCCCTTGAACCTAAAATAAAAGTTGGAAAGAAAAAAATTGGAAAGAAAAAAAGGAACTTAAAGA
GAAGAAAAAGATTGTATCTAGTAGTTTTACTAAGACTATAAAATTTCTGACGGCTCCACTACCTCCTCAA
GATTGAGAACTAAACAACATGAGAAGCACAATTACATGCCAAAGATTCTTTTTGCTGTCTTCATTTGTAG
CATCCCAGTGGAATGTCTTTGAAAAAAATTTTTTTTATCTGTATTATCTCACCTGCTCTGAGTATTGGTG
ACAGTGATATATGCATTGTGATTAGACGCCTAGCCTCCTGAATATAATGTATTTCCAGTATATTGTCCTT
CTGAATAGCCTGTTTACAATTCTTTGAACATTGCCTGCCAATAATTTAGCAAATTGTTATTGAATGTCAC
AGCTTGATTATAGAACATAGTAAGAAATCAACAAATTGAACACCAAACTGAATTTAATGCTAAAAATTAT
CCTTTTAAAAAATAATGTATTACTAATTTTTACTCATGAAATTTAACATTTCCAATCATTGCTTAGTTGT
TGACTCAACACTCAAAAATAATATATGCTACTTTTAAAATCCCAAAACCTCCAGATTTGTGTACTGCCAC
CAGGTGTTGACAGGTGCCTTGATTCTTCTAGTTTGTGGTTCCAGAGATAAGGTCAGGGTCCTGATACAGC
AAAACCACCATTTGTCTTTGTTAAACTGAAATGAGAATGCGTTCCTTATTGGAAAGAAAAGTTACACGGT
TTTATTATTATCATCAGTACTTAGAGAAGACTTAAAAAGTACAACTTAAAATGAACTCAAAGTTTCTGTG
ACTAGGAAATGATATGACTCAGGGAATTTAATACTTGGGATCCAAAACAAAGAAAACAAAATGACCCATA
AAGAACCATGTTGTTTATGAGGGCAAACTATAGTAAGCAAACAATATTAACTTCAAATGAGCACTGGAGA
AAAATCCTGATTCTTTAAAATTGTTTTTAATATTATTCTCTTAAACTTAGTGATACCCAAAAAAGAATCA
AAATTTTGTGGAGAGGAATATAATAACTGGTTGTCTTATCTGTATTAACAGGATTTTGTAAAAGCATTAT
TATTTCTGTCAATTGATTTTTAAAACATCTATCAACTTTTTTTCTTTTGTGTATAGATATCAATGTATCT
CATAGATTGCTTCCCTTTTTTAAATTAAAAAGTATAAATCTTTATAAAAATTAACTATAACTTTATGAAA
GTATGTTTAAACTTGAGCAGATTTTGTAAAAATTTAATGTGTAGAACATGTGTTGTTTTCAGCAACAGCT
TAATTTCTTTAGTCACTTAACCTTTTTTAGACTTTTGTTTTTAAAAATATTTCTTTTTTTCACTCTGAAT
CATACCTAGGAATCAAGTCTCTCTAGCCTTTGTAATATATTGAAAAGACTTGAAGGCCATTTTGCCTTCA
AACTTTTTTCCAGGAGTTTGTCCTTAAACCTCTAACATCTTATAAGTTTCCTCATAGTTTTTCACATTTC

FIG. 7C (Cont.)

TGTTTTATGTGTGCTTCCAATTAAGATGGTATTCTTCTGATTTCCTATTCCTGTGTCTTCCTGCTATGTG
GAGTCTTCACAGATTTTTAGCAGCCAGGCCAGGAGATTGTATTCCTTCCTATATTGGCAGGTTGGATTCC
CCCTGAATTAACTCTTCCATTCAGAGGCTGCCACCGTTCTAGTTCGTGTCTTGAAGAATTGTATCACCCT
CCTAACTGATATTTTAACAATAGCTGCAAACTCCTTATTATATGACACTTAAATAGCATAAGAGCTCCTT
TTGCAGCACCTGACATCTTTTGAGGTTTATAGATTTGTTCAAAATGAAGGATGTACAAAAATATTAAAAA
TTTAACTTTTTAAAACTTAGATTAAGATGGCTTTATGCCATGGTATGTTGCTATCTACTCCTCCCATTGT
CTCTTGAGCCCACTGCATTCCAGCTTTAGTCCCTATCCTCGGAAACTGCTGTAGTCAGTCTGTGACTTTT
GTGTTGCCAAATTCAGTTGTCGGTTCTAAGGTGTCAGTTTTACTTAATCTGTCAGCAGTATTTGACAGAG
TTGGTCTTTCTTCCTAGAAACACATTCATTTGCCTGCCGGATATTTCCTGCCTTACTGGCTGCTGAATTC
TAGTCTCCTTTCTACATCCTCATCTATTTGGTCATCTAGAAATGTCCTAGGGCTTTGGCCTCTTCTAGGC
GTCACTCCCAAAGTGGTATTCTGCAGTCATGGAGAATGACACATCTGTAGGCATATGACTCCCAAGTTTC
TCAGCACCTGATGTGATGTATACTTATTTGTTCATTCCCTCTCTCCTTTCTCCTAAATATAAACTCTGTG
AGAATAGGGACTTTGTTCCTGTTCACCACTGTGTCTGCAATGCATAGAACAGTATCTAACACGTAATATA
TACTCATACTTTACATTGAATGATTTCTTAATTTATGGGTCATTCATCATTAATCTTGATCATAATAATG
AATCAGCCGAAAACAGCACTTTTTTTAAGAAAAGTGTGTGTTATGTCTAGTTTATTTCAATAATACTAAG
ACAACTATCTCCTTACTACCTGAATTTATTTCAGCACAACCGATTAATTTTAATTGCTATGAGTTAAAAA
CTTTAAATACAGTGAGTTTTTTTAAATTCAGATAGAGATGTTTTTTAGCTTACTGCTTTTAAAAGACTGC
AATTTAAAGGTTCTGTTAATTCTTCAAAAAAAGATAAATTAAGTGCTTCATTTTCCTGCATAGTAAATCA
TTGACGTTCCTAACATTTTTTTCAATAACTTATAAATTTTCTTTGCTTTGTTTGTGTTGTGACACGTTGTG
TAAATGAGATTTGATATCAGAAGTAGGATCTACAAAACAAACACTAAATACTGGGGTTAGTACTAACGTT
TTCACTGAAGATGGACCCAGAAAAGTAGCCAAACACAGTGTCACCCCGAGTCCATTCTGAGATACATACT
GGAAAATTATAGTAATCGGTTCATTCAGGAAACCAAGTGACAATAGGTTAAGCCATGAGTAATATAAGTA
ATATAAGTAACATTTCTTTATCTTCCACTATTAAAAAAAAACTTGTAAATCTTTATTTAAATGAACACCA
AATTAAAGAAAACTGAGCCAAAGAAATGTAAGTCTAAAATGAAATGCTCAATTTTGATTTATCAGAGATA
TAAGCCTTACTAAGTTTTAAGTTAACAAATTTGGACCTTAACACATATTAATCTAAATTAATTAATTCGA
CCTTTGTTTTCAGTTTTAGAGAAATGTAAACTTGTTCAAAAATATAGCAGAATATAAACTATTTAAAATA
ACAGTTTATACTTGCATACCATTTGAAATGCTTTGTTTTTGCTTGTGTTCTCTGCTAAATTTTTTTTCCA
TTGAATCTGTGCTGCTTCTTTGCCAATGTTTTCCACTGTAGAATCTCCATCTCGCAACCTTGCTTCTCGT
GAGCGCATTTACAAAAATTATGGTGTAGCTGGGCCTGCCTCTGCTCTCTCATCTCTGTCTCACAAACTGA
AGGGTGGGTATACATGCATTCATGGATGGGCCATTCTTAATGAACATAAGGAGTGTCATTAAAGATGTTT
CCGTTCGTCTCAGTCATGTTCATGCCATTCCATTTTTTTAATTAAAGTTTATCATTTTATTTACATTTAT
ATATGTTTGAGTAATTTATGATGCTCCTATTCAGTATTATAATATAGATTATCCCAGTAGCTATGCATGT
TTATTACATCTATAGGTTAAACATTACTCTTACTTAATTTTAAAACTTTATGAGATCATTAAAATTAAAA
TAGGTATAAGGAAAGAATTACCTAATTGGGGGAATTTTTGAAATCATTTTTATCAGAAAAAGATGATATA

FIG. 7C (Cont.)

TGTGCAAGGCATAAAGCACATTTTTTAGTCTTAAACTTATTGTTATATAATATAAAAATCATTTTACTAT
TTTAGTCTTTTATGAGAAACACTGATAATGAACTTAAAGTTTTTAAGTTTAAATTAGTTATTAGGACTCA
TGTGTCTATTTATATTTATATGTAAACCTACCTGTCCTATCTGGCATAAATTTTTCTAATATTGTTTTCC
TAGTGACTAAGTTTTAATATTTTAAACTTAGAAATGTTTAAACTATTGACAATTGACAAAATTTCAGACA
ATTTAAAAATATGTTTTTGGTTTTTTGAAACACTACAGATGCCTACTTAAATATTTTGTCTTAAAGTATT
ATTTAATTAAATTTAAATCTTGTAAATCTTTTAAAATCTTGTATTTAAATAAAATTTTATCAAAAAGAAC
TTTTACAGCAATGCCTAACATATTGTATAAGTTTTTCAACTAATTACTGATTTTCTTTTTTTCTTAGAAA
TAGATAAAACAGCTATATGTTTCTCATTATACAATTGACAGTATAAACATATAAATAGGAAATATAAAAA
TATACTAAATAGTATTGTACAACCTGTGCTATATAGTATATAGTATTGTGTGTAATAGCATATAGTATCA
TGTAACCTGATATATGCTATATATCATGCCATGTGATATATGCATATAGTATTATGATATAGTATGATCC
TGATAATTTAAGATTTGGGCATGAAAAAATGTATGGGTCATTTAGTGAATGAATGCTTACCATTTAACAT
GTTTAGTAACATTTAACTTGCTTGCCCTAAGTTTCTATCCTGTCATTATTATTTCTTCAGGTTTCCTTTA
AAGTTAGAAAAATGTTTGCATATTATCATTTAAATGTAAAAGTACAGTCATTAAATAAATTAGGAGATGA
ATGTGAAAGTATTACGTATAGTCTGAAGATTTTTAGCAAACTGTTTATATTTGTTGGTATTTTGAGCAGC
CACAACATACAATTTTTAGTAATATTTAATAACATGCTGCAAAACATTTGAAACACAAATGAAGCAGATA
AACATAAATTAGCACAGGGGCTTACCCCACTTAACAAGCATAGTTTTTTTAATATATAAAATACGTTTT
GGAAAAATAAATTTTTCAAAAAGATTTAGTTATCATTTGAGAAATACATCTGAAAAAGAAATATTTCTGC
CATTATTTGTATGCCTAAACTTCAACAGGTATTTAGCTGTCACCACTTACAGATCTTAAGAAAATATTCA
CCACTATTAGAGATATAATAAGATATACAAATGCCTATTCTTTCTAACACTATGTAATAAACTTTTTTGC
TCACATATGACAAGTGGTGTTCCTGGTATTTGGCAGATTCCATTTTTCAGGCAACCACAGAGGTTGTTTT
CATGATGAGTAAATAACCTACCATTGTAAGTTCATATGCATTCCTAGAATAGAGGTAGCATCAGCAGGTA
TTCACCATTCCTTTGCATGCAGCTGTTGTGCAGGTCAACCACTAAGACACATCTGACACAGGGAGTAGGT
AATCTTTGTCACGAACCCTTCCTATTTGTTAGAAATCCTACACAAGTTGTCCTTTTTTATAAATTAGAGA
GAAAACCTCTTTCAGTTTACAGATGGATTTTTTGGAGAAAGGGATACCAAATATAAAAGACTTACTAATT
GTTTGTCTAGATTCCCATTATGTGTGGTTCAGTTTCTGAAATAAATGTGATGATAAAGGTGATAAACATG
TCTCCAGCTGTCAGATTAATAACAAAAAACAAGTATTCCAAACATCACATACTCAAAATTAATGGCCATG
ACTACTGATTTAATCTACCAAATATAATTTGTTTACCAAATTTGCCATATGCTGTTACTAGGTCAGTAAG
ATTAGATGGGTAGCAATTTTTTGAACTACTTTTGAACAGTTTAAGGGTACTTATTCATAGATCACATCTG
TTTATCTGTGCTCTCCCAAGACAGCATTGATAGTTAGAATTCTAAATTGGGATTTTTTTAACCCTTTTTT
CAAAACTTAGCCCCATCTGTTAATACTGTATTTATAAAACAGAGCACATAATATGATAAAGGAGGTTAAT
GATTGAATAATGAAGCTTTGCAAGAAACTAAAAAGCATTATGTTTTAGTTACTTTTATTCATCCAAAGAA
CAGGAAAAATTATCTTAAATATTGGCATGTTGCAATTAAACATTTAGTTCATCAGTGTGCCCTGTATAAA
GTACTTGCCATACTCTATTATTTCACCATGTAATTACTCAGTTTGCAAGCATCTAACCCTTGCACATCAA
TAACTAATGTCACCTCTGTCCTGTGGCCTTGGGAGCCTTAATTGTAAAAAGTAGACTTCTGGAGAAGCTG

FIG. 7C (Cont.)

AATACTTGGGAGTAGCAGAAGAAAAAAATCAAGAAAATTGGAATATATTACTCATTCAACACATATTTAT
TGAATACCTACTGTATTCCTGGATTCATTCTTGGTATTACATCAGTGAAGAGTAACAGACAAAAATACCT
GCCCTTGACAAAGACTGGGGCAGATTCTCCAGCACTACTGTCCTGAGCCATAGAGAAATAGAGCGTGACT
ATACACACTTAACACATGCACGGAAGCATAAAAAACATTTTCCTACATCATCTGAATTTGTTCACATCCT
TTTTTCTTTTAAAAAATAATAACATGCAGTTATAGCCAGTTAACAAATCTACCTTAATTTCCTAGGAACT
GTCTTTGAAAAAATATAAATACTTCCAGATAGGTTTATGGATTTTCAGTTTTTTATACCACTTGAAACCC
TTCAGTCAGATTGCTTTTCTCCTAACAACTAACTGGTATCACTTGCACTAAGAGTAGAAGTTTTTATTTT
AAGGAGGAAAGGTGATGTTGAAGTTTGTACCATTTACTTGGGTCACAGACAGCCTGGCTCTAATGCCTCA
AAGAAAAGCATAAAATAGAATGAAGGAGAGACACTGAATGAAGGCAGGGTGCTAAAAACAATTAATGTCC
ATGCAGAAACATCTAATGCTTTGCCTTAGAAAAGGGAGGTGATTCTTCTTTTCATCCTGTTTTTCTGTCA
TTCTCCTGACTCCTTGTTTTGAGGGTCCACAGTTCAGACTTTTACCACTCATTCTGAGGATCCACCGTTT
CTGTGGTTTCCAAGGGAACACAGGCTCTGAGTTCTAAGCAGCTAAGCTTCCTGAACTTTTGGAGTGTAAC
CTGTTTATAAATAATTAAATAACAGCTTCAGGGCATTCATGTGCTCATTGTAAACTAGTCTAATCTGATC
ATAAAACAGAGTGCCTCTTAAGCAACTCTTTGTTAGCCTAATTGTATGCATACACTTAAAAATTATAATT
GTGTCTATGCATAAATTCAGTTCTCTAATTCAACAAAACCCATACCGTTGCCCTAAGGATGCGAGGTATC
ACTCTGCTGGAAATTTAGCTCTACTCTACATTTAAAATACAAGTTTTCACATTAAATAATTTCTTATTCC
CCAAAAGATTAATTTCTGTCTCTTTCTAGTCCCTCACTGAATTTAAATTCTAACTAGTTATTGCACTAGG
GCAGAGGTTGAGATATCACTGATAGTTCACACTGGATTTGTTCAACCTGTTGTTTTGCGTCCATGAAAAT
AGTTTTTGGTGGTAATGTTGTGTAATGATGTGTAGAAATTTTATTAGAAATATTTCCCCCTTCTTTCCTT
TATTCTTCAAGTATTTTAGTATGTATGACAAACAATATAAATTTTGTAGCTATGTTTTTTTATTTCAGTG
TTTAGTGGCTAAATTATCAGTAAGTTATAATTTTATTAATAAGTTTCACTGTAAAATGGACCATACAGGT
GATCGAGGAAACATCTCAACATCTTCTAAACCAGCCTCTACATCAGGAAAATCAGAGCTGTCCTCTAAAC
ACAGCAGATCGCTTAAACCTGATGGACGTATGAGCCGGACTACTGCTGATCAGAAGAAGCCAAGGGGCAC
AGAAAGTTTATCTGCTAGTGAATCCCTCATCTTAAAATCTGATGCTGCAAAGTTGAGGTCAGATTCCCAC
AGTAGGTCATTATCCCCCAACCATAACACCTTGCAGACATTGAAATCTGATGGGAGGATGCCTTCTAGCT
CCAGAGCTGAATCCCCAGGACCAGGTTCTCGGTTGTCATCTCCTAAGCCAAAGACTCTCCCAGCCAATAG
GTCTAGCCCATCGGGTGCTAGTTCTCCACGCTCCTCCTCACCACATGATAAAAATCTACCTCAAAAAAGT
ACTGCTCCTGTTAAGACAAAGCTTGATCCTCCTCGGGAACGTTCTAAATCAGACTCTTACACACTTGATC
CAGATACCCTCCGCAAGAAGAAAATGCCCCTCACAGAACCTTTGAGAGGACGGTCAACGTCACCAAAACC
AAAATCAGTACCAAAGGATTCTACAGATTCCCCTGGATCTGAAAATAGAGCTCCCTCTCCCCATGTGGTA
CAGGAAAACCTCCACAGTGAGGTGGTCGAAGTCTGCACCTCAAGTACTTTAAAAACAAATAGTCTAACAG
ACAGCACCTGCGATGACAGCAGTGAATTTAAGAGTGTGGATGAAGGTTCAAATAAAGTTCATTTTAGCAT
TGGAAAAGCACCACTGAAAGATGAACAGGAAATGAGAGCATCTCCCAAAATAAGTCGAAAATGTGCTAAT
AGACACACCAGGCCCAAAAAAGAAAAATCGAGTTTTCTTTTCAAAGGAGATGGATCCAAGCCTTTAGAGC

FIG. 7C (Cont.)

CAGCCAAGCAAGCCATGTCTCCTTCTGTGGCCGAATGTGCCAGAGCTGTGTTTGCTTCCTTCCTCTGGCA
TGAAGGCATAGTACATGATGCAATGGCTTGTTCTTCTTTCCTAAAGTTTCATCCTGAACTTTCCAAAGAA
CATGCTCCTATAAGGAGTAGTTTAAATAGCCAACAACCTACAGAGGAAAAAGAAACCAAGTTAAAAATA
GACATTCATTAGAAATATCATCTGCACTGAATATGTTTAATATTGCACCCCATGGACCAGATATATCTAA
GATGGGTAGCATCAACAAAAACAAGGTATTGTCTATGCTTAAGGAACCACCTCTGCATGAAAAATGTGAG
GATGGGAAAACCGAGACCACTTTTGAAATGTCCATGCATAACACAATGAAGTCTAAGTCTCCTCTTCCCT
TAACTTTACAACATTTAGTGGCTTTTTGGGAAGACATCTCTTTGGCTACTATCAAAGCTGCTTCCCAGAA
TATGATTTTTCCAAGTCCTGGTTCCTGTGCAGTTCTTAAAAAGAAAGAGTGTGAGAAAGAGAATAAGAAG
TCCAAAAAGGAAAAAAAGAAAAAAGAAAAGGCAGAAGTTAGGCCCAGGGGTAATTTGTTTGGAGAGATGG
CCCAGCTGGCAGTAGGAGGACCAGAGAAAGATACCATCTGTGAACTGTGTGGGGAGTCACATCCATACCC
GGTGACCTATCACATGAGACAAGCTCACCCAGGTAAATGATACTGTTGAATGTACGTATAAGTGCTTTTT
TCTTTAATGAACCAGATCACTTTATTTGAGCTGTTCTATGAATTTTGTCAAAGGATAGGGAATTTATAGT
ATCTTAGAATGTCATTTTTAAAGTACATTATCAGTACAGGGTTTTGTGAAAAACAGATAAATTCTAATAT
TATGATGGCCAGGTCATTTAGTGCTATTTCACTTTCATGTAGCATGTTTTAAAAAATATTATGTGTTACC
CAAAGGGTGTGCCATTAATGTGTCTGTCTCACACAGCAGAAACAGTGGCATGCCCATACACACAGGGCAT
CTCCTTTGATTTTACTATTTTCCTGTTCAGAATTGCAAATTAAATTAGATTAGATTGATTTCTATAGGCT
TTTTCCTACGGAAGTGATATTGTTTTATCAGAAGACTGCATTTTCAGTAAATGTAATGATTTCTGTAACA
TTGACTAATATTCCAAATTCACCTAATACAAATTTGGTTAATTTTTTTCTTTGTCTACATATTATACCTC
AAATGTCTTATGAATATGTGATTTCTGAAAATATATCATTGTTATAGAACTTTTATACTTGTATTGTCTA
ATTTTATTGACATAATTAAGTATATCTAAATATACCTATATTCTATCTCTCTTTTAATATGCCTGATTAG
AAACTAAGTATCTCTCATATTTGGGGCATCATTTAATTGATTGCTTTTTGATCAAGTAAGCTATTTTTCT
GATATAGTTAATAGCCTGAAAAATAAGATATCTACTTCAGTATTTTGCTTTCTTTGAGAAGGTAAATCTG
TCATTAATGTATGAGTAATAAGGATCAAACTATTAAGGACACTTGGAGTGTTAAATATTTATTTTTGGTA
TTGTTTCAAGGTTGTGGCCGATATGCTGGTGGACAAGGTTACAATAGCATTGGGCATTTTTGTGGAGGAT
GGGCTGGTAACTGTGGTGATGGTGGCATAGGAGGAAGCACTTGGTATCTGGTATGTGATCGCTGTAGAGA
AAAATACCTCCGCGAAAAACAGGCTGCTGCAAGGGAGAAGGTATTTTATTCCATTTGGAGCTATACTTTT
AATGATATGGATACACTGTATAAAAATACCTTGTTATAATCTTACTACATCAGATAATTCCACATAGTTG
ATATTAAAAGATCAGCTTTTATAATGGAAATCATATACAAATTTAATATTTGTACTAAGTCAAATGCTTT
TAATTTTAAAAATTAACTATATATTGGAATAACACTAGATAACCTCTGCTACATATGCCTTATTGACAAA
TATTTGTTGTGTAACTCTTTATTATTAATTGTCTGTTATTCTCTCTATGGAGAGCTTTCCTTTTCACCTT
CTTTCTCTTTTCCTCTTTTTTTGGCTCCTTTGTTTTCCTATTCCATATCTACTCTCTCTTTTCTTTATTC
ACTCTAGTGGCACCTAACTAAAAAATTTCACTGAATACACGCACTGAAATGATTTACTTTTTAAAAAAAT
GAATTACATTTAGATTTAACTAGTTAGGTGTTAAATTTTTCTGAAGAAGGAAAGGAAGTATAGTTTGTGT
TTGATACAAAATTGTCTTGGTCAGCCCAGGATGAATATGAAATGAATGTTGTTTTTTATAATCTTATTAT

FIG. 7C (Cont.)

CTTAAAATAGCTTTACAAGTGTTTAATAATTTTTATTGGAAACTCAAAATACTTAGCTTAAGAAACTAAG
GATTTTAATGTAAGTCAGAAAACATTAGTTTGATTTTTTTCTTCGCCAGGTCAAACAATCTAGGAGAAAA
CCAATGCAAGTCAAGACCCCTCGTGCCTTGCCCACCATGGAAGCTCACCAGGTGATTAAAGCCAATGCAC
TCTTCCTGCTGTCCCTGAGCAGTGCAGCAGAACCGAGCATTCTGTGTTACCATCCTGCAAAGCCATTCCA
ATCTCAGTTGCCCAGTGTAAAAGAAGGCATTTCTGAGGATCTTCCTGTGAAAATGCCTTGTCTCTACCTG
CAGACATTAGCTAGGTAATAAAATTTTGCTGTTGTTTTTTAATCACCTTTGGATTAACAGCGATTGTTTA
TTGATATCTAGGGTAGTTCGGTATTTGACCTACACTTTATTAGCTATTGTGTACTATAAACAAACTTCCA
GGCATTTATTTTTTGAGTTGCCTTGACTGACATAATGACTTTATGGTAATAGGTATTTAAAAAACTATAA
AAATGCTTCATCAATTTGCATTGTATTAATACACAACATGTCTTAGAAAATAAGACTATAGCTATCTTTT
ACTCTTTGGTAGGCTGACTTCACTCTGTTAGTGCGAAATGCTGAAGTGTAAAGAAAGTGTGTTTCCTTAG
CAGTCTTTTATTTCGTAAATTATTCATTCTGTTAGCATTTAAATGAATACCAACTGGGCACCTACCAGCC
TTGTGCTAGGCCCTGAATGTATGAATATAACAAAATCCTGGCTTCTATGTACTCATACTCGGATGTCAAG
TCAGACATGTTAGTGAAACATTTGAAATGCCATGTGAGGAGTGCTACAATAGAAGTATGTATGTAAGATG
CTGTTAGAGCATAAAAGATGGAGAGTATCTGAATCTTCCCCAGGAAATCAGAAAAGGCTTCCCAGAGGGT
CTGAGCCTTTAGTAGAGTCTCAAAGGATAAATAGAAATCTGTCAGGCAAGCGACAGGAAGAAAGCGACTC
TTGGAAGAATAACCCAGGTGAGTAAAGACACAAATGAAATCTCATTACACATTTCAGGAATCACGGGTTG
TTAAAGGACTGGCTACTGGAGGAAATATGTGAAAGCCCGTTCAAAGTGATTGGTTCACCCAAGTAATGTC
GGGCTCTGTAGCCCAGGTTAAGATTGCATTTTATCCCATGAGCAGAGGAAACAGTGGAAGAATTTTAAAC
AGAGAAATACATGAACTGGTTTGCAATTAAAAAATCACTGTGGAATGTGGAAGCTAATGTGGAGACTAGA
TAAAAGTGCATTACTGGAGATAGAAACCTGTTAGTATTCTGTTTTCATATATTGGACCTCAGTGGTGCAG
CCTGTACTTTCACACATCATGCACTGACACTCCAAAAGAGCCTTTCATATACCAAAACCAAATTTTTTTC
ATCAGCTGACAAATGAAGGTAATCTAGATATTGCCCACTGACATGGCTTGCCGACCAACAGTTCCATTTT
GGAAATTGTCCTCTTTGTGTAGCAGAGTTGTATGGTTTTTAAAATTTTGTGCTTACTATTACAATAAAAT
GAATAAGCAACAAAAAATGAAAATATCAGACTAAGTACATTTGAGACTGAGGTGGAAATCATCAGTATGCC
AAAATACAATAGATCTTTAGTGTGAATCACACCACTCAGTGGACTTAGGTTAGCAACTATTTGTTCATTT
TGAAAAGGAAAGAATCAAATTGTAAAACGTGAAAAATGCTAACACAGCATAATTATAGATTTTTTTCTTT
TTAGCTGTCTGGGGAATGGGCACCCCTTCCACCCTGAACCACAGAAAATTTCATATATCTAATATTTTTC
AAATATGATCTTATGTATGTTCCTACCCAAAAAAGTAACTGCTTGTATTTCAGTGGTCTGTGCAAGAAAT
AATAAGCATGAACCAAGGCAGTGATGATAGGGAATGAGAAGAGAGAATGGCTCTGAGAGGAAACCTAATA
TCATGGGCTTGAAAGATGATGATGATAGAGGGCTAAGCCTACTACAACACTGGAAATATTTTAGCTTAAG
CAACTGGATGGTTGGTGGGCTTATTCACCAAAACACTGGAAGATGGAAAAGTTCTCAAAAGGAAAGAAAC
TGAGTTCAATTTTGGATTTGAAATGTTCGTGGTACCTGGAATGTTGATGAATAAAATTATCAGACTTTTA
TTTTCACCTACCTACATCTACGATTATTTTAATGCTTTGCCTTTAACTATGATTTACATGTGCTGCTTTT
CCTGTTATGAAAGAGATTAAAAATGGAGAGGATCTGTATTGCCATCATGCTTTAAGTTATTGGGTTTGAT

FIG. 7C (Cont.)

TTAATGCAGGCATCATCATGAAAATTTTGTGGGCTATCAAGATGACAATCTATTCCAGGATGAAATGAGA
TATCTACGTTCAACATCTGTACCTGCCCCGTATATATCAGTAACTCCTGATGCAAGTCCTAATGTATTTG
AAGAGCCAGAGAGCAATATGAAGTCTATGCCACCAAGGTATTTTAGTTCTCTCCTGTCTGTTGAATAGCT
AGTGTTTGGTGGAAGAAAGACTTTGAACTAGAAAAGAGTCCTGTAGAAGTTCTTTAATACATCTGTGAGC
CAGTTTTGCTAACTGCTGGAGCAGTAAGAAAAAGCATACATGTATGACTAAGGTAAGGTCCTTGATGGGA
GAGGCAGACTAGTTGGAGAGAAGAGATCAACTAGTGAAGGAATTAAAGATTACATTATATGACATTACTT
AATGCTGTAGTAAATCAGAGTAGGGAAGGGTTACTTTGAGTTTTCATGGGAGCAGTGGCATTGAAAATAA
ATCTTAAACTTCTTGGATTATTGTTTACAGTGCCTCCTAACTTAGGTATGGTAGTATCAGAGTAAAGAGC
TTCTCGGAAAGCTGAATAGAAACTTGTTACAATAATGTAATACACAAGAAAATAGAGGCCAGGCGCTGTG
GCTCACACCTGTAATCCCAGCACTTTGGGAGGCCAAGGCGGGTGGATCACCTGAGGTCAGGAGTTTGAGA
CCAGCCTGACCAACATGGTGAAACCCTGTCTTTACTAAAAATACAAAAAATTAGCCGAGCATGGTGACAC
ACACCTGTAATCCCAGCTACTCGGGAGGCTGAGGCAGGAGAATTACTTGAACCTGGGAGGCAGAGGTTGC
AGTGAGCTGAGATTGCACCACTGAACTCCAGCTTGAGGAAAAAAAAAAATAGAGTACCACTGAAACTTTT
TTAGAGGACGAATGATGTGATAAAAATGCAAAGGTAGTCTCACAGTGACAATTGAGAAGCTGACATATGG
ATTAAAGAGATATATTTTGTAGGAAAAATAAGTGTGACTTGTTCACTAACTGGATAATGAAAAAGATAAG
TTTAAGATGACATGAAGATTTCAGTCACGAATAACTGTGAACATGGTATCATTGGAAAGGAAGACATTTG
CTGAATGAAAAGAGAATGTGCTTATTAAAAGAGCATGCCACTGTGTTACTACTATACAACTATAATTATA
AACTAATATAATAAATACTTTAATGAGCGCAATGGGACATATATATCCAAATGAGGTTTTTTTTTTTTTT
CATTAAAAATACATGCAACTTCTCCCCTCCCCAACTGTGTGGATTACTCGTCAGAATTTCTTTGAAGCTG
CTCTTGACATTTTCTCCAGAGTGCAGTGCAACCTTTTATATCTTTAAAAGTGATAAAGTATTTCTAAAGG
AGATACACTTTTTAAAAGAGTTAGAAACTGTTTTGAGGCTAGTCTGACAAGTGTGATTCTCATTGGGTTA
CTATTACCCCTTAGGATCAAAATCCAGGAGGCTGAGGCAAGAGGATGGCTTCAGCCTAGGATTTTGAGGT
TACAGTGAGCTACGATTGTGTCACTGCACTTCAGCCTAGGTGACAGAGCAAGACCCCTTCTATTTAAAAA
AAAAAAGTTGATGAATAAATGAATTCATTAAATCAGTGGTTCTCAATTGAGGGTGATATTTGCCTCTCTG
TTGACATCTGGAAATATTTGGAAATAACTTTGTCACAACTGGGCTAGTTGAGTGGGCATCCTAGTGAGTT
GAGGCCAGGGATGTTGCTAACCATCCTACAGGAGGCAAGACAGCCTAACAAGGAATTACCTGGCTCAGGG
TAGCCATTCAATTAAAGATGTCATCTTTGCTTTCTTCTTTGGATTTTCTTGTGTTGCTTGAATTCTTTCA
CAAGCAATTTTTTTTTTTTTTTTGGTAAAAAGTCACTTTTTAAATTTGTGTAATTTTTTTTAAGTTAGTAG
AAAACTTCCTCTGAAAACAGAACAAATGTCTGTGCTTTATAGTAACACCATATATAAAGTGAATTAAGTT
AATGTTTCCCTGTATTCTAGTCATTCTGGAACCAAGCAACCTATACTAACACCCAGGGACATTTACTGCC
AATCAGTTATGTACAGTATTTATAGTCTATTCAAACAAGAATGTACATAAGCTTAGAGAAGTGGTGAGTA
AAGAAAACACCTAGGCAGTTAGCCGTCTATTAGAAAATAGATAATTTTACCAAGGGACACAGGATTTCAA
ACCTGGCTTGAATGATGGAAAAAACTCCAGAACCAACGGTGAGCAAAAATATTCCAATTTGAATTCAGGT
GACAGAAAAAGGAGCTCACGAAAAGAATAGTTTCTAAATTTGTTTTAGAGAAATAAGAAAGAGAAGGGAT

FIG. 7C (Cont.)

TTCTCTTTTTTTATAAAATGTGTCAATAAAGGAAATTGTATAGCTCTCTTAATAACTTTGTAAGTATTTT
TAAATGTTGCTTTAATAAATAGAAAAGCTGTTAGTTTACTTAAGCCTGAATAAAACCATTAAGTTCTTTT
ATAGAGTGTAAATACAACACTGGTGCCAAAAATCAGTTTGTTACCTCTCATGACACCTTGATGCAGCCAT
CCTCCAAGGGCTTTGGGCAACATTTCCCAAGAGTGAGAAACCTCACAGAACACTGAAGACACCAAAAGAA
AACTTTGGAACCAAATTTTGCTTCCTGTTTTATTAGGTTTTCATGTGTACATATCCATTTTCTTTCTATT
TGGTGCACTTACGATTATATCTGACTGTTTTTCCTGAATATTATGATACATGAATTCCACCCCAGTGCTT
TTGATTCTAAAAGGAGCTTGGAAACCTTTCTTCTTTTTCATTTAAAATACAAAGTAGATTTAAGAAAACC
ATAAGTTTTAAGGTACAATGCTGAAATCAGTCAAAATGTTACTGCATTTGAAAAGATCAAATTATGATTT
AAAGAGAGATTATCAATTTGGCTTTGATTTTGTTTCTCCACATGAAATATTGAGTCACATATTTTGCATC
ATTATAAGTATAGTTACATTTCATTCAGCTCTTCTGAGTTTGTATCTGTTGCATTGTTCCATGTACAGTT
TAGAAACCAGTCCCATAACTGATACTGATCTTGCAAAGAGAACTGTCTTCCAAAGATCATACTCAGTTGT
TGCTTCCGAATATGATAAACAACACTCCATTTTACCTGCACGAGTTAAAGCTATTCCTAGAAGAAGAGTT
AACAGTGGAGACACTGGTAAGTATGAGGATAAAAAAGAATATTGAGTGATCTGACTACTACAAATAAAAA
AATTGTTTTATTTGCATATAATTTTTAAAATTTAATTTTTGAAGGAAAAGGCATGGGATAATTTCTAATG
TGTGATTGACATTCCTTCTATATGACATAGCTATAAATGTGCATCTCTAAATTTTGCATCTTAGTTGAAG
GGAAATCTGGAGATCATTCAGTGATTGTTCGAGAATAAATTGACCTTTACAATCTTACTTGTTAGGTATC
TAAGCCAAATGTTACAACCATTATCCCTTCCACTAAACTTTTGTGGACCAGGAGTTCCAATGACGTACAC
ATTCACAGTTATCTCTCCACCCCAACTGAAGCTTGATAACTCTTGGAGCTGCCATCATTCTAAGTAGATA
ATAAAACTTTGGGGATATAAATAGCCCTTAATCGATTTAAAAAAAAAAAAAAAACAGTTACATGATCTGG
ACCAGTTGGTATCAACAGCCCCAAATTGGAGCTGGGGATTCTACCTCAAGAATAATTTTAAAAACCCAAG
AAGAACAGGGTAATATAGTGATCAATTATCAGAGAGATCACTTGCTAAAATGAAGATTTGGCCTAAAAAT
TATAGTCAGATGATTAAGTTATCTTACTGAAGACTTTTAAGAAAAACATTATTGAAGATTGTCCAGCAAT
TTATAGGTTCATTCAACAAATATTTTTGACCTCCTGTTAAGAAATGTTTCTTATAAAGCCATCTTTTAGA
AAATGATGCAGATGAGATGTAGATTTCATTTAGAGAAAATATAAATCACTTAGCTTTTAGAGTGTTTTAG
AAAAGGTGAACTTTAGATTCAGCTCTGATTCAAAACCCACCTCTACAACTTAATAGCTATATGACTTTCA
GAGAGTAACATATTTAATCTTTCTGAACCTTGGTTTCCTCAGTAAAAGTTGAAATTGTTATGATTTGTGT
CATGTTCAAAAAACCAATGACAAAGGCTTTAAGTGAATATATTAGATATTATTATCTTAAATATATATGC
ACTGCCTATGAAAATTAATAATTTTCTTTTTCTTTAATAGAAGTTGGTTCTTCCCTTTTGAGACATCCGT
CTCCTGAGCTTTCTCGGCTAATCTCAGCCCACAGCTCTCTTTCTAAAGGAGAACGAAATTTCCAGTGGCC
AGTTTTAGCTTTTGTTATACAACATCATGATCTAGAAGGTCTTGAAATAGCAATGAAACAGGCCCTAAGG
AAATCTGCTTGTCGAGTTTTTGCTATGGAGGTATCAAGACATTAATGAAATTACTGATTCATTGATTATA
CAAATCATGTGATGATTCTATTTCACGATGCCACTTTTTTACCAACAGAAATTGTGTGAAATTAAAAGGC
ATTAGCCAATTAAAAGTATTAAGTGTTCCTATAAAAATCAGACTCTAAAGTTTATGAATATAAATGAATT
TAGAATTTCATATTTAAGCACCCTAAAGAAATTTATTTCTGTATTGCTTTACTATTTGAATCTTGAGATT

FIG. 7C (Cont.)

ATCTTTTTTTTAAAAGCTTTTTATACTCAGAATGTCATTTTATTAGAATGAAATGACAGAGTAATCATGG
AAAGAAGATAAGGAGTAGGGCTTTTGAGTGGTAAGTTGACCAGTAATAACTTCTCTGGGCCTTTGGTCTC
TGGAAATAATAGGATTACTGTATATTACAGGCCTATATATAGTAAATCTGTGTTTTTATCAAATGTGATA
AATAACCTACCACTTCATGGATGGGAATTATATGAATATATTTAAGTAAATGGTTGCTTGCCTAGAGCTT
GAGATACACTTTGTGTTCATCCAGATGCAAGTTGGAAAAAATGTGCTTGAATAAATTAATATTAAAATGA
ATTTTCAAAGTAAAATGTGATTTGAAAAAATATTTTGGTATTGTATCTTATAAATTATTTTTCCTGTTTT
TTTTAAATTAAAACCCCAAATTATTAACTGTTTCAAGTTCCGTGTGCTTTCAGTGAAATAAAGGTCAGAT
TTTCAAGGTGCCAAGCATAGTAGCCCATGCTTGTAATCCTAGCACTTTGGGAGGCGGAGGAGGGAGGATC
ACTTGAGCGCAAGAGTTTGAGACCAGCGTGGGCAACATGTGAGACCTCATTTCTACAAAAAAAAAGTTTT
AAAATCAGCTGGGTGTGGTGGTACACACCTGTAGTCCCAGCTACTTGGGAGGCTGAGGTGGGAGGATCAT
TTGTGCCTGGGTGCTTGAGGCTGCAGTGAGCCATGATCACACCACTGTACTCCAACCTGGGTGACAGAGC
GAGACACTGTCTCTTAAAAAGAAAAACAAATAGTAAAACTATAAGGCATTTTTTTTAATTAAAAAAGATT
TTCTAGTATCTTTCTTTGAAGTCTTAATCCATGGAGGTACTTTATTTCTGAGTACTTTTTAAACTCATGT
ATTTTATTCTTGAACTCATTTAACCGTCATTTCTTCAGGCTTTCAACTGGCTTCTGTGTAATGTCATCCA
AACCACTTCTCTCCATGATATTCTGTGGCATTTTGTGGCATCACTGACTCCTGCACCAGTGGAACCAGAG
GAAGAAGAGGATGAAGAAAATAAAACAAGCAAAGAAAATTCAGAACAAGTAAATGAAATTTTTGTTTTGA
TTGTGCATATTTTTATAGAAACTGGTAGTATACCTTCAAATAGTCCAATAATTTGCATGAAATCATTCGC
AGATCTAACTTGAAAGCAAAAAGAATATTTTAGTGCTATGGGCAAAGTATTAATAATGAGACCTGGATTT
TATAGAAGGCAGCCTGTATAATGGAGAGAGCATTGAATTAGGGCACTAGGAGCCTGAGTTCAGCCTCATT
TCTACCCTATTGTAGTTGTATGACTTGTAGGCCTCGGTTTCCATGTCTGTAAAATGAAAGTAATCTAGGT
GACATTTATCTTATTCCCAGTCACTCTGAAATTATGTGAATGGCATTTTAGGTTAATTTCCAAGGATATC
AAGCAACATTATCATAGTCAAATTCTTAAAACTCACAAACAAGACACCATGAGCAAGAACTAACAAAAAC
AATAGACAGTAGAAATAGACCCTCAACAATGGTTGTAATTATCTATGTAAATGTAGAATAATGTGTTAAT
ATGCTTAAAGAAATAAAAGAGAAACTTTAAAATATGAGAAGAAATTGTAAGAAGAAATATGAAGTGATGA
ATTTGATAAAGAACTAAAGAAAACATAAATACTAATCTAAGTATAATTGATATTTTTAGTTTTGAGATTT
TATAGCATGTCAGTGAAAAAATTGGCTAAATATAAGAGAATGATGGATTCGATAAAGAACTAAAGAAAAT
ACGTAAAAATTAATCTAAGTATAATTGATATTTAAAAAACAATCAGTTGGACATTTTATAGCATGTCAGC
AAACAAATTGGTTAAATATAAGAGACCTGTAGAAATTATCTAGACTTCAACACAGAAAAAGTAAATAAAA
AATACAAGTTGCTAAGAGCAATGAAGGGCAAAATGATGTACAACTTACCTACTTGGAGTTTCAGAAGGAG
AAGACAGAATGGAAGAGAGACAGTGTTTAAGAGTTAATACTTGAGAATTTCCCAGAATTGATTACAGATA
ACAACCCATTGAGTCAAGAAGCCCAGTAAACCCCAAGCAGAATAAATACAAATCATGGTGGACAAATTAT
AGTGAATCACCTGAACACCAAAAACAAAGAAAGAGATCTTTTAAGCAGCCACAGAAAAAAATATTAGCTT
TCAAAAGAGGGACAGTGAGAATAATTGCTTAATTTTTGGTAGCAACATTACAAGTTAAAATACTGAGTTT
GTTTAAAAGGCTGTCAGTTGGTTTTTTTCAACGTGCTGAAAGAAAATACTTGTTAACCCAGTTGAAGGGT

FIG. 7C (Cont.)

CTTTGAAGAACAAGACCAAAGACATTTCCAGAATAAAAACTGGGAGAAATGGCCATGGAGTATCAATGAA
GAGAAAAGAAAGTGTAAATATGAGGGCATATCTTAAAAAACATTGACTATGTAAAAGTAATGATATGTC
ATGGTGATGTACAAAATGATAAAAGATCAATCCTGGATATGTATCTACCTAATACTGTAACCTTAAAAAA
AGTAACAATTGACAGACTGCAAGGAAAAATAGGACAGTCTACAGTTACAATGTGAGATTGTCATATACCT
GTAACAGCTATCTGTTCCTGCATAACTACCCCAGAACTCACTGGACTAAAACAGTTGTTTATTTGCTGAC
AGTCTGTGGGTTGGCAATTGCAGCAAGGCTCCACTGAGAGGAATGACTCTTTCCTGTTTTGGTTACATAG
TGTGCTTCAAGTGGTACCCCCTGAGCTCTTTTATCCTCCAGAATGCTGGCCTAGGTTTGTTCAGATGCCA
GAAGCATTCAAGAAAGAGAGCACAGAAGCTGCAAAGCCAAAATGGCGAACACTAAACTCATATGCCATGC
TTCTGCCACCTTCCATTAGCTAGTATAATTCACAAGGCCGGTCAAATTCAAAGACTGAGAAATAAACTCC
ACCTGTTGATGGAAAGAGCGACAGAGAATTTGTGGCTGTTTTGTGTATAGTACCATAACACTCTTTTTAG
TACTGGATAGGTCAGGCAGAGAAAAAGAATCAGAAAGTACACAGATTTGAATGATTGACAGTCTTGATAG
AATATACAAAACATTGCATATAGTTGTTTACATTCTTTTCAGATACACACAAATGTCTATGGAAATTGAC
TGTTTACTGGACACATAAAGCAAGTTTTAACAAACTTGAAATAATTGGTTTTCTTCCCACCATGTCCTCA
GTCTTTATTGCTAGTATATAAGAATTAGATAACAAAACAATAACAAGAAAAATATTTATAGGGAAATTAA
GTAACGCTTCCAAATGAGTTGCATCAAAGAAGAATTATAACAGAAAATATTTTAAATGGAATGGCAATAA
TAGTACATCTCAAAACTTGTTGTTTGGCAGAGTTCTAGTTATAGTTACGATGAAACAGCCAGTGTCAGCA
TTAGTTCTTATAGTAAGTAACAAAAAGCTGGGCAAAATATTTAAAACAATTGTTCATAGGCTCTGAGGAG
TGACCAGTACAGGGCTGTAATCCTTGAGAGAAGAAAAGGGCATGAGGTAAGCCCCACAATTGGGAAAAGA
GCCCAAGCAGAGTACGTCAGTTGTGTTGGCAGAGATCAAAGTTTAGGACTGTAACTTTGGGATGTGGGAA
GCAGGGCACTAGTGGTACAGAGCTGCAGAAAGGGAGTCTAAAATTTTTGCATAAAAATATCCCTAGGGTC
CTGGCCACTCTTAGACTGGGCATGCAATTTCTCTGGAGGATCTAGCAGTGGAAATGAATTGTAAGCTGAG
AACTGAACAGATTCTTAGCTTCAGAGCTGGGTTCTGAAGTTTTAGTCCAACCAGAGGTGGGGTGAGCGTG
ATGAATACTCCTGGCATGCCCTTGAAACCCCAGAAAGACCATACTCAAGGAATACAGACCATGCCTTAGG
AGTAAGGGCAGTGCCTAAAATCAAGGGCAAAACTGAAATAACCCCAGTCTAACAAAGTCGAATGCCAAGC
CTTGATGGAATCTAGATGGCCTGCTATCTCCCTGTAAGAACAAAACTACATTCTTTAGAAGACAATATAA
ACCAGAACTTCTATATCAGTAGAAGATAATATAAACCAGAACTTCTATATCAGTAATCAATATATGCACA
AAGAAGGAGGCAAAAAGCAACCATCTTTTACTTAGCTCAGTGACATAGTTTAAAAAGTTTGATGGGCTTA
CATTGGTAGCAAGATGGAAGAACAAACATTCTTTGCTGTGGAGTAGCAGCTTCTTAGAGAATGGTTTGGT
AAGATCTATCAAAATTCACATTAAAAATCATTCAGTAATTCCACTTTTATGAAGTTCTCCTTATCATATA
TGCATGTGTGAAAAGACAGATATACAAGTTGATTCATTGCAGAATGTTATATAAAAACAAAAGATTGGAA
ACAACCTAAATGACTGTTCTGAAGTGGACTGATGAAATAAACTATGGTATTTTTATTCATCAGAATACTA
TGCAGTGGGATAATATATGTTACATACATATCTAATAAGTAATAATCTCAAAGATAAATTATTGTTAAAA
GAACACAGATCAGTTTGTTTCCAGTGCTGCCATTTGTGTAAATGAACAATATTTATAGACAGTCCAAGAA
ACTGGTAATAGAAATTGCCAGTGGGAGGGCATCTAGGTGGCTGGGCTGTAGAGACAGGGAGACTTTTTAT

FIG. 7C (Cont.)

GGTATTTTTTTATACCTCTTGAATATTTTATTATGATGTGTGTTATCTACTCAAAATAATAAAAGTTAT

TCCATAGTTAATATTATTAATGGAGCCATCTGAGGGTTGTAATGAGAAATGAAATTCAACCCCTACTTCT

CTTTCCTAGCTGTGGTCCATTTGCGTAGAAAGGAGCTTTTTTTTCTAATTCACATAAAAATGCTGTATGA

GTTAGTGACCACCCCAACTTCTAAACATATGTTATTTTTTATACATAAACATACACACAAAACATACCTA

CATATATGTATGTGTATATATCCATACACATACATATATATGCACACACACTACACATACACATGCATAC

ACATGTGGATTCACCCTACAGGTATCTTTGTGAGTACACTAGAATTGATACATTTATTCATTTGCATGCT

GATTTTGCTTGTGACTAAACTTACAGCTTTTTTCCCTAAAATAATACAAGCATAATTAGTTAAAATTACT

GTATCTTTCTGGGTACAATTTGGTTTTGTTGTTTGTATTTCTGTTACATGACCATTTTTTAAGTATACAT

AATAGTCTTTTGTGAAGAGGATTCCTTCCAGCACACAAACTGATAAACTTGTTTCAATTTCTGCCTTAGG

AGAAAGATACAAGAGTATGTGAACATCCACTCTCAGACATAGTGATTGCCGGGGAAGCTGCTCATCCTTT

ACCACACACCTTTCACCGCTTGCTGCAGACCATCTCAGACCTTATGATGTCTCTCCCCAGCGGCAGTTCA

TTACAGCAAATGGCCCTGAGGTAATTTTGGTATCCACATATCCTAGGTACATTGGACAAGAGAGTTTATG

GAATATTCAAAGTATGAAATGCTCCAAAAAAAGCTCTTTAAATAGTAAGATAGAATCCCTACATTATATA

GATGGTGCCTCCCTCCTTACAGTCATAATTTTTAGAATGGTCCTTCCTCTTAGTTAACATTTGTTTGCCC

TCCTGTAAAATGTGGCTAATGTAATTCTTAGTGCCCTAAATTATCACTGTAGCAATCTCCCTCACTTTCC

CCAGTCTCCTACCTCAAATCACTTAAATGTCCCAAAAAGAGAGAGGGAAAATGAAATCTCAAAAACAAAA

ACCAAAATAGAGTTTTGACTTGAAAAGAATCTTGGGGAAAACAGAGCCTGGTTGTATGCACCCAGTCCTA

AAAGCACCTTAAGGAGCATCACAGATGCTCAACAGATTCCAATTTCAATTTGAAATGTGTTGAGAATTTA

GCATTGCTTTTACACTGTGAACCTTGTTACTAGATTCACATACTGGACTCACACTTATAAATAAATTCTC

CTAATTAATGTATACAAGAAATAGATTGATGGAATGCTTGGGCTTCCCATGTTACTAATGATAAGACCAG

TGGAAGAGAGATTTCTCTTTGTCCTCCTCACAAGATTTTTGAACTACAAGATAAACTATACCCTGATGAA

TTAGTATGGCATTGTAAGAGTAATAAATTTGAGGGGTTGTTGCAGTTGGTGTACCACTTGTTTACACAAT

AGATTCATTACCCTTTTTGCTTCTGTAGCCTTGATCTTCATCTGTCTAATTCTTTTATATTTAAAATGGG

TCAACTTTCCTTAGAATTTACCTTGTTCCAAAGAAGTTACCTTTATTTCTCAAAAACAAAAACAATAGGA

ATGATTTTCTTCCCTGAATTTTTAAAATGTCTGTTACTAGAACATTAAAATTTCTTGAGATATTAGCTAC

AGAGTACTCATCTAAGAGTTCCTTAGATGTTCCTGGAAAATAATTATTTCGTATATTGCTTATATATCGC

CTTTTTAGGTGCTGGAGTCTCAAATTCAAGCAATCTGATCACCAGTTCCTTCATCAGAGCAACGTCTTTC

ATCACATTAACAATATTTTGTCAAAGTCAGATGATGGCGATAGTGAAGAGAGTTTTAGCATCAGTATACA

GTCTGGCTTTGAAGCTATGAGTCAGGTCAGTCATTTCAGTTATTATCCTGGTTGTCCTGTTAGTTAATAA

TACATCAAAGGAGAAACTGTAAGTTATTCATAATCAATTTGATCCTGTCTTCCATTATGTTTTATCTTAT

ACCTGTTTGTTTTATCATCACGAAAGATTTGCTTTTAAGTATCATAAGTACTTATATTTGTTTCTGATAG

GAATTATGCATAGTAATGTGCTTAAAGGACTTAACCAGCATTGTTGACATAAAAACTTCAAGCCGACCTG

CCATGATTGGCAGTTTGACAGACGGCTCCACAGAAACCTTTTGGGAATCAGGAGATGAAGATAAAAACAA

AACTAAGAACATCACCATCAACTGTGTAAAAGGAATCAATGCCCGCTATGTGTCTGTTCACGTGGACAAT

FIG. 7C (Cont.)

TCCCGAGATCTTGGGGTAAGAAAGCAAACGTGATTTACGGCTCTTTAGCTCTTTTCAGATCTTAGTATTC
ATGCACTTTCATTTCTGAATTTAGCAACAAGCTTTATCACCTGGAATTTCACCAACCAAACATCATTGCT
ATAATCCCCAAATAAATCTTAAGTCTAAAAACAAATTAATATGATTGGGAGCACTGTGGAATTCCATTTC
TGAAAAGAGGTCTGATTACAAATATACCATGGCTACAGCTAAGCAAAATGAAAGTCTGCTCTACAATTTT
CTGCTGCCATTCCCTTGGTTAAGATTTTCCCGTGACCTGGAAGTCCTCCCCTTAAACTCTGCTGATCAAT
TCTTCCAGGGTCTCTCAAACTCAGCAGAGAAATTCTAAGTAACTCCTCTAAAAAATTACTCTTTCCCTCT
GCTGATTCTTTTTGTATTACTCTGGTGGCACTTAATAATAATCTTTGACCTATAGTGTAATCAGCTTTTT
TTTTTTTTTCTGAGATGGAGTCTCCCTCTGTCACCCAGGCTGGAGTGCAGTGGCACAATCTTGGCTCACT
GCAACCTTCGCCTCCAGGTTCAAACGATTCTCCTGCTTCAACCTCCTGAGTAGCTGGGATTACAAGCACA
CGCCACCATGCTTGGCTAATTTTTGTATTTTTAGTAGAGACAGGGTTTCACCATGTTGTCCAGGCCGGTC
TCAAACCCCTGGCCTCAAGTGATCTGCCCACCTCAGCCTCCCAAAGTGCTAGGATTACAGACATGAGCCA
CTGCACCCAGCCTATCTTCAAGTGTCTACTTTGCCACAGTCCTCATGAAATAAAAAATAAGTTTCAGACT
GTCCCAAATAATCATAATTTATATTCTCTTCAGCCTAGTTCATCCATGTGTTTCAACTGAATTAAATATT
CTTTTATAAAAGGCACTAAACAAGAAAAAAGAGTCCTATTTGCTTGAGTATTAACAACCAAGAAAGAAAT
AGCACTAACTGCCAGACTGCCTTTCTTCTACCTCATTTAGAATTTTTTTCCTCAGAATGGATGTGGCTTG
CTAGCAGATACAGTATTAATGGCTCTCCTTGAACCATTGCCTGGCTTCTCCTGTGCCATTTGCATATTTC
CTTTCTCAGGAAGAGCCACAGTGGTAGGATTGGGTCTCAGATAACCTGGATGCAGGCCAGTCTGCAATCA
GAGCAACCTCCAACTCCTGTACATCAGTGCAGGTTCTATTCCTCCCTGGTATTGAGTAAGTAAAAGAGGC
TTAGCTAATATAATATGAGCTATTTCCTCCTCAGACCTAAGAATTTCCACTGGTGTAACTACTTTATCTT
ACTGGAAAGTCAAGTGTAACAAAGCAAAACATTTTTGTAGCTAGAACTCACTGTTCAGTGCAAAGCTATC
TTTGGCTCATGGTACATTTTAAGCAAGGACATACTCTCCCTCAGAACAATGATTGCAATCAATTTAACAC
TTCTGTCTTTTCTAAGAGGAAATAATCATAACAGTATTCATTTTCAAAATTCCCAACATGTAAGCTGACA
TCTACTTTCCTTTTAACAGGCTTCCTCTATGTTATAGGTTGAGCATTCCAAATCTGAAAATCCAAAATGC
TACAGAATCTGAAACTTTTTGAACACAGATATGACACTTAAAGGAAATGCATATTGGAGCATTTCTGGTT
TTAGATATTCAGATTTGGGGTGCCCAGCCAGTAAGGATAATGCAAATAGAGTATTTCAAAATCCTAAAAA
ATCCCTAATCCAAAACACTTCTAGTCCCAAATATTTCTAATAAAGGATACTCAACCTGTATGTATGTTTT
CCTTGAGTTATGTACCTCCATGTTCCTCAACCTGCCTACCACAGAGCCTTGTACACAGCATTTGTTGATT
TGAGTTGTATCAGCCTACAGCACTCATATTATGCAGCTCTCCAAGGAATTAATGTTAATCTATTTCTTGA
TGTGCTTTGCGTAAAACTTATTCAGCCTTAAGATATTTGACACTAGTTTGAACATGTATTGAACTTGTAC
TGTTTGACATTTATTTTGTGTATTAATGTTGCCTTCCCTAGTTTGGCAAGTATCTTGGGGGATAGAACCT
CCTCTCATATATCCTACTTCAAATCTGTAAGGAAGTCTGGGTACATTGTGACACTCATAAGTATTTGTTA
GTTCAGTTACCTTCCCTCTTTATACTTCCAAAAGTAATGAAAATATAGCAACAAGAGTCTGACATAAGTG
ACAAGCAGATTTGTTGAAAGGCTTCATGAGGAAGGAATCTGAATATTTAGACTTTGAATAAGGAGAGGGA
ATGTCAAGCTGTGAGAGAGCACCTGGAGAGAGGCTGAAATGTGCAATTTAAGATGGAGTTTGTGAGAATG

FIG. 7C (Cont.)

AGACTAAAGTTATAGGAACCGTGGTTAGTTGGAGGGATGGGGTGGGGTCAATCAGGAAGGACCATAAGAG
ACAGGCAGAAGAGTTGATGTGGTATTAGTAGGTCATGAGAAACCATTGTAAGTTCTGAAGCAGGAATATA
GCATATTAACTATTGTGAATTGTCTATTTCAGAATAAAGTTACCTCAATGACCTTCTTAACTGGCAAAGC
AGTAGAAGATTTGTGCAGAATAAAGCAGGTAATTGAAATTTTGTCATTAAATGTTTCGCTACCTAGAGAG
AAATTTCTTCTTCTCAGCCTTCACTATTGAATTCCACCCTTGGCACACAACCAAAGTATTATAGGGAATT
ATCTATTTACAGAACACTAAATTGACAAGTGGTCCAAAACATAGGAATAGTAACCACCATCCCTGTGCTG
GACATCTCACCTGTTTTCCTAAATGTTCCCCAGTCATGAGCAATTATATTGTACCTACAGTCTCCCTACC
CTACTCCCCAACAAAGACTCAGGGTATCTTAAAATTTATCACAGATCCCATTCACACTTAAAACCTTACT
TCACCTATACTTTGAGTTAATACAGGTTATTGTCCTCTGGCCTGAAAAATCTGTCTGTTATAACACTTAT
AACACTGCAGCTATATCCAGGTTGCAAGTCAGTTTAAACCAACTTTAGAAACAAGTTAAGTTTTATCTAG
GCATGTGTCTGAGACTGTGCTCAAGCTCCCTTACTTGTATTCATGAAACTTTGTCAAATCTGTTCCTCAC
TGGCTACTTTATCTCACAAAAAGTTGGCCAATCGCTTGCTTGCTTGCTTGTTTTCAAATCACATTGAAGG
AATCAATTAAGATTTTGGACTAAACATATAATAAATTTTGTTTAAATTGTTGAAGAATTTGGGAAAATAA
TCCTATTCAATGAGATTGTGTTTGTTTATACTTAATACCCCTTTTTGAAAATTGACATTATTAATTAAAA
TAATATCAACTTAATGTCTATTTAAATCACATAGAAATCGCCAGGTCATTTCTTGGTTATTAAATGCCAT
AAGAACAGTTTTTATTTTATGAAGGGAATAGTGTCAAGAACTATTTCACAGTATATTAACATTTAATCCT
TGAAAAAAAAAGTCATATTCTCAATGAAAATTAGTGAAATAAGGAATCACAAGTGTGAAGTTACATATTA
TGTAATTTTTGTTCAAAAGTAAAACATATTAAGTAACTGCACTTTAAAGTCCCTTATCTTTAAATGGTAC
TTTAATGTGAGGATGCACAAAAAAAGAACCCTTTTCTGATCTTGTGAGGTTTCCACTTACAGATGATATA
GATAAAGTACAGTCATATAAATTATTTGTAATTATTTCACTCATATAATTTTGCTCGGAAGCCATATCGT
AGTCAGGCCTGGATTTTAATTCTCAATTCCACCATTTACTGAAAATCCCTTAACCTGTATTAACCTTAGT
TTCTTCATCTGTGTAATAGCTACTATAAATAATATTACTTATCTTCACCTGGTTGAAATAAGAAAATCAG
TGTGAAATAACCTCATAACCTTTACTCTGTGCAATTCTTTGTTATTTGAGCTTGCTGGTATCAATGCTAA
GTCCAGCACAGTGATAAAAGTGATCCAGCTGAATCAGGTTCCTGCCTCTTTTCTACTCAACCAGGTTGAT
CTGGATTCCAGGCACATTGGCTGGGTAACAAGTGAACTTCCAGGAGGGGATAATCACATCATAAAAATTG
AATTAAAAGGCCCAGAAAATACACTGAGAGTTCGACAAGTCAAAGTCCTGGGCTGGAAAGATGGTGAAAG
CACAAAAATAGCTGGCCAGATTTCAGCCAGTGTGGCCCAGCAGAGGAACTGTGAAGCTGAGACTCTGCGA
GTATTCAGACTGATTACGTCTCAAGTGAGTGTCCTTACAACATATTCTAGCACAGGATAATTGATGTAAT
ATATTTTAAGAGTGTAACAAAATATTTTGTGAAACTTATTACAGAAATTTCTGGCTATAAATGTTGCCCA
TTTTTTCTTTTCATAGCCCTAAACACCTGAGTTCCATGTTGCATTTGTAATTAAGAAAAATAGTGGTGTA
TATTAGCAAGAGTAGCATATTATAAAACCTGCGGAATCAGCTAATGAGTCCTCTGGCCAATATAGTGTTA
ATGCCTGTCATTAATTCCTTCTCACATGCATATCTTCATCAGGTATTTGGAAAGCTCATCTCTGGAGATG
CTGAACCTACACCAGAACAAGAGGAAAAAGCACTATTGTCATCACCTGAAGGAGAAGAAAAAGTATACAA
TGTATTTATTTGTATTCTAAAGATATTTATTTCCCTTTTTTATTCTTTTTTTCAGTGAAATAATTCATTT

FIG. 7C (Cont.)

ATTGCTGTATATTTTGATGGATATGTAATAACAGTTTTATGCAGTTCATATTTGTTCTTAGAAAGATGAA
GGAACTATCTAAAAGAAATTCATTATTCATGTATAATCTAGCTAGTATTTTAAGTAACAGCAAATTTGCT
CTATACCTTGGGTTTTTGCATTCATTTGTAATCATTTCTGTGCTATACCCCATCAGTTATCTTCTCCCTC
CTCCATTGTCCCTGTCCTTCACAGTTCAGCTCAAAAGTACTGTCTTCTTCATGAAACTTTTTTACGATTT
ATCCTCTTCATGAAATTTGTTTATGATTTCCCCAAACAAAAGCAGTTTTCTCTCTGCTGGAGTTCATAAT
AATCTGTATGTGTCTCTTCTTCATTTTTCTCTTATGTTTATCTACATGGATGTTTTCTCTCTTCTACTGA
ACCATAGCTTCTTAAAGACCAAGTCCATGTCTAATTTGTCTTTGTATCCATCATGGTAGCATCACACACA
TGTTTAGTAAATTTTTATTAGAATAACTACTCTTTGTTACTGTTCTTGAAATTTCTTGCAAAAATACAGT
TGCTTTACTTTTTCGGTCCTGACTAAAACACTATACCTAAAACTTTTGTACTTCATCCATTTGCAAAAAG
AGAAGTCAACTCTGACTAGTCTCAATATTCTAGTGTCTTTAAATGCTACAAATAATCACCTTGGCAGCCC
TTTGAAAGATAAATTTCAAGGATTTCCCTTGTCTCACCCTGTGTTTCTTAATACAGTAGTATCTAATCAT
TGTCCTGTTTTTGTTTGAGGTCTGAAAAAAATAAGATTTCTTAAATGCTGGTAACTTCTTTCAACATCTT
TTGGAGATTTCATTTGAATGACTACAAGACTGTGTAACTACCTGTTAAGTCAATTGAATTTTAGCAGATG
TCAACTCTGTACTAAACAATTGTGAGAATGGCAAGCCCTCAAAAAGCTTGCATTCTGTTCTTGGTTATGA
ACCCTCTGCATTCCCCTCACCCCCCCCAAAAAGAAATCAACAAAGATACTATATAGTATAAAAGCAAGTT
ATTAAATGTGTGAAAAAAATTGGATCATTGTGCCCTGGAGTGGTCAGAGAAGGCTTCTTAGGGGATATTG
GACTGGAGTTAGATCTGAAAGAGAATGAAGGGATTCAAATGAGATTAGTAGAGAGAATGGGAGCAAGGAC
TGATCAGAGAGACTGGCCTAAGGGTGGGAGAGTGTATGCTGAGGAGTTAAGGTTGAGTAGGAAAGGTTAT
ACTGTCATGTGTGTGCCCATGAAATAACATGATTTTTAAGAGAATCTTTTTTTAAGTTAGATTATTGAAG
CACAATTTACATACAGAAATTCCTCATTTTAAACTGTATCATTCAATGAATTTTTACTTGTGTACACTAG
TGAAATCATTATCACAATCAAGTTTGTTTTGTTTTGTTTTGCTTGAGACCGGGTCTCTCTCTGTCATCCA
GGATAGAGTGCAGTGGTATGATCACGGCTCACTGCAACCTCAACCTCCCGGGCTCAATGGATCCTCCTGT
CTCAGCCTCCCAAGTAGCTGGAACTACAGGTGCACGTCACCGTGCCCAGCTGATTTTAATATATCTGCAG
AGATGTGGTTTTGCCATGTTGCCCAGGCTGGTCTCAGACTCCTGGGCTCAAGCAGTCTGCCAGCATTGGC
CTCCCAAAGTGCTGAGATTACAGATATGAGCCACCATGCCCAGCCCACAACCAAGTTTTAAAACACATCA
CTCCCCAAATTTCTCTCATGTTCCTTTGCAGGCAATCCCCCAACCTCACACTTAGAGCCTAGCAACTACT
GAACTATATTCTGCCAGTGTTGTGTTGCCTTTTCCTGGATGTCATATAAATGGAACCACTCAGAATGTAG
CCTTTTTGTCTTGTTTCTTTCACTTTAGTGTAATGCTTTTGAGATTTATCCATGTTGTAGCATGTAGCCA
TGGTTCATTCTTTTGGTTGCTGAGAAGTGTTCCATTATATGGATTTACCGTAATTTGTTTATCCTTTCAT
TTTTTGATGGATATTTGGGTTGTTTCTGCTGTTTGGCTACTATTAGTAAAGCTGCTGTGAACACTCACAT
ACAGATCTTTGCAGGTCTTTTACCAATTATGTGTTTTCAAATATTTTCTCCTAGTCTGTGTCTTATCTTT
CAGAGAACAGAAGTTTTTAAGTTTGATAAAGTCCAGTTTTTTCTTGTTTTTTTGATTCATGATTTTTATG
TATGGTCTAGAACCCAAGGTCACACAGATATTCTCTTCTTTTCCTTTAGAAATGTTATAGTTTTAGTTCT
TTTCTTTAGAACTGTATACATTTTAATTTTTATGTGCAGTGTAAGAATTGAGGCTTATCTTTTGCATATA

FIG. 7C (Cont.)

GATGTTCAATTGTTCTACTACGATTCATTGAGAAGACTATCATTTATCAATAGTCAATTTACCATAAATG
GTAGGTCTGTTTCTGGACTCTATTCTGCTCCATTGATCCATCAAAGTGTCTTACTTACTGTAGCTTTATA
AAAAGTCTTGATATCAGGTTCTAACTTTGTTCTTTATCTAAGTTATTTTGGCTATTCTAGATCTCTTGCA
TTTCCATATAAAGCTTAGAATCAGCTTGACCGTTTCTTTAAAAAAAAAAGGGGGGGGGCGGTGGGGATG
GAATTTTGACTGGAATTAACACCAAATTGATAGTTTAGGGAGAATCGCCATGTCAATAATATTGAGTCTT
CGTATCTGTGAACATGATATGTATCAGGGGTTTTCTTACATCTGTTTAAAATTTCTCTCAGCAGTGTTTT
GTAATTCATTGTACACATCTTGTACATATTTTATTAAATTTATTCCTAAACATTTAACATTTGTAAAGCT
ATTGTAAATGGTATTTTTTATTTCACTTTCCAATTGTTCATTTCTAGTGTATAAAAATAGAATTGACTTT
TGTATATTAGATTTCTACCCTGTGATCTTAAATTCACTTACTAATTTCAGAAACTTTTTATAGACTCTTT
GGGGTTTTCTTAGATAATCATGTAGTCTTCAATAAATTTGGGTTTTTTCCTTTCTAAACTATATGCCTTA
AATTTCTTTTCTTATATTATTGTGTTATTGCATTGATTAAGCCCTTAAGCGCCATGCTGAATAGAAGTAA
TGAGAACAGATAGCTCTGACTTGTTCTGGATCTTGAAAAGAAAGTATAAACCATTCATTATTAAGTGTGA
TGTGAACTGTAGATTTTTTGGGGGTGAATCTTTTTAATAAGATTGGAGAATGTTTTCTTCTATTCCTAGT
TTGCTGAGAATTTCTATCAGAATGGATTCTTTTTTAAGAGACCTGGTCTTAACTCTGTCACCCAGACAAG
AGCACAGTGGTACCTTTATATGTTTCTCTTTCTTCATTTCTTTTATTCCGTAAGATAATCCATATATTGC
TATGCATTTTAGTCAACATGTGATACTAGCTTGTATACAGTTCATTTTCCTTCAGTGAAAAAAAAAACTA
GGGGATGGTAGCTACATGATATAGTGCTTCTTTTAGAAGTAATAAAAATGCTGTAATATTGACTGACGAC
GATAGTTGCACATATCTGAATGTACTAAAAACCATTGAATTCTATGCTTTAAACAGATGAATAGCATGGT
ATGTGAACTATATCTCAATAAAGATGTTTTTAAAAAGCAAAAATAAATGATGAAAGAGGTAAACAAGATG
AAAGAACTATCTAAAAGAGACTCATATATAATCTAACTAGTACTTAAGTAGCAAAATAAATGCTCTATTC
TAAAAATTCACTTTCTTTAATAGATAACAGAGCTGTTTCAGTTATCTGTTTCTTTTTGGGTAAGCTTTAG
TAGTTCTGACACTCAAGCAATTTGTCCATTTCATCTAAGTTTCTGGATTTATTGCCATAAGTTGTTCATA
ATATACCCTTATGTCTTTTTAATATCTGTAGAACCTGTAGTGATGTGTCTTGGTGATTTGTGTCTTCATT
CTTTTTTTCTGAAATAGTTTCTCTAAAGATTCATCAGTTTGATCTCTTCAGAGAACTAGCTTTTTGTTTC
ATTGATTTTGCCTCTATTTTTGCTTCTTTTAATAATCACAACTTTATTTCTTTCCCTATGTTTGCCTTGTA
TTCATTTGTTCATCTTTTTCTGACTTCTTAAGGTCCAAGATCAGATCGTAGACTCCAAGACCTTTCTTTT
CTCATCTAAGTATTTAATGCTATTATTTTCTTCTAAGCACTACATTAGCTGCATTTCACAAATTTGGGGT
ATTCTGTTTTTATTTTCATTCAATTCACAATGTTTTCTTAGTTTTCTTATTCCCATTTGATTTCTTTTTT
TTTTTTTTTTCTTTTTTTTTGAAATGGAGTCTTGCCCTGTCGCCCAGGCTGGAGTGCAGTGGTGCAATC
TCGGCTCACTGCAAGCTCTGACTCCTGGGTTCACGCCATTCTCCTGCCTCAGCCTCCCAAGTAGCTGGGA
GTACAGGCGCCCGCCACCATGCCCAGCTAATTTTTTGTATTTTTTTTAGTAGAGATGGGGTTTCACCACG
TTAGCCAGGATGGTCTCGATCTCCTGACCTCGTGATCCACCCACCTCGGCCTCCCAAAGTGCTGGGATTA
CAGGCGTGAGCCACTGTATCCGGCCCCATTTTGATTTCTTCTTTGACCCTTGGGTAATTTAGAAGCACCT
TGTTTAATTCCCAAATATTTGGGAATTTTCCTGTTAGCTTTATATTATTAATTTCTGGTTCAGTTTCATT

FIG. 7C (Cont.)

GTGGTCAAACTGTATTGTATACTTCGTATAATTTCAGTCCTTTTAAAATTGTTAAGATTTGGATTCTGGC
CTATAATATAGTCTGTTTTAGTGAATGTCCACGTGCACTTCAAAAAAATGTGAACTCTGCTGTTCTTCTT
TGAGGGGTTCTATAAATATCAGTTAGTTCAAGTTGATCAATAATATTCAAGTCTTTAAGAGCCTTAATAT
TCAAGTCTTTAAGAGCCTTACTGGTTTTTGGTTTTTTGCTTGTTTACTTGTTCTGTTAAGTACTGAAAGA
AGAGTTTTGAAGTATCCAACTAACTGGATTTGTTTATTTGGAATTCATTCTACCTGGTAGCTGATCTCAA
CATTCTAATGGACTCCAAAAAAAAAGTTTTGGTTTTGTAGATGATCAGGTTTTTCCTCATTGTTAGGGCG
AAAGGGACATTCTCTTCTGGCTCTCTATCTTAAGAAATGTAAAACCAAGCATCATTTTTGATTCTTAAAC
AAAAGAGTTTCTTACCTCAGTTTTCTTACCTGTAAAGTAGGCAAAATATTACAATTTACCTTCTGGGGTT
GTTGCGAAGATTAGATAAGATTTGTGTGTGTGTGTGTGTGTGTGTGTGTGTGTGTGTGCGTGTGCACA
CACGTGCATGCATATATATATATACACACACATATATACATATGTGGCACTTAGAAGAACAGCGTGCACA
TAATAAGCTCTATAAAATTTTAGCCTTTATATTTTTCCTTATGATACATTTCTTTGATGACTTGGTGTTC
CGATAGCTTAATTTAAGACCACTATCATCACAGAGGTTTGTTAGGACACTTTCCTTTTAAACAAATGTTA
TTTTCCTGGATTGTTCTTCAAACAATTAAATGTGGGATGTGAACTAATAATGTTTACAATTTAGAAATAG
ATTTAATCAAAGCTACTCAAATTGACTACATTAAAGAAATTTGTGAAAGGAGAATATACTTCTCTGAATT
TCCTAAGTTCTGAGATTTTGTTCTTTTTATTTCAAACTTTATCCTTTGTCTTAGTATTATAAGCCTCAAT
TTAAAATAAATTTACTTTAAAAATATATACACAAAATTATTTCTCAAGTTACTTTGAAATATCACATATA
CAAATTTTATTTAAAGAGACCACTTCATTCTTTTTTTTTTTTTTCTTTTTCTATGTAAAGGCAACATCAG
ATGCTGACCTGAAAGAACATATGGTTGGAATCATATTCAGCAGGAGTAAGCTGACTAACTTACAAAAACA
GGTTGGTTAACAGCTATTTCATTGTCTTCATTAGTTTTGTGTGTGTGTGTGTGTGTGTTTGTTTGTTTGT
CTGTTTGTTTGTTATTAGGGTATAAAGCAGGGATGTCCAATCTTTTGGCTTCCCTGGGCCATATTTGAAG
AAAAAGAATTGTCTTAGGCTACACATAAAATACACTAAGGCTAACAATAGCTGATGAACTAAAAAAAAAA
TTGCAAGAAAAAAAAATCTCCTAATACTTTAAGAAAGTTTATGAATTTGTGTTGGGCCACATTCAAAGCC
ATCCTGGGCCACAGGCAGTCCCCCGGCTGCAGGTTGGATGAGCTTGGTATAAAGTATTTTGAAAAATTTA
TGAAGGCTTTTTTATGCTCGCCCTTTTATAGGTCCTGCAGAATGTGCCTGCCATTTTTTAGAGAGGAATG
AGTATTTTGGCATACCTTCATCATTTTAAAGATTTTACTTATGAAAACTTGCTTACCTTGCTGCTATTTG
TTATGGGTAGATTTTTTATTTGGTGTCAAATACCCAGCTATATCAGATTTGATTTGCATTTCCCATATTT
CTTTTCCCCCATTCTTCTGTGTGTTGGCTGAGCAATTAACAGTGTTAACTATACCAGTGTTAATATTTTT
AAATATAACCAGGTGAGGAAATAGCGCTATATTGTTCATATAATGGGGTGCTACATAACATAAAAATATC
ACTTCAAAAGTCAAATAAAATATTGATTTTAAATTAACCTATTATTCTAACTTTTTTTTTTTTCGAGAGG
GAGTCTCGCTCTGTTGCCCAGGCTGGAGTGCAGTGGTGCGATCTCGGCCCACTGCAAGCTCCGCCTCCTG
GGTTCACACCATTCTCCTGCCTCAGCCTCCTGAGTAGCTGGGACTACAGATGCCTGCCACCACGGCTGGC
TAATTTTTTTTTTTTTTTTTTTTTTTTTTAGTACAGACGGGGTTTCACCGTGTTAGCCAGGATGGTCTCG
ATCTCCTGACCTCGTGATCCACCCGCCTCGGCCTCCCAAAGTGCTGGGATTACAGGCATAATATTTTTGT
ATTTTTAGTAGAGACGGGGTTTCACCGTGTTAGCCAGAATGGTCTCGATCTCCTGACCTCATGATCCACC

FIG. 7C (Cont.)

TGCCTCGGCCTCCCAAACTGCTGGGATTACAGGTGTAATTTTTTTGTATTTTTAGTAGAGACGGGATTTC
ACCATATTAGCCAGGATGGTCTCGATCTCCTGATCTCATGATCCGCCCGCCTCGGCCTCCCAAATTGCTG
GGATTACAGGCGTGAGCCACGGCACCCAGCCCTATTCTAACTTTCTACACTATTATTCTTTTCAATGAAC
TACAACATGAATTTATTTTTGCTTTATCTTTCTAGCAGTGTTTCATTGAATCTTAGATGCTTTCAATTGT
AAAATGTCATGTATAATTTCAGTATTGTGAATCTTATCAGCTATAAAGCACCTTATGAACATAATGGTAA
ACCATGAGAAAAAGTGCCTTCAGTGATAAAATATGGTGATTGGTTTTTGACGTGCTAAACTGTAAGCATA
GGCATTAATAACTTGCATATAATCAGTTTGCACATAGTAGTTGATTTAAATATTTCCATTTTTATTGTGG
CTCCCTTAGCTTTACTTGTTTCTTAGATGAGTTAAGAGAATGACATATGATGGAGAATTAACTGGGAGAA
TAGTATTAAATTGAGTATCAATTTACATTCTTGTCTTATTCTTTTGTTTGCTTGTTTTGCTAGGAGTAGT
AAATCAAACTAACCCTATATTTTTACATGTTCTGTGTTAACTTTAAATAGGTGTGTGCTCATATTGTCCA
AGCTATTCGCATGGAAGCTACCAGAGTCCGTGAAGAATGGGAACATGCTATATCAAGCAAAGAAAATGCC
AATTCTCAGCCAAATGATGAAGATGCCTCCTCTGATGCCTACTGCTTTGAGCTGCTCTCTATGGTTTTAG
CACTGAGTGGCTCTAACGTTGGCCGGCAATATCTGGCTCAACAGCTAACCCTGCTTCAGGATCTCTTCTC
GCTGCTTCACACAGCCTCTCCTAGAGTCCAGAGACAGGTGACTGATCACACTACAGCCTTTCCATTGCTT
TTGTTACTTGAAACATTGTTAAAAGTTGCAATGCAAAGAGAATTATCTAAGGACCCTAAGTATAGATTTT
TATTTCGTATTTTGTTATATTTTGTTTGGGGCCTGTATTTTACTCCCTTTTTTACTGTTTATAGTGAGAG
TATAGAATAGTAAAATATGTTCCATTTTATTAATGTGTTGTGATAAGAGAGTATTCTGGCTACTGATTAC
CATATTACCATGAAATATATAATGTCATTTAGCCCTGACCAGAAAGAAAAGGTATTTTTTTTCGTGCTGC
CTTGGGTTAGTAATTACCACTACTATTACCATTTGAATAGTATGTATATCATATTTTCTTCCTTCACAAA
ATGTAAAATAGTGTTTAAATCATATTTCTTTTCTTAAAGATTTTGAAGTTACAGAATGGTAGTTAGGTAC
ATTAAAAAATGAAGCCTGGGATGGGGTACAGTGACTTATGCCTGTAATCCCAGCACTTTGGGAGGCAAAG
CTGGGAGGATCCCTTGAGCCTAGGAGTTCAAGGCTGCAGTGAGCTGTGGTTGCTCCACTGCACTCCAACC
TGGGCAACAAAGCAAGACCCTGTCTTTAAAAAAAGAAAAGAGAAATAAAAGAAACCTTAAAACATTAGTC
TTTACATGGAATTCTCTCATTTTATTTTTCTTACCAGGTAACCTCTTTACTAAGAAGAGTTTTGCCTGAA
GTAACCCCTAGTCGTCTGGCCAGCATCATAGGAGTGAAATCCCTCCCCCCAGCAGATATCAGTGATATCA
TTCACTCAACAGAGAAAGGAGACTGGAATAAGCTGGGTATCTTGGACATGTTTCTAGGATGCATTGCCAA
AGCACTCACTGTACAGCTAAAAGCCAAAGGAACCACCATCACTGGAACAGCTGGTACCACTGTGGGCAAA
GGAGTTACAACAGTTACTCTTCCGATGATTTTCAATTCCAGGTTAGTTATTGCCTCTATTTTAGTACCAA
AACAGAATAGAGTGAGCTACTGTTCAGAAATTTAAGACATAATTTCAGATTTTACCTTGTTAGGTTACTC
ACCAAATAAAATCCATAAACAACTGGCTAATATCTAAAAAGGTCATGTATATAATAAAAGTGTCATTTAT
AATTAGTGGGGAATAGAAAGTAGGCTGAATATGTGATGTCAGAATATTTGGATATCCATGTTAAAAAAAA
TTCTAGATACCTACCTCTCACCATATACAAAATTAAACTTCAGTTTTAGGTAATATGTTTTTTTGCCACA
ATAAAAAGAAATAAATATGGGGGAATAAAGTAAAGTTCAGGTCAACTAAAGCTTTATGTACATTTCTTTT
TAAAACTGTACTGGGACAAATTATAGAAGAATATTTTTGTAATCTTCAATTTGATAAGACCTTCTTAAAC

FIG. 7C (Cont.)

AAAACACAGAACCCAAAATCATATAGGAAGATATTTATAGATTTGACTATATAAAAATGAAAATTACTTG
ATAGGTGATAATATTTAAATGTTTTAAAATATAGGGAAATAACTTAGAAAAATACTTAAACCTATATAAT
AGACAATGACTTGTTAGCATAATATAGAAGTATGACTACAAATCAATTTTAAAAAGGCAAACAACTGATA
AGAATAATAAATGACAAGAACAGTCAGTTCACAGAAAAAAACTTATAAATGCCAGTAGTCAGTTCACAGA
AAAAAACTTATAAATGCCAGTAAACAAATGAAAACACCTCACTACTAATCAGAGAAATGTAGATTAAAAT
AATTGCAAAATATCTTTGATGCTTTGGCAACATTATGAGGAAATAGGCATTTTCATCTCATATAAATTGC
TGCAGCCTTTTTGGATATCTGTTTATAATATCTAACTATATTTTAAATATGCATATCTTTTGACCTACCA
ATTCTACTTCTAAAACTTTCATGCATTTGCACCAAGGTATATATGCAAGGATGTTCTGTAATTGTGTGTA
ACAGTAGAGAATTAGAGACATCTGAACAGTGCTACTTGTAGAGCCAATCCATGACAATATGCAGATAACA
TCAGAATGTTAATCATTGTATCACTTCTTTCCTGTAGTCTTGCTAGGAAAAAAGTCAGCTGAACTAAATA
GTAGTGTGCTTAGTGATACAGTGAATTTATATTCCGGTTAAGCTCCACATTATCCGCATGTGCCCTAGAA
ATAAGTCGTGTGTGGTCCCTGGACTGTACTTCTAAAAGATGCACACAGAAATAATGTGCAAACAGAGAAA
TACTTGAAAGGGAACTCAAATAACCTTAACTGCTGTCTTGGGATTTGGGGTAATGGTTTGATGAATTTTC
TTTTTAAATGTTTTAATTGATTCAGTCACTTAAAAATCTAAAATGCTGCATTCTGAAATAACATTTTCAT
CTTTTTCATTTGTTACTACTACTGATAATTTATTGGCTTTTTAAGTGCTAATTTTTCTTGTAGTTATCTC
CGACGAGGTGAAAGTCATTGGTGGATGAAGGGCTCAACCCCTACCCAGATCTCAGAGATCATCATTAAAC
TTATCAAGGATATGGCAGCAGTAAGTTCCCATTCTTCTGTTTTGGCAGTGAAGTGCGGCAGGAAGCTGAC
ACAAAACAGCTTACTCTGCTGAATTGATAGGAGATGTAGATTAGTGTAACTTTACTTAAAGACTATTTGT
AGTATGTTAACTATCATGCTGTTTGTCTTTTCAGTGAGTGATAATTTGTCATTTATGTAAACCATGTTCA
TTTCAAATTTTCCAGTTAATTTGTGTGGGAATTGTTACGTGACTTTAAAATCTAATAAAATAAAATATGC
TCTTTCAGACCCTAAGAAAGAACTTGATTCAAAAAACCTAAAGGAAAAAAAGAGGAAGAGAGCTCTCGAA
AGTGGAAGTTTCTCATTCTCCTCAGTCCTCATGGTTTTTAAACCCTTTATTCTTCTTTATTAATGTCATA
TACCCTCTGTCTTAAGATGGTGGCTTCCAAAGGAGATCTGGGAGTGTGGAGGACAGGGAGTTACTTTACA
GAATGCCTGGCTCTGATTAGTTGCTCCTTGTCATTTTCCACACATTGTATTATTTCTAGGAGGGCAGCCT
GAGAAGGACAAGATAGTATGGAATGTAGAGTCAGAAGGAATAGAAGGCAGCTTGGAGAAGGAGGAGGAAT
TGAACTGCCCCTTAAATCATGTGGATATGAGAAGTGGGAGGATTTTCTGGGGGAAAGATGAAGTTCTATC
ACTTTTCCCAACAGCGTGGATATTTTCTCAACCTCTGTGGCAAACAGACTTTCTCAGGGTGTTCATTGAA
TTAAAATATTTAGGAGTAATATTTAGGAACACCTAAATTATATGATAGTTAAATGTTTGTTCATTACAAA
TCAAGGTAGCAAATAAAGGTAGTTGCAGTTTGAACCTGTTTATATTTTAGGTTCCTGTAATACTCATCTA
AAGCAGTTAGCTTCACTGTGTAAATTTTATGCTAAGTGACAAACTTCTCAAACATAGATAACCTTAGTAT
TTCTGTTATGTTTTTATCAGATGTGAGAGTAATTGCCCTTGATTTCCAGGAAAAGAGTATTGAGAACTTA
ATTTTTTATTTATTTATTTTTAAATATCAAAATGATGATTAGAAGTTGAATTTTCCATAGGATCACGAAG
AAATTTTAGTTCAAAAGTTTGTGCCCATAATCTAAAATTCCATGGTCTCACTAAAAACAAATATTTCCTT
TGATAGGAGATGTTATTTAAGAAAAAAGAGTTTACTATGGTAATACATTTCTGGTCACTTATTAAAATAC

FIG. 7C (Cont.)

TCTGTTCTGCTCAATAGGGTCATCTGTCAGAAGCTTGGTCCCGAGTGACAAAAAATGCTATTGCAGAAAC
CATCATTGCCTTGACCAAGATGGAAGAAGAATTTAGGTCTCCAGTGAGATGTATTGCAACAACTAGAGTA
GGTTTTGCTTTGTTTTGTTTTGTTTTAAATTTGGTGTGTATCATTGCGTGTTCTTTTTTAGTAATAGATT
TAAACAAATTTTAATCACTAAGTCAACATAATTATTTTTTAACCAAATACCGTATTTATTGAAAAAGTAT
AAAGGGCTTTTATATTATGAACTAGTCGTTACTTCTCACTGTTATGTGTTCTGTGTCACTTGTTTTTGTT
ATTGTTTAGGAAGCCAAGGGTACACTGGTTAGAAAAGGCTAATTACATTGTACATTGTTTGCGTGTTGTC
TTTCTAATGATCTGTTTGCTGTAGTTTACCACAGTAAGTTTAGTGCCAGCATTATGCTGTGATAGACCGA
AGGTCCTTTGGAGACAAGACCCCTGCCTATGCCTGGTTGTTCCTAATGTAGAGCCCTGTAACTTACTTAC
AGGATTTATAGGTCTTACTTCTAAAAAGCAAGAAGTGCTTGTCCAGGGCAGGGTCAGGGTGGAAATCTTT
GAGGAAATGAGATTGCATTCTTCAGATGACACATTTATAGTAAGTTTTAACCTGCTAGATTTCATGTCCC
ATATACTTCCAGAAGAGATTTGAGATTTCCTTGAAGGAGGGCAGTCTGACAACGTTAGGAAGAAGTGAAT
GCTGGTAAAAATTGCTTAGGTTAATCCTCAGAAATCTGAAGAAGATAAACTATATATCCCTAGGGCGGAA
AAAGTCAATTTATGCTATCTTGCTATTATTGACTGTGACACCTGAAATAGGTATTTTTGACAGTAATCCT
TTCCTACCACTCATGTGTTGCTTTCTTTCAGTCTGCATTCCCCTTCCTCCTTGCATGCATTATTTCTTTT
TCTATTTTTCTGTCCCTATTTTAACATCTCTTGCTTTCTGTATCCAATAACACTCACATGCACTTCTTAG
AGTTGAGCTAGTTAAGTCATTTTCTATTCTTCATTAATGAGGGGATATATCATTCTATATAAAACTGAAG
CTTACCCTTTAAGCCTCAGAAATTTTTAACTATTTCTGAAAACAGTTGTCTTTTTTTTTTTTTTTTTTTT
TTTGAGACAGAGTTTCACTCTTGATGCCCAGGCTGGAGTGCAATGGTACGATCTTGGCTCACTGCAGCCT
CCGCCTGCAGGTACAAGCGATTCTCCTGTCTCAGCCTCCCAAGTAGCTCGGATTACAGGCATATACCACC
ACACCTGGCTAATTTTTTTTGTATTTAGTAAAGACTGGGTTTCACCATGTTAGTCAGGCTGGTCATAACC
CCCTGACCTCAGGTGATCCACCCACCTTGGCCTCCCAAAGTGCTGGGATTACAGGCATGTGCCACTGTGC
CCGGCCCTATTTTGGAGAACAGTTTTCTAAAGCTTTTAGACATGTATGTATTTCTGACAAAGTGCACCAA
GTATAGTATTAGGCTTTCTGGGGCAACAAGGGGCAACAAAGACTTCTGAGGAACTTTTATTATCTAGAAG
GATTTAATGTGTACCTGACTACTCATGGGACTGTACACAATTTAGCAGTTGCTGTACCACCTTCTTTGGC
ATTTAATGATACTAAATGGAAAAATATTCAGAAGACATTAGTAGTAAATATTAAATATGCCAATTCATTT
ATTCATATGTTGTTTACATAGTAGACCAATAAAGGATAATTTTATTTGTCAGATAGAAGACAGGGTGGTT
CATCAGAGAAACAGTCACTTGTTCAGTAGATATCTGAGTGCCTCCTGTGTGCATGGCACATAGGACAGTG
ATCGTGTATGCCTGCTACCACATCAGGAAGACTTGAGTGCCACTGAGTATCTATGTATTTTCAAAATCAG
CCAGCATTTATTGAGCTGTTGTGATGTGTCACAGTCAGCATTTCATAAGTCTTTCCTAAAAATTCAGTGG
TGTAACAGCCTTCCCTTTCAACAGCTCTGGCTTGCTCTCGCATCCCTATGTGTTCTTGATCAGGACCACG
TAGATCGTCTCTCCTCGGGGAGATGGATGGGAAAGGATGGACAACAAAAACAAATGGTAAGATCAGAATT
TTGTAAGAATTTATCTTGCTTTCCTTTACAGTAAGCTTTAGCTTAGCTTAAAAACAAACAAACAAACAAA
AAACACATCAACATAAACAGTTAGTGGATCTCTTGAAAGATTGTGTCCCTTCGGCCAAGTTCATCTCACA
AGTCTATTTCAGAGAGTCCCTACTTCATAGTATATGGAAACTTTAGGGGCTTTTATTTAAGTATATTAAA

FIG. 7C (Cont.)

GAGCTTTCTTCTTCTCTGAGTCATGTTTGCATCATATCAAAATTTATTTTTAGCCAGAGTCTGATTTAGT
GACTAGATATTTTACTAAAATGTAATCAGTCTTATGGTAGGAAGGAAATAAAGCAATAACACAGGCAACA
TGACACACCACCTGTTCACATATATACTTAAGTAGGTTTGATGGGTATCTTTAAGTTCACTAGAAAGGAA
AACTTTATATAGGCCCTTTCACCATTTTCTTATTAATGTTCAAGTTTCAAAAATAAACAGTTTCTTCCTT
TGGCATACAGAATGTTTAGATATATAATGGGGCAGACATTTCTTAAGTCTCTAAGTAACAAAGTATACCT
GTTCATTGTATTAATCATTGAACCTGCAAAGCACATTAATGATTGGATTTGGAGTTTTGAGAGATTTTTA
TAGTTAAGTACATTTGCAATAATTCTGTTTAATATTCAGATTCTAAATTCTTAATAGACTTCCGAATAAC
GGTTTATTTTTGTAAATAAATTATATTCAATTTGTATGAGAGTCTGAGACTTGCTTGTTAATCTAAGTAA
CGTGGAAATGTCTTATTTTAGCCTATGTGTGATAACCATGATGATGGTGAAACTGCAGCAATCATTTTAT
GCAATGTCTGTGGAAATTTATGTACAGACTGTGACAGATTCCTTCACCTTCATCGAAGAACCAAAACTCA
TCAAAGACAGGTGAAGATTTTTGTCTCTGGAGCATAAAATATGTTCAGTGAATTTTGAAATAAATGTGTG
AAAGAGGCTTTGTGTAGTAGGGGGAAAAAGTGGACTTTGGAATCAAAGACCTTGGTTGAGTTCACAGCTG
TCTCGCTTACCATCTATAAATAGCAAGTTGTTTTATCCTTAGAAACACTTAATTTCTCCATTTATAAAAA
AGGGACTGCTGTGAAGATTAAAGAGAAGATTGGAAATATTCAAAACTTCTTAGAGTGCTTAAATGAAAGC
CATTATTATTATTGAATAATTAAATTTTATACTCTCCCTTTCAGAGTGATAAATAAGCATATTTTTCCCT
GTTCTTTAATGAAATAATAGGTCTTCAAAGAAGAAGAAGAAGCTATAAAGGTTGACCTTCATGAAGGTTG
TGGTAGAACCAAATTGTTCTGGTTGATGGCACTGGCAGATTCTAAAACAATGAAGGCAATGGTGGAATTC
CGAGAACACACAGGTAAAAGGTTTAAAGATTGAGCCATGCCTTTAAAACCCACAAAAAAAGATTAAACCG
TGCCAACTGATTAAACTGTGAATAATTTTGAGTGATATTCTGATGTTTAATTATGACATCATTGATCTAT
ATATTTACTAAATATATAGAGTGTTCTATGGTGAAGAGAGCATTAGACCAAAAGTCAAGAAACCTGATTT
GCCACTAACTAGCTGTGTGGTGTCGAGCAAGTCACTTAACCTCTGGAACTCATTGACTTCATTTATAAAG
TGAGAGGATCACAACTAATGGGGCTCCATAGATAAAATACATTTCTATTGATAATTCCCTTCTAGTTCTG
CTAGTTGTTGCCCCACAATAAAAATTGCTGCACTAGATGATCACTAAGATCTCTATTTATTATAAGGTTG
TATGATTTTATGATATTTAGAGGTTTTTGTAGACCTAATGCTTCTGAAGGTGTTGTGAATGGTACTGTTT
CCATTGATAGCAATAAAATAATTAACAAAAATGAATAGACATAAAACAAAAGGTAACCTATGTATGTTAA
ATGTATTTTTATCTCTAAAACATAGTTTTCATTTTGCTGCTTTTCTAAAGTAAATCTTGTATATTCCTAG
TTCAAAGTTATGTTGAATCTTACAAATTCTCAGTTTTCAGCACATCTGCAGTCTGCCATTTGACTGACAC
GAACTTCCAGTGTTGGAGTTAGGTGTAAATCCGAATCAATTTAATTCTAGGGTGACTTTGCATGCTGCAA
GAGCATGACCTTCTTTTCTCATAGTTGATTTCTTCCTCCTATAATCTGTCAGTGCTGTATACTGCATTAA
TAAATGTTCTAATGTCAAACCATCCTTGTAAACCATCCTTTTTAAATAGATTTTTCTGTAAATATTGCTG
AATTCAATATATTGATATTAATTATAGTTAGATTTTTATATCTGTGTTTAAAAATCAGCTTGGTCTGTAA
TTTTCAAATCTTCACGTTCTTTTTCTTATTGCTCTGTTCTTGTTTTATTGATTCTGTTTCTTCTTTAAGT
ATTTCAAACATATTTAAATTCCTTTTCAAATTGCAGAGTTCCTGAGGTAGGAATTCTGTTTTTCAAGTTT
CATACTCTGATGATAGGCTTTATACCATGCCTTATAATTTTGTTATATATAGTTAAAGATTTCCCTAACT

FIG. 7C (Cont.)

TCTGTGTATTTTTATTTAATTTTTGGTTATCATATTTTTTATGGTATTGTGCATTTGGAGTCAGGGGCTT
GTAACAGCTGCTCAGTCTGGTAACTTGACTAGAAGTCTAGTCTGTTTCTTTCACTGAAAAAAAATATTAG
TCGAGAGTGTATTTGGCTTCAGATAGGTCTTTAATTTCTTTTTTTGTGTCTCATTATTTACTTTATAATT
AGGACAACTTAGAAACCTTCCGTTCTAAAACTGTCAGGCTGATTTCCCAAGGATAGCAACTTATACAAAC
CTAGTTTGCTTTTTAAAATTTAGTTCTGTTAACATATCTAGAAAACATCCATAAGAAGGATTTTTATTTT
TCTGCTTGAACCTAGGCAAACCCACCACGAGTAGCTCAGAAGCATGTCGCTTCTGTGGTTCCAGGAGTGG
AACAGAGTTATCTGCTGTTGGCAGTGTTTGTTCTGATGCAGATTGCCAGGTGAGTATATAGTGACACAGG
CCATCCCATTGTCCATGTTCCCCTGTGACACCTTTACTTCATACAGAAAAGAGTTTTAGCTCAGCGTCAC
TCCAGCTTCCTAAATGAGTGTATTACCTATGTGAAGCATCAAATGCCTTACCAAAGTTGAAGAATGGGTC
AAATAAGGCTCTCAAGCCCAAACCACACTCTTTTTGTATGTTTCTCAGTTACCATGATCATATGTATTTA
ATATCTACTTTTGTACTAGAAACAGTTAAAAATTTATGAACTGTATTTCCTTTATCTCTTACAGACATTA
TTCACTTATTTCCTTAAAATACATTTTCAACATCTAAGAGTTCTTTAATCCTGAACATATATAAACATAT
TCTATGTTGTCCAAATGTTTTTGGTTTCTCAATTAATAAGAATGTGGATATGCTCAGAGAGTCAAAGGTA
CCTTTTTAAAAAAAAAAAAAATCTGCATTTTGGTGATGCGGAGAGTGGTGACTGGGAAATTATACATTGG
GGAACTTTTTTTATTTTTTATTTTTTTGAGACGGAGTCTGGCTGTGTCGCCCAGGCTGGAGTACAGTGGC
ACGATCTCGGCTCACTGCAACCTCCGCCTCCCGGGTTCAAGCGATTCTCCTGCCTCAGCTTCCTAAGTAG
CTGGGATTACAGGCGCGCGCCACCATGCCTGGTTAATTTTTGTATTTTTAGTAGAGATGGGGTTTCACCA
TATTGGTCAGGCTGGTCTCAAACTCCTGATCTCGTGATCTGCCCACCTCAGCCTCCCAAAGTGCTGGGAT
TACAGGTGTAAGCCACGACTCCCAGCCAGGAACTTTTTGCTTTATAGCTGTGCATGATGACAAATATGAA
ATTATAATTCACTTATCAGCATTCCCTTTATAGAGAGTGGCATTTTTTAAAAATCGCATCAAAAAAAAAA
AACTTTGTTAAGAAGCCTAATTTATATTCAAACAAAGATTAGAAATAACTTTACTTTGTTGTTACTTGGC
CTGCATAGATACTTCCTGTGGGAAAGTAATCTTTGGAAATTTATATAATAAGGAAAATTACCAGAATGTG
TGCTTTTTTACATACTTGTGTAACATTGTAATTCATCTTTAACAGGAATACGCTAAGATAGCCTGTAGTA
AGACGCATCCTTGTGGCCATCCATGCGGGGGTGTTAAAAACGAAGAGCACTGTCTGCCCTGTCTACACGG
CTGTGACAAAAGTGCCACAAGCCTGAAGCAAGACGCCGATGACATGTGCATGATATGTTTCACCGAAGCG
CTCTCGGCAGCACCAGCCATTCAGGTTGCCTCAGCTTTTAAAGTATTGAATGTATCCAGACATTAAGATG
GGGAATATATTTGTCAAATAAACATTGATTGAGGCCGGGCGCAGTGGCTCATGCCTGTAATCCCAGCACT
TTGGGAGGCCGAGGCAGGTGGATCACGAGGTCAGGAGATCGAGACCATCCTGGCTAACACAGTGAGACCC
CGTCTCTACTACAAAAATACAAAAAAATTAGCTGGGCGTGGTGGTGGGTGCCTGTAGTCCCAGCTACTCA
GGAGGCTGAGTCAGGAGAATGGCATGAAGCCAGGAGACGGAGCTTGCAGTGATCTGAGATGGCACCACTG
CACTGCAGCCTGGTGACAGAGCGAGACTCTGTCTCAAAAAAAAAAAAAAAAAAAAAGCAGTTGATTGAA
ATCTTTTTTTATATCACTAGGCAGAAGTGTTCTTTTAATCTATACATGTACCAGGCTAATGAGGAGCAAA
TTCTGCCTCTTTATGCTGTGCTTTCTATGTTGCATGCTCAGCTTTAATTTGTGATTTGTGTGAACCTCTG
TAATCAACAGAATGTATAAAATATTCAGAAGCCAGGGGGAAATAATTAGATTATCCCCCAGTAGCTAAGG

FIG. 7C (Cont.)

CTCTTCTTAATTTCCAAAATCCAGAATGGTATTTTTACAACATTATATAATTGATCTATACATAATGATA
CATACTTCTATACATACACAAGTTACTGTGCACTAAATAGGTTTTTTTAACTTTTGCCCATTGCTTATAT
TTTCAGTTCTCATGATTCCAAGATAATAATAGTCTCCAAAAGAAAATCATAAGTCAGTAATTTCTTCTTC
TTTCTGTGAGATACAAAATTGAATAATTTTACTTTTTTTCCTAACCTAGCTTACTTTATATAAGTGGCAT
GAATGTTAAAAAGCAGGAGAAGCCAAAGGCCTAGTTAATAGTATCCCAATTTACTGTAATGAAATTTAGT
AAATAATAATGTCCCAATTTCAGTGTCCCAATGAATTTTCATTATAGTAAATTTCTTGATTTTTCTCTTA
CCTGCTTTAAGTAGTGCCTTGCATTAAATAATCTCCCAGTCACTCAACTGTTTATCATTATTATATTTGC
TTATGTCCTTTTCTTTTGTTTATTTAAGCTGGATTGTAGTCACATATTCCACTTACAGTGCTGTCGGCGA
GTATTAGAAAATCGATGGCTTGGCCCAAGGATAACATTTGGATTTATATCTTGTCCCATTTGCAAGGTAT
GGAAAGAATCTGAAATCATGTACTTTCTTTTTCTTTTGTTCTTTCTTTTCACCTTTCAAAATAAACATAT
GTCAGTATCTCTTGGTTTTACCCACCAGCCCCTAGCAGTTTCTTCCCTTCTCATTCATGTGGAACCTGAG
AATATAATCTCTCTGTTATAATGCATCTCAAAACAGTAATTGTCCATTTAAAACTGATTACATTCTGTTA
AACATATTACATGAGAAAGTTCATTTAAACATCGTGATGCATTAAAGGGCATGCATCTCTACTCTCAGAC
CACTAGAGAGCTCAGTTGACATAACATGACAACGGCTACCAAAAAGAAGAATGATCCTCTGGTGTTTGTA
GAAACTGATACCTGCCATTAAAGAGTGAAATTGGAACCCTCAGTACCACTAGAACAGATTCTTTTAGAGC
TTAGTTAAAACAAGGAGAAAGTTCTTGGCATTTTGACACATTTGTACAAAGGTAGTCAGCAAGTAGGAAG
TTGTTTTGGCAAGCTAATAATGATTAACAAAAAGCTGTTTTTGAAGAATGTGGCAGTACTTTCCCTATTA
ATTCATCGCCCCTTTTTGTTCTATTAAGCTCTCCCTATTTTCTTATCTTCGTATTTGCAAACTAATATAA
AGGGTAGAATGTGGAAAGACTTAGCACAATCATTGTCTAGATAGACTGAGGAATAATCAAAAAGATTGTA
GTATTTTGCTCTCCCCTATCATATGGTGCTACAAATATTAATAGATACATGAAAGTTTTACAGCAAATAC
TACCTGTTCACTTCTGTCACCTGGCGTTCTGCCTTCCCCTCAAGGAAGCAAAACACACACACACACACAC
ACACACACACACACACACACACACACACACACACACACCAAACACAGAGCGTGTCTTATTTGTGGC
AACAAGGTAACTTTGTTTCCACAATAGCTAGGGCAACAGGAGATATATTTCAGACGCAGGAAATATAAAG
CTAATAAAATGGAATTTTCATGCTCTGTGTCCCATTTGCCCCATTTTCCCTGCTCTTGGAAAAATATGGG
CTTCTAAAGAATTTACAGAATGTTTTTCAAATGACATTTTATTTAGAATATGTGTGCTGTCTGGTTATCT
TCTAGCACAATGCTTGGCACTTAGGTGCATGCTAAGTGTTTGTTGAGTTGGTTAATAAATGATTCTGCTA
AAGAGTGTTCATTTTTTATTGCAGAACAAAATTAATCACATAGTACTAAAAGACCTACTTGATCCAATAA
AAGAACTCTATGAGGATGTCAGAAGAAAAGCCTTAATGAGATTGGAATATGAAGGTCTGCATAAGAGTGA
AGCTATCACAACTCCTGGTGTGAGGTTTTATAATGACCCAGCTGGCTATGCAATGAATAGATATGCATAT
TATGTGTGCTACAAATGCAGAAAGGTATGCTATAAATTATACTGAGAAGTTTTAAAAACTAGAGCTTACC
TATATGATTAAGAATTCAAATTGTACAGTGATATCTAATTATTCCATCTTAAGCCTGAAGTTAAAAATAA
GATAGCTTGGTACAATGTTTCCCAATGTTTCCAGTAAAACTTGTTTACTTAACTTGTTTGGGGATTCTTT
ATTTAACCTGAACAAACTTTTCGAAACATGCAGTATTTCTGTATACAAGCTGCTTCCCATCAGTAATAAC
CTGTTGGCCCAGGGCAATTCCTTCTCGAATAAACTTCTCTCACTTGACTCTGCTAACCATTCCTTCCTTA

FIG. 7C (Cont.)

AAACCCTTAATTCCTTGGCTTCCAGGACAACACACTCTTTTTCTGTCCTCCTTCCTTTCTAGTCATTTAT
CTTTAACTACTTCTTCTTTTTTTTTTTTTTAACCTACCCCTTACATATTTGTTTTCCTAGAGCTCCATTCT
TGCCTACTTAATAAATACTTCCTTACCTTGGGTGACCTCTTTTACATCTATACCTTCACCTACCATGTAT
ATGTTTATGACCCCCCAAAATTTTTGAGATTTAGTTACAAATAACCAACTGCGTACCAGACATTTGGATC
TCTCACACATACTTCAGAGTTCACATGTCAGGTATTATATTCATCAATCTTGGCCGGGCACAGTGGCTCA
CACCTGTAATCCCAGCACTTTGGGAGGCCAAGGTGGGCAGATTTCTTGAGCTCTGGAGTTTGAGACCACC
CAGGGCAAGATGGCAAAACCCCATCTCTACAAGAAATACAAAAATTAGACAGGTAGGTTGGCATCTGCCT
GTAGTCCCAGCTACTTGGGGGACTGAGGCAGGGGAATCGCTTGAGTCCAGGGGGTTGAGGCTGCAATGAG
CTGTGTTTGTGCCACTGCAGTCCAGCCTGGGTGACATAGTGAGACCCTGTCTCAAAAAAAAAAAAAAAGA
CTTTACCAATCTCTGATCTTTATTGACAAAATCCTATCAATTCTGTCTCCAGATCTCTCTTGAGTCCTTT
TTTCTTTCCATTACATCTCCAGCAAACCTAATCATTTTCCTTGGTAATTACAGTAGCCTTCTTCCTGAGC
TCGGGTGTAGAACCCCTAATTCCTCTGTTGCATCCCTTACACTGCTGCTAATTAATACTTCTAGATCTAA
AATCTAACTGGATCACTCTTCTACTTATAATACGGTAGCCCAGTCTCCCTCTCCAGTCTCATCTCCCAAG
ATGCTACCATTTGCTCTCCATTTGCTGCCACATACCAAATAACTTGCATTTCCCAAACTCAGCCCTGTCT
GCTCACCCACTGACACCCCCATGCCATTGCACAGGCCATTGGTGTTTAAAGGATGCTCTTCTCTACCTCC
CCCTGCATATTTTACTCTGACCTGCCACCCCCAACCCCATACACACATGCTGTCATGCAGAGCCTAATCT
GTCTTGTCATACCTCGGGCTTCAGCTCAGGTTTCACCTCCTCTGTAACATACCCCCATCTCACTTCCATC
AACACCACCACCACATGATTTTGGTATCTTGCAGGCATCTAGCATAGAACTCCCTATTCTGCATTATGAC
TACTGGACCACTTATCTCTCTGCCCTACTTGATAAGTTCCATGAGGACAAAGAGTATGTTTTTTCATTTT
TCTATCTCTAGTACTTTGCACTTACTAGATACAAAGTTAAGTGGAGAATGAATAAATGAGTGAAAGAATG
ACTACATGAGAAAGGTGCATAGTCTCCCAATGTAGCAAAAAGAAAATACAGAGGATGAATGGATGTCTAA
GTAGAGAGATGATAGCCAGAAAGGCAGATAAATACATGCACACCCAATAGTGCACATTTATGAAGCTTGT
ATTGTTACAAATAATAAAATAGTATTTCTGTGTGTTTCATGTACTAAACATTATAAATGAATATTGTGCT
ATTACAGGGTAGCAGTCAAATGCTTAGGAAGCCAAGCAGAGGATATAGAAAAGTGAAACAGCTGGAGTAA
GCAGTCCCCAAGACAAACCGAAATACTTCCAGGGTTAGGTTTAGCTGGTGAACGACCGTTTATAACCTCT
GCATCAATGGATCCTGTCTTTGGACCTGTTTTTCTAGTATAGATAATAGATTTATATTGACTCAGTTTGT
TTATTCCCAATCCGGACATAGCTTTTTGACTATGAGACAATCAGTGCATGCAAATTGTCCCAGTTCCTTG
GCCTCACTTAATCTCTGCCCAGGGCAAATACAGATAAATCACCCATCATGATATTTTTATTTATTCATGA
TAATTTTATTTATTCAAATTCTATTTATGCAAGTGTCTGTATTGGAAACTGTTGAGTTCCTGCCTACTGC
ATAACTTTATAACTATGAGCAGAATTCTGAACAGAATTATCAAATTTGCCTTTTTTTTTTTTTTGAGACG
GGGTCTCACCATATCACCCAGGCTGGAGTGCAGTGGCATGATCTCAGCTTACTGCAGCCTCCACCTCCTG
GGCTCAAACAAGCCTCCCACCTCAGCCTTCTCAGTAGCTGGGACCACAGGTCCTCACCACCACGCCTGGC
TAATTTCTGTGTTTGTTTGTATTTTTGATAGAGATGGGTTTTGCCATGTTGCCCAGGCTGGTCTTGAACT
CCTGAGCTCAAGGAATCTGTCTGCCTCACCCTCCCAAAGTGCTGGGATTACAGGTGTGAGCCACCATGCC

FIG. 7C (Cont.)

CAGCCGGCCTTTTCTTCTTAAAAAATGTGTGATCAGAGGATGCTTAAAATTACTTTTTCTTTCCCATTA
GCCTTGGAATTATAATTCTATACTAATTACTTTATGTATATTTTGTTCTACAGTATTATAAATTGGGAAC
TGCTAAGCATATTTATTAAAACAGTAGAAGGGGATATGTATTTTAATATTTCAAAATGAGAAAAATTTCT
CAAACTTTACCCTGAAAAAAGCATAGCTTTTACTACTTAATATTCTGTTGATATTTACTTGGAATATTAT
ACTTTTTTGTTTTGACAGGACAATGTAACTGCCTACTTTAAGCTTGAATCCATTTGAGAGTCGAAATAGC
TTTAGGCCAGGCATGTGGCTCATGCCAATAATCCCAGCACTTTGGGAGGCCAAGGCAAGAGGATCACCTG
AGCCCAGGAGTTTGAGACCAGCCTGGGCAGCATAGGGAGACTCTGTCTCTACAAATAATTAAACAATTAG
CCGGGTGTGGTGGCGTGCACCTATGATCCTAGCCACTCAGGAGGCTGAGTTGGGCGGATCGCCTGAGCCC
AAGAGGTTGAGGCTGTCGGGAGCCATGATTGCGCCACTATGCTCCAGCCTGGGCAACAGAGTGAGAGCCC
GTCTCAAAGAAACAGAGAGAGAGGTGGAAGAGGAGAAGAGAAGAGAAGGGAAGGAAGGGAAGGAGGGAAG
GAAGGTAGGAGGGGAAGAAAGAAAAAGAAGAAATAGCTTTATTTCTTACCCTGATCCACCCTACATACAG
TCAGCAAGCAATATGGGCATGCACTTGGCATTTCAAGGGATGGTCTAGTAGATAATGGTATTTTCTAAAA
CCCCTAGATCTTACTTTCACTATGCCCATACTGTATCTCCCATGCCAGAGTTTTCTTTTTTCCTGCTGTA
ATCTAGATGTGTTTTCTCCACAGGCATATTTTGGTGGTGAAGCTCGCTGCGATGCTGAGGCTGGACGGGG
AGATGATTATGATCCCAGAGAGCTCATTTGTGGTGCCTGTTCTGATGTTTCCAGGGCTCAGGTAGCCAGA
ACATTTTATTAGAAACAACAGTTTAGAAATGTTAAATAGTATTATTTTTTAAACAATAATATGGTGGGAA
TGTAAATCAGGCTTTTCTCCTCAGTATTTTCTGATATTTGTTCAGTGTTGTATAATTTTTCACATTATTT
CATATATATTATTTCCTTTGGGCGATATTTTTATTTTATAATTTTGTCTTCCATGAAATGATCACCATAG
TTAAACAATGTAATAAATTTTCTTATTTTCTTAGTTTCTTAAACGTGCAGTGAAACTTTTAGGTTTTCCC
CTCTTCAGTGAAATGTTCACAGTACATCTGTGAGATTATAAGAGAGGTTAATTTCATTAATTTTCAGTTT
GACCAGCCATAAAACATTCATAAAGAAATTAAGTACCTTGCTTATTAAATCAGATAGATTATGATGGAAA
TGGAATTAGAACTTGGATCTTTGTCCAGACCTTTTGGACAGGCCACATATTTATTTGTTAGTTTTCAAAC
ATGTGTATCATCAGTTTTTCAATCAATTTTTAGAGTTATGTAGGCCCTCAAAATATGAATTAAGGAGCTG
TCTATGTATATGCCTATCTTAAGTGTGATTGAAATAGTCTCACTATGATCTTGTGTCTGTCTCTTCTCTT
TTGCTATAGATGTGTCCCAAACATGGCACAGACTTTTTGGAATATAAATGTCGCTACTGCTGTTCAGTGG
CTGTTTTTTTCTGTTTTGGAACAACACATTTTTGTAATGCTTGTCATGATGATTTTCAAAGAATGACTAG
CATTCCTAAGGAAGAACTACCACACTGTCCTGCAGGTATGCTTTTAATATTTTAAAATCACGATTATGAT
CTATATACCATAGTTTTATGTAAACATTATATGAAAGCTCTGTTTCAAGTGACAGAAACTCAATTCAAAC
TAGCCTAAAGAAGCAGGAGGAATTCCTTGATCCTTGTAAGCTTATGACTTTCTGGGTGAATTAGGAAGCA
GGCTCATCATCATGAGTGAGAAGTTAGCTGTGACGGAGCAGATCTCATGGGGAGTGAGAATGAAGTCTAC
TAAGGATTGGTGAAAAGATGGCTGTTCAGCACTAAAAAGTCATATGAAGTTCAATATTACAGAACCATTT
AAAAGGATTCTGTGATTTTTTTTTTTTTTTAACGAAGCCTGGAACCGTTGCCATAAAATGAACCAAGTGA
TTTAATCTAGAATGGCTGGGAATCAGTAGTGTAGTGAGCATCAGAAAGTCAAGGGAATTAAAGAAACCAC
TCAGAATACAGGAGAAATTATTGTCTATGGAAAGCAGGCTGAGGGGAAAGAAGTATGAAACCAAAAAGAA

FIG. 7C (Cont.)

GCTGAAAATACTGGAAGAGGACAGGAGGCTAGTGGCAACGGTGAGGTGGAATACCAGGCTTCACGGAAGT
GAGAGAAGTGGAAGGAGAGGTCCGTGCAACCATAGGAGAGAATTTTACATAAGATATATCTGAAATTAGT
GAAAATACATGCACAAGTACATACAACACAATATACCGTGTTGTCAAAGCTAGAAAACACACACTGCCAT
CTGCTGCCTATCAGAGTGCAAGTGATAGACCTCTCCGGAAAACAGCTTAATAGTGCCTCTCAAAATTACC
AGCGTATCAACCCTTCAGCACTCCCTCTTCAGGGATATAGCTACAAATGTGAGGACAGTAAAAAAGGGCA
AATAAACAAGGTTATTAACTACAGCTTTGCTATGATAATAAAAATGTATAAACAATGCTAGTGTCCAGTA
GGGTAGTGGCTAATATTACGCATCAGTTTAAAAAAAAAAAAGAGTGAGGATGGTGTTTCTGTGTGCTGAT
TTGGAAAGATCTTCAGGAGATAGCATCAGATGAAAAAAGTAAATTAGGCCAAGTGGTGTGACTGACACCT
GTAATCCCAGCACTATGGGAGACCGAAGCAGGTGGATCACTTGAGGTCAGGAGTACGAGACCAGCCTGGC
CAACATGGTGAAACCCCATCTCTACTAAATGTACAAAAATTAGCCAGGCATGGTGGCGGGTACCTGTAAT
CCGAGCTACTCACGAGGCTGAGGCCAGAGAATCACTTGAGCCTGAGAGGCGGAGGTTGCAGTGAGCCAAG
ATTGCGCCACTGCACTCCAGCCTGGGCGACAGAGCTGTTTCAAAAAAAAAAAGCAAATTGCAGAACAGAG
TATGCAGTATGCTGCCTTTTGTAAGAGGGAAAATGAGACTATCTAGTCATATTTGTTTATATTTACATAA
AGAAACCCCTGGAAAGATACTCAAGAAACTAATACTATTGATTAACTATTGGGAAAAGCAAGAAAAAGAT
GAGGGTAGAGACTAGGGAAAGTTGCTTCCAATTGTGTTATCATTTTTAACATTTTGATTTTAAACCATGT
GAAACATATACTATCCATTTCAAAATAAAGATAAGTAGGGTTTTTTCAAGTATGACTACTTTTTACCATT
TGCTCATGTCAAATAAAAATTGTTTTACTGTTTCTCCTCAAATACTGTTTTTTTTTAATAGAAGTAGCAG
GCTTTGAAAGAAGCAAGGCCAGAATGATGTGAAGCCAGGTTATGGAGGATAATGGACAGAACAGAGATGT
GAGCCATGCTTGGAGGGAGGGGGTGATGTGCTGGAGGTCAGCAAGTGAAGGGAGTGTGGAAAGGGCAGTA
TTCTAGATGACTCTAGATGACTTGAGCTTGGAGGAAGGGCAATTATTGAATGAAAGTTGTAGGTTGTGGT
CTGGAAAGAAATAGGAGCCAAGAGAAAAATCAGTCACACGTTGTAGCCATATGACCTGGAGGAGCTTGGG
AGATAACCAGCCTCCAGTTGAGAAAGATTTAAGGCAAGCAGTATCTTCAGGGGAAATCTAGATTTTACTT
AAAGTTTCCTCTATGTTAAAAAACAGAAATAAGAATGCTAAAAATAAGGAAGTTAACAATGAAACACTTT
AGAGAACTCAGTGGTGGGTAGTAGCTGAGAGAGGAGGGTCAGGTTTCCTCACAGGATCAGGGCAGCCAAC
ACAAAGGAATCACAGGAGGGAGGCGGGGGAGGAGCCAGAGTTGGCAGAAGGAAGGAATGACCTCGGTCCT
GGGCATTTTCACACATATTTGCTCCATTTTTACAATCTGCGAGTAGATGGTATTATCCCTATGTTATCAA
ATGGAAAATTGAGGGCTAGGGAGGTTAATGAACTGGCCTAAGAACATACACTGAGATTGAGGTATACTCT
CCCAGCCTCACACATCCCTCTAACTCATCCATTCATTTAGAGAACTGGAATAGAATAAAGGAGATCCCAC
AGGGATGTGAGTAGGGAAGATGGCCATATACAGTTTACTTAGAAGGACAGAAGAAGCAATTCTCTAACCA
CTCTCAACCCTGTTAATTCTAATATTTTTAGATAATCAGTCTTCATCCATTCAAGCTGCTATAACAAAAT
ACTGTAAACTGGGTAGCTTATAAACAGTGGAAATTTATTCTCACAGTTCTGGAGACCAGGAAGTCTAAGA
TCTAGGAATTAGCAGTCGAGGTGTCTGGTGAGGACCCACTCTCAGCCTCATAGGTGGCACTTTCTTGCTG
TCGTGGAAGGGCAGGGGGCCTCTCCTGGGTCTCATTGATAGGAAGAGCACTAATCCCATTCATGGATTCC
ACCCCATGACCTCATCACCTCCCACAGCTCCACCTCCTAACACCATAACATTGGTGTTAATGTTGTAGTC

FIG. 7C (Cont.)

TCAGCAGTGCACCAAGATATAACAGTCTCTCATTGTCTGAGATAATGCCAGGAGTTCTTTGTCCTACCTC
CAAGAAGATTAAGGAGCACAGATACAAAGGTGAGGTTAGAGCGAAAGTTTAATAAGCAAAAGAAGAAAGC
TCTCTGCCAGCAGAGAGGGGGGCCCAAACAGGATGCTCCCGTGAGGCTGGGGCCCAGGGTTTTTATGGAC
TGGAAAGGGGAAGGAATGTGCTTAGTCTGTGGGCTGTCTTGGCCCGCAGCGTGACTCAGCTTGGCCCGGG
ACCCTGGCCCAGGAACCCACTGGAGCCCACTGTGCCTATGCCCACAAAAGGAGAGAGCCCCCTGACTATA
CAAAGGACAAAGGCATTTCTATCCCAGGTCTTGTCCTTTATCTGATTGAAGGTTTTTCTGTCTGTGCAGC
CGTGGGCATGTCTTTAGGCACAATGCCCTGTGCTAGTTCCCTCATCGGTGCCTGCAGCTTGACTTTTTTT
CCCCAACTGCTTTTTATGTTATATGGGGATGAGGCACTGACCTGTGGACCTGGGGCTCTCTGGGGACCCT
TCCCTTGCTATCTACCTAAGGCAAACTAACTCCTTTCATTAACACGTCAGTATATAAATTTGGAGGAGCA
CAAAAACATCCAGACCATAGCATAATCCCTCTATCCATTTCTTTCTAAAATATTTATTGACTACCTTCTC
GTGCCAGGATACTTAATCTTCACAGCACCCCATGAGTTAGGTATTGCTGTGTCTATTTTAAAGATGAGGT
ATCTAAGAATCAGAAAAAATAATTTTACTTCAGTTTCATATCTACAAAATGAGGATAATCGTTTCTGCCT
CCTATGACTGTTAAATGGTTAAGTAGCTGATATACTAGAACAGTGCCTCAGTAGTAAGCACTCAGATGTT
TGCAGGTGTGTTTTCACTATTTTTATTTCTCACCACCATGTTGGATTGTGAACACCTTGAAGATGGGAGC
CATGCACTTTTCATCTTTAATCCCAAGTACCTAAGAATGCCCTTCATATATTAGGCATGCGGTAAATATT
TGTTGAGTAAATGACTCATTTTTTCCTTGAAAAAACCCAAGGGCTGCAGTTTGTGTCACCACCATTGATA
TGTTGTGTATCTGAACTAGATCTGCCATTGAGTGTCCCCATCCTGCGCACTCTCCCCCACCCACTGGTGG
GGTGGGCACCAATCTGCAGTGTGATTTGGAGCAGGAGCTACTGAACTACTTTCTAACAGGAATAATTAAC
TTTCTAGCAAACCTCTGGCATCCTCCCATGCTGACCCATCCTGAGGTCTGTGCCTGCATTTGTCTGAGGT
GGCACTCATTGCCACTCTCATGCCTGTTAGCTCTAACCTGAAGTTGACTTCTCTGAGATTAGCTGTCTTC
AGTTTGACACTCTAATGTCTTGGTCTTACTCTTGTACAGAACTTACTTTTTATTCCTCTAGATCAGGCCT
CAGTTTGTGGTTGTTCAGTAATAGTAGTAATAGCCAACATTTATTGGGTATTATACTGTGCAGTCTAAGA
GCTTTATAAATGCTAGCCTTTTATCCATCATGGTTTCCTTCTCTTATGTCAGAAATGTTTTTAAACCTAG
AAAAGGTAAAGTAAATGAGACGTCATTCCTCATTGATCAGTGTAAGCTCATTCCATCCAATCTCGTGATA
TTTTTCTCTCAAGCACAATCAGAATTTAGATTTATTATTTTGAAAACTAGCTGTAGAAAACTAATGCAGA
GTTCCTATTCCTTCATCTACTATTAAATAGGGACTCTGCTTTCAAGTATAAGCCTAGCGTGTTTTTCTGA
CAAAGTAAGCCTCCTGGTTTCTAAAGGAACTAAAAATCTTTTCTAAATGATATGAAACCCATGACGTGAA
GCACATTAATATAATAATTTTCTTTTTTAAAATACTGTTTTTGGTACATTTGATAGGCCTACTTTGATTA
TTATCAACAAATTCATATCTTCCCCAAAGTGTTTTTTCCACATTGTATTTTATAACATTGTTCATGTTTT
TAACCTGATAACTTTCATTTTCCTGCTAATATCCTTCAGGTACTTTTAAAAATTACAGGAATCATTGGCC
TTCCCATTTTACCAGTGTGGGCTTTTTCATCAGTAAAAATAAAAGGGAAAACATGGCTTCTTTAAACTTA
AATGTTTTTACTTATAGAAAAACATTCTACACAAAAATCTCCCTGTTTTCTATTCAGAAAAATAATGTTC
TGCCAGACTAAATTGAGGGGTTTTGTGACCTTTTTTGTTCATTACTCTGTTTTAAAATGATATATCTGAT
GCATTTATTAATAGAAAAAGATCTGTAGCTCGAAGTGATCCTCTCTAGGCAGGATATAGTGAGTAAGGGA

FIG. 7C (Cont.)

CCCCATCACTTCTTCCATTGTACATATCTGTGTTGAATTTTTTATAGTGAACATTTTTTACTTTTGTGAT
CAGAAGAAAAATTTCTAAATGTTATATTTGTATAACCATAGTCATGTTATTTCTTTGAATAACCTATCAG
TGATTTATATTTCTGTGAGGTTTATATGTGTGTATTCTTAAAACATTATTTTCCTTTGCCTCCTTCAAAT
TTATACAGGTCCCAAAGGCAAGCAGTTAGAAGGAACTGAATGTCCACTCCATGTTGTTCATCCACCCACT
GGGGAAGAGTTTGCTCTGGGATGTGGAGTGTGCAGAAATGCCCACACTTTTTAGAACACGCAGATCCTTT
GTCTACAGAGAGAAAAATTGCCTTCATCCCCCAAGAGGATGCGGTGAAGTTTAAACTCTGCTCAGGATAA
GGACGGGACCATTTTTACATCCATGAAAATGAACCATTCACAGTGCAAGAAGGATACCAAATACCATGTA
CATAATTCTTGCTATGAAAAGTTTCCCCATTATTTTGGTTTATCTTCTTTTGAACAAATGACATCAAACT
TGTGAGGTGTTTGCATGTGGCCATTACCGTCATTGGCCTGTGAAGCATTGGACATTTATAGATAATTGAT
ATAAAAGAATCGCCATGCCCATGGACTAAGAACGATGCTGGCTTTCAAGCAAAAAAGAAAAATAATCATT
GTTTATTGTATACTGCCTTTTTGTAATCCTGTACAATTGCATCACGGGTGGGGATAAAAAGAGGAATATT
CTGGTTTATTTCCTAGACTGTTATTTAAAAAAAAAAAAAACATTGTGTTAGGACAGCATATAAATGTAAT
AAGTATCACACTGTATATAAACATATCAATGTTTGTCCTGTATAAGAATTACTAAATTACAAATGCAATT
TCATTTAAACTTCTAGGTTAAGTTTGAGCCTGAAATTTTAATGAAGTGCAATACTGAGTGTGCCTCATTA
TCTTGCAGCTGTAAACATATTGGAATGTACATGTCAATAAAACCACTGTACATTTTTATACAGTGATAAA
GTCTACCACTGTGGGAGGTATTGTTTAAAAAACAAAATTTGAACACCTTTAAGGTCTAAAAGTCCAGTTT
TCCTCAGAAAGAAATTTACTAACACAACACATTCATAATTTTCAAAACTGTTAGAGAAAATAAGAATAGT
AATGAAGTGCAATGTTGGAATCTTAAACCCTAAGCAGAAGATCATAAATATATATATATATATTCGTAGG
TAAATATATTCATACCAAAGACAGAAGAAAGCATTTAGGAAATTAACTTCTATTTTAACTAGCAGCATTT
TTAACTTTATTTATTTATTTATGAGACAGGGTCTTACACTGTCACCCAGGCTGGAGTACAGCGGCGTGAT
CTCAGCTCACTGCAGCCTCCAACTGGGCTCAAGCGATCCTCCAGCCTCAGCCCCCTGAGTAGTTGGGACT
ACAGGCATGCACCAGCACCATGCCCAGCTAATTTTGTAATTTTTGTAGAGATGGGGTTTTGCCATGTTGC
CGAGGCTGGTCTCAAACTCCTAGACTCAAGCAATCCCCACTGCTTTGGCCTCCCAAAGTGCTAGGATTAC
AGGCGTGAGCCATTGCACCCAGCCCCTTTTTGAAGTTCATATAAAGTAATAAAATCACTAATTTTTTATT
CATTTTCTATAGACAACGGTGTGTTTAGGTACATCTTTTTGACACTCGAGTCATGAAATTGCCAAATTAT
TGATTGTTGACTCATCATACATCAGATTAGCAAAACTTTTGTTGTTGTTGTTGTATTTGAGACAGTCTCA
CTCTGCTGCCCACACTGGAGTGCAGTGGCACCATCTTGGCTCACTGCAACCTCCACCTCCCAGGTTCAAG
CGATTCTCCTGCCTCAGCCTCCCAAGGAGCTGGGACTACAGGCGTGTGCCACCTCACCCAGCTAATTTTT
GTATTTTTAGTAGGGATGGGGTTTCACCAGGCTGGTCTTGAACTCCTGACCTCAGGTGATCCGCTCGCCT
CCGGCCTCCCAAAATTCCGGTATTACAGGCGTGAGCCACCGCGCCTGGCCAAGACTAGCAAAAGTTTTAA
TCACATTTTGTTCTAAATTCCAACTGTGGGAAATATAGAACTTAATTTGTCAATATAGAATTACTGACAA
ATTTAATGACATTTGTGTTAAGCATTTATGAGAAATTTAAAACAATCTTTGCCTTGAAGGAACTTAAAAA
ATAAAGATCAGATCTGAGCACAGGTAACTATTTTACAGAATGTTCTAATAAGTTTCATAAAAATATCCAA
GCCAAATGCTTCAGGATTTAGGAAAAATCATTATTGTTTTGTCGTTGGGAGTGTAGCTAAGAGGCCATTT

FIG. 7C (Cont.)

AAGCTGCCTTTTGAAGAATAAGTAGCATTTCAAGGAGCAGAGATGTGGAGAAAGGCATGAGAAATACCTA
AGTAGGAAAATCTAGAATATGATCAAAGAACAGTAAGTATGAGTGTTCAAGCTTAGGATTGACTGAAAAT
GTTTCCAGAAAACACAAAGTACGTAGAGAGACTAAAGCTGTTACAAGAAAACTGGAGGGGAGAATGCAGT
GAGGACACTGTCAGTATATTTGACTTGACACTGTCAGTATATTTGACTTAAATTCACAGGCCACAGGAAT
GAAACTAACCTTGAGAATGCCACACAGATAAGAGACTTTATGGACACTTAATAGCTGCGAAGAATACCAT
CTTGCGTCAGTTAACTTTGCTGGCAAACTGGTCAGCTCAGTTTGTAAATCGTAGAGGAAAAGAAACAAAC
TATTGAGATGGCTTGGCTAAAAAAGCCATCTCAAGTTATGAAAGGGATAAAATCAACAAAGCTGTGTAGT
GAATACTCACAATGACTTCAACTTATCTTCATTTATGAGGAAGTCACTTTTAGTCAGGATCTCTAGCACC
TCAAAACCAGAGAACATAAACATCTTAGCAATAAATTATGACAAAGCACAGGAAGGAGTGGCTTTGGCAG
GCATTTTTAGCTCAAGCATCCTACACACAAGGACCATCCTTCAAACACTGCATGTAACATCCAAGGCAGG
AGACAGAAAGCAGAATCACAGTGGTAGATGTCAGTGAATCTTCCTGGAAAGAAATTGTTTTTCCGTTATA
TTTTCAAGCCTAGGAAAAGCCATTTTTCTTAGTATTATGGCTAGACTGTTTAGGCCTAAAATCTCCCTAT
TTTATCAATAAGCTTATTTGGTTTTGGTTTTTGGTTTTTTGAGTTTTTTGGGTTTTTTTTTTTTTTTTTA
AGAAAGGGTCTCACTCTGTCGCCCCAGCTGGAGTGCAGTGGCGTTATCTCGGCTCGCAGCAACCTCTGCC
TTTTGGGCTCAAGTGATCCTCCCACCTCAGCCCCAAGTAGCTGGGAGTACAGGCACGAGCCACCATGCCC
AGCTAATTTTTGTAATTGAAACAGGGTTTCACCATGTTGGCCAGGCTGGTCTCAAACTCCTGAGCTGAAG
CGATCTACCTGCCTCAGCTAGGATTACAGGTGTGAGCCACCGCACCCAACCTCAATAAGCTTATTTGATA
AAATATATGCAATGCTCCCTTTATTCACTTTTCATTCAGAATGTTTAGTAATTTGTATTGTTTTTCAGAT
TTTCAGCCCAATATATCTCCCTGCCCACTGTGTCACTGTATTCTACCTATACATCATCACGTGTTTCTGC
TATTGGCTGTATGATGGAACACTGCGGCTCATTTTCCTGAAAACTGCCGATAGTGCATAGAGTGCTGGGA
TGGAAACCAGAAGCTTTGAATTCAAGCCTTGGTTCTGCCTTGTTTTTGCTTGGGTGGCCTTGAGTCAGCC
ACATACCTTTTAAAATCTCAATTTATTAGAAATTATTCCAAATCAAAATCAAATGAGAAGGTATATACAA
AAGTGCTTTATCCCACAATAAACTATTCAAGAGAGAGCAAAGGAGAGGACATTTACTCAACACCTCCTAA
AAGGCAGCCAGTGAAATTAGGCATTTTATTTAATCCTCCTGGCAACTCTGAGAGTAAAGCATTATTAATC
CCATTTTGGCTGTTTAAAGAAATTATTTGCACTAGATTCCAGCTGTAGTTTAGCTTCAGAAAAAAAAATC
CTGAGATGTGAATTCACAGCTTTCTGGGTTTAAAGCCCAAGCTCTATCACATCATGCTATTATTGTTACA
TTACTGCTAGTTCTATGAAAAGAAATACTAATTTATGAAATACATCTTATCCAAAATGGTTGGGACCAGA
AGTGTTTCTGATTTCGGGTTTTTTCAGGTTTGGGAATATTTGCATTACCAGTTGAGCATCCCAAATCTGA
AATCCAAAATGCTCCAGTGAGCATTTTATTTGGGTATCAGGCATGTCAGTACTCAAAGTTTTAAATTTCA
GGACACTTATCGTATGGCCAAGGTTGCACAGGGGACAAGACAGCATATGCCTCCAAGAGTGTTCAGTGTC
GTCAGGAGGTACCTCCACCCAGATTTCCCTTCAGGGGAGGCCCCACCTCAAGGAGTCCAGTTAGCTGACA
GCCTCCAGCTTTAATCACCCCCACATATGACCCAATGTCACACTCCTCCAGGGCAGCCCCAGCCTGTGAT
AGAGTTCAGATGGGGTTCTCGGGCCTGGCCATTTCTGCCCAAGCGGCACTCCTGCGTGCGCGGTCTTGCG
TAAGAACTCAGGCCGACTGAGACTGTCTTACAGCTGCCCTGCAGTCGGAGGCTTTTCCTACCCAATCTTT

FIG. 7C (Cont.)

CCTTCTCTCTTCTTTCCTAGATGCCAGACCTGCATCACAGTCTAATGGCTCTCCCTGCCCACTCCTGCTC
CCTCATCACTTTATCTTTCATAGGGATTACCCCCAACAGATTTTCTGCACTTCTAACTTAATCTTGGCAT
CTGCTTCCTAGAGGACCTGCCTGACACAGGAGGGTAATACATTTTAAATGACTTACTTATGGCTTCATTT
CTCAAATGTCTTAGGGTGGCTTAGAAAAAA

FIGURE 8A (SEQ ID NO:4)

GCTTGCCAAACGATTCAGGTGCCAACAATACTAAATTCACTACAGAGAAGTGTACAGGCAGTGTTGGTTG
GAAAGATTCAAGTCCAGGACTGGTTTAGCAATGGCATTAAGAAAGCAGCTTTAATGCACAAGTGGCCATT
AAAGGAAATATCTGTTGATGAAGATGACCAGTGTCTGCTTCAGAATGATGGATTTTTCTTTATTTGTTA
TGCAAGGATGGATTATACAAAATAGGCTCTGGATACAGTGGAACAGTTAGGGGTCATATATATAATTCTA
CATCTCGTATCAGAAACAGAAAAGAAAAGAAGTCTTGGTTAGGATATGCCCAGGGTTACTTGTTATATCG
GGATGTGAATAACCACAGTATGACAGCCATAAGAATAAGCCCCGAAACGCTGGAGCAAGACGGCACTGTA
ATGTTACCAGCTTGCAGATGTTGCTTGACACATTCCTGAAGCTGCTGTCTTATAATGTCATACACGGGTA
AAGAGCGGACACGGGAAGTTGTCAGTGTGACGCCGAAGGAAGACCCAGCCCTCAGCCCCAGCCCTCAAGC
CTGAAGAAGCCTGCTGTCATTTCATCACTTCTTTGACACGGACTACAGTTTCTTCAATAAAATCATTTGC
TTTTTCCCTGACAAGGGATACTACTTCTCTGTAGCTTTTCATCAAGAAGAGAAGTAGTAAACTGTCAGAT
TTATAGGTGGTTACTGAATACCATGTTTAAAATGAACAT

FIGURE 8B (SEQ ID NO:5)

GCAGCTTCAGAGTGACAGAGGAACTGTCTCAACATCTTCAAGACCAGTGTCTACATCAGCAAAGTCAGAG
CTGCCCTCCAAGAACAGCAGATCAGTTAAACCTGATGGGCGTGTGAGCCGGACTACTGCTGACCAGAAGA
AGCCACGGGGCACAGAAGGCTTATCTGCTAGTGAATCCCTCATGTTAAAATCTGATGCTGCAAAGTTGAG
GTCAGACTCCCATAGTAGGTCACTGTCCCCTAACCATAACACTTTGCAGACACTGAAGTCTGATGGAAGG
GTATCTTCTAGCTTCAGGGCTGAATCCCCAGGACCAGGCTCTAGGTCATCCTCTCCTAAGCCCAAGACTC
TGCCGACTCCCAGGTCTAGCCCATCTGGTGCTAGCTCTCCACGCTCCTCCTCACCGCAGGATAAAAATCT
ACCTCAGAAAAGCACAGCTCCTGCTAAGACAAAACTTGACCCACCTCGGGAGC

FIGURE 8C (SEQ ID NO:6)

TTTTTTTTTTTTTTTTTTCCTTTTTCGTTTTTTTATTCTCTTTCTCACATTCTTTCTTTTTAAGGACTGC
ACAGGAACCTGGACTTGGAAAAATCATATTCTGGGAAGCAGCTTTGATTGTAGCCAAAGAGATGTCCTCC
CAGAAGGCCACTAAGTGTTGTAATGTTAAGGGGAGCGGAGACCTAGACTTCACTGAGTGATGCATGGACA
TTTCAAAAGTGGCTTCCGATTTTCCGTCTTCACACTTCTCATGTAGAGGTGGCTCCTTAAGCATAGACAG
GACCTTATTTTTGTTGATACTTCCCATCTTGGATATGTCTGGTCCGTGAGGTGAAATGTTGAACATATTT
AGGGCAGATGATATTTCCAACGAATGTCTATTTTTTAACTTGATTTCCTTTTCCTCTGTGGGTGGCTGGC
TATTCAAACTACTTCTTATGGGAGCATGTTCTTTGGAAAGTTCAGGATTAAACTTCAGGAAGGAAGAGCA
GGCCATTGCATCATGTACTATGCCTTCATGCCACAGAAAAGAGGCAAAGACAGCTCGGGCACACTCAGCC
ACGGACGGGGACATGGCTTGCTTGGCTGGCTCTAAAGATTTGGCTCCATCTCCTNTTGAAAGAAAGTTAG
ACTTTTCTTTTTTGGGCCTGGTGTGTCTATTAGCACATTTCCGACTTATTTTGGGGTGATGCTCTCATTT
CCTGTTCA

FIGURE 8D (SEQ ID NO:7)

TAAGCTTGCTCTGTCCCTGCCCCGTACATCTCAGTAACTCCTGATGCAAGTCCCAATGTCTTTGAAGAGC
CGGAGAGCAATATGAAGTCGATGCCACCAAGTTTGGAAACGAGCCCGATAACTGACACCGACCTGGCTAA
GAGAACTGTCTTCCAGAGGTCATACTCAGTTGTCGCTTCGGAATATGATAAACAACACTCCATTTTACCT
GCACGAGTTAAAGCCATCCCTAGAAGGAGAGTGAACAGTGGAGACACGGAAGTTGGGTCTTCTCTCTTGC
GACATCCGTCACCGGAGCTTTCCCGGCTTATATCAGCCCACAGCTCTCTCTCCAAAGGAGAGCGAAACTT
CCAGTGGCCAGTCTTAGCTTTCGTCATACAGCATCATGATTTAGAAGGGCTGGAAATCGCAATGAAGCAG
GCCTTAAGGAAGTCGGCTTGCCGTGTGTTTGCTATGGAGGCATTCAACTGGCTTCTCTGTAATGTCATCC
AAACAACGTCTCTGCATGACATTCTCTGGCACTTTGTGG

FIGURE 8E (SEQ ID NO:8)

ACGAAGGGCTGCATAAGAGTGAAGCGATCACGACGCCGGGCGTCAGGTTTTACAATGATCCAGCCGGCTA
TGCCATGAACAGATACGCATATTATGTTTGCTACAAATGCAGAAAGGCATATTTTGGTGGTGAAGCTCGC
TGTGATGCTGAGGCTGGACAAGGAGACGACTACGACCCCAGAGAGCTCATCTGTGGAGCCTGTTCTGATG
TGTCTAGGGCTCAGATGTGTCCCAAACATGGAACAGACTTTCTAGAATACAAATGTCGCTACTGCTGTTC
AGTGGCTGTCTTCTTCTGTTTTGGAACAACACATTTCTGCAATGCTTGTCATGATGATTTTCAAAGAATG
ACCAGCATTCCTAAGGAAGAGCTCCCACACTGTCCTGCAGGTCCCAAAGGCAAACAGCTAGAAGGAACTG
AATGTCCACTCCATGTTGTTCATCCGCCCACGGGGGAAGAGTTTGCTCTTGGTTGTGGAGTGTGCAGAAA
TGCTCACACGTTTTAGAACTTTCAGATCCTTTGTCTACAAAGAGGATAGTTGCCTTCATCCCCTGGGAGG
ATGCAGTGAAACTTTAAACTCTGCTCAAGGATAAGGAACGGGGACCATTTTTACATTCTGAAAACGAACC
ATTTTCCAGTGCCAGGAAGTGATGCCCCAAATACCTG

FIGURE 8F (SEQ ID NO:9)

TTTTTTTTTTTTTTTTTTGACGCTCTCACTGTGTAGAGCACAGTGGTTTACTGACGTACATTCCAATATG
CTGACAGCTGCAAGGTAGTGAGGCACACCCAGTATTGCACTGCATTAGAGCTTCAGGCTCAAACGTAACC
TACAGGTTTAAATGAGACTGCTGTGTCATTTAGTAATTCTCATACAGGACAAACACTGATAGCTTTATAT
ACAGTCTGATACTTATTACAATTATAGGCCTTACTAACACAATTTTTTTTTTTAAATAACAGTCTAGGAA
AGAAACCAGAATATTCCTCTTTTTATACCCACCCGTGATGCAATTGTACAGGATTACAAAAAGGCAGTAT
ACAATAAACAGTGATTATTTTTCTTTTTTTGCTTGAAAGCCAGCATCATTCTTAGTCCATGAGTATGGAG
ATCCTTTTATATCAATTATCTATAAATGTCCAATGCTCCACAGGCCAGTGACGGTAATGGCCACATGCAA
ACACCTCACAAGTTTGATGTCTTGGTTCAAAGATGATAAACCAAAACAATGGGGAAACGTTCGTAGCAAG
AATTATGTACACAGTATTTGGCATCACTCCTGCACTGGAAATGGNTCGTTTTCAGAATGTAAAATGGTCC
CGTTCTTATCCTGAGCAGAGTT

FIGURE 10

5´-GAAGGGTGGGGCCAAAAG-3´ (SEQ ID No.10)
5´-GGATGCAGGGATGATGTTCT-3´ (SEQ ID No.11)
5´-GGTGGTGAAGCTCGCTGTGATGCT-3´ (SEQ ID No.12)
5´-CGTGTGAGCATTTCTGCACACTCC-3´ (SEQ ID No.13)

FIGURE 11

5'-GACTGGTTTAGCAATGGC-3' (SEQ ID No.14)
5'-GCCATTGCTAAACCAGTC-3' (SEQ ID No.15)
5'- GCAATTGCTAAATCAGTA -3' (SEQ ID No.16)

FIGURE 12A: SEQ ID No.17

```
 400                                       nnhsmtairi spetleqdgt vmlpdchteg
 421 qnilftdgey inqiaasrdd gfvvrifats tepvlqqelq lklarkclha crislfdlek
 481 dlhiistgfd eesailgagr efalmktang kiyytgkyqs lgikqggpsa gkwvelpitk
 541 spkivhfsvg hdgshallva edgsifftgs askgedgesi ksrrqskpyk pkkiikmegk
 601 ivvytacnng sssviskdge lymfgkdaiy sdssslvtdl kghfvtqvam gkahtcvlmk
 661 ngevwtfgvn nkgqcgrdtg amnqggkgfg venmatamde dleeeldekd eksmmcppgm
 721 hkwkleqcmv ctvcgdctgy gascvssgrp drvpggiegc gsgesgcavc gcckacarel
 731 dgqearqrgi ldavkemipl dlllavpvpg vnieehlqlr qeekrqrvir rhrleegrgp
 841 ivfagpifmn hreqalarlr shpahvkhkr dkhkdgsger gekdaskitt yppgsvrfdc
 901 elravqvscg fhhsvvlmen gdvytfgygq hgqlghgdvn srgcptlvqa lpgpstqvta
 961 gsnhtavllm dgqvftfgsf skgqlgrpil dvpywnakpa pmpnigskyg rkatwigasg
1021 dqtflridea linshvlats eifaskhiig lvpasisepp pfkcilinkv dgscktfnds
1081 eqedlqgfgv cldpvydviw rfrpntrelw cynavvadar lpsaadmqsr csilspelal
1141 ptgsralttr shaalhilgc ldtlaamqdl kmgvasteee tqavmkvysk edysvvnrfe
1201 shgggwgysa hsveairfsa dtdillgglg lfggrgeyta kiklfelgpd ggdhetdgdl
1261 laetdvlayd caarekyamm fdepvllqag wwyvawarvs gpssdcgshg qasittddgv
1321 vfqfksskks nngtdvnagq ipqllyrlpt sdgsaskgkq qtsepvhilk rsfartvsve
1381 cfesllsilh wswttlvlgv
```

FIGURE 12B: SEQ ID No.18

```
 446                             ifats tepvlqqelq lklarkclha crislfdlek
 481 dlhiistgfd eesailgagr efalmktang kiyytgkyqs lgikqggpsa gkwvelpitk
 541 spkivhfsvg hdgshallva edgsifftgs askgedgesi ksrrqskpyk pkkiikmegk
 601 ivvytacnng sssviskdge lymfgkdaiy sdssslvtdl kghfvtqvam gkahtcvlmk
 661 ngevwtfgvn nkgqcgrdtg amnqggkgfg venmatamde dleeeldekd eksmmcppgm
 721 hkwkleqcmv ctvcgdctgy gascvssgrp drvpggicgc gsgesgcavc gcckacarel
 781 dgqearqrgi ldavkemipl dlllavpvpg vnieehlqlr qeekrqrvir rhrleegrgp
 841 lvfagpifmn hreqalarlr shpahvkhkr dkhkdgsger gekdaskitt yppgsvrfdc
 901 elravqvscg fhhsvvlmen gdvytfgygq hgqlghgdvn srgcptlvqa lpgpstqvta
 961 gsnhtavllm dgqvftfgsf skgqlgrpil dvpywnakpa pmpnigskyg rkatwigasg
1021 dqtflridea linshvlats eifaskhiig lvpasisepp pf
```

FIGURE 12C: SEQ ID No.19

```
 499                       gr efalmktang kiyytgkygs lgikqggpsa gkwvelpitk
 541 spkivhfsvg hdgshallva edgsifftgs askgedgesi ksrrqskpyk pkkiikmegk
 601 ivvytacnng sssviskdge lymfgkdaiy sdssslvtdl kghfvtqvam gkahtcvlmk
 661 ngevwtfgvn nkgqcgrdtg amnqggkgfg venmatamde dleeeidekd eksmmcppgm
 721 hkwkleqcmv ctvcgdctgy gascvssgrp drvpggiogc gsgesgcavc gcckacarel
 781 dggearqrgi ldavkemipl dlllavpvpg vnieehlqlr geekrqrvir rhrleegrgp
 841 lvfagpifmn hreqalarlr shpahvkhkr dkhkdgsger gekdaskitt yppgsvrfdc
 901 elravqvscg fhhsvvlmen gdvytfgygq hgqlghgdvn srgcptlvqa lpgpstqvta
 961 gsnhtavllm dgqvftfgsf skgqlgrpil dvpywnakpa pmpnigskyg rkatwigasg
1021 dqtflrides linshvlats eifaskhiig lvpasisepp pfkcl
```

FIGURE 12D: SEQ ID No.20

```
1000                                           a pmpnigskyg rkatwigasg
1021 dqtflrides linshvlats eifaskhiig lvpasisepp pfkcllinkv dgscktfnds
1081 eqedlqgfgv cldpvydviw rfrpntrelw cynavvadar lpsaadmqsr csilspelal
1141 ptgsralttr shaalhilgc ldtlaamqdl kmgvasteee tqavmkvysk edysvvnrfe
1201 shgggwgysa hsveairfsa dtdillgglg lfggrgeyta kiklfelgpd ggdhetdgdl
1261 laetdvlayd caarekyamm fdepvllgag wwyvawarvs
```

FIGURE 12E: SEQ ID No.21

```
1000                                           a pmpnigskyg rkatwigasg
1021 dqtflrides linshvlats eifaskhiig lvpasisepp pfkcllinkv dgscktfnds
1081 eqedlqgfgv cldpvydviw
```

FIGURE 12F: SEQ ID No.22

```
1028        dea linshvlats eifaskhiig lvpasisepp pfkcllinkv dgscktfnds
1081 eqedlqgfgv cldpvydviw rfrpntrelw cynavvadar lpsaadmqsr csilspelal
1141 ptgsralttr shaalhilgc ldtlaamqdl kmgvasteee tqavmkvysk edysvvnrfe
1201 shgggwgysa hsveairfsa dtdillgglg l
```

FIGURE 12G: SEQ ID No. 23

1028 dea iinshvlats eifaskhiig lvpasisepp pfkcl

FIGURE 13A
(SEQ ID No.24)

AATAACCACAGCATGACAGCCATAAGGATAAGCCCTGAAACACTGGAGCAAGATGGTACTGTGATGTTA
CCAGATTGCCACACTGAAGGTCAAAATATTTTATTCACTGATGGAGAATATATTAATCAGATAGCTGCT
TCAAGAGATGATGGCTTTGTTGTCAGAATATTTGCCACAAGCACTGAACCTGTTCTACAGCAAGAATTG
CAACTTAAACTGGCTAGAAAATGCTTACATGCCTGTCGTATCTCATTATTCGATCTGGAAAAGGACTTG
CATATTATAAGTACAGGATTTGATGAGGAGTCAGCAATTCTTGGTGCAGGACGAGAGTTTGCGCTAATG
AAAACAGCAAATGGAAAGATATATTACACTGGCAAATACCAGAGTCTTGGAATCAAACAAGGTGGTCCT
TCAGCAGGAAAATGGGTTGAGCTACCAATTACAAAATCTCCAAAGATAGTACACTTCTCAGTTGGACAC
GATGGCTCTCACGCCCTTTTAGTTGCAGAAGATGGGAGCATATTCTTTACAGGATCTGCTAGTAAAGGA
GAAGATGGAGAATCAATTAAGAGCAGACGGCAATCCAAACCTTATAAACCTAAAAAGATAATTAAGATG
GAAGGAAAGATTGTGGTATATACAGCCTGCAATAATGGAAGTAGTTCTGTTATTTCTAAAGATGGAGAA
CTCTACATGTTTGGAAAAGATGCCATTTACTCTGATAGTTCAAGTTTGGTAACTGATTTGAAGGGCCAT
TTTGTAACTCAGGTAGCTATGGGCAAAGCTCACACTTGTGTTTTAATGAAGAATGGAGAGGTGTGGACA
TTTGGTGTAAATAATAAAGGACAGTGTGGACGAGATACTGGTGCCATGAACCAAGGTGGAAAGGGTTT
GGAGTTGAAAATATGGCAACAGCAATGGATGAAGACCTGGAAGAAGAACTAGATGAAAAAGATGAGAAG
TCTATGATGTGCCCTCCAGGCATGCACAAATGGAAGCTGGAGCAGTGCATGGTTTGCACTGTCTGTGGA
GACTGTACAGGTTATGGAGCCAGCTGTGTCAGTAGTGGACGGCCAGACAGAGTCCCCGGAGGGATCTGT
GGTTGTGGTTCCGGAGAATCTGGTTGTGCTGTGTGTGGATGTTGCAAGGCCTGTGCAAGAGAGTTAGAT
GGTCAAGAGGCAAGACAAAGAGGAATTCTTGATGCAGTGAAAGAAATGATACCTTTAGATCTTCTTTTA
GCTGTCCCAGTGCCCGGGGTTAACATTGAAGAACACCTTCAGTTACGACAAGAAGAAAAACGGCAACGT
GTAATCAGAAGGCACAGATTAGAGGAAGGAAGAGGCCCCCTTGTATTTGCTGGTCCTATTTTTATGAAC
CATCGAGAACAGGCTCTAGCCAGACTCAGATCCCATCCAGCACACGTAAAGCATAAACGGGACAAGCAC
AAAGATGGAAGTGGAGAAAGAGGCGAAAAGGATGCAAGCAAAATCACAACATACCCTCCAGGCTCTGTG
CGATTTGACTGTGAGCTCCGGGCAGTCCAAGTCAGCTGTGGATTTCACCATTCAGTGGTTTTAATGGAA

FIG. 13A (Cont.)

AATGGAGATGTCTATACATTTGGTTATGGGCAGCATGGGCAGCTAGGACATGGAGATGTCAACTCCAGG
GGATGTCCCACTCTTGTTCAAGCATTGCCAGGCCCTAGCACACAAGTCACTGCAGGCAGCAACCATACG
GCAGTACTTTTAATGGATGGACAGGTCTTCACATTTGGAAGTTTTTCTAAAGGACAACTGGGCAGACCA
ATTTTGGATGTGCCATATTGGAATGCAAAGCCAGCTCCCATGCCTAACATTGGATCAAAATATGGAAGA
AAAGCTACTTGGATAGGTGCAAGTGGGGACCAAACTTTTTTACGAATTGATGAAGCACTTATTAATTCT
CATGTACTTGCTACATCAGAAATTTTTGCCAGTAAACACATAATAGGCTTGGTACCTGCTTCTATATCA
GAACCTCCTCCATTTAAATGCCTTCTGATAAATAAAGTGGATGGGAGTTGTAAAACTTTTAATGACTCA
GAACAAGAGGATCTGCAAGGATTTGGTGTGTGTCTTGATCCTGTATATGATGTAATTTGGAGGTTTCGA
CCAAATACTAGAGAGCTGTGGTGTTACAATGCGGTGGTTGCTGATGCCAGGCTTCCCTCTGCAGCAGAC
ATGCAGTCCAGATGTAGTATCCTAAGTCCTGAACTTGCCTTACCAACAGGATCAAGGGCCCTCACTACC
CGATCTCATGCAGCTTTGCACATTTTAGGTTGTCTTGATACCTTGGCAGCTATGCAGGACTTAAAAATG
GGTGTTGCAAGTACAGAGGAAGAGACTCAAGCAGTAATGAAGGTTTATTCTAAAGAAGATTATAGTGTG
GTAAACAGGTTTGAAAGTCATGGAGGAGGCTGGGGTTATTCTGCCCATTCAGTAGAAGCTATACGTTTC
AGTGCCGACACTGATATTTTACTTGGTGGTCTTGGTCTGTTTGGAGGTAGAGGAGAATATACTGCTAAA
ATTAAGCTGTTTGAATTGGGTCCTGATGGAGGAGATCATGAAACTGATGGTGACCTTCTTGCAGAGACT
GATGTATTGGCTTATGACTGTGCTGCTAGAGAAAAATATGCAATGATGTTTGATGAGCCTGTTCTCCTG
CAAGCTGGGTGGTGGTATGTGGCATGGGCCCGAGTGTCAGGACCCAGCAGTGACTGTGGATCTCATGGA
CAGGCATCTATTACCACAGATGATGGGGTTGTTTTCCAGTTCAAGAGTTCAAAGAAATCAAATAATGGT
ACAGATGTTAATGCGGGTCAGATACCTCAGTTATTATACAGACTTCCAACCAGTGATGGCAGTGCTTCA
AAAGGCAAACAGCAAACCAGTGAACCTGTACACATTTTAAAGAGGTCTTTTGCAAGAACTGTCTCAGTG
GAATGTTTTGAGTCATTGTTGAGTATTCTTCACTGGAGCTGGACCACCTTAGTCTTAGGAGTT

FIGURE 13B
(SEQ ID No.25)

ATATTTGCCACAAGCACTGAACCTGTTCTACAGCAAGAATTGCAACTTAAACTGGCTAGAAAATGCTTA
CATGCCTGTCGTATCTCATTATTCGATCTGGAAAAGGACTTGCATATTATAAGTACAGGATTTGATGAG
GAGTCAGCAATTCTTGGTGCAGGACGAGAGTTTGCGCTAATGAAAACAGCAAATGGAAAGATATATTAC
ACTGGCAAATACCAGAGTCTTGGAATCAAACAAGGTGGTCCTTCAGCAGGAAAATGGGTTGAGCTACCA
ATTACAAAATCTCCAAAGATAGTACACTTCTCAGTTGGACACGATGGCTCTCACGCCCTTTTAGTTGCA
GAAGATGGGAGCATATTCTTTACAGGATCTGCTAGTAAAGGAGAAGATGGAGAATCAATTAAGAGCAGA
CGGCAATCCAAACCTTATAAACCTAAAAAGATAATTAAGATGGAAGGAAAGATTGTGGTATATACAGCC
TGCAATAATGGAAGTAGTTCTGTTATTTCTAAAGATGGAGAACTCTACATGTTTGGAAAAGATGCCATT

FIG. 13B (Cont.)

TACTCTGATAGTTCAAGTTTGGTAACTGATTTGAAGGGCCATTTTGTAACTCAGGTAGCTATGGGCAAA
GCTCACACTTGTGTTTTAATGAAGAATGGAGAGGTGTGGACATTTGGTGTAAATAATAAAGGACAGTGT
GGACGAGATACTGGTGCCATGAACCAAGGTGGGAAAGGGTTTGGAGTTGAAAATATGGCAACAGCAATG
GATGAAGACCTGGAAGAAGAACTAGATGAAAAAGATGAGAAGTCTATGATGTGCCCTCCAGGCATGCAC
AAATGGAAGCTGGAGCAGTGCATGGTTTGCACTGTCTGTGGAGACTGTACAGGTTATGGAGCCAGCTGT
GTCAGTAGTGGACGGCCAGACAGAGTCCCCGGAGGGATCTGTGGTTGTGGTTCCGGAGAATCTGGTTGT
GCTGTGTGTGGATGTTGCAAGGCCTGTGCAAGAGAGTTAGATGGTCAAGAGGCAAGACAAAGAGGAATT
CTTGATGCAGTGAAAGAAATGATACCTTTAGATCTTCTTTTAGCTGTCCCAGTGCCCGGGGTTAACATT
GAAGAACACCTTCAGTTACGACAAGAAGAAAAACGGCAACGTGTAATCAGAAGGCACAGATTAGAGGAA
GGAAGAGGCCCCCTTGTATTTGCTGGTCCTATTTTTATGAACCATCGAGAACAGGCTCTAGCCAGACTC
AGATCCCATCCAGCACACGTAAAGCATAAACGGGACAAGCACAAAGATGGAAGTGGAGAAAGAGGCGAA
AAGGATGCAAGCAAAATCACAACATACCCTCCAGGCTCTGTGCGATTTGACTGTGAGCTCCGGGCAGTC
CAAGTCAGCTGTGGATTTCACCATTCAGTGGTTTTAATGGAAAATGGAGATGTCTATACATTTGGTTAT
GGGCAGCATGGGCAGCTAGGACATGGAGATGTCAACTCCAGGGGATGTCCCACTCTTGTTCAAGCATTG
CCAGGCCCTAGCACACAAGTCACTGCAGGCAGCAACCATACGGCAGTACTTTTAATGGATGGACAGGTC
TTCACATTTGGAAGTTTTTCTAAAGGACAACTGGGCAGACCAATTTTGGATGTGCCATATTGGAATGCA
AAGCCAGCTCCCATGCCTAACATTGGATCAAAATATGGAAGAAAAGCTACTTGGATAGGTGCAAGTGGG
GACCAAACTTTTTTACGAATTGATGAAGCACTTATTAATTCTCATGTACTTGCTACATCAGAAATTTTT
GCCAGTAAACACATAATAGGCTTGGTACCTGCTTCTATATCAGAACCTCCTCCATTT

FIGURE 13C (SEQ ID No.26)

GGACGAGAGTTTGCGCTAATGAAAACAGCAAATGGAAAGATATATTACACTGGCAAATACCAGAGTCTT
GGAATCAAACAAGGTGGTCCTTCAGCAGGAAAATGGGTTGAGCTACCAATTACAAAATCTCCAAAGATA
GTACACTTCTCAGTTGGACACGATGGCTCTCACGCCCTTTTAGTTGCAGAAGATGGGAGCATATTCTTT
ACAGGATCTGCTAGTAAAGGAGAAGATGGAGAATCAATTAAGAGCAGACGGCAATCCAAACCTTATAAA
CCTAAAAAGATAATTAAGATGGAAGGAAAGATTGTGGTATATACAGCCTGCAATAATGGAAGTAGTTCT
GTTATTTCTAAAGATGGAGAACTCTACATGTTTGGAAAAGATGCCATTTACTCTGATAGTTCAAGTTTG
GTAACTGATTTGAAGGGCCATTTTGTAACTCAGGTAGCTATGGGCAAAGCTCACACTTGTGTTTTAATG
AAGAATGGAGAGGTGTGGACATTTGGTGTAAATAATAAAGGACAGTGTGGACGAGATACTGGTGCCATG
AACCAAGGTGGGAAAGGGTTTGGAGTTGAAAATATGGCAACAGCAATGGATGAAGACCTGGAAGAAGAA
CTAGATGAAAAAGATGAGAAGTCTATGATGTGCCCTCCAGGCATGCACAAATGGAAGCTGGAGCAGTGC

FIG. 13C (Cont.)

ATGGTTTGCACTGTCTGTGGAGACTGTACAGGTTATGGAGCCAGCTGTGTCAGTAGTGGACGGCCAGAC
AGAGTCCCCGGAGGGATCTGTGGTTGTGGTTCCGGAGAATCTGGTTGTGCTGTGTGTGGATGTTGCAAG
GCCTGTGCAAGAGAGTTAGATGGTCAAGAGGCAAGACAAAGAGGAATTCTTGATGCAGTGAAAGAAATG
ATACCTTTAGATCTTCTTTTAGCTGTCCCAGTGCCCGGGGTTAACATTGAAGAACACCTTCAGTTACGA
CAAGAAGAAAAACGGCAACGTGTAATCAGAAGGCACAGATTAGAGGAAGGAAGAGGCCCCCTTGTATTT
GCTGGTCCTATTTTTATGAACCATCGAGAACAGGCTCTAGCCAGACTCAGATCCCATCCAGCACACGTA
AAGCATAAACGGGACAAGCACAAAGATGGAAGTGGAGAAAGAGGCGAAAAGGATGCAAGCAAAATCACA
ACATACCCTCCAGGCTCTGTGCGATTTGACTGTGAGCTCCGGGCAGTCCAAGTCAGCTGTGGATTTCAC
CATTCAGTGGTTTTAATGGAAAATGGAGATGTCTATACATTTGGTTATGGGCAGCATGGGCAGCTAGGA
CATGGAGATGTCAACTCCAGGGGATGTCCCACTCTTGTTCAAGCATTGCCAGGCCCTAGCACACAAGTC
ACTGCAGGCAGCAACCATACGGCAGTACTTTTAATGGATGGACAGGTCTTCACATTTGGAAGTTTTTCT
AAAGGACAACTGGGCAGACCAATTTTGGATGTGCCATATTGGAATGCAAAGCCAGCTCCCATGCCTAAC
ATTGGATCAAAATATGGAAGAAAAGCTACTTGGATAGGTGCAAGTGGGGACCAAACTTTTTTACGAATT
GATGAAGCACTTATTAATTCTCATGTACTTGCTACATCAGAAATTTTTGCCAGTAAACACATAATAGGC
TTGGTACCTGCTTCTATATCAGAACCTCCTCCATTTAAATGCCTT

FIGURE 13D
(SEQ ID No.27)

GCTCCCATGCCTAACATTGGATCAAAATATGGAAGAAAAGCTACTTGGATAGGTGCAAGTGGGGACCAA
ACTTTTTTACGAATTGATGAAGCACTTATTAATTCTCATGTACTTGCTACATCAGAAATTTTTGCCAGT
AAACACATAATAGGCTTGGTACCTGCTTCTATATCAGAACCTCCTCCATTTAAATGCCTTCTGATAAAT
AAAGTGGATGGGAGTTGTAAAACTTTTAATGACTCAGAACAAGAGGATCTGCAAGGATTTGGTGTGTGT
CTTGATCCTGTATATGATGTAATTTGGAGGTTTCGACCAAATACTAGAGAGCTGTGGTGTTACAATGCG
GTGGTTGCTGATGCCAGGCTTCCCTCTGCAGCAGACATGCAGTCCAGATGTAGTATCCTAAGTCCTGAA
CTTGCCTTACCAACAGGATCAAGGGCCCTCACTACCCGATCTCATGCAGCTTTGCACATTTTAGGTTGT
CTTGATACCTTGGCAGCTATGCAGGACTTAAAAATGGGTGTTGCAAGTACAGAGGAAGAGACTCAAGCA
GTAATGAAGGTTTATTCTAAAGAAGATTATAGTGTGGTAAACAGGTTTGAAAGTCATGGAGGAGGCTGG
GGTTATTCTGCCCATTCAGTAGAAGCTATACGTTTCAGTGCCGACACTGATATTTTACTTGGTGGTCTT
GGTCTGTTTGGAGGTAGAGGAGAATATACTGCTAAAATTAAGCTGTTTGAATTGGGTCCTGATGGAGGA
GATCATGAAACTGATGGTGACCTTCTTGCAGAGACTGATGTATTGGCTTATGACTGTGCTGCTAGAGAA
AAATATGCAATGATGTTTGATGAGCCTGTTCTCCTGCAAGCTGGGTGGTGGTATGTGGCATGGGCCCGA
GTGTCA

FIGURE 13E
(SEQ ID No.28)

GCTCCCATGCCTAACATTGGATCAAAATATGGAAGAAAAGCTACTTGGATAGGTGCAAGTGGGGACCAA
ACTTTTTTACGAATTGATGAAGCACTTATTAATTCTCATGTACTTGCTACATCAGAAATTTTTGCCAGT
AAACACATAATAGGCTTGGTACCTGCTTCTATATCAGAACCTCCTCCATTTAAATGCCTTCTGATAAAT
AAAGTGGATGGGAGTTGTAAAACTTTTAATGACTCAGAACAAGAGGATCTGCAAGGATTTGGTGTGTGT
CTTGATCCTGTATATGATGTAATTTGG

FIGURE 13F
(SEQ ID No.29)

GATGAAGCACTTATTAATTCTCATGTACTTGCTACATCAGAAATTTTTGCCAGTAAACACATAATAGGC
TTGGTACCTGCTTCTATATCAGAACCTCCTCCATTTAAATGCCTTCTGATAAATAAAGTGGATGGGAGT
TGTAAAACTTTTAATGACTCAGAACAAGAGGATCTGCAAGGATTTGGTGTGTGTCTTGATCCTGTATAT
GATGTAATTTGGAGGTTTCGACCAAATACTAGAGAGCTGTGGTGTTACAATGCGGTGGTTGCTGATGCC
AGGCTTCCCTCTGCAGCAGACATGCAGTCCAGATGTAGTATCCTAAGTCCTGAACTTGCCTTACCAACA
GGATCAAGGGCCCTCACTACCCGATCTCATGCAGCTTTGCACATTTTAGGTTGTCTTGATACCTTGGCA
GCTATGCAGGACTTAAAAATGGGTGTTGCAAGTACAGAGGAAGAGACTCAAGCAGTAATGAAGGTTTAT
TCTAAAGAAGATTATAGTGTGGTAAACAGGTTTGAAAGTCATGGAGGAGGCTGGGGTTATTCTGCCCAT
TCAGTAGAAGCTATACGTTTCAGTGCCGACACTGATATTTTACTTGGTGGTCTTGGTCTG

FIGURE 13G
(SEQ ID No.30)

GATGAAGCACTTATTAATTCTCATGTACTTGCTACATCAGAAATTTTTGCCAGTAAACACATAATAGGC
TTGGTACCTGCTTCTATATCAGAACCTCCTCCATTTAAATGCCTTCTG sphingosine-1-phosphate

FIGURE 16A (SEQ ID NO:31)

MGPTSVPLVKAHRSSVSDYVNYDIIVRHYNYTGKLNISADKENSIKLTSVVFILICCFIILENIFVLL
TIWKTKKFHRPMYYFIGNLALSDLLAGVAYTANLLLSGATTYKLTPAQWFLREGSMFVALSASVFSLL
AIAIERYITMLKMKLHNGSNNFRLFLLISACWVISLILGGLPIMGWNCISALSSCSTVLPLYHKHYIL
FCTTVFTLLLLSIVILYCRIYSLVRTRSRRLTFRKNISKASRSSEKSLALLKTVIIVLSVFIACWAPL
FILLLLDVGCKVKTCDILFRAEYFLVLAVLNSGTNPIIYTLTNKEMRRAFIRIMSCCKCPSGDSAGKF
KRPIIAGMEFSRSKSDNSSHPQKDEGDNPETIMSSGNVNSSS

FIGURE 16B (SEQ ID NO:32)

Coding sequence: 244 to 1392

1 gtcgggggca gcagcaagat gcgaagcgag ccgtacagat cccgggctct ccgaacgcaa
61 cttcgccctg cttgagcgag gctgcggttt ccgaggccct ctccagccaa ggaaaagcta
121 cacaaaaagc ctggatcact catcgaacca cccctgaagc cagtgaaggc tctctcgcct
181 cgccctctag cgttcgtctg gagtagcgcc accccggctt cctggggaca cagggttggc
241 accatggggc ccaccagcgt cccgctggtc aaggcccacc gcagctcggt ctctgactac
301 gtcaactatg atatcatcgt ccggcattac aactacacgg gaaagctgaa tatcagcgcg
361 gacaaggaga acagcattaa actgacctcg gtggtgttca ttctcatctg ctgctttatc
421 atcctggaga acatctttgt cttgctgacc atttggaaaa ccaagaaatt ccaccgaccc
481 atgtactatt ttattggcaa tctggccctc tcagacctgt tggcaggagt agcctacaca
541 gctaacctgc tcttgtctgg ggccaccacc tacaagctca ctcccgccca gtggtttctg
601 cgggaaggga gtatgtttgt ggccctgtca gcctccgtgt tcagtctcct cgccatcgcc
661 attgagcgct atatcacaat gctgaaaatg aaactccaca acgggagcaa taacttccgc
721 ctcttcctgc taatcagcgc ctgctgggtc atctccctca tcctgggtgg cctgcctatc
781 atgggctgga actgcatcag tgcgctgtcc agctgctcca ccgtgctgcc gctctaccac
841 aagcactata tcctcttctg caccacggtc ttcactctgc ttctgctctc catcgtcatt
901 ctgtactgca gaatctactc cttggtcagg actcggagcc gccgcctgac gttccgcaag
961 aacatttcca aggccagccg cagctctgag aagtcgctgg cgctgctcaa gaccgtaatt
1021atcgtcctga gcgtcttcat cgcctgctgg gcaccgctct tcatcctgct cctgctggat
1081 gtgggctgca aggtgaagac ctgtgacatc ctcttcagag cggagtactt cctggtgtta

FIG. 16B (Cont.)

1141 gctgtgctca actccggcac caaccccatc atttacactc tgaccaacaa ggagatgcgt
1201 cgggccttca tccggatcat gtcctgctgc aagtgcccga gcggagactc tgctggcaaa
1261 ttcaagcgac ccatcatcgc cggcatggaa ttcagccgca gcaaatcgga caattcctcc
1321 cacccccaga aagacgaagg ggacaaccca gagaccatta tgtcttctgg aaacgtcaac
1381 tcttcttcct agaactggaa gctgtccacc caccggaagc gctctttact tggtcgctgg
1441 ccacccccagt gtttggaaaa aaatctctgg gcttcgactg ctgccaggga ggagctgctg
1501 caagccagag ggaggaaggg ggagaatacg aacagcctgg tggtgtcggg tgttggtggg
1561 tagagttagt tcctgtgaac aatgcactgg gaagggtgga gatcaggtcc cggcctggaa
1621 tatatattct acccccctgg agctttgatt ttgcactgag ccaaaggtct agcattgtca
1681 agctcctaaa gggttcattt ggcccctcct caaagactaa tgtccccatg tgaaagcgtc
1741 tctttgtctg gagctttgag gagatgtttt ccttcacttt agtttcaaac ccaagtgagt
1801 gtgtgcactt ctgcttcttt agggatgccc tgtacatccc acacccccacc ctcccttccc
1861 ttcatacccc tccctcaacgt tcttttactt tatactttaa ctacctgaga gttatcagag
1921 ctggggttgt ggaatgatcg atcatctata gcaaataggc tatgttgagt acgtaggctg
1981 tgggaagatg aagatggttt ggaggtgtaa aacaatgtcc ttcgctgagg ccaaagtttc
2041 catgtaagcg ggatccgttt tttggaattt ggttgaagtc actttgattt ctttaaaaaa
2101 catcttttca atgaaatgtg ttaccatttc atatccattg aagccgaaat ctgcataagg
2161 aagcccactt tatctaaatg atattagcca ggatccttgg tgtcctagga gaaacagaca
2221 agcaaaacaa agtgaaaacc gaatggatta acttttgcaa accaagggag atttcttagc
2281 aaatgagtct aacaaatatg acatccgtct ttcccacttt tgttgatgtt tatttcagaa
2341 tcttgtgtga ttcatttcaa gcaacaacat gttgtatttt gttgtgttaa aagtactttt
2401 cttgattttt gaatgtattt gtttcaggaa gaagtcattt tatggatttt tctaacccgt
2461 gttaactttt ctagaatcca ccctcttgtg cccttaagca ttactttaac tggtagggaa
2521 cgccagaact tttaagtcca gctattcatt agatagtaat tgaagatatg tataaatatt
2581 acaaagaata aaaatatatt actgtctctt tagtatggtt ttcagtgcaa ttaaaccgag
2641 agatgtcttg tttttttaaa aagaatagta tttaataggt ttctgacttt tgtggatcat
2701 tttgcacata gctttatcaa cttttaaaca ttaataaact gattttttta aag

FIGURE 16C (SEQ ID NO:33)

```
  1 mgslyseylnpnkvqehynytketletqettsrqvasafivilccaivvenllvliavar
 61 nskfhsamylflqnlaasdllagvafvantllsgsvtlrltpvqwfaregsasitlsasv
121 fsllaiaierhvaiakvklygsdkscrmllligaswlislvlgglpilgwnclghleacs
181 tvlplyakhyvlcvvtifsiillaivalyvriycvvrsshadmaapqtlallktvtivlg
241 vfivcwlpafsillldyacpvhscpilykahyffavstlnsllnpviytwrsrdlrrevl
301 rplqcwrpgvgvqgrrrvgtpghhllplrssssleqgmhmptsptfleqntvv
```

FIGURE 16D (SEQ ID NO:34)

```
   1 atgggcagct tgtactcgga gtacctgaac cccaacaagg tccaggaaca ctataattat
  61 accaaggaga cgctggaaac gcaggagacg acctcccgcc aggtggcctc ggccttcatc
 121 gtcatcctct gttgcgccat tgtggtggaa aaccttctgg tgctcattgc ggtggcccga
 181 aacagcaagt tccactcggc aatgtacctg tttctgggca acctggccgc ctccgatcta
 241 ctggcaggcg tggccttcgt agccaatacc ttgctctctg gctctgtcac gctgaggctg
 301 acgcctgtgc agtggtttgc ccgggagggc tctgcctcca tcacgctctc ggcctctgtc
 361 ttcagcctcc tggccatcgc cattgagcgc cacgtggcca ttgccaaggt caagctgtat
 421 ggcagcgaca agagctgccg catgcttctg ctcatcgggg cctcgtggct catctcgctg
 481 gtcctcggtg gcctgcccat ccttggctgg aactgcctgg gccacctcga ggcctgctcc
 541 actgtcctgc ctctctacgc caagcattat gtgctgtgcg tggtgaccat cttctccatc
 601 atcctgttgg ccatcgtggc cctgtacgtg cgcatctact gcgtggtccg ctcaagccac
 661 gctgacatgg ccgccccgca gacgctagcc ctgctcaaga cggtcaccat cgtgctaggc
 721 gtctttatcg tctgctggct gcccgccttc agcatcctcc ttctggacta tgcctgtccc
 781 gtccactcct gcccgatcct ctacaaagcc cactactttt tcgccgtctc caccctgaat
 841 tccctgctca accccgtcat ctacacgtgg cgcagccggg acctgcggcg ggaggtgctt
 901 cggccgctgc agtgctggcg gccgggggtg ggggtgcaag gacggaggcg ggtcgggacc
 961 ccgggccacc acctcctgcc actccgcagc tccagctccc tggagagggg catgcacatg
1021 cccacgtcac ccacgtttct ggagggcaac acggtggtct ga
```

FIGURE 16E (SEQ ID NO:35)

MATALPPRLQPVRGNETLREHYQYVGKLAGRLKEASEGSTLTTVLFLVICSFIVLENLMVLI
AIWKNNKFHNRMYFFIGNLALCDLLAGIAYKVNILMSGKKTFSLSPTVWFLREGSMFVALGA
STCSLLAIAIERHLTMIKMRPYDANKRHRVFLLIGMCWLIAFTLGALPILGWNCLHNLPDCS
TILPLYSKKYIAFCISIFTAILVTIVILYARIYFLVKSSSRKVANHNNSERSMALLRTVVIV
VSVFIACWSPLFILFLIDVACRVQACPILFKAQWFIVLAVLNSAMNPVIYTLASKEMRRAFF
RLVCNCLVRGRGARASPIQPALDPSRSKSSSSNNSSHSPKVKEDLPHTDPSSCIMDKNAALQ
NGIFCN

FIGURE 16F (SEQ ID NO:36)

1 atggcaactg ccctcccgcc gcgtctccag ccggtgcggg ggaacgagac cctgcgggag
61 cattaccagt acgtggggaa gttggcgggc aggctgaagg aggcctccga gggcagcacg
121 ctcaccaccg tgctcttctt ggtcatctgc agcttcatcg tcttggagaa cctgatggtt
181 ttgattgcca tctggaaaaa caataaattt cacaaccgca tgtacttttt cattggcaac
241 ctggctctct gcgacctgct ggccggcatc gcttacaagg tcaacattct gatgtctggc
301 aagaagacgt tcagcctgtc tcccacggtc tggttcctca gggagggcag tatgttcgtg
361 gcccttgggg cgtccacctg cagcttactg gccatcgcca tcgagcggca cttgacaatg
421 atcaaaatga ggccttacga cgccaacaag aggcaccgcg tcttcctcct gatcgggatg
481 tgctggctca ttgccttcac gctgggcgcc ctgcccattc tgggctggaa ctgcctgcac
541 aatctccctg actgctctac catcctgccc ctctactcca agaagtacat tgccttctgc
601 atcagcatct tcacggccat cctggtgacc atcgtgatcc tctacgcacg catctacttc
661 ctggtgaagt ccagcagccg taaggtggcc aaccacaaca actcggagcg gtccatggca
721 ctgctgcgga ccgtggtgat tgtggtgagc gtgttcatcg cctgctggtc cccactcttc
781 atcctcttcc tcattgatgt ggcctgcagg gtgcaggcgt gccccatcct cttcaaggct
841 cagtggttca tcgtgttggc tgtgctcaac tccgccatga acccggtcat ctacacgctg
901 gccagcaagg agatgcggcg ggccttcttc cgtctggtct gcaactgcct ggtcagggga
961 cggggggccc gcgcctcacc catccagcct gcgctcgacc caagcagaag taaatcaagc
1021agcagcaaca atagcagcca ctctccgaag gtcaaggaag acctgcccca cacagacccc
1081tcatcctgca tcatggacaa gaacgcagca cttcagaatg ggatcttctg caactga

FIGURE 16G (SEQ ID NO:37)

MNATGTPVAPESCQQLAAGGHSRLIVLHYNHSGRLAGRGGPEDGGLGALRGLSVAASCLVVL
ENLLVLAAITSHMRSRRWVYYCLVNITLSDLLTGAAYLANVLLSGARTFRLAPAQWFLREGL
LFTALAASTFSLLFTAGERFATMVRPVAESGATKTSRVYGFIGLCWLLAALLGMLPLLGWNC
LCAFDRCSSLLPLYSKRYILFCLVIFAGVLATIMGLYGAIFRLVQASGQKAPRPAARRKARR
LLKTVLMILLAFLVCWGPLFGLLLADVFGSNLWAQEYLRGMDWILALAVLNSAVNPIIYSFR
SREVCRAVLSFLCCGCLRLGMRGPGDCLARAVEAHSGASTTDSSLRPRDSFRGSRSLSFRMR
EPLSSISSVRSI

FIGURE 16H (SEQ ID NO:38)

1 gagtcagccc ccgggggagg ccatgaacgc cacggggacc ccggtggccc ccgagtcctg
61 ccaacagctg gcggccggcg ggcacagccg gctcattgtt ctgcactaca accactcggg
121 ccggctggcc gggcgcgggg ggccggagga tggcggcctg ggggccctgc gggggctgtc
181 ggtggccgcc agctgcctgg tggtgctgga gaacttgctg gtgctggcgg ccatcaccag
241 ccacatgcgg tcgcgacgct gggtctacta ttgcctggtg aacatcacgc tgagtgacct
301 gctcacgggc gcggcctacc tggccaacgt gctgctgtcg ggggcccgca ccttccgtct
361 ggcgcccgcc cagtggttcc tacgggaggg cctgctcttc accgccctgg ccgcctccac
421 cttcagcctg ctcttcactg caggggagcg ctttgccacc atggtgcggc cggtggccga
481 gagcggggcc accaagacca gccgcgtcta cggcttcatc ggcctctgct ggctgctggc
541 cgcgctgctg gggatgctgc ctttgctggg ctggaactgc ctgtgcgcct ttgaccgctg
601 ctccagcctt ctgcccctct actccaagcg ctacatcctc ttctgcctgg tgatcttcgc
661 cggcgtcctg gccaccatca tgggcctcta tggggccatc ttccgcctgg tgcaggccag
721 cgggcagaag gcccccaggcc cagcggcccg ccgcaaggcc cgccgcctgc tgaagacggt
781 gctgatgatc ctgctggcct tcctggtgtg ctggggccca ctcttcgggc tgctgctggc
841 cgacgtcttt ggctccaacc tctgggccca ggagtacctg cggggcatgg actggatcct
901 ggccctggcc gtcctcaact cggcggtcaa ccccatcatc tactccttcc gcagcaggga
961 ggtgtgcaga gccgtgctca gcttcctctg ctgcgggtgt ctccggctgg gcatgcgagg
1021 gcccggggac tgcctggccc gggccgtcga ggctcactcc ggagcttcca ccaccgacag
1081 ctctctgagg ccaagggaca gctttcgcgg ctcccgctcg ctcagctttc ggatgcggga
1141 gcccctgtcc agcatctcca gcgtgcggag catctgaagt tgcagtcttg cgtgtggatg
1201 gtgcagccac cgggtgcgtg ccaggcaggc cctcctgggg tacaggaagc tgtgtgcacg

FIG. 16H (Cont.)

1261 cagcctcgcc tgtatgggga gcagggaacg ggacaggccc ccatggtctt cccggtggcc
1321 tctcggggct tctgacgcca aatgggcttc ccatggtcac cctggacaag gaggtaacca
1381 ccccacctcc ccgtaggagc agagagcacc ctggtgtggg ggcgagtggt tccccacaac
1441 cccgcttctg tgtgattctg gggaagtccc ggcccctctc tgggcctcag tagggctccc
1501 aggctgcaag gggtggactg tgggatgcat gccctggcaa cattgaagtt cgatcatggt
1561 aaaaaa

FIGURE 16I (SEQ ID NO:39)

MESGLLRPAPVSEVIVLHYNYTGKLRGARYQPGAGLRADAVVCLAVCAFIVLENLAVLLVLG
RHPRFHAPMFLLLGSLTLSDLLAGAAYAANILLSGPLTLKLSPALWFAREGGVFVALTASVL
SLLAIALERSLTMARRGPAPVSSRGRTLAMAAAAWGVSLLLGLLPALGWNCLGRLDACSTVL
PLYAKAYVLFCVLAFVGILAAICALYARIYCQVRANARRLPARPGTAGTTSTRARRKPRSLA
LLRTLSVVLLAFVACWGPLFLLLLLDVACPARTCPVLLQADPFLGLAMANSLLNPIIYTLTN
RDLRHALLRLVCCGRHSCGRDPSGSQQSASAAEASGGLRRCLPPGLDGSFSGSERSSPQRDG
LDTSGSTGSPGAPTAARTLVSEPAAD

FIGURE 16J (SEQ ID NO:40)

1 gcgcggccca tggagtcggg gctgctgcgg ccggcgccgg tgagcgaggt catcgtcctg
61 cattacaact acaccggcaa gctccgcggt gcgcgctacc agccgggtgc cggcctgcgc
121 gccgacgccg tggtgtgcct ggcggtgtgc gccttcatcg tgctagagaa tctagccgtg
181 ttgttggtgc tcggacgcca cccgcgcttc cacgctccca tgttcctgct cctgggcagc
241 ctcacgttgt cggatctgct ggcaggcgcc gcctacgccg ccaacatcct actgtcgggg
301 ccgctcacgc tgaaactgtc ccccgcgctc tggttcgcac gggagggagg cgtcttcgtg
361 gcactcactg cgtccgtgct gagcctcctg gccatcgcgc tggagcgcag cctcaccatg
421 gcgcgcaggg ggcccgcgcc cgtctccagt cgggggcgca cgctggcgat ggcagccgcg
481 gcctggggcg tgtcgctgct cctcgggctc ctgccagcgc tgggctggaa ttgcctgggt
541 cgcctggacg cttgctccac tgtcttgccg ctctacgcca aggcctacgt gctcttctgc

FIG. 16J (Cont.)

```
601 gtgctcgcct tcgtgggcat cctggccgcg atctgtgcac tctacgcgcg catctactgc
 661 caggtacgcg ccaacgcgcg gcgcctgccg gcacggcccg ggactgcggg gaccacctcg
 721 acccgggcgc gtcgcaagcc gcgctcgctg gccttgctgc gcacgctcag cgtggtgctc
 781 ctggcctttg tggcatgttg ggcccccctc ttcctgctgc tgttgctcga cgtggcgtgc
 841 ccggcgcgca cctgtcctgt actcctgcag gccgatccct tcctgggact ggccatggcc
 901 aactcacttc tgaaccccat catctacacg ctcaccaacc gcgacctgcg ccacgcgctc
 961 ctgcgcctgg tctgctgcgg acgccactcc tgcggcagag acccgagtgg ctcccagcag
1021 tcggcgagcg cggctgaggc ttccgggggc ctgcgccgct gcctgccccc gggccttgat
1081 gggagcttca gcggctcgga gcgctcatcg ccccagcgcg acgggctgga caccagcggc
1141 tccacaggca gccccggtgc acccacagcc gcccggactc tggtatcaga acgggctgca
1201 gactgacacc ctcggcccac gactgtcttc ccaagtttta cagacttgtt ctttttacat
1261 aaaggaattt gtaggaaatg cagccaaagg tgcagtcgga aaagatgcag ggaaatgta
1321 tttatgcagc gacaccccac aatgtgaaca aacagacaaa aaatctgtgc cctcgtggaa
1381 ttgacgttct gcttgggaac acagaaaaga actcggtgat gaaataatgg agatgattcc
1441 agtgacaaac gacagagatg gtgatggtgg tcagggaaga cctctctgca gaggtagtga
1501 cttgtgatgt gagctgagac ctctgtcctg ggaagaccaa aagaaaagca tttcaggatg
1561 agggaatggc atgcgcaaag gccctgaggc tgaaatgtgc ccatgtgttc taagaaatgc
1621 agcgatgctg gtgtgcctgg agcagggacg gagggggaga atgggaggag acaaggagct
1681 gaaggagtag ttcccgaagg accttgtggg tgatatagag gacttcgctt ttgctctgag
1741 tgaggtggga gccatagaag cttctaagca gaagagggac ttgccctaat tcaggtgatc
1801 acaggtgtct tgtggcctcc atgggaggtt gaaaaccaca gaaggtgaag gggggctgca
1861 ctgagccaca ggaacaatga tggagattcc agctaagccc agaccccgtg gattctagat
1921 agattttaga ggcagcagac agaattactg aggaattgag tgtaagagtg gaataaagtt
1981 atcaaggaca atgccaaggg tggggcaccc ccaaatttga ctttgggaga ctcagccaaa
2041 tcctatctgg taataaaatt tctttttttat ttttcttttc tttctttctt tcttttcttc
2101 tttttttttt tttgagttgg gatcttgtgc tctgtcaccc aggctggagt gcaatgggca
2161 caattatagc tcactgcagc ctggaactcc tgggatcaag cctggagttc ctgcttcagc
2221 ctccctagta gctgggacta caggcatgca ccaccatgcc cagttaataa aatttcttca
2281 aatgcaaaa aaaaaaaaa aaaaaa
```

FTY720
2-Amino-2-[2-(4-octylphenyl)ethyl]propane-1,3-diol
hydrochloride

A) B)

D)

Pain behaviour of adult rats in the formalin test with and without 10 µM S1P

METHOD FOR ALLEVIATING PAIN USING SPHINGOSINE-1-PHOSPHATE AND RELATED COMPOUNDS, AND ASSAYS FOR IDENTIFYING SUCH COMPOUNDS

BACKGROUND OF THE INVENTION

The invention concerns the use of S1P (Sphingosine-1-Phosphate). Other aspects of the invention concern a method for screening pharmaceuticals and methods for the treatment of pain.

Pain is a complex subjective sensation reflecting real or potential tissue damage and the affective response to it. Acute pain is a physiological signal indicating a potential or actual injury. Chronic pain can either be somatogenetic (organic) or psychogenic. Chronic pain is frequently accompanied or followed by vegetative signs, which often result in depression.

Somatogenetic pain may be of nociceptive origin, inflammatory or neuropathic. Nociceptive pain is judged to be commensurate with ongoing activation of somatic or visceral pain-sensitive nerve fibers. Neuropathic pain results from dysfunction in the nervous system; it is believed to be sustained by aberrant somatosensory processes in the peripheral nervous system, the CNS, or both. (For an overview of pain mechanisms, see for example Scholz and Woolf, 2002; Julius and Basbaum, 2001, Woolf and Mannion, 1999; Wood, J. D., 2000; Woolf and Salter, 2000.)

Chronic pain results in individual suffering and social economic costs of tremendous extent. Existing pharmacological pain therapies are widely unsatisfying both in terms of efficacy and of safety.

Up to now, two classes of analgesics are mainly employed for the treatment of pain: Non-opioid analgesics, mostly acetaminophen and NSAIDS (non-steroidal anti-inflammatory drugs) and opioid (narcotic) agonists (wherein "opioid" is a generic term for natural or synthetic substances that bind to specific opioid receptors in the CNS, producing an agonist action). Unfortunately both analgesic classes, opioids and non-opioids, have several unwanted side effects. The most serious side effects of opioids are the possibility of inhibition of the respiratory system and after long-term treatment the possibility of addiction (Schaible H. G., Vanegas H., 2000). NSAIDs, a major class of non-opioids, on the other hand, can induce a variety of gastrointestinal complications such as ulcers and bleeding, but also kidney damage (Schaible H. G., Vanegas H., 2000). It has been estimated that in the U.S.A. about 16.000 patients die every year because of severe gastrointestinal complications caused by conventional NSAIDs.

In light of the severe drawbacks connected with state of the art pain treatments, there is a great need for novel classes of pain modulating drugs. Especially in light of the vast gap between the fast advancing understanding of the neurobiology of pain and the unmet clinical need to provide effective treatments without the drawbacks of state of the art treatments, efforts need to be directed to the discovery of new targets for novel classes of analgesics. Thus, it is the object of the present invention to provide a new means for the development and provision of a new class of pain modulating drugs.

This object is solved by the use of S1P or functional fragments or derivatives thereof for the preparation of pharmaceutical compounds that alleviate pain.

DESCRIPTION OF THE FIGURES

FIG. 2: PAM is expressed in DRG neurons as well as in neuronal cells in rat spinal cord.

Panel A: RT-PCR analysis with RNA (40 ng) of spinal cords from control animals or animals treated with zymosan after 24 h, 48 h and 96 h. The lower panel shows the mean±SEM of 7 experiments. Student T test: *$p<0.001$.

Panel B: Western blot analysis using a 7% SDS-PAGE gel with rat spinal cord lysates of control animals or animals treated with zymosan after 24 h, 48 h and 96 h (40 μg) with anti-PAM antibody and anti-ERK1/2.

Panel C: Quantitative RT-PCR analysis with RNA (40 ng) of spinal cords from control animals or animals treated with formalin for 1 hour.

Figure 5:
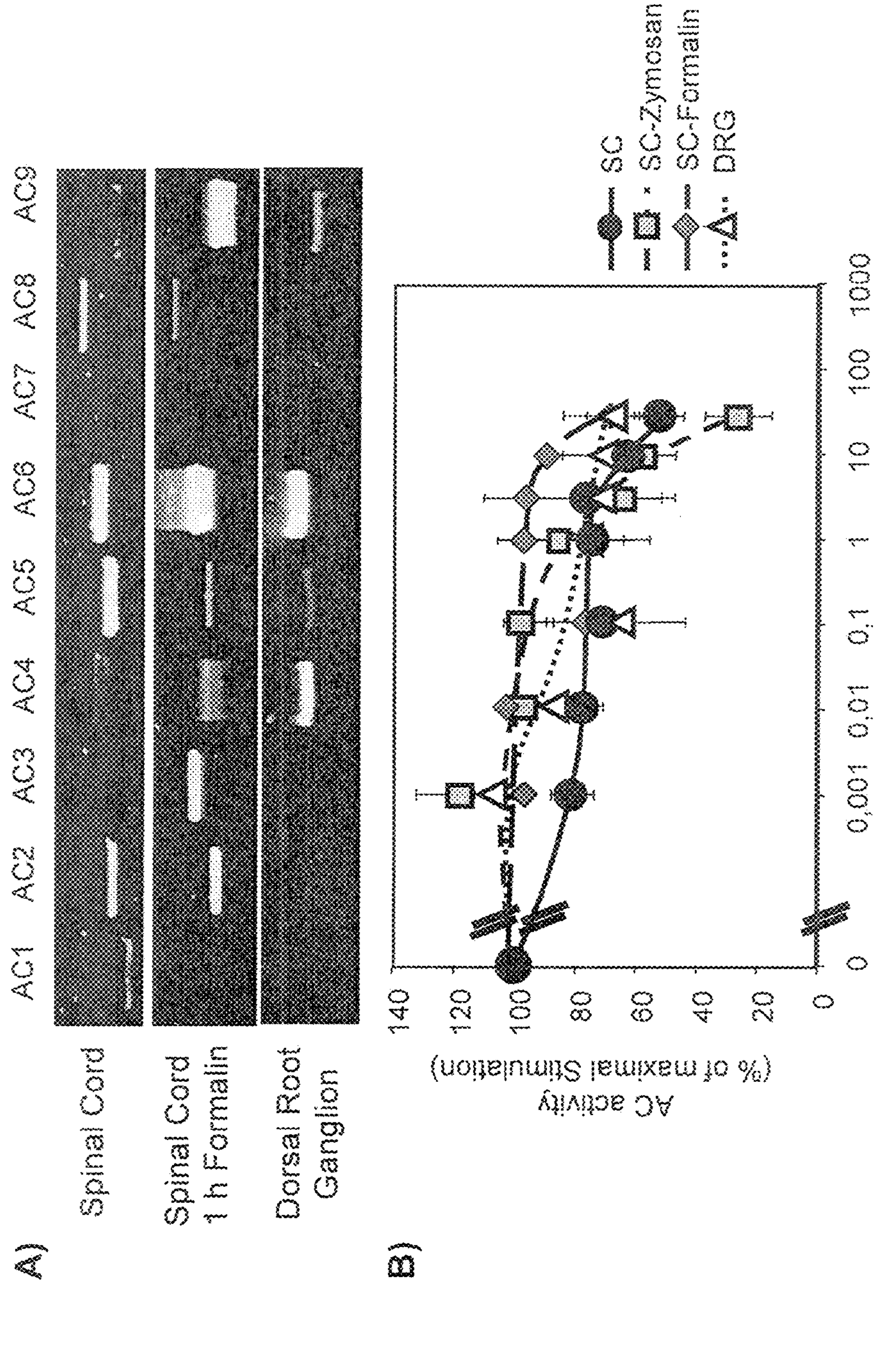

FIG. 5: PAM inhibits Gαs-stimulated AC activity in spinal cord lysates.

Panel A: RT-PCR was used to determine AC isoform expression in spinal cord and DRG RNA (40 ng).

Panel B: Lysates of spinal cords or DRG (10 μg) were assayed for AC activity in the presence of 80 nM Gαs as described in Material and Methods. The mean±SEM of at least 3 determinations done in triplicates is shown.

Figure 6A:
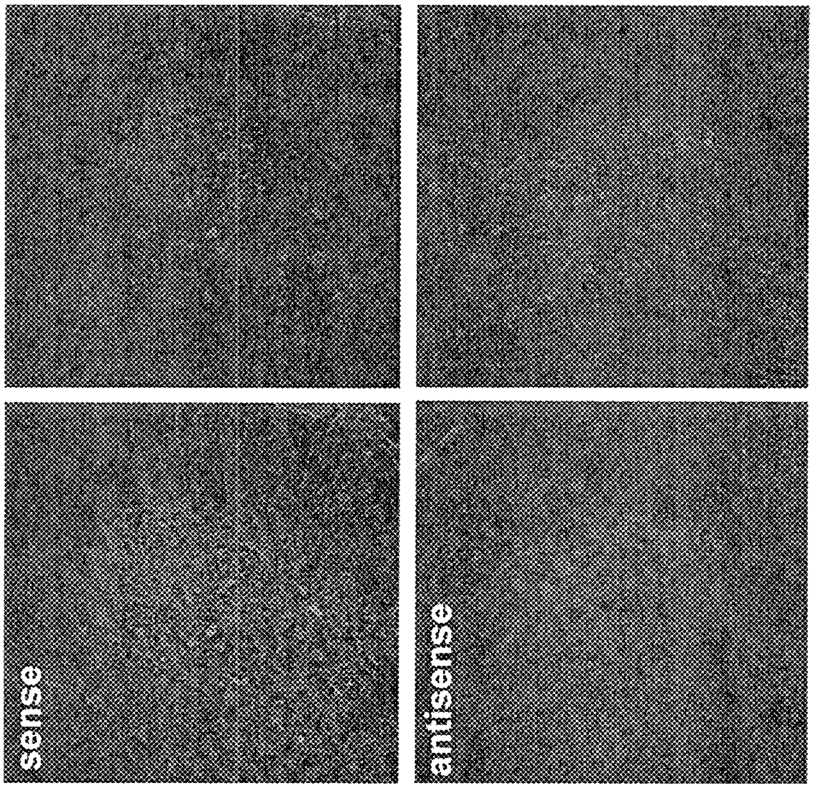
Figure 6:
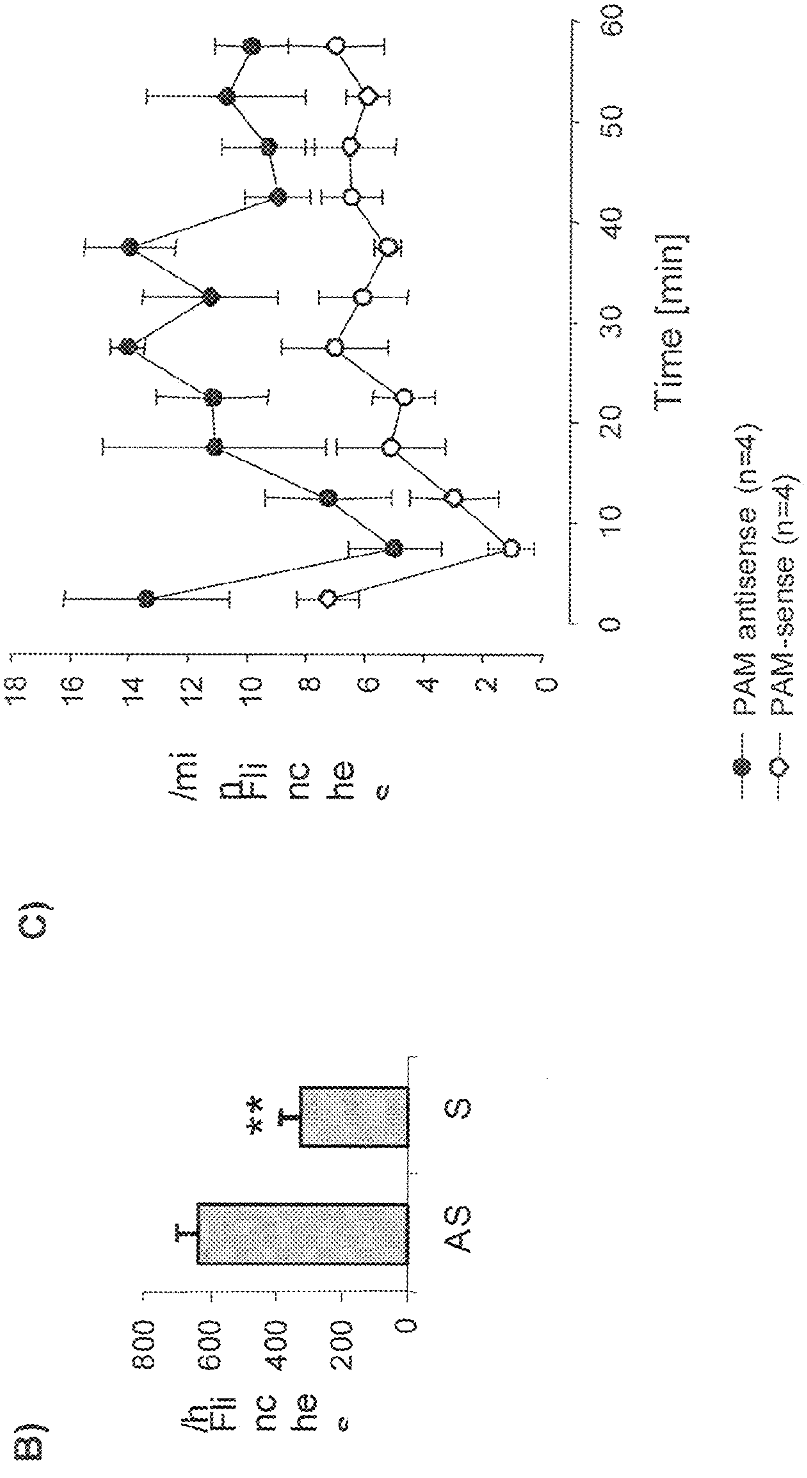

FIG. 6: Intrathecal application of antisense ODNs against PAM increases nociceptive behavior.

Panel A: Adult rats were given intrathecal sense and antisense ODN as described. After formalin treatment, the spinal cord was removed and subjected to immunohistological analysis using anti-PAM antibodies (green) or anti NeuN (red).

Panel B: Formalin assay of animals treated with sense or antisense ODNs as described in the material section. The total amount of flinches over 1 hour is shown. The mean±SE of at least 4 determinations is shown.

Panel C: Formalin assay of animals treated with sense or antisense ODNs as described in the material section. The number of flinches during 1 hour is shown. The mean±SE of at least 4 determinations is shown.

FIG. 7: Protein (FIG. 7B), genomic (FIG. 7C) and coding nucleotide sequence of human PAM (FIG. 7A) according to NCBI accession numbers AAC39928 (protein sequence; SEQ ID No. 1), AF075587 (coding sequence; SEQ ID No. 2). Human PAM is located on Chromosome 13q22; its genomic sequence is publicly available under NT_024524.11 (Start: position 24679861; Stop: position 24962245; SEQ ID No 3); FIG. 7C shows the contiguous sequence from position 24679861 to position 24962245.

FIG. 8: EST-clone coding sequences for rat PAM:

FIG. 8A: AW921303 (corresponds to by 960-1394 of hs cDNA; SEQ ID No. 4)

FIG. 8B: AW918711 (corresponds to by 8188-8632 of hs cDNA; SEQ ID No. 5)

FIG. 8C: BQ201485 (corresponds to by 8966-9633 of hs cDNA; SEQ ID No. 6)

FIG. 8D: BE112881 (corresponds to by 10311-10830 of hs cDNA; SEQ Id No. 7)

FIG. 8E: AW441131 (corresponds to by 13569-14152 of hs cDNA; SEQ ID No. 8)

FIG. 8F: BF409872 (corresponds to by 13569-14807 of hs cDNA). (SEQ ID No. 9)

Figure 9:
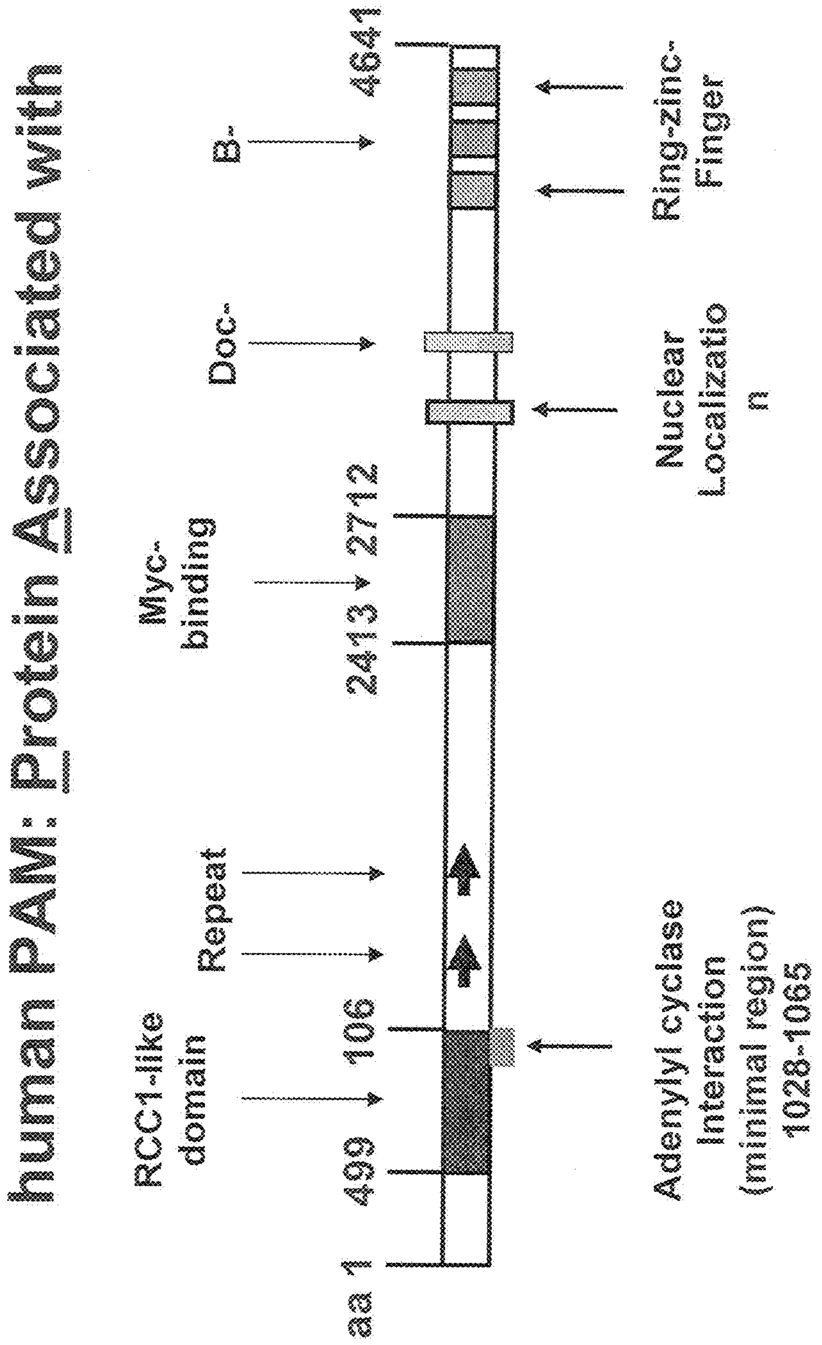

FIG. 9: Overview of domain structure of human PAM according to Guo et al., 1988/Grossberger et al., JBC 1999 and Scholich et al., JBC 2001)

FIG. 10: PCR Primers for rat PAM RT PCR.

FIG. 11: Antisense Oligodeoxynucleotides for inhibiting rat PAM expression and control oligonucleotide.

FIG. 12: Different PAM hs polypeptides for the use in the context of present invention. The polypeptides are fragments derived from the polypeptide according to SEQ ID No. 2.

FIG. 13: Different PAM hs polynucleotides for the use in the context of present invention.

Figure 14:
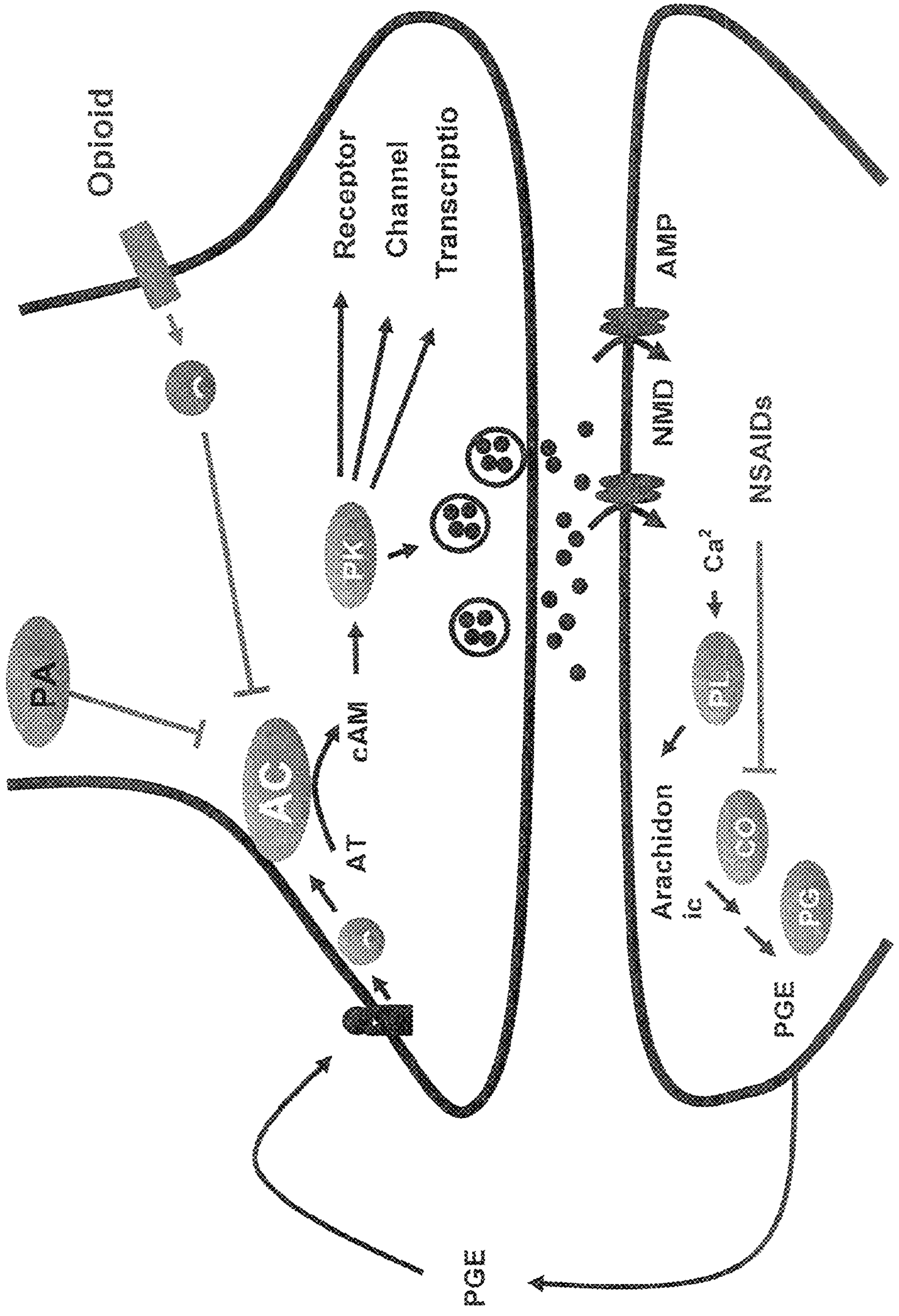

FIG. 13A: cDNA sequence coding for the protein fragment according to SEQ ID No. 17 comprising nucleotide positions 1317 to 4366 of hs Pam cDNA (SEQ ID No. 24);

FIG. 13B: cDNA sequence coding for the protein fragment according to SEQ ID No. 18 comprising nucleotide positions 1482 to 3332 of hs Pam cDNA (SEQ ID No. 25);

FIG. 13C: cDNA sequence coding for the protein fragment according to SEQ ID No. 19 comprising nucleotide positions 1641 to 3341 of hs Pam cDNA (SEQ ID No. 26);

FIG. 13D: cDNA sequence coding for the protein fragment according to SEQ ID No. 20 comprising nucleotide positions 3142 to 4046 of hs Pam cDNA (SEQ ID No. 27);

FIG. 13E: cDNA sequence coding for the protein fragment according to SEQ ID No. 21 comprising nucleotide positions 3142 to 3446 of hs Pam cDNA (SEQ ID No. 28);

FIG. 13F: cDNA sequence coding for the protein fragment according to SEQ ID No. 22 comprising nucleotide positions 3228 to 3839 of hs Pam cDNA (SEQ ID No. 29);

FIG. 13G: cDNA sequence coding for the protein fragment according to SEQ ID No. 23 comprising nucleotide positions 3228 to 3341 of hs Pam cDNA (SEQ ID No. 30);

FIG. 14: PAM signaling according to the above findings.

Figure 15:
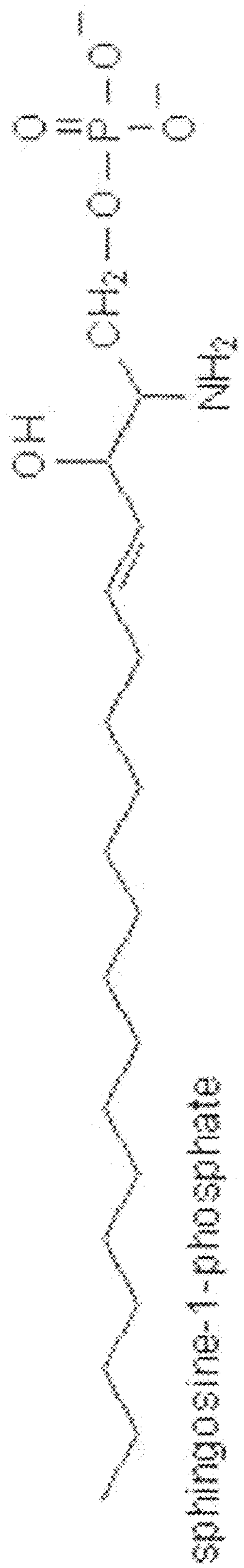

FIG. 15: Structure of Sphingosine-1-Phosphate.

FIG. 16: mDNA and amino acid sequences of S1P receptors:

FIG. 16A: amino acid sequence of $S1P_1$ (SEQ ID No. 31);

FIG. 16B: mRNA sequence of $S1P_1$ (SEQ ID No. 32); the coding sequence starts at position 244 and ends at position 1392;

FIG. 16C: amino acid sequence of $S1P_2$ (SEQ ID No. 33);

FIG. 16D: mRNA sequence of $S1P_2$ (SEQ ID No. 34); the coding sequence starts at position 1 and ends at position 1062;

FIG. 16E: amino acid sequence of $S1P_3$ (SEQ ID No. 35)

FIG. 16F: mRNA sequence of $S1P_3$ (SEQ ID No. 36), the coding sequence starts at position 1 and ends at position 1137;

FIG. 16G: amino acid sequence of $S1P_4$ (SEQ ID No. 37)

16*h*) mRNA sequence of $S1P_4$ (SEQ ID No. 38), the coding sequence starts at position 23 and ends at position 1177;

FIG. 16I: amino acid sequence of $S1P_5$ (SEQ ID No. 39)

Figure 17:
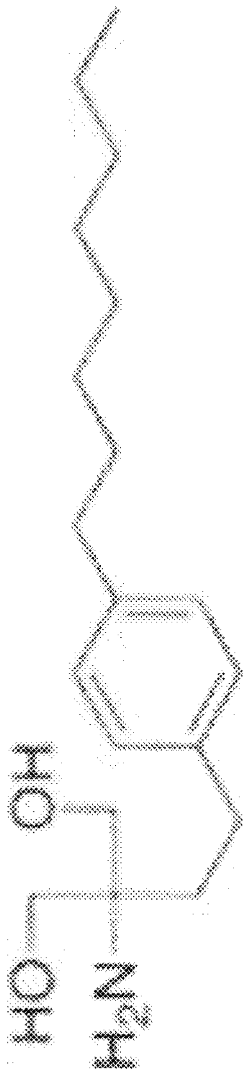

16*j*) mRNA sequence of $S1P_5$ (SEQ ID No. 40), the coding sequence starts at position 10 and ends at position 1206;

FIG. 17: Structure of FT720

Figure 18:
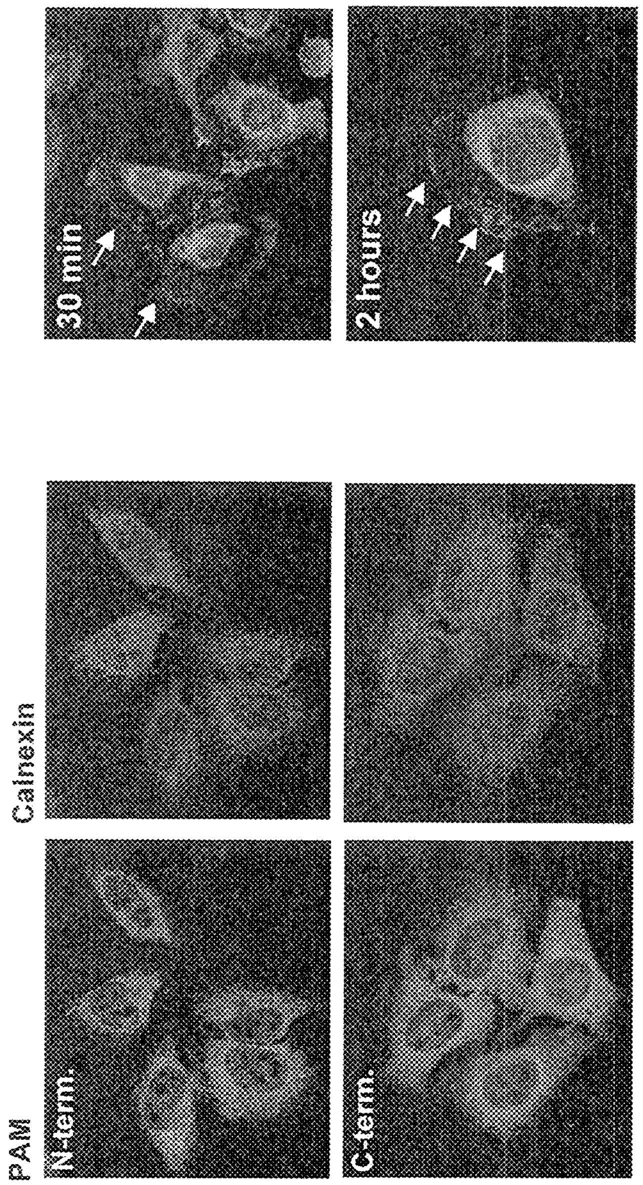

FIG. 18: PAM translocates from the ER to the plasma membrane in HeLa cells after serum stimulation.

Panel A: Serum starved HeLa cells (24 hours) were fixed and stained with anti-PAM antibodies (green) and anti-Calnexin antibody (red) as described above.

Panel B: HeLa cells were treated with 10% fetal bovine serum for different times and stained with anti-PAM antibodies to monitor the subcellular localization.

Figure 19:
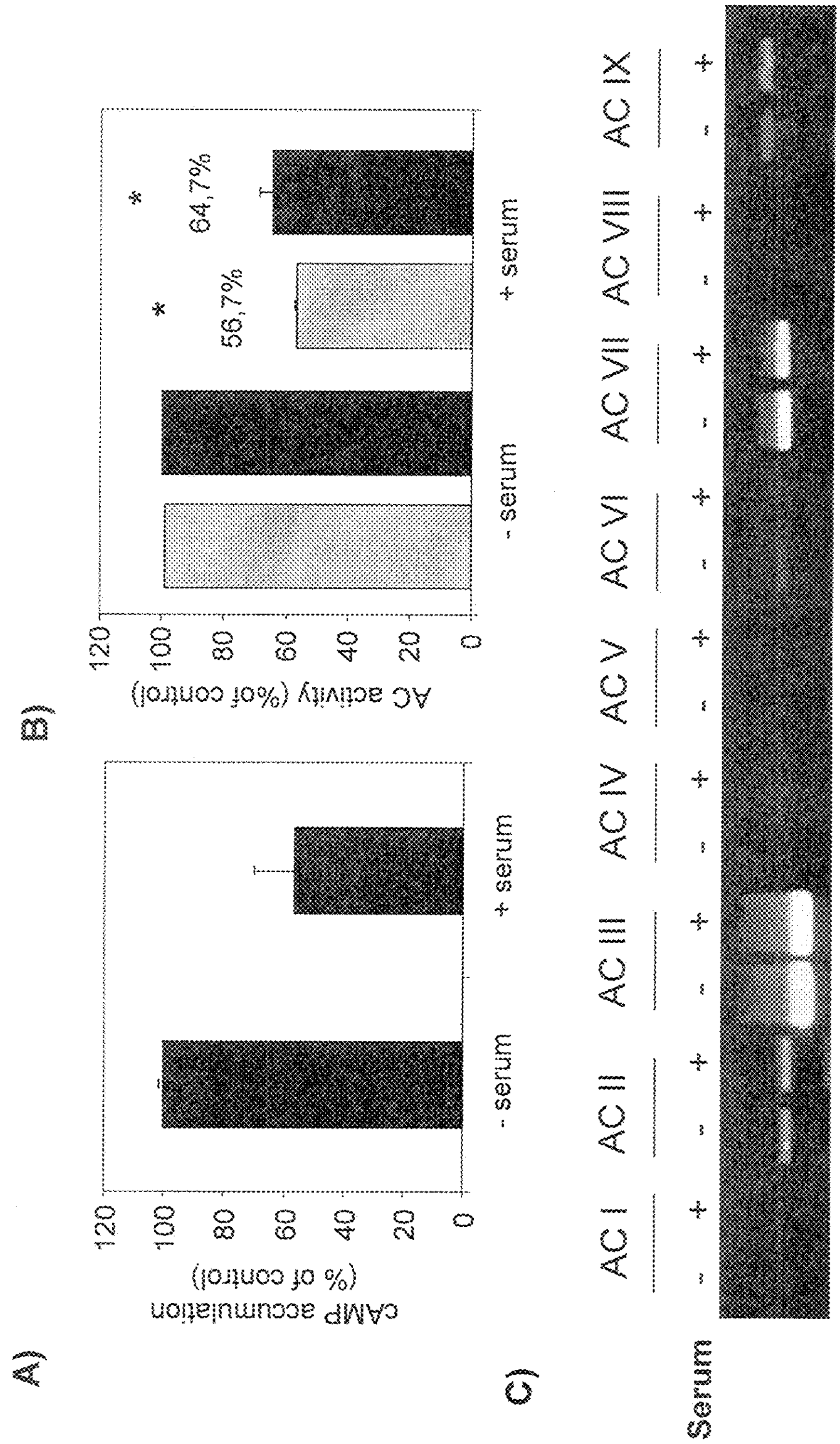
Figure 19:
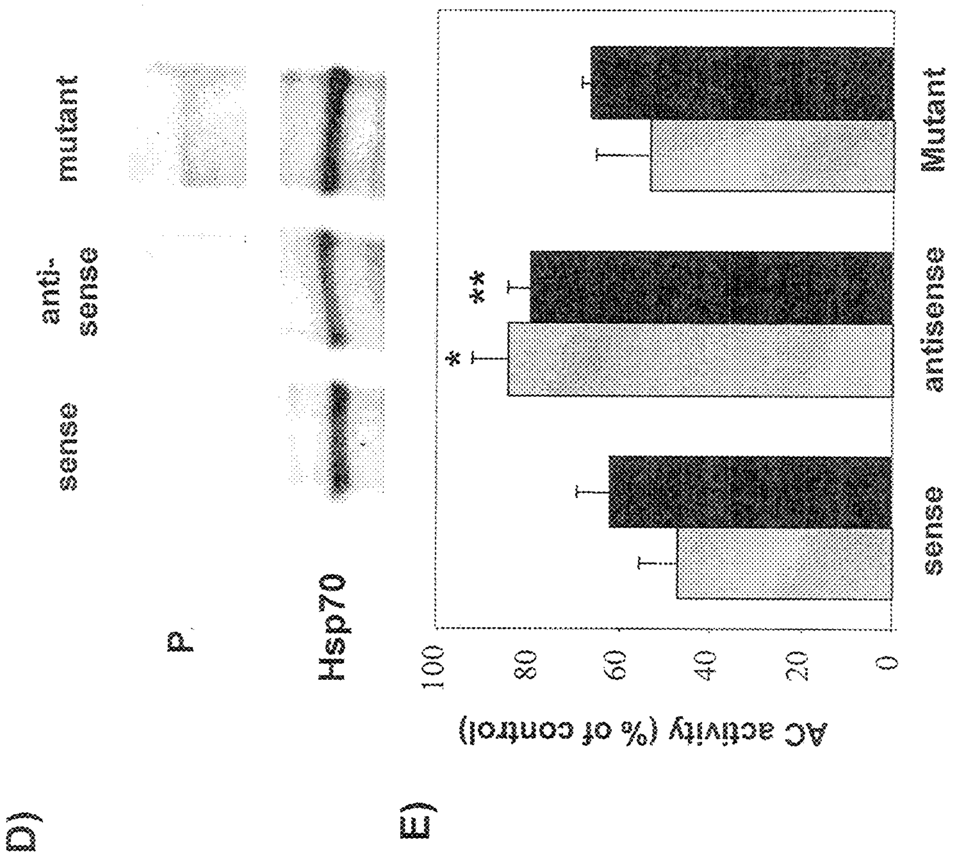

FIG. 19: Serum-treatment of HeLa cells decreases AC activity through a PAM-dependent process.

Panel A: cAMP accumulation in HeLa cells was measured in the absence and presence of serum as described above. The mean±SEM (Standard error of the mean) of three determinations is shown.

Panel B: Adenylyl cyclase activity of HeLa cell lysates was measured in the absence and presence of serum as described in Materials and Methods section. The $G_s\alpha$* (80 nM; grey bars)- and forskolin (100 μM; black bars)-stimulated specific activities of ACV were 124±10 pmol/mg/min and 464±89 pmol/min/mg, respectively. The basal activity was 11.75±2 pmol/mg/min. The mean±SE of at least 2 experiments each done in triplicates is shown. Student T test: *$p<0.001$.

Panel C: RT-PCR analysis of the AC isoform expression in serum starved HeLa cells and after 1 hour incubation with 10% FBS.

Panel D: Serum-starved HeLa cells were transfected with 3 M each of antisense, sense, and antisense ODN harboring three point mutations (3M-as) as described in above. Cells were harvested and subjected to Western analyses using 7% SDS-PAGE (30 μg protein) with anti-PAM antibody and anti-Hsp70 antibody.

Panel E: Serum-starved HeLa cells were treated with sense, antisense, and 3M-as ODNs as described above. After 24 hours the cells were incubated for 30 minutes with 10% FBS. Cells were harvested and AC activity in presence of $G\alpha s$* (80 nM; grey bars) and forskolin (100 μM; black bars) was determined as described above. Data from at least 3 experiments measured in triplicates are presented as the mean±SEM. Student T test: *$p<0.01$, **$p<0.05$.

Figure 20:
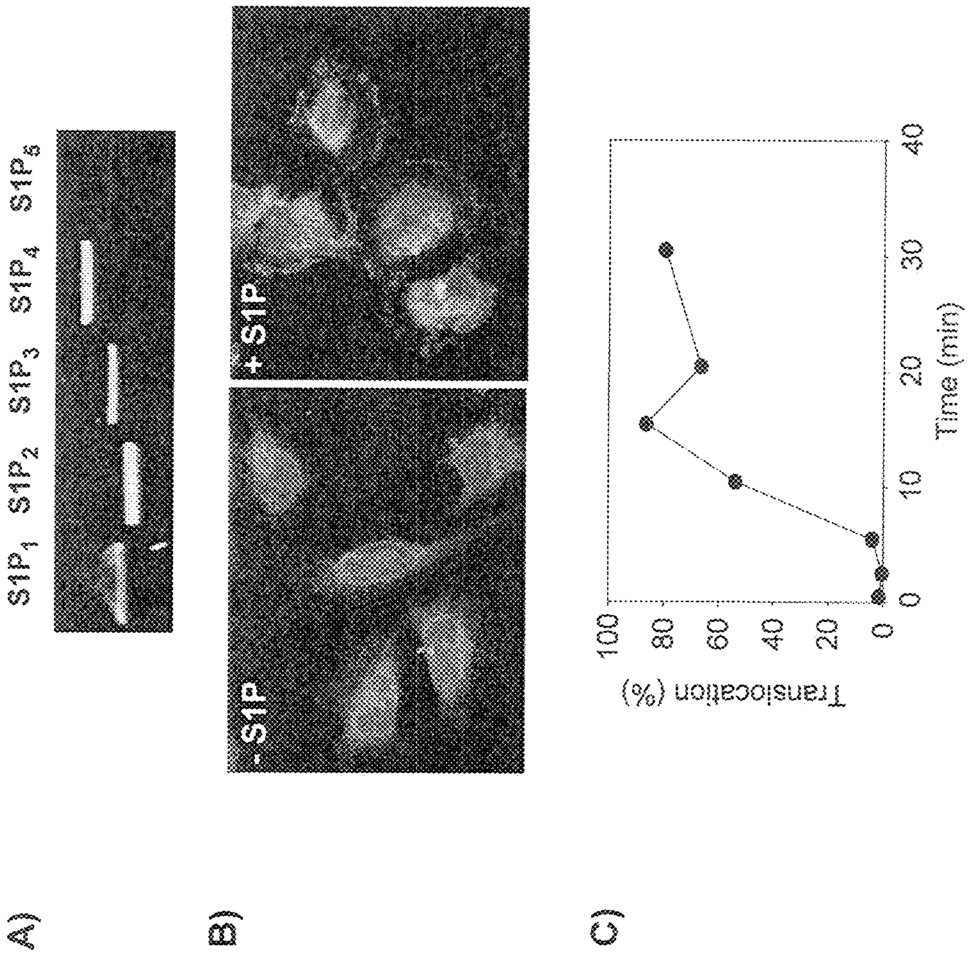

FIG. 20: S1P induces translocation of PAM the plasma membrane and inhibits PAM-dependent AC enzyme activity. Panel A: RT-PCR analysis of the S1P receptor isoform expression in serum starved HeLa cells.

Panel B: HeLa cells were treated with 0.5 μM S1P for 30 minutes and stained with anti-PAM antibodies to monitor the subcellular localization.

Panel C: Time dependence of PAM translocation in HeLa cells. Serum-starved HeLa cells were treated with 0.5 μM S1P for different times and stained with anti-PAM antibodies to monitor the subcellular localization. The percentage of cells exhibiting PAM-translocation is presented.

Figure 21:
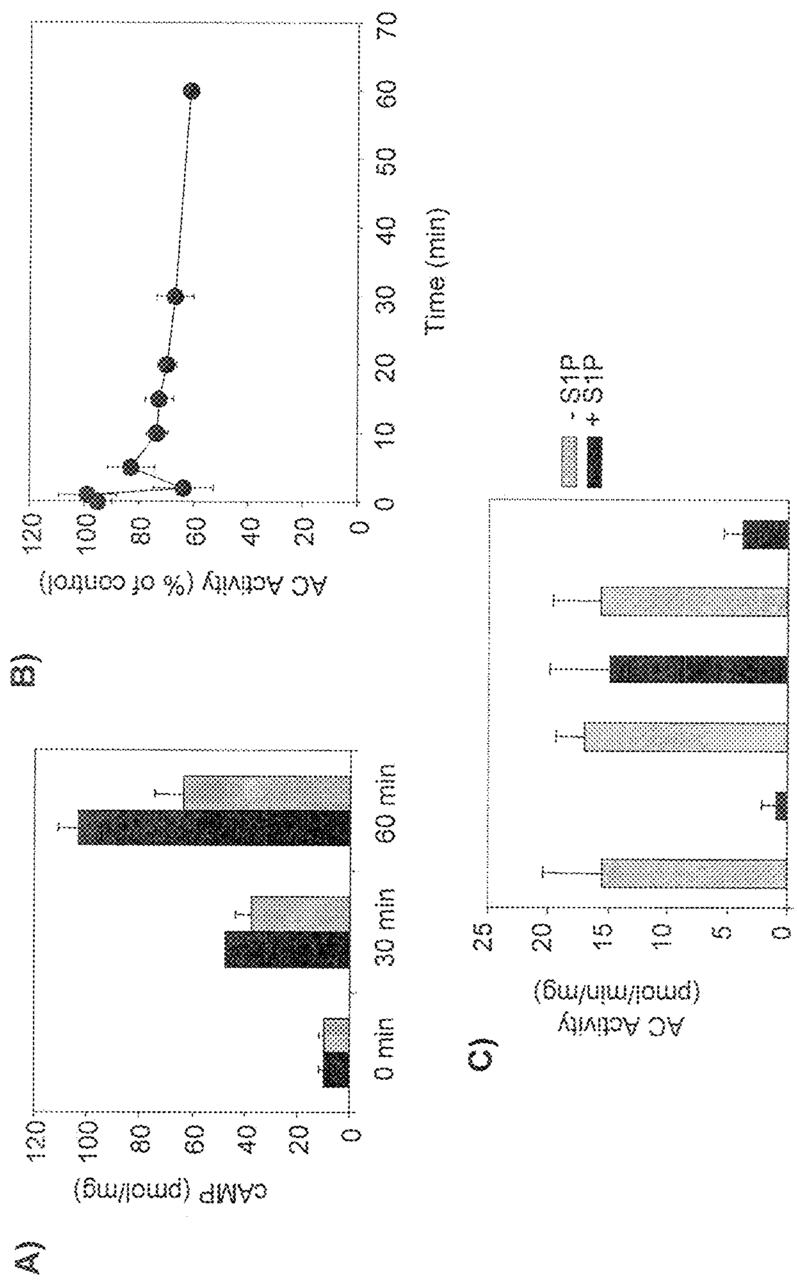

FIG. 21: S1P-treatment of HeLa cells decreases AC activity through a PAM-dependent process.

Panel A: cAMP accumulation in HeLa cells was measured in the absence (black bars) and presence (grey bars) of 0.5 μM S1P at varying times as described in Materials and Methods section. The mean±SEM of three determinations is shown.

Panel B: Serum-starved HeLa cells were treated for varying times with 0.5 μM S1P. Cells were harvested and AC activity in presence of 80 nM $G\alpha s$* was determined as described in Material and Methods. Data from at least 4 experiments measured in triplicates are presented as the mean±SE.

Panel C: Serum-starved HeLa cells were treated with sense, antisense, and 3M-as ODNs as described in the Materials and Methods section. After 24 hours the cells were incubated for the indicated times with 0.5 μM S1P. Cells were harvested and AC activity in presence of Gαs* (80 nM) was determined as described above. Data are presented as the mean±SEM of three determinations.

Figure 22:
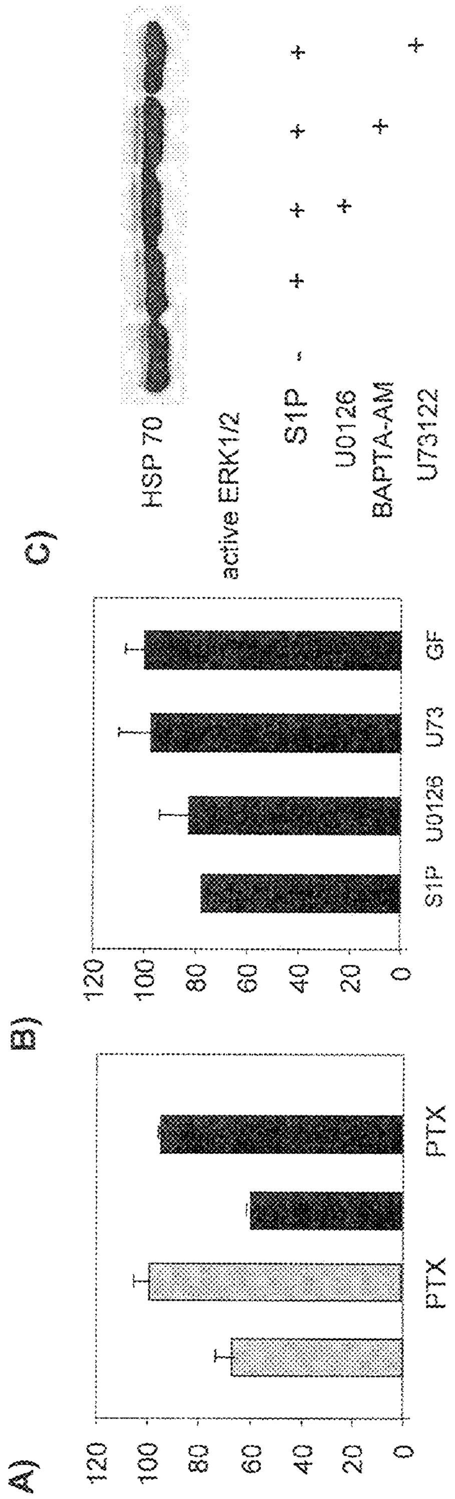
Figure 22:
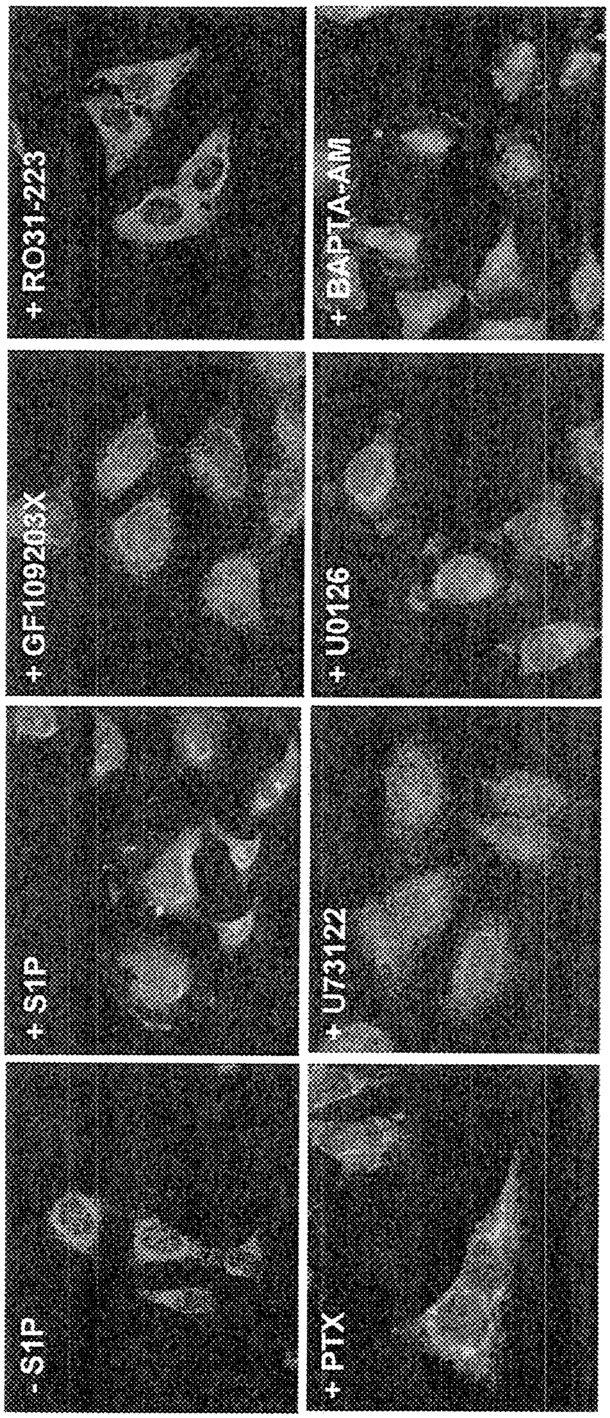

FIG. 22: PAM-translocation and PAM-dependent inhibition of AC enzyme activity is mediated by the PLC/PKC signaling pathway Panel A: Serum-starved HeLa cells were treated with 0.5 μM S1P for 3 (grey bars) or 60 (black bars) minutes. Prior incubation with S1P the cells were incubated for 24 hours with 1 μg/μl pertussis toxin (PTX). AC activity in was determined presence of 80 nM Gαs*. Data from at least 2 experiments measured in triplicates are presented as the mean±SE.

Panel B: Serum-starved HeLa cells were treated with 0.5 μM S1P. Prior incubation with S1P the cells were incubated for 20 minutes with 10 μM U73122, RO31-8220, BAPTA-AM or U0126. AC activity in was determined presence of 80 nM Gαs*. Data from at least 2 experiments measured in triplicates are presented as the mean±SE.

Panel C: Western Blot analysis of HeLa cells treated with 0.5 μM S1P for 10 minutes. Prior incubation with S1P the cells were incubated for 20 minutes with 10 μM U73122, BAPTA-AM or U0126. Cells were harvested in boiling Laemmli buffer and subjected to Western analyses using anti-active ERK1/2 antibody. Anti-Hsp70 antibody was used as loading control.

Panel D: HeLa cells were treated with 0.5 μM S1P for 20 minutes and stained with anti-PAM antibodies to monitor the subcellular localization. Prior S1P-treatment were the cells incubated for 24 hours with 1 μg/μl pertussis toxin (PTX), for 20 minutes with, 1 μM GF109203X, 10 μM U0126, BAPTA-AM, U73122 or Ro31-223.

Figure 23:
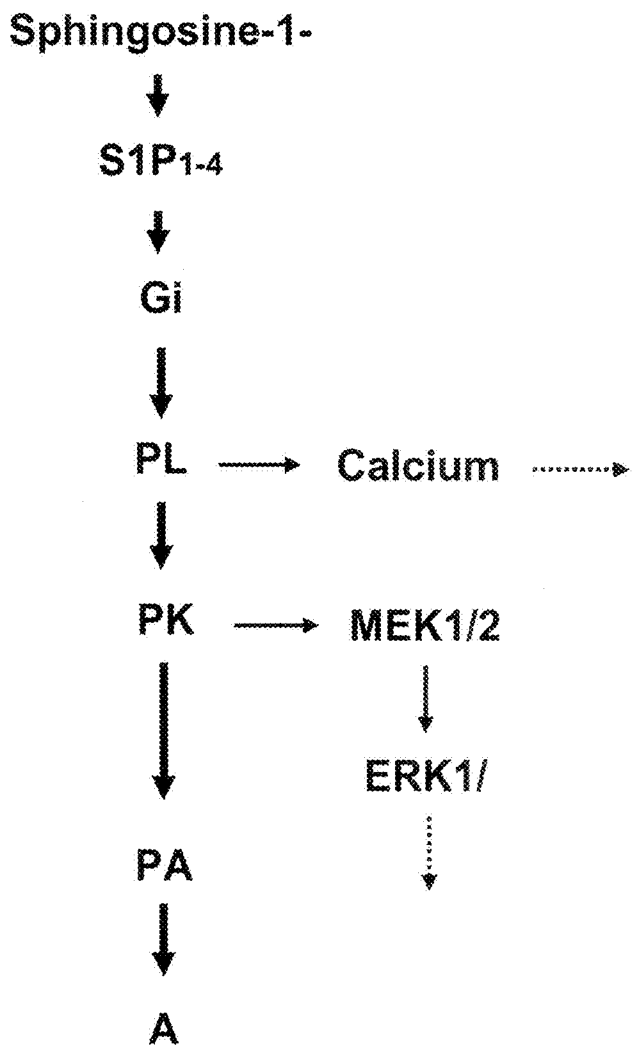

FIG. 23: Schematic of the proposed signaling pathway leading to PAM translocation and PAM-dependent inhibition of AC enzyme activity.

Figure 24:
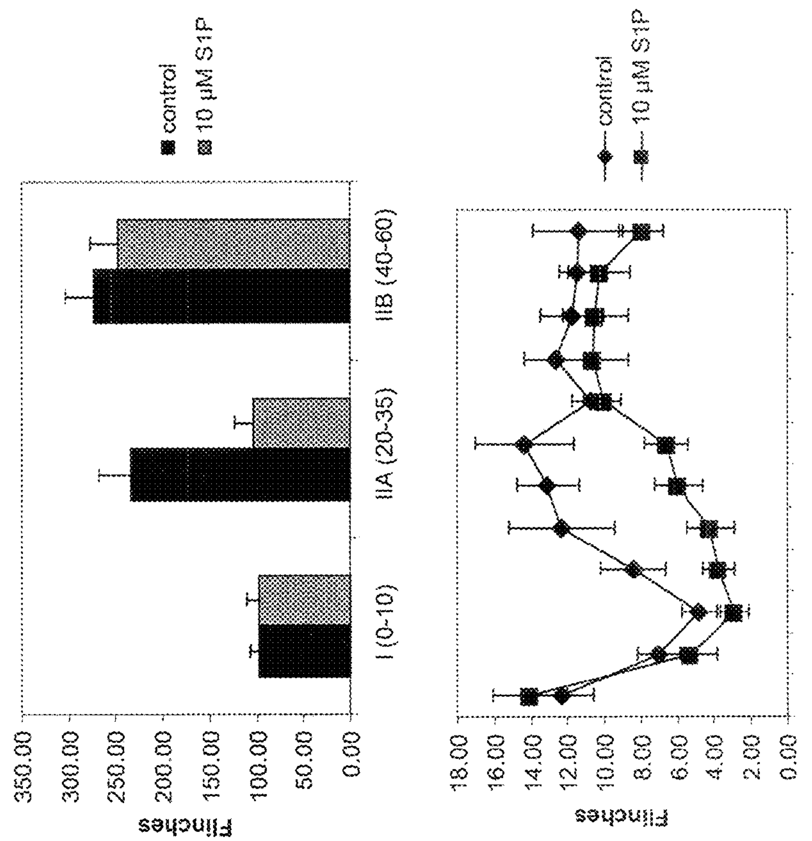

FIG. 24: Pain behaviour of adult rats in the formalin assay with and without application of S1P over a period of 60 minutes. 20 μl of 10 μM S1P or 20 μl PBS/DMSO were given to adult rats by intrathecal application 15 minutes prior to formalin injection. After formalin injection, flinches were counted in 5 minute intervals over a time-period of 60 minutes. The mean of six animal experiments+SEM is shown.

DETAILED DESCRIPTION OF THE INVENTION

The invention is based on findings of the inventors that demonstrate for the first time the implication of S1P in nociceptive processing and its ability to decrease pain (a U.S. Patent Application filed May 20, 2004 listing the same inventors, entitled "Method for alleviating pain using protein associated with Myc and related compounds, and assays for identifying such compounds," the contents of which are incorporated herein by reference, describes a similar role for protein associated with Myc). The term functional with respect to S1P or the term S1P function refers to the ability of S1P to interact with at least one of its receptors and preferably to activate the receptor, or to lower intracellular cAMP levels or to mediate the translocation of PAM (Protein Associated with Myc) from the endoplasmic reticulum to the cellular membrane; more preferably it refers to its ability to enhance PAM activity (i.e. the ability of PAM to interact with AC and/or to lower AC activity and/or to decrease pain) and/or to inhibit AC activity and even more preferably to its ability to decrease pain. The term functional with respect to S1P receptors or the term S1P receptor function refers to the ability of S1P receptors to interact with S1P, more specifically to mediate the receptor-typical signal triggered by the S1P interaction and more specifically to influence pain processing triggered by the S1P interaction.

A fragment of S1P can be any fragment that is smaller than the wild type molecule according to FIG. 15. A fragment of PAM can be any fragment polypeptide or polynucleotide that is shorter than the corresponding wild type. A fragment of an S1P receptor can be any fragment polypeptide or polynucleotide that is shorter than the corresponding wild type.

A derivative of S1P or of a S1P fragment can be any modification of the molecule having S1P function or any other kind of modification, such as a chemical or biological modification e.g. leading to the stabilization of the molecule, or modulating its specific targeting to e.g. certain cells or facilitating its entry into or uptake by cells; one known modification being the hydroxylation or methylation of S1P. Useful are suitable modifications or additives for ensuring or facilitating its targeting to the site of need and its entering the cell. On the other hand, a local application, such as an intraspinal application using suitable catheters, etc. or the like is possible for ensuring its targeting to the spinal cord. Other useful additives include salts (for physiologically tolerable organic or anorganic salts, see, e.g. Remington's Pharmaceutical Sciences, p. 1418, 1985), buffers or the like for its stabilization, etc.

Since S1P is internalized by cells via specific receptors, it can be applied externally and will then be internalized specifically. A modulation of S1P targeting can e.g. be gained by cloning and expression of the S1P receptors in the cell of want. A cell type specific expression can be ensured using appropriate promoters/enhancers of genes which are known in the art.

The present invention is based on studies of the inventors, that demonstrate for the first time the surprising implication of S1P in sensitisation mechanisms within the spinal cord and dorsal root ganglia (DRGs).

S1P (Sphingosine-1-Phosphate) is a phosphorylated derivative of sphingosine, the structural backbone of all sphingolipids. This extracellular (serum-borne) sphingolipide known to regulate a variety of cellular processes by binding to one of five specific G-protein coupled receptors (GPCRs), named $S1P_1$ to $S1P_5$, that are differentially expressed in different tissues, each regulating specific cellular actions (for a review, see. e.g. Payne et al., 2002; and Spiegel and Milstien, 2000). Known functions of extracellular S1P include, e.g. the regulation of cellular migration, cell survival or angiogenesis. Apart from its extracellular actions it is also known to act as an intracellular messenger (for a review, see. e.g. Payne et al., 2002; and Spiegel and Milstien, 2000). Its implication in nociceptive processes, however has not been known so far.

PAM (Protein Associated with Myc) is a giant protein of 510 kDa. The protein, genomic and coding polynucleotide sequences of PAM are known in the state of the art and are, e.g. publicly available from the NCBI (National Centre for Biotechnology Information; National Library of Medicine, Building 38A, Bethesda, Md. 20894, USA) data base under the accession numbers AAC39928 (coding sequence; SEQ ID No. 1), AF075587 (protein sequence; SEQ ID No. 2). Human PAM is located on Chromosome 13q22; its genomic sequence is publicly available under NT_024524.11 (Start: position 24679861; Stop: position 24962245; SEQ ID No. 3). Alternatively, the protein and coding sequence are publicly available under KIAA0916 protein Accession NP_055872 (protein sequence) and NM_015057 (coding sequence).

For rat PAM, the following EST-clone coding sequences are publicly available:

AW921303 (corresponds to by 960-1394 of hs cDNA; SEQ ID No. 4)

AW918711 (corresponds to by 8188-8632 of hs cDNA; SEQ ID No. 5)

BQ201485 (corresponds to by 8966-9633 of hs cDNA; SEQ ID No. 6)

BE112881 (corresponds to by 10311-10830 of hs cDNA; SEQ ID No. 7)

AW441131 (corresponds to by 13569-14152 of hs cDNA; SEQ ID No. 8)

BF409872 (corresponds to by 13569-14807 of hs cDNA; SEQ ID No. 9).

PAM was originally identified by its ability to interact specifically with the transcriptional activating domain in the N-Terminus of Myc (Guo Q., et al., 1998). PAM has recently been described as a powerful inhibitor of AC activity (Scholich K., Pierre S., Patel T. B.: Protein associated with Myc (PAM) is a potent inhibitor of adenylyl cyclase. J. Biol. Chem. 2001, Dec. 14; 276 (50):47583-9), but there has been no evidence of its function in nociceptive processing and sensitisation, so far.

Rather, PAM is believed to be playing a role in presynaptic growth regulation: PAM mRNA has been known to be highly expressed in specific anatomical regions, including hippocampus, dentate gyrus and cerebellum. Both PAM and Myc expression in the brain of adult rats and mice is confined to the maturing Purkinje cells in the cerebellum and granule and pyramidal cells in the hippocampus (Ruppert C., et al., 1986; Yang H. et al., 2002). None of these cell types, however is known to be involved in pain processing and sensitisation.

PAM homologues in *Drosophila* (highwire) and *C. elegans* (rpm-1) have been shown to play a crucial role in presynaptic terminal organization (Zhen et al., 2000), the regulation of synaptic growth (Wan et al., 2000), synaptogenesis, and neurite growth and targeting (Schaefer et al., 2000). These findings led to the assumption that highwire, rpm-1 and their mammalian homolog PAM might act as negative regulators of synaptic growth (Chang et al., 2000; Jin Y. 2002). Accordingly, a dramatic increase in PAM expression in the cerebellum, hippocampus and dentate gyrus was found during the major synaptogenic period in these structures (Yang et al., 2002).

During brain development in rodents, PAM expression is turned on shortly after birth, up-regulated during the first two weeks, and, thereafter, PAM expression remains elevated during adulthood (Yang et al., 2002). So far, nothing has been known about the expression and regulation of PAM in the spinal cord and DRGs and its function in sensitisation mechanisms and regulation of pain.

Previously, it has been demonstrated that human PAM is a potent regulator of cyclic AMP (cAMP)-signaling and inhibits the enzyme activity of several adenylyl cyclase (AC; E.C.4.6.1.1) isoforms at nanomolar concentrations (Scholich et al. 2001).

The ubiquitous cyclic AMP (cAMP) second messenger system is one of different signal transduction mechanisms translating extracellular stimuli to intracellular signals and responses. Upon extracellular stimulation, G-protein coupled receptors (GPCRs) modulate plasma-membrane bound enzymes or ion channels via trimeric GTP-binding regulatory proteins (G-proteins). One of the enzymes modulated in its activity by GPCRs is the adenylyl cyclase (AC), a cAMP generating enzyme. Thus, the incoming extracellular stimuli influence the intracellular concentration of the intracellular mediator cyclic AMP. A rise in cAMP levels affects the cell by stimulating protein kinase A (PKA), which phosphorylates specific intracellular target proteins and thereby alters their activity.

Each type of cell has characteristic sets of GPCRs, enzymes modulated by those GPCRs, specific subsets of adenylyl cyclase (AC) and target proteins, that, acting together with more unspecific or generally occurring players (such as the ubiquitous cAMP), enable each cell to make its own distinctive response to incoming extracellular signals. It is for example known that the cyclic AMP (cAMP)-second messenger plays a major role in the regulation of synaptic plasticity (Bailey et al., 1996; Xia et al., 1997; Brandon et al., 1997); on the other hand it is involved in metabolic processes and cellular proliferation. Thus, the role of the ubiquitous cAMP messenger system and its different components varies according to different specializations of different tissue and cell types.

So far, 5 different GPCRs acting as SIP receptors are known in the art termed $S1P_1$ to $S1P_5$, (for a review, see, e.g. Spiegel, S., and Milstien, S., 2000). The protein and coding polynucleotide sequences of the different SIP receptors are known in the state of the art and are, e.g. publicly available from the NCBI (National Centre for Biotechnology Information; National Library of Medicine, Building 38A, Bethesda, Md. 20894, USA) data base under the accession numbers: NM_001400 (SEQ ID No. 32; nucleotide sequence of *homo sapiens* endothelial differentiation, sphingolipid G-protein-coupled receptor, 1 mRNA (EDG1/$S1P_1$); NP_001391 (SEQ ID No. 31, protein sequence of *homo sapiens* endothelial differentiation, sphingolipid G-protein-coupled receptor (EDG1/S1P.sub.1); NM_004230 (SEQ ID No. 34, nucleotide sequence of *homo sapiens* endothelial differentiation, sphingolipid G-protein-coupled receptor, 5 (EDG5/$S1P_2$) mRNA; NP_004221 (SEQ ID No. 33, protein sequence of *homo sapiens* endothelial differentiation, sphingolipid G-protein-coupled receptor, 5 (EDG5/$S1P_2$); NM_005226 (SEQ ID No. 36, nucleotide sequence of *homo sapiens* endothelial differentiation, sphingolipid G-protein-coupled receptor 3 (EDG3/$S1P_3$) mRNA; NP:005217 (SEQ ID No. 35, protein sequence of *homo sapiens* endothelial differentiation, sphingolipid G-protein-coupled receptor 3 (EDG3/$S1P_3$); NM:003775 (SEQ ID No. 38, nucleotide sequence of *Homo sapiens* endothelial differentiation, G-protein-coupled receptor 6 (EDGE/$S1P_4$) mRNA; CAA04118 (SEQ ID No. 37, protein sequence of *Homo sapiens* endothelial differentiation, G-protein-coupled receptor 6 (EDGE/$S1P_4$); NM_030760 (SEQ ID No. 40, nucleotide sequence of *homo sapiens* endothelial differentiation sphingolipid G-protein-coupled receptor 8 (EDG8/$S1P_5$) mRNA; NP_110387 (SEQ ID No. 39, protein sequence of *homo sapiens* endothelial differentiation sphingolipid G-protein-coupled receptor 8 (EDG8/$S1P_5$).

Another aspect of the invention concerns S1P or a functional fragment or derivative thereof for the use as a medicament, preferably a medicament for the prevention or treatment of pain.

A further aspect of the invention concerns the use of S1P or functional fragments or derivatives thereof for the alleviation of pain. The term “alleviate,” as applied to pain, means the ability to prevent, lessen, or abolish pain, or to otherwise make pain more bearable.

Moreover, the use of S1P or functional fragments of derivatives thereof for identifying compounds that alleviate pain is encompassed by present invention. The compounds preferably have, mimic or enhance S1P activity. Most preferably they have the ability to alleviate pain.

The compounds can for example be identified by their ability to a) mimic, restore, activate or enhance S1P function (i.e. its ability to interact with at least one of its receptors or fragments thereof and preferably to activate the receptor, or to lower intracellular cAMP levels or to mediate the translocation of PAM from the endoplasmic reticulum to the cellular membrane; more preferably it refers to its ability to enhance PAM activity and/or to inhibit AC activity and even more preferably to its ability to decrease pain) or PAM function (i.e. its ability to lower intracellular cAMP levels, to interact with other factors like AC, especially with AC, to inhibit AC or its ability to lower the pain perception) or b) increase the serum level of S1P (e.g. by activating or enhancing the production of S1P or diminishing its extracellular degradation) or c) enhance the expression of at least one S1P receptor (i.e. by activation of its transcription, transcript stabilisation, translation or its posttranslational processing; by modulation of its posttranslational modification or by activation of its stabilisation or inhibition of its degradation, etc.) or d) interacti with enzymes responsible for production or degradation of S1P.

Another aspect of present invention regards a method of alleviating pain comprising administering to an individual a sufficient amount of S1P or a functional fragment or derivative thereof.

The compounds of the invention—including S1P and functional fragments and derivates thereof—may further be used to alleviate inflammation as well as pain, meaning that the compounds may be used to prevent, lessen, or abolish the inflammation or otherwise make it more bearable.

Administration should suitably be performed in a way that allows for targeting of S1P to the site of action (DRG or spinal cord), e.g. by systemical administration of S1P derivatives or formulations to the bloodstream (e.g. intravenous or oral application) or by local (e.g. intraspinal) application of S1P or its fragments or derivatives thereof.

Another aspect of the invention concerns a method of screening for pharmaceuticals useful for modulating and/or preventing pain, comprising the steps a. Providing a sample containing PAM or a functional fragment or derivative thereof and not containing S1P,
b. Providing a second sample containing PAM or a functional fragment or derivative thereof containing as well S1P,
c. Contacting at least the first sample with a compound,
d. Measuring the PAM activity in the samples,
e. Determining the ability of the compound to mimic S1P function.

The method can further comprise a step, wherein the cell is contacted with S1P instead of the compound and wherein the PAM activities according to c) and d) above are compared to the PAM activity in presence of S1P.

Another example refers to a method comprising the steps, a) providing two samples comprising a cell expressing an S1P receptor or a functional fragment or derivative thereof, and
b) contacting one sample with the compound, and
c) measuring the receptor activity in both samples.

A method according to another aspect of the invention comprises the steps, a) providing two samples comprising a cell expressing an S1P receptor or a functional fragment or derivative thereof, and
b) contacting the samples with S1P, and
c) contacting one sample with the compound, and
d) measuring the receptor activity or the interaction of S1P and receptor in both samples.

PAM or the S1P receptors can be derived from any sequence available that allows for their specific purpose according to the different aspects of the present invention. Preferably, PAM or the S1P receptors are of human.

For the different aspects of present invention it is also preferred, if PAM or the S1P receptors are isolated polypeptides or oligo- or polynucleotides. Isolated in the context of the different aspects of present invention means at least partially purified from a natural source or recombinant molecules (which can, of course, also be purified or partially purified).

An assay is any type of analytical method to monitor a biological process. For the use in drug screening, the assay needs to be reproducible and is preferably also scalable and robust. The assay is preferably suitable for high throughput screening of chemical substances for their ability of modulating (preferably diminishing) and/or preventing pain. High throughput screening mostly comprises the screening of approximately 500.000 different compounds for a certain ability. The type of assay depends e.g. on the type of molecule used (either polypeptide or polynucleotide) and the "read out", i.e. the way in which S1P, PAM or S1P receptor activity is determined (see below).

Different types of such assays are commonly known in the state of the art and commercially available from commercial suppliers. Suitable assays encompass radioisotopic or fluorescent assays, for example fluorescence polarization assays (such as those offered commercially by Panvera, Perkin-Elmer life sciences (e.g. LANCE) or Packard BioScience (e.g. HTRF or ALPHAscreen™)) for measuring the interaction of a labeled member with a non-labeled member (e.g. PAM or fragments thereof could be labeled and their interaction with AC could be monitored).

Simple biochemical assays are suitable, e.g. for determining the interaction between a potential pharmaceutical compound and a receptor or a functional receptor fragment or derivative. More elaborate assays are also capable of determining whether the compound is able to activate a given receptor and is thus mimicking S1P activity.

More examples include cell based assays, wherein a cell line stably (inducibly or not; chromosomal or episomal) or transiently expresses a recombinant protein of interest. These assays comprise e.g. reporter gene assays, wherein the regulation of a certain promoter or a signal transduction pathway of a member of a signal transduction cascade is measured according to the activity of a reporter enzyme, the expression of which is under the control of said certain promoter. For this type of assay, a recombinant cell line has to be constructed containing the reporter gene under the control of a defined promoter that is to be investigated itself or that is regulated by the signaling cascade under investigation. Suitable reporter enzymes are commonly known within the state of the art and comprise firefly luciferase, *renilla* luciferase (e.g. commercially available by Packard reagents), β-Galactosidase. Suitable cell lines depend on the aim of the assay but comprise mostly cell lines that are easy to transfect and easy to cultivate, such as, e.g. HeLA, COS, CHO, NIH-3T3, etc.

Assays for measuring the intracellular ion level comprise e.g. FLIPR (fluorometric imaging plate reader, commercially available from Molecular Devices) assays, wherein an argon laser light source combined with a cooled CCD camera allows for parallel measurements in 384 well plates transient ion signals (such as $Ca^{2+}$, etc) within cells (e.g. neuronal cells or other cells (e.g. cells recombinantly or naturally expressing certain ion channels). FLIPR assays allow e.g. for monitoring of intracellular calcium using certain fluorochromes, such as Fluo-3, Fluo-4, or monitoring intracellular pH using BCECF or BCPCF pr specific FLIPR assay kits, or detecting membrane potential changes using e.g. DiBAC or specific FLIPR assay kits, or monitoring of membrane polarization. For the monitoring of other intracellular ions, e.g. zinc or sodium, other dyes known in the state of the art can be used. Other types of assays and other types of read outs are commonly known to persons with skills in the art.

For the measurement of cAMP levels, e.g. AlphaScreen, fluorescence polarization or HTRF technology is suitable.

For the determination of ion channel activity (which control e.g. intracellular ion concentrations and can thus be employed for measurement of intracellular ion concentrations) e.g. membrane potential sensitive assays and dyes can be used such as DiBAC or Molecular Devices' membrane potential assay kit on FLIPR technology; mitochondrial membrane polarization measuring JC-1 dye with FLIPR technology; ion sensitive dyes such as Fluo-3, Fluo-4 or Molecular Devices calcium assay kit for intracellular calcium concentration measurement; sodium sensitive dye e.g. from Molecular Probes for measurement of intracellular sodium; assays based on patch-clamping or atomic adsorption spectroscopy-based Rubidium ion efflux measurement for determining of intracellular potassium concentrations, and so on. Further automatical devices and analytical methods for detecting certain changes and states within cells are known to the person of skill in the art and comprise, e.g. the Acumen detector (fluorescence-based laser scanning reader that allows for 3 dimensional reconstitution of distribution of suitably labeled objects) by ACUMEN bioscience.

For measurement of GPCR activity, e.g. cAMP measurement, for example by means of the AlphaScreen™ cAMP detection system by Packard Bioscience, Ca2+ mobilisation-assays or reporter gene assays are suitable.

The PAM polypeptide is preferably a polypeptide that comprises or consists of the sequence according to SEQ ID No 2 or is encoded by a polynucleotide comprising or consisting of the sequence according to SEQ ID No 1 or 3. The S1P receptor polypeptides are preferably polypeptides comprising or consisting of one of the amino acid sequences according to SEQ ID No. 31, 33, 35, 37 or 39 or are encoded by polynucleotides comprising or consisting of one of the nucleotide sequences according to SEQ ID No. 32, 34, 36, 38 or 40 or by the coding sequences comprised within these mRNA sequences.

The PAM polynucleotide is preferably a polynucleotide comprising or consisting of the sequence according to SEQ ID No 1 or 3 or a polynucleotide comprising or consisting of a sequence that is able to hybridize with the above polynucleotides under stringent conditions. The S1P receptor polynucleotides are preferably polynucleotides comprising or consisting of the sequences according to SEQ ID NO. 32, 34, 36, 38 or 40, polynucleotides comprising or corresponding to the positions 244 to 1392 of SEQ ID No. 32, 1 to 1137 of SEQ ID No. 34, 1 to 1062 of SEQ ID No. 36, 23 to 1177 of SEQ ID No. 38 or 10 to 1206 of SEQ ID No. 40, or comprise or consist of a sequence that is able to hybridize with one of these polynucleotides under stringent conditions.

Stringency describes reaction conditions that influence the specificity of hybridisation or annealing of two single stranded nucleic acid molecules. Stringency, and thus specificity of a reaction depends, inter alia, of the temperature and buffer-conditions used for a reaction: Stringency, and thus specificity, can e.g. be increased by increasing the reaction temperature and/or lowering the ion strength of the reaction-buffer. Conditions of low stringence (and thus low reaction and hybridisation specificity) exist for example, if a hybridisation is performed at room temperature in 2×SSC-solution. Conditions of high stringency comprise e.g. a hybridisation reaction at 68° C. in 0.1×SSC and 0.1% SDS solution.

Hybridisation under conditions of stringency within the different aspects of present invention is preferably understood to be:

1) Hybridising a labelled probe with a nucleic acid sample to be analysed at 65° C., or in the case of oligonucleotide probes, at 5° C. below the annealing or melting temperature of the duplex consisting of oligonucleotide and sample (annealing and melting temperature are in the following understood to be synonyms) over night in 50 mM Tris pH 7.5, 1M Nacl, 1% SDS, 10% Dextran Sulfate, 0.5 mg/ml denatured salmon or herring sperm DNA.
2) Washing for 10 minutes in 2×SSC at room temperature.
3) Washing for 30 minutes in 1×SSC/0.1% SDS at 65° C. (or in the case of oligonucleotides: 5° C. below the annealing temperature).
4) Washing for 30 minutes in 0.1×SSC/0.1% SDS at 65° C. (or in the case of oligonucleotides: 5° C. below the annealing temperature).

Oligonucleotides for the use as hybridisation probes are polynucleotide and preferably DNA-fragments having a length of 15 to 30, preferably 20 nucleotides. The annealing temperature is determined according to the formula Tm=2×(number of A+T)+4×(number of G+C)° C.

For preparing a 2×SSC or a 0.1×SSC (or any other kind of SSC dilution), e.g. a 20×SSC solution is diluted accordingly. 20×SSC consists of 3M NaCl/0.3 M Na-Citrate×$2H_2O$.

Before performing a hybridisation reaction, the polynucleotides are, if wanted after performing electrophoretic separation (then: Southern Blot (DNA) or Northern Blot (RNA)) or without electrophoretic separation (then: slot or dot Blot), transferred to a suitable membrane, e.g. a nylon or nitrocellulose membrane. Hybridisation is performed using a suitably labelled probe. Suitable labelling techniques are e.g. radioactive labelling or labelling using fluorescence dyes. The probe is a single stranded polyribo- or polydesoxyribonucleotide being single stranded naturally or being usually double stranded and having been made single stranded by denaturation. This probe binds to the DNA or RNA sample (which is also in single stranded state) by means of base pairing.

The PAM fragments are preferably fragments comprised within the above sequences ID No. 1, 2 or 3 and the derivatives are preferably derived from the above sequences ID No. 1, 2 or 3 or from fragments thereof. The S1P receptor fragments are preferably fragments comprised within the above sequences ID No. 31 to 40, more preferably fragments comprising or consisting of positions 244 to 1392 of SEQ ID No. 32, 1 to 1137 of SEQ ID No. 34, 1 to 1062 of SEQ ID No. 36, 23 to 1177 of SEQ ID No. 38 or 10 to 1206 of SEQ ID No. 40 and the derivatives are preferably derived from these sequences.

The functional fragments or derivatives thereof are preferably capable of inhibiting adenylyl cyclase (AC) activity, more preferably that of AC Type I, V or VI (with respect to the S1P receptors, most preferably capable of inhibiting AC activity when activated by S1P binding or binding of a molecule mimicking S1P).

According to a preferred embodiment of the different aspects of present invention, the functional fragments or derivatives of PAM comprise or consist of amino acids 400 to 1400, preferably 446 to 1062, 499 to 1065 or 1028 to 1231, and more preferably 1000 to 1300 and even more preferably 1000 to 1100 and even more preferably 1028 to 1065 of the human PAM sequence, preferably of the human PAM sequence according to SEQ ID No. 2, or if they are encoded by the respective polynucleotide fragments, especially if comprised within the sequences according to SEQ ID No. 2 or 3.

If the functional fragments or derivatives thereof are polynucleotides, it is preferred, if they comprise or consist of polynucleotides encoding the above polypeptide fragments. More specifically, it is preferred if they comprise or consist of positions 1482 to 3332 (encoding amino acids 446 to 1062) or 1641 to 3341 (encoding amino acids 498 to 1066) or 3228 to 3839 (encoding amino acids 1038 to 1231) of the human PAM cds. It is even more preferred, if the human PAM cds from which the fragments are derived has the sequence according to SEQ ID No. 2.

According to one preferred embodiment of present method for identifying pain modulating compounds, a cell expressing an S1P receptor and/or PAM, preferably a recombinant S1P receptor and/or PAM is used.

The cell can be any type of cell, e.g. a eucaryotic or prokaryotic single cell organism (such as bacteria, e.g. *e. coli*, or yeast, e.g. *s. pombe* or *s. cerevisiae*) or cell lines derived from multicellular organisms (such as HeLa, COS, NIH-3T3, CHO, etc), wherein mammalian cell lines are preferred.

According to another preferred embodiment, a modified cell, having a lower S1P receptor activity as compared to its unmodified state, is used. This way, it can be tested, if the chemical compounds to be tested for their ability of modulating (preferably diminishing) and/or preventing pain, are able to enhance or restore the lowered or totally abolished S1P receptor activity.

The modification can be any type of modification (stable or transient, preferably stable), that leads to a decrease of S1P receptor activity and/or PAM activity (i.e. their ability to lower intracellular cAMP levels, the translocation of PAM, to inhibit AC or their ability to lower the pain perception), S1P receptor or PAM transcript steady state level (i.e. by inhibition of S1P receptor or PAM transcription or transcript stabilisation) or S1P receptor or PAM protein steady state level (i.e. by inactivation of S1P receptor or PAM translation or its posttranslational processing; by modulation of its posttranslational modification or by inactivation of its stabilisation or by increase of its degradation). This can for example be achieved by using dominant negative mutants of S1P receptors or PAM, antisense oligonucleotides, RNAi constructs, by generating functional or genomic S1P receptor or PAM knock outs (which can e.g. be inducible) or other suitable techniques known within the state of the art. For an overview of the above techniques, see for example: Current protocols in Molecular biology (2000) J. G. Seidman, Chapter 23, Supplement 52, John Wiley and Sons, Inc.; Gene Targeting: a practical approach (1995), Editor: A. L. Joyner, IRL Press; Genetic Manipulation of Receptor Expression and Function, 2000; Antisense Therapeutics, 1996; Scherr et al, 2003.

According to a preferred embodiment, a PAM knock-out cell is used. Suitable cell lines for the generation of knockouts are well known in the state of the art and comprise e.g Current protocols in Molecular Biology (2000) J. G. Seidman, Chapter 23, Supplement 52, John Wiley and Sons, Inc; or Gene Targeting a practical approach. (1995) Ed. A. L. Joyner, IRL Press.

The S1P activity can either be determined directly, e.g. by its ability (or the ability of its fragments and derivatives) to interact with at least one of its receptors or their functional fragments or to trigger the translocation of PAM to the cell membrane, or it can be determined indirectly, e.g. by its ability (or the ability of its functional fragments and derivatives) to lower intracellular cAMP levels, to modulate ion concentrations within the neurons, to inhibit AC function, or its ability to modulate, especially decrease pain perception. Suitable techniques for measuring the above parameters are well known in the state of the art (see also above): The cAMP levels can e.g. be measured by HTRF or ALPHAscreen™, the ion concentrations can e.g. be estimated by patch clamping or suitable dyes, the pain perception can e.g. be measured by means of the formalin test or tests of mechanical or thermal hyperalgesia, or the hot plate test etc. The interaction with its receptors can e.g. be determined by cAMP measurement, $Ca^{2+}$ mobilisation or reporter gene assays.

Another aspect of present invention concerns a method of identifying a compound that alleviates pain comprising a) Selecting a compound that modulates or mimics the activity of S1P as a test compound, and
b) Administering said test compound to a subject to determine whether the pain is alleviated.

The subject can be any subject with the ability of perceiving pain, preferably it is a mammal, either a non-human mammal or a human (i.e. within a patient study).

The modulation preferably alleviates the pain, meaning that it prevents, lessens, or abolishes it; or that it otherwise makes the pain more bearable for the subject. According to one preferred embodiment of the invention, the compound is an S1P receptor agonist (for a review, see for example Mandala et al., Science 2002) and more preferably FTY 720 (2-Amino-2-(4-ocylphanyl)ethyl)propane-1,3-diol, see FIG. 17) or a functional derivative or analog (analogs are known in the art, see e.g. Brinkmann et al., JBC, 2002) thereof (i.e. a derivative or an analog having the above-indicated capability of modulating pain), preferably a phosphorylated derivative (see Mandala et al., Science 2002). Suitable are also physiologically acceptable salts of the compound or its derivatives or analogs.

According to yet another aspect of the invention a method of alleviating pain comprising administering a sufficient amount of a pharmaceutical compound with the ability to bind and activate at least one of the S1P receptors and/or the activity to activate PAM function to an individual is concerned within the scope of the application. One suitable example of such a compound is an S1P receptor agonist (for a review, see for example Mandala et al., Science 2002) and more preferably FTY 720 or a functional derivative or analog as defined above, preferably a phosphorylated derivative thereof, or a physiologically acceptable salt of the compound or its functional derivative or analog.

In the following, the invention is illustrated in more detail by means of examples and figures. However, the examples are not meant to limit the scope of the invention.

EXAMPLES

Investigation of PAM Expression Pattern and Function of PAM and S1P

1. Materials

S1P was purchased from Tocris (Ellisville, Mo.), the anti-Hsp70 antibody and the anti-Calnexin antibody from BD TransductionLabs (Bedford, Mass.). The anti-active ERK1/2 antibody was obtained from Promega (Madison, Wis.). Pertussis toxin, U0126, U73122, and Wortmannin from Tocris (Ellisville, Mo.), RO31-223, BAPTA-AM and GF109203X by Sigma (St. Louis, Mo.).

2. Preparation of Animal Sections:

Wild type Sprague Dawley rats were purchased from Charles River Wiga GmbH (Sulzfeld, Germany). The animals had free access to food and water prior to the experiments. They were maintained in climate- and light-controlled rooms (24+0.5° C.). Each animal was used at one occasion only. In all experiments the ethics guidelines for investigations in conscious animals were obeyed, and the procedures were approved by the local Ethics Committee. After killing, adult rats were fixed by perfusion with 4% paraformaldehyde in 0.1 M phosphate buffered saline (PBS, pH 7.2) for one hour. Tissues were cryostat-sectioned in the horizontal plane at a thickness of 14-16 μm. Sections were mounted on Superfrost Plus Slides (Fisher Scientific Co., Pittsburgh, Pa.) and stored at −80° C. until use.

3. Preparation of Riboprobes:

The riboprobes were generated as described previously (Yang et al., 2002). Antisense and sense riboprobes of rat PAM were obtained with T7 and T3 polymerases, after linearizing the plasmid with Hind III (antisense) and BamHI (sense), respectively (see Yang et al., 2002). In vitro transcription was performed in the presence of [35S] UTP-αS (ICN, Irvine Calif.), linearized PAM cDNA, NTP at 37° C. for 1 hour according to the manufacturer's recommendation (Promega, Madison, Wis.). The RNA transcripts were purified using RNA Probe Purification Kit (Pequlab, Erlangen, Germany).

4. In Situ Hybridization:

In situ hybridization was performed as described earlier (Yang et al. 2002): Sections were fixed in 4% paraformaldehyde in 0.1 M phosphate-buffered saline (pH 7.2), pretreated with 0.25% acetic anhydride and 0.1 M triethanolamine, rinsed with 0.2×SSC and dehydrated with serially increasing concentrations of alcohol. Sections were prehybridized with prehybridization solution (50% deionized formamide, 0.6 M sodium chloride, 10 mM Tris-HCl (pH 7.6), 50 mM EDTA, 0.025% sodium pyrophosphate, 0.02% Ficoll, 0.02% BSA, 0.02% polyvinyl pyrrolidone, 10 mM DTT, and heat-denatured, heterologous nucleic acids (0.005% yeast tRNA, type X, 0.05% yeast total RNA, type I, 0.05% salmon testes DNA, type III)) for 2 hours at room temperature; hybridized with riboprobes in hybridization solution (2.5×106 cpm/section), 50% deionized formamide and 50% hybridization buffer containing 0.6 M sodium chloride, 10 mM Tris-HCl (pH 7.6), 50 mM EDTA, 0.025% sodium pyrophosphate, 0.02% Ficoll, 0.02% BSA, 0.02% polyvinyl pyrrolidone, heat-denatured, heterologous nucleic acids (0.005% yeast tRNA, type X, 0.005% yeast total RNA, type I, 0.05% salmon testes DNA, type III), 100 mM DTT, 0.0005% polyadenylic acid, 10% dextran sulfate) at 50° C. overnight. Sections were rinsed with 2×, 1×, 0.5×SSC at RT (room temperature). After digestion in 20 μg/ml RNase A (Sigma, St. Louis, Mo.), sections were washed in 1× RNase buffer, 2×, 1×, 0.5×SSC at room temperature, and in 0.1×SSC overnight at 45° C. Sections were dehydrated with serially increasing concentrations of alcohol, exposed to Kodak Biomax MR film (Kodak, Rochester, N.Y.) for 3-7 days at −80° C.

5. Antibody Generation and Immunofluorescence Staining:

Antisera were raised commercially in rabbits using peptides consisting of amino acid residues 135-153 and 4601-4614 of human PAM corresponding to the SEQ ID No. 1, respectively (BioTrend, Cologne, Germany). The antiserum was commercially produced by BioTrend, Cologne, Germany, according to standard procedures. To monitor the distribution of PAM in spinal cord and DRG slices, the slices were permeablized in 0.1% Triton X-100 for 5 minutes. The slices were blocked for 1 hour in 3% BSA in PBS and then incubated for 1 hour with anti-PAM antiserum (1:50 dilution). This was followed by incubation with FITC-labeled goat anti-rabbit antibody in PBS containing 3% BSA. The slices were then washed with PBS and mounted using Fluoromount™.

6. RT-PCR:

Total RNA from rat spinal cords and DRGs was isolated by guanidinium isothiocyanate/phenol/chloroform extraction (Chomczynski and Sacchi 1987). 2 μg of total RNA were annealed with 0.6 μM of each of oligo (dT) primer and reverse-transcribed using reverse transcriptase (Promega, Madison, Wis.) for 30 minutes at 37° C. The cDNA was then immediately used for amplification. Oligonucleotide primers used for the amplification of rat GADPH were 5"-GAAGGGTGGGGCCAAAAG-3" (sense; SEQ ID No. 10) and 5"-GGATGCAGGGATGATGTTCT-3" (antisense; SEQ ID No. 11; Trajkovic et al. 2000). Oligonucleotide primers for the amplification of AC isoforms were chosen as published by Xu et al. (Xu et al. 2001). Primers for rat PAM were 5"-GGTGGTGAAGCTCGCTGTGATGCT-3" (sense; SEQ ID No. 12) and 5"-CGTGTGAGCATTTCTGCACAC TCC-3' (antisense; SEQ ID No. 13). The PCR product corresponds to the human PAM cDNA nucleotides 13692-14064. The corresponding rat sequence was derived from the EST clone AW441131 (SEQ ID No. 8). For semiquantitative PCR, SAWDAY DNA Polymerase (Peqlab, Erlangen, Germany) was used. After an initial denaturation step at 95° C. for 5 minutes, 30 cycles were performed with 1 minute at 95° C., 30 seconds at 55° C., and 10 seconds at 72° C., followed by a final 10-minute extension step at 72° C. Quantitative PCR was performed using the TaqMan™ system and reagents (Applied Biosystems, Weiterstadt, Germany) according to the instructions of the manufacturer.

67 Purification of Full Length PAM:

PAM purification was performed with some modifications as published previously (Scholich et al. 2001). Shortly, HeLa cells were grown in DMEM medium with 10% fetal bovine serum and 1% penicillin/streptoMycin. Confluent cells of forty 150 mm dishes were harvested with 1×PBS, 1 mM EDTA and pelleted for 5 minutes at 400×g. The cells were resuspended in TED buffer (50 mM Tris-HCl, pH 8.0, 1 mM EDTA, 1 mM DTT) containing 125 mM NaCl, 20 μg/ml of aprotinin, 20 μg/ml leupeptin, 1 mM benzamidine, 5 μg/ml soybean trypsin inhibitor and lysed by 2×5 seconds of sonication. The homogenate was centrifuged at 27000×g for 30 min at 4° C., and the supernatant was loaded on a Q-Sepharose XK16 column (Amersham, Pharmacia, Piscataway, N.J.) and eluted with a gradient of 150-350 mM NaCl in TED according to instructions of the manufacturer. The fractions were analyzed by Western blotting according to standard procedures; positive fractions were pooled and the NaCl concentration adjusted to 1 M. The protein was then loaded on a Phenyl-Sepharose XK16 column (Amersham, Pharmacia, Piscataway, N.J.) and washed with 300 mM NaCl in TED according to instructions of the manufacturer. The flow through and wash fractions contained PAM. They were pooled and the buffer exchanged for the aforementioned TED buffer containing 100 mM NaCl using Centricon 50 (Amicon, Beverly, Mass.) according to the manufacturer's instructions. The protein was then loaded on a MonoS 5/5 FPLC column (Amersham, Pharmacia, Piscataway, N.J.) and washed with the loading buffer (100 mM NaCl in TED) according to instructions of the manufacturer. The flow through was collected and applied to a Mono Q 5/5 FPLC column (Amersham, Pharmacia, Piscataway, N.J.). The protein was eluted with a gradient from 150-400 mM NaCl in TED. Positive fractions were pooled and the buffer exchanged for 50 mM Tris-HCl, pH 8.0, 1 mM DTT using Centricon 50 (Amicon, Beverly, Mass.) and stored at −80° C. The stored PAM was used within 3 weeks.

8. Expression and Purification of Recombinant Gsα:

The hexahistidyl tagged constitutively active Q213L mutant of Gsα (Gsα*) was expressed and purified as described in Graziano et al., 1991. To ensure maximal activation of the Gsα*, the G protein was incubated with 1 μM GTPγS in the presence of MgCl2 (25 mM) for 30 minutes prior to use in AC activity assays.

9. Adenylyl Cyclase Activity Assays (AC Activity Assays):

Spinal cords were lysed in 25 mM Hepes, pH 7.4, 1 mM EGTA and cell membranes were prepared as described by Kassis and Fishman. Aliquots were stored at −80° C. until use. AC activity assays were performed in a volume of 100 μl for 15 min at room temperature in the presence of 100 μM $MgCl_2$ as previously described (Patel et al., 2002). Gsα* (80 nM) or forskolin (100 μM) were used to stimulate AC enzyme activity in membranes (10 μg protein).

10. Spinal Delivery of PAM Antisense and Sense Oligonucleotides:

Rats were anesthetized with ketamine (60 mg/kg i.p.) and midazolam (0.5-1 mg/kg i.p.). The skin was incised above the vertebral column from vertebrae Th13 up to L3. Muscle tissue around L2-3 was cleared away. The processus spinosus of L3 was removed and a laminectomy was done at L2. Polyethylene catheters (ID 0.28 mm, OD 0.61 mm) were then inserted into the peridural space so that the tip of the catheter reached Th9-10. The catheter was fixed with cyanacrylate glue, externalized in the neck region, and the skin was sutured.

11. Infusion of PAM Oligonucleotides:

The sequences of the oligodeoxynucleotides (ODNs) were chosen from the rat PAM sequence as follows. Sense: 5'-GACTGGTTTAGCAATGGC-3'(SEQ ID No. 14), antisense: 5'-GCCATTGCTAAACCAGTC-3' (SEQ ID No. 15), and antisense ODN harboring three mutations (3M-as; mutations are underlined): 5'-GCAATTGCTAAATCAGTA-3' (SEQ ID No. 16). Three days after surgery, rats were placed into a "freely moving system" (CMA, Stockholm, Sweden) and antisense (n=5) or sense (n=5) oligonucleotides (2.5 mg/ml in artificial cerebrospinal fluid) were infused through the catheter at a flow rate of 0.05-0.1 μl/min for 100 hours using a microinfusion pump (CMA, Stockholm, Sweden).

12. Formalin Test:

Within 15 min after stopping the infusion, the formalin test was performed. 50 μl of a 5% formaldehyde solution was injected subcutaneously (s.c.) into the dorsal surface of one hind paw. Flinches were counted in one-minute intervals up to 60 min starting right after formalin injection. Flinches of 5 min intervals were summarized as mean flinches per minute. To compare the nociceptive behavior between groups, the sum of flinches during the two phases of the one-hour observation period were submitted to the Students t-test. α was set at 0.05.

At the end of the formalin test, the rats were killed, the lumbar spinal cord and dorsal root ganglia (DRGs) were excised, snap frozen in liquid nitrogen and stored at −80° C. until further analysis. To determine PAM expression, spinal cord slices were analyzed immunhistochemically using the above anti PAM antibodies.

13. Zymosan-Evoked Inflammation:

For induction of an inflammation, 2.5 mg zymosan A (Sigma, St. Louis, Mo.) suspended in 30 μl 0.03 M phosphate buffered saline (PBS, pH 7.5) was injected subcutaneously into the midplantar region of the right hindpaw. Such intraplantar zymosan injection is known to induce a reliable model of thermal and mechanical hyperalgesia rats (Meller and Gebhart 1997). Rats were killed by cardiac puncture under deep isoflurane anesthesia 24-96 hours after the Zymosan injection. The lumbar spinal cord and dorsal root ganglia (DRGs) were excised, snap frozen in liquid nitrogen and stored at −80° C. until further analysis.

14. Immunofluorescence Staining:

To monitor distribution of PAM in HeLa cells, cells were grown on glass coverslips in DMEM with 10% FBS and 1% penicillin/streptoMycin (Gibco, Karlsruhe, Germany). To visualize translocation of PAM HeLa, cells were serum starved overnight and subsequently treated with 10% serum for 2 hours. Wherever indicated, cells were preincubated for 30 minutes in the presence of different concentrations of inhibitors. The cells were fixed in 4% paraformaldehyde (Sigma, Taufkirchen, Germany) in PBS for 10 minutes and then permeablized in 0.1% Triton X-100 for another 5 minutes. The coverslips were blocked for 1 hour in 3% BSA in PBS and then incubated for 1 hour with anti-PAM antibody (1:50 dilution). This was followed by incubation with FITC-labeled goat anti-rabbit antibody in PBS containing 3% BSA. The cells were then washed with PBS and mounted. For the analysis confocal (BioRad, Hercules, Calif.) and regular fluorescence microscopes (Nikon, Duesseldorf, Germany) were used.

15. cAMP Accumulation

Spinal cord samples were sonicated and centrifuged at 4° C. for 20 minutes with 18.000×g. The supernatant was used for cAMP measurements. The cAMP accumulation in the cells was determined by the cAMP Detection Kit (Assay Design Inc, Ann Arbor, Mich.) according to the manufacturers instructions.

16. Antisense Oligodeoxynucleotides

The sequences of the oligodeoxynucleotides (ODNs) were chosen as published previously (Scholich et al., 2001). Sense: 5'-CTGTTCATGCCGGTT-3', antisense: 5'-AACCGGCATGAACAG-3', and antisense ODN harboring three mutations (3M-as; mutations are underlined): 5'-AATCCGTATGAACAC-3'. HeLa-cells were plated on 35 mm dishes (300,000 cells) and grown in DMEM medium (Gibco, Karlsruhe, Germany) containing 10% FBS and 1% penicillin/streptoMycin for 24 hours. The ODNs (3 μM each) were introduced into the cells by transfections using Tfx20 (Promega, Madison, Wis.) in 1 ml serum-free medium according to the instructions of the manufacturer. Two hours later, 1 ml DMEM (Gibco, Karlsruhe, Germany) containing 10% FBS was added. The cells were then incubated for 6 hours. Then the medium was exchanged against serum-free DMEM (Gibco, Karlsruhe, Germany), followed by an incubation for 16 hours in serum-free DMEM (Gibco, Karlsruhe, Germany) before being treated with 10% serum or 500 M S1P. The cells were then used for Western blots by adding boiling 1× Laemmli buffer or they were harvested for AC activity assays as described above.

17. Purification or the PAM Activating Serum Factor:

188 ml fetal bovine serum (Gibco, Karlsruhe, Germany) were adjusted to a final concentration of 0.3 M NaCl. The serum was then loaded on a Phenyl-Sepharose 15/10 column (Amersham, Pharmacia, Piscataway, N.J.). After elution from this column, as well as after all following columns, the flowthrough and all eluted fractions were collected and analyzed for its ability to induce translocation of PAM in HeLa cells. The flowthrough was then loaded on a Q-Sepharose 15/10 column (Amersham, Pharmacia, Piscataway, N.J.). The column was washed with 400 mM NaCl in TE (50 mMTris/Cl pH 7.4, 0.5 mM EDTA) and eluted with 1 M NaCl in TE. The eluate was loaded on a Superdex 200 pg Gel filtration column (Amersham, Pharmacia, Piscataway, N.J.).

Protein was eluted with TE according to instructions of the manufacturer and the fractions were analyzed for their ability to induce translocation of PAM in HeLa cells. Positive fractions were pooled, loaded on a MonoQ 5/5 FPLC column (Amersham, Pharmacia, Piscataway, N.J.) and washed with 400 mM NaCl in TE. The protein was eluted with a gradient from 400-1000 mM NaCl in TED. Positive fractions were pooled and loaded on a Superdex 50 pg Gel filtration column (Amersham, Pharmacia, Piscataway, N.J.) according to instructions of the manufacturer. Protein was eluted with TE according to instructions of the manufacturer and the fractions were analyzed for their ability to induce translocation of PAM in HeLa cells. Positive fractions were pooled, stored at −80° C. and used within 2 weeks for mass spectrometry or biochemical assays. S1P was detected employing phthaldialdehyd-labeling followed by HPLC separation as described by Caligan et al.

18. Results Demonstrating the Implication of PAM in Nociceptive Processing:

The above experiments of the inventors using RT-PCR, immunohistochemistry and in situ hybridisation, demonstrate for the first time that PAM is expressed in sensory neurons of the spinal cord as well as in dorsal root ganglia (DRGs) of adult rats. PAM mRNA was detected by RT-PCR at similar levels in the spinal cord and dorsal root ganglia throughout development (E14-adult). PAM-expression is upregulated 24-48 hours after zymosan treatment of rats as shown by western blot and RT-PCR.

The major adenylyl cyclase isoforms, which are expressed in the spinal cord and DRGs, are AC type 5 and 6 and AC type 4 and 6, respectively. No major changes in AC isoform expression were observed after zymosan treatment in spinal cord. Hence, Gαs stimulated AC activity in membrane preparations from spinal cord and DRG was inhibited by PAM. Consequently, it was found that treatment with antisense but not sense oligonucleotides against PAM increased formalin induced paw flinching in adult rats. Accordingly cAMP accumulation in the spinal cord of rats treated with antisense oligonucleotides to PAM was elevated as compared to control rats.

Addition of purified PAM to spinal cord lysates resulted in an inhibition of Gαs-stimulated AC activity of spinal cord lysates from control and zymosan treated animals (FIG. 5*b*). At 30 nM Gαs-stimulated AC activity was decreased by 50% in spinal cord lysates of control animals and 70% in lysates derived from rats treated with zymosan for 96 hours.

Figure 1:
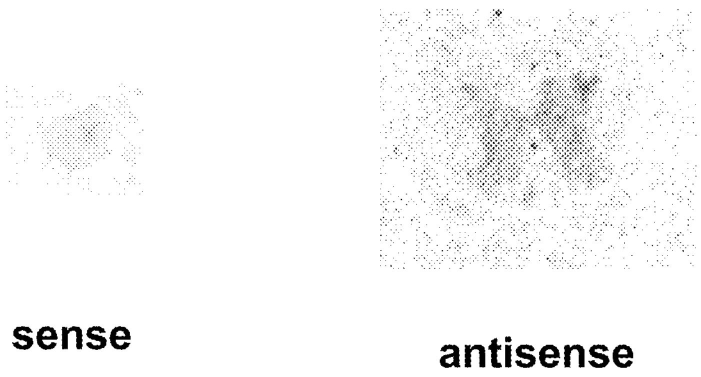
FIG. 1: PAM is highly expressed in spinal cord neurons. In situ hybridization using horizontal sections of spinal cords hybridized with sense or antisense probes against rat PAM.
Figure 2A:
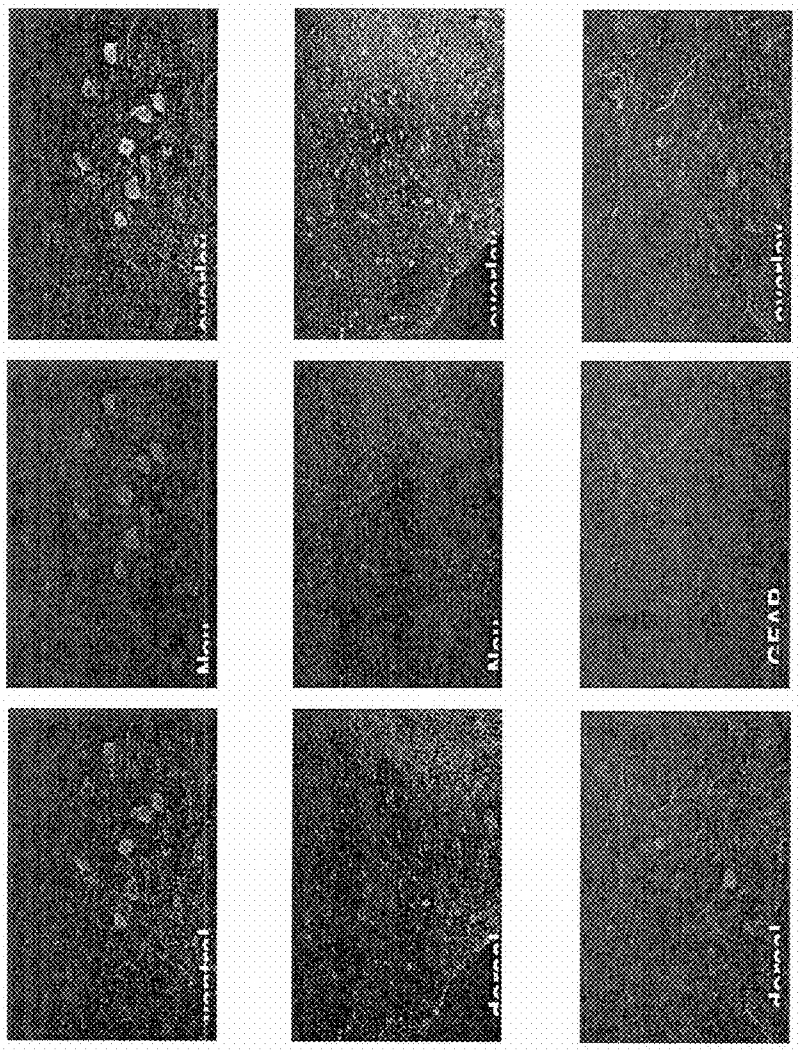
FIG. 2A: Immunohistochemical analysis of rat spinal cord sections. The sections were stained with anti-PAM antibody (green) and anti-NeuN or anti-GFAP (red) to visualize neurons or glia cells, respectively. The overlay of both signals is presented in the right panels. The objects were magnified 20×.
Figure 2B:
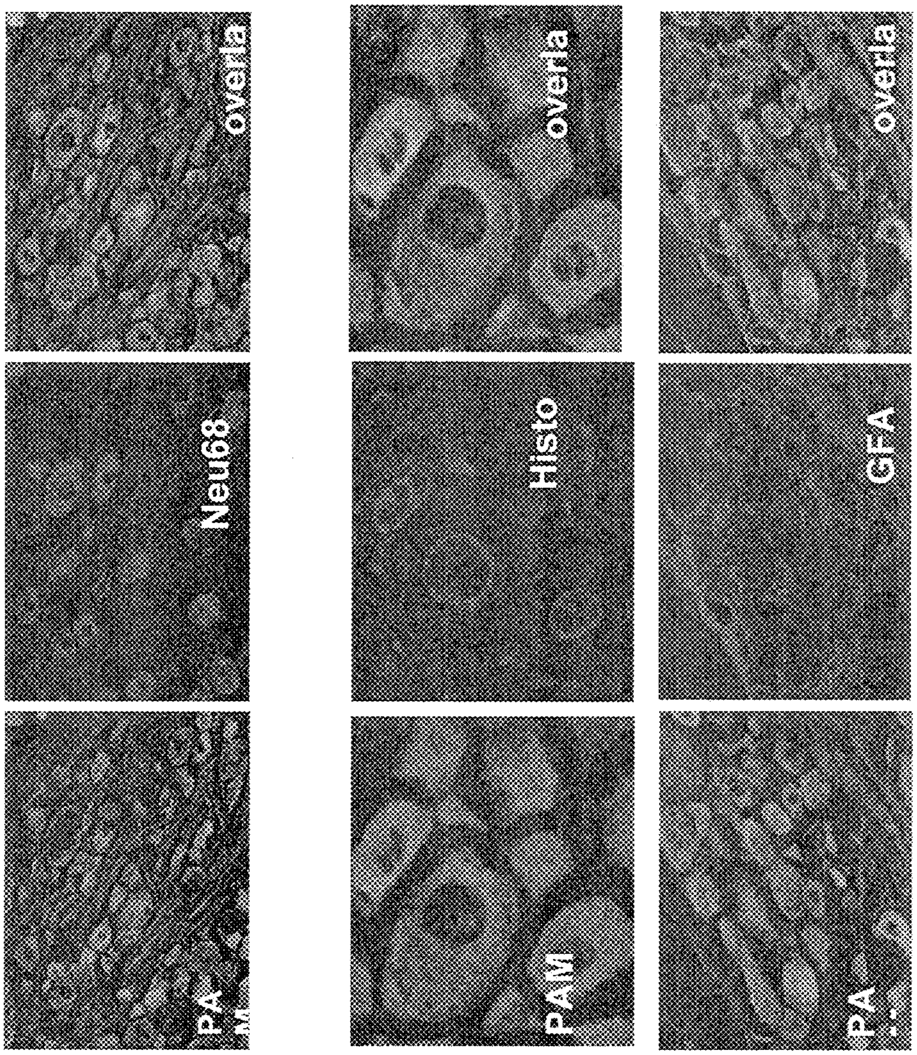
FIG. 2B: Immunohistochemical analysis of rat DRGs sections. The sections were stained with anti-PAM antibody (green) and anti-Neu68, anti-Histon or anti-GFAP (red) to visualize neurons, nuclei or glia cells, respectively. The overlay of both signals is presented in the right panels. The objects were magnified 40× except for the Histon staining, which was magnified 63×.

To determine if PAM is expressed in the spinal cord, first in situ hybridization was performed. This led to the detection of a clear signal for PAM mRNA throughout the gray matter but not in the white matter of the spinal cord of adult rats (FIG. 1). To define more precisely the cell populations that express PAM in the spinal cord as well as in DRGs, antibodies against PAM using peptides corresponding to the amino acid residues 135-153 and 4601-4614 of human PAM were generated. The immunohistochemical analysis revealed that PAM was co-localized with anti-NeuN but not with anti-GFAP immunoreactivity (FIG. 2*a*). More specifically, PAM expression was detected predominantly in dorsal horn neurons (FIG. 2*a*) while non-neuronal cell populations exhibited very little PAM expression. Especially high PAM expression could be detected in DRG neurons (FIG. 2*b*). Here, PAM immunoreactivity was located in the axons as well as in the cell body of both large- and small-diameter neurons (FIG. 2*b*). Interestingly, no PAM was detected in the nuclei of the cells as demonstrated by co-staining with anti-Histone antibody (FIG. 2*b*). As could also be seen in the spinal cord, PAM expression was not detected in GFAP expressing cells.

Figure 3:
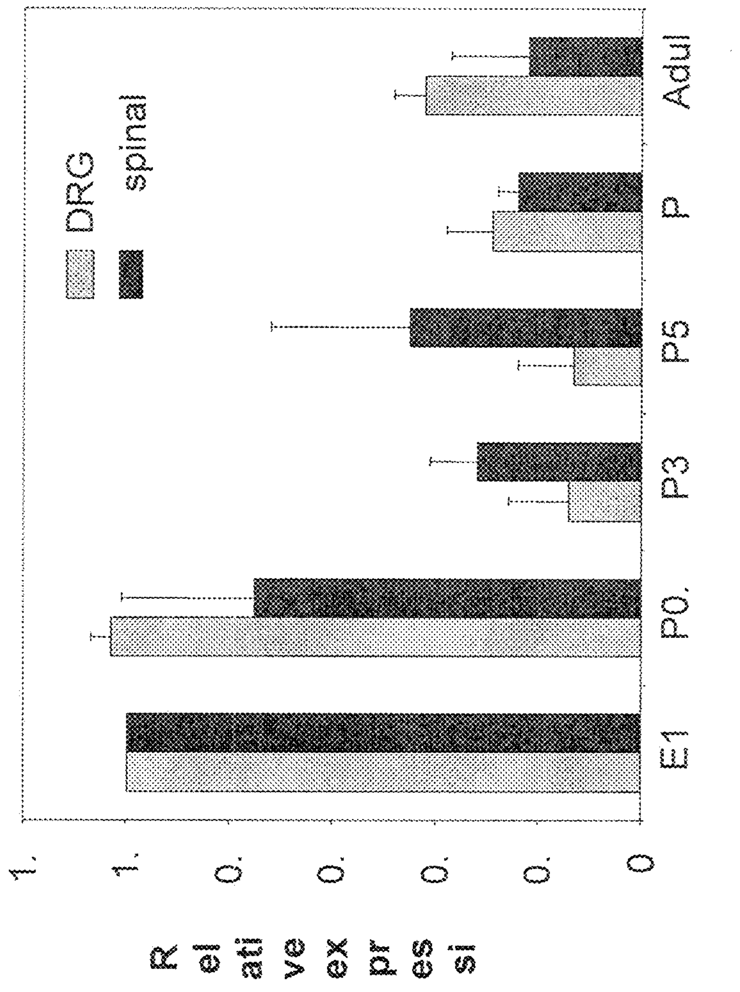
FIG. 3: PAM is differentially expressed in DRGs and spinal cord during different developmental stages. Quantitative RT-PCR (Taqman™) was used to detect PAM in RNA (40 ng) of spinal cord, and DRGs of embryonic rats day 16 (E16), postnatal day 0.5 (P0.5), 3 (P3), 5 (P5), 9 (P9) and adult rats. The mean±SEM of at least 3 determinations is shown.

Since PAM expression in the brain is differentially regulated during development in rats and mice (Yang et al. 2002), the inventors investigated if PAM mRNA expression also changes during development in rat spinal cord and DRG. To this end, PAM mRNA expression was determined using quantitative RT-PCR. PAM mRNA was found to be highly expressed in the spinal cord and DRG in late embryonic stages (E16) until shortly after birth (P0.5; FIG. 3).

Interestingly, shortly after birth the expression declined to 30-40% of the embryonic expression and then remained constant throughout adulthood (FIG. 3).

Figure 4:
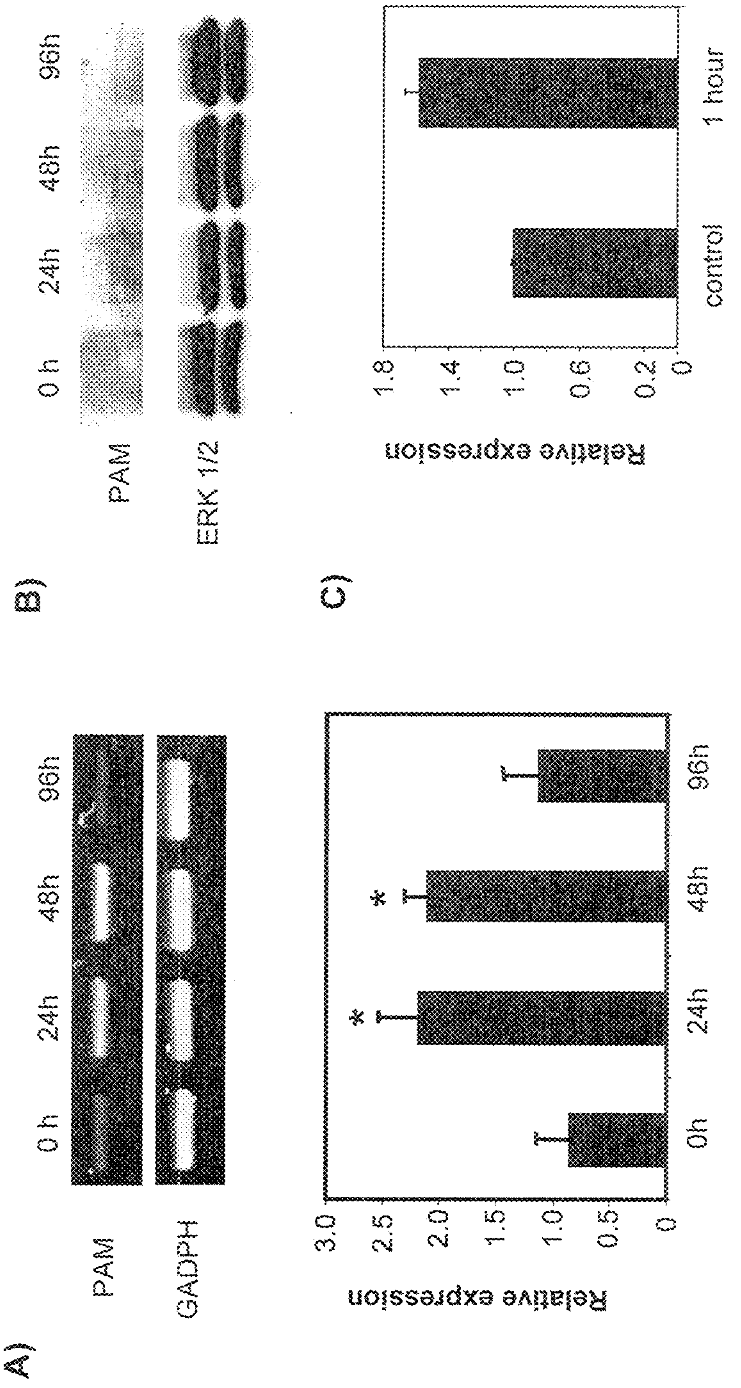
FIG. 4: PAM is upregulated in the rat spinal cord after zymosan and formalin treatment.

Next, it was examined if PAM expression in the spinal cord is regulated by nociceptive stimuli. Therefore, spinal PAM expression was monitored after zymosan and formalin injection in the hind paws of adult rats. PAM mRNA was upregulated about two-fold at 24 and 48 hours after zymosan treatment (FIG. 4*a*). Accordingly, PAM expression was upregulated at the protein level 24 hours after zymosan injection and stayed elevated for 96 hours (FIG. 4*b*). 96 hours after zymosan injection, PAM mRNA expression declined. This reduction in PAM mRNA expression was not reflected at the protein level (comp. FIGS. 4*a* and *b*). Notably, PAM mRNA was also upregulated in the spinal cord of rats 1 hour after formalin injection (FIG. 4*c*).

Since PAM is known to be a powerful inhibitor of adenylyl cyclases type 1, 5 and 6 (Scholich et al. 2001) it was investigated if PAM is able to inhibit AC activity in spinal cord and DRG lysates. Two major AC isoforms are detected by semi-quantitative RT-PCR in the spinal cord. These AC isoforms are type 5 and 6 (FIG. 5*a*). Notably, both isoforms are inhibited at nanomolar concentrations of PAM (Scholich et al. 2001). The AC isoform expression pattern in the spinal cord was not significantly altered 24-96 hours after zymosan injection. Interestingly, 1 hour after formalin injection a shift in AC isoform expression was detected (FIG. 5*a*). The mRNA of AC type 5 is down-regulated and the mRNA of AC type 3 and 9 are up-regulated.

As could be shown by the above experiments, addition of purified PAM to spinal cord lysates resulted in inhibition of Gαs-stimulated AC activity in spinal cord preparations. Addition of 30 nM PAM decreased Gαs-stimulated AC activity by 49% in spinal cord lysates of control animals (FIG. 5*b*). Gαs-stimulated AC activity in spinal cord lysates derived from rats 96 hours after zymosan injection exhibited higher sensitivity to PAM inhibition as compared to untreated animals (70% inhibition at 30 nM; FIG. 5*b*). In contrast, inhibition of AC activity by PAM in spinal cord lysates from animals treated for 1 hour with formalin was inhibited to a lesser extent (25% inhibition at 30 nM; FIG. 5*b*).

In DRGs the predominantly expressed AC isoforms are AC type 4 and 6 (FIG. 5*a*). Gαs-stimulated AC activity in DRG lysates was decreased by 32% in presence of 30 nM PAM in contrast to spinal cord lysates (FIG. 5*b*).

To examine a possible role of PAM in spinal nociceptive transmission, animals were infused with PAM sense and antisense oligonucleotides by lumbar intrathecal catheters before performing a formalin assay. PAM expression was decreased in spinal cord neurons as observed by immunohistochemistry (FIG. 6*a*). Infusion of PAM antisense oligonucleotides caused a significant increase of the nociceptive response following formalin injection as compared to PAM sense treatment ($p=0.007$; FIGS. 6*b* and *c*). The hyperalgesia in PAM antisense-treated rats was accompanied by increased licking and biting behavior. Since PAM is an inhibitor of AC activity (Scholich et al. 2001), basal, Gαs- and forskolin-stimulated AC activities were determined in spinal cord lysates of sense and antisense-ODN treated rats. The experiments showed a significant increase (20.7%) of the basal AC activity in antisense treated rats (Table 1). In contrast, no significant changes were detected in Gαs- and forskolin-stimulated AC activities indicating that the total amount of AC was not altered by the ODN treatment (Table 1).

The above experiments showed that PAM is localized in the cell body and axons of both spinal cord and DRG neurons (FIG. 2*a,b*). Only very little immunoreactivity was detectable in the nucleus suggesting different functions for PAM in neurons and cancer cell lines.

Central sensitization after prolonged nociceptive stimuli is based on neuronal and synaptic changes in the spinal cord (Woolf and Costigan 1999; Woolf and Salter 2000; Ji and Woolf 2001). The finding of the inventors that Pam is expressed in sensory neurons of the spinal cord and DRGs led to the newly formed hypothesis, that PAM could be implicated in synaptic changes during spinal nociceptive processing. The above findings that PAM was up-regulated after nociceptive stimuli (FIG. 4*a*) supported this hypothesis that PAM may play a role in synaptic changes during spinal nociceptive processing.

Furthermore, the surprising finding of the inventors, that PAM is expressed in sensory nervous of the spinal cord and DRGs led to the question whether PAM is capable of inhibiting AC activity in spinal cord and DRG, as well.

The above experiments showed for the first time that PAM is a potent inhibitor of Gαs-stimulated AC activity in spinal cord preparations (FIG. 5*b*). AC activity was decreased by 50% after addition of 30 nM PAM. To achieve comparable inhibition using the α-subunit of the inhibitory G-protein, Gαi, 200-800 nM Gαi has to be used (Wittpoth et al. 1999). The inhibitory action of PAM was even stronger in spinal cord preparations of animals treated for 96 hours with zymosan (FIG. 5*b*) and could be explained by the elevated amounts of endogenous PAM in the spinal cord after zymosan injection (FIG. 4*a,b*). Inhibition of Gαs-stimulated AC activity in spinal cord preparations from formalin-treated animals (25% inhibition) was less pronounced as compared to control or zymosan-treated animals (50% and 75%, respectively).

Notably, in animals treated with formalin for 1 hour a shift in AC isoform expression was observed (FIG. 5*a*). AC of type 3 and 9 are up-regulated while AC type 5 is down-regulated. To date it is not known if PAM is an inhibitor of AC type 3 and 9. Therefore, these isoforms may not be inhibited by PAM or the tested PAM concentrations were too low to achieve an inhibitory effect. Since PAM is a giant protein of 510 kDa, it is technically not possible to test PAM concentrations greater than 30 nM. Nonetheless, according to the dose response curves shown in FIG. 5*b*, higher PAM concentrations might result in a stronger inhibition of Gαs-stimulated AC activity in the tested spinal cord preparations.

Interestingly, PAM was a less effective inhibitor of AC enzyme activity in DRG than in spinal cord preparations. The different inhibitory efficiencies of PAM in spinal cord and DRG preparations are most likely due to the observed differences in AC isoform expression. The major AC isoforms that are expressed in the spinal cord are type 5 and 6 that are both strongly inhibited by PAM (FIG. 5*a*; (Scholich et al. 2001)). In DRGs AC type 4 and 6 are the dominant AC isoforms (FIG. 5*a*). Since it is unknown if PAM inhibits AC type 4 either this isoform is not inhibited by PAM or, again, the tested PAM concentrations were too low to achieve the inhibitory effect. However, according to the dose response curve shown in FIG. 5*b* it is seems likely that higher concentrations of PAM would result in a stronger inhibition of Gαs-stimulated AC activity in the DRG preparations.

Most surprising, however, were the findings, that PAM activity had an influence on the nociceptive behavior of the test animals: This could be demonstrated for the first time by experiments of the inventors showing a significant increase in basal AC activity (Table 1) and—more important—a significant increase of the nociceptive response following formalin injection as compared to PAM sense treatment (FIGS. 6*b* and *c*) when endogenous PAM expression in the spinal cord was decreased by infusing animals with PAM antisense oligonucleotides (FIG. 6*a*).

19. Determination of the Analgesic Effect of PAM

The above-listed evidence for the analgesic effect of PAM could for example be supported by the following hypothetic experiment: The analgesic effect of PAM, e.g. in the formalin model of acute pain, could be determined directly by intrathecal application of e.g. a peptide corresponding to amino acid residues 1028 to 1065. This peptide represents the minimal region found to be capable of mediating PAM-adenylyl cyclase interactions as determined by the yeast-two-hybrid system and AC activity assays. The peptide could be applied in a complex with the bioporter lipofection reagent (commercially available at Peqlab, Germany). This approach would allow the peptide to enter the tissue and mimic the actions of physiological PAM towards ACs.

20. Results Demonstrating the Influence of S1P on PAM Signaling

To investigate PAM expression and localization in HeLa cells, two antibodies against PAM where employed, which are directed against peptides corresponding to the amino acid residues 135-153 and 4601-4614 of human PAM. Comparison of immunohistological staining of rat brain showed that both antibodies recognized the same brain regions which also exhibit PAM mRNA expression (Yang et al., 2002). In serum starved HeLa cells both antibodies showed colocalization of PAM with calnexin, an endoplasmatic reticulum marker (FIG. 18*a*). After addition of serum to the cells, a partial translocation of PAM to the plasma membrane was observed (FIG. 18*b*). PAM appeared at the membrane 20-30 minutes after serum treatment and started to disappear from the membrane after 1 hour serum incubation. The cellular distribution of PAM in HeLa observed with the antibodies used differs from the cellular distribution described by Guo et al. Since Guo et al. used a portion of PAM to generate antibodies that includes common motifs for nuclear proteins cross-reactions with nuclear proteins by this antibody are possible.

Since PAM is a potent inhibitor of AC enzyme activity, it was next investigated if the translocation of PAM from the ER to the plasma membrane results in an inhibition of AC activity. Serum-treatment of HeLa cells reduced the intracellular cAMP accumulation (FIG. 19*a*). Additionally, serum-treatment decreased $G_{\alpha s}$- and forskolin-stimulated AC activity to 56.7% and 64.7%, respectively, as compared to untreated cells (FIG. 19*b*). The observed decrease in AC activity was not due to a change in the AC isoform expression or due to an increased AC expression since no changes in the mRNA expression of AC isoforms was detected (FIG. 19*c*). To determine if the decrease in stimulated AC activity was mediated by PAM, the amount of endogenous PAM was decreased, employing antisense oligonucleotides against PAM as previously described in Scholich et al., 2001. As shown in FIG. 19*d*, in HeLa cells treated with antisense ODN the amount of PAM, as determined by Western Blot analysis, was decreased as compared to cells treated with sense or mutant antisense ODNs. Reprobing the same blot with anti-Hsp70 antibody showed that the loading of proteins was the same (FIG. 19*d*). However, the treatment of HeLa cells with antisense ODN reduced the serum-induced inhibition of $G_{\alpha s}$- and forskolin-stimulated AC activity significantly (FIG. 19*e*). Importantly, transfection of HeLa cells with sense or mutated ODNs had no influence on the serum-induced inhibition of $G_{\alpha s}$- and forskolin-stimulated AC activity (FIG. 19*e*). These data suggest that endogenous PAM exerts an inhibitory influence on AC activity after stimulation of HeLa cells with serum.

To identify the serum factor that induces PAM translocation to the plasma membrane the factor was purified using reverse phase-, anionic exchange- and gelfiltration-columns. After each purification step, the fractions were tested for their ability to induce PAM translocation and AC inhibition. According to the purification properties, the serum factor could be identified to be slightly hydrophobic (Elution from the Phenyl-Sepharose column with 0.3 M NaCl), possesses a strong negative charge (elution from MonoQ and Q-Sepharose columns at 0.7 M NaCl) and has an estimated molecular weight under 500 according to the retention time on the superdex 30 gelfiltration column. According to the physical properties several candidate substances were tested, from which only sphingosine-1-phosphate induced PAM translocation.

S1P can bind to a family of five G-protein coupled receptors. Therefore it was investigated by semi-quantitative RT-PCR if HeLa cells express S1P-receptors. The mRNA of four of the five S1P-receptor isoforms ($S1P_{1-4}$) was detected in the HeLa cells (FIG. 20*a*). Next, it was tested if purified S1P exhibits the same properties toward PAM activation/translocation as serum. First, HeLa cells were treated with increasing concentrations of purified S1P. PAM translocation to the plasma membrane occurred in 70-90% of cells treated with 0.1-5 μM S1P treated cells. PAM appeared at the plasma membrane after 10 minutes incubation with 500 nM S1P and started to disappear after 1 hour of incubation (FIG. 3*b,c*). Most importantly, treatment of HeLa cells with 0.5 μM S1P reduced the intracellular cAMP content (FIG. 21*a*) as well as the $G_{\alpha s}$-stimulated AC activity (FIG. 21*b*). $G_{\alpha s}$-stimulated AC activity decreased within 3 minutes after incubation with S1P and before partly recovering. 5-10 minutes after begin of the S1P treatment, $G_{\alpha s}$-stimulated AC activity decreased once more FIG. 4*b*). Antisense ODN against PAM eliminated the inhibition of $G_{\alpha s}$-stimulated AC activity at 60 minutes after incubation with S1P (FIG. 21*c*). Taken together, these data demonstrate for the first time that inhibition of AC activity in HeLa cells by S1P is achieved through two different mechanisms: A fast PAM-independent AC inhibition (3-10 minutes S1P treatment) and a delayed, PAM-dependent AC inhibition (10-60 minutes S1P treatment).

It has been demonstrated that by binding to its respective receptors, S1P can potentially activate four different G proteins, Gi, Gq, G12, and G13 (Hla et al., Science, 2001; Kluk et all, BBA, 2002; Siehler and Manning, BBA, 2002; Spiegel and Milstein, JBC, 2002). From these, only Gi is pertussis toxin sensitive. Pertusis toxin-treatment eliminated the inhibitory effect of S1P on $G_{\alpha s}$-stimulated AC activity (FIG. 22*a*) and PAM translocation to the plasma membrane (FIG. 22*b*). Thus, it seems likely that the inhibitory G-protein, Gi, is responsible for the fast, PAM-independent inhibition by S1P.

Next, further elements of the signal transduction pathway that causes translocation and activation of PAM were elucidated. Since $S1P_{1-4}$ receptors have been described to couple to $G_i$, $G_q$ and $G_{12/13}$ (Hla et al., 2001; Kluk et al., 2002; Siehler et al., 2002; Spiegel et al., 2002) and translocation of PAM as well as AC inhibition is pertussis toxin-dependent (FIG. 22*a*) the above data suggest that PAM activation in HeLa cells depends on $G_i$ activation. Previously it has been described that S1P can activate phospholipase C (PLC) as well as ERK1/2 signaling through activation of $G_i$ (Kluk et al., 2002; Siehler et al., 2002; Spiegel et al., 2002). Thus, it was tested if PLC activation is involved in PAM translocation, and it could be found that PAM translocation and late phase AC inhibition was abolished in presence of the PLC inhibitor U73122 (FIG. 22*a*). PLC converts phosphatidylinositol 4,5-biphosphate to inositol 1,4,5-triphosphate ($IP_3$), a calcium-mobilizing second messenger, and 1,2-diacylglycerol (DAG), an activator of protein kinase C (PKC) (Rebecchi et al., 2000; Wilde et al., 2001). Calcium imaging showed that S1P induced a PLC-dependent calcium increase in HeLa cells. However, this calcium decrease was not necessary for PAM translocation since pre-treatment with BAPTA-AM did not interfere with PAM translocation (FIG. 22*a*). Yet PKC inhibitors GF109203X and RO 31-8220 eliminated PAM translocation and AC inhibition, respectively (FIG. 22*a*). These data suggest that S1P activates PLC through the inhibitory G-protein, Gi. Subsequently, PLC actions result in a calcium-independent PKC activation which is necessary to mediate PAM translocation and the delayed S1P-induced AC inhibition.

Since it has also been shown that S1P can activate the ERK1/2 signaling pathway (Kluk et al., 2002; Siehler et al., 2002; Spiegel et al., 2002), it was tested if EK1/2 is activated by S1P in HeLa. ERK1/2 phosphorylation was detectable after incubation of HeLa with S1P using anti-active ERK and anti-phosphoTyr[183] ERK antibodies (FIG. 22*b*). Surprisingly, ERK1/2 phosphorylation depended on PLC activation (FIG. 22*b*), $G_i$, and PKC activity (data not shown) but was independent of an increase in intracellular calcium. However, ERK1/2 activation was not necessary for PAM translocation or inhibition of AC activity (FIG. 22*a*). Altogether these findings show for the first time that S1P induces PAM translocation and subsequent inhibition of AC enzyme activity through a signaling cascade that includes Gi, PLC and PKC. Interestingly, S1P induced additionally ERK1/2 activation and an increase of intracellular calcium concentrations, both of which were not necessary for PAM translocation or inhibition of $G_{\alpha s}$-stimulated AC activity.

The signal transduction pathways regulated by S1P are the focus of intensive research (Kluk et al., 2002; Siehler et al., 2002; Spiegel et al., 2002). It is well known that S1P receptors can inhibit AC activity through Gi dependent mechanisms (Kluk et al., 2002; Siehler et al., 2002; Spiegel et al., 2002). However, here, it was shown for the first time that inhibition of AC activity over prolonged times after S1P stimulation is not due to a direct inhibition of AC by the inhibitory G-protein since the delayed AC inhibition depended on PLC- and PKC-activation. Moreover, the data of the inventors suggest that the prolonged inhibition of AC activity in HeLa cells after S1P-treatment depends on the translocation/activation of PAM to the plasma membrane. This translocation is regulated by Gi activation and PLC/PKC signaling. Since PAM is a potent inhibitor of AC enzyme activity S1P-induced PAM-dependent AC inhibition may be a result of direct interactions between PAM and AC although this still has to be determined.

The above experiments of the inventors led for the first time to the finding that PAM is localized at the endoplasmatic reticulum in HeLa cells and translocates to the plasma membrane after serum treatment. PAM translocation was accompanied by a decrease in $G_{\alpha s}$- and forskolin-stimulated AC activity as compared to untreated HeLa cells. AC inhibition was mediated by PAM since pretreatment of the cells with antisense oligonucleotides against PAM prevented AC inhibition. In the following we identified Sphingosine-1-phosphate (S1P) as the serum factor responsible for PAM translocation. Treatment of HeLa cells with 0.1-5 μM S1P induced PAM translocation to the plasma membrane in 80% of the cells within 10-30 minutes. S1P reduced AC activity by two separated mechanisms. Initial AC inhibition was not mediated by PAM but was pertussis toxin sensitive. After prolonged S1P-treatment AC inhibition depended on PAM translocation. S1P actions towards PAM translocation and PAM-mediated AC inhibition were pertussis toxin-sensitive and required PLC- and PKC-activation. Taken together, these data identified for the first time a regulator of PAM activity. Moreover, it could be shown that long-term inhibition of AC activity by S1P is mediated by the translocation of the AC-inhibitory protein PAM from the ER to the plasma membrane.

21. Determination of the Analgesic Effect of S1P

To determine the analgesic effect of S1P, S1P was delivered to the spinal chord by intrathecal application.

21 a) Implantation of Lumbar Intrathecal Catheters:

Rats were anesthetized with ketamine (60 mg/kg i.p.) and midazolam (0.5-1 mg/kg i.p.). The skin was incised above the vertebral column from vertebrae Th13 up to L3. Muscle tissue around L2-3 was cleared away. The processus spinosus of L3 was removed and a laminectomy was done at L2. Polyethylene catheters (ID 0.28 mm, OD 0.61 mm) were then inserted into the peridural space so that the tip of the catheter reached Th9-10. The catheter was fixed with cyanacrylate glue and was externalized in the neck region and the skin was sutured.

21 b) Infusion of PAM Oligonucleotides.

Three days after surgery rats were placed into a "freely moving system" (CMA, Stockholm, Sweden) 20 μl of 10 μM S1P were infused through the catheter.

21 c) Formalin Test:

Within 15 min after stopping the infusion the formalin test was performed. 50 μl of a 5% formaldehyde solution were injected subcutaneously (s.c.) into the dorsal surface of one hind paw. Flinches were counted in one minute intervals up to 60 min starting right after formalin injection. Flinches of 5 min intervals were summarized as mean flinches per minute. To compare the nociceptive behavior between groups the sum of flinches during the one-hour observation period were submitted to the Students t-test. At the end of the formalin test, the lumbar spinal cord and dorsal root ganglions (DRGs) were excised, snap frozen in liquid nitrogen and stored at −80° C. until further analysis.

21d) Results:

20 μl of 10 μM S1P or 20 μl PBS/DMSO were given to adult rats by intrathecal application 15 minutes prior to the formalin injection. Then, flinches were counted in 5 minute intervals over a period of 60 minutes. A significant decrease in the number of nociceptive responses for phase 2A (20 to 35 minutes after formalin injection) could be detected as compared to PBS/DMSO-treated animals (see FIG. 24). These experiments clearly demonstrated that exogenous S1P acts as an analgesic.

22. Determination of the Analgesic/Antinociceptive Effect of S1P Receptor Agonists The analgesic/antinociceptive effect of S1P receptor agonists, e.g. FTY 720 could for example be supported by the following hypothetic experiment: The analgesic/antinociceptive effect of e.g. FTY 720, e.g. in the formalin model of acute pain, could be determined directly by intrathecal or intravenous application of e.g. FTY 720 and consecutive testing of its analgesic/antinociceptive effect by means of e.g. the flinch test. This approach would allow the molecule to enter the tissue and mimic the actions of physiological S1P towards ACs.

LITERATURE

Bailey C. H., Bartsch D., Kandel E. R.: Toward a molecular definition of long-term memory storage. Proc. Natl. Acad. Sci. U.S.A. 1996 Nov. 26; 93(24):13445-52;

Brandon E. P., Idzerda R. L., McKnight G. S.: PKA isoforms, neural pathways, and behaviour: making the connection. Curr. Opin. Neurobiol. 1997 June; 7 (3):397-403;

Bek M. J., Zheng S., Xu J., Yamaguchi I., Asico L. D., Sun X. G. and Jose P. A. (2001) Differential expression of adenylyl cyclases in the rat nephron. Kidney Int 60, 890-899;

Brinkmann, V., Davis, M. D., Heise, C. E., Albert, R., Cottens, S., Hof, R., Bruns, C., Prieschl, E., Baumruker, T., Hiestand, P., Foster, C. A., Zollinger, M. and Lynch, K. R., (2002), The Immune Modulator FTY720 Targets Sphingosine-1-Phosphate Receptors; the Journal of Biological Chemistry, Vol. 277, No. 24, June 14, p. 21453 to 21457;

Caligan, T. B., Peters, K., Ou, J., Wang, E., Saba, J., and Merrill, A. H., Jr. (2000) Anal Biochem 281, 36-44

Chang Q. and Balice-Gordon R. J. (2000) Highwire, rpm-1, and futsch: balancing synaptic growth and stability. Neuron 26, 287-290;

Chen, Z., Nield, H. S., Sun, H., Barbier, A., and Patel, T. B. (1995) J Biol Chem 270, 27525-27530

Chomczynski, P., Sacchi, N.: Single-step method of RNA isolation by acid guanidinium thiocyanate-phenol-chloroform extraction. Anal. Biochem. 162, (1987) 156-159;

DiAntonio, A., Haghighi, A. P., Portman, S. L., Lee, J. D., Amaranto, A. M., and Goodman, C. S. (2001) Nature 412, 449-452

Graziano, M. P. Freissmuth M. Gilman A. G.: Purification of recombinant Gs alpha. Meth. Enz. (1991) 195: 192-215;

Graziano M. P., Freissmuth M. and Gilman A. G. (1991) Purification of recombinant Gs alpha. Methods Enzymol 195, 192-202;

Guo Q., Xie J., Dang C. V., Liu E. T., Bishop J. M.: Identification of a large Myc-binding protein that contains RCC1-like repeats. Proc. Natl. Acad. Sci. U.S.A. 1998 Aug. 4; 95 (16):9172-7);

Grossberger, R., Gieffers, C., Zachariae, W., Podtelejnikov, A. V., Schleiffer, A., Nasmyth, K., Mann, M., and Peters, J. M. (1999) J Biol Chem 274, 14500-14507;

Hla, T., Lee, M. J., Ancellin, N., Paik, J. H., and Kluk, M. J. (2001) Science 294, 1875-1878

Jin Y. (2002) Synaptogenesis: insights from worm and fly. Curr Opin Neurobiol 12, 71-79);

Julius and Basbaum "Molecular mechanisms of nociception", Nature, volume 413, 13. September 2001, pp. 203-209;

Kassis, S., and Fishman, P. H. (1982) J Biol Chem 257 (9), 5312-5318;

Kind, P. C., and Neumann, P. E. (2001) Trends Neurosci 24, 553-555;

Kluk, M. J., and Hla, T. (2002) Biochim Biophys Acta 1582, 72-80

Mandala, S., Hajdu, R., Bergstrom, J., Quackenbush, E., Xie, J., Milligan, J., Thornton, R., Shei, G., Card, D., Keohand, C., Rosenbach, M., Hale, J., Lynch, C. L., Rupprecht, K., Parsons, W. and Rosen, H., (2002), Alteration of Lymphocyte Trafficking by Spingosine-1-Phospate Receptor Agonists, Science, Vol. 296, April 2002;

Meller S. T., Gebhart G. F. (1997), intraplantar zymosan as a reliable, quantifiable model of thermal and mechanical hyperalgesia in the rat; Eur. J. Pain 1, 43-52;

Nair, B. G., Parikh, B., Milligan, G., and Patel, T. B. (1990) J Biol Chem 265 (34), 21317-21322;

Nestler, E. J. (2001) Nat Rev Neurosci 2, 119-128

Patel T. B., Wittpoth C., Barbier A. J., Yigzaw Y. and Scholich K. (2002) Functional analyses of type V adenylyl cyclase. Methods Enzymol 345, 160-187.

Snyder S. H. (1985) Adenosine as a neuromodulator. Annu Rev Neurosci 8, 103-124;

Payne, S. G., Milstien, S., and Spiegel, S. (2002), Sphingosine-1-phosphate: dual messenger functions; FEBS Letters 531 (2002), p. 54 to 57;

Postma, F. R., Jalink, K., Hengeveld, T., and Moolenaar, W. H. (1996) Embo J 15, 2388-2392

Rebecchi, M. J., and Pentyala, S. N. (2000) Physiol Rev 80, 1291-1335

Ruppert C., Goldowitz D., and Wille W. (1986), Proto-oncogene-c-Myc is expressed in cerebellar neurons at different developmental stages, Embo J5, 1897-1901;

Sato, K., Tomura, H., Igarashi, Y., Ui, M., and Okajima, F. (1997) Biochem Biophys Res Commun 240, 329-334

Schaefer A. M., Hadwiger G. D. and Nonet M. L. (2000) rpm-1, a conserved neuronal gene that regulates targeting and synaptogenesis in *C. elegans*. Neuron 26, 345-356);

Schaible H. G., Vanegas H.: How do we manage chronic pain? Baillieres Best. Pract. Res. Clin. Rheumatol. 2000 December; 14 (4):797-811;

Scherr M., Morgan M. A., Eder M., Gene Silencing Mediated by Small Interfering RNAs in Mammalian Cells, Curr Med Chem. 2003, February; 10 (3): 245-256;

Scholich, K., Mullenix, J. B., Wittpoth, C., Poppleton, H. M., Pierre, S. C., Lindorfer, M. A., Garrison, J. C., and Patel, T. B. (1999) Science 283, 1328-1331

Scholich K., Pierre S., Patel T. B.: Protein associated with Myc (PAM) is a potent inhibitor of adenylyl cyclase. J. Biol. Chem. 2001, Dec. 14; 276 (50):47583-9;

Scholz and Woolf "Can we conquer pain", Nature neuroscience supplement, volume 5, November 2002, pp. 1062-1067;

Siehler, S., and Manning, D. R. (2002) Biochim Biophys Acta 1582, 94-99

Snyder S. H. (1985), Adenosine as a neuromodulator. Annual Reviews of Neuroscience 8, 103-104;

Spiegel, S. and Milstien, S. (2000), Functions of a new family of sphingosine-1-phosphate receptors, Biochimica et Biophysica Acta 1484, p. 107 to 116;

Spiegel, S., and Milstien, S. (2002) J. Biol. Chem 277; 25851-25854;

Trajkovic V, Samardzic T, Stosic-Grujicic S, Ramic Z, Mostarica Stojkovic M. Muramyl dipeptide potentiates cytokine-induced activation of inducible nitric oxide synthase in rat astrocytes. Brain Res. 2000 Nov. 10; 883 (1):157-63;

Wan H. I., DiAntonio A., Fetter R. D., Bergstrom K., Strauss R. and Goodman C. S. (2000) Highwire regulates synaptic growth in *Drosophila*. Neuron 26, 313-329);

West, A. E., Chen, W. G., Dalva, M. B., Dolmetsch, R. E., Kornhauser, J. M., Shaywitz, A. J., Takasu, M. A., Tao, X., and Greenberg, M. E. (2001) Proc Natl Acad Sci USA 98, 11024-11031;

Wilde, J. I., and Watson, S. P. (2001) Cell Signal 13, 691-701

Wittpoth C., Scholich K., Yigzaw Y., Stringfield T. M. and Patel T. B. (1999), Regions on adenylyl cyclase that are necessary for inhibition of activity by beta gamma G(iα) subunits of heterotrimeric G proteins. Proc. Natl. Acad. Sci. USA 96, 7723-7730;

Wood, J. D. "Pathobiology of Visceral Pain: Molecular Mechanisms and Therapeutic Implications II. genetic approaches to pain therapy", American Journal of Physiological Gastrointestinal Liver Physiology, 2000, volume 278, G507-G512;

Woolf and Mannion "Neuropathic pain: aetiology, symptoms mechanisms, and management", The LANCET, volume 353, Jun. 5, 1999, pp. 1959-1964;

Woolf J. and Salter M. W. "Neuronal Plasticity: Increasing the Gain in Pain", Science, volume 288, Jun. 9, 2000, pp. 1765-1768;

Xia Z., Storm D. R.: Calmodulin-regulated adenylyl cyclases and neuromodulation. Curr. Opin. Neurobiol. 1997 June; 7 (3):391-6;

Xu, D., Isaacs, C., Hall, I. P., and Emala, C. W. (2001) Am J Physiol Lung Cell Mol Physiol 281, L832-843

Yang H., Scholich K., Poser S., Storm D., Patel T. B., Goldowitz D.: Developmental expression of protein associated with Myc (PAM) in the rodent brain. Brain Res Dev Brain Res 136, 2002, 35-42;

Zhen M., Huang X., Bamber B. and Jin Y. (2000) Regulation of presynaptic terminal organization by *C. elegans* RPM-1, a putative guanine nucleotide exchanger with a RING-H2 finger domain. Neuron 26, 331-343);

STANDARD LITERATURE FOR LABORATORY METHODS

If not indicated otherwise, laboratory methods were or can be performed according to standard methods listed in the below standard literature:

Sambrook et al. (1989) Molecular Cloning: A Laboratory Manual. Second edition. Cold Spring Harbor Laboratory Press, Cold Spring Harbor, N.Y. 545 pp or Current Protocols in Molecular Biology;

Current Protocols in Molecular Biology; regularly updated, e.g. Volume 2000; John Wiley & Sons, Inc; Editors: Fred M. Ausubel, Roger Brent, Robert Eg. Kingston, David D. Moore, J. G. Seidman, John A. Smith, Kevin Struhl.

Current Protocols in Human Genetics; regularly updated, e.g. Volume 2003; John Wiley & Sons, Inc; Editors: Nicholas C. Dracopoli, Honathan L. Haines, Bruce R. Korf, Cynthia C. Morton, Christine E. Seidman, J. G. Seigman, Douglas R. Smith.

Current Protocols in Protein Science; regularly updated, e.g. Volume 2003; John Wiley & Sons, Inc; Editors: John E. Coligan, Ben M. Dunn, Hidde L. Ploegh, David W. Speicher, Paul T. Wingfield.

Molecular Biology of the Cell; third edition; Alberts, B., Bray, D., Lewis, J., Raff, M., Roberts, K., Watson, J. D.; Garland Publishing, Inc. New York & London, 1994;

Gene Targeting: a practical approach (1995), Editor: A. L. Joyner, IRL Press

Genetic Manipulation of Receptor Expression and Function; D. Accili, Wiley-Liss., USA, 2000; ISBN: 0-471-35057-5.

Antisense Therapeutics, S. Agrawal, Humana Press, USA, 1996, ISBN: 0-89603-305-8.

Remington's Pharmaceutical Sciences, Edition 17, 1985.

Abbreviations Used:

AC, adenylyl cyclase; Gαs, α subunit of the stimulatory G protein of adenylyl cyclase, Gαs*, constitutively active (Q213L) mutant of Gαs; Gαi, α subunit of the inhibitory G protein Gi; Gβγ, βγ subunits of heterotrimeric G proteins; ODN, oligodeoxynucleotide; PAM, protein associated with Myc; RCC1, regulator of chromosome condensation; S1P, sphingosin-1-phosphate; TED, 50 mM Tris-HCl, pH 8.0, 1 mM EDTA, 1 mM DTT.; RT, room temperature;

Table 1

Basal AC activity is elevated in spinal cord lysates of antisense treated rats. Spinal cords lysates (20 μg) were assayed for AC activity in the absence or presence of 80 nM Gαs or 100 μM forskolin as described above. The mean AC activity±SEM of spinal cord lysates from at least three rats per group, each measured twice in triplicates, is shown (ns=not significant).

TABLE 1

| Condition | | AC activity (pmol/min/mg | |
|---|---|---|---|
| basal | | | |
| sense | | 102.7 ± 6.6 | |
| antisense | 1 | 24.0 ± 6.2 | (p ≤ 0.01) |
| Gαs | | | |
| sense | | 398.8 ± 16.9 | |
| antisense | | 432.6 ± 17.2 | (ns) |
| Forskolin | | | |
| sense | | 283.9 ± 25.7 | |
| antisense | | 316.2 ± 24.3 | (ns) |

The invention claimed is:

1. A method of alleviating pain associated with nociceptive processing or sensitization in the spinal cord and dorsal root ganglia, the method comprising administering to a subject experiencing pain a compound that activates a sphingosine-1-phosphate receptor in the spinal cord or dorsal root ganglia or enhances PAM (protein associated with Myc) activity in the spinal cord or dorsal root ganglia, wherein the compound is sphingosine-1-phosphate or a salt thereof or FTY 720 or a salt thereof, thereby alleviating pain associated with nociceptive processing or sensitization in the spinal cord and dorsal root ganglia in the subject.

2. The method of claim 1, wherein the compound is administered intrathecally.

3. The method of claim 1, wherein the compound is administered intravenously.

4. The method of claim 1, wherein the compound is administered orally.

5. The method of claim 1, wherein the subject is a mammal.

6. The method of claim 5, wherein the mammal is a human.

7. The method of claim 1, wherein the compound is sphingosine-1-phosphate or a salt thereof.

8. The method of claim 7, wherein the compound is administered intrathecally.

9. The method of claim 7, wherein the compound is administered intravenously.

10. The method of claim 7, wherein the compound is administered orally.

11. The method of claim 7, wherein the subject is a mammal.

12. The method of claim 11, wherein the mammal is a human.

13. The method of claim 1, wherein the compound is FTY 720 or a salt thereof.

14. The method of claim 13, wherein the compound is administered intrathecally.

15. The method of claim 13, wherein the compound is administered intravenously.

16. The method of claim 13, wherein the compound is administered orally.

17. The method of claim 13, wherein the subject is a mammal.

18. The method of claim 17, wherein the mammal is a human.

19. The method of claim 1, wherein the pain is nociceptive pain.

20. The method of claim 19, wherein the nociceptive pain is chronic nociceptive pain.

21. The method of claim 19, wherein the nociceptive pain is acute nociceptive pain.

* * * * *

SEQUENCE LISTING

<160> NUMBER OF SEQ ID NOS: 40

<210> SEQ ID NO 1
<211> LENGTH: 14807
<212> TYPE: DNA
<213> ORGANISM: Homo sapiens

<400> SEQUENCE: 1
tcttggagcg ttctcagttt ctcaacagat cttcacttgc taggcagcca gaagccggcg 60
gcagtggcgg caccgcctcc tcctcacatt cccggggtgg cggggttaga tgagcggccc 120
cagtcgcggc gccgggggcg ctgttcatgc cggttcccga cggctccgtg gctgctgcgg 180
ggctggggct ggggctaccc gccgcggact ccccgggtca ctaccagctg ctgctgtcag 240
gccgggccct ggccgaccgc taccggagga tttataccgc tgcgctcaat gacagggacc 300 agggggggcgg cagcgctgga cacccagcct ccaggaataa gaaaatttta aataagaaga 360
aattgaaaag aaaacagaag agcaaatcaa aagtgaagac aagaagcaag tctgaaaact 420
tagagaatac agtaatcata ccagatatca aactacatag caatccttct gctttcaata 480
tttactgtaa tgtacgccat tgcgttctgg aatggcagaa aaaggaaata tcattggcag 540
ccgcatctaa gaactctgtg cagagtggag aatcagatag tgatgaagaa gaggaatcca 600
aagagccccc tatcaagctt ccaaagatta ttgaggttgg cctttgtgaa gtttttgaat 660
tgatcaaaga gacacgattt tctcatccat ccctgtgtct caggagtctc caagccctgc 720
tcaacgtgct gcagggccag cagccagaag tgctccagtc tgagccacct gaggtcctag 780
agtctctctt ccagcttctt ttggaaatca ccgttcgaag tactgggatg aatgacagca 840
caggacagtc cttaacagca ctttcctgtg cttgcctctt tagtctggtg gcttcttggg 900
gagaaacagg aaggacactt caggccatct ctgctatcct caccaacaat ggaagccatg 960
cttgccaaac tattcaggtg ccaacaattc taaattcgct acagagaagt gtacaagcag 1020
ttttggtggg aaaaattcaa attcaggact ggtttagtaa tggcattaag aaagcagctt 1080
taatgcacaa gtggccatta aaagaaatat ctgttgatga agatgaccaa tgtctacttc 1140
agaatgatgg atttttttctt tatctattat gcaaggatgg attatataaa ataggctctg 1200
gatacagtgg aacagttagg ggccatatat acaattctac atcccgtatt agaaacagaa 1260
aagaaaaaaa gtcttggtta gggtatgctc agggttattt attatataga gatgtgaata 1320
accacagcat gacagccata aggataagcc ctgaaacact ggagcaagat ggtactgtga 1380
tgttaccaga ttgccacact gaaggtcaaa atattttatt cactgatgga gaatatatta 1440
atcagatagc tgcttcaaga gatgatggct ttgttgtcag aatatttgcc acaagcactg 1500
aacctgttct acagcaagaa ttgcaactta aactggctag aaaatgctta catgcctgtc 1560

-continued

```
gtatctcatt attcgatctg gaaaaggact tgcatattat aagtacagga tttgatgagg   1620
agtcagcaat tcttggtgca ggacgagagt ttgcgctaat gaaaacagca aatggaaaga   1680
tatattacac tggcaaatac cagagtcttg gaatcaaaca aggtggtcct tcagcaggaa   1740
aatgggttga gctaccaatt acaaaatctc caaagatagt acacttctca gttggacacg   1800
atggctctca cgccctttta gttgcagaag atgggagcat attctttaca ggatctgcta   1860
gtaaaggaga agatggagaa tcaattaaga gcagacggca atccaaacct tataaaccta   1920
aaaagataat taagatggaa ggaaagattg tggtatatac agcctgcaat aatggaagta   1980
gttctgttat ttctaaagat ggagaactct acatgtttgg aaaagatgcc atttactctg   2040
atagttcaag tttggtaact gatttgaagg gccattttgt aactcaggta gctatgggca   2100
aagctcacac ttgtgtttta atgaagaatg gagaggtgtg gacatttggt gtaaataata   2160
aaggacagtg tggacgagat actggtgcca tgaaccaagg tgggaaaggg tttggagttg   2220
aaaatatggc aacagcaatg gatgaagacc tggaagaaga actagatgaa aaagatgaga   2280
agtctatgat gtgccctcca ggcatgcaca aatggaagct ggagcagtgc atggtttgca   2340
ctgtctgtgg agactgtaca ggttatggag ccagctgtgt cagtagtgga cggccagaca   2400
gagtccccgg agggatctgt ggttgtggtt ccggagaatc tggttgtgct gtgtgtggat   2460
gttgcaaggc ctgtgcaaga gagttagatg gtcaagaggc aagacaaaga ggaattcttg   2520
atgcagtgaa agaaatgata cctttagatc ttcttttagc tgtcccagtg cccggggtta   2580
acattgaaga acaccttcag ttacgacaag aagaaaaacg gcaacgtgta atcagaaggc   2640
acagattaga ggaaggaaga ggccccccttg tatttgctgg tcctattttt atgaaccatc   2700
gagaacaggc tctagccaga ctcagatccc atccagcaca cgtaaagcat aaacgggaca   2760
agcacaaaga tggaagtgga gaaagaggcg aaaaggatgc aagcaaaatc acaacatacc   2820
ctccaggctc tgtgcgattt gactgtgagc tccgggcagt ccaagtcagc tgtggatttc   2880
accattcagt ggttttaatg gaaaatggag atgtctatac atttggttat gggcagcatg   2940
ggcagctagg acatggagat gtcaactcca ggggatgtcc cactcttgtt caagcattgc   3000
caggccctag cacacaagtc actgcaggca gcaaccatac ggcagtactt ttaatggatg   3060
gacaggtctt cacatttgga agtttttcta aaggacaact gggcagacca attttggatg   3120
tgccatattg gaatgcaaag ccagctccca tgcctaacat tggatcaaaa tatggaagaa   3180
aagctacttg gataggtgca agtggggacc aaactttttt acgaattgat gaagcactta   3240
ttaattctca tgtacttgct acatcagaaa tttttgccag taaacacata ataggcttgg   3300
tacctgcttc tatatcagaa cctcctccat ttaaatgcct tctgataaat aaagtggatg   3360
ggagttgtaa aacttttaat gactcagaac aagaggatct gcaaggattt ggtgtgtgtc   3420
ttgatcctgt atatgatgta atttggaggt ttcgaccaaa tactagagag ctgtggtgtt   3480
acaatgcggt ggttgctgat gccaggcttc cctctgcagc agacatgcag tccagatgta   3540
gtatcctaag tcctgaactt gccttaccaa caggatcaag ggccctcact acccgatctc   3600
atgcagcttt gcacatttta ggttgtcttg ataccttggc agctatgcag gacttaaaaa   3660
tgggtgttgc aagtacagag gaagagactc aagcagtaat gaaggtttat tctaaagaag   3720
attatagtgt ggtaaacagg tttgaaagtc atggaggagg ctggggttat tctgcccatt   3780
cagtagaagc tatacgtttc agtgccgaca ctgatatttt acttggtggt cttggtctgt   3840
ttggaggtag aggagaatat actgctaaaa ttaagctgtt tgaattgggt cctgatggag   3900
gagatcatga aactgatggt gaccttcttg cagagactga tgtattggct tatgactgtg   3960
```

-continued

```
ctgctagaga aaaatatgca atgatgtttg atgagcctgt tctcctgcaa gctgggtggt   4020
ggtatgtggc atgggcccga gtgtcaggac ccagcagtga ctgtggatct catggacagg   4080
catctattac cacagatgat ggggttgttt tccagttcaa gagttcaaag aaatcaaata   4140
atggtacaga tgttaatgcg ggtcagatac ctcagttatt atacagactt ccaaccagtg   4200
atggcagtgc ttcaaaaggc aaacagcaaa ccagtgaacc tgtacacatt ttaaagaggt   4260
cttttgcaag aactgtctca gtggaatgtt ttgagtcatt gttgagtatt cttcactgga   4320
gctggaccac cttagtctta ggagttgaag aacttagagg attaaaagga ttccagttca   4380
cagctacact cctagattta gagagactgc gctttgtggg tacctgttgt ctgaggttat   4440
tgcgtgtcta tacctgtgaa atttacccag tgtcagctac aggaaaagca gttgtagaag   4500
aaactagcaa attagcagag tgtattggaa aaaccagaac tttgttaaga aaaattttat   4560
cagaaccact tgatcactgc atggtgaaat tggataatga tcctcaagga tatctcagtc   4620
aacccttgag tcttctagaa gctgtccttc aggaatgtca taatactttc actgcctgct   4680
ttcattcttt ctacccaact cctgccttac agtgggcttg cctttgtgat ctgctgaatt   4740
gtttggatca ggatatccaa gaagcaaact tcaagacatc aagtagccga ctccttgcag   4800
ctgttatgtc agctctgtgt cacacgtctg ttaagctgac ttccatcttc ccgattgcgt   4860
atgatggaga agtattacta cgatcaattg ttaaacaagt tagtacagag aacgactcaa   4920
cactagttca tcgttttccc cttttggtgg cacatatgga aaaactcagc cagagtgaag   4980
agaatatctc agggatgaca agcttccgtg aagttctgga gaaaatgctg gtcattgttg   5040
tgctaccagt caggaacagc ctgaggagag aaaatgaact cttctcctcc cacctcgtct   5100
ctaacacctg tggattactg gccagcattg tcagtgaact gacagcgtca gccctgggat   5160
ctgaggttga tggacttaat tctcttcact ctgtaaaagc tagtgctaac cgatttacaa   5220
aaacaagtca gggcagaagt tggaacactg ggaacgggtc ccctgatgca atctgttttt   5280
cagtagacaa acctggaata gttgtggttg gtttctctgt ctatggagga ggtggaattc   5340
atgaatatga attagaggtg ttggttgatg atagtgaaca tgcaggagat tcaactcatt   5400
cccacagatg gacatctctg gaattagtga aaggaacgta cacaacggat gactcaccca   5460
gtgatatagc tgagatcaga cttgacaaag tggttccttt aaaggaaaat gttaaatatg   5520
ctgtgcgctt gaggaactat ggaagccgta cagccaatgg agatggagga atgaccacag   5580
ttcagtgccc tgatggtgtg acattcacat tcagcacgtg cagcttgagc agtaacggca   5640
caaaccaaac cagaggacag atcccacaga tactctacta taggagtgaa tttgatggag   5700
atttacaatc ccaacttctg agtaaagcca atgaagaaga taaaaactgt agcagagcat   5760
tgtctgttgt aagcactgtc gttcgagcct ctaaggacct cctgcacaga gctcttgctg   5820
tggatgctga tgacattcca gaactgctga gttcttccag tctgttttcc atgctgctcc   5880
cccttattat agcctacata ggaccagtag ctgctgctat tcccaaggtg gctgtagaag   5940
tctttggcct tgtccaacaa ttgcttccgt cagttgccat tttgaatcag aagtatgcac   6000
cgcctgcctt caaccctaat cagtcgacag atagcaccac aggaaaccag cctgaacagg   6060
gcctctctgc ttgtacaacc tccagtcact atgctgtcat agagagtgag cacccgtata   6120
aacctgcctg tgtgatgcat tacaaggtga cattcccaga atgtgtgagg tggatgacaa   6180
tcgaatttga ccctcagtgt ggtactgcac agtcagaaga tgtccttcgt ttgttgattc   6240
ctgtcagaac tgttcagaat tcaggatatg gaccaaaatt gacatctgtt catgaaaatc   6300
```

-continued

```
ttaattcatg gatagaatta aagaaatttt caggatcctc tgggtggcct actatggttt   6360
tggtgttgcc aggaaatgag gcccttttt cattggagac tgcatcagat tatgtgaaag    6420
atgacaaagc ttctttctat ggttttatgt gttttgcaat tggatatgaa tttagccctg   6480
gacctgatga gggagtcatc caattggaaa aagaattagc caatcttggt ggggtttgtg   6540
cagcagctct gatgaagaag gacctagcac ttcctattgg taatgaatta gaagaagacc   6600
ttgaaattct tgaggaggct gcattgcagg tgtgcaaaac ccattctgga attcttggaa   6660
agggtctagc tctttctcat tcaccaacta tattagaagc acttgaggga aatttaccac   6720
tccaaatcca aagcaatgaa cagtcttttc tggatgattt tattgcctgt gtcccaggat   6780
caagtggtgg aaggcttgca aggtggcttc agccagattc atatgcggat cctcagaaaa   6840
catctttgat cctgaataag gatgatattc gttgtggttg gcctaccacc ataactgttc   6900
aaacaaaaga ccagtatggg gatgtggtac atgttcccaa tatgaaggtg gaagtgaaag   6960
ctgtccctgt ttctcagaaa aaaatgtctt tacaacaaga tcaagcaaag aaacctcaaa   7020
ggattcctgg cagtcctgca gtaacagctg catcttctaa tactgacatg acttatggag   7080
ggctggcatc accaaagcta gatgtttcat atgaaccaat gatagtgaag gaagctcgat   7140
atattgccat aacaatgatg aaggtttatg aaaattattc atttgaagaa ctacgttttg   7200
catcaccaac tcctaagaga cccagtgaga atatgctgat ccgtgtcaat aatgatggga   7260
cttattgtgc aaattggact ccaggggcta ttggactcta cactcttcat gttaccattg   7320
atggcattga aatcgatgct ggtctggaag taaaagtaaa agacccacca aaagggatga   7380
taccaccagg aactcagttg gtcaaaccaa agtctgaacc tcagcctaat aaggttcgaa   7440
aatttgtggc caaggacagt gcggggcttc gcatccgtag ccacccttcc cttcagagtg   7500
agcagatagg catagtgaaa gtcaatggaa ctatcacttt tattgatgag atccataatg   7560
atgatggtgt gtggctgagg ctgaatgatg agacaataaa gaagtatgtc cctaacatga   7620
atggttacac tgaagcctgg tgcctctctt ttaatcaaca tcttggcaag agtcttctgg   7680
tccctgttga cgaatctaaa actaatactg atgacttttt caaagacata aactcctgct   7740
gcccacagga agcaacaatg caagaacaag atatgccatt cttgcgagga gggccaggca   7800
tgtacaaggt agtgaagacg ggaccttcag gtcacaacat cagaagctgc cctaacctta   7860
gaggtatccc aattggaatg ttagttctgg gaaacaaagt caaagcagtg ggagaggtaa   7920
ccaattctga agggacatgg gtgcaactgg atcagaacag catggtagag ttctgtgaga   7980
gtgatgaagg agaggcatgg tccttagcta gagacagagg cggaaaccag tacctccgac   8040
atgaagatga acaagctctt ctggatcaga attctcaaac tcctcctcca agccctttct   8100
cagtgcaagc ttttaataaa ggggcaagtt gcagtgccca aggatttgat tatggactcg   8160
gaaatagcaa aggtgatcga ggaaacatct caacatcttc taaaccagcc tctacatcag   8220
gaaaatcaga gctgtcctct aaacacagca gatcgcttaa acctgatgga cgtatgagcc   8280
ggactactgc tgatcagaag aagccaaggg gcacagaaag tttatctgct agtgaatccc   8340
tcatcttaaa atctgatgct gcaaagttga ggtcagattc ccacagtagg tcattatccc   8400
ccaaccataa caccttgcag acattgaaat ctgatgggag gatgccttct agctccagag   8460
ctgaatcccc aggaccaggt tctcggttgt catctcctaa gccaaagact ctcccagcca   8520
ataggtctag cccatcgggt gctagttctc cacgctcctc ctcaccacat gataaaaatc   8580
tacctcaaaa aagtactgct cctgttaaga caaagcttga tcctcctcgg gaacgttcta   8640
aatcagactc ttacacactt gatccagata ccctccgcaa gaagaaaatg cccctcacag   8700
```

-continued

```
aacctttgag aggacggtca acgtcaccaa aaccaaaatc agtaccaaag gattctacag   8760
attcccctgg atctgaaaat agagctccct ctccccatgt ggtacaggaa aacctccaca   8820
gtgaggtggt cgaagtctgc acctcaagta ctttaaaaac aaatagtcta acagacagca   8880
cctgcgatga cagcagtgaa tttaagagtg tggatgaagg ttcaaataaa gttcatttta   8940
gcattggaaa agcaccactg aaagatgaac aggaaatgag agcatctccc aaaataagtc   9000
gaaaatgtgc taatagacac accaggccca aaaaagaaaa atcgagtttt cttttcaaag   9060
gagatggatc caagccttta gagccagcca agcaagccat gtctccttct gtggccgaat   9120
gtgccagagc tgtgtttgct tccttcctct ggcatgaagg catagtacat gatgcaatgg   9180
cttgttcttc tttcctaaag tttcatcctg aactttccaa agaacatgct cctataagga   9240
gtagtttaaa tagccaacaa cctacagaag aaaaagaaac caagttaaaa aatagacatt   9300
cattagaaat atcatctgca ctgaatatgt ttaatattgc accccatgga ccagatatat   9360
ctaagatggg tagcatcaac aaaaacaagg tattgtctat gcttaaggaa ccacctctgc   9420
atgaaaaatg tgaggatggg aaaaccgaga ccacttttga aatgtccatg cataacacaa   9480
tgaagtctaa gtctcctctt cccttaactt tacaacattt agtggctttt tgggaagaca   9540
tctctttggc tactatcaaa gctgcttccc agaatatgat tttccaagt cctggttcct   9600
gtgcagttct taaaaagaaa gagtgtgaga aaggaaggaa taagaagtcc aaaaaggaaa   9660
aaaagaaaaa agaaaaggca gaagttaggc ccaggggtaa tttgtttgga gagatggccc   9720
agctggcagt aggaggacca gagaaagata ccatctgtga actgtgtggg gagtcacatc   9780
catacccggt gacctatcac atgagacaag ctcacccagg ttgtggccga tatgctggtg   9840
gacaaggtta caatagcatt gggcattttt gtggaggatg ggctggtaac tgtggtgatg   9900
gtggcatagg aggaagcact tggtatctgg tatgtgatcg ctgtagagaa aaatacctcc   9960
gcgaaaaaca ggctgctgca agggagaagg tcaaacaatc taggagaaaa ccaatgcaag  10020
tcaagacccc tcgtgccttg cccaccatgg aagctcacca ggtgattaaa gccaatgcac  10080
tcttcctgct gtccctgagc agtgcagcag aaccgagcat tctgtgttac catcctgcaa  10140
agccattcca atctcagttg cccagtgtaa aagaaggcat ttctgaggat cttcctgtga  10200
aaatgccttg tctgtacctg cagacattag ctaggcatca tcatgaaaat tttgtgggct  10260
atcaagatga caatctattc caggatgaaa tgagatatct acgttcaaca tctgtacctg  10320
ccccgtatat atcagtaact cctgatgcaa gtcctaatgt atttgaagag ccagagagca  10380
atatgaagtc tatgccacca agtttagaaa ccagtcccat aactgatact gatcttgcaa  10440
agagaactgt cttccaaaga tcatactcag ttgttgcttc cgaatatgat aaacaacact  10500
ccattttacc tgcacgagtt aaagctattc ctagaagaag agttaacagt ggagacactg  10560
aagttggttc ttccctttttg agacatccgt ctcctgagct ttctcggcta atctcagccc  10620
acagctctct ttctaaagga gaacgaaatt tccagtggcc agttttagct tttgttatac  10680
aacatcatga tctagaaggt cttgaaatag caatgaaaca ggccctaagg aaatctgctt  10740
gtcgagtttt tgctatggag gctttcaact ggcttctgtg taatgtcatc caaaccactt  10800
ctctccatga tattctgtgg cattttgtgg catcactgac tcctgcacca gtggaaccag  10860
aggaagaaga ggatgaagaa aataaaacaa gcaaagaaaa ttcagaacaa gagaaagata  10920
caagagtatg tgaacatcca ctctcagaca tagtgattgc cggggaacgt gctcatcctt  10980
taccacacac ctttcaccgc ttgctgcaga ccatctcaga ccttatgatg tctctcccca  11040
```

-continued gcggcagttc attacagcaa atggccctga ggtgctggag tctcaaattc aagcaatctg 11100
atcaccagtt ccttcatcag agcaacgtct ttcatcacat taacaatatt ttgtcaaagt 11160
cagatgatgg cgatagtgaa gagagtttta gcatcagtat acagtctggc tttgaagcta 11220
tgagtcagga attatgcata gtaatgtgct taaaggactt aaccagcatt gttgacataa 11280
aaacttcaag ccgacctgcc atgattggca gtttgacaga cggctccaca gaaacctttt 11340
gggaatcagg agatgaagat aaaaacaaaa ctaagaacat caccatcaac tgtgtaaaag 11400
gaatcaatgc ccgctatgtg tctgttcacg tggacaattc ccgagatctt gggaataaag 11460
ttacctcaat gaccttctta actggcaaag cagtagaaga tttgtgcaga ataaagcagg 11520
ttgatctgga ttccaggcac attggctggg taacaagtga acttccagga ggggataatc 11580
acatcataaa aattgaatta aaaggcccag aaaatacact gagagttcga caagtcaaag 11640
tcctgggctg gaaagatggt gaaagcacaa aaatagctgg ccagatttca gccagtgtgg 11700
cccagcagag gaactgtgaa gctgagactc tgcgagtatt cagactgatt acgtctcaag 11760
tatttggaaa gctcatctct ggagatgctg aacctacacc agaacaagag gaaaaagcac 11820
tattgtcatc acctgaagga gaagaaaaag tatacaatgc aacatcagat gctgacctga 11880
aagaacatat ggttggaatc atattcagca ggagtaagct gactaactta caaaaacagg 11940
tgtgtgctca tattgtccaa gctattcgca tggaagctac cagagtccgt gaagaatggg 12000
aacatgctat atcaagcaaa gaaaatgcca attctcagcc aaatgatgaa gatgcctcct 12060
ctgatgccta ctgctttgag ctgctctcta tggttttagc actgagtggc tctaacgttg 12120
gccggcaata tctggctcaa cagctaaccc tgcttcagga tctcttctcg ctgcttcaca 12180
cagcctctcc tagagtccag agacaggtaa cctctttact aagaagagtt ttgcctgaag 12240
taacccctag tcgtctggcc agcatcatag gagtgaaatc cctcccccca gcagatatca 12300
gtgatatcat tcactcaaca gagaaaggag actggaataa gctgggtatc ttggacatgt 12360
ttctaggatg cattgccaaa gcactcactg tacagctaaa agccaaagga accaccatca 12420
ctggaacagc tggtaccact gtgggcaaag gagttacaac agttactctt ccgatgattt 12480
tcaattccag ttatctccga cgaggtgaaa gtcattggtg gatgaagggc tcaaccccta 12540
cccagatctc agagatcatc attaaactta tcaaggatat ggcagcaggt catctgtcag 12600
aagcttggtc ccgagtgaca aaaaatgcta ttgcagaaac catcattgcc ttgaccaaga 12660
tggaagaaga atttaggtct ccagtgagat gtattgcaac aactagactc tggcttgctc 12720
tcgcatccct atgtgttctt gatcaggacc acgtagatcg tctctcctcg ggagatggat 12780
tgggaaagga tggacaacaa aaacaaatgc ctatgtgtga taaccatgat gatggtgaaa 12840
ctgcagcaat cattttatgc aatgtctgtg gaaatttatg tacagactgt gacagattcc 12900
ttcaccttca tcgaagaacc aaaactcatc aaagacaggt cttcaaagaa gaagaagaag 12960
ctataaaggt tgaccttcat gaaggttgtg gtagaaccaa attgttctgg ttgatggcac 13020
tggcagattc taaaacaatg aaggcaatgg tggaattccg agaacacaca ggcaaaccca 13080
ccacgagtag ctcagaagca tgtcgcttct gtggttccag gagtggaaca gagttatctg 13140
ctgttggcag tgtttgttct gatgcagatt gccaggaata cgctaagata gcctgtagta 13200
agacgcatcc ttgtggccat ccatgcgggg gtgttaaaaa cgaagagcac tgtctgccct 13260
gtctacacgg ctgtgacaaa agtgccacaa gcctgaagca agacgccgat gacatgtgca 13320
tgatatgttt caccgaagcg ctctcggcag caccagccat tcagctggat tgtagtcaca 13380
tattccactt acagtgctgt cggcgagtat tagaaaatcg atggcttggc ccaaggataa 13440

```
catttggatt tatatcttgt cccatttgca agaacaaaat taatcacata gtactaaaag  13500

acctacttga tccaataaaa gaactctatg aggatgtcag aagaaaagcc ttaatgagat  13560

tggaatatga aggtctgcat aagagtgaag ctatcacaac tcctggtgtg aggttttata  13620

atgacccagc tggctatgca atgaatagat atgcatatta tgtgtgctac aaatgcagaa  13680

aggcatattt tggtggtgaa gctcgctgcg atgctgaggc tggacgggga gatgattatg  13740

atcccagaga gctcatttgt ggtgcctgtt ctgatgtttc cagggctcag atgtgtccca  13800

aacatggcac agacttttg gaatataaat gtcgctactg ctgttcagtg gctgtttttt  13860

tctgttttgg aacaacacat ttttgtaatg cttgtcatga tgattttcaa agaatgacta  13920

gcattcctaa ggaagaacta ccacactgtc ctgcaggtcc caaaggcaag cagttagaag  13980

gaactgaatg tccactccat gttgttcatc cacccactgg ggaagagttt gctctgggat  14040

gtggagtgtg cagaaatgcc cacacttttt agaacacgca gatcctttgt ctacagagag  14100

aaaaattgcc ttcatccccc aagaggatgc ggtgaagttt aaactctgct caccataagg  14160

acgggaccat ttttacatcc atgaaaatga accattcaca gtgcaagaag gataccaaat  14220

accatgtaca taattcttgc tatgaaaagt ttccccatta ttttggttta tcttcttttg  14280

aacaaatgac atcaaacttg tgaggtgttt gcatgtggcc attaccgtca ttggcctgtg  14340

aagcattgga catttataga taattgatat aaaagaatcg ccatgcccat ggactaagaa  14400

cgatgctggc tttcaagcaa aaaagaaaaa taatcattgt ttattgtata ctgccttttt  14460

gtaatcctgt acaattgcat cacgggtggg gataaaaaga ggaatattct ggtttatttc  14520

ctagactgtt atttaaaaaa aaaaaaaaca ttgtgttagg acagcatata aatgtaataa  14580

gtatcacact gtatataaac atatcaatgt ttgtcctgta taagaattac taaattacaa  14640

atgcaatttc atttaaactt ctaggttaag tttgagcctg aaattttaat gaagtgcaat  14700

actgagtgtg cctcattatc ttgcagctgt aaacatattg gaatgtacat gtcaataaaa  14760

ccactgtaca tttttataca gtgataaagt ctaaaaaaaa aaaaaaa               14807
```

<210> SEQ ID NO 2
<211> LENGTH: 4641
<212> TYPE: PRT
<213> ORGANISM: Homo sapiens

<400> SEQUENCE: 2

```
Met Pro Val Pro Asp Gly Ser Val Ala Ala Ala Gly Leu Gly Leu Gly
1               5                   10                  15

Leu Pro Ala Ala Asp Ser Pro Gly His Tyr Gln Leu Leu Leu Ser Gly
            20                  25                  30

Arg Ala Leu Ala Asp Arg Tyr Arg Arg Ile Tyr Thr Ala Ala Leu Asn
        35                  40                  45

Asp Arg Asp Gln Gly Gly Gly Ser Ala Gly His Pro Ala Ser Arg Asn
    50                  55                  60

Lys Lys Ile Leu Asn Lys Lys Lys Leu Lys Arg Lys Gln Lys Ser Lys
65                  70                  75                  80

Ser Lys Val Lys Thr Arg Ser Lys Ser Glu Asn Leu Glu Asn Thr Val
                85                  90                  95

Ile Ile Pro Asp Ile Lys Leu His Ser Asn Pro Ser Ala Phe Asn Ile
            100                 105                 110

Tyr Cys Asn Val Arg His Cys Val Leu Glu Trp Gln Lys Lys Glu Ile
        115                 120                 125
```

-continued

```
Ser Leu Ala Ala Ala Ser Lys Asn Ser Val Gln Ser Gly Glu Ser Asp
    130                 135                 140

Ser Asp Glu Glu Glu Glu Ser Lys Glu Pro Pro Ile Lys Leu Pro Lys
145                 150                 155                 160

Ile Ile Glu Val Gly Leu Cys Glu Val Phe Glu Leu Ile Lys Glu Thr
                165                 170                 175

Arg Phe Ser His Pro Ser Leu Cys Leu Arg Ser Leu Gln Ala Leu Leu
            180                 185                 190

Asn Val Leu Gln Gly Gln Gln Pro Glu Val Leu Gln Ser Glu Pro Pro
        195                 200                 205

Glu Val Leu Glu Ser Leu Phe Gln Leu Leu Leu Glu Ile Thr Val Arg
    210                 215                 220

Ser Thr Gly Met Asn Asp Ser Thr Gly Gln Ser Leu Thr Ala Leu Ser
225                 230                 235                 240

Cys Ala Cys Leu Phe Ser Leu Val Ala Ser Trp Gly Glu Thr Gly Arg
                245                 250                 255

Thr Leu Gln Ala Ile Ser Ala Ile Leu Thr Asn Asn Gly Ser His Ala
            260                 265                 270

Cys Gln Thr Ile Gln Val Pro Thr Ile Leu Asn Ser Leu Gln Arg Ser
        275                 280                 285

Val Gln Ala Val Leu Val Gly Lys Ile Gln Ile Gln Asp Trp Phe Ser
    290                 295                 300

Asn Gly Ile Lys Lys Ala Ala Leu Met His Lys Trp Pro Leu Lys Glu
305                 310                 315                 320

Ile Ser Val Asp Glu Asp Asp Gln Cys Leu Leu Gln Asn Asp Gly Phe
                325                 330                 335

Phe Leu Tyr Leu Leu Cys Lys Asp Gly Leu Tyr Lys Ile Gly Ser Gly
            340                 345                 350

Tyr Ser Gly Thr Val Arg Gly His Ile Tyr Asn Ser Thr Ser Arg Ile
        355                 360                 365

Arg Asn Arg Lys Glu Lys Lys Ser Trp Leu Gly Tyr Ala Gln Gly Tyr
    370                 375                 380

Leu Leu Tyr Arg Asp Val Asn Asn His Ser Met Thr Ala Ile Arg Ile
385                 390                 395                 400

Ser Pro Glu Thr Leu Glu Gln Asp Gly Thr Val Met Leu Pro Asp Cys
                405                 410                 415

His Thr Glu Gly Gln Asn Ile Leu Phe Thr Asp Gly Glu Tyr Ile Asn
            420                 425                 430

Gln Ile Ala Ala Ser Arg Asp Asp Gly Phe Val Val Arg Ile Phe Ala
        435                 440                 445

Thr Ser Thr Glu Pro Val Leu Gln Gln Glu Leu Gln Leu Lys Leu Ala
    450                 455                 460

Arg Lys Cys Leu His Ala Cys Arg Ile Ser Leu Phe Asp Leu Glu Lys
465                 470                 475                 480

Asp Leu His Ile Ile Ser Thr Gly Phe Asp Glu Glu Ser Ala Ile Leu
                485                 490                 495

Gly Ala Gly Arg Glu Phe Ala Leu Met Lys Thr Ala Asn Gly Lys Ile
            500                 505                 510

Tyr Tyr Thr Gly Lys Tyr Gln Ser Leu Gly Ile Lys Gln Gly Gly Pro
        515                 520                 525

Ser Ala Gly Lys Trp Val Glu Leu Pro Ile Thr Lys Ser Pro Lys Ile
    530                 535                 540

Val His Phe Ser Val Gly His Asp Gly Ser His Ala Leu Leu Val Ala
```

-continued

```
545                 550                 555                 560

Glu Asp Gly Ser Ile Phe Phe Thr Gly Ser Ala Ser Lys Gly Glu Asp
                565                 570                 575

Gly Glu Ser Ile Lys Ser Arg Arg Gln Ser Lys Pro Tyr Lys Pro Lys
            580                 585                 590

Lys Ile Ile Lys Met Glu Gly Lys Ile Val Val Tyr Thr Ala Cys Asn
        595                 600                 605

Asn Gly Ser Ser Ser Val Ile Ser Lys Asp Gly Glu Leu Tyr Met Phe
    610                 615                 620

Gly Lys Asp Ala Ile Tyr Ser Asp Ser Ser Ser Leu Val Thr Asp Leu
625                 630                 635                 640

Lys Gly His Phe Val Thr Gln Val Ala Met Gly Lys Ala His Thr Cys
                645                 650                 655

Val Leu Met Lys Asn Gly Glu Val Trp Thr Phe Gly Val Asn Asn Lys
            660                 665                 670

Gly Gln Cys Gly Arg Asp Thr Gly Ala Met Asn Gln Gly Gly Lys Gly
        675                 680                 685

Phe Gly Val Glu Asn Met Ala Thr Ala Met Asp Glu Asp Leu Glu Glu
    690                 695                 700

Glu Leu Asp Glu Lys Asp Glu Lys Ser Met Met Cys Pro Pro Gly Met
705                 710                 715                 720

His Lys Trp Lys Leu Glu Gln Cys Met Val Cys Thr Val Cys Gly Asp
                725                 730                 735

Cys Thr Gly Tyr Gly Ala Ser Cys Val Ser Ser Gly Arg Pro Asp Arg
            740                 745                 750

Val Pro Gly Gly Ile Cys Gly Cys Gly Ser Gly Glu Ser Gly Cys Ala
        755                 760                 765

Val Cys Gly Cys Cys Lys Ala Cys Ala Arg Glu Leu Asp Gly Gln Glu
    770                 775                 780

Ala Arg Gln Arg Gly Ile Leu Asp Ala Val Lys Glu Met Ile Pro Leu
785                 790                 795                 800

Asp Leu Leu Leu Ala Val Pro Val Pro Gly Val Asn Ile Glu Glu His
                805                 810                 815

Leu Gln Leu Arg Gln Glu Glu Lys Arg Gln Arg Val Ile Arg Arg His
            820                 825                 830

Arg Leu Glu Glu Gly Arg Gly Pro Leu Val Phe Ala Gly Pro Ile Phe
        835                 840                 845

Met Asn His Arg Glu Gln Ala Leu Ala Arg Leu Arg Ser His Pro Ala
    850                 855                 860

His Val Lys His Lys Arg Asp Lys His Lys Asp Gly Ser Gly Glu Arg
865                 870                 875                 880

Gly Glu Lys Asp Ala Ser Lys Ile Thr Thr Tyr Pro Pro Gly Ser Val
                885                 890                 895

Arg Phe Asp Cys Glu Leu Arg Ala Val Gln Val Ser Cys Gly Phe His
            900                 905                 910

His Ser Val Val Leu Met Glu Asn Gly Asp Val Tyr Thr Phe Gly Tyr
        915                 920                 925

Gly Gln His Gly Gln Leu Gly His Gly Asp Val Asn Ser Arg Gly Cys
    930                 935                 940

Pro Thr Leu Val Gln Ala Leu Pro Gly Pro Ser Thr Gln Val Thr Ala
945                 950                 955                 960

Gly Ser Asn His Thr Ala Val Leu Leu Met Asp Gly Gln Val Phe Thr
                965                 970                 975
```

-continued

```
Phe Gly Ser Phe Ser Lys Gly Gln Leu Gly Arg Pro Ile Leu Asp Val
            980                 985                 990

Pro Tyr Trp Asn Ala Lys Pro Ala  Pro Met Pro Asn Ile  Gly Ser Lys
        995                 1000                1005

Tyr Gly  Arg Lys Ala Thr Trp  Ile Gly Ala Ser Gly  Asp Gln Thr
    1010                 1015                 1020

Phe Leu  Arg Ile Asp Glu Ala  Leu Ile Asn Ser His  Val Leu Ala
    1025                 1030                 1035

Thr Ser  Glu Ile Phe Ala Ser  Lys His Ile Ile Gly  Leu Val Pro
    1040                 1045                 1050

Ala Ser  Ile Ser Glu Pro Pro  Pro Phe Lys Cys Leu  Leu Ile Asn
    1055                 1060                 1065

Lys Val  Asp Gly Ser Cys Lys  Thr Phe Asn Asp Ser  Glu Gln Glu
    1070                 1075                 1080

Asp Leu  Gln Gly Phe Gly Val  Cys Leu Asp Pro Val  Tyr Asp Val
    1085                 1090                 1095

Ile Trp  Arg Phe Arg Pro Asn  Thr Arg Glu Leu Trp  Cys Tyr Asn
    1100                 1105                 1110

Ala Val  Val Ala Asp Ala Arg  Leu Pro Ser Ala Ala  Asp Met Gln
    1115                 1120                 1125

Ser Arg  Cys Ser Ile Leu Ser  Pro Glu Leu Ala Leu  Pro Thr Gly
    1130                 1135                 1140

Ser Arg  Ala Leu Thr Thr Arg  Ser His Ala Ala Leu  His Ile Leu
    1145                 1150                 1155

Gly Cys  Leu Asp Thr Leu Ala  Ala Met Gln Asp Leu  Lys Met Gly
    1160                 1165                 1170

Val Ala  Ser Thr Glu Glu Glu  Thr Gln Ala Val Met  Lys Val Tyr
    1175                 1180                 1185

Ser Lys  Glu Asp Tyr Ser Val  Val Asn Arg Phe Glu  Ser His Gly
    1190                 1195                 1200

Gly Gly  Trp Gly Tyr Ser Ala  His Ser Val Glu Ala  Ile Arg Phe
    1205                 1210                 1215

Ser Ala  Asp Thr Asp Ile Leu  Leu Gly Gly Leu Gly  Leu Phe Gly
    1220                 1225                 1230

Gly Arg  Gly Glu Tyr Thr Ala  Lys Ile Lys Leu Phe  Glu Leu Gly
    1235                 1240                 1245

Pro Asp  Gly Gly Asp His Glu  Thr Asp Gly Asp Leu  Leu Ala Glu
    1250                 1255                 1260

Thr Asp  Val Leu Ala Tyr Asp  Cys Ala Ala Arg Glu  Lys Tyr Ala
    1265                 1270                 1275

Met Met  Phe Asp Glu Pro Val  Leu Leu Gln Ala Gly  Trp Trp Tyr
    1280                 1285                 1290

Val Ala  Trp Ala Arg Val Ser  Gly Pro Ser Ser Asp  Cys Gly Ser
    1295                 1300                 1305

His Gly  Gln Ala Ser Ile Thr  Thr Asp Asp Gly Val  Val Phe Gln
    1310                 1315                 1320

Phe Lys  Ser Ser Lys Lys Ser  Asn Asn Gly Thr Asp  Val Asn Ala
    1325                 1330                 1335

Gly Gln  Ile Pro Gln Leu Leu  Tyr Arg Leu Pro Thr  Ser Asp Gly
    1340                 1345                 1350

Ser Ala  Ser Lys Gly Lys Gln  Gln Thr Ser Glu Pro  Val His Ile
    1355                 1360                 1365
```

-continued

```
Leu Lys  Arg Ser Phe Ala Arg  Thr Val Ser Val Glu  Cys Phe Glu
    1370                 1375                 1380

Ser Leu  Leu Ser Ile Leu His  Trp Ser Trp Thr Thr  Leu Val Leu
    1385                 1390                 1395

Gly Val  Glu Glu Leu Arg Gly  Leu Lys Gly Phe Gln  Phe Thr Ala
    1400                 1405                 1410

Thr Leu  Leu Asp Leu Glu Arg  Leu Arg Phe Val Gly  Thr Cys Cys
    1415                 1420                 1425

Leu Arg  Leu Leu Arg Val Tyr  Thr Cys Glu Ile Tyr  Pro Val Ser
    1430                 1435                 1440

Ala Thr  Gly Lys Ala Val Val  Glu Glu Thr Ser Lys  Leu Ala Glu
    1445                 1450                 1455

Cys Ile  Gly Lys Thr Arg Thr  Leu Leu Arg Lys Ile  Leu Ser Glu
    1460                 1465                 1470

Pro Leu  Asp His Cys Met Val  Lys Leu Asp Asn Asp  Pro Gln Gly
    1475                 1480                 1485

Tyr Leu  Ser Gln Pro Leu Ser  Leu Leu Glu Ala Val  Leu Gln Glu
    1490                 1495                 1500

Cys His  Asn Thr Phe Thr Ala  Cys Phe His Ser Phe  Tyr Pro Thr
    1505                 1510                 1515

Pro Ala  Leu Gln Trp Ala Cys  Leu Cys Asp Leu Leu  Asn Cys Leu
    1520                 1525                 1530

Asp Gln  Asp Ile Gln Glu Ala  Asn Phe Lys Thr Ser  Ser Ser Arg
    1535                 1540                 1545

Leu Leu  Ala Ala Val Met Ser  Ala Leu Cys His Thr  Ser Val Lys
    1550                 1555                 1560

Leu Thr  Ser Ile Phe Pro Ile  Ala Tyr Asp Gly Glu  Val Leu Leu
    1565                 1570                 1575

Arg Ser  Ile Val Lys Gln Val  Ser Thr Glu Asn Asp  Ser Thr Leu
    1580                 1585                 1590

Val His  Arg Phe Pro Leu Leu  Val Ala His Met Glu  Lys Leu Ser
    1595                 1600                 1605

Gln Ser  Glu Glu Asn Ile Ser  Gly Met Thr Ser Phe  Arg Glu Val
    1610                 1615                 1620

Leu Glu  Lys Met Leu Val Ile  Val Val Leu Pro Val  Arg Asn Ser
    1625                 1630                 1635

Leu Arg  Arg Glu Asn Glu Leu  Phe Ser Ser His Leu  Val Ser Asn
    1640                 1645                 1650

Thr Cys  Gly Leu Leu Ala Ser  Ile Val Ser Glu Leu  Thr Ala Ser
    1655                 1660                 1665

Ala Leu  Gly Ser Glu Val Asp  Gly Leu Asn Ser Leu  His Ser Val
    1670                 1675                 1680

Lys Ala  Ser Ala Asn Arg Phe  Thr Lys Thr Ser Gln  Gly Arg Ser
    1685                 1690                 1695

Trp Asn  Thr Gly Asn Gly Ser  Pro Asp Ala Ile Cys  Phe Ser Val
    1700                 1705                 1710

Asp Lys  Pro Gly Ile Val Val  Val Gly Phe Ser Val  Tyr Gly Gly
    1715                 1720                 1725

Gly Gly  Ile His Glu Tyr Glu  Leu Glu Val Leu Val  Asp Asp Ser
    1730                 1735                 1740

Glu His  Ala Gly Asp Ser Thr  His Ser His Arg Trp  Thr Ser Leu
    1745                 1750                 1755

Glu Leu  Val Lys Gly Thr Tyr  Thr Thr Asp Asp Ser  Pro Ser Asp
```

-continued

```
    1760                1765                1770

Ile Ala  Glu Ile Arg Leu Asp  Lys Val Val Pro Leu  Lys Glu Asn
    1775                1780                1785

Val Lys  Tyr Ala Val Arg Leu  Arg Asn Tyr Gly Ser  Arg Thr Ala
    1790                1795                1800

Asn Gly  Asp Gly Gly Met Thr  Thr Val Gln Cys Pro  Asp Gly Val
    1805                1810                1815

Thr Phe  Thr Phe Ser Thr Cys  Ser Leu Ser Ser Asn  Gly Thr Asn
    1820                1825                1830

Gln Thr  Arg Gly Gln Ile Pro  Gln Ile Leu Tyr Tyr  Arg Ser Glu
    1835                1840                1845

Phe Asp  Gly Asp Leu Gln Ser  Gln Leu Leu Ser Lys  Ala Asn Glu
    1850                1855                1860

Glu Asp  Lys Asn Cys Ser Arg  Ala Leu Ser Val Val  Ser Thr Val
    1865                1870                1875

Val Arg  Ala Ser Lys Asp Leu  Leu His Arg Ala Leu  Ala Val Asp
    1880                1885                1890

Ala Asp  Asp Ile Pro Glu Leu  Leu Ser Ser Ser Ser  Leu Phe Ser
    1895                1900                1905

Met Leu  Leu Pro Leu Ile Ile  Ala Tyr Ile Gly Pro  Val Ala Ala
    1910                1915                1920

Ala Ile  Pro Lys Val Ala Val  Glu Val Phe Gly Leu  Val Gln Gln
    1925                1930                1935

Leu Leu  Pro Ser Val Ala Ile  Leu Asn Gln Lys Tyr  Ala Pro Pro
    1940                1945                1950

Ala Phe  Asn Pro Asn Gln Ser  Thr Asp Ser Thr Thr  Gly Asn Gln
    1955                1960                1965

Pro Glu  Gln Gly Leu Ser Ala  Cys Thr Thr Ser Ser  His Tyr Ala
    1970                1975                1980

Val Ile  Glu Ser Glu His Pro  Tyr Lys Pro Ala Cys  Val Met His
    1985                1990                1995

Tyr Lys  Val Thr Phe Pro Glu  Cys Val Arg Trp Met  Thr Ile Glu
    2000                2005                2010

Phe Asp  Pro Gln Cys Gly Thr  Ala Gln Ser Glu Asp  Val Leu Arg
    2015                2020                2025

Leu Leu  Ile Pro Val Arg Thr  Val Gln Asn Ser Gly  Tyr Gly Pro
    2030                2035                2040

Lys Leu  Thr Ser Val His Glu  Asn Leu Asn Ser Trp  Ile Glu Leu
    2045                2050                2055

Lys Lys  Phe Ser Gly Ser Ser  Gly Trp Pro Thr Met  Val Leu Val
    2060                2065                2070

Leu Pro  Gly Asn Glu Ala Leu  Phe Ser Leu Glu Thr  Ala Ser Asp
    2075                2080                2085

Tyr Val  Lys Asp Asp Lys Ala  Ser Phe Tyr Gly Phe  Met Cys Phe
    2090                2095                2100

Ala Ile  Gly Tyr Glu Phe Ser  Pro Gly Pro Asp Glu  Gly Val Ile
    2105                2110                2115

Gln Leu  Glu Lys Glu Leu Ala  Asn Leu Gly Gly Val  Cys Ala Ala
    2120                2125                2130

Ala Leu  Met Lys Lys Asp Leu  Ala Leu Pro Ile Gly  Asn Glu Leu
    2135                2140                2145

Glu Glu  Asp Leu Glu Ile Leu  Glu Glu Ala Ala Leu  Gln Val Cys
    2150                2155                2160
```

-continued

```
Lys Thr  His Ser Gly Ile Leu  Gly Lys Gly Leu Ala  Leu Ser His
    2165                 2170                 2175

Ser Pro  Thr Ile Leu Glu Ala  Leu Glu Gly Asn Leu  Pro Leu Gln
    2180                 2185                 2190

Ile Gln  Ser Asn Glu Gln Ser  Phe Leu Asp Asp Phe  Ile Ala Cys
    2195                 2200                 2205

Val Pro  Gly Ser Ser Gly Gly  Arg Leu Ala Arg Trp  Leu Gln Pro
    2210                 2215                 2220

Asp Ser  Tyr Ala Asp Pro Gln  Lys Thr Ser Leu Ile  Leu Asn Lys
    2225                 2230                 2235

Asp Asp  Ile Arg Cys Gly Trp  Pro Thr Thr Ile Thr  Val Gln Thr
    2240                 2245                 2250

Lys Asp  Gln Tyr Gly Asp Val  Val His Val Pro Asn  Met Lys Val
    2255                 2260                 2265

Glu Val  Lys Ala Val Pro Val  Ser Gln Lys Lys Met  Ser Leu Gln
    2270                 2275                 2280

Gln Asp  Gln Ala Lys Lys Pro  Gln Arg Ile Pro Gly  Ser Pro Ala
    2285                 2290                 2295

Val Thr  Ala Ala Ser Ser Asn  Thr Asp Met Thr Tyr  Gly Gly Leu
    2300                 2305                 2310

Ala Ser  Pro Lys Leu Asp Val  Ser Tyr Glu Pro Met  Ile Val Lys
    2315                 2320                 2325

Glu Ala  Arg Tyr Ile Ala Ile  Thr Met Met Lys Val  Tyr Glu Asn
    2330                 2335                 2340

Tyr Ser  Phe Glu Glu Leu Arg  Phe Ala Ser Pro Thr  Pro Lys Arg
    2345                 2350                 2355

Pro Ser  Glu Asn Met Leu Ile  Arg Val Asn Asn Asp  Gly Thr Tyr
    2360                 2365                 2370

Cys Ala  Asn Trp Thr Pro Gly  Ala Ile Gly Leu Tyr  Thr Leu His
    2375                 2380                 2385

Val Thr  Ile Asp Gly Ile Glu  Ile Asp Ala Gly Leu  Glu Val Lys
    2390                 2395                 2400

Val Lys  Asp Pro Pro Lys Gly  Met Ile Pro Pro Gly  Thr Gln Leu
    2405                 2410                 2415

Val Lys  Pro Lys Ser Glu Pro  Gln Pro Asn Lys Val  Arg Lys Phe
    2420                 2425                 2430

Val Ala  Lys Asp Ser Ala Gly  Leu Arg Ile Arg Ser  His Pro Ser
    2435                 2440                 2445

Leu Gln  Ser Glu Gln Ile Gly  Ile Val Lys Val Asn  Gly Thr Ile
    2450                 2455                 2460

Thr Phe  Ile Asp Glu Ile His  Asn Asp Asp Gly Val  Trp Leu Arg
    2465                 2470                 2475

Leu Asn  Asp Glu Thr Ile Lys  Lys Tyr Val Pro Asn  Met Asn Gly
    2480                 2485                 2490

Tyr Thr  Glu Ala Trp Cys Leu  Ser Phe Asn Gln His  Leu Gly Lys
    2495                 2500                 2505

Ser Leu  Leu Val Pro Val Asp  Glu Ser Lys Thr Asn  Thr Asp Asp
    2510                 2515                 2520

Phe Phe  Lys Asp Ile Asn Ser  Cys Cys Pro Gln Glu  Ala Thr Met
    2525                 2530                 2535

Gln Glu  Gln Asp Met Pro Phe  Leu Arg Gly Gly Pro  Gly Met Tyr
    2540                 2545                 2550
```

-continued

```
Lys Val Val Lys Thr Gly Pro Ser Gly His Asn Ile Arg Ser Cys
    2555                2560                2565

Pro Asn Leu Arg Gly Ile Pro Ile Gly Met Leu Val Leu Gly Asn
    2570                2575                2580

Lys Val Lys Ala Val Gly Glu Val Thr Asn Ser Glu Gly Thr Trp
    2585                2590                2595

Val Gln Leu Asp Gln Asn Ser Met Val Glu Phe Cys Glu Ser Asp
    2600                2605                2610

Glu Gly Glu Ala Trp Ser Leu Ala Arg Asp Arg Gly Gly Asn Gln
    2615                2620                2625

Tyr Leu Arg His Glu Asp Glu Gln Ala Leu Leu Asp Gln Asn Ser
    2630                2635                2640

Gln Thr Pro Pro Pro Ser Pro Phe Ser Val Gln Ala Phe Asn Lys
    2645                2650                2655

Gly Ala Ser Cys Ser Ala Gln Gly Phe Asp Tyr Gly Leu Gly Asn
    2660                2665                2670

Ser Lys Gly Asp Arg Gly Asn Ile Ser Thr Ser Ser Lys Pro Ala
    2675                2680                2685

Ser Thr Ser Gly Lys Ser Glu Leu Ser Ser Lys His Ser Arg Ser
    2690                2695                2700

Leu Lys Pro Asp Gly Arg Met Ser Arg Thr Thr Ala Asp Gln Lys
    2705                2710                2715

Lys Pro Arg Gly Thr Glu Ser Leu Ser Ala Ser Glu Ser Leu Ile
    2720                2725                2730

Leu Lys Ser Asp Ala Ala Lys Leu Arg Ser Asp Ser His Ser Arg
    2735                2740                2745

Ser Leu Ser Pro Asn His Asn Thr Leu Gln Thr Leu Lys Ser Asp
    2750                2755                2760

Gly Arg Met Pro Ser Ser Ser Arg Ala Glu Ser Pro Gly Pro Gly
    2765                2770                2775

Ser Arg Leu Ser Ser Pro Lys Pro Lys Thr Leu Pro Ala Asn Arg
    2780                2785                2790

Ser Ser Pro Ser Gly Ala Ser Ser Pro Arg Ser Ser Ser Pro His
    2795                2800                2805

Asp Lys Asn Leu Pro Gln Lys Ser Thr Ala Pro Val Lys Thr Lys
    2810                2815                2820

Leu Asp Pro Pro Arg Glu Arg Ser Lys Ser Asp Ser Tyr Thr Leu
    2825                2830                2835

Asp Pro Asp Thr Leu Arg Lys Lys Lys Met Pro Leu Thr Glu Pro
    2840                2845                2850

Leu Arg Gly Arg Ser Thr Ser Pro Lys Pro Lys Ser Val Pro Lys
    2855                2860                2865

Asp Ser Thr Asp Ser Pro Gly Ser Glu Asn Arg Ala Pro Ser Pro
    2870                2875                2880

His Val Val Gln Glu Asn Leu His Ser Glu Val Val Glu Val Cys
    2885                2890                2895

Thr Ser Ser Thr Leu Lys Thr Asn Ser Leu Thr Asp Ser Thr Cys
    2900                2905                2910

Asp Asp Ser Ser Glu Phe Lys Ser Val Asp Glu Gly Ser Asn Lys
    2915                2920                2925

Val His Phe Ser Ile Gly Lys Ala Pro Leu Lys Asp Glu Gln Glu
    2930                2935                2940

Met Arg Ala Ser Pro Lys Ile Ser Arg Lys Cys Ala Asn Arg His
```

```
    2945                2950                2955

Thr Arg  Pro Lys Lys Glu Lys  Ser Ser Phe Leu Phe  Lys Gly Asp
    2960                2965                2970

Gly Ser  Lys Pro Leu Glu Pro  Ala Lys Gln Ala Met  Ser Pro Ser
    2975                2980                2985

Val Ala  Glu Cys Ala Arg Ala  Val Phe Ala Ser Phe  Leu Trp His
    2990                2995                3000

Glu Gly  Ile Val His Asp Ala  Met Ala Cys Ser Ser  Phe Leu Lys
    3005                3010                3015

Phe His  Pro Glu Leu Ser Lys  Glu His Ala Pro Ile  Arg Ser Ser
    3020                3025                3030

Leu Asn  Ser Gln Gln Pro Thr  Glu Glu Lys Glu Thr  Lys Leu Lys
    3035                3040                3045

Asn Arg  His Ser Leu Glu Ile  Ser Ser Ala Leu Asn  Met Phe Asn
    3050                3055                3060

Ile Ala  Pro His Gly Pro Asp  Ile Ser Lys Met Gly  Ser Ile Asn
    3065                3070                3075

Lys Asn  Lys Val Leu Ser Met  Leu Lys Glu Pro Pro  Leu His Glu
    3080                3085                3090

Lys Cys  Glu Asp Gly Lys Thr  Glu Thr Thr Phe Glu  Met Ser Met
    3095                3100                3105

His Asn  Thr Met Lys Ser Lys  Ser Pro Leu Pro Leu  Thr Leu Gln
    3110                3115                3120

His Leu  Val Ala Phe Trp Glu  Asp Ile Ser Leu Ala  Thr Ile Lys
    3125                3130                3135

Ala Ala  Ser Gln Asn Met Ile  Phe Pro Ser Pro Gly  Ser Cys Ala
    3140                3145                3150

Val Leu  Lys Lys Lys Glu Cys  Glu Lys Gly Arg Asn  Lys Lys Ser
    3155                3160                3165

Lys Lys  Glu Lys Lys Lys Lys  Glu Lys Ala Glu Val  Arg Pro Arg
    3170                3175                3180

Gly Asn  Leu Phe Gly Glu Met  Ala Gln Leu Ala Val  Gly Gly Pro
    3185                3190                3195

Glu Lys  Asp Thr Ile Cys Glu  Leu Cys Gly Glu Ser  His Pro Tyr
    3200                3205                3210

Pro Val  Thr Tyr His Met Arg  Gln Ala His Pro Gly  Cys Gly Arg
    3215                3220                3225

Tyr Ala  Gly Gly Gln Gly Tyr  Asn Ser Ile Gly His  Phe Cys Gly
    3230                3235                3240

Gly Trp  Ala Gly Asn Cys Gly  Asp Gly Gly Ile Gly  Gly Ser Thr
    3245                3250                3255

Trp Tyr  Leu Val Cys Asp Arg  Cys Arg Glu Lys Tyr  Leu Arg Glu
    3260                3265                3270

Lys Gln  Ala Ala Ala Arg Glu  Lys Val Lys Gln Ser  Arg Arg Lys
    3275                3280                3285

Pro Met  Gln Val Lys Thr Pro  Arg Ala Leu Pro Thr  Met Glu Ala
    3290                3295                3300

His Gln  Val Ile Lys Ala Asn  Ala Leu Phe Leu Leu  Ser Leu Ser
    3305                3310                3315

Ser Ala  Ala Glu Pro Ser Ile  Leu Cys Tyr His Pro  Ala Lys Pro
    3320                3325                3330

Phe Gln  Ser Gln Leu Pro Ser  Val Lys Glu Gly Ile  Ser Glu Asp
    3335                3340                3345
```

```
Leu Pro  Val Lys Met Pro Cys  Leu Tyr Leu Gln Thr  Leu Ala Arg
    3350                 3355                 3360

His His  His Glu Asn Phe Val  Gly Tyr Gln Asp Asp  Asn Leu Phe
    3365                 3370                 3375

Gln Asp  Glu Met Arg Tyr Leu  Arg Ser Thr Ser Val  Pro Ala Pro
    3380                 3385                 3390

Tyr Ile  Ser Val Thr Pro Asp  Ala Ser Pro Asn Val  Phe Glu Glu
    3395                 3400                 3405

Pro Glu  Ser Asn Met Lys Ser  Met Pro Pro Ser Leu  Glu Thr Ser
    3410                 3415                 3420

Pro Ile  Thr Asp Thr Asp Leu  Ala Lys Arg Thr Val  Phe Gln Arg
    3425                 3430                 3435

Ser Tyr  Ser Val Val Ala Ser  Glu Tyr Asp Lys Gln  His Ser Ile
    3440                 3445                 3450

Leu Pro  Ala Arg Val Lys Ala  Ile Pro Arg Arg Arg  Val Asn Ser
    3455                 3460                 3465

Gly Asp  Thr Glu Val Gly Ser  Ser Leu Leu Arg His  Pro Ser Pro
    3470                 3475                 3480

Glu Leu  Ser Arg Leu Ile Ser  Ala His Ser Ser Leu  Ser Lys Gly
    3485                 3490                 3495

Glu Arg  Asn Phe Gln Trp Pro  Val Leu Ala Phe Val  Ile Gln His
    3500                 3505                 3510

His Asp  Leu Glu Gly Leu Glu  Ile Ala Met Lys Gln  Ala Leu Arg
    3515                 3520                 3525

Lys Ser  Ala Cys Arg Val Phe  Ala Met Glu Ala Phe  Asn Trp Leu
    3530                 3535                 3540

Leu Cys  Asn Val Ile Gln Thr  Thr Ser Leu His Asp  Ile Leu Trp
    3545                 3550                 3555

His Phe  Val Ala Ser Leu Thr  Pro Ala Pro Val Glu  Pro Glu Glu
    3560                 3565                 3570

Glu Glu  Asp Glu Glu Asn Lys  Thr Ser Lys Glu Asn  Ser Glu Gln
    3575                 3580                 3585

Glu Lys  Asp Thr Arg Val Cys  Glu His Pro Leu Ser  Asp Ile Val
    3590                 3595                 3600

Ile Ala  Gly Glu Arg Ala His  Pro Leu Pro His Thr  Phe His Arg
    3605                 3610                 3615

Leu Leu  Gln Thr Ile Ser Asp  Leu Met Met Ser Leu  Pro Ser Gly
    3620                 3625                 3630

Ser Ser  Leu Gln Gln Met Ala  Leu Arg Cys Trp Ser  Leu Lys Phe
    3635                 3640                 3645

Lys Gln  Ser Asp His Gln Phe  Leu His Gln Ser Asn  Val Phe His
    3650                 3655                 3660

His Ile  Asn Asn Ile Leu Ser  Lys Ser Asp Asp Gly  Asp Ser Glu
    3665                 3670                 3675

Glu Ser  Phe Ser Ile Ser Ile  Gln Ser Gly Phe Glu  Ala Met Ser
    3680                 3685                 3690

Gln Glu  Leu Cys Ile Val Met  Cys Leu Lys Asp Leu  Thr Ser Ile
    3695                 3700                 3705

Val Asp  Ile Lys Thr Ser Ser  Arg Pro Ala Met Ile  Gly Ser Leu
    3710                 3715                 3720

Thr Asp  Gly Ser Thr Glu Thr  Phe Trp Glu Ser Gly  Asp Glu Asp
    3725                 3730                 3735
```

-continued

```
Lys Asn  Lys Thr Lys Asn Ile  Thr Ile Asn Cys Val  Lys Gly Ile
    3740                 3745                 3750

Asn Ala  Arg Tyr Val Ser Val  His Val Asp Asn Ser  Arg Asp Leu
    3755                 3760                 3765

Gly Asn  Lys Val Thr Ser Met  Thr Phe Leu Thr Gly  Lys Ala Val
    3770                 3775                 3780

Glu Asp  Leu Cys Arg Ile Lys  Gln Val Asp Leu Asp  Ser Arg His
    3785                 3790                 3795

Ile Gly  Trp Val Thr Ser Glu  Leu Pro Gly Gly Asp  Asn His Ile
    3800                 3805                 3810

Ile Lys  Ile Glu Leu Lys Gly  Pro Glu Asn Thr Leu  Arg Val Arg
    3815                 3820                 3825

Gln Val  Lys Val Leu Gly Trp  Lys Asp Gly Glu Ser  Thr Lys Ile
    3830                 3835                 3840

Ala Gly  Gln Ile Ser Ala Ser  Val Ala Gln Gln Arg  Asn Cys Glu
    3845                 3850                 3855

Ala Glu  Thr Leu Arg Val Phe  Arg Leu Ile Thr Ser  Gln Val Phe
    3860                 3865                 3870

Gly Lys  Leu Ile Ser Gly Asp  Ala Glu Pro Thr Pro  Glu Gln Glu
    3875                 3880                 3885

Glu Lys  Ala Leu Leu Ser Ser  Pro Glu Gly Glu Glu  Lys Val Tyr
    3890                 3895                 3900

Asn Ala  Thr Ser Asp Ala Asp  Leu Lys Glu His Met  Val Gly Ile
    3905                 3910                 3915

Ile Phe  Ser Arg Ser Lys Leu  Thr Asn Leu Gln Lys  Gln Val Cys
    3920                 3925                 3930

Ala His  Ile Val Gln Ala Ile  Arg Met Glu Ala Thr  Arg Val Arg
    3935                 3940                 3945

Glu Glu  Trp Glu His Ala Ile  Ser Ser Lys Glu Asn  Ala Asn Ser
    3950                 3955                 3960

Gln Pro  Asn Asp Glu Asp Ala  Ser Ser Asp Ala Tyr  Cys Phe Glu
    3965                 3970                 3975

Leu Leu  Ser Met Val Leu Ala  Leu Ser Gly Ser Asn  Val Gly Arg
    3980                 3985                 3990

Gln Tyr  Leu Ala Gln Gln Leu  Thr Leu Leu Gln Asp  Leu Phe Ser
    3995                 4000                 4005

Leu Leu  His Thr Ala Ser Pro  Arg Val Gln Arg Gln  Val Thr Ser
    4010                 4015                 4020

Leu Leu  Arg Arg Val Leu Pro  Glu Val Thr Pro Ser  Arg Leu Ala
    4025                 4030                 4035

Ser Ile  Ile Gly Val Lys Ser  Leu Pro Pro Ala Asp  Ile Ser Asp
    4040                 4045                 4050

Ile Ile  His Ser Thr Glu Lys  Gly Asp Trp Asn Lys  Leu Gly Ile
    4055                 4060                 4065

Leu Asp  Met Phe Leu Gly Cys  Ile Ala Lys Ala Leu  Thr Val Gln
    4070                 4075                 4080

Leu Lys  Ala Lys Gly Thr Thr  Ile Thr Gly Thr Ala  Gly Thr Thr
    4085                 4090                 4095

Val Gly  Lys Gly Val Thr Thr  Val Thr Leu Pro Met  Ile Phe Asn
    4100                 4105                 4110

Ser Ser  Tyr Leu Arg Arg Gly  Glu Ser His Trp Trp  Met Lys Gly
    4115                 4120                 4125

Ser Thr  Pro Thr Gln Ile Ser  Glu Ile Ile Ile Lys  Leu Ile Lys
```

-continued

```
    4130                4135                4140

Asp Met  Ala Ala Gly His Leu  Ser Glu Ala Trp Ser  Arg Val Thr
    4145                4150                4155

Lys Asn  Ala Ile Ala Glu Thr  Ile Ile Ala Leu Thr  Lys Met Glu
    4160                4165                4170

Glu Glu  Phe Arg Ser Pro Val  Arg Cys Ile Ala Thr  Thr Arg Leu
    4175                4180                4185

Trp Leu  Ala Leu Ala Ser Leu  Cys Val Leu Asp Gln  Asp His Val
    4190                4195                4200

Asp Arg  Leu Ser Ser Gly Arg  Trp Met Gly Lys Asp  Gly Gln Gln
    4205                4210                4215

Lys Gln  Met Pro Met Cys Asp  Asn His Asp Asp Gly  Glu Thr Ala
    4220                4225                4230

Ala Ile  Ile Leu Cys Asn Val  Cys Gly Asn Leu Cys  Thr Asp Cys
    4235                4240                4245

Asp Arg  Phe Leu His Leu His  Arg Arg Thr Lys Thr  His Gln Arg
    4250                4255                4260

Gln Val  Phe Lys Glu Glu Glu  Glu Ala Ile Lys Val  Asp Leu His
    4265                4270                4275

Glu Gly  Cys Gly Arg Thr Lys  Leu Phe Trp Leu Met  Ala Leu Ala
    4280                4285                4290

Asp Ser  Lys Thr Met Lys Ala  Met Val Glu Phe Arg  Glu His Thr
    4295                4300                4305

Gly Lys  Pro Thr Thr Ser Ser  Ser Glu Ala Cys Arg  Phe Cys Gly
    4310                4315                4320

Ser Arg  Ser Gly Thr Glu Leu  Ser Ala Val Gly Ser  Val Cys Ser
    4325                4330                4335

Asp Ala  Asp Cys Gln Glu Tyr  Ala Lys Ile Ala Cys  Ser Lys Thr
    4340                4345                4350

His Pro  Cys Gly His Pro Cys  Gly Gly Val Lys Asn  Glu Glu His
    4355                4360                4365

Cys Leu  Pro Cys Leu His Gly  Cys Asp Lys Ser Ala  Thr Ser Leu
    4370                4375                4380

Lys Gln  Asp Ala Asp Asp Met  Cys Met Ile Cys Phe  Thr Glu Ala
    4385                4390                4395

Leu Ser  Ala Ala Pro Ala Ile  Gln Leu Asp Cys Ser  His Ile Phe
    4400                4405                4410

His Leu  Gln Cys Cys Arg Arg  Val Leu Glu Asn Arg  Trp Leu Gly
    4415                4420                4425

Pro Arg  Ile Thr Phe Gly Phe  Ile Ser Cys Pro Ile  Cys Lys Asn
    4430                4435                4440

Lys Ile  Asn His Ile Val Leu  Lys Asp Leu Leu Asp  Pro Ile Lys
    4445                4450                4455

Glu Leu  Tyr Glu Asp Val Arg  Arg Lys Ala Leu Met  Arg Leu Glu
    4460                4465                4470

Tyr Glu  Gly Leu His Lys Ser  Glu Ala Ile Thr Thr  Pro Gly Val
    4475                4480                4485

Arg Phe  Tyr Asn Asp Pro Ala  Gly Tyr Ala Met Asn  Arg Tyr Ala
    4490                4495                4500

Tyr Tyr  Val Cys Tyr Lys Cys  Arg Lys Ala Tyr Phe  Gly Gly Glu
    4505                4510                4515

Ala Arg  Cys Asp Ala Glu Ala  Gly Arg Gly Asp Asp  Tyr Asp Pro
    4520                4525                4530
```

```
Arg Glu  Leu Ile Cys Gly Ala  Cys Ser Asp Val Ser  Arg Ala Gln
    4535                 4540                 4545

Met Cys  Pro Lys His Gly Thr  Asp Phe Leu Glu Tyr  Lys Cys Arg
    4550                 4555                 4560

Tyr Cys  Cys Ser Val Ala Val  Phe Phe Cys Phe Gly  Thr Thr His
    4565                 4570                 4575

Phe Cys  Asn Ala Cys His Asp  Asp Phe Gln Arg Met  Thr Ser Ile
    4580                 4585                 4590

Pro Lys  Glu Glu Leu Pro His  Cys Pro Ala Gly Pro  Lys Gly Lys
    4595                 4600                 4605

Gln Leu  Glu Gly Thr Glu Cys  Pro Leu His Val Val  His Pro Pro
    4610                 4615                 4620

Thr Gly  Glu Glu Phe Ala Leu  Gly Cys Gly Val Cys  Arg Asn Ala
    4625                 4630                 4635

His Thr  Phe
    4640
```

<210> SEQ ID NO 3
<211> LENGTH: 290040
<212> TYPE: DNA
<213> ORGANISM: Homo sapiens

<400> SEQUENCE: 3

```
cttcagcttg gagtactaaa tatattctat gaaatatact ttattttaaa gtgcaatata     60

tttgtcaaga atgcactatc ttattaccct taaaaagaga aggtcactga agagtaaagc    120

atgtcttcac tcttcaagcc taagcttttt cttttttttt tcccaaattg ttctcagcta    180

ccaattttgt ttttaaattc cccaatacat tgttgtacaa atccaggaaa caaacgcaga    240

ctttaccaca gcattttcag cagtctcgat gtacctaata atatacatac ttcctgtgtt    300

tgtagtcttg tagctttagt acaatattaa ccctttaaat gaaacaacac taatctgtcc    360

tcttatatac acgttatggt tcctgccctg ttatttacta catcagcacg ggtagcttcc    420

tttaaaaaca aaatcgttaa agatgagagt aggaaaaatg taaatgtgat aagagttcaa    480

aaaactgtgg tccaggtttg caatgttaag tggaaaagaa cgactaaatc tgtgatcaca    540

aggggaaaga tgaagccata gtcttattac atgggcacag gacagagaga tctcttttgc    600

gaaatgagca taccaaccac aaagaataaa acatactacg cccgtaataa aatgggcaca    660

ggcaggattt gccgtagttc aatgctattc tttgagggcg aatgtgtcgt gggtgaactg    720

ctgtctagcc cattccgaca cccaagccgc ccaggcggcc cccacgcccc ccggctgcag    780

ccctccctgt acacacaaat gcacacacgc ccagcccggc cgctggagga actaagatgg    840

cagcgcagaa agcacggggg ccgagctcgg tggggtgggg aaagaaaagc aaagccctct    900

gtgtttttc attctgtata ggtccccctc tttccccaaa cacaagggct gcgtaaggca    960

ttcggtagta gagctcgcag gagcggcggg aggggacgct tgctttgcat actgccagaa   1020

acccacgtct ccgatctgca gcgacggttc aggcgaccct cgcgacttgt gaccacactc   1080

tccttcacgt ccccttgaca gtagaagtaa gggtgactcc aaatgccttt ttctttctgg   1140

catgcgcccc actcccccgc catcccaggg gagccttcca agttgcccag ctgccaaggc   1200

ggtagctgtg gcagttgcag ggaccgggga gcgcgccgtg cggaggcagg aagaggagga   1260

ggaggagaaa aaacgctgca ctggctatca attttgagga gagcgaccgc tgccgctgcc   1320

gtggaaggaa acgctgccaa ccgcaacaga aatgccactc tcggatacct aagtgagcat   1380
```

-continued

```
gtgtgcgact ctgcgcacgc ctagttgcgc agctcaatga catcgggctt cttagcaagt   1440
tatccagttt ccgggttttg agtgtaccca tcaggctccg taggggcctg tctgggactg   1500
aacagcagta aagattgaag cgaaattaat gaatggtggg aagagcccgg agaccagggc   1560
agccacgcgg gtcaatgtcc actagaaact ctaaatgggc agtgactgca cattccacca   1620
cctgagcctg cgctgtaaat gttttctgtg caagcaacat tcattcattc agccaacatc   1680
tatttccctc ctgttcaggg ctagaccctg tgctaggagc ctgtgatggt tgaacagaca   1740
ccattgctac cctacggaaa acctagtgtt ttgtttagta tgtgctacca tttgtgaaaa   1800
ttcatgtgcc aagttggaca tcctagatcc tttaagtcct ccctcaatct catgtagtgg   1860
gtattctttt gagcattatt cagaggagat aatttgccca aagccagaca agtattaagt   1920
agcagagtca ggatccaatt ccagggctgt ctgatttcag agccttttag ctaccctgct   1980
aggtcttgca atagtaatgg gccctctcat tgcttacctg tcaggcctta gaattcttag   2040
aatttagctg cctctacacc attgtcttgg ttctcactcc agggttaggg gctgcctggt   2100
caacactgag gtctttaact gtgctgaagc attaggatag aaatttagtc taataaatac   2160
ttactggata cctactacat gcaaagtcct gaagtggctg aaggagacac aaaagcagca   2220
agctctgaag gaacttaggt aaggaaacaa gacaaataca aaaacttaac agggctaatt   2280
acagtactaa aatactatga ttccacatgt cttgtccttt gttcctatgt ttatcccact   2340
gctaattatc tttaaaaaaa ctaaatgaaa tccatccatt atttaaagct tcagaaaaaa   2400
atgcattgct ttcagcaacc ttccacccta aaactagaat taatttactt tcctattcct   2460
tgttgtttgc acttctcaaa cactaaggag gatttttaa catttatttt attttttttt   2520
aagagaaggc catccgaaga agaggcacag atataagaac tagtacatag atgaaagata   2580
cagtactggg atgacagaac ttataaatta ttttgtcagg actgtaaatt aggaaactct   2640
tcaaattgag agtcaaagga taaaacgtag taggaatcaa agtgcattgg cacgtatatt   2700
tctagagcat atacttagat ggggttcgta ggttagcttg gaacaaagga ctgagcaaat   2760
gttacttttt tatagacaac aacaagatat gtgatggatc tgacattttc agacgctata   2820
cagtctccgt cacaattatt gtttcagatc gcattcaaga attatcttta aaaatgtaag   2880
tttgggcaga aaaaaataaa ccattaaatg accactgcca agagataaaa gtgcactctt   2940
aggtgagtga ggagtcaata aaaaagagta atttaaaaaa tattattgct ccgttgagaa   3000
caagaatttg ggaatgactc tggcttgtga atactagcct atctgttata ctttcacaca   3060
caaaatactt tcacacacaa aaaagaatgt gctagattac tacctgtctt tgtaagtaaa   3120
agctgtgtta aacaagcgta aatcctaatg acaaaaacca tataaaataa gatcgctaaa   3180
ggcacttcta attgggatgg ttttctctgc cttaaactct gaattaacca gcacaattca   3240
cagtaaatct tcctgttggc agcagagcct tggagaagag gtagcagaag agcgtgccac   3300
tcctcctctg gcgatgggca cgttcccccct tgctttctgg tcctcgttct tccacctgga   3360
gggaacctga agtcgaacgt cagtagctga cagcctcccc agcactttcc ttactcttct   3420
tcaagctgcc agtaaaaccc ggagaagtgg actacttcag attccgcaca acccaacagc   3480
cccaaaccca aagccccgag gcggagggag tggtggcgga gagggggtgg ggaggaaaag   3540
gggcggcagt tactgagcat gtgcgaggag tggcgcatgc tctgtgaggc cggcagcttc   3600
ccattgcggg tagccccggc ggtggtggcg gtggtagcgg tggtggcggc ggcagtggcg   3660
gcaccgcctc ctcctcacat tcccggggtg gcggggttag atgagcggcc ccagtagcgg   3720
cgagggcggc gcggggggga ggaggagaag aaggaggagg agaaggaggt cgctgtcttt   3780
```

-continued

```
gtagtctccc tgctgcggga gccagaggcc gccgccggag ccgtcgtcgt tggaaaaggg   3840
ctgtgtgtgc gcgcgcgtgt ctgcccgccc ggcccgcggg gacgaggcgg cggcggcggc   3900
ggcggcggcg aggatgatga tgtgcgcagc gactgcctcc cccgccgccg cctcctcggg   3960
gctcggcggg gacggattct acccagccgc caccttctct tcctccccgg cgccgggggc   4020
gctgttcatg ccggttcccg acggctccgt ggctgctgcg gggctggggc tggggctacc   4080
cgccgcggac tcccggggtc actaccagct gctgctgtca ggccgggccc tggccgaccg   4140
ctaccggagg atttataccg ctgcgctcaa tgacagggac caggggggcg gcagcgctgg   4200
acacccagcc tccaggtgcg tccccagggt gcccttcctt gcgccccatg ccgcccttcc   4260
ttgcgcccca tgccgcgcgt gcacccgcgt gtgtgtgtgc ttgcgtgtgt gtacctgcgc   4320
atttattgag ctttcagtcc gctctggatg tctgttggca ggagcactta tcgagatagg   4380
agggtgcggt ggctgcagtt tctcgtgtgt gtgtgtgtgt gtgtgtgtgt gtgtgtgtgt   4440
gtgtgtgtct gcctgcctat gtggggggat agtgaggggt ggtaggggaa cctgtgatgc   4500
tggaaaaggc gatggtgctg gtcggctgtg acacgtgtgt gtatcgttga ggtaggaggt   4560
ggcatgggta gagagggtaa gaggatgata cacgaagaga attgcaacag tggcaaggga   4620
agtggcgttt tcagtgtctc tgccgcaatg ttatttgcac gtgccgcctc tcccatgaca   4680
ttccttccag ccctttccac ctcccttcaa tctgcctttc accaagagga gtcatggtat   4740
agattggttg agttttggat aagcaggccc gagggatagg cgtgaggttt gctttaaaaa   4800
gatttatgaa taagggacgc agatggagat ctgtgtggat gcgaaaggtg tctgatagag   4860
atttttagag ctgtactttg ataaccgggc cttttggtct tctagaaatg aggttgcagt   4920
tactcttgtg atctgatgtc ccatcggcca tttctcttca tcctctgttc gatttcctct   4980
gttacttaca ggctttagag tagagagggt tttgtaggga aaaggggaaa actgcagaac   5040
ttcagaatat gacagctggt acagcgttca actgccacta gctagaaaat ctgaatagcg   5100
cgtagatttg tctcttttac ttgggttggc tacaccttca gcttccttga tgtagatgtt   5160
cagttggttt catttttcttt ttcttaaaat gtgggtgctt ttttttgctg agggctctcc   5220
tattgttttc ttttccatgc ccttacatgc cgcataccct gaaggttggt gactgacttg   5280
tttcaccagc tttgacagtg gtaattggga gttggcttca tctttttttt cccacagctt   5340
cttgcagtac atggggaaaa catagtagga aactgtcaaa atgagttaaa gagtttactg   5400
ttatttattg aatgtgcaat ttattaggca attgttaggt gtctttttct cccattatga   5460
aagggacgag gctgtaagtc aggtatttgt agcttatcac taggtatcat ggcttatctg   5520
ttggagacag ttgtaaagct ggagctttgt tcacactttt tctaggttaa ccagttttct   5580
catgtctgtg attgtttaca ggattgggca cagcagtagt tttaccatat ggatgtaaac   5640
gtgtgtaact attttttgct atctgaactg aaggccagaa tggcacaagt ctgtttcttg   5700
ctaatgcttt tgaaaatagc acaaaactac gtgagacagt ttgccctgat aattaggtat   5760
aattttgatc tgtaaatctc taaattatgg caccgcagga acatctttac aaactcctct   5820
caaagaattt aaatttattt tgtgtatggt ttccagactt atgcaataat ttttgacttg   5880
tatattcctg ttttgacttc ctactactag tgtaatatga tttctgtgta tctagaacta   5940
tattaacggt tttagacaaa attaacatag attaatcata taacatttgt gaatgatttt   6000
ttagcccttg gtccattttt gtacaagccg tcaatgaaaa gtaatgaaga attagttcaa   6060
gtatttcaag aactactcat ggaaatcagc attatgttat gatattgcct gctaatgctt   6120
```

-continued

```
gttcaacgca acattattgt ttatttaagt tcacattatt ttattacaaa aagtagcctg   6180
caactactct attgatgatt tgattaagaa ttaaatcaca tttcttatta aagatgttga   6240
ggaaagtaga cttggggttt cggctctgaa tgaatgatag aattatttgt atagggacac   6300
aagttaaagg agaagatgat atcttttaga gagactgaat ggagcaataa tagagaatga   6360
agctctagtg agcatcaggt ttaaaggtgt gagagaaagg agacagtgaa ggaaacggaa   6420
tcaaaattaa gaagaaaatc atgaaacagt agcctctgtg gctctaggag agtggattga   6480
aaattctcag aagtggtaaa tgttgaagaa agtgagaacc gttttcaggt cattgataac   6540
ttttgaggaa gtggtcagaa tagagggatg tggtgaggag tgaatggaat gtgtttttgg   6600
taactcaagg ggatttcaaa gttgagggaa ggatattcaa gtataggagg ttgggtggga   6660
tatgcaaata tgggaggcta aatggagaga cagagtgaag aagtgagaga ggggataatt   6720
gataggaaaa ggtcaaaggg atctcaggga caggaagagg tcaaagggat ctcagggata   6780
gagttaaggt gacaggtgga gaggttagcc attgaaaaaa ggagcagtta atatagaagg   6840
ggtggaggtg agtacttgta aatataaaga ctgggagttt attgaggata ggcatcatat   6900
cctattcgtt ttgataatcc caatgtctag cacatttttt ggcatgaatt ctgtaaacat   6960
caagtgcctg ctctgtgcca ggcagtattg cagatgctga agatgtagcg gtgagcaaga   7020
tagacaaagt ctctgccgtc ttggaaaatc cactccaatg ggagaaatag acaactcata   7080
atttcactta gtaataagta actgtgaagg caataaaacc tatttcatgt gatagggcaa   7140
tttgtagtgg ggctatttta ggtaacatgg tcaggaaatg tctctttgag agttggcatt   7200
taaattgaat tgccatgatg aggaggcaga tgtagaggaa gaatgttctg ggaatttata   7260
aaggccttga aatgggaaca ggcttgtgtt caagaaacaa aaacatgatg agtgagttat   7320
cagtcaatgt caaatgaatt aattactctt tgctttaggt gtacagttga gaagttgaga   7380
gtttcaaacc taatggactc agtgactttg atgacagtct aacaaagtgg ttaagagctt   7440
gggcacagaa gctagactgg ttttgcatcc tggttttgtc atttgctagc tgtgtaactt   7500
tgagtatatt acataacttc tatgcctcag ttttttaaat atgtagaatg gggatcataa   7560
tactaacatg aattgttttg tagattaaat gaatcaatgt atgtgcttgg catgttgact   7620
gctatgaaat attagttact gttttttgtc tgtttgtttt tgctgagaat gaggggtgtg   7680
gggacttgaa gagaaggcaa ggatcatgtc ttactctttt atttttggtc tcagtgactg   7740
tgtagaatgt gggaataact ctttcattta tccagtgact gaatagatat atttttggat   7800
gaatgaggcc aatcaaaatc ggaacattct gttggggaaa ggggttggac aggaaatgta   7860
tgaaggaatg tatgatctgt tctgaatgtg aatggtggta taaccatgca cttgggaggc   7920
accatagcac agtggctaaa tgttagagca ctggaggtag actcccttag ttcacgtcta   7980
cctttttcta cttgtgttaa attgggcaag ttaattagac tttgtctgtt tctttacttg   8040
taactttgta gtgttatcaa aaggacatta tgtccgcacc tggtaagtgc ccatgaaatg   8100
ttacctgttg ttattattaa aatcacattt aaaattccaa ccagcatggc actgtatgtt   8160
tttccacaca aaatagaaat ggagaaaacc tagttgagtt gatttagggt taaagaaaaa   8220
agaaatggaa ggttttgggg acagtgtttg actatatggt aaaaaggaaa gtgatgccaa   8280
gagggaactg atagactgga agataaagag gagtcagagt atctgggtcc tgaagtccta   8340
gaagaacaat gttagtgaaa acaatagagg ggattgtgac caaaatgggg aatctaaact   8400
taaccccctt agttttttca gctgctttat ctctttcttg ttagaaatgg tatttgagtc   8460
catccttcag atgcatggga ttttggttgt aagaggttaa gtagtcattt tagcaaaagt   8520
```

-continued

```
tcagggatta ttttatttta cttattttga ggcaggctgg agtgcaatgg tgtgaacata   8580
gctcactgca gcctcaacct cttgggctca agtgatcttc ctgcctcagt ctcctccagt   8640
agctgggact acaggcatgc accaccatgc ctggcttgtt ttttattttt tgtagacaca   8700
gggtctcacc atgttgtcca ggctggtctt gaactcctga gcttaagtga tcctcccacc   8760
tccacctccc aaagtgctgg gattatgggt gtgagccacc atgctcagct tgctcaggga   8820
ttattacttg gcactaacca ttggccctat aaaaatttat aagacacaaa ttctagactt   8880
gagtttactg tctatctgga agtgcaagat acaaaggcag atacttatag aagtgttaaa   8940
tgaaatgacc aagaaagtat aacctactat gacaaaggca tggcattcta ggctggctta   9000
aaagcatcag cagagacagg aaagcacagt ttgtatgtag gtaacagtag gaattctgtt   9060
agagctagaa tgcaggtgtc atgaaggaca gtagtggaat tcattctgga aatggaggct   9120
ttggctagga tggggcatct tgaagaccaa ggtaagaatt agattttatt cagtagacac   9180
tgatcaccct tgatggtttt aagctatgaa gagacgttat ttattgtagg aatatgtcag   9240
gaagtaatgc gggattgaat ctgtatgtgt acatctgtat ttgtgcatag gtagtaattt   9300
tcttcatgta gctgttatat cagtggaatc ctgtatagtg tataaacaca agttaaggca   9360
aaaactgctc tattggtata ctggtaggta gaaatgtgaa atgaattagt ttcctaactc   9420
aagagaagaa aaaaatcttg cctctgggct taaaaggaaa ataaaaatgt caatctaaaa   9480
atacttttgt cctttaatat atttgtttaa aaaatcaaca gaatagtctc acttttttct   9540
caaaaaccag attaaacatt taggttttct gaggaggggt taggttaatt gaggtttaat   9600
ttatatacaa taaaattcat cctctttaaa tgttcatttg aagagtcctg aaactatcac   9660
cacagtcaag tatagactgt ttccatcact tcatataaaa agttctgtca ggccctccta   9720
cccctggtta ctgaccgctg caaatcagtt ttctgtcact aatattttac cttttctaga   9780
atgtcatata aatctagctc cttaagggca gggcccccag gtattgttca tctttctgtc   9840
ttgtatctgt atttcctgta agtggaagct agaccttaag ggtttattag gtgttcatta   9900
gaaaattttt tagcaagaat attgtatatg gcgctgggta ctgcatgttg catcccatcc   9960
agaggttgtg aggttgtctc actatttaat atgttaaatc tgattacttg ggtaagacgg  10020
tacctactag atttcatctc tgtaaatgta tgctttttcc atttgtaaag aacaagtaat  10080
cacagggtaa aaatttgagc acattgtgaa tgccttttac ctaatgcttt tagcattctt  10140
tgataatcct tgtctgagtc aataatttca ttaggggttg caaaatgatg aattaaaaaa  10200
taattctgtt atttcttcta tgtttattag ctggtactct tctgcaaaga agagttggcc  10260
ttcactgact gtcagtgaaa tgtagtttct cctaatccag cagcataaat gcttaattct  10320
cttccctcat tagccaaatt ggtgtaatag tccagtggtg gtgtggcagg tgctgtggtt  10380
aggctttcag atcccgcttt caggcacatg ttcccctagc tcttggcaat attggcagct  10440
aaaactgatt gcagctgagt cccactccac gcattgccct gagccaagag ttgcctcccc  10500
cagagtcatg cctcctcttc aggggcagtt tacatctaat atctatacag tgtagggata  10560
taaatgccta gcgcttttgc tataagacaa gccaaccttg aagtctatcc caacaccaga  10620
gagctctccc atgggtctgg ctgagggctt cctgggactg cattgcagat caactccttc  10680
ctctgttcag tcttacgtct ttcactgccc cacagttgtt ggttcggagg gcactccgca  10740
ataaacttcc ggtgtgcaca tctgcatttg agagtctgtt tcctgggaac cctcctaccc  10800
aaagcagttg gtgccaggag tggtctcaga aagtagactt tacagtgagg ttttgaagct  10860
```

-continued ggattattgg ctggctggct ggcaatgaga atcgattctg gtgctagatg gagcactaat 10920
actgataacg cttggcatgc actgtagcta tgcaacttaa aactttcact ggtggtgagt 10980
tggaatgcta ttcctgttga agggaatgca ctggtgagtg cactaggctt ttgagaagtt 11040
cagagaaatt aattatgagg acaatcatca gatggctttt ggtaaataac attgatagat 11100
tggagaaaga tgatgcaagg tggaagataa ttgggggcaa aatgtaaaag gaaatttatt 11160
tagcatcatg taaagaaaca catatacagt aagaggaaaa atctaaggct tcaacccaaa 11220
acttaatttt aagggtagca gagcaccaag gtaggtagaa ttctctctca gctatgctaa 11280
ggtcagtgtt ctggttgggc aggaatcctg acccttagga tggggcatct gagtgcactt 11340
gaaaaccctg aaaccccaaa ttcctcttaa ccctctgggc ctgcagaagt ggccttcttc 11400
tactagctag aggggttgct tgcagactgt gctgtccctc ttacccccag ctcctcctct 11460
ctcgcctact gactatcacc aaaccaacaa ctagggttaa gtcacaagaa cacctagttc 11520
ggggtgctgg atctgcgaag ggaggaaggg actgtacaca caaacacaca cacacacacg 11580
ttcccaaact gcaccaaggc accccaaagc accaccacag acacaaaaga ataccatggg 11640
atatttcaga attttaaagg aaacacagca atatctgtca caaattacta gcttgaggta 11700
gttcacggtt ttgacattag ctcatgccac atttcttttg atgatgtcat atttttgcag 11760
ggttggattt ttactagttg tgatacagat caagcactgt gcaaaaatca gtgtggaaca 11820
ggaaaggagg gtggcatgtt cagtctgatt ccaagtttga gaagttgttc tgtgtctaac 11880
aggcacacat gtcatattat caagtaattg aagtttttgt ttgtttgttt gttttgaggc 11940
agagtctcgc tctgtcaccc aggccagagt gcagtggtgc gatctcggct cactgcaacc 12000
tccgcctgcc aggttcaagt gattcttctg cctcagcctc ctgagtagtt gggattacag 12060
gcgtgtccca ccacactcgg ctgatttttg tatttttact agaggtgggg tttcaccata 12120
ttggtcaggc tggtctcgaa ctcctcacct cgtgatccgc ctgcctcgtt ctcccaaagt 12180
gctgggatta caggcgtgag ccactgcgcc tggcccagta tttgtagttt ttaagaagga 12240
aataaaaata tttttcttcc aatttatgtg ttattttttc aaatgtctac tcatttgtta 12300
ggacatgaat tcttgttatt tggatctaac tacttaataa acactactgt ttggtatttc 12360
ttttggccta tgagtgcatg gaaaaattac cgatgatggc tgtgcatggg cccaataaaa 12420
gggttttcat tcaccagtgc tgatctagca actgctgctg ctgaatatcc agcctgacag 12480
cagcagagat caatcatcct tcaagcaggc caaccagtcc ttatacagtg gaaaggacca 12540
tgattcattt tgattggatt tgagacatat tctgggtctg aatttgtctt tccagcaggg 12600
tctcacccag gactactgtt tgagggcttg caggatgttt gatcctctac tacagggatc 12660
atttcagaat aagggaccca ctgttatgtt atgttatgtt atgttatgtt atgttatgtt 12720
atgttatgtt atgttatgtt atgttatgtt ttgagacgga gtcttgctct gttgcccaag 12780
ctggagtgca atggcgtgat ctcagctgac tgcaacctcc gcctcccggg ttcaagcagt 12840
tctcctacct cagcctcctg agttgctggg actacaggtg cacatcacca cgcccagcta 12900
atttttgtgt ttttagtaga gacggggttt caccatgtgg accaggatgg tctcgaactc 12960
ctgacctcgt gatccggcca cgtcagcctc ccaaagtgct gggattacag gcgtgagcca 13020
ccgcgcccgg ccgggaccca cttttataga ataggagaat catttgtccc atcttgcacc 13080
acaccgtcca gaagctgatg acttgataga gcagtaaaac agtcctttga tggcacagct 13140
gatgatgaga tcctgcagct tgggcatgat gccctgcaag ggtgaggcgc ccattctcca 13200
gtgttcccag taggaagatc acatgaaatt aggagtggct ccgcatagca tcactctgtg 13260

```
aatcacctgg gcagtttctg cttcccatct ccatagctct gatggcaagg ggttaaaaga  13320
tcctggttct cagaagagaa acatttccaa cagagggcgc tatgagaatc ctgttatact  13380
ttaaagtaca gctgccacta ggatttgggg ctccttttct aaataaagaa gtcaccaggc  13440
tgggcacgat ggctcacgcc tgtaatccca gcactttggg aggccgagat gagtggatca  13500
cgtgaagtca ggagttcgaa accagctcag ccaacatggt gagaccctgt ttgtactaca  13560
aatacaaaac aattagccgg gcatgttggc gcgtgcttgt aatcccagct aattgggagg  13620
ctgagtcagg agaactgctt gaacctggga tgtggaggtt gcagtgagcc gagattgcgc  13680
cactgcactc cagcctgggc aatagagcaa gactccatct caaaacaaaa aaaaaacaac  13740
aaaaaaagaa gtcaccattt ggacagggtt aatgtccttg ttcatgtgga ggaggtaggg  13800
ctgtgttcca cagtggagca tggaggtttg gcacacaggt gatctataag gtgtctcttg  13860
gtacttcctt gtccagtgtt tgtggtaaat ggacacgaga aaggcccagt gaccacccca  13920
tgaagtcagc cacctggacc aacagaaata ctagccatag attaaaggaa tctagaatgg  13980
ctagtagaga agagttgttg atatcaattt taccgtctgt agtggctggg gctgtggttt  14040
gacccacttt ccttcctctg gaaagtttct ccaggaaatg acactcacca gaattctgga  14100
ggaacttttt ccatgcctta tttgaagcaa gtgaatccta attgtataat aggcgaaata  14160
tagtgaatcc tgtattgtgg aacccagagc ccctgcccag cactgatgtg ctcaaaattc  14220
ccccacgact gctgggaaca ttggttggct acagactctt ccctagttcc aatatgggca  14280
ttgcctttgg caataggtga tggccctagg tgatggatca ttcttggggg cagcctgaat  14340
gaactggttg atcggggcat tttatggttt ttagtgctac tgtaactagt ttagtttttc  14400
ctatttttca gttgtttgat atgaatatat aacaatacag ttgcttttga atgttaacct  14460
tgtatctctg atcttgttaa gctcatttat taactttaat agttttgtaa attccctggg  14520
atgttctgtg taaataatca tattgtcttt ctttctgatc tctagattct cctacccctc  14580
agcccctact ttattccaat tacttaattc tcccttgttt ttaatctgag agaaaaacaa  14640
ctacaaatta atcttacagt tttttaaatc attaagtatg atattagctg taggtgtttc  14700
aatggcctct atcaatttga agatattccc tagtattcct actttgctga tagtttttat  14760
tttttatatt ttaatttttt tttttttttt ttttgagaca gagccttgct ctgttgccca  14820
ggctggagtg cagtggcata atctcggctc actgaagcct ctgcctcccg ggatccagca  14880
agtctcctgc ctcagcttcc tgagtagctg ggattacagg cacacgccac tatgcctgac  14940
taatttttgt atttttagta gagatgagat ttcaccacgt tggccactct ggtcttgaac  15000
tgctgacctc aggtgatcca cctgcctcag actctgaaag tgctgggatt acaggcgtga  15060
gccatcgcac ccggcttgct gatagttttt aattataaat gtgtattgag ttttgtcaaa  15120
tgcttttcct ctacctgtta aaatgatcat atagtaagag aacaaaagga aaattgaatt  15180
acattaatta atttttgaat gttaaattaa ctttgcattc ctgggataaa accatcatat  15240
ttggaatgta ttgctgaatt tgatttgctg gtattatgct aagaattttc aggtttatat  15300
tcatgaggga tattggtctg taatcggttt tttttctttt cttttcttgc taatcctgtc  15360
aggctttaga attagttatc ctcgtctcat aaagtgagtt acatagtaat cctaccctac  15420
ccagtcctac ccaattttta aaatgtttgc gtaagattgt tgttatttct tcttgaatgt  15480
ttgacagaat tcaccagtgg caccatctgg tcctggaatt ttattttggg gaagcttttg  15540
acaaattcac gttctttaat agttagagcg ttattcagat tttctgttat tattcatgtc  15600
```

-continued

```
aattttggta acttgtattt ttttggagaa gttcattcat ttcatacttc taagttgttg  15660
aagtttttag catgaagtta tccatagcat tctttcatta tcctttaagg tctatgggat  15720
ctctgataat aactccctcc ttttttaaaa aaaatatttt tttaagagca gttttaagtt  15780
catagcaaaa ttgagaagag ggtacagaga ttttccatct atccctttcc cccactcacg  15840
catagcctca tccatatcaa catcccccac cagagtggca tttttgtggc cattgtttaa  15900
cctccactga cacatcataa tcactctcaa gtccagagtt tacattaggg ttcactcttg  15960
gggttataca ttttttggtt cagaaaaatg tataatgaca tgtatttatc actgtagtat  16020
catacagaat attttcactg ccctcaatat catctgtgct ccacctattc ctgtttctct  16080
gccactcaac cccaggtaat cacttactgt ctccatagtt ttgccttttc cagaatgtgc  16140
tatagttgaa atcatacagt atgtggcctt ttcagattgg tttccttcac ttagtaatgt  16200
gcatttaggt tcattctttt tttgtgtatg agacttgata gctcatttct taccactgaa  16260
taatccacca tgtagatgta ccagaatttg tctgttcacc tacaatttgg tgagtttgga  16320
ggacaattgg gttgcttcca agttttggca attatggata aagctgctct aaacatctgt  16380
gtgcaggttt ttgtgtggac atacattttc ttttttagaa attgacaaat gacattgtat  16440
gtttttataa tgtacagcat gatgttttga agtacatata cattggggaa tggttaaatc  16500
tagtggacat gttttcagct cctttgggtt aataccagaa acagtgattg tgggatcacg  16560
tgctaagagt aggtttagtt tttgtaggaa atcaccaaac tgtcttacaa agtggctgtt  16620
tcatttttca tttccaccag caataaatga gagttcctct tgcattaaag cctcgccaac  16680
atttgatgtt gtctatgttc tggattttgg ccattctgat aggtgtgtag tagaatctcg  16740
tttttttttt tcatttctct gatgacatat gatgtagaac atcttttcat aacgcttatt  16800
tgccatctat atatcttgtt cggtgaggtg tctgttaagg tctttgcccc atctttaatt  16860
gagttgtttg ttttcttatt gttagagttt tgagagttct tggtattctg tgagggtgta  16920
actgaggaga tggggaaaaa agttcttggt attttggata acagtccttt atcagatgtg  16980
tcttttgcaa atattttctt tcaatctgtg ccttgtcttc tcgttctctt ggcattgtct  17040
tttgcagagc agaggttttt aattttagta ttcagcttat taattatttc tttaatggat  17100
tgtaccttgg tgttgtagct aaaaagttat ctaggttttc tcctgtgtta ttttctaaga  17160
gttttatagt tttgcatttt acatataaag tccgttttcc attttgagtt aatttttgtg  17220
aagggtgtaa ggtttgtttc tagattcatt tctttgtatg tgatccaaag aaccaacttt  17280
tggctttctt aatttttctct attattgatc tgtttttctat ttcattggct tttccatcat  17340
cattgtaatt tatttctttc tactttcttt aagtttactt tgctgttcta atttcttaag  17400
gtggaatcct aggccattga ttttaaattt ttcttccaat ataagtattt aaagctatga  17460
atttttatct gggctgtgct ttagttacat cccacaaatt ttgactgcta tatatttgtc  17520
atttagttca aattattttc caatttattg tttaaaatta ttacaacttt cagatatggt  17580
gttttcttac atattaatat attattgtta ttactttcta atataaacct tgtatgattt  17640
tgatctttaa catttattga gatttgtttt attgcccagg atatgttctg tcttggtgat  17700
tgtattatac acacttgaga agaatgtgtt cggtcatctt tggacatgaa gttctataaa  17760
tgtcagttaa agttggatga taagtgttgt ttggatgttt atgtttttat atttaaagtt  17820
tctcctctta ggcaactagt atagaacctt gcccttaaaa aaagaaatcc actgtcaatc  17880
tttgcctttc aattggagtg tttagattat taatatttaa tatgattaat tattgacata  17940
tttaccatat caacagtgat aggtctgcca ctttattgtc ttctgtttct cttttttttgt  18000
```

-continued

```
tcctttcttc ctccttttct gcttctttgg gattatattt tgggattatt gggagtattt  18060
cattttagtt gctctattgg tcttttcagc aatatctctt tgtatttact ttttttatgc  18120
cctagggatt acagtatgca tacctaactt tttacaggct acttagggtt attattatac  18180
taattcactt aaaacacaga aaccttgcaa ccctacagat ccttttattc tcccctcccc  18240
cagagacctt tatgttatag ttgtcatgca tactatactt ggcaaacatc accaaacaat  18300
gttatagttt ttgttgtcga cagtcatgtg tactttatag aacttagagg aaaaatctag  18360
tattttgtgt tttcctatat atttattgtt tctattgctc tttcttcatt cctgaagatg  18420
cagcatttcc tttcagccta atgttgacct tagcttttct agcagatcag tctgctgggg  18480
atacattctc tttgttttc tttgagaatg tatttatttt actttcattc ctaaaggata  18540
ttttaggtgg atatataatt ccgagtagat gcttgcttcc ttgagcacct caatgatgcc  18600
atttagctgt cttttcactt ctctgatttc tggtgaaaaa tctttgtaat gtaaacctta  18660
ttcccctctg tgtggtgtgt aattttttc tagctgcttt caaaaatttt ttctttgttt  18720
ttggttttca gcagcttaat ttgatgtgta tctagtcatt ttctttaagt ttatcctctt  18780
tgaagagtac tgagcttctc aaatcggtaa atttttggct ttcactaagt ttagaatgtt  18840
ttctaccatt gtgtctttct tctgacctta caaaattcta gtggcaatta tgataaaact  18900
tttgagattg tttcacaggc ctctaactgt tcagtctcct atcaattttt tttctctgtt  18960
tttcagatga ggttattttt attgatacac gttcaggttc acagactctt ttctcccatc  19020
tccattttct tattgagtcc aaccagtgaa ctttttatgt attgtttatt tcacttttaa  19080
catttacatt tggttcttta aaaaaaaaac aaaaaaaaaa aaacaaaaaa aaacttctct  19140
ttccctgccg agaacctctt tccattccat tcagttgtcc ttgtctttcc tcaatgtagc  19200
atatttatag tggttgcctt ccagtcattg ttggataatt acaacatgtg catcgtctta  19260
gggttggcat cttttgattg tctcttccct tgaagttgtt cacatttttc ttgtgttttg  19320
cattgtgaga atttgggatt gtatcttgga catggttaat gttatgtttt gtaaactcta  19380
gggtttatta taattctctg gaggatgttg tgtttttttgt tgtttagggg atccctttct  19440
gtgtcttact ctttttcagg acttcttacc cattttccat catatcagtt tcttttctca  19500
gttcctctgg ccagaaagag ttttaacttg gaattttaac ttttgggttg tagccctgta  19560
atgcagtgat ctcttcctgg ccttcaggca aagctgttag tgaaaggaga aaaacaacca  19620
aactgggaaa tttactcttc tgtgaatcac ttttccaagt tttgactccc ctccagaatt  19680
tgcttttatt tgtttttcag agtcctgaag tactttttttt gtctttttaa aaattttgcc  19740
caaagtagtt gtaaacagtg gggaaaatag gctgttttgg ggtttatgcc aatgtactgg  19800
aaccagaact ctcttatctg gctttaaaaa aagattttcc cttttattga tttttagcag  19860
cttgactgta ttgtacctaa atatggtgtg tgtgtgtgtg tgcatgcgca cgcacacacg  19920
tctgtgtctc tgtgtgtgtg tatcctgctt ggtatccttt cagtttgtta gatctgtgtg  19980
atgtcaattt ttatttaact tgcaaatttt ggcctttatt tcctcaaata ttatttcaga  20040
ctcaatttct tatttccttc tgggaatcca attatatata tatgatactg tttgatatca  20100
tatgtgtcta taatcatata tatgacatat ttatatgacc agatagtaaa taacttagac  20160
tttatgggcc atagagtctc tgttgcaacc atgcagctct gttctttagt ttgaaagcaa  20220
ccacagacaa tatatataaa tggataagca tggctgtgtt ccaatataac tttatttaca  20280
aagatagaca ggaagctgtt tttggcatgt agactatagt ttgctgaccc ctgagtaggt  20340
```

-continued

```
ggtaatcgtt gctggagcta cattgtgaat tcagggaatc aaagaagtgc aaaacagaaa  20400
tgttggaaat aactacaatg taggtagcgg ggtgcataaa aatgaggagg taggagatat  20460
ggctagaaag atatgttagg actaggttat tatgttccct gtattgcttt atttgaaaat  20520
agtatggaac aatcataggg tattttttgt ttgttttctt ttttttgtct gtttttctga  20580
gacggagtct cactccgttg ccaggctgga gtgcagtggg gcgatcttgg cttactgcaa  20640
cctccgcctc ctgagttcaa gagattcttc tgcctcagcc ttctacatag cagggactac  20700
aggcacccac caccacgccc agctaatttt tgtattttta gtagagatgg gatttcacca  20760
tcttggccag gatggtcttc atctcttgac ctcgtgattt gcccgcctcg acctcccaaa  20820
gtactgagat tacaggcgtg agccactgcg cccagccaat cataggtttt taagcaatgt  20880
aatggtagag ttaaactttc aatttataaa gataatctct agtagtgtta tagaggatga  20940
atgaaaagga gcagatctgc aaagcagggc tacctttaaa gagacagttg cagtaactct  21000
gacaagtgaa aatactgaga aaagataatg ggaatagatg gaataaagtg gatttaatga  21060
tatatttagc aggtgactag atctcaagtg caaatataat aatgattttc atctagatag  21120
aaagggagga agagctagtt tctcaagagt ccattcttgg gattcttctc tctgaatttt  21180
cttctttggt tgtctcaggc ttatgatttc agatatgcat ttgacttcct ggtctgtggt  21240
ttttaggtaa aacctctttt cttaagttct agcctgtatt ttgaaaagtc tactgctagg  21300
attctctcag tcctgttcag atacattatg ttcagtatat tcaaagtctc ctcgtgaaca  21360
tactgtcact cacaaactgc ctcttttccc ttaggccagt gaaaccgaag tctgagatag  21420
gttcttgagg ttggcaataa gaaattataa tgagccaaca cccactcact tcacctcctt  21480
ttttcaggag gcagggaaaa gtgggaaagt gaggctggac atgggagtat ttagaaatag  21540
tgtttaataa tgtttaaagg gcaagaagga aggcagtagc ttaaggaagg agacaaataa  21600
ttaatctttt ggattagata acctgtagga gatgttctta gtgtcctagc catatccctt  21660
tggcatccat ttgcatactg tcttctgcaa acatctatga ctatctgcct gaaaagaaac  21720
acacttggcc tgtgtgcagg gcaactcaca tgcgccagag agttaatgcc ttcagaaaaa  21780
ctttccacca gtgatggatg gggagttggt agataaatac ctttgtctca cctgcattta  21840
ggataactga gccatgtttt ctgctgtcta ccagagttct ccactggttc aggccctagt  21900
tccccatcag ggtaactggc ttcataatat gtcctttctt gacttccttc ttttccctgt  21960
tttacttttg ttttccctac tggtgttttt cctgggatca cctctcaaaa taactactgc  22020
acttgaattc ttgaattgac gtctgcttct ggggaaaccc aaaccaaggt agacatttga  22080
atttggcatg ggaataataa taaaaatgtg tttagcactt actaaatacc aggcataatt  22140
ctaagtgtga catcatccag tgggagaggt actgttttca ccctattgta tggatgagag  22200
aactgaggca cagagagatt aaagtaatac caagatcaca gtgctggtaa atgacagagc  22260
ttgtatttga acccaagtca tttgtttcta aattctgtac tcttaaccta tcttgacata  22320
gcaggctgaa ggaaaagggc aaggatagta aaaaagagag agagaatggg aataattaat  22380
agagtaaggc cctgggttag agatcatttc aaggtgggtg gaagaaaagc aaagggagta  22440
catttgtaat ggtgtctcta ttttattggt taaatagatg gttagattct ctgctctgag  22500
ttgatgggta ggggagggat tttgaagtag ctggaaaggt tctagatttt tatggtagat  22560
gtaccttgat agagaactta actggctcta gaccagcagt ctaatgatgt tcagtaactc  22620
caatagctat tattgtttag ggttgttata gcttattgaa caaggtttgt aactaaccag  22680
tatagaagtg aatatagaac atgagcagat agctcacatt agaagtgata tatgtagtaa  22740
```

agacttaagg gacaggaaga ggaagaaaaa ggagccagta aagaagactg agaaggaacc 22800
accatcagag gtagaaggaa cactaaagta gaggttctag aagctggcgg gacagggggc 22860
agggatgtaa agaagtaggc actgtttggt agttatcgta tgtaggagaa tgtgaaggat 22920
aaagactgaa gatgggcagt tgaattggct actagaaagt ttgtggtatt gagaagtctc 22980
atagacttgc atgagtttga tagtaaggtg ttaaaaaact tcaatacaat gaagtttttt 23040
tttttttttt tttttttttt tttgagacag ggtctcactt tgtcatccag gctggggtgc 23100
agtggcatga ccatagctca gtgcagcctc taactcctgg accaaagcga tcttcccacc 23160
tcagccatct gagtagctgg gactacaggc acatgccacc gtgcctggct aatttttttt 23220
tttttaatag agacggggtc ttgctatgtt gcccaggcca ggaccatttt tttcttcaag 23280
aaatttagtg atgaagaggg atagaggatt acttaaactt ttttcccctt ttgaattgga 23340
gaatgacagt aggcctctaa ggttagaaac cacagaaaaa aagcataaag ggtaaacaaa 23400
gagagggatg tatggttgag caaaatctca aggatggtga atgaaatggg atctggtgta 23460
tgagaggaag tgcatacttg gatagagtaa gagctgtctc ttttgggatg ggggaaggag 23520
gaagtttcag atttgaaaag gtctcaggga catattttta gccttttttat gtttctgtga 23580
agaattccag attcttttc tgatctgttt tctagatctt aaattttcta ttcagctgtg 23640
tcctgtacac ttaaatccac ctatggagtc tgtagtgtca gttatttttc atgtctagtt 23700
tgattttttt tcaaatgtgc ttggttgttc cccattccct gcagatattt taatgatagt 23760
cttttatttc tttaaatttg atacacatgt tcttgttgca atctttccga aaatcccacc 23820
atctgaagtc tatataggtg tctttctgtt gcctagttct gctgttctca ctcagagtgc 23880
cttgtatctc tgtgttctta gttatttgct tgctctcatt cctcttgttg ttctctgagg 23940
cctgggatga atagattgta ttcatgatat cattagaaag tgttacagtt ttacaattgc 24000
ttcaaggctt gagtttccct ggcctaccta gcctatgttt acttaagagt acaaatatgc 24060
atgaggcagg gtctatagcc aaagcttttc agagagttct cttcccctca cttatgctcc 24120
cttccatatt cccctaccct cttttctttt tccttctgct gctctgccca ttgccaaggt 24180
agctttattt atagtcctcc ccccatgtga agacttccaa ataagatcaa gagactgaag 24240
ctatatataa gaaatctgtt ttcatctctc ccctaaatca agttgaactg ttaaaatctc 24300
tttcttatta ctaattagcc ggctaggtta agtaaataaa agttttctac ttagtaatga 24360
gataactatt cctccctaat ttattcattg atgcttgaac atgataggag tatcattaca 24420
ttaattacac agaatgaatc tggcttctat ggaaaagctt cagtttacat aaggtgcttc 24480
atagattgat ttttaaaagt tggtcttgta tccagtgacc ttgataattc ccttgttaat 24540
tctttatttg tggattattt tgtattttct ataaatataa ttatctacaa ataaaaaatg 24600
ctttactttt aatttttaac cattatgact tttatttcat ttgcatcact tactgacctt 24660
caatattgtg ttaacagaag tggtgatagt acaaatcctt gcattttcct cctatgccta 24720
agtggaaata cttaattttt caacattcag tatagttgaa tacactgtta aaagtaggtt 24780
ttttatagat aatctgtatt agattaagta aaatctgttc ctggttcacc aaggagtttc 24840
atcactagtg gttgttgagt tttaaaaata ctttttctgt ttctattgaa gtgatcatat 24900
gttttgtttc ttttgttctg ttattatatt gaattatgtt gattatgtat ttattctttc 24960
cacatgttgt tagacaaaat tatttgtagg taaatggctc tctctttttt taaaaataaa 25020
aggggtaata cacataccat aaattcaccc ttttatacaa cttattggtt tccagtatat 25080

-continued

```
tcacaaagtc atacaactaa acatttttgt ctctccataa atcccaaagc tattagcagt  25140
cagtttctat tctcctttct atcagttttt ggcaactact acttcctgtt tttatgaatt  25200
tgcctaccta gacattacat ataaatggaa ttatacaatt tatgaccttt tgttgccatt  25260
gtttctttca cttagcataa tgttttcaag gttcatccat gttgtagcat gagtcagtac  25320
ttcattcttt ttttatgggt aaacaacatt ctcttatatg gaagtgctac actttataca  25380
ttcattagtt ggtgagcatt tgggttgttg ctatttttg gctgtgcagt atttttgctt  25440
ctatgttcat aggagatatt ggtctgaaat ttttgtattt tgaaatgttc tcttcaaatt  25500
ttgatatcag agttatgctt gtcttatgag ttgggaaatg tttcttcttt ttatattgtc  25560
taaaagagtc taacattgat aatgtttgaa agaactacca gtgaattttt aaagtatttg  25620
gaagaattca ccaacaaagc catccgagtc tagagttttc tttgtggata gattttgatt  25680
agggatccag tttttttca atatatagaa gactattcag atattacatt ttttttccct  25740
tgtttaatgt tgagaagtta catttttca aggaatttat ccattttatt tgtcaaattt  25800
atgggcagca tctgtagtga tgtctccttt cttatttctc atattggtaa tttgtgcttt  25860
tactttttc ctgaccattt ttgctctagg tttattatat ttatttcatt ttattttaaa  25920
atatttgcta tatatttaat tcacaaataa ttgtacttat acatggggta taatatgata  25980
ttttgataca tgtttacaat gtgtaatgat caaatcagga taattagcat atttatcacc  26040
tccgacattt atcattttat catttctttg tcatgagacc attcaaaatc ctctcttcta  26100
gctgtttgaa gttgtataat acattgttgt ttatgatagt caccctgtgg tgctatataa  26160
cactcaaact tactcctact ttctagctct gattttgcat ccattagcca acccctggct  26220
actcttcaac aactcttcta ctttctactt ttatgagatc aacttttta gcttccacat  26280
atgagtaaaa acatgccata ttcatctttc tttgcctggc ttctttaact taagataatg  26340
tcctccaggc tcatccacgg tgctgcaaat gacagaattt tactcttttt taatcactaa  26400
atggtatttc attgtgtata tatatcacat tttctttatc cattcatctg ctcatggaaa  26460
cgtaggttga ttccacatct tggctattgt gaatagtgta gcagtgaaca tgggagttct  26520
gaatcttttc aacatacgga ttttttcct ttggatatac acccagtagt ggaattgctg  26580
gatcatatgg tagttctgtt tttagttttt tcaggagcct ccattctatt ttccacaatg  26640
gttgtactaa ttcacattcc catcaacagt gtagttctac tttctccaca tcttcaatag  26700
catttatttt ttgtcttttt gttatgtata ctaatctttt cagagaacca atttttggct  26760
ccctgataac ctctattgaa tgtctgcttt ccatttcatt ggtatctact cttattttta  26820
tttcctttct actacatatt ttgcatttaa tttgtggttt tctttctagc ttcttgagtt  26880
gtaagtctag ataatttact ttcagtgttt tttttttcag tatatgcatt tatgtgtatg  26940
caaaaggaga tgcattttgt ggaagtactg cgttagcagc attctaccga ttttgttatg  27000
tcaaatttca ttttcatttt atggaaaata ttttctgatt tccattgtga ctagttcttt  27060
gacccatagt ttatttagaa gtcttgtttt tttgattgcc aaacatttgg gaatttctta  27120
gttgtttgtt ttttttaat ttctcgttta atttttccat gaccagagaa ttaccttatc  27180
attcagtcct tggaaatttg tttagacttg gtctgtggtc cagcatatta tctattttgg  27240
taaatgttct atatgcactt gaaaagaata tgtattctat tgttgttgga tatgtttctg  27300
tatgtatgcc aattaggtca ggttgattaa tcatggtttg tttgtttgtt tgttttgaga  27360
cggagtctcg ctctgtcgcc caggctggag gacagtggtg tgatctacgc acactgcaac  27420
cgccacctct cgggttcaag cgattctcct gcctcagcct cctgagtagc tgggattaca  27480
```

ggtgcgtgcc accacgcccg gctaattttt gtatttttag tagagacggt atttcaccat 27540
gttggtgagg ctggtctcga acacctgacc tcatgatcca cctgccttgg cctcccaaag 27600
tgctgggatt acaggcatga gccaccgcgc ctggccgatt aatcatgttt tcaagttttt 27660
ctatgtcagt gctgttttgg tctctacttg ttctatcagt tacagagagg tatgttagaa 27720
cttactcttt caattgtgga tttgtatttt cccatttaac ttctgtcaat tttactttat 27780
atattttgaa gctgtgttac tggatgcatt caaatttagg agtgttatga tttcctaatg 27840
atttgaccct tttgccattt agaaatgctc ttttcatttc ttttaatact gttgccttaa 27900
aaattacttt gtcaaatatt aaaatagcca ctccaacttt ttttgggaca ctggagagtg 27960
tgcttgagat acatcttttt ctgtcctttt agcatgtatc ctttcattta aaattatgat 28020
attacagtta ttaaaggaag actttccttc agtatttctt gtaatattgg tctcttgaca 28080
gtgaattatg tcagctttca tggatctaaa aacatcttta tttttgtctt cattcttaca 28140
ggatactttt agaatccttt atgtgaatta tatcagcttt catggatcta aaaacatctt 28200
tatttttgtc ttcattctta aaagatacat tcttaaaggt tacatgattc caggttactt 28260
tcccccacct ctaacccca tccctccact ctaccacctc cccctcccca ccccccagcc 28320
cttttcaaca caaagaatgg aaactatcaa ttttattgtt cctttaagca tatctcttct 28380
ctggctgctt taaagatttt ctctttatgc tttgctttta gcaatatgac catgctgtgc 28440
ctaggtatgc ttttctttgg attttcctgc ttaaagttcc ctgagtttct tgaatctctc 28500
agttgatttc tttcttcact tttgggaaat tgtcagtaat tatcttgtca tatattgctt 28560
ttgttccatt ctttttctc tctttctggg attccaatta tatgaatatg agaccatctg 28620
actttgtccc acatgtctcg ttctctgttt ggttcatccc atttttgttt ccgtgattga 28680
attctgttat ttatttattt atttattttt ggcctgtttg caagtctgtg aaacctgttt 28740
ttctgtaact tactctgctt ttaaaatcat atgagaagtt cttaatttca gatgtttatt 28800
tttcagtttc agaatgtcca cttggttctt tttttataaa ttatgttgaa aattgccaat 28860
tgcattattt tacacatatt gttaatctct gcatctcagg tacttgcctc ctaacgttaa 28920
tatctgggtt ttctgtgagt ctgactaatt ttctggtttt ctcttgatta tgtgtctgcc 28980
acatattttg cttcttttga tgtcccttaa tgtgtttact tagtgtcccc gaactagact 29040
aacactgtgt atgaatgaac atgattttct ttcagatcat gtgttttctc ctagagaggt 29100
gtgctctttg ctgtgtcaga cagatagaat gaggagtttg attatctcaa tccagtgagg 29160
gattacatag accgctccct ccctctacta ggattctgtc ttcttacgga agttttctct 29220
tccctttga cccagcctct ttttttttt tttttttttt ttttttgaga tggagtcttg 29280
ctctgtagcc caggctggag tgcagtggcg cgatcttggc tcttggctcg tcacaacctc 29340
tgccttccag gttcaagcga ttctcctgcc tccgcctccc tagttgctgg gattgcaggc 29400
gtgcaccacc atacccagct aatttttttgc atttttagta gagacggggt ttcaccatgt 29460
tggccaagct ggtctcgaac tcctgacctc aagtaatctg cccgcctcag cttcccaaag 29520
tgctggtatt acaggtgtga gccaccgcgc ccagccttga cccagcctct ctatcatcct 29580
tcagtgttcc agttacattt ctgaggagat ataccactgg gaaagctgtc tatgtatcta 29640
gagcttttct agattccagt ctgtcatttc agcccacatg ggcatctaaa gcactactag 29700
tctcttgttt cctttattag agttcctctg cttaagccaa gctcagtcct tactcatgcc 29760
caagctctgc agttaccccc atggaagaac aagccagtgg tctcagctgc cttggaagtg 29820

-continued

```
ctcttccacc tctggatttt ttgttctttt agtcctcatt gcttccacag ctttcttacg  29880
ttggttagtc tggtctttga agcaggcgca ttggcctgcc tcctatctaa tcacttactt  29940
tagggaagtg gaagtcagaa gtttatcttt ataaaaagaa aaggcagata attttaggag  30000
tgcttatttt tataagcata gtgatgtttt gaatagtttt atctgtgttg catactcata  30060
gctataaagc attttttcc tttctgatat gggcctgttt atcaaaatat gccccagatc  30120
tggggcgagc aaacaaagac ccacagacca atgaggccca attcttgttt ttatgtagcc  30180
tgtgaactaa aagtggtttt tacattttta aaaggttgaa aagaaaataa aaaaggaaga  30240
gaatgttttg tgagcattat gtgaaatttg gaagttttat tgtaatatat gcacactcct  30300
ctctttatgt gctgccgatg gctgctttcg tgctgtaacc attgagtagt tgcaacagag  30360
atcttgtgac tcacaaagtg taaaatattt gctgtgtggc cctttgcaga aaaaatttcc  30420
ctattcctgc tttacatcac aggctcagga attttttatt tcttattact aagagaaatt  30480
aagcaaaaga ttgaaaccat tttattccag aagttctgta aatttggatt tattaaaatc  30540
ttagcatttt agaggattta caaggaacct cagtctcctt catctcttta ttttgcaaat  30600
gaagcagatt tgagtgaaag aggttttaaa attatgacta catttttggt ataaagtata  30660
ctcagtaata agctgataga gaaactattg atctatatca ctgaataatt tgcaaaattg  30720
atttgttctt atattgcaga agtatttgat ttttcttaag cagtgtagct cttaagaaaa  30780
tatttttgga atttttaaag taaatatttt aagataaata tttaaggcat gttaatagcc  30840
ttttcctttt attgtcaacc acaattcttt caaatctgat ggatatgaag ttatttttgt  30900
gagaagactg aaagtcttac aggaccaatt ccagacattc ttcattaagc ttcgattgat  30960
ttagaatata aagccctaaa tcatcagaaa ttccaagtta aattgttaat gtgtaagact  31020
ggtttttaga gtttctcttt tatattccca tcctcagata ttgtgaaagg tttaagctta  31080
gttctcaaat atagagatat aatggtgtgt tatattacta gcaaatggca tttttaaatt  31140
ttccaatgtt gaatacaaat tttgtttata taattttcaa cttattactg gctcttttag  31200
aaaacttcta cctcttcctc tgcaaaccaa atcaacaaca acaacaaaaa acacagtaaa  31260
agtaatttat aattaatttg ggaatagcta gttcttggat ggcctgtact taagaattga  31320
tgggttcaga ttcataagaa ttgttacaac caattaaatg ccatcatgca tagaaagaag  31380
tattttagaa atgtacgtaa agtcatttga actttaaaga agttccatta gataaaacag  31440
acacaaacat tggtctctaa ttgggaaaat ttgagtcagt tataacttgt ctttaggaaa  31500
tctatctgaa tttggattta tatattctac ttctctgaaa attggtttgg aataaatttt  31560
gatgctttta taagttatat agaaggggct aacctcttag tagttatgta ttcctgttgc  31620
tcaaatacct gatttcactc aggtaatctt taatataaag gaaagttggt ttcctaaata  31680
gtatgaagaa tacgtattgt gttttattta tttatttgtt catctgatat ttattgacca  31740
tccctgatgc ttcacattga tgcaggtgct gaaagtacac agttgaaata gacattcatc  31800
atgccctcac aatgctagta gttgagtaga ttctataagc aggtatatgt atttatgttt  31860
agcatttggc actgttaatc tttctctttc tctttacttt tatggcatac tatcttgtgg  31920
aaatctcatc cacatacata gtttccatga cctcctttgt actaaagtct gtgcaaaata  31980
atcccaagga taactcctta gtgggccttt ctggctagag atgctttaaa tgcactcatg  32040
tcgataccat agatgtagat accttatttt aatctctgag taaggcatgt agctgtagct  32100
ctcaacttcc tcatttctcc ccttcctcac tctttctctt atactttctc tttctcttaa  32160
aatactcgtt gagtactata tcccaggaac ttttctggac agaggctaga gtagtgaaca  32220
```

agaaagacag ggcccctgca ctattggagc ttttagcttg gcgaggaagc aatacattaa 32280
acagttccat acataattac agttattggc tgtacaatga aacataaata tacgatgaat 32340
gagagtgtat attagggaaa ctcatccagt gtggggagtt agacttaagt gacacttatg 32400
ctgagacctc gaagataagt agtggttagc aggagaagac gtggtagaga atttcaggaa 32460
gagggaaaac ctttgtgaaa gttgtgatga agcttaacag gttcagacaa ctgaaagaat 32520
atccttcttg ctggagtatg atgaatcagg tggaaaagaa tgcaaaatga ggcaggagag 32580
attgatggag gtcagttatt ggaagaggat cttttaaacg atgtcggtgc ttttggactt 32640
tatcttaaga gaattgagaa gatactgatt tttaagctgg ggaattatcc actcaggttt 32700
gtgtctttaa aagttgagtt aggttcctat gtgaagaatg gattgaaggg tatggatgtg 32760
cagaaatgag ttaagctttt gcagtggtcc aggtaagagg tggtggtaac ctagcttatt 32820
agcattgcag cagtaaagat ggtgtggaca gattcaataa ctgtttatga gatataattg 32880
accagatttt gtgattattt tgatttcaag agtgaaactg aaggcaatgt caaggataac 32940
attttcatct gcttgttact cttgtctatt tgttgacatt ttggtatttt gaagttacac 33000
atcttcaaaa tcaaacccat tacttttttt ccagcaggct aactcttcct tctaacttct 33060
ctatttttaa gagtgacatt gtctacctcc aagtgaccta ggcttaaaat ttttctcttt 33120
tgtcactgct gttactaaat tagttaccaa atcttaagga cttgacccct tcagcatctg 33180
gaacaacctc ctccccttcg ttctccctgc attccctctt ccccccgact tcatcctttt 33240
ttctttatta cagcagtagt atcctcttgt tagatcacta aactgtgctt tccattcaag 33300
tctctgagct ccttggggac aagaactgtc tttttcattt tgtgtcttta ctactttgca 33360
tctcagcatg gtgaacataa aacatattaa gtgaaatgaa aataaaatgt tttccttgct 33420
tcttgtttct tgcaccataa ttcttattct ttatcacata ttttttttctg tttctcaaaa 33480
gttattcagg ggcttccttt tgcttaaaga ataatttggt cttaggacta tgtgataatg 33540
aagtatccag actggctgct ggagacataa agtatatgag ctggggattt tcctatagta 33600
gtttagtaaa aagtggctct taagtccctt tgcaccgtag ccctcactac caaaaagagc 33660
agattttttt tcttggaaac atcactgaca tttgtaaaca tcccactatg gataaagtat 33720
aaaacacttc atttgatgcc tttttaatgt tttaagttta tgtttttgca gaattcaaat 33780
ttgtattatc atttaatata tattgtatat tgcttagctg ccccatgtta tcttctcaat 33840
agctacttta tatgttagta tcttatatgt gtatgtaaag tatattgttt cacataaaga 33900
aattttgcaa gaaaaagatc caaatgtcta ctttggaaat acccattttt gatagctttg 33960
tatgtcctaa tatgaacatt catatttttt tcccattttt cttttaatat ttaggaataa 34020
gaaaatttta aataagaaga aattgaaaag aaaacagaag agcaaatcaa aagtgaagac 34080
aagaagcaag gtaaagctgc tggtaattga taaggaatag gactttttca tatggtgatt 34140
tgaataaaaa tgccaagatt aaaaaatata attaaaccat tttattagta tgtgctgaag 34200
taattttgta aaagcccttt atgatttggt tcctctttta gtttcatctt tcttttgggt 34260
gtttcttttc tttcttgcct ttttttttc tttttgaaa cagggtcttg ttttgtcacc 34320
caggctggag tccagtagtt tcctgggctc aagtgatcct tccacctcag cctcctgagt 34380
agctgggact acaagtaaat gccaccacaa ccagctaatt gttaaatttt ttgtagagac 34440
agggtctcac ggtattggcc aggcttgtct cgaactcgtg ggctcaagca atcctctcac 34500
ctcggcctcc caaagtactg acattgcaga catgagccac tgtgcccagc ctatttctgg 34560

```
gattttcttg accagtagcc tggaagttaa tatctggatg ttgaaaatta tttgctattt  34620
attcttatta tctttgatca gtcctttggg gaacatatcc atttctgttc tctttttca  34680
atctgactac aggtactaga aacttgagta aaattagctt gtaaactggg acttggattt  34740
gggttcatca tatgcctttc ttgacaggaa ttagggaaac ttggtgtgtc catattgttc  34800
tgagcctctt ttgactgttg gtagctctgc aaaagaaaag gcaatatgga atatttgaat  34860
taggtgagac cttagaaacc aagaatctat tttcacctaa tgcagagatc tctataaaat  34920
ccatcttttt tatactgaac attttcagtg accagagcac ttgatataac agtctctttt  34980
ctattgaaca tctagacaga aggaagagag gagtcgtaac tatgattcct gaatagcttc  35040
actttgagtt aaagaaacaa tagatttgct gggcctgtat agcaactata gaggcaattg  35100
tttcctacac ttttaagtta gtgtttttac tattgtaact gagagaaatc tacttcaaag  35160
tagcaaacct aaaataaaat gaaaggttgg gggatggcat ttatttggtg gctctatctt  35220
gagacacaga tggatccggg gatgaaatga tatcattggc tgggtgcagt ggctcacgcc  35280
tgtaatcccc gcactttggg aggccgaggc tggcagatca cgaggtcaag aggtcgagac  35340
catcctggcc aacatggtga aaccctgtct ctacgaaaaa tacaaaaatt agctgggcgt  35400
ggtggtgggt gcctgtagtc ccagctactc aggaggctga ggcaggagat tgcttgaacc  35460
cgggaggagc aggttgcagt gagctgagat cgcaccactg cactccagcc tggcgacaga  35520
gtaagactcc gtctcaaaaa taaataaata aataaaaata atcaaaccca tattttcagc  35580
tcttgcttct gccttcctct gtgtgtggac ttattacctg tgactgaggc tgaggctgcc  35640
agtagctcca actccatttg ctctgagcaa gaggcaatct cttatactag tcatagcaga  35700
aagtcttggg taggattttc ggtttacctg catcatttgc tttgaccacg gagatacggg  35760
atactttggt tagactgagt tatattttta accctgagat gggcagtggg tgagcaccct  35820
ggtgaatagg ccacatgaaa tgagggagga atagttaccc taaggaaagt gttgccgggt  35880
aggcagaaaa ataatctgtt cactgtatcc cttctcatta cttctgcttc tgggatagag  35940
gagggaagtg gagcgcattg tcaatataca gaaaacctct aacaaataca gtcattccaa  36000
cctctatccc ttttcaactt tttggtgcta tgtgcaaatc ggagtatggg aatcttgaat  36060
atcttttaag ttttttaag gtttcatttg gtgattttcc tgaagtggtg gcatatgata  36120
tccaggaaga ggtgaggaga agtcaaggtc ttttgtcccc ttcaattcgg cctccaacta  36180
gctttgtgcc cttagtaatt cagtttttt cctcttgctc tcagtatttc tatatcttct  36240
ttttaagagt agtttgagat aacagtgatg taagtaagtt cattcattta ttcctcaaac  36300
attaattgca tgctgagtat gtgcaggcat tatgctggat gtttgggata caaagatgag  36360
taagaggcat tttttgctca tggaaagcat ataaagtagt aaaatggtgt tgttagtctc  36420
cttgacctgt attacttttt ccagattatt tttcatctac cctctttctg aaagttattt  36480
ttaaaatgcc atttagctgg cattttatct actttatatc tactttatat atattttata  36540
tatatgtata tatatatgta tatatatata tatatatata tatagccatt atatctactt  36600
tatggctatc atcaacccct ctatttctcc tcatccatca gtcatctcct ttatttaatt  36660
tccatcttac ccaggttaga taccagtctt tctttttaga aaaactctta tttaatctgt  36720
aacaaattac aaaaacttga tggtttaaat taacactcgt tatcttacag ttctggaaat  36780
ctgaagtcca aaatggatct cactgagcta aaatcaaggt gtcagcaagg ctttattcct  36840
tctggaggct ctaggaggga atctgttttt ttgcctttcc agtttctata gtagaggctg  36900
ctcagatgtc ttgggttgtg gccccccttcc atcttcaaag ccagtggcgg ttggttgagt  36960
```

-continued

```
tttctcatgc ggcatcactg atagttttct gttgttttat ctcctcctct tactgtccag  37020
cctccctctt tcacttgtaa ggacccttgt gattacattg gcccatccag ataatctgtg  37080
catttcaaaa tccttagttt aatcacatat acagagtccc ttttgccatg taaggtaata  37140
ttcacctggg ttctggggaa ttagggtata gaagtttttg gaggctatta tttacctacc  37200
atatctccct tgtatatttg ttgcattaat ctgacaaaac tcaatcttgt gtgaatccag  37260
ttattttgtc cctcccttaa ggtgagttcc atgtgctgcc aaagagagtt acacaagagt  37320
taactgataa tgatacacat tcatgatcat caatctcaag tataccatag ccagactatc  37380
ttattatttt ttctggtcaa atagttctct tttcttctgt gattatttca gacctttgcc  37440
atgctcctca aacctctgat aaattctacc ttccagcaca tgacttcact ttcttacagg  37500
agaaatcaaa ttcattactc agaaaagttc ctcaacttcc taatcccaaa tgcgtctgtc  37560
ttcaggcttc tcagtagctg agcctgacat agagatttga agtttgcagt tcagtaagtt  37620
ttgaaagtta acattcatgc atagaagcac tactgcagtc aaagttcaga acatttctat  37680
catctccagg ggttttcttt tttttttcttt cttttttttt ttttttttt gagacggagt  37740
cttgctctgt ctcccaggct ggagtgcagt ggtgtgcgat ctcagctcac tgcagcttct  37800
acctcctggg ttcaagcaat tccctgcctc agcctcctga gtagctggga ttacaggcac  37860
cagccaccac gtccagctaa tttttgtatt tttagtagag acaagatttc accatgttgg  37920
ccaggctgtc tcaaactcct gacctcaggt gaaccacccg ccttggcctc ccaaagtgct  37980
gggattacag gcacaagcca ccgtgcctgg ccggttttct taccctctgc tgattccatc  38040
cctccctata accctggctg tagacaacca cagatatatt ttctgtcact gtagattagt  38100
tttcattttc tagaacttca tataaatgtg atcatattgt gagtgctctt ttttttttaa  38160
atctggtgtc tttccctcag cataatgatt tgtgttaatg ttgttgtata tcaatagttc  38220
attccatttt tttgctgatt ttatatacat atatatgcac ttgtgtgtgt atgtgtgtgt  38280
gttcagtttt cttgggtgca tactgaggag tggaatgttt aggtggtttt tcctttgatt  38340
tgccagaagg actcataaat ctcacaagca atttatactc atggctaaga tttattacaa  38400
caaaggatac agagcaagca gcaggaaaaa ggtatgtgtt tgtgatgtat aggaagttat  38460
ggcataggct tcctagttct tcattgactg agctttcatg tcagaaagaa agacatgctt  38520
tctctctggc agtgaactac agagaaatgt gtatattgtt tttgctcagg tgagttttag  38580
aattcaagac tttgtgggtt tggtcacaca gacatatctt gttagtcaat cagacatggt  38640
aagtgaaact caggtacaca ttgtaaagct tgatgttcgt acatgcagag cagtctgaca  38700
ggccaggagg catggtccat tgctctgtgt gttcataaca caatcatcaa tcactaccac  38760
aaagaaaact ctaaacatcc acattcccaa aggttagcca agggtcaatc atggtttcct  38820
tggggaaata caaggagtaa gcaatcatgc ctgcagcgtt aactttttcc tcagagtggg  38880
cacggtaaat gtacgtttag tttagctttt tttttttttt tgagacagag tttcgctctt  38940
gttccgcagg ttagagtgca atggcacgat ctcggctcat tgcaacctcc gcctcccagg  39000
ttcaagcaat tctcctgcct caggctcccg aggagctggg attacaggca tgcaccgcca  39060
cgcccggcta attttgtatt tttagtagag acggggtttc tccatgtgga ggctggtctc  39120
gaactcctga cctcaggtga tctgcccgcc ttggcctccc aaagtgctgg gattacaggc  39180
gtgagtcact gcacccggcc tgtacattta gctttttaag aaactagaaa actcttttcc  39240
aaagtggttg ttccaatctg tagtcccacc agtggtatat gaccaatcta gttgcttcat  39300
```

-continued

```
atctttgcaa acatatggta ttcgcttttt aaattttagt cagcctacta agtaggggtt  39360
tcccattgtg gttttagctt gcttttctct aatgactaat gatgtgaaat cttttcatgt  39420
acctttttgcc attcttattt ttttgatgtg aaatgtctgt tcagatcttg cctcttattt  39480
ttgtaattgt cttcttctta ttgaattgcc agagtttctc atatattcta aatacaagtc  39540
ttttgtcaga tatctgcatt ccaaatacat ttctcctgtt ctgtggcttg cttttggggg  39600
aagaattgcc attttaatga tattgaattt tccaatccat gaacatggta tatgtctcca  39660
tttatttaag tctttaaatt tcactcagca acactttttt gttttcagtg tgtagggctt  39720
acacatattt tattactttt atttacaatt attatatatt tttgatgtta ctgtaaatgc  39780
agttattttt gaaaatttat tttgctttga gatgatttca gtatgaatgc agtgtgtatg  39840
tgtttgtgtg cacctaagtc tgtgtaattt tatcacatgt gtaggtccat gtgactctta  39900
ccacagtctg gatatacagc agttccatca caaggattct ctgtgatatc ctttatagcc  39960
acaggtatct tccttcctca ccctctcctt agcttctggc aaccactgat ctgttcagca  40020
tttataattt tgccatttta agaatgttgt ccagtgaaat tgtacagtat gtaatcattt  40080
aagattggtg ctttttttcc ccacttggca aaatgtcttt gagattcaca cacattgttg  40140
catattgttt gttccttgat gagtaagcat ttcatggtat ggatgtacta tagtttgttt  40200
aaccatttac ccattaaaag atatctgagt tgtttctagc ttttgactat tttaaaagaa  40260
tgctattacg aacattcgtg tactggtttt tgtgtgaaca taagttttta tttctctggt  40320
gtaaatgtcc aagaacataa ttgctggatt atatggtaag cacatattta gttttgtagg  40380
aaattgctgt actttcttcc agagtggctg taccatttta catgaccatc agcaatgtat  40440
aagtttctcc tcatccccac cagcatttgg tgttgtcact atttatttta gccattctga  40500
taggtgtgta ctatatctca ttttaatttg cattttccta gtagctaatg atgttgaaat  40560
tcttttcatg tgcttattca ccctttgtgt aaatatcttc tatattgatg tgtttattcc  40620
tatcttttgc ccatttgtta attggattcc ttgtttgttt ttactgttga cttttgagaa  40680
ttctttatat attctgaata ctcatccttt gttggatatg tggtttgcaa atattttctc  40740
ccagtctgtg acttcaatgc tattattttt gaaattacat tttttcagtt gttcattcct  40800
agtatgtgga tatactactc atttttatat agtaatttta tatcctgtga ttttgttaaa  40860
tctgcatact atttctggta acttttttgc agattcctta agattctcta catgtttttt  40920
tacaagtaaa aacatttctt ttttagaaaa tacttcttgc ctttttccct tggctggata  40980
ggatattttc cttgcactag ataggatatc cagtacaatg ttgatgagtt gctgagagta  41040
gaccaatttg cctggatcac aatcttagag ggaaagcatt cagtctatta ccatgttagc  41100
tgtggttatt ttgtagatac cctttatcaa gttgagaaaa ttcccttcta ttcctaactt  41160
agactttttt tttttctatc atgaatcgat actggatttt tgtcaagtga tctttctgtg  41220
tttatttgaa gtataatata ttttttctct gttacaacag tggttgcttt tccagtgttg  41280
tgccagcatt gtccctgggt taaacctcag ttggtcataa tgtattactt ttttatatat  41340
tgttggattt gaatagctaa tacttgtaat atctctggat atttggatga gatatttgta  41400
atatctctta tacatatatt cataagttat atgccatgcc aatttaactt tttgatgtat  41460
ttcttattta acaagtgtat ttttttttttc caattcttta tggaagaaga gtcgaatatt  41520
tgggaccaag tgtttttggt acttgaggta tcattttgtt tatcttagat acttcctgga  41580
catactctaa ttattggaag ttgaatttct aaaatatttt aaaacagctt tttatattta  41640
taatataaat gttgatcttg aaattgtagt tgctgtctga tgaataaaat attgggcata  41700
```

aaagagaaac tgtttagtct taacaaatta ccaatcacat gatttttagc ctttatcaat 41760
actgataggt gagagagagc ttagggaagc atctacagtt tacttggcat tactgttact 41820
tgaatgagaa tgaaatgagc tgatgaaaat taagtgtttt tttgggaggc cctcatttct 41880
gtgtaaactt ctatatctac ttttaaaagc attcaaaatg caatctaatg tttgtagtag 41940
gtcattgaga ctctacagtg tgtctagagt ctcttaggaa gtcgtaaaat gaatttcctt 42000
tgatacagaa ctctaagagt taagctttgt tgagtctatt cctgtcatgg cgatacaaga 42060
atatttctaa gtttttgcc catccttttc cagcccttgt cagattggtt ggttattgct 42120
gcattgctca aaaaatagtg aggtatagaa aaggggacta gaagttgggt ccatagactt 42180
agactgtctc tgctgtgtca cataatgtgt cttctgcaag tcagttagtg tgtctaatct 42240
ttacttttat gtaaaatggg acttgatgat agaaaagagt gtgaaatgga aatattctgt 42300
tttgtatttc agtctgaaaa cttagagaat acagtaatca taccagatat caaactacat 42360
agcaatcctt ctgctttcaa tatttactgt aatgtacgcc attgcgttct ggaatggcag 42420
aaaaaggaaa tatcattggc agccgcatct aagaactctg tgcagagtgg agaatcagat 42480
agtgatgaag aagaggaatc caaagagccc cctatcaagc ttccaaaggt aagccactga 42540
gttctattaa tatttagatg tgtaacctgc aggtgttctg gctataatgc atatatacgc 42600
attgctaaaa tactttgctt tatgtaaaat tgcacactaa aaataacacg gcttatgggc 42660
aaaaatagat ttggagcaga aaaggaaaac tctgcaactt tataactaag gtgctaacaa 42720
agtcaataat tgataattca ctggaaagcg caggaaggga gatcagtggg ttggagtctg 42780
ttatagggc aattaaaaaa tgtacaaaag cagtagggtg gaaatgctag tatagaggca 42840
ttgagccatg gcagatggaa gtagagctct gagccagtga gccgagagta aggtgggcac 42900
aagagaaagc caagagccct ggaaagctgg gaggtgctcc tcacctggga tgcaggtatg 42960
cgtttttatt tttcttgaaa tagaactaca aagcctctca gctgtgtagt agcagggctg 43020
agagcctttt cctttctgcc taagcttata attgtactct tgatattgtg gtttcccttg 43080
attaggaaaa aaaaaaatca cctatgaacc aactgaactt ctgcattatt ctgatattac 43140
tcccttattt accaggagca tataaactag ttggtatttc tataatagaa gcatgtattg 43200
taggccgggc gcagtggctc tcacacctgt aatcccagca ctttgggagg ccaaggcggg 43260
tggatcacct gaggtcagga gtttgagaac agcctggcca acatggtgaa accctgtctc 43320
tactaaaaat acaaaaatta gcccggcatt gtggcagtcg cctataatcc cagctactca 43380
gaggctgagg caggaaaatt gcttgaaccc aggaggcgga ggttgcagtg agccgagatc 43440
atgccattgc actccggcct gggtgacaga gtgagactgt ctcaaaaaaa aaaaaagaaa 43500
ctggctgggc gtaatggctc acgcctgtaa tcccagctct ttgggaggcc aaggcgggcg 43560
gatcacgagg tcaggagatc gagaccatcc tggctaacac ggtgaaaccc cgtctgtact 43620
aaaaacacaa aaaaaactta gcccgtcacg gtggcgggcg cctgtagtcc cagctactcg 43680
ggaggctgag gcaggagaat ggcgtgaacc cgggaggcgg agcttgcagt gagccgagat 43740
ggcgccactg cactccagcc tggacaacag agctagactc catttaccaa aacaaaaaac 43800
ctgtattata gaactactct cagtttactc tgttctgttt aagtattggt atatttaaga 43860
ctggaaggtc tatatatata tatatatata tatatatatt tttttttttt tttttttttt 43920
tttttttttt tttgagacgg agtctagctc tgttgcccag gctggagtgc agtggtgcca 43980
tctcggctca ctgcaagctc cgcctcccag gttcaggcca ttctcctgcc tcagcctccc 44040

-continued aagtagctgg gactacaggc acctgccacc gcgcccggct aatttttttt tgtattttta 44100
gtagagacgg ggtttcaccg tgttagccgg gatggtctcg atctcctgac ctcgtgatcc 44160
gcctgcctcg gcctcccaac gtgctgggat tacaggcgtg agccactgca cccagcctgt 44220
tatatatatt ttttctatat agtagatata gttaatattt acaacaaaag aataggtgaa 44280
aatatagaca tttttaaatg gtgcctttat atgacttatg catattgctt ttttctaaac 44340
agagctattc aaaatgattt tataattata aatgatttat gactattgcc tttttactaa 44400
actgatacct taaaattatg ccttgaaagc ttatacatat ccacaaggga ttgtgtaaat 44460 atttttttact acttggaaat agcagcataa atggaacctg gtctgagttc ttttgcacat 44520
tttatggtgg ctgttcctaa gtacaccacc atccttaatc atattgtcag gttcttctca 44580
ccttattctc ggcagatggc ttgcttcata tttcatagag taatacaagt tttgtgaact 44640
tactcagctt cttgatcagc catcttcaca tgtccttttt gcctcctgtt ttagagtggg 44700 accctttttct ttttcttatt tcctttgtct gcaatgtcct aactgtacct actctaatag 44760
ctccttcctt ccttcctttg ctttcctttg ctttcctttc ctttcctttc ctttcctttc 44820
ctttcctttc ccttcctttc tcctttttttc ttttcccttt ccttttccct tttcctttgc 44880
ctttcccttt cctttccttt ctttcacgga gttttgctct tgctgtccag gctggagtgc 44940
aatggcatga tcttggctta ctgaaacctg tgcctcctgg gttcaagcaa ttctcctgcc 45000
tcagcctcct gagtagctgg gattacaggc atgtgccacc gcgcctggct aattttgtat 45060
ttttattaga gatggggttt ctccatgttg gtaaagctgg tctcaaactc tggacctcag 45120
gtgatctacc caccttggcc tcccaaagtg ctgggattac aggtgtgagt caccgtgcct 45180
ggccaatagc ttctttcttt aacctaaaac aaacatgttt atctttaata tgggagctgc 45240
tctacataga aattatggtc tctaattgta atttcttatg cttaactagg agagattgag 45300 ataaaaaaaca tagttgagtt aggacgtagg gctggaggac ttgtataatt tactttttag 45360
ttagaatacc aattctgtgt atgtgtgagt cacactgtat tatagtaatt gtgctactta 45420
agttcaatat tgtgagagaa aacaaaagcc tgggtaaatt ttttacacag gtatgcagat 45480
tttgaatagt aaactgtagt tcaaattaaa ttgcataaac aagaacaatg gattcctagg 45540
gtgtttaaaa acatcaggat tagtgagtat taaatgaaat atcaggcatt cttaagataa 45600
ccttttgcag cataattaac agagtcaaag ggtatctttt caaagaaaat taaagaagat 45660
cagatagccc aagtgattaa tactgaattt tctaccaagt actgacctgt ctgcaaacag 45720
ggttagcatg ggttatggag ccaaactgct ggggttcaaa caccattaaa attactagct 45780
atgtgacact ggaagttatt tgacacatcc gtgcctcagt tttgtcatct atagattggg 45840
ggttgcatct acctcatagg gttgtagtga caatttaaat gaattaatgg atgttgagtg 45900
cttgagagaa cagtacctgg cagaaagaag tgctcggtaa atgatatata tagttgtaag 45960
tgtcagttta ggtgcaaaca agaaaatgtg taggtgcaaa tgaatttgag ttacttgtca 46020
aggaactctt cagtttatta aaaaaattat gcaagcaaat gaaacttcta gagaatcagt 46080
gcaatcacct gatgaatgag aggtaaagag aggaagaagt gatgagatgc ctctatgcag 46140
aggcaagcag atactatggg tggggagtga aactttcagg tgatattttt tggcagccat 46200
ttccatgaca tgaaggattg acactgagga cgaaattagt ctcttaaggt ttgaggtgat 46260
gggatttgaa ggcaagtggg aaatgttggc atttttcttt tccctttgac cttctctgtg 46320
cctcagcccc aaatgctgct attatcctag tttgctcctt ttctttgttc ctctgttgct 46380
cctcctaagt gtgtggctgt cccattcctt cttgcctgag gtttctgttt cttgtactct 46440

-continued

```
ttttttttt tccttaacat gattaagaca gtttttaatc tgttgttgaa gtgttgttgt  46500
aatacagttt tatttttccc attcttgagt tttaaattat tatttagtta ctaataaatt  46560
gagtttgact gttatataga ccttgattgt caccctttg ctttttgctt ttgtttttgt  46620
gttttgcgga tcagtaatca ttgatgtatt taaacgagct ttctattccc tgaatgcttc  46680
tacattaagt tttttaacca gctcaaactg tcactaaaat ctacatcctc taaaacttta  46740
cagattttat agctacataa tttttattat ttttgttttt attttcattt tgagacaggg  46800
tctggctctg tcactggggc tggagtgcag tggcgtgatc tcagctcacc gttaacttcc  46860
gcctcctggg ctcaagtgat catcccacat tagcctccca tgtagctggg actacaggtg  46920
tttgccacca ccccaggata ctttttgtat ttttagtaga gatggggttt tgccagattg  46980
cccaggctgg tctcgaactc ttgagctcaa gcagtctgac cgcctcagcc ttccaaagta  47040
ctgggattac aggcaggagt caccgtgcct ggtgcataat ttttaaatag taacgcttag  47100
aagtcatatt tcccatctga acccatttga agccagtcat gccacattat taaaagattt  47160
agacttacct aggatcattt ctttcttaat tcagtatatt ctttttgaat ttgtagccag  47220
cattatatta ggtcctgaga acaaaaggat gagacataat tcctgccctc aagaaagcat  47280
tgtcttgtag ggataagaac caggtcaata aatattctct agtgccttaa ggattgatag  47340
ggagtgctag atatagtgga acacgttaga gaaaggactc aacactggct gagatagagc  47400
aagagagaga gagcaggaag ctaaatcatg aagggcctta tgtgccatgt aattgattca  47460
gatgttatct cataattagt aaatattgaa gattttaagc aaaagaatat catcagactt  47520
gcatgattgc atcagactca ccaccctgta gttatgaata tgccttacta acactggagt  47580
aactttgtac tccagtaagt aagtaacttt gtactccagt tagtaagtaa ctttgtactc  47640
cggttagtaa ggcatatcca taactacagg gtggtgagtg agactggaga cagaggaacc  47700
atttaggcag ttattgcagt tgtctagaga gtgttaatga gggttggaat tatggtagtg  47760
acagtgtttt gaatatagga aatgttaagc agaattgaca ggaattagta ataaattggc  47820
tataacgact gaaaaagaag gcagaatcta aagatattct taaaggtttt gtgtggtgag  47880
ggcctttact gaaagaggga atactggatg aggaacagtg cttggctgaa atgatgatca  47940
agtttagttc acatgctgat tctgaggtaa atgtgaagta tccagtgtgt gctatgtagg  48000
gctgaagttc aaaaaataag tgtcagctag aaaaatagat ttgggagtta tcactatgta  48060
ggcacaagtt gaaacaaatt tctgtgagag atcggagggg gtgggatcaa gaacattgtt  48120
tgaaaaaata gctttgaaaa gttgaaaagt tttgaaaagt tctcttcctc tgagtgtgaa  48180
gagaagggaa gaagatggta gtagtcatag ataaatttgt taggcaagga actcagaaac  48240
ttcacactca tactttcttt cttttttttt ttttttcaa gatggagttt cactctgctt  48300
gcccaggctg aagtgcagtg gcacgatctt ggctcactgc agcctccacc tcctgggttc  48360
aagtgattct cctgcctcag cctcccaagt agctgggatt acaggcatgc gccaccatgc  48420
ctggctaatt ttgtattttt agtagagatg gggtttcacc atgttggcta ggctggtttg  48480
caactcctga cctcaggtga tctcccaacc ttggcctccc aaagtgctgg gattataggt  48540
gtgagctacc acacccggcc tcacattcag aattctccat cttagccttc tcctcctctc  48600
tttctgctgc tgcctcttcc ccctcctttt ttctctgtct ctagattttt aaattttta  48660
ttatttgtag atattatctc tgtaccaaat atttgcttta tacaaacaat tttaaaagac  48720
agtatacttc actctatggt aatatgtaaa tataattttg atttcctttt gagcttttc  48780
```

-continued

```
aaatataaaa gtataggaag tgattttagg accttttaac taaacaagat acaattttta  48840
agggtaaaga attaattatt aaatccaaat gtgatgtaac taaactttta tgatcacact  48900
tagtcatgaa ataataaagt cacgtttgga aatatatgat ttgagaaggg caaaataaaa  48960
ccttgaaaga ctctttatat atcatttttc tttggccaaa tatattttta tctcactttc  49020
ctagcatatt agactggctg tatcaggtaa ttatttgggc ttcatgtttc tttatctttc  49080
aaatatgata gataaccttc aaaatttaat tatttgagag cagcagtaaa ggtaaaattc  49140
agtaaattta caaaagacta ttttctgaag agaagtgcga aagcatgtgt tgggtaatta  49200
gttatagttc gttatggaaa gtattgaagc ttcttgtgtt cttttattgt tataattatt  49260
atttttatta aatatcacat ttatttattt tgctaattat acatatttat tgtagatgat  49320
ttgaaaaatc agaacatttt tctaaagagg tattaaaaat cggaagtaat atttgaaata  49380
ccattaacca aaatataccc caatataaac atttttattt cttttgtcat tttttctatg  49440
tacacattaa aatgtttttt acacacaaat gaaataatac tatattggca ggactatatt  49500
ttttctcctt acactcttcc ttcctgatac tgaaggaggg agaaatatgt gttttcattg  49560
actataagac ttcaaactgt tttaaagtct actttcaaag ttcaaacttt tggtaaaata  49620
ctttatactt agccaaacag cagaaaaaga cttatttaag aacatgtctg ttacctctgt  49680
gcaataatcc atagctaaat attaaaaatt ctttaatagt tgcagaactt gaggttgatt  49740
tttgttgtgt attgaatata tattactatt ctgaaaatga atgttttccc atttgttaaa  49800
caaaaagtct acaatgaacc aagatgtgga taattagtga gactctcaca gtgtttaacc  49860
cagacagatg aagagttccc tatcatcatt gtgaccaaag ttttatgggc cagtctcact  49920
aaaaccggct agctctgttt ctaggcagcc cacctgagtt gcctattgcc attcacttgt  49980
tattacacct taaacttacc agagagatca agaacctgtt cattaggcag tcttactgtt  50040
tctggcaagg ttcaataatt ccgttgtcac cgtaggaaac tgtatctata ataaatgaac  50100
cttagccaaa aatgtcatct gtgaaaaatc ctcttggatt tatgaaaaat catggttggt  50160
agcagagtaa gcaatctgaa agaataacag aatatagtag tcttccattg gcttgagaat  50220
agagccccat attttgtact ctggagatct ttgacttcac atttctcttt cctgtaagta  50280
cataagcaga tggaaatctt ggacagcatg ttcttgtttt ctagtccatt ccaggaaaag  50340
aaactatatc aaatgtgaaa gtttaatcac ttaatgtgtt taatcaattg aaactctatg  50400
cagactcttc tgtaatatta gctataatca agtctgttag cattttagat aacttctcca  50460
aagacagtcc tcctagttat ttgacttctt agctatatct gttgtttcca gaaaacttgt  50520
aaatgttaat cagaactaca attgacttac cttcagccga cttgcttctg gtttagaaaa  50580
tgtatttctg agatgcagtg gtttttagc aaacaattta gtgaataaat taaacaaata  50640
tttaatgtgt gcctaccata tgctaggtaa ttggctaggc atgggaggta ttaagccgtt  50700
taagacatgt tccttgtata ttggaagata atacaagccg tttaagacat gttccttgta  50760
tattggaaga tcccaacatg gttgggaaaa tgaaaacaaa aatagttata ctgtaatgta  50820
ataaatgcta taacagaggt ctgtattgag tatgaattat atagcatgac taatttaccc  50880
tattagatta taaactctta gaggacaggg tctagtatac cttcatattt cctaaagtga  50940
gtttgcacaa tatgagtgct taggaggtat ttatgtaata tatgaattaa tgcaaaaata  51000
tcagcagaga gaatattctt ccactgttgt gttcaataga attaatggtt ttgggagttt  51060
ctactaatta gtcttatttc aatttttctg ttacttctcc aaacaattta attaatactt  51120
cttgaactgg ttctcagaat gttgacattg cctgagaaat ggaatttgtc ttttgtttta  51180
```

tcagtcttat gaaggtatat ccttaaactc attcattgca atttgctctc tcaatcttta 51240
gtaacaaatt tatctctttt gctggatata gagtctgatt tttcttgcac ctgatgagga 51300
atagtaagat aattaaagga aaagtaccag tgatattttt agctaagcag ttttaaattg 51360
ttttgtgatc atcctacaag aagggatacc aactataaat aataatatag tgattgtacc 51420
attatagaaa aggctaagac gaaaagctcc ttgtaaaatc tttttactat atgtgctgtg 51480
ttgactttat ttctggttat aggtaacaat taacatgact tttgacaaaa agagtactga 51540
attttccttg agtacaatca aatgaacttt gcaaattaat atagtttatt tcttctgagt 51600
gaatgcaatc tagtctctag ttcattgtta taagccattt tcatgatgtt ttattatggc 51660
tccattatac atatacatta tcatttgctg tggaagtaac ttgtaccaac taaactgctt 51720
agaaagtgtt actagcttac atgtcataaa gtatatatat tttttccttt taaatagatt 51780
attgaggttg gcctttgtga agtttttgaa ttgatcaaag agacacgatt ttctcatcca 51840
tccctgtgtc tcaggagtct ccaagccctg ctcaacgtgc tgcagggcca gcagccagaa 51900
ggcctccagt ctgagccacc tgaggtccta ggtaagagcc aaggctcatt cagtgaagca 51960
tttaaaagtg aatataatta ataatagagt attgtacact tcaaaattgt taagagaata 52020
tttctaaagt tctcactaca gaaaatgtta agtacttgag gtgatagatg ttaattagtc 52080
cacattttat tcatgaatca taacatcact ttataccccca taaatttata taattataaa 52140
ttgtcaattt gcagttttta aaaagtgaag agcttctctt atgaagcaca cacaatagcc 52200
tgtaatgcag tctttattta attgtggtac ggaaacagca ggggtataag ttctagagta 52260
ttttttctg tgttccactg aagttatggt ttaagagttg aagttcgtgc acacacattt 52320
ctcaattagt atgatgaagc ggggggcaaa caaaacataa atccctggaa tccagaaata 52380
atcctcaaac cttaaggtca ctattaactg aaatcgttct tattaaactt ttggccaaaa 52440
tagctaacat tcactttctc taacttgtta ctctcaatag ttttaaaaaa caggggaaaa 52500
ggaaataaat gccacaaagc caaaacagta caattagttt ctaaattgag gggactttttt 52560
tttgtattca tcataaataa aaatctattt gtgttatgga ttaaacttct gacttagcaa 52620
ctttcattaa gtaaataaag tgttcgcttt tcttaaagta tgttccgatt cttgcctttc 52680
atatcagtga cccagactca acatgtaatc ctttaaataa gataggagct tttacttaaa 52740
aggtactaag gaatagaaat atagatggaa gcataatttt taactggtta attgcttttt 52800
ttctccgatg ctaactatgg gtctttaaac tatctaaagt tttctagatc cttctattat 52860
tataggaaaa ttctcagaag tactagagct gtggttctca ttatgtggtt ctcaattctc 52920
attagcatgt atcagagtta tcggggactt ccctatggtg tttctgattc catagacttg 52980
gggtggggcc caaaagtttg tatttggaat tagtttcttg gtgatacaga tgctggtttg 53040
aggagtacac tgctggttta gactaaaact tggtcctttt tttccgactt ggctatttag 53100
attttgtagg acccacctgt gagaaccaaa ctgcatgaac ctaactacat gtcagatttt 53160
tctttttgg tcgcatgtgg ggactcagtt attgtgtttg acttttgttt gttttaatga 53220
gagggaggat gctggtcatt gaatcaagct gaggattttt taaaaccacc cccctcacat 53280
acacagttat taaaagctat taccaaatag aagctgtcat gttggcaggc aagcaccgtg 53340
ttggttattg ttatgatagc accagtgatc atattaatat tgtgaagtgc tgcttggctt 53400
gacagcattt tactgaagat ttgatttatt ttatttaaca atattttgct cggttttctt 53460
ggatttggtt tgttagttag caaataattg gaatgttgaa atacccgcga agacttggat 53520

-continued

```
gtcgtatttc ctactttgaa catgttattt ctttcctcct aagtcttcta ccattctcat  53580
gtctcatgtc agttgttata tactttcctt tgtatccatt ctgtacatac tttctttcct  53640
ttattctttt aaaactagaa cttgttctta atactggctt tggcatataa tatgtgcttt  53700
agtcttatct tccatcaaaa ctttcacatt attggctggg tgtggtggct tatgcctgta  53760
atcccagcac tttgggaggc tgaggcagga ggatagctta aggctgggag tttgggacca  53820
gtctgggcaa cttagacccc tatctctcca aaaaaaaaaa aaaaaaaaaa aactgggcat  53880
ggaaatgagt gctactcaag aggctaaggt gggaggaccg ctcgagccca ggagtctgag  53940
gctacagtcg gctgtgatca tgccactgcg ctgcactcta gctgggtgac agaatgagac  54000
ctcatctcta ccaaaaaaaa aacccccaaa aaatcccaca aaacccaaaa atatttcacc  54060
ttattaatct gttcattttt attttcttgt ttaaagtttc aaattctgct gtactgcctt  54120
tcgtctgtct tccatccttt cagtgtttac tgctgatctc gtcactgctt tggcttattt  54180
ttctatgtaa gggatttatt atcacttcat gttttctatt ttgttaaatt agctcaaaga  54240
taaaagcact gatttggttc ttttatacta aatttctttt gaaacttgcc tctcctcctt  54300
tttttaatct aatatcacaa tcttattggt tatccttttt ttcccattcg gttgttttcg  54360
tgttattcat gaaaatatgt gtatatttat ataactctta ctgtggaaca tcttgatgat  54420
tagtatacac caagcttctt ctctttgcaa atagattttg atttttaaat tatctattta  54480
aaaatatatt tccttatatc catatattct gttcaattag attatattct cgagtactca  54540
ctgaaatgta atagcacccc ctttgttatg tgctaagaat gtgcgatact attgctgtta  54600
ttatggaact tagcatcaga gagttggata tgtgtataat tacaaatgtg gataaatcgt  54660
atggaggaaa gtagaaggag ttctgagagt cctttttttgt tttttgagac ggagtctcgc  54720
tctgttgccc aggctggaat gcagtggtgc gatcttggct cactgcaact tccacctcct  54780
gggttcaagc tattctcctg cctcagcttc ctgagtagct tggactacag gcgcgttcca  54840
caatgcccgg ctaatttttg tatttttagt agagacaggg tttcactatg ttggccaggc  54900
tggtctcaaa ctcctgacct caggtgattt gcccacctca gcctcccaaa atgctaggat  54960
tacaggcatg agccactgcg cctggccaag attccttttt taacttaaaa atttttttatt  55020
tatttatctt tagggacagg atcttactat attgcccagg gtagcctcaa accctggact  55080
caagtgatcc tcctgcctcc acctcccaag tagctgtgac tataggtaca cactgctgca  55140
cccagctcct tctgagagtc tttaacaggc tccctgaaga tgtgacatat gagatttaga  55200
gggtgaatag gagggagtga attcgattat aagtgctcta ggcagaaata acagcattta  55260
gtaaggctct gagacagaaa ggagaatgaa tgaaaagaag agcaatatgg ctagaatgtg  55320
gagagtgaag gaaacagtct tgtgacaggt gaggaaggag gcagggacat gcagagcttt  55380
acatgccatg ttaaagaatt tgattagtgg gctaggagga atggaaagtc attctctatt  55440
tcattacatg aagaatattg ttttttaaat agccttattt tcttaaatta tttgtttaaa  55500
ctattgacta ttttctttcc ctggattctt aacctttttg aaagggtaga gacattcttt  55560
gtcatgtttg ccaataccct agtgtagaat agttgccagt gtgtgagagt tcggtatata  55620
tttgctgaat aatcaacaga tgtactcact gaaggataat aattggagga aggatgggta  55680
gatggaaata tggacaaaca gggatagatg aaaggatgga gggaaggaag gatagctgga  55740
ggaaaaggta gaggaaagga taaatggaaa aaaatggaag tataggatgt gtacagacaa  55800
gtgaagagag gaagggggaa agaaaagaag acagaaggga ggaagaaatt aacaaaggag  55860
tgaaagaatt ttaagtagac aatcagattt ttggtttgaa attctccctg gctattgggg  55920
```

caaaagcgaa tggtaagaga taatttctta acacttttta tcaaagagat gatgatagca 55980
tggattggaa agatgatgat gagataggga aaagtggagt tatccattag gaagtaaaat 56040
aaacaggact taatttggga ttagctatgg aagatgaggg attggtaggg gctgcctggg 56100
tttctgtaag ttaccagata acccacaggt ggcattttag tttttagaga attgcagtac 56160
attactcctc tttctcttgt tctcctcctt ctctcccttc cctttccctc tcttcatgtt 56220
tctcagtttt tctttttcta actctctttt tccctctcca tctgattatt cactctataa 56280
ggattttcaa gtctccgttc tatggaagaa atacccagat gtctgttgat tgaatcttag 56340
atggaggtgt tcagggaatt ttgtgcagag acctctgctg gttgtaaaac atttgtgtgt 56400
gtgtgtgttt catcttcacc actaaatgac tttatgattt aggaaaaatc ttttgatacc 56460
acatatctca atttcattat taaaggggga gaatatctgt cctattgact tggaggtttt 56520
tctagggtat aaatgaatta catcctaagt gtgaattgct attatgttaa tgatatagcc 56580
aattttatat taaagcacat tattgcatat gttttatgtt tctattactt tgaaaatata 56640
tacataattt cctggacact taacatttta agaagcctcc taatctaaaa ggtaaaataa 56700
gtatgacaag tagtctatta cttgatagga tgagtttctt gaatatgtga atgcctctag 56760
gcaagcttgt tttaaaagac cttagattgt ctttttttac taagaaaaat aaggagttga 56820
actgaatgtt ctttaagacc cttgttacat aaatatttta acttttgggg aagagagtaa 56880
ctagaaagaa actaaagcaa agtaattgtt ctagattcct taaatttcgt ttataatgag 56940
acaaagtaaa aataaataaa tatacgcata taatgttccg tatgttggat gaatataatt 57000
gaattctatt ttatccacag agtctctctt ccagcttctt ttggaaatca ccgttcgaag 57060
tactgggatg aatgacagca caggacagtc cttaacagca ctttcctgtg cttgcctctt 57120
tagtctggtg gcttcttggg gagaaacagg aaggacactt caggccatct ctgctatcct 57180
caccaacaat ggaagccatg cttgccaaac tattcaggta tttcatattt atatctgctt 57240
agaagtttat aagatgacaa gttacagttt cgtctcaatt tctgtcaata ggaattctgc 57300
tttttctcac tcattacagt agcttaatct gtccaagatt gatacataaa taatctacag 57360
tatttcaatt aagtgatatg tatgtttaac tctgaagctt taaatataat aaaatgaatt 57420
ttggccagac ctcttaaatc tttaagctgg tctttgcctt aacaccatag ccttctcttt 57480
ccttgctgtt ttcttgctgt ctgcgttctc ccttcttccc atctttccct gagtttttta 57540
gtatggaatt cattcatggt tttaaatatc ttttctctat tgaaagaaaa agatatggta 57600
tcaatctgat atatttttga ttggttgatt atgatttttt tatgaattga ttcgtttctg 57660
agttacttca gctgtgtata aaacatttta ggcttttaat attcagttgt ggaacaaaca 57720
agctcatcac cattttagtg gtgggaaaaa taatccttat aggcaaactt gacttaatta 57780
tttgggaagg ctctggaaat tgagaaagaa gttatgatct taagacctga ctgtctactc 57840
ttctctggcc ccttgggcaa ccctagggca ggtggaaggg atgcctcaat cctgttatta 57900
gcagaccaaa gatagcaaaa ggagtatatt ggtcattttc tgtcttattc agtgattttg 57960
aactctcctg gtcaaacaag acccattccc ttactcaaga tttctgctct tttcttcctt 58020
tctgccttgc ttggaatcct tttgtccctt tttatggtcc ttaattattt tgaagttgct 58080
ctaatacagt ggttttcaag ctgtgttctg tagacatgct ttcagggttt ggcaaatgtt 58140
taatttaaat atatgtttaa aatatgcaaa tattttaaaa attgtaataa agtaacacaa 58200
acattcagat accatatacc agattttaat aggatagtga ccaccaacat atgagcttat 58260
gaattttgat atgatttgct tttatataga gacttaggaa tgccattaga gctcatagca 58320
ggagtataag aactacgttc atggaaagcc tcccagagga tatgaggtga gatctaaact 58380
aatgagttga aatcagccag gagaaatttt tggtgttggt ggtgtagaga gagaatgttc 58440
taggtatcca catgctaagg catggaggtg agagtaagag tgaaatattt gaaagctgaa 58500
agaagtttag tatagctata gcatagagag ctgtcaaata gcgtagccac agcatacaga 58560
gctggcaaat aacagagaca ggactcgagg gcttatctgt ctccaatatt tatgctcaat 58620
cactagacaa cacaaaacta cttgatcctc tgaatcaata gctgcagttc tctacagacc 58680
tgccacatca ccacatcccc aactctagcc taaactccat attaaagccc attaccttaa 58740
catggcttgc agtgctcttc atgatttggc cttttatcta ccaacttcat ttcccaaaac 58800
tctcctggcc tgactgttgg tagagggaga aaagctttcc ctgagaatgt gtgcattaag 58860
tccgttttca cgctgctgat agagatgtac ccgagactgg gcaatttaca aaagaaagag 58920
gtttaatgga tttatagttc cacatggctg gagaaacctc acaatcatgg tggaaggcaa 58980
ggaggagcaa gtcatgtctt acgtggatgg cagcaggcaa agagagcttg ttcagggaaa 59040
ttcctcttta taaaaccatc agatctcgtg aggcttattc gctatcatga gaacagcaca 59100
ggaaagactt gcccccatga tccagttacc tcccactggg tcccttccac aacacgtggg 59160
aattcaagat gagatttgag tgggaacaca accaaaccat atgagtatgt gtaactcttc 59220
acatctcaga tttgttttgg cacccaaatg catactactt gtccatttca taaagcttaa 59280
cagagagttt aaagcagggt agacatggta gtactgcaag atgctgtatt gaaagacact 59340
gaaatccttt ctggagggtt gaactcttga cttcaaaggc tttctgcaaa taaaacacta 59400
tttattgcat ttgagctcag aaacaaatta ataaaaaaag cacatggaaa aaggcaccat 59460
tattgagaat tagcagaaac aaatatggta gaatcaatcc tgccaagtcc ttagatattg 59520
aaattatttg atatagaatg tgtatgtgta tgaatatata aagtatggtt aaagtaataa 59580
aagaaaatat caaaagtatg attaagtagt gagaatataa aaagtagtca gacattagga 59640
aaaaaaacaa atcgaactcc tagaaatgaa aaaccaaata attacaatta gaaacttaaa 59700
atgggttaac tattgtataa tatggttgaa gatggaaatg gtgaactgaa agataaagag 59760
gaagaaatta tctagaatgc aacagagaga caaggagaga aatatggaag ataaaataag 59820
aaacatggat cgagaatgac aaaatctaat gtaatacaat ctgagttcca caaggcaata 59880
atagatttgt ggagatagag tacttgaaat aatggctaag attttacaga attggtgaat 59940
gacatggaat cccaagagta aggaagtcta ccttgcttga gatttgcttc ttatagatga 60000
acttttagtt ggtacttttt gctggcatgc gaaatatcat tctgaacaat ttattgtctt 60060
atgaatgatg atgtattacc aaagtatctt tgttctgtgt ttgtaacatt taaaaatgtt 60120
ttttcattat ttttcttctc ttttgattag gtgccaacaa ttctaaattc gctacagaga 60180
agtgtacaag cagttttggt gggaaaaatt caaattcagg actggtttag taatggcatt 60240
aagaaagcag ctttaatgca caagtggcca ttaaaagaaa tatctgttga tgaagatgac 60300
caatgtctac ttcagaatga tggatttttt ctttatctat tatgcaagga tggattatat 60360
aaaataggct ctggatacag tggaacagtt agggtaatgt gattccttac agttccttaa 60420
ttatacagag ttataaccat aatgaattgt gttctgtgtg tttctagttt catttctaga 60480
atatgatcta attttagtgt aataatattt atttgaaaac cataattgaa atacatgcat 60540
taaatgtcat tcacccattt gtattatttt tcattgatta ttaattatga aaccactgat 60600
atactaactt ttgttttttt tgcagggcca tatatacaat tctacatccc gtattagaaa 60660
cagaaaagaa aaaaagtctt ggttagggta tgctcaggta agaaactatc cacaataaac 60720
caaaatttc ttatctttta caacatgtga tttgtccttg tttaatcagt aatatcactt 60780
ctatttaaac agaaatgata atatattttt actaatatgg ccataataac tgaatagtgt 60840
agcgtaaaga acactgtctc agaactcata agaggttcaa ttttagttct ggccctgctt 60900
cctactagct gtatgactgg acaactcagt taacttattg ggtcctctgt tatttagctt 60960
taatatggga ttaaacatac cttctttaga gttcttgtgt aagtgagcct ctagataaga 61020
attgaagacc acctttatca ttagcacatt ttttttttta attgagacag aatctcgctg 61080
tgtcacccag gttagagtgg agtggcacag tctcggctca ctgcaacctc tgcctcctga 61140
gttcaagtga ttcttgtgcc tcagcttcct gagaaggccc atgccaccat gcctagctaa 61200
tttttttgta tttttagtag agacagggtt ttgtcatttt ggccaggttg gtctcaaacc 61260
cctgacctga agtgagccac ccgcctgggc ctcccagagt gctgggatta caggcctgag 61320
ccaccccacc cagcctcatt agcacattta aattggaaat gtatacatgt cctgaggcca 61380
aattagggtt tcttaccaca gactctttca ttttagtcta gattcagtac tttctaggaa 61440
acagtgtttg gcctactcag tagacagcta cctgcatgaa gaatatgcaa agaatcacaa 61500
gagagaaaga aaagccctgg gtttttgtgt cttaatgctg tgatcttatc tcctgaccaa 61560
catagtcaga taggtgttag ccttttacaa ggtcagcagc cagatggata cattactcct 61620
cttatggaga aaagcaaatg aaggatggac aagagggact agaaatattt ttttccatac 61680
agtacctacc tgaacagtga agcccaagtt cctttgtata aggataaaga ataaagattt 61740
ccctgcatgc ctgccttgct gagcttgtga gatttgttgt caggatcaaa tgataaaaga 61800
tatttgaaag tcttttgaaa actatggaaa ttactattgt tacatgaaga ataattctac 61860
tgtatcacct attggggaga atttgaaatt aaattttttt ttttttttgg agttgtagtt 61920
ttgctcttgt cgctgaggct ggaatgcagt ggcgtgatct cagctcactg caacctccgc 61980
ctcccaggtt caggcgattc tcttgcctca gcctcccgag tagctgggat tacaggtgcc 62040
caccaccacg tccagctaat ttttgtattt ttagtagaga cgggtttaac catgccggcc 62100
aggcttgtct cgaactctta atcccaggtg atccacctgc ctcagcctcc caaagtgctg 62160
ggattacagg cgtgagccac cgcccccagc ctgaaattaa attttagata acaaattagt 62220
ttctcagtaa ttgtctctta aaaattgaac ttagtttaaa atatctcatc agatttttat 62280
ttgccactct attgtgtttt atctaagaaa taatgccgtg gaaagtatat tattatagca 62340
gtgtgttcaa tggcatacca caccttctga aaccactatg ctattcattt tcaaatagca 62400
aactcaatac ttgttatttt tcttaaagta cttgttaaag taacagtgat cattcatatt 62460
atttacttgg caagtggtat ggtcattttg aacaaaatgt ttgtaactgt actgtcctgt 62520
ttagtatacc taattatgtt tctgggaata tgttacatca attttcaata atgtatgact 62580
tttcctctaa ttgagaggaa tgttcttata tttttaatca ttaatatctt ttagacatca 62640
atattgatgt attattgtac ctcaaaaacc tgtaatatgg agctgtatgg ctgctgtttc 62700
tgctgaatta gtaataaata ttttaacagg aaaatttttt gctgttatca gggttattta 62760
ttatatagag atgtgaataa ccacagcatg acagccataa ggataagccc tgaaacactg 62820
gagcaagatg gtactgtgat gttaccaggt atgtttcaag tagtcatttt ttctccacaa 62880
gcaattttaa gaaatgtgca tgttaagcta tttagacaca taaagaatga ttagcaaggg 62940
atagtgcttg cttataaaag ggttttaaaa atcttgacat acaaagcatt ttatagtcta 63000

-continued

```
cgtgaagtta atacatatca agagaataga catagaaata taacaagttt taatatttgt  63060
tttcaaactt ggccgtctat ggcctaatct ctgacctcac cccaccactg ctgaattagt  63120
ggggtgatgt aactgtgttg ctcttaataa aaatcagaac tctggctctc atgtgactca  63180
gtataaagaa ccttctgttt atttttactt taacaacagt gcagttgggt tttcctcctt  63240
atttaattta atttaatttt atttaattta atttaatttt attttatttt attttatgtt  63300
aaaggggttt cagagacaga gagtttaggg taggtcagga attttttttt ttaatttcat  63360
catttatgct tcttatgctt cttaatactt tgataaaggt ctttggacac agtttatttt  63420
gctttaattt tgaggctttt atatattcac ttaaatcact gctaaattat caggcagtag  63480
gtctccaatt ttgatgaatg ctggaaaaat gcatattctt tattgtaaga tctttgaatt  63540
tgtttataat gttgatactt tctgaggctg tttatattaa aatcttgagt gtctaatgtg  63600
tctgtcaata atttcatagt agcaatatta cttgtaagcg tttgaccatc tgaaagtgag  63660
agctacttct gaagagtgca ttgagaagaa taattgctcc tgggctgcat gtttattttt  63720
aaatataatc ttaataattt catcaaacat ttatttgaac cttactacat atacatagat  63780
acatattagt gtacatgaca ctatgttaaa gtaaatatga catttcatgt ccatttcaga  63840
aatagaggag ctttggaaag cggatgactt aataaaatca ttttgaaaat aaccatctat  63900
tttcagatat gtctacaggg tttttttttt tttttttttt ttcattacaa gtcctggacc  63960
atgtctttgg tcataataat aataataata atgacaataa tattaaaaaa tacttttaat  64020
aacatgcaca ctcccccccac atatttatac atatattgaa agtaatcatg tttgttgtat  64080
aaaaatcata tgaacaaaaa agaatgaatt gaaataatta taatcccact tcccatatat  64140
aaacactatg aacatattgg taaatatcct tctcgtattt ttcctttgtg tatatgtcca  64200
tacttgtaaa aaagtgtgat catatgctac atattgcttt tttaatctat ctctttcact  64260
taatattctg aaaatatttc taggtcatta aatagtcttc tacaatgtca cttaaatgtt  64320
acaaaatata ttccattgat taatgtttga gaatgaaagc cttccagggt tttgctatat  64380
aaattacact gtaatgagcg ttcctatcgt gctgtctttg tgccagtcat tttaggataa  64440
tgacatagaa gaaaaattct aaattgacac atcccatccg ctataacaca tgggtactaa  64500
tatcaaggat ttacttctga gaaaccctgc acatttaata gagactgtga cttattgata  64560
agacaatttg aaaatatgtg cctacagctg ttttatttat tctgccttga taaaaaaatt  64620
actcgttaat gtctttattc agtttaaatc tcgttgcttt gtttaacttg tgaaatgcaa  64680
ctttgaacaa tacaagtgtg gctttctgtg tttcataagt gtgtgctgta ttagtggtga  64740
agaatgaacc aaacttcagg aagatagtcc catatttgtc ttcagaactg gcagatgttg  64800
cttgatatat tcctgaagat acaagcttaa aatattacat gatggataaa gaaaggataa  64860
agagaaaatc ttgaaatcac gtggcagaag actcctccct caagcctgaa gaagcctttt  64920
gtaattttct tgtttctttg acctggactg aattttcatc caatagcact ttttgttttt  64980
cgtgggtagg aatagctctg ctctgtagcc ttccaatcaa ggagcagaag taaattgtca  65040
ggtttataga tggtaatgaa taccatgttt caagttgaca taaatcaggt aattccttga  65100
gcttcatgtt ccagcttgtc ttacagtata gtttatttaa aaagtatttc aaccttgttt  65160
tgatgaactt aaaacatact tttttatct gataattgtc attttattct ttaaacctcg  65220
gcttatctta cagattgtat ctttatgtca ttttctctcc atgtctggtg acaggttgcc  65280
tcagttcatg aggctttttg ctactcttct tgcgccgctt cactcctcac ccctgcgttt  65340
atctgaaatt ataatgagtt tttcttcttt gctttttagt ttaaaatctt actgcttaga  65400
```

```
gcttgagaag catctttctt gcgcctcttt gtgttctgta cagtggacta ggaactcttt  65460
cttttgattt ctcctctctt tgattaccaa gtctcttggg ctaccagtgg gccttgtctc  65520
ccagtttcta tttccagttt gtgatccctg aattctctat ttggtaaggg tctgcctgtg  65580
ttttgcatat ttatgataag gaagtatgct agtatgaagc tcctgggcaa agataaagaa  65640
taatccagct tattcgggtg ggctccatta ctgcatttca aaatcagaat tttatgtttt  65700
gttgattcag gtgcaactag aaatgaaatg ttattttttg ttttggtatt gtgattaatg  65760
gagagattca tcctagtttt ctgcagttat tttgggaagt atgtgtgtgt gtgtgtgtgt  65820
gcttttaact tgcttgctga aaatttgttt ttccaaaagg acagaattta tccttgatgt  65880
tgattttgct tgtagttttg tgttatttag tagcaatcac taacacgtgt tcctgtggtc  65940
cttctgtaat actggtatcc cttgttacaa ttgagcttgt gcattatttt gatcaaagta  66000
tatggtgtac tattctatgg agatacatgc agtattgatg aaatatggta ttctagccaa  66060
gatacatgac tgctttgaga taaaaataaa agcataagca tatatttgtc tgctcttgtt  66120
ggacaaacat ttaaaaagtt tagagcacac taaatgctaa aaatgctgtg aataaacatt  66180
gaatttttaa gtgggaaatg tacaactggt tttgaatatc cattttacaa agcaagggat  66240
atctgtagtt ggacacaata gatgtcaaat acagaagctt taggtcgtat ttttctgtga  66300
cactaatgac tgtgatgtat gtctgagagt agagtgttgc ctccattgca tgtgattgta  66360
ttgaaatgat tgtaaccaac attatagttt gttcatcgtg gtgcatgttt actgtcagac  66420
tatatctaat actaattcat tttgaaatta ggtgggatct caggtccttg gttatggaag  66480
atttataaat ataagcaaaa atgtaataag tatgattagt tgaattagtt tctgctaatt  66540
tataattctt tattaaaaag cacagtctcc ttttgagttt atccttattg cgtggagaac  66600
tctcattttg acttcaacag aggagtaaat tcattttgca aggtgtttgc ttgtattgta  66660
atataaatac tttttctttt gcacagattg ccacactgaa ggtcaaaata ttttattcac  66720
tgatggagaa tatattaatc agatagctgc ttcaagagat gtaagtatcc tgaatcttaa  66780
gtagctagtg taaatggaat tccttttcct taaattattt agcttttatt agatagactg  66840
tagagccttg aacgacctct ttatgtaatg taatgctgtg gatgttttat ttttcttagg  66900
atggctttgt tgtcagaata tttgccacaa gcactgaacc tgttctacag caagaattgc  66960
aacttaaact ggctagaaaa tgcttacatg cctgtggtat ctcactattc gatctggaaa  67020
aggacttgca tattataagt aagatagcaa attaagtgtt ttccctatat tttaattttc  67080
aatttttcat actcttaaaa atgaacattg tgttttcacc agttcagctt atgttgtagc  67140
agctattttg tgtctgttac tattaatata aaggataatt ttgaattaat atgaataaat  67200
aactgggaaa cacagtcttt aaacaaagta tgatatttga agaccattct aaggaattga  67260
ctaataattt ctcttttttg ctttgaatag agcaaaagaa aataaaattt aatgagaatt  67320
atggatggat attggtgaat gtcattagtt tatatgctgc atcatttttc aactatttaa  67380
aaatttgaaa acttacgttg taaatgttat tacaacaata tacatagttc tctcgttgaa  67440
atttttaaag tttttacttg aatagatttt caaggtaact atagaatgat ctcatagatt  67500
gtcaaaatgg taattggcct tacacacgga tcagtaatct ttcacttgga tagagaaata  67560
cagataacca cagagtattt cttgggctta gattatttac ttttgtaatg ttgtaaaagt  67620
aattaggatc atgagttctc ctgagagttt tagttttggc ttgccatgcc actccaggtt  67680
taatagtgac cttccgtaac ttgtagggtt ctttgcaaga tccatctttt ttgactgtta  67740
```

tctcattaca tttcataaac ttggcattag tgctttactt tctatattct aattatgtag 67800
tatttttata attcttccct agaaaaatct tgaattgaaa ttacagattt aaaattttta 67860
aagcccataa actagttagt agtttgtata gctggacaaa gtcataaaat gtaccatatg 67920
taaagctaca attactcata gttttacaat ttgaaaatat gcataaggat ctgtgtgtgt 67980
atatgcatat ttacatatat atatatttga attgatggag tagctatata agatgtcttt 68040
ctgtagaaaa agacataggc agagaatctg aaatacttta attcaaatat ctgcatggca 68100
ttgttccaag cttgaatgac tctgtgtctg gactaacctc tccaaccttt atatatgctt 68160
atttgtaaac caagtggtat agttgtgaga atcaaatgag ataaattttg tgaattgtat 68220
aatgcctggt acctaataaa cgctcaataa aactttgagc atttatacat taattcaagg 68280
aatattgctg acattgaatt tttaaatttt tttgtcgtat atttaaaaaa ttaatttggt 68340
actggtttgg aacaagagaa acagattatg ataactttat ctttccttgg agtactatac 68400
ctatggttaa tatttttaaa aatttgagca catgacattt tgtcatcctt gtttttttagt 68460
gattttgaat tgacattgca atcacttaaa atagtgcatg ttgtatttag aattcttcat 68520
attagaaatg caatagtatt tattagtctc gtatttcagg tacaggattt gatgaggagt 68580
cagcaattct tggtgcagga cgagagtttg cgctaatgaa aacagcaaat ggaaaggtaa 68640
attattctct ttggattaaa aatgagcatt ctctgattta agagattaaa atacaatctg 68700
ttgattagtt tatatagttt gcatgtttaa gaagaatcat cttttaaatt ttgatttaaa 68760
attatttttt ataagataaa attttattca tgtagggaac agtacaggca tgcctcattt 68820
tattgtgctt agttttgtta cacttcacaa ataattgctc tttttacaaa ttgaaggttt 68880
gtgacaaccc tgagttgagc aagtctgttg gcatcatttt tctaaccgcc tgtgctcact 68940
ttgtgtctct gtgtcacact ttggtaattc tcgaaatatt tcagacttct ttattattat 69000
tatatctgtt atggtgatct gttatctttg atgttactat tgtaattatt ttagggtgct 69060
gtgaattgtg cctatagaag acaggaaact taatggataa aagatatgaa aaagctatta 69120
tgaactgtgt cttcttggca aaatatgtgt atttcttgct caactcccag aagctgaata 69180
gtgtaaaaaa gagtttgttt ttatgtgaat tttattttttc aataaaatat tgatgtcctt 69240
tttttcctc atgtgaaacc tgatgcacta ttccaaaaag taccataatt cctttttttt 69300
tttaatacat aagatatatt acactggcaa ataccagagt cttggaatca aacaaggtgg 69360
tccttcagca ggaaaatggg ttgagctacc aattacaaaa tctccaaaga tagtacactt 69420
ctcagttgga cacgatggct ctcacgccct tttagttgca gaagatggga gcatattctt 69480
tacaggatct gctagtaaag gagaagatgg agaatcaagt aagttgagtg atcaactatg 69540
catttaataa aaataaatgc tttattttag taaaaataaa actttattaa gataaagttt 69600
atgaatttca ataacaccac accaacttta tatatatatc attgacttga tgtaactgct 69660
taataaatac atattgaatg aatgaggaac ttattttact ttccaggatc taacaagaat 69720
acatgtgaat tacaacttgg gaaaaaaagg agattttaga tatgtgttag tagaatggta 69780
ttaataatgc aatagctaat ttagagattg ggccctccag gagtttggta gaaaactaat 69840
attactcact gagaatttga atgtacttca gggaatgagg atctagcaat gatagcgtaa 69900
atattaattg accagatgag gctagcaggt tcactgattt taaatgacat gttgggaagc 69960
ccaggccttt gtgaaaataa acaaatagtg tcataaatgc aaataatatg ggtttttttt 70020
ttagctttat atacaaacca ttattattat tatttgtaca tagaggtctt gatttaatct 70080
aatttctttt ttaaagctaa gagcagacgg caatccaaac cttataaacc taaaaagata 70140
attaagatgg aaggaaagat tgtggtatat acagcctgca ataatggaag tagttctgtt 70200
atttctaaag atggagaact ctacatgttt ggaaaagatg ccatttactc tgatagttca 70260
agtaagttaa taaaaagttt tacttttatg caaagaagtt tcaatactag ttatgtatga 70320
caaagacata tctagaaaat ttatgttggt ggcatgcttt ctctacattt tttacatttc 70380
cttccaaatg tgaaatattt cgaaagagaa attttctgtc atatcttgtc actaggagca 70440
ctgtccctag tttcatgcaa agctaatcat agagcttggc aagggaagct tcgctgtagc 70500
tgtgacttct gtggatgttt tccctagact caggtgctta tgggacatgt ccctgggaca 70560
gtggtagtat cctgaagaag tgattttcat gacatagcta gtttataatt gttgaagtat 70620
tttatctccc ccattagggt gtttggctgg gatgatctgt cttatttact attctatccc 70680
cagtgcccag cacagtgtct ggcacattgt agggtctcaa gaattatttt ctagtgcctg 70740
ggtgactgat aaaccaaaag tttgagaagt ggatatgagg ggtagaacta gctaaatggt 70800
tttatattta taaatgctaa tctcaaaaac ttgtcatatt tggttactag attttctttc 70860
tagcagctag aaatgaatat aatgagtgaa gcatcccact tggaaggatt ttatgtgtga 70920
taaatatgta aagcctttga gtttctttgt aaaaaaggaa actagaatta atgaagttta 70980
tgattagaaa tatatgtaat tgtcccatgc tggggaaatt acacctgtag aacatttata 71040
gcaattaatt attaagtgga ggtgtaccca gatgataagt gaactggctt aatgttgtaa 71100
tatttagatt ctcaattggc tgcagctatc agagtaaatc aaaatttggg agtgggttct 71160
tgtacagttt aaaaataata ttcaatataa ttgttgcttg ctaacatcca ctgggtagag 71220
ctgatggaaa cttgtatatt tcttcaacat atatttattg agcatgggtg atacattagt 71280
gattgatgga cctgacagac ctggatactg cctttttgag gatccgagag acagttgggt 71340
attacagaac ttaaatattg gggaagtggt attgaatggt tatggacata gactgagatc 71400
ctagcaccaa cacttttttt ttttgagagg gagtctcact ctgtctccca ggctggagtg 71460
cagtggcaca atctcagctt actgcaacct ctgcctccta ggttccagcg attgtcccac 71520
ctcagcctcc caagtagctg agattatagg cacgtgccac aacacccagc taattttttg 71580
tatttttttgt atttttagta gagacgaggt ttcactgtgt tggccaggct ggtctcgaac 71640
tcctgacctc aagtgataca ctcgcctcag cctcctcaag tgctgggaat acaggcgtga 71700
gccaccgcgc atggcccttg gcaccaacgc ttttaattgg gtaacagttt acttaatctt 71760
taactgggta acagtttact aaacatttaa gagttttctt tttgtttttt tctacctgca 71820
aaaaatagat aatgatagca cctgcttcat atagttgtta tgaagattat aggaggtaga 71880
acttaagaaa tgcttagcac atcatgtaag gtctcaaagc atgtcagcta gtactgttaa 71940
taataataat aaataactac tgttttatat atatacacac acccttacct ttttcaaatg 72000
tgctaaatat taaaagtgga aatttttgag gtataattaa caaaaagacc taaactagtg 72060
aaaggtgaaa gtgaaggcca ccttaaggta gtgatatctg agctaataat gtagaacagt 72120
tttcccaaag cataatatga gattgatact atttgtaatt taaataaaac aaatacttga 72180
taacatgttt ttattttaat gtatattgga aaaataataa tctttgattg ttaatgttaa 72240
agatgcttca atcaatttag agttgataca aaacatatta aatagataat atgagtggca 72300
cttggatatg acaaatataa tgaaagtaat acatgaataa gtgaagttta gaaaataact 72360
gtgtattgga ttgtggaaga aagcattgta ggttgaaaag gattaaaaaa tactgttttg 72420
aaaagtctca ctggtttcta cataaacaat ttcatgtcaa tatactatgg caagtatttt 72480

-continued

```
actttgtttt gctgaggcag gtcaaagcag gtaaaataaa ttatttatgg actcctttgt  72540
gcttagacca gaaaagtttg aaagtactgt ggagaggtat taccatttgg aggaagcatt  72600
caggagaagt aagcttgaga gaaagctaca gtaaagatat gtcccaagtc tggatgataa  72660
tgttttagga ttcactgaag ctacgttaca aagttacaaa gttaattcag tgatactctg  72720
ccagtctttt ggctacttat ttctcatttt gttgagttat tttgccccag aaataaacgg  72780
ttctgcattg aggtagttct tttactaggc tcagaagggc ctttttgttg tttttactaa  72840
atttgtttct ttcctatagg tttggtaact gatttgaagg gccattttgt aactcaggta  72900
gctatgggca aagctcacac ttgtgtttta atgaagaatg gagaggtgtg gacatttggt  72960
gtaaataata aaggacagtg tggacgagat actggtgcca tgaaccaagg tgggaaaggt  73020
aggtctttaa ttcttagata ttaaaatttg tgttgtcttt tcattagttt ttcagaacaa  73080
catagtgaaa agtcttgttc ttttcaaaat gagtggctct tctttttctt tttgttccta  73140
tttaaatttt ttttaaaaat tttatgggta gatagtaggt atatgtatgg ggtacatgag  73200
ttgttttgat acaggcctac aatgtgtaat aataatcaca gggtaaatgg ggtctccatc  73260
atctcaagca tgtatccttt ctttgtgtta tgagcactcc agttatactc cctcagttgt  73320
taaagtatac aaaaaattat cgccaactgt agccaccctg ttgtgctatc aaatagtaga  73380
tctcttgtat ctaattatat ttttgtgcca actaaccatc ccatttccca cccactctcc  73440
ctgactaccc ttcccagtct ctagtaacca gcattgtact ctctatcttc atgagttcaa  73500
ttgttttaat ttttagctcc cacaaatgag tgacaacatg tgaagttggt ctttcggtgc  73560
ctggcttctt tcacttaaca taatatcctc cagttacatc cttgttgttg caaatgatag  73620
gatctcagtg ttttttatgg ttaaatagta ctaccttgtg tttatatgcc acattttctt  73680
tatccactca tctgttgatg gacacttagg ttgcttccaa atcttggcta ttgtgaatag  73740
tgctgcaata aacatgagag tgcagatatc tctttgatgt actaatttcc tttcttttgg  73800
gtatatccat agcagtggga ttgttggatc atattgagtt ctagtttcag tttttttgggg  73860
aagctccata ctgttctctc cagagtggct gtactaaatt tacattctca ctaacagtgt  73920
acaagtgttc ccttttctcc acatcctctc caacatttgt tattgcctgt cttttggata  73980
aaagccacgt taactgggga gagatggtat ctcagtgtag ttttgatttg catttctctg  74040
atgatccatg atgttgagca ccttttcata tacctgtttg ctattcatat gtctactttt  74100
gaaaaatgtc tattcagaac tttttcacat tttttaattg gatttgagtg gctctttgac  74160
gttatatttg tgaattagga aaaccactga atttcttatt tatttgataa tatttactga  74220
taaaatatca ctggaaaaac aaatacactt tagatttttt atttttgagc aaatgtgctg  74280
gcttactcca atcatcttct aaattctaca taaaatagtg cttctttggc ttagcatctt  74340
tgatgactgc attactccag aaaagtcttt tccaaacatt tttttattag ctgctgttac  74400
acgacatgtt ttaaatttta accatttttg gcagcaatct ttctggcgta tattatcttc  74460
ccatttaaca gcacatgcta cctgtaattt aacctgttct tgacaactaa gagtgatcct  74520
tatgaatatc tgacacttta ccaagaaaag actaaattgt agacacacct tcttcacaat  74580
atcctttgct ccaaccctca ggccattgaa gagaacaaag ggctttctcc tttgattgcc  74640
ctgtttgctg tggtcttgtt ttgttgttgt ggttgtaaat agcatgtcta cttcttgccc  74700
tcaattttta tatctagctg ctatcgttat gtttataact ttcactccaa tttctgattt  74760
tggtcaagag attaaaccat acatatatat tattagaact aagcgttgaa ctttggttaa  74820
agtaccaata atttcgagga ttaatgctgt ataaattaac aaaacctggt ttttctgttt  74880
```

tgaggctttg atgtcagact catctggatc tcagaaaccc accattcttt gtctttgcct 74940
tattcgtgtg tctgtgtgtg tatttaaaat gcatcacttt aaaaatgagc aagttactag 75000
aatatattgg caaatgaaga aggaacaaaa gaaagaaaag aaatggatta cttcacaatg 75060
gaaatacttt gatttattac taaattagtg aacttgtttt ggataataac tgctaggaca 75120
aaggggagaa tcgggttttt ttaatatata atatgaatat atattcagat tatgttttat 75180
aagaagtctg aactaaacaa cattgtttcc ttattctgaa actcttgtga aaattgagcg 75240
tacatttaca cctatgttct agattcttca gtgacatttt gtaataatca aagtaaaatt 75300
gttaaaagat ttttttaata agaatcatac ctaccctgct ggtaagtaat gaattagaaa 75360
gcagatgagt aaagtaagac acatacagtg catactgatt gcagagtcat aacagatgct 75420
ggggagaatg tggagaaagg ggaatgctca tacttggcta gtggaaatgt aaattagtac 75480
agcaactatg gaaaacatag atttttcatt cgtatgaagg tgactcaaaa aactgaaaat 75540
ggagctgcca catgatctag caattccact tctgggtata tgtatcaaaa agaaaggaaa 75600
tctgtatgtc agagagatgc ctgcattctc aggtttatca tagccatatc cacaacacca 75660
agatatggaa tcaacttaag tatccatcaa cagatgaatg agtaaagaaa atgtggtaca 75720
tacacaatag aatattattc atccctaaaa aagaatgaaa tattgttatt tgcagaaaca 75780
tggatagaac tgaaggacat gatgttaact gcaataaaat aaaccaggga cagagacaaa 75840
tatcactcat atatgggaac taaaaaattg atttcatgga gatagtaaat agaatagtga 75900
ttaccagaga cttgtaagga tagtgggagg gggagaggaa gagtggttgg ttaataggta 75960
caaaaataca gttagagaga aggaataagt tctaatgttc aggagcagag tagggtgaat 76020
gtcgttaaca acaatatatt gtgtatttca aaatagctag aagagagaat ttagaatatc 76080
ccagttatct tgacttgatc ccagttaccc agatttgatc attagacatt atatgcatgt 76140
atgaaaactc acatatatgc cataaatagg tataacagtt atgtatcaat ttaaaacgaa 76200
cgtaaaggaa tattttaaaa gtttatttaa accaggaaag tacagaacat attgaaatat 76260
taaaaaattg tgtctctacc atgtcttgtc attttttttc agttaaaaaa aaatcacaga 76320
taagattcaa gtgccccata tccccccttcc aaggcttatt atcatattcc atttctcccc 76380
agagctaacc gcgatcatga ctttgataag catacgttca atcatgttct tatatatttt 76440
tacatgttct tttatatttt atgtgtaaaa taatattgca taatgatgtc tgttttacac 76500
ataaaatata ctactgtttt atgtgttttt ataagtgtta atctgttatt tacatttttc 76560
tacaaatttt tttttctcat cattctgtta gaaatatgtc catgttggta catataaatc 76620
taaatgattc atgttaacta atgtgtaata taccacacag tgaacatgct atagtgtatc 76680
cattctcctg ttgatggatg ggcttatttc caatttttca ttgttataaa tgagtttaaa 76740
acctccttta taaatgtttc ctggaaaacc tgtgagactt tctctgatgt aattgctcta 76800
ttgtggattt cagttttact ggatttttct tgaaagagat tgtaacaatt tatactctca 76860
ccagtagagt tggattttcc acatcacatc tgatattgac agactgattt ttgtcagttt 76920
ggtggctatg aaatgatact gtaatttttt atttgttaca ttgaagtata atatgcatgc 76980
aggaaaatat acatagtatc ttgatgaatt ttctcaaatt gattgtattc atgtaatcag 77040
cacccagatt aagaaaccac atattaccag cagcccagaa agccccactg tatgttcctc 77100
tctgcccttc agttaattac cataaattag ttttcttttt atacttgata taagtgaaat 77160
catgcagtat gaactctttt gtgtccagtt tctttttatt gttttatgtt tatgaagttc 77220

-continued

```
atacatattg ttacaagtag ttatagattg ttcatttttg ttctattaaa ttatatatag  77280
atactacagt tttaaaattg tttctagtat ttgggcattt ggatggtttc cagttttggt  77340
tattatgaat aatgttgctg tgaacattct agtaaatgtc ttttggtgaa agtgtttatt  77400
catggctttt gggtatatac ctaggagtag aattgctggt tctctcactt ttcttttaat  77460
tttcattccc ttgattatta atactgagtt tgaacatctc ttcaaacttt attttactta  77520
ctaaaaattg atttgtagga gctttttac gtattatgtt ttatatatct ttgactaacc  77580
tgtggtttac agtttcattt gttatgtata attttaaaat tttgatgtca aaattttcaa  77640
ccttttcctt tataaatttt tgatgaatgt agcctggtga gagattttat tttccatata  77700
aattagaacc agctttattt gcttggcatt gtgattgaga ttccattgac tgtaaagatt  77760
aatttgagga taatagttcc agtattggaa tgattaaatg agtaatgctt atagagctag  77820
ttacaaatag tgctcagtac attttagcta tgattattga aaatagtcac tgaggcttcc  77880
ttcaggatca ctttattcta atcctagata tagctagctg atgcttggtt atctaatttt  77940
tctgcttgcc catagattag aagtggcaaa accccaaaag gctatatatg ctatgagttt  78000
atttcttggt tagatagacc tgtattgagt gatagctgta tgttaaatgg atgtgatagg  78060
tgtgagagaa taagattgac taagaataag agatattatg agcaagactt aacctcataa  78120
cttagatcct ttaggaaagt caaatataaa aaataattac ttgactccca cagatttgtt  78180
ctcctgtcat agggtcttat aacactgtgt tccttcaaaa ccctaccagt tgtagtttac  78240
atttttattt ggttatttga ttaatgtctg tctttcttac tacattataa gcttcataac  78300
agctcagtat taccgtcttc agtttctaga gcagaggtct gcagagtata acctgatgtc  78360
attttttat atagccctct aagctaaaaa ttgattttac attgtaagga ttgtaaaaaa  78420
tgtgacaaag atttgtatgg gccacagagc ctaaattatt tactggctct ttataaaagg  78480
tttgctgatt tcttgccgtg aaggaatccc tggagtatag taggtgttca atttagaaaa  78540
aaagatgaat gaattgtatt gtaacaccat tttaaaaagt tgttaggtga ggtataaaca  78600
ggcactgagg aggtagtgac tgactgcctg gaaaaggtag caagtgcttt aatagggaat  78660
gacttctgag ctgaattttt gaaggctgaa gtttctctac tagatgagat aggcagagac  78720
atcttgtaaa tgaggaagga agaggcagag ggagcaagaa tgaacaaagg ccctgagcat  78780
atggaaggac acagggtgtt tggagagcag agggaaaaga aatgagattg gagaaaatta  78840
ggagccatct tgtgcctact gcctcttgct gagttttgtt cttctgaaga ccttggaagg  78900
tcactggagg tttgtaaatt atgaagttgt catgtgcttt gggagggtga ttggtggcag  78960
taggaggatg atctagagtg gggaactctt ggcttggagc atggttggga ggctttcttt  79020
ggtctgttga atgaaagtgt tggtagtgag gatggaaaac aggaaaagat ttaaaagtat  79080
gattgacaga aggtaacagc caagagacat ttgacaatag ccttccttgc cttcttttgc  79140
agaaatgaaa tggggagagt gtttattagt ggtccctaaa ttaaaattta tttttgttac  79200
tcaaatttaa gcatttcttt gtataattgc ttggattagc atgctgtcat tttttaaact  79260
gggaaatata gtcatccatc ttttatacat gaaagtaacc tgtataaaaa ttacaaattg  79320
atctgtcaaa tagggtttgg agttgaaaat atggcaacag caatggatga agacctggaa  79380
gaagaactag atgaaaaaga tgagaagtct atgatgtgcc ctccaggcat gcacaaatgg  79440
aagctggagc agtgcatggt ttgcactgtc tgtggagact gtacaggtta tggagccagc  79500
tgtgtcagta gtggacggcc agacagagtc cccggagggt aagagacaat gattcctact  79560
aaagaacatg tgcagaacac atttctttgc aaaatcattc cggagtatac tctactatta  79620
```

atattttttt cttaaagacc agtggcatct tcacttgatc ttagccaaaa ggccaagaaa 79680
gtattataat tcttataatt gttttctgtt ataataattt ataatttaat gtcatctcta 79740
aggttgcctt tctttcattt gattcattta aaccattatt taaaaacaga ccataagttt 79800
ttcaagactt ggggctgtac ttttatttgt attattttc aaagcctatt taatgctaga 79860
tatctattat atttctttct gttgaacatg aatcttttct aaataaaatt atcgatatca 79920
taaagagtac ttgattagat atatagtttt gttttaaatt aaatgtacca tttataaatt 79980
tagaaacgtt gtatgcttgc ttctaaagtt acatcatacc tgctatattt atccttgttc 80040
tcaatggacc acatttttca gggttctata ttattgtcaa tttacagtta atatgtaagt 80100
ttggcagaat aagaatgcag gttttctgct aggatgttag gaagaatttt gaatctattt 80160
tctacattgc tagttatagc cactataaca tgatgggata ttctttgtgt gatcagcttt 80220
gtaataattg gctgatttgg gggagtagag aaaattttgt gaagagaagc ccagaaggaa 80280
gacagccatc cctgcctctt gaccttcctc tttgtcaact ctgtaatagt tgcttcttcc 80340
caaatattgt ctggatctaa taggagttta tttctaagtt tatatttggc ctttcatagt 80400
taaataggtc atatataaca ggccttttct ttaaggctgc tgagatatga tttttttttt 80460
ttttttgaga cggagtctcg ctctgtcgcc caggctggag tgcagtggcg ggatctcggc 80520
tcactgcaag ctccgcctcc cgggttcacg ccattctcct gcctcgacct cccaagtagc 80580
tgggactaca ggcgcccgcc actacgcccg gctaattttt tgtattttta gtagagacgg 80640
ggtttcaccg ttttagccgg gatggtctcg atctcctgac ctcgtgatcc gcccgcctcg 80700
gcctcccaaa gtgctgggat tacaggcgtg agccaccgcg cccggccatg aacttttaaa 80760
aacaaatttt ctttacatta ttagtataag caataaagtc gtctttatca aaggataata 80820
tttattctgt agtgctttat gtttggctct gttttctgtt ttttaagcac ctaacttctt 80880
tatttttaaa tttaatttgg atgcagaaag actctgatta ttttttaaca atgttggaat 80940
tgaaatttat tctcctggat ctctccaacg ctatttccat taaaattcag tgttagctgg 81000
gtgtagtggc ccatgtctgt aatcccagca ctttgggagg ctgaggccag aggatcactt 81060
gaggccagga gtttgaaacc agcttcagca gcatagcaac acccctaact caaaaaaatat 81120
ataataaaaa taaaatttaa tatccccact ctctgagctt aagcagccag tatatatcgt 81180
gaacaaaatc tataaattat ctggtccctt ttgaaattaa ttattcttcg tttttttcctc 81240
cagagactta cataatttat aataattatt catagactta catggacaat actaaccaag 81300
tataataatt gctttatgaa tgaagcaaac tgaatatatc agaatattaa ggactattaa 81360
gctgacttca attattataa aattgtgact acatatctta ttatgataaa gtacatataa 81420
aattgaccag cttaaccatt tttaagtaga cagttctgtg gtattaaatc cattcataat 81480
gttgtgcaac tattaccacc atgcatctcc ataacttttc atcttgtaaa actgagactc 81540
tgtaactgtt aaacaatgac tcctcattct tccctctccc ctgcctctgg catccactat 81600
tcttgttttc tttctgtgtc tgattgacta ctctaggtac ctctcatata aagagaatca 81660
gagtatttgt cttttttgtg actggcttat ttcacttagc ataatatcct cagttcatcc 81720
aggttgtcac atatgtcgga acatctttgc tttttgaggc tgaataatat tctattgtat 81780
gtatattacc acattttgct tatccattca ctcactgatg aacactttgg ttgcttccac 81840
attgtaacta ttgtgagtaa tgcgctgtga agatgagtgt acaaggagct ctttgagacc 81900
ctgttttcag ttcttttggg catataccca gaagtggaat tgttggacta tatggtaatt 81960

-continued

```
ttatttttaa tcttttgagg aactgccata ctatttttca cagcggccaa ccatttttaca  82020
ttcccaccaa tagtgtacag atgttccagt ttctccacat ccttcttaac acttatgatc  82080
tgttattttg gtagtggcat cctaatgggt gtgagatagt atctcattat agttttgatt  82140
tgaatttctc cagtgattag tgatgttcag catctttcca tatacttttt ggccatttgt  82200
agatctttgg agaaatgcta ttcaagtcct ttgctcactt ttgaatcagg ttgtcagttt  82260
cttttgttgt tgttgatgag ttttaggaat tctctatata gtttgaatat taattcctta  82320
tcagatatat gatttgaaaa taaaaagttc tgtctgtggg ttgtgttttt actctgttga  82380
tgttgtcttt tcaagcagaa aatttttaaa attttcatga agtccagttg tctattgttt  82440
tttggttatt gtcgcctgtg cctttggtat catatccaag aaattatttc ccaatctagt  82500
gttgtgaagg gttactgtta tcttttcttc ttcttttttt ttttttgatt atactttaag  82560
ttttagggta catgtgcgca acgtgcaggt tagttacata tgtatacatg tgccatgttg  82620
gtgtgctgca cccattaact cgttatttaa cattaggtat atctcctaat gctatccctc  82680
cccgcttccc ccaccccaca acaggccccg gtgtgtgatg ttccttttct tctaagagtt  82740
ttttgttttt ttttgtaata gttttaggtc ttacatttag gtctttgatt cattttgagt  82800
taatttttgt atatgctgct agagaagtgt ccagatcaag ttttcccagc aatgtttatt  82860
gaaatgatta tcctttctct attgaaccat cttggctcct ttgtcaaaaa tcatctgacc  82920
atatatgtga aggaagattt ctcagctgtc tattctatcc cattggtctg tatgactgtc  82980
tttatgccac accacattgt tttgattact gtagatttgt agtaagtttt gaagtcaaaa  83040
ccgagtactt tgttcttctt tttcaagatt gtttggctat ttgaggtccc tagagatttt  83100
ctatgaattt taggataggt ttttctattt tgtaaaaacc atcattggga ttttgatagg  83160
gattacaatg aatctgtaga ttgctttggg tagtatgaac atcttaaaaa cattaagtct  83220
tctaatccat gaacatagat gtgtttctac ttatgtcatc tttaatttct ttcagcaatg  83280
ttttgtagtt ctcatttcac ctcattggtt aattactaag tgtattcttt ttgatgctat  83340
ggaattgttt ctgtaatttc cttttcatat tgttcattgt tagtgtctag aaatacaact  83400
gatttttgtg tgttgacttt gtatcttcct actttgctga attcattttc tctattggtt  83460
tttttgagtg caatctttag ggttttctac ttatgagatt gtattatctg tgaacataga  83520
taattttact tcttcctttc tgctttggat gacctttatt tcttttcctg tccaattgcc  83580
ctggctagaa cttctagtgc tgtttaggat tggtcaaagt gagcatcctt gtcttcttcc  83640
tgatattacg aggaaaagct ttcagtctct caccattatg atgttcactg tgtgtttttc  83700
atatgtggtt tttatgttga gatcatttcc ttctattcct agtttgtcta ctgtttttat  83760
tatgaaaggg cattgaattt tgtcaaatgc tttttgtaca tcaattgaga tgatcatgtg  83820
tttcttttct ttcattctgt taatgtgtta cattacatgg attgattttc atttgttgca  83880
ttccaggagt aaatcccact tcgttatggt gtataattct tttaatatcc tgctgaattt  83940
gttttgttag tattttgttg aggattttca catcattatt cataagggat attggtctgt  84000
aggggttttt ttttttgcct ccccctgccc ctctccctcc tccctttctt ctctttctcc  84060
ttctccttct tctttcttct cctcctcctc ttcctccttc tccttctttt cctccttctc  84120
cttctcctcc tgctcctcct cctcctcctt ctccttcttt tcctccttct cctccttctc  84180
cttcttttcc ttcttccttc ttcttctttc ttctcttctt tcttcttctt tttcttcatc  84240
ttttgtctga cattggtatt ggggtaatcc tgacctcaaa gaatgaattc ttgttctctc  84300
ctcttcagtt ttttggaaaa ttttgagaat tggtgtcata aacactattt taaaaatagt  84360
```

gtcagtcagg catattactg tgtcacagtt tttactgtgt agtaagtgat cttccaaatt 84420
gtttataatg cttgctttta aaagtgacac atttcacagg gtgtctagct atgtctttta 84480
aactgctgcc agatatgttc ttccttttgt accttctgaa atctgtataa cctggggttc 84540
aacaaggctg tcaaaagttt caagaactga tctgatgaac tacattaaag ctataccttc 84600
tacaaaatat gtgactaaga agttactttc cctgacccca agtcagtttc tgggagtgtc 84660
tttgtcaaca tataccccat atggttcaca atcgatatga aagggctgaa ggagaaaaag 84720
aacaggtaat tggactctgt gaaaggagag aatgggaggt gaaggcatgt aaagaagaga 84780
gggggaagga gacatatatg tgtttgtgtg tgtgtatata tatgtgtgtg tgtgtgtata 84840
catatatata tacatatata tgtattattt tttcctttcc aatgtgtgaa tgtttttatt 84900
tcctttgtgt gtgtgtgtgt gtgtgtgtgt gtgtgtgtgt gtgttacttt acgttctggg 84960
atacatgtgc agaacgtgca ggtttgttac ataggtatac acatgccatg gtggtttgct 85020
gtacctgtca accggtcatt aggtatttct cctaatgcta tccctcccct agccccccacc 85080 ccccaacagg ccccagtatg tgatgttccc tttcctgtgt ccatgtgttc tcattgttca 85140
actcccactt atgagtgaga acatgcagtg tttggttttc tgttcctggg ttagtttgct 85200
gagaatgatg gtttccagcc ttcattcatg tccctgcaaa gaacacgaac tcattctttt 85260
ttatggctgc atagtattcc atagtgaata tgtgccacat tttctttatc caacctatca 85320
ttgatgagca tttgggttgg ttccaagtct ttgctattgt gaataatgat gaaataaacg 85380
tacatgtaca tgtgtctttg tagtaggatg atttataatc ctctgggtat atacctagta 85440
atgggactgc tgggtcaaat ggtatttctg attctagatc cttgaggaat taccacactg 85500
ccttccacaa tggttgaact aatttacact cccaccaaca gtgtaaaagc gttcctattt 85560
ctccacatcc tctccagaat ctgttgtgtc ctgacttttt aatgatcacc attgtaactg 85620
gcgtgacatg ttttctcatt gtggttttga tttgcatttc tctaatgacc agtgatggtg 85680
agcttttttt cgtttgttgg ctgcataaat gtcttcgttt gagaagtgtc tgttcttatc 85740
cttcgcccac tttttgatgg ggtggtttgt tttcttgtaa atttaagttc tgctgcataa 85800
ataaatgtct tcttgtaaga agtgtctgtt catatccttt gcccactttt tgatggggtt 85860
gtttgttttc ttgtaaatgt gtttaagttc tttgtagatt ctggatatta gccctttgtc 85920
agatgagtaa attgcaaaaa ttttctccca ttctgtaggt tgcctgttca ctctgatgat 85980
actttctttt gctgtgcaga agctctttag tttaattaga tcccatttgt caattttggc 86040
ttttgttgcc attgcttttg gtgttttagt catgaagtct ttgcccatgc ctgtgtccta 86100
aatggtatta cctaggtttt cttccagggt ttttatagtc ttaggtctta tgtttaaatc 86160
tttaatccat cttgaattaa tttttgtata aggtgtaagg aaggggtcca gtttcagttt 86220
tctgcatatg tctagccagt tttcccagca ccatttatta aatagggaat gggaaggaga 86280
catattacat gaagctggca agcttaggct ctgttgctga aggctaccaa cacctgcctt 86340
cacttatctg ctggacagca acattgtttg attgttttta gccaaccaac ccatctgggt 86400
cacttaatcc taaagcttct ggtgcttcac taactgcaaa aagactttta aaggattgtt 86460
tttaaagtag tgactttgat gatagtcgaa tctgtgtgta ttttctgtag aaatatacca 86520
attatgccta ttgggagttt aatcagtctt gtttttaatt attctgctat ttatatcttt 86580
tctttaaaat gaacaatcgt gatctaaaga ggtgatttca ttgcttactc atttaacaat 86640
ttcaaaaatg tggaaaataa gttatagaaa agagttttaa agacaaatta ggaatatctc 86700

-continued

```
agttgtcttt tttttttttt tttgtatttc cccctaggat ctgtggttgt ggttccggag  86760
aatctggttg tgctgtgtgt ggatgttgca aggcctgtgc aagagagtta gatggtcaag  86820
aggcaagaca aagaggaatt cttgatgcag tgaaagaaat gataccttta gatcttcttt  86880
taggtaattt tgattgatta tactatgcta cactgagttg tcctcaactc agtaagtctg  86940
acagtttaaa caatttcttt tagatatatg ttaataaatt aggataataa ttaatgtatg  87000
caatactgct tttacggtaa ctgacaatat gacattgttt aagggatgag attctttttt  87060
tttttttctt tttttgaga tggagtcttg ctctgttgcc aaggctggag tacagtagct  87120
caatctcagc tcactgcaac ctccgccttc taggttcaag tgattgtccc atctcggcct  87180
cccgagtagc tggaattaca ggtgcccgct accacacctg gctaattttt gtatttttag  87240
tagagacggg gtttcaccat gttggccagg ctggtcttga actcctgacc tcaggtgatc  87300
tgcccacctt ggcctcccaa agtgctggga ttacaggtgt gggccaccat gcctagccag  87360
aatgagattc tttttccctt tttggctaag aattattaaa gtaaaaatat tgtgtgtttt  87420
agacaatgtt tttgctagct tttactttct tgaattttat gtagttctgt catagctatt  87480
atataacata tatgttgttg ttgttgttgt ttttggccaa tcatctagct gtcccagtgc  87540
ccggggttaa cattgaagaa caccttcagt tacgacaaga agaaaaacgg caacgtgtaa  87600
tcagaaggca cagattagag gaaggaagag gtaagatgta gctacagaga aaaagtacat  87660
gaaaatccac tttcctaccc tatcctgaaa ccactgaaaa gttcacacaa taaactaatt  87720
tggtaagaaa tcatcaaaat taaaattagc aatattctga taactcatat aatgggaaaa  87780
tattcagggt attcatgctt cttctaataa catacgttta ggtatttata attgtgctaa  87840
taacatactt ttaattcagc agggtgttta tggcataagt cagccatatt aagaactgtg  87900
ccatctgcct actatcaata actattagaa atggcaactt tttaaaaata gatattctca  87960
caacttgtcc ttcacccgga ctttggactc atctatttga ccgtggaaca aaattcaatt  88020
tagtcttttt catttctatt ttcttactca tttatgctca ttatcatttg gacatagtcc  88080
tgctatgctg ccctccagtt cagcacataa ctatgctttc atgtgtcctt ttttggaaaa  88140
acctcattct agttatttac aggaagagta agatggcagg tctgcaggtt tcatttgcaa  88200
agataggtct attgtttatc ttttcctcat tgtttatgag cttaaaagtt tcttagctta  88260
aaaatacatt taactggcca ggcacggtgg ctcacgcctg taatcccagc actttgggaa  88320
gctgaggcag gcagatcaca agatcaagag atcaagacca tcctggccaa catggtgaaa  88380
ccccatcact actaaaagta caaaaaaatt agctgggcgt ggtggtgtgc gcctgtagtc  88440
ccagctactc aggagactga ggcaggagaa tcacttgaac ctggcaggtg gagcttgcag  88500
tgagccatga tcgcaccact gcactccagc ctggcgacag agtgagactc catctcaaaa  88560
gaaaacaaac aaaaaaaatt taactgtggt tataattggt atttgaatac gcaaagataa  88620
atatatgtat tactaaagat ttccttgctc agtaaatttt tttttgtag gattaagaca  88680
aattgttatg gaagtctatg attttattcc tccaataggc aaaattttga ttagaaatgt  88740
ttactgatat tgcatatttt aaatgcttat tagaaatggc atgatatttg atgcatgaaa  88800
taaacctttt acccatttaa ccatcattat atttttttct agctattctt tttgttaata  88860
tatggaataa gtagtaaaat gtataataca catggtgaat tctagtttta ctaaacttaa  88920
attgtaaaac atatacttgg cacatgaaga gtgttcttca tagcatctga taagtgatgt  88980
tgattgataa ggtgaatatt tactattgtt tggctttgct tgcataatgt cctttaaagg  89040
atattttaat gagattaata tagatactgt cagtatttac attatataag tatatgggaa  89100
```

```
aattgcatgt taaatatttc ttacaaaaca ggatagaatt aagtttctga tgtggtaatt  89160
aataattttt tatgttgata taattttttc agattagtta ccattctatc tgtttgctac  89220
ctgtttcttc tttctttaga aatattaggt tgagcgacat gaatgaacct acaaaatgca  89280
gctatttctt acatttaaac tacagtatag cacatcctta cacttaatta ttcacattta  89340
attacttgcc taatgcggtg tatcttgtta ctctttttct cttccctcta aaaaagctat  89400
tcttctctag gtatagtata tttgtgcata taggaaataa aggaacattg aatcgtgcat  89460
tgataacttg acataacttg gtgattgcag aatattcttt tgccatttat ttttaaattt  89520
gacataaacc tgtgaaacat aattgtaaac attaaccctt taaagttaaa aaaaaaatcc  89580
tccactagct aaatatttaa agaaattatg ttgttgtatc tgactttcca aagatagatt  89640
gaggttctag gcacttagtg tatattttgt gacaaatagg tttcatctgc agtcctaaat  89700
atatagaaca tcagtagaaa cactttgttc agattattgg tgtacataaa ttttatcttg  89760
tccttatttt ttggtagaac tctttcttag atcaccctcc ttcatgtttg gtaaaacaat  89820
atatagtgaa tatcttttct tgagtggaat cttcagtatg aacctcaatt atcacagtcc  89880
ttgctttcca tggcactaaa attaacagaa atgtgtgcac attggaacca tgtcctcccc  89940
tttcacagtc accacagtta cctagaatca tgcgaaagga ggacagagtt cccgtatttc  90000
tgtgtttcag ttaacacagc actatgcaaa gtgatgcctg cttgtatgtt ttgtttgttt  90060
gtttatttat ttatttattt tgagatgaag tctcactctg ttgcccaggc tggagtgcag  90120
ctgcacaatc ttggcccact gcaacctctc cctcccaggt tcaagcgatt ctcctacatc  90180
agcctcttga gtagctggga ctacaggtgc ccgccaccac gcctggctaa tttttgtatt  90240
tttagtagag gcgaggtttc accatgttgg ccaggctggt ttcaaactcc tgacgtcaaa  90300
tgatccacct gcctcagcct cccaaagtgt tgggattata ggtgtgaggc actgtgccca  90360
acctatttta ttttaaatga atatttttgc atttggacaa gaattctaac tatgtattca  90420
tttttaaaa aatcaaactt cagagtcatt cagtgacttt ggaaatcctt atactgtatt  90480
aagtaattaa aaatctattc tgatatgaca cttttatgat tttatcttta tattattctt  90540
agcactccat taagcaattt ttatttaaaa acaaattttt ataagaaaac aaaattagat  90600
gaatatgata tacttacact tccatagaga taaaacaaga aagataaata ccaaaatatt  90660
aacaatgctt tttcctgaca ggtgagttta tagatatttt ttattttctt ctttacaatt  90720
tgtttcctaa atattctcca ataagcatat tagtgtataa atagagtaaa agttatgttt  90780
tacaactgaa gccattttaa aaaaatactg attaggttta aggcatccat actttgctta  90840
cctttgcttt ttaaaaaata tttttatttt aattggatgg aggactctct ttcaggtgct  90900
gtgcttttca ttactttctg gccatggttc tcaaggtggt ctcaaaggga ccagcatcac  90960
ttgggcactt gttagaagta ccagttctca ggccccactt cagatctcta ctgaaacaaa  91020
aaactggggg agtacagcca gtaaactgtg ctttaatagc gttccaggtg attctgatgg  91080
tcccaaagtg tgagacttag tgtgctaggt cagttgtttg cactttgcgg tttgatccaa  91140
tgaccttctg catcagaatc acctgggcct aatgaatcag aatttatggg tcaagggtct  91200
tggaaataga tctgagtcac ttgcacagtg ttctaaggct cttctctggc actgtgctag  91260
aaaagattgt agtggctttg ctcccatgag gaatagaaac atcaaataaa atgttagtgt  91320
tccggctgcc atacatacag atctttttatt tctttggcct gttgatactt tttagaaact  91380
aaaaatttag tagtatgtta ataattatac ttactagtaa ttggctttta cctgtgttaa  91440
```

-continued

```
cattccagaa tttaagaatt aggttatgtt agattatttt acttgacttt tctgtctcat  91500
cttatttacc aagtctgaac taagtttttc atagatgatc agaactctgg gctctagttc  91560
tttttttttg agtcacagtc ccactctgtt acccaggctg gagtgcagtg gtgcgatctc  91620
ggctcactgc aacctccgcc tctcggtttc aagcgattct cctgcctcgg cctcccgagt  91680
agctgggatt ataggcatgc accaccacac ctggctaatt ttgcattttt gttagagatg  91740
gggtttcacc atgttggcca ggctggtctc aaacttctga cctcaggtga tcagcctccc  91800
aaagtgctgg gagtacaggt gtgagccact gcgctcggcc tgggccctag ttcttgtact  91860
aaagccttgc tcagacagct tcaggcctat tgacgtaatt tagttactgt tttatgacac  91920
caggtctctt ataatggaat gtgttattga aacccaagaa agcaatgata ttactgcttc  91980
ttcatacatt tggaactttt taattttaaa tctttgtgtt attaatagtc tagttaattt  92040
ttttaattta tctttttagg tattaatagt attcatttat agattttagt tcaatggttt  92100
gtgataactt gtcttttta gattatattg ggttgattga tgtattaatt taactgtgca  92160
agtgaagtgc ttattcagtg aaattcttaa gtagggctct tgaagtcatc agaagaacta  92220
gtggatgatc atatcaatga ttttatcctt atattccttt tcagcactct gtttcgtaag  92280
gaaaattaaa cttcaataat gttagctttt tcttctttct tctaagtatc caagtttcat  92340
aattgtgagc tgtagatggg ctaaacccat gtcctggctt acatgggaga gtcccatttt  92400
ataggtgtcc aggcatattt cttttttttt tttttttttt tttttgaga cggagtctcg  92460
ctctgtcgcc caggctggag tgcagtggtg ctatctcggc tcactgcaag ctccgcctcc  92520
tgggttcaca ccactcttct gcctcagcct cccgagtagc tgggactgca ggcgttcacc  92580
accacaccgg gctaattttt tgtatttttta ctagagatgg ggtttcactt tgttagccag  92640
gatagcctca atctcctgac cttgtaatcc gcctgccttg gcctcccaaa gtgctgggat  92700
tacaggcgtg agccaccgcg tccggcatgt tgctattact ttttaagccc ttaaaaccat  92760
tatggttttc ttgatttgac gcatcaaatc caatattagc tgatattcca gtgacacata  92820
aaagtctctt tttaaattaa agtattatat gaagaattta gagagtataa gtaagaaaaa  92880
atagatcagc ataacccttt atacaaagag aaccattagt agaattttgg tgtaacttct  92940
cacacttttt tacttatttc atataatttc atactgtgat agatattggt gtcctgtttg  93000
tattcccttt aatattatat catgaaattt ttttgtgctt tattgcaaat accatattaa  93060
agtaatatag gaatttaggt caaggttttg cataaaccta ttccttaatt caattattgt  93120
ttttatttcg ttgtcatctt ctaatcaagt tttacttatt tctagttata tcattgactg  93180
aattttgttt tacatttttg cttagtgtta taatacatat atttttatgt tttgcttgta  93240
ttgtacccct accttcccat ttccatcccc ccctcaaagt aaatgttaat agtctaatat  93300
cttactctat taaaatataa tcatgtacag agacttacac atatgtgaaa gtgtagacat  93360
atgtttattt acaaaagtag tattctgtat atacatttgc aacatctttt tctcatttta  93420
caatacaaga agaacacact gtaggtcagt aaatgtggat ctaccacatt ctatacagta  93480
actacctaat atcataatat ggctatacca tagtttatat aaccattatt tattgatggg  93540
cattcaggtt attgtaagtt tttgtgggtt ttactgtaat aaatattctt aaacttagag  93600
ctacatatta gtgtttgtat agtagagctt tcccaaaata gaatgtgtgg ggcagagagt  93660
atatatctgt cttaaatttt aacagataat tcacattgtt ttaaaaatgt tataggaatt  93720
tgtttatact ccctagacta atgtataaga gtagtgtttt cctctagcat cacctgtatt  93780
cattattctt ttatttattt atttatttat ttattttttg tagaggcagg atcttgctat  93840
```

-continued gttgcccagg ctggcctcga acaactgggc ccaagtgacc ctcctgcctc agcctcccga 93900
gtagctagga ctgtacaggc atgtgccacc acacctgggt ttagttattc tttttaattc 93960
ttggaaaaca gtggtgaaca atgttatctc attgttaatt taaataacac aaaatcatat 94020
tctgtgtaaa attatttcat aaatctcatt ttaatggctg cgtattattc catttagtag 94080
atgtattata gtttttaatt actttcattt gggtattttt aaaatgttgc tataatgaat 94140
aaagttgtag taaacacctt tgaggtgaaa tcctttaaaa atattttaga gttttcttta 94200
ggatagattc ctagggtgca gttactagat caaaggataa taatttttat gatcttgaaa 94260
tatatcacca agagcttttct gaaaggcttg tactatttaa cactgccact tattccatgc 94320
tttttctgcc tacctgccta cagatgaact ctgaattacc cattgtctac acatgagtgt 94380
agcttctatc taaacctggt tatctcatac ccctatttta ctcactcctc tcccaatgaa 94440
agaaataaat caccaagttc tatttataca gccttcttaa ttctttaata gctttttaat 94500
atctactttt cagaatctta ctgtttcctt agctgaggct tcttttcttt gcctatctga 94560
cagcaaaaag ccttttaact ggccttacct ccagtcttat cttctaagcc attagccacc 94620
ttctttccag aatattcatt ctgcaataca gatcagatca gtagcacttc tctgtttaaa 94680
accaaaaggc tattcatagt ccttaggatg aaggatatac ttttatctct acagcctcat 94740
ctctctctat tctcatttct tttcccttgc ccttcctttt tttcccctac ctctgaacct 94800
ttatgctact tgttacctcc tttatttgac ctcatcttat gtggtggttt cttttatctc 94860
tacactgtct accttcccac cctcaagttt tgttagcttc tcctctagtt tgtgtgcctc 94920
cttttgttat agcatactgt cataatttct tgtttagttg tgtgtaaacc ctccctcccc 94980
tcattagaat gtgagcttct tgaagcagag attgtatctt gtttatcaag ggttcccaga 95040
acttcacatg gtacctgtta gtaccatgat ttgtagtata tttttgttga ctaattgaaa 95100
gcaggttagg gacttatcat ctctagaatg aagttttgtg gtataaaaag gttttaatta 95160
tctgtttttt tgcatacctc tccaagcaaa tttcccaaga cttttgctcc atcacatata 95220
ctctgtaaaa gtcagctaca tgtattttta atgactatac aatattgttt aatatcttta 95280
tgcttttata aaatcctaat ttatatccta ttccttttaa ctggaatgcc ctctcttcct 95340
ttccttttct cttgttaaac tttttgtcat tctttgaaac cttgctgatt gtcctgagtt 95400
tatttagtat cttttcttac ttcaggacat aatgtgtata gatttctttt atagcattta 95460
ttgtaatatt tcatagtttg tgtttttatt tctgtttttt tccctagtgg actgaattcc 95520
agtgagacct gtatctttgt cattatattc atttcaccta gtgtctgcta aataaaagat 95580
aatcagaaaa tttggtgaat aaattagtga ctcaactata tttaaagaaa cattatttta 95640
gcccatggga tacaatagta ttttcgagcc caattgcttt aatttttaga catgattgcc 95700
cccgtgcctt cttgatttat aaatcaaaag attctaaaaa gattgaattt agcaagacat 95760
taaacgggtg tgggtgtgat gtattttcat gaggagaaac aatattgtag gcagaccata 95820
gaaatcagaa aatggtaata taacaatatt attaccttaa tatctataac ttttttatat 95880
agttggaaaa tactttttat agtaatttat atatctgctt tgtaacaatt gagaaatcat 95940
gcatgttaag aaaataaggc attttgttca tatttgttca tatttgaaat atcaatttta 96000
ttacatttta gaaatggaac tcagtttaca taaccttagc ctgagaaaat aattggtact 96060
gcattattga gaacttattc ttctgttaac attaaattag catgtttcta tctgtagtag 96120
tcatagaata tgttattcat ggtttttcat acaatttgag gtatttgcat ttttgtttat 96180

-continued

```
atctagaaac ataattgaaa tatggttcct ttacccactt gtacatttaa tgaagggtac  96240
tttgatattt aatttgacat ttatgaaatt ttattagagg gcagtaggct caatttgtcc  96300
catcattaga aaaattaaac tgaagatcaa tagagaatca tgaaaaaact tgttttaaat  96360
aaaaatgttc agtgcttata tagtgtcata attcctgttt cagttaatgg taacctgtca  96420
aatttagagt gttttcaaat ttgaagacat ttttgatgtt gttaaaactc aaggaaacta  96480
tagttctgct gtataagaaa aaaacctaaa attttaagtt gtaactaaaa tttatttttc  96540
ttttcaaggt aaataaatgt taatgggaaa aatgatttat tttattttat taaaataaat  96600
ttggctgtat attttttcct taaataccat ataagtggaa agagctataa tctgtgtggg  96660
tatgtattta tatatgtata tatatatgta catagtggca ctttagaaga aatgatttaa  96720
tgaaagatgt ttccaaaatg ttatttgggt taggtgcccc ctttaccatc aatataaagc  96780
ccaagctcct ttctctctct ctctctctct cgttctctct ctctctctgt gtgtatacat  96840
atatctatat gcagaatata gacatttttg ttttgttttt gatcatctgg ttttcttaac  96900
ctctatttat gatttgtagt aaactcggta acatttttat tttggttttg tagcaagatt  96960
aatacaaata ttaaacctgg aagagcttgt taaaacttaa tggttaattt aaaaattagt  97020
ttttatgttt caatggaaaa gatatctgtc ttcaacgaat acatggttta ctgactttga  97080
atatatatga tattaaaaaa gtatttgtaa gataatttga ttgatttaaa ttgaacttct  97140
tgattatcta tttgagacta ttagtaacta cacaataatt ttatgagtat acaagacggg  97200
ttttgtactt tataaattat atttaagata ttaactttta tgtgaaatgg tgattaggtt  97260
atgggtgggg gtggggggct ggagtgggga aattggaaga aaagtataat gtccaaaacc  97320
gttaagaata aatttttatg ctttttagtt tgaattattt tttgttcatt atagtgtttt  97380
cattttgtga gtttttctat gcacatacaa aatgtttctc ctcaggcccc cttgtatttg  97440
ctggtcctat ttttatgaac catcgagaac aggctctagc cagactcaga tcccatccag  97500
cacagctaaa gcataaacgg gacaagcaca aaggtatttg gtcttcctta tcacctaggt  97560
gggatacttt cccaatttct tccactcatt tgaattttgt ctctgggaaa atgcacaaac  97620
ctgattcttc tactttgctt ctatcatgat gtagcctgag gagaaagaac attctgaaag  97680
tgataccgtt tgtcagtgac tgtcatgctt cttgtttttt tgttgtcgtt agctttcata  97740
aaggagatat tttacaatat atcttttcct tgtccatttc ttttcaaatt tcaaaaagtt  97800
aagggaaggt ggaaaaaata attattgctt tctgtcttac atcctttatt atttgctctt  97860
taatgactgt gatctggcct tttacaattc ttttttgaat gctgtttata tgctttagga  97920
taaacaatat tactaaattc agtatattaa atgatgataa taagactgcc attacacttt  97980
tccactgttt attaattaag tttatataaa caacaaatga atatacaaat atttgatggt  98040
tgtgggttaa gtagagataa gtgcaagcaa agcacgaatc atgaagactt tctctagtcc  98100
ctggtgatgg tcagagggct atcctagtct gtgaggaagt aggaatctag ctcggtgttg  98160
tcctttgaga tctcagagtt ctgggttaat taaatatatt cttaaagcat gcttattttc  98220
ttgtaaacca caaattatgg gtcagctaag atcaggaaag aatttaatac aaggaattta  98280
taaatttata taaaattttt gccttgtatc ctggcctttg aaccagtgtt cttccttagc  98340
tagcacaact taaaactccc atttcttaa atgcctaaga taggtcctgc aaaatagaat  98400
aggaagtttt aaaaacatgc tttccatgta gacaaattaa tctaattaat gtttggatcc  98460
ttttcttttt tttgctgcaa aattgtcata gtctaattta aaaaaatttc ataggcaata  98520
tagtataatc cactttattt ttatttgcct ctttcagtct gtcagtttgc cactcaaaac  98580
```

-continued aaaaacataa acaaaataga caaaactcat ctttagtaaa ggtgtaaata gagcacaact 98640
taagatatac tctgcagaaa taaaaatagt gttttaaatc taatgcaatt aaccacagta 98700
aaatttgtga ttactttatt tactgagtgc tctaacaatg ccataaatat ttaaggaatt 98760
ttcaacctaa gacagctgat tccaaaaaga aaagatacat atataaggaa taatatttgg 98820
ggtatgcaat gaaattgtta tttgccagaa tgtctgatct tttatgattt ctactatgtc 98880
acaattagaa cagatttttt cagtttcttt cttcccccaa atatatgaaa gtgaagtttt 98940
cccaatagtt taactgaggt taaatattca catttcatga aacagtttaa aacctttca 99000
gctccatgtt agtatctcat ggacaagtat ctttaccctt tccagatttt taaatgaaac 99060
gttaaatgaa aaccaaggtt acatatttaa agcaaacttt tcccaatgtc acataatgat 99120
tggctataga aattattcag tgaggctggg cgcagtggca catgcctgta attgcagcac 99180
tttggaaggc tgaggggtg gatcacttga ggtcaggagt tcgaggccag cctggctaac 99240
atggcgaaac ctcatctcta ctaaaaatac aaataataat gataacaata ataagcccag 99300
tgtggtggca catgcctgta atcccaggta ctcaggaagc tgaggcatga gaacaataat 99360
cacttgagcc tgggaggcag aggttgcagt gaaaaaacaa gttattcaat gatagctagt 99420
cttcaagttt gcttgtcatg gggttacttt ataacaagtt tctttgtata cttgtaacca 99480
ctctgtaagg acctactttg taatatcaca gtgtaggacc agttttattg gattttaggg 99540
ttttatagag tgagatagtt ttatcttttt actccccaaa tacatttaca atgcaaataa 99600
taatttatca attggtaccc tattttttg tgaagagtat taatttactg ctcactaatt 99660
tccctccagc cactaaccat ttacactcac tgtcttgtca tttaattatc tctccattca 99720
ctgcttttac ttttacgaca tgttgaacat ccctaatttg aaaattcgaa atgctccaag 99780
atctgaaact ttttgagcac caacatgaag cccccaagtg ggaaattcca cacctgacct 99840
cctgtgacag gttgcagtcc cagcacacag cttattcagt gtcctaaagt gaaagcaatc 99900
ctctcagccc tcttcagcta tgataaagct tttccatgca cagcatgatg gtgacgccaa 99960
tcacagtttg tctacgtggg tggctgggtg gctgaggtac ctttgctttc tgatagtgca 100020
gggatacaaa ttttcatgca ccaaattatt taaaatattg cataaaatta tctttcggct 100080
atgtgagtaa tttgtatatg aaatatcaat gaatttcatg tttagacttg ggtcccatcc 100140
ccaagatatc tcataatgta tatgcaaata ttccaaaatt tgaacaaact ccaaaatcca 100200
aaacacttct ggtcccaagc atttcaaata agggatgctc aacctgtaca tattttcagt 100260
cttttaataa gtatttttc tacatatatt tttctcttca ccttacccag tttatcttct 100320
agtttatcta ctgagaagtt tatggtattg attgctatgt tctatcctac atttaattat 100380
gttggtacaa attataggat ggtaatagtt aaaatttttt agactgtgac ttttttgtga 100440
gggtgtaagg agagtaagaa ctgtggattt attgttaaca ggactaagtt ctaagatgga 100500
aagttggaga acttctgggt gattggagaa aattcagaga aggtcagaat tcatcctata 100560
caggcagata ttgactaaag gcaaagcaga gtatatagac tgaatcaata agtaaaattc 100620
catataaaat acagtaaatt attctaaaat gtgcctataa actatattcg aaacagaatt 100680
aacatttgtt tcagctattc agtaccttac acagaaaaat gtgttaatag tgtacatagt 100740
taggaacatc tgaattgttc tagagatagt cctaaaatct attttaaaat gactgatttg 100800
aaaatctgaa ggcacactga taaacatctg agtctatttt actcttactt tctgtttgga 100860
aatggtgcag tgtgatgaaa atattatagc ctttggaatt aggcttcaat tttatttctg 100920
aatttgtcat ttactagaac tacatggctg tgcaaaatgt cttaatctct ttggcttcag 100980
ttttcttatt ttaaaaacaa gaatagtaat tcttaactga ttgtgttgct atgaagatta 101040
aaatatatgt gtgtagtctt tgcacaccca catatgtagt ctttgcacat ataaatcctc 101100
catgaatact agctttaata ttttgaattg aattatttgt tttctctttc agaattatct 101160
taaaggtaca atatttgaga tttattaaat gcatagttta tttttacaaa ggatttaagg 101220
tttcaaccat ttggtggtgg taaaatgcat gagccttatt tatgattaaa ctctaaattt 101280
gtcctaccat ttatgatttt gggctggtta cttaacccct taacccttca agccttagtt 101340
ttttcatctg taagatggac aaagaatacc tatattatca gattgcttta ttcattaaag 101400
aaagtaacaa tagtaaatat tgattgagca cttttcatat tttatttaat tctcatagga 101460
acctgatgag ttacatatca ttgttgctat attatagata ggaaagctag gaccagaagg 101520
tccagtgtcc agttgtcata caactagcaa atgagaagag ccaagattcc agtccaagtt 101580
cttaagttcc agtactccca agcactcatc cactgtggta tttaattgtt tacagtgttc 101640
agttagcaca cagcaagtgc ttagtaaatt gcaactactt ttgtccttgc tgatttgttt 101700
taatgatttt gctccaagta ctcactgtgt tctgtggtag tttctgttat atgcatgact 101760
gtaggattac cctccaaaag tatagatttt agtaaaaatt aaaattagaa gttagagtcc 101820
cttagatact gaaccctctt ttttctctgt gtatacaaat atgtgtatat aattatatat 101880
aatgtgtaca tacatataat attttagtta catagttgcc aaggctttgt agctactgta 101940
gtttcagtgt tacatggtat acacacacac acacacacac acacacacac acacacaaca 102000
tattcatctt agggaaaata cagatgtgct catacttaaa tggccaatta taagattatt 102060
cacatctgtc aattttttat tgacaatgtt taatttttta tatagatcta agctttggtc 102120
ttattgctgc tcattaacac tttactgaat aatgagcttg aacagatttt tttttttttt 102180
ttgagacagg gtctcactct atcacctagg ctggagtgca atggcatgat cacggctcac 102240
tgcagccttg acctcccggg ctcaggtgat tctcccacct cagccaccca agtagctggg 102300
actgcaggta ttcaccacca cacccagcta gttttttgta tttttagtag agacagggtt 102360
ttaccatgtt gcccaggctg gtcttgagct cctaggctca agtaatctgc ctttctcagc 102420
ctcccaaagc cctgagatta caggtgtgaa ccaccatgcc cagcttgagc agaattaatc 102480
ttgctgaatt cacttgctgg ttcttgaatt tggactaaat ttttggccac ttattaagtg 102540
ccttttttct ttgataaact ttggttaatg tctgagttat aggaattata ctcaattttt 102600
tgatatcaaa taccatatac agatatatat ataaaatata tattttaatt ctgccactgc 102660
tgctgataaa gattaagacc ctcatctcaa tttttttact tgtaagattt tcactgtcta 102720
taataattga gaagttgttt tgtacagtta cagtttgttt caatgaacaa aatgtttcta 102780
gtattatttt gacctctaaa taacagctgc tacttttttta gtcattgtgg ttgtattcac 102840
taaattacca acctttaaaa ataatctcct tccttgatgc tatgtctcta ttgtgggatt 102900
tatgcctata tttaatctcc tactcaaggg aggagacaaa atgctaaatt caaaggtaaa 102960
accttataac taggcatcaa tacatttata taaagtggaa tgatacttga aatgtttaat 103020
taagtctggc agaatcatat gaacacaatg tattttctat gttaaatctc atttggtttt 103080
aataattaga catttttacc aattgagata aagccgtaaa atttctttac atctggcgtc 103140
ttattaaata gcctttggaa gatatgtatt tgtgtgtgtg tgtgtgtgtg tgtgtgtgtg 103200
tgtgtgtatg tgtgtgtgtg tgtgtaggct tttgcatata ttttaccatt ccactatctt 103260
tccaacatga ggaggctttg aactgagtat attttatttt ggatggagtg aaactaaatg 103320
ttgttggttt tttttttttt tttttagtcc atccattctt tgatttaatt tggcaaaccc 103380
acattagata atttagcaga agaggaatta tatcttcatc ctattatagt aaaacctctc 103440
actaattctg aatttatgat atttgagatg cagtatttgt gatctttttt gagtaaaaaa 103500
ttcaaaataa tttcttcctc tgaattttca gggtcatact tataagggga aacctgtcta 103560
aaatcactag cttttcaaac caagggctca agaaatgaag gattccttca acgtgccttc 103620
agcctctggg tccagcagtt aattcttgta tgttaaagga cttttatgtt tatggtacat 103680
tttaaatgta atattggcct attttgaaat ataatgtagg taaccacact ctatttattg 103740
tagcatttag tttaatctgt aatctgtact gcttgaaggt aacaaaactg aatttttact 103800
tcagtgttct gtatgattaa gacgtttcca gtaagccaca caggcctacc tgttctatgt 103860
tattccgaat tagtgaggtt ttactgtcct agtgtcgtaa agagtttcag tcttcttgaa 103920
attataggca tttagttacg gaaaggaaag taataatgta ggtagatttt gtctcacctg 103980
gatgttacta aaggttaggt aaaaaaagaa taaacacaaa atgatttaat attattctgt 104040
ttaacattct aaaatgcaca atgaaaatac aggatagaaa gtgtgtgtct gtagattcac 104100
atatgtatct tcatataata cacacttgtt tagagttgct ataccacttg agagtggttt 104160
agactagttg aacttgtgaa attccttcca gatttacatt tattctgtgt acaaggaatt 104220
tgaatcttga tgatataaag gtcatatgtt agtgatgtat agaagtacat tgtgattaga 104280
aaaagtaagt tgttgttatt tacacattcc aaacaaaaat ttttatattc tggaatgtgg 104340
tttttgatgc tatggttaga ttgttggaaa attcaaagtt ggattgcaaa agccaagggt 104400
aaagaaaagg cttaaagcaa gctcaatgaa ggaaattgtg agaagggagg aggaaagaag 104460
gagtgaaagc agaaaaaagg tttggttgag ggtagtgatt ggggacaggg agaaaaccac 104520
aaagcaatat ggctgaaggt gatggtggca caggaaacat gaataagaat aggccattga 104580
actgcaatat attgaataaa gctctttggt ctttatacat tttgaaaagt tcagttgagt 104640
ttcaaaatac ttatgggcag tgtagccttt ctaagatcta tttaggaaat ctaagtcact 104700
tgtgaatcca ttagcaattt tttaaaaatg gctagtacta acaatatcac taagtttaaa 104760
ataattgtta aatgactttg catgcagtaa ttttttatgg aaactaaatt ttcccatata 104820
aactgttaca ttttaaattt tgttatttct ataacttaat gacccgttta ttacataagg 104880
ttttatccat aaccagatct tatctctgtt tttattaatt tagtgatatt tgcaaatgga 104940
agtatatagt ctatcttttc aaaattcctt ctttgcaggt agattcttga tctatcactt 105000
ctaacagcta cagattcttc ttgcttgttc cttttaacat ttttctcttg ttcttccata 105060
ataaactgat ttaaattttt attttgaaga tgaataatgg cttaatcata attcacaaat 105120
tataacactt gcagatggaa gtggagaaag aggcgaaaag gatgcaagca aaatcacaac 105180
ataccctcca ggctctgtgc gatttgactg tgagctccgg gcagtccaag tcagctgtgg 105240
atttcaccat tcaggtagcg gctggaactt tagggtataa ctgcgttttt acaattgtgc 105300
tcagtaactt atttcttcag atttgatgaa catagcctgt taactgtgtg ttaaaagctg 105360
tagcgtggca gtctctcaaa tctgtaagac ctttgtattt attacagaat ctctttaaac 105420
aactatggca tgatggaaca ggtacttgtc tagagatcta acttctagtc tgtcttcctg 105480
tggacttctt ttataattca agacagtctg gaagatgaaa taatccttta aatctctttc 105540
agttctagaa tgctgtggtt tttgtaacat gttcccatat tttgttaatg ttcagtgata 105600
aatgtatgtc aacaaattta ctttcttaaa atgtagaaaa taattaaatt cttagtaaat 105660

-continued

```
tattggcatt tgggttagct tttgctgtac tgttcaacct ttataaaaac aaaaatgtta 105720
aattccttcc ttgaagatta tttgataagg tattaacaga cattaaagtt ctgctgtttc 105780
attgatgttg tacgtaattg tgcagacctc ctatcctaga taggagagaa caatatttta 105840
tatgtagtta ctcattatta agaagatttt acagttgacc tgaaccagtg tgttaataag 105900
aattaatgtt attaaatggc atttatacga atttttaagt gtgtattatg aaaaaattat 105960
acatttatat gacctacaaa aatatttttc agaactaaaa ttaatttctc attaaataca 106020
aatttgtcct tcagttacct atttttaatg gttctataaa tcttaaatag tgaaaattac 106080
actgctttta gtatagttgt gatagaaatg taaaatgcat ataatgaaaa aataaagctg 106140
tgtgttttgg ttgcagtggt tttaatggaa aatggagatg tctatacatt tggttatggg 106200
cagcatgggc agctaggaca tggagatgtc aactccaggt acttgctaac ttttcatttg 106260
aagatccaga gttatttttt cttctgtttt cttttccttc ttttttcttt cttttctctt 106320
tttaagtata tatttctaga attaaaataa tattatacca ctgctttgca aagtgtggcc 106380
catgaattat tggtggtttc tgatcttatg gttgagtgct tttgtagaga taaaggattt 106440
tgtagtttca ggagaaaagc tgatatatat tttaaatagg agagtgatta tgattgtcac 106500
aaaatatcac tatattctta gcaattatct ttttaaaggc tgtgcatggc aatagaaaaa 106560
tagtgaattg tatttttaaa aaatgtcagc aatggattca aacatattcc tgatgtctgt 106620
tttgaaattt tggtctaata acatgcagtc attgaagctt ttgaataatt tttggacaga 106680
acctattggt ctctctgatt aactcttttg acttattgca aatagtagta gagagactgg 106740
tggtaatttc ctaatatccc tacttcattt gttttagttt tagttttagt tcgtgacatg 106800
atcgtgcagc taaagattcc ctttctcagc ttccattgca gcaggatgtg gccatgtgaa 106860
cttaagtgat aggtgccact ttggaatctt gctgttaaag ggaaagggtg tacctttcca 106920
tttgtccttc tctcttccca gcttgctggc tggaatgaat atgtggaagc agaaactaaa 106980
gaagtcatca cagagataag ttggagactg tgtactgaga atggcagaat cataagatgg 107040
gaataggctg ggtctctgac accatgaact gcctcatcag cttcttaaat tgcatgcttc 107100
ttgcgtgaga aataaacttg tatcttgaag tccctcttac ttgtctttca ttacagcagc 107160
cgagtttgta ttctacgtaa tgcagtcaga atacttttgg tcaaaagtaa tagaaaatcc 107220
atctttatta gttcaggtct tccagaaagc agatgccaag acaggattag atatgcaaag 107280
aatttattag atacatgtag ttttgaccct atgaaaggag aaagagaagg aagaatcggg 107340
taggagtcta ggttccagca taacattaag agagttttag ccaggccagt gatgtgtccc 107400
caagctgagg atacctttgg aagggtcctg cattgggcag gaatagacca acattcatac 107460
cttcaccatg ttcagtcaca gctggtagca ccccagggga cgaatgtcct cgtgcatcca 107520
aagggacagc acctgaggct gttataatag ttaactctgc tctctgtagc agattgtctt 107580
gaaggagatc tgagtggtct gtgtctgtgg ttgtctcacc atggaaacag gagtatttat 107640
gaagtctgga aagatagaga gcagcttcaa gccagacttc actcagcaat tcacttagct 107700
gcaaaaactt accttttgac cttctactct gccttattct tcctcgcagt cacagtgtat 107760
atgccagaat caaggggact tctatggttt ctcctttaca tacagtgaaa gaaagagaac 107820
ttaccttcac atagtcatta aataaaattc aaggttgtca ctgtgtcttg aactcactct 107880
actattgtgg cagggatgga attctgccat ttacatggta aagattagtg attcttaacc 107940
ctggctgtat attagaatta cttagggaat ttgaaaaaat atcatatgtg gattctacat 108000
ccagcatttc tgagagatgt gtgtgttgaa aggcttgtgg gtgggacagg ggtggggagt 108060
```

-continued ggtccttgat aggatgccag catcagagtt ttttctaaaa ggtccccaga ttctatatgt 108120
atccaggatg agaaccactc tctacccttc gagctgaggc agggtcagat ctgtgggcac 108180
tgcataaaaa atggcaacaa aagggaatgt cctgagttat gtttatgaat gttgttgcta 108240
atgataagag acgattgaga tatcattgag ttgaacttct tattaaaaac acaactgaaa 108300
cataaaattg atactactat caagaggttt gtaaaactat cacaatcata aatatttaat 108360
gactaatatc atacttgcaa agagcaaaag atgtgtttgg cagaattact ttatcagatg 108420
tgtctgctgg atatgacata ataccaacag tgttgagcaa ttactgtcac aggtgttaga 108480
tgccaactga tattttgctt tgcaattgag taacattact gaaatgcaga ggctgaatct 108540
gggtagtaat tacagttggc cctctgtacc tgtgggttct gcatctgtgg attcaatcaa 108600
tcttgacaga aaacatagtt aggcctacga taattgcatc tgtactgcac atgtacagat 108660
gtttttgtct tgttattatt tcctaaacaa cagagtataa caactattaa catggtgttt 108720
acattgtatt aggtattata agtaatctag agatgtttta aagtatacag gaggatgtgt 108780
agtttatgta caaatactat gccaatttat ataagggatt tgagcatccc tagagtttgg 108840
tagctgcagg ggatcctgga accaattccc catggatgct gagggatgac tataacctgt 108900
gtggggaaga acgtggcaac tttttgttct gtttctcatt tgagagttgg gacacagaag 108960
aagagggttt atttgtatca tcgtggctat tgttgttgtt atttagctgg tggttatttt 109020
gtgagccata gaaactggga aaggtgcatt gcagttagat aagatggggt ctcagtcatg 109080
tatgcagcaa agagggcact tcacagaaaa taattggcaa atagtatttc atggtcttgc 109140
cagagtggaa agggaagtag tgaaaagcat ggccatgtta tagtcaggtt atgttatctt 109200
actgtgcact tggcactcag aagaatgagc agcatgagca caacatcctt ccacaccaca 109260
ctgaggtgtg ttggccgctg agagggaagg tgttcatgtc agcttttaaa atgaagagat 109320
tacctaaaaa cattacttcg tggtcctgat tataccagtg aacaccattc ttcgattccc 109380
aagtctgaag agatataggg cagtttcagg ccagacttcc tcaggtaata atattgtagc 109440
aatatgctca atattttaaa ttgcttgaat ttatcgtctt catgaaatac gatagcattt 109500
aatgttgaaa caaaatatca gggtttctta tgaagattaa acattggtag gatctacaca 109560
gtggtatagt aactggtaga tgctacatag tcatcgaacc tggaactgta gaggcaaggt 109620
tcagctcttc acttcttacc aaccatatga ctataatttc ttaagattaa acactggtgg 109680
gatttgtttt aactgcccaa agttgttctt ttccagcatg gaatgttttg gtccttgttc 109740
cattgagtgg taactgaaag actgattaca tgaagtgtgg gcagagctac aacggataat 109800
gcagtagtca tacctatata ctgtgcctag tggattagat attcatcaag accgcttcag 109860
tcttaagcac tcagttaccc tgtctgtctg gacttttgtg gaacttggaa agtagcaacc 109920
aagaactctg ttattaattc agaaaggagt tgattatgtc tatagaggaa caatcttggg 109980
aggaacaaag cttctatagc atatgtatta actacaacaa agcaaaacat ttacagatag 110040
ttgaaataaa gggttacagt tggagaatat gtttgaaaag tctctagtaa tcaagagctg 110100
ttaactggaa tttactatat agcacacatt aataatgtgt tgtttaagat caatattgtg 110160
gtatgcatga taatgaagat ggaaaagtgt tattgatatt ctctttattt aatgtgttat 110220
attgccagaa tgactgagtt cagtctctag gttgggtcct gattctgtca cttggtagct 110280
atatgatctt ggccaggtta cttaatcttc ttgtgtctca gtttctcaag tttaaatatc 110340
cataatctga tgatactttc ttcttctgtg atgcagccct actttatttc cctttgactt 110400
tatgccccac agccctctac ttttttactc ttttttcacc ctttttttaa ctttatttcc 110460
tactcaagtt aaagactgtt gcttaatttc ttcacctata ctcttaccag tttcttcagt 110520
tttcccactc tcttggtcgt ggtgctagga catgataaaa ccgcaaacat gaatcaatct 110580
taatatttcc tatgcctata cttaggcttc tggaaggtaa gaaatcacca tacctatgca 110640
gattgatact taatttccag attcaaccag ttcctgtaca atggtcatta atcctcctgt 110700
tgtgtagtat tgaactattt gacttaatac cttttgagag tttgatgaaa gacatggggt 110760
ctctatgaaa aatacaagaa tatacactta aaaatttgct tgcaaattta ggagatcttt 110820
tgaagctcac tcatggactt cctagaagtc ctttatatct gagttgaaaa ctcctgctct 110880
cggtatgtat ctattccatc taccaccaca ccttttctcg aatcttcaaa ctctccactc 110940
acctgtttcc tccttttagc ataggatctc catgtacatt gcaacagatg taagaaatta 111000
ttcagcccac caaccctgca aacctacttc catccatacc acttctctgc ttctttcctc 111060
atgttacagt taaagaggaa cctgttgtgt ccttgctatg aaacctagct gtcttttcct 111120
tagagatcta tttctgtttc ctgtcttctc tctaaccttt gtctttagcg tctttatttt 111180
gagtcacctt ttaaacttcc tcaaatctct tatcattaaa aaaaaaaaat cctctccttc 111240
agcttcattt ttcctttagc tgctggctct cctttctttt tccctttagt gctgggatac 111300
ttagagctac tttgtgtatt ctctgactcc ttatctgctg cattgtggtg cctgcttcca 111360
ccaaagagac ctccttctgc taaatcgagt ggttaggtgt atgtctcctt agagcatttg 111420
gcatgtactt tattttccac gcttgaaacc tactcctcca atgagtctcc ttgagttctt 111480
tctttctgtg tggtttattc tagatgtctg tgagctgttc ttcctcggtc tgtatctaaa 111540
atgttagaag agactcataa gggaaattag gatctcttct tttctctctc aaagagtctt 111600
cctagatctc attcattctc atagcttaag tgaatattac cactatctac tctgttgctt 111660
aagcaaaaaa aatcttcctt gccccatatc gatcatctgc caagtttcat caattctgtt 111720
ccttacatag ctatcaaagt caccatctct ttcactctgc actgctccta gttaaggcct 111780
tcatcataaa ttacccaaac tactatataa tttttaaaat ttaaagtgtc ataattacat 111840
ttctcaaaag cagagctctc ctgctatgtg tggactattt ctataatggt tgtgtttcta 111900
attacagata atggttacta aaaatggctg ttaaaagtag gaaaggatac taggatgtca 111960
tttatcataa tagttactgt tcattaagtg ttaactgtgt gccagacgct gatccaagta 112020
cttgacacgt atgggcctct ttactgttca caggaactct gtgggggtag acaccgtttg 112080
ttagtattct ccatgtgata aagaggaaac tgaaatacaa aaagaatgaa aaacttgttc 112140
gaagtctggt cgcattatta ttaagttggg gagccaggat tcacaaccag ccagtctagc 112200
tttaaagcct gagcttgtag tcactgctct aatgcctctc atgatactgt gttttgactc 112260
attaactgtg attctaagat ctaaacttat agcttagtga taaaagttag aaaagatgat 112320
cataaaatta tttcatctag ttcctggatt gaatttctgt taaggcatta catgattttt 112380
atttcatcca ataattattt ataaagatct ctaacaggcc agtcagtata cagagtacca 112440
gattaaaaat aaatgtagca ccagtttttc agaaattatt atgtgtctat aattagggta 112500
attacattta gaagatcttt ttgatgatct ccttaaagtc agcaactgtc tttttcatct 112560
ttgtttacct agtacctgga atggagatag gcgtttagca cttaaatgtt tactgaatat 112620
tcttatgagt gccttttatc tttcctactc cttgttgcat tgcttactta ttgtttttat 112680
tttagttgag ttttgtaaga aattgactta cttttttttt ttttaaccta ggggatgtcc 112740
cactcttgtt caagcattgc caggccctag cacacaagtc actgcaggca gcaaccatac 112800
ggcagtactt ttaatggatg gacaggtctt cacatttgga agtttttctg taaggaattt 112860
ttaaaacatt aataatattg cattatacca ttgccttata atttgtctat attagctctt 112920
ttttctgttt ccagaatata atataacaat tatattataa ttgttacata tgcatatttc 112980
atgccttcat ccccaacaca cactaaacct gaatgatatt ctttgaagta attttcctct 113040
ctagctcagc attagaattt attgaattta acagctttgt tagaattgga catgtttatt 113100
tcagattaaa gtcttttaag cattcaatag agctaattct gtcataggaa aggttatttc 113160
tcatctaact tgtagagatg aatttttctt aacacataga actatgctat tttgtaacct 113220
tttaaaagcc tagttttttt tatttgattt gtttaaaatt atactttctt ttttcctttt 113280
ccaccctctg agtctatccg cctgtctgtt acataggcgc ttgtgcacat tctctccctc 113340
tctctgcacc aaagcttaaa gagtgaaaat gctctaagaa ttttgtgtag tttgggcata 113400
gtagatatca agaaaaatct ttgcgagact gtgctaatac tcttgtacca tttcagatgt 113460
ggataattac taagaactct tgaacctaag tgtctgagat gacatttaca gcttttgatt 113520
ttttaaaaac tgtaaatgtg tacttaaaat attttatttg aaaatggttt caaacttaca 113580
gaaagattgc acaactaaga acagtgtgta gaatatctgg ttagtgtctt taaccagatt 113640
cacctattgt taacatttg atccagcatt tgctttatta ttgcacatgt ggctgttctc 113700
tttctcacac acgcagtgtg tgtgtatgca caaatgtgtg tgtgtacgta tgtatataaa 113760
atattttttt ttctcaaatc ctttgacaat gtcttgtgta cattatggcc cgttacctcc 113820
tacatacttt agtttgtatt ttgtgaattg acctaataat tattttttgg catttctttc 113880
ccctccaatc taggatcagg cattacattt gcctgttgtg tgtctttagt ctcctttaat 113940
ctgtaacatt tctacagcta tgtattgtct attataacat tgacattttt gaagagtata 114000
tagtactgtt ttgaaaaata gaatcctctt catttttgtt tctttgataa tgtcctcatg 114060
tttagatgca ggttgtgcac ccaggccaag atactctgta agttatgttg tgtttgccct 114120
cactgcatca catctgaagg ctcagaatgt ccatctgctc ttcattgatt atggacattt 114180
tgatcacctg atcaaatgtc tgatttctgt actgtttctc ctttgaaact ataagcaacc 114240
tgtaggttga cacttttaag atgcctgctt ctcatcaaaa tttcccccta gatttagcat 114300
ccattgatca ttctttcctg agctagtctt tactataatg tttaaaaaat ggtgattttt 114360
ttcaactcca gtaggcactt ggccttttac tctaagcaag agccctcctt tcctgtttac 114420
ttgtttttct acttattatt ggtatagact caggtatttg tattttcttc attatcatct 114480
ttaattattt gggtgcctag attatctccg atttggccag cagtagcccc ttcaagttgg 114540
ctcctgtatt cttgtgacat gccccttcat tttttggagt gcttcctttc tttccagcat 114600
aacaagttgt tcagggttta tcttgtacag gccctgtatg actgtcctag aatcagccat 114660
ttctccaaga accctgattc tttttagtgg ggaatagtat tagacactaa ctgggcacta 114720
gaagtgttca ttgctacagg acgtctttgg atctctggta tgcatatatt tatatgtcca 114780
catatatgta tgtattttag aaatcatagg ccaggtgtgg tggctcatac ctataatccc 114840
agcactttgg caggccagtg taggaggatc actcaagccc aggagtttga gaccagcctg 114900
gacaacatag tgagacccca tctctattaa aaaaattagc tgggtgccgt ggcacatgcc 114960
agtggtccta gctgctcagg aggttgaggt aggaggatca cttgagccct ggaggtcgag 115020
gctgtagtga gagctgtgat tccatcattg ccctctggcc tggacagcag agcaagatcc 115080
tgtctcaaaa agaaagaaaa agaaccccac tgtgacttct acttccaatc cattcccaca 115140
aggttctttc ttacctgtcc tgttctatat ttatgtactt tcttcctcag taagaatctt 115200
tcctctcaac aatatcaata tatttatttc tcacttagtc cccagatatg tctaaaatag 115260
ttttatattt gctttgcctg tacaagttca aaaaaacaaa ctcactgaaa ggtcattctt 115320
gctctttccc ctcccacctg ctccccaccc caagtctgaa ggtgtatagt caagcactgt 115380
ccatgagtgg cctggattct ctctctcact cctttcagtg gaaattgtga ttcctttgga 115440
atagagtggg gctcatttgt ttcagtttaa gattcccctc accctatcct ttgattaagt 115500
tttatttcat ttttaaaata tatagaacat ttacatgttg ctaaaaatta agttatacaa 115560
aaattgtata ctcaagaggt gtcacttcct cccatatcct tgacattcct gcctccccac 115620
acctttcatt ccatacttgg aggtaatgaa tgtcattgtt ttacagttta ttcttcttgt 115680
gtttcttctt gtgaagatat ataagcatgc agacacacta ttttatatat atatacctat 115740
atatgtatgt atgtgtatac acagttatgc actgtataac agtattttgg tcagtgatgg 115800
actgcgtatg ctaaggtgtt cccataagat tataataagt actttgacta taacttttct 115860
atgtttacat gcagaaatac ttactaatgg gttacagttg cctacagtat tcagtacacc 115920
agcatgctgt acaggttggt agcctaggag caataggcta caccatatca cctaagtatg 115980
tagtagatat accgtctagg tttgtataag tccactctga tgttcgcagc atcacagaat 116040
cacctaatga cacatatttc agaacatatc cctgtcatta agtgacatgt gactgtacat 116100
aaatatatat atttcccctt tcccgttttt taaaggtaat agcctatata tgctcttttg 116160
cactttgctc ttttcgcttc agcatctctc ctagaaatca ctccatatca attcataaag 116220
ctcttcattt ttttttttac ctccatgtaa taccccattg tgtgtatata tgatagttta 116280
ttcattcagt ttctcatgtt tatatattta cgtggtttcc aatactttgt aatggtagta 116340
gtgaatattg ttagaggtgt atctttgaga taaattccta gaagtgagat tactgtgttg 116400
aaggttaatg cctatgtagt tttgtgagat attaacaatt ctcctgtatt ttgctttcac 116460
actaacggtg tatgagattg cctgtttcca cagaattgcc aacagaatgt gttgtggtac 116520
ctttaatttg tgccagtctg atgggtgagg aatggtcctg cttacttcca agttcctttg 116580
cctttagttg gtgctctgat cctcaaagtt cggatccata tttagtattt tggcattgaa 116640
ggttaacttt ctttttgggg gcatgtgttt ccctgtgctt tttctaactt cttcacacgc 116700
ctctgtcctc cttcttaaga acttccctgt tcgtgctttg cacatgctca ggtttgcagt 116760
agccggtggg tggagagaac tcttggaatt tggctcttct gcttacagga aacatagaga 116820
tcatgacacc cgctgtctcc ttccactgct gaaggtttga gtcacatata gatttgtttg 116880
cacagcatat ttttgtgtct tttgaggtgg ttatgtgagt gataagattt gacgtcagac 116940
agtcattgtc ctccagtccc agcagtccta gttgtgaact tttatgaatt taaatgtggc 117000
ttatttataa ccacattctg gtccttatgg ggttgtccag gtatctaaca catttttgga 117060
ctgcttttct tcatattagt tggtagtaag ggaatacata tttatttcaa tagtcaatga 117120
aaaagataac taatttattt ttcctccaaa agcagaatat atccctgaat atgatatatt 117180
ttgctcacta tttacttttt tttttctttt tgagacagag cctcactctg tcatccaggc 117240
tagaatgtag tggcatgatg atctcagctc actgaaacct ccggctccca gattcaagca 117300
attcttatgc ctcagcctcc tgagtagctg ggattacagg cccatgccac cacacccagc 117360
taattttcgt atttttagta gagacgaggt ttcaccatgt tggccaggct ggtctcaaac 117420
acctgacctc aggtgatcct cccatctcgg cctcccaaag tgctgggatt acaggcgtga 117480
gctactgcac ctggcccctg tttacatttt tgtgctctct tatttttgtc aaaaaataag 117540
gacagatctt aaaagagtat gagaaataaa tgttgagtgt tttggctgct tctctaatca 117600
tgtgcttgcc atgtttcctt ccctggttct gtccagggat tgaagctcag ttgcttccac 117660
agttagtttg tggctgtgtt ttcttgctgt gctacctggt ggttggatga gaacgtgacc 117720
agagtgttcg cagtgctcca ggctcccttg ttccagaatg ctgtgagggg agagaggtcc 117780
cgagccaggg gtggaagaat atctattgag tcaatgtcag cattctttta ttctttttca 117840
gctacaggct tactagtgag aaacttccta ttacttttta aattaaactc ttacctgacc 117900
aggtccctat agagagccat acttttaaac tggttaatag ttatttactt aaaatatcat 117960
atcttaccat tgattgtgct gtttatttta aaacataaat gaaataattt agggacatat 118020
catgtgaaaa caacattaca tatttttcta attgtattca cagtttcagt atttattttg 118080
gtctttttac atggatattc tcagattata tgagttcaat agtgactttc ttttatacta 118140
tcaacttact atgtcaaagt gactttttaa atgaacaatt tggaatacta atattttaac 118200
atattgtgtg tatttgtcgt acttttcatt taaatgtagg tgaagacaaa gtattttgga 118260
gatacttctt gcgtggaaaa tatttcaaac tttttttttaa aaaataatgc actttttaag 118320
actttccagg aataatagaa attattttat tactttataa atatttggtc caaattctta 118380
catattgtat ttattttaaa aacccaaact aacaattggt gaaaaataag gtttcataga 118440
ttgattttta tctactgcct ccttaacttt atgaaaatta gattgtttac acagcaatat 118500
tgctaatatg gtttatttaa tcttttagaa aggacaactg ggcagaccaa ttttggatgt 118560
gccatattgg aatgcaaagc cagctcccat gcctaacatt ggatcaaaat atggaagaaa 118620
agctacttgg ataggtgcaa gtggggacca aactttttta cgaattgatg aagcacttat 118680
taattctcat gtacttgcta catcagaaat ttttgccagt aaacacataa taggtaatac 118740
cagaaataaa caaatgcccc ttccaaactc ttgtcttgat tgatagtaaa tggtttatct 118800
ttccctttaa tgaaatgtac ttttgtagct ttttgttttc tttctgctca aagaaattta 118860
aacaaagcct gtaaatgtct ccgtttatat gtgtctctat gctgaaagaa tggaataatt 118920
gggagatctg gaaaccacag tatttgtgag ctagacagtg gtagaactat aaactaaatt 118980
ctagtaggat aaaatccata ttagagtaag agagttttat gcattgttta ttgctaaata 119040
aatgttagaa attaattttt atgggaggtt atataaatcc aactttgaaa tttcacgaag 119100
accaagttat caatctgtac tgtgtccatg atactgtgaa taattatata atagagtggt 119160
atagcaagag attaggagca tgtgttgtgg atttagacat cttgaggttt tattcctaat 119220
tctcccactt aaagattttt taattactta gcctctttta ttctctgctt attcacctga 119280
gaaatggaga taatactact ttatgggttt tggagaattt aaaagggtaa tatatattaa 119340
aattatatat aaatattttt ttcttaaggc ttggtacctg cttctatatc agaacctcct 119400
ccatttaaat gccttctgat aaataaagtg gatgggagtt gtaaaacttt taatgactca 119460
gaacaagagg atctgcaagg atttggtgtg tgtcttgatc ctgtatatga tgtaatttgg 119520
aggtaagcat ctcagtttat aaaatagtca ataagttttg atgcagttat actcttatgg 119580
taatataaac tttatttaca ggtggacttt tcacatgtga gtactctcct gtttatctaa 119640
taactgcaat tctgtctcag tgattcacag ggacctttat actgtagcat agtggttaag 119700
agcatgcatt ttaagcaaca ctacctaggt ttatcccagc tccacaactt gctttctgtg 119760
tcaccctgga gaagttactt tgactgtgtg cctcagtttt ctcatttatg aaatggggat 119820
gctaatacta cagaggtgca tactaggtgc catataagtg tttgctatta tcattataat 119880

-continued

```
tattaatttt actgttgaga gttctgttgt tatttttagt ctgtcatcaa tcctgtttat 119940
attgtataga attcattcta ttttttgttc tcataattat tattaactat gaggaggaaa 120000
ttatgccaaa gacaataaag aataaagaag ataattgagc ttgcccttta agaatgtgca 120060
ttaaaaaata ctcttactgg tagagaaata tacaggatta tatgcattct ggaaattata 120120
aaaacataga gataaataag gcacaaaaga gactcaagaa attatgttgc atttgtttga 120180
aatttattgt ggtgctgggc cgggtgcggt ggctcacgcc tgtaatccca gcactttggg 120240
aggccaaggc gggcagatca cgaggtcagg agatcgagac catcctggct aacacagtga 120300
aaccctgtct ctactaaaaa tacgaaaaat tagccgggcg tggtggcggg cacctgtaat 120360
cccagctact cgggaggctg aggcaggaga atggcgtgaa cctgggaggc ggaatttgca 120420
gtgagccgag atcgcaccac tgcactccag cctgggcgag actctgtctc aaaaaaaaaa 120480
aaaaagaaaa aaaaattatt gtggtgcttt atatacaaaa tgaataaata agttaccctt 120540
cttagtgttt ctagctttgg atactaatag gaggtgtacc ctgccatcac cacagtggct 120600
catcacaggg ctgagcactt ctttcctttt gcggccggcc ttagtaggca agattccagt 120660
aagttgaaag gttgaagtag tgtgagtgag gagacttttt ctctgtcttc cttcttctac 120720
ccatgcctgc ttgcattctc atcagacagc caagttctaa gaggccatgt ggtagcaatg 120780
ggatagatga tctcaaatgt cttgccaact ccttggtaat tttcttccgt gttccaaaat 120840
agagattaat aacgaggctt gcattcagag tgaagagact gctgcacttc ccaggttgct 120900
ggccagcttc ctctcttatt tgggcatttt atgagaaggc gtagtggcca gtattgagtt 120960
gagtacatct caaatcaatt acatctccct ggcagcattg tgcagggtag atgaaataac 121020
aagagactat gggtgagtgg tcttttgtga tcattcttat gaagacatga ggtattaaga 121080
accaaagtta gaatggtcac agtgggatag aatggagggg atagagagga gaaaagatgt 121140
aaagatagaa ttggctgcag ttacttaccg attagaagtc aatgttcaag agacttagtt 121200
accaaagagc aggctctggt ttggacttag gtgtaaattg atgttttact gttttgtagt 121260
tcttacatgt tttattttta aatgaagtaa atttgcatta gcaaaacaaa aataaaaatt 121320
ggcagtgtgg aatctgtttc tggatgcatt cactaagtta gcaataacag tataactaag 121380
cgtaacagta aaaacttact tgaactagaa ccatttccgt ggggtcttaa cagaactctc 121440
aagtatgatg ttcagctggt tgaaccttgt cttttccatt tatggtagta gcaatgggac 121500
agatgatctc aaatgccctg ccagctcctt gatcaatttc tccattgttg gaaaacagag 121560
attaagagat gttttggtaa aacagctgag aggtattttt ctttaaatca ggatcagaat 121620
ttctgttatc ctgacttctg gctgctttgt gtcttttgtg tttttcaatg gggcacttaa 121680
attttataat tatcatatgc attgcacatc caatattagc ttactttgac tttccttctg 121740
gcctgcatct gcttcatttt atattcttta ggagccaact ttgcctgagt aattagaaac 121800
aacatctata aagagcagat aaatgttaag aacacctgtt ttatttccca catacaaatt 121860
tacacaaata atatgtgaat ttgtgttatt ttttaaaaaa caaagcaaaa atacatacag 121920
gaaaaaggat ggtcatactc tgtatctgtt tcttttccca taccgaattc cactagcctt 121980
ctctgtggat cacaagtatg aagtttgatt tatatcatct gacacctttt aaaatgcatg 122040
tatttttctt tttatgtaaa taaaaacata cctactctaa aagttagatt ttttgctcaa 122100
aaataattta gagatctttc caagtcagta tttaaagaac agcttcatta ttaaaattgt 122160
ggaattctgt agtctgggta taccaaatat acttaactgt ttgcccatca gtgaacattt 122220
tagatttttt ttaatattac gatactacct acaatgctac agtgaacaaa tacacaggta 122280
```

-continued tctacacaca gagttttaca cacatgtgga agtatttctg caagctagct tttaaaatgt 122340
agaattgctg agttaaaaga taggctcaca gaattgtaaa atgactgagg taagtctgaa 122400
tcactttaga agtttatttt tccaaggttg aggagatgcc tgggaagaaa agacaagcca 122460
cagcaggatc tgtgccctgt actttttctg aagaggtttg aggccttcag catttaaaga 122520
ggaaaagaga gcaggaggag aaaaggaaaa gaaaaaatga gaggatgtgg tcacattctt 122580
gtaaggtttt gattaggctt actgaatcca catgttgcac atgaaaagga aggggtagag 122640
ggaacagtga attttgtatt tggagttaaa gtaaacatag agtagaggaa gcagtcaaat 122700
actcattcat ctggggctgg ggcgggtggg gcttggtggg gggatgggca gataatttct 122760
agtatcttct tgtctcttac catgaatttt ccagaaccaa aaagagattt gaatccatgg 122820
atattagaaa ctatgtgttt ctattattta ccatcaagag agttagtgaa actgttgaac 122880
actaaagacc aaggggaaat cttaaaagca accagagaga aaagaatgat tacctaaaca 122940
atgagatcaa cagaacttcc caaaagcaat aatgcaataa tattaatgct actagttata 123000
gaagctacca taatatattt tctcccaaat gctattttaa gtgcttttta aaaataattt 123060
aaaatttttt aattgtggta aaaaaacagt ataaaattta ccatcttaat cattttgaaa 123120
gtctgcagtc agtggtgttt agtgtattta tgttattgtg aaatagatca tcagaacttt 123180
tttttcttgg aaaactgaga ctctatagtt attaaacaat agcttgcatc cctcacttcc 123240
cgacccctaa aagaggtaaa gaagtggaga tagtttttg aagtttttgt tacaaaagag 123300
atcagagaaa tgggatgatg aagacgttgt gggttcctaa tagtttttaa ttggttttta 123360
ctgtttattc atatggttga acatccacat ccattctatc tgtgcttcct ttctatggat 123420
agcattccat gtccttgcca atttttgcta tggattgatt gtttctagct cttatacatt 123480
gaggatattg tagctgtgtc tcacaggtac acttcacatt tttcttcaac ttgtcctttg 123540
tctttaaact tttttaatgg ggtatttgtt gagtttcata tttatatgta tgtatcaaaa 123600
ctttatacag tcaagtatta taatctacat tactattttc tgtattaagt attataatct 123660
acgttactat tttcaaatta tttcactttt agtgatatag tttttttata tgtttagctt 123720
agatccagaa gataatgagc tacatttgtc ctctttaagc tgactatatt atttattctc 123780
tttgtatcat cagttatgtt ttaggaattt tttttaaaaa caaaaccaca ttgaggtgct 123840
gtaattattc tttttcttta aaggtttcga ccaaatacta gagagctgtg gtgttacaat 123900
gcggtggttg ctgatgccag gcttccctct gcagcagaca tgcagtccag atgtagtatc 123960
ctaagtcctg aacttgcctt accaacagga tcaagggccc tcactacccg atctcatgca 124020
gctttgcaca ttttaggtag ggttgcgatt tgatgtacca ttaattcaca ttaatgtgtg 124080
ctgtccaggg ttttttttta gagtatttaa atttatatgt aattctgtct tgtttgttaa 124140
ataataataa tgtacaaaat aagttaaatc ctctaagagg ctaattccac agaaaacaat 124200
acatgagacc tgtactaaca ctatcaaaga tttatgtatg cccaattatt taattttcac 124260
agaggtagac ccttaaaaat aatgtttttg ctcaacttga atgtataaac ttttaaagat 124320
atgataaaat tttcaagtat ataatattta atttatgtat attatgttaa ataaattcta 124380
taaaatgtaa tgaattttat atacatcttc tgtttcttct tatataacac agttttccac 124440
agcatatcaa cttcattctt atttaattac tttgagatgt agtacttatt taattacttt 124500
gagatgtagt gcaatatatt attttgtaac tggaaatttt atatcactct atgtaactat 124560
gtattttgtt gcttttaaaa atgatcctta aaaagactca ttttcagact ctagcacttg 124620
caggtgtgaa atcatattcc taaatataat taccatatca taaatataac tctttgtttc 124680
ttttttctca aatttcattt tggtttctat tgtagacatc caaaactagt gttgattaag 124740
tttgtgtgac actaatgtgt cttcctcaaa tagcacttta agaatcaaac taatttggag 124800
tttcataaaa ggaagaacct tgtaagaatt caaaggttaa gtgatttcaa cttttcagag 124860
atccagtttt gtgtaaaagg ttgtcgtatg gcaagtttaa atatgatcat taatcagaca 124920
agggataatt tgtattggtt ttaagcattc ttccatgaaa tgatgtttaa agcttggagt 124980
aacattctga gtttatttat tttaatttat cccctatagc atttaatgtc atcaatacca 125040
taggacattt taatttcaag gagttaaatt ttgtttcttt gttgttttag gttgtcttga 125100
taccttggca gctatgcagg acttaaaaat gggtgttgca agtacagagg aagagactca 125160
agcagtaatg aaggtttatt ctaaagaaga ttatagtgtg gtaaacaggt ttgaaagtat 125220
gtatacttcg gtttaggaaa tgttgtctta caactgaaat atatatggat cttttaaaac 125280
atagattatg atttatatat tctaggtcat ggaggaggct ggggttattc tgcccattca 125340
gtagaagcta tacgtttcag tgccgacact gatattttac ttggtggtct tggtctgttt 125400
ggaggtagag gagaatatac tgctaaaatt aaggtaaagt tcatcaacaa tgttgtcctt 125460
ttttgtttga acatactgat tttgacttaa tttattattt tattatttaa tgtctaattt 125520
ttttcctttt taactgggtt tattttgttt ttaatgcttc tttttaaaaa gcgatagaga 125580
aaacattgct aaaatcgaat acagtaatac taaatttttt aaatttattt atttattatt 125640
attatacttt aagttttagg gtacatgtgc acaatgtgca ggttagttac atatgtatac 125700
atgtgccatg ctgatgcgct gcacccacga acttgtcatc tagcattagg tatatctccc 125760
aatgctatcc ctccccccctc cccccacccc acaacagtct ccagagtgtg atgttcccct 125820
tcctgtgtcc atgtgttctc attgttcaat tcccacctat gagtgagaat atgcggtgtt 125880
tggtttttttg ttcttgcgat agtttactga gaatgatgat ttccaatttc atccatgtcc 125940
ctacaaagga catgaactca tcattttttta tggctgcata gtattccatg gtgtatatgt 126000
gccacatttt cttaatccag tctatcattg ttggacattt gggttggttt caagtctttg 126060
ctattgtgaa taatgccgca ataaacatac gtgtgcatgt gtctttatag cagcatgatt 126120
tatagtcctt tgggtatata cccagtaatg ggatggctgg gtcaaatggt atttctagtt 126180
ctagatccct gaggaatcgc cacactgact tccacaatgg ttgaactagt ttacagtccc 126240
accaacagtg taaaagtgtt cctatttctc cacatcctct ccagcacctg ttgtttcctg 126300
actttttaat gattgccatt ctaactggtg tgagatggta tctcattgtg gttttgattt 126360
gcatttctct gatggccagt gatggtgagc atttttttcaa gtgttttttg gctgcataaa 126420
tgtcttcttt tgagaagtgt ctgttcatgt ccttcaccca ctttttgatg ggttgtttg 126480
tttttttttct tgtaaattgg tttgagttca ttgtagattc tggatattag ccctttgtca 126540
gatgagtagg ttgcaaaaat tttctcccat tttgtaggtt gcctgttcac tctgatggta 126600
gtttcttttg ctgtgcagaa gctctttagt ttaattagat cccatttgtc aattttgtct 126660
tttgttgcca ttgcttttgg tgttttagac aagaagtcct tgcccatgcc tatgtcctga 126720
atggtaatgc ctaggttttc ttctagggtt tttatggttt taggtctaac gtttaagtct 126780
ttaatccatc ttgaattgat ttttgtgtaa ggtgtaagga agggatccag tttcagcttt 126840
ctacatatgg ctagccagtt ttcccagcac catttattaa atagggaatc ctttccccat 126900
ttcttgtttt tctcaggttt gtcaaagatc agatagttgt agatatgtgg cattatttct 126960
gagggctctg ttccgttcca ttgatctata tctctgtttt ggtaccaata ccatgctgtt 127020
ttggttactg tagccttgta gtatagtttg aagtcaggta gtgtgatgcc tccagctttg 127080
ttcttttggc ttaggattga cttggtcttg cgggctcttt tttggttcca tatgaacttt 127140
aaagtagttt tttccaattc tgtgaagaaa gtcattggta gcttgatggg gatggcattg 127200
aatctgtaaa ttaccttggg cagtatggcc attttcacga tattgattct tcctacccat 127260
gagcatggga tgttcttcca tttgtttgta tcctctttta tttccttgag cagtggtttg 127320
tagttctcct tgaagaggtc cttcccatcc cttgtaagtt ggattcctag gtattttatt 127380
ttctttgaag caattgtgaa tgggagttca ctcatgattt ggctctctgt ttgtctgttg 127440
ttggtgtata agaatgctta tgatttttgt acattgattt tgtatcctga gactttgctg 127500
aagttgttta tcagcttaag gaggttttgg gctgagatga tggggttttc tagatataca 127560
atcatgtcgt ctgcaaacag ggacaatttg acttcctctt ttcctaattg aatacccttt 127620
atttccttct cctgcctaat tgccctggcc agaacttcca acactatgtt gaataggagt 127680
ggtgagagag ggcatccctg tcttgtgcca gttttcaaag ggaatgcttc cagtttttgc 127740
ccattcagta tgatactggc tgtgggtttg tcatagatag ctcttattat tttgaaatat 127800
gtcccatgaa tacctaattt attgagagtt tttagcatga agggttgttg aattttgtca 127860
aaggcctttt ctgcatctgt tgagataatc ctgtggtttt tgtctttggt tctgtttata 127920
tgctggatta catttattga tttgcatata ttgaaccatc cttgcatccc agggatgaag 127980
cccacttgat catggtggat aagcttttg atgtgctgct ggattcgttt tgccagtatt 128040
ttattgagga tttttgcatc aatgttcatc aaggatattg gtctaaaatt ctctttttg 128100
gttgtgtctc tgcccggctt tggtatcagg atgatgctgg cctcataaaa tgagttaggg 128160
aggattccct ctttttctat tgattggaat agtttcagaa ggaatggtac cagttcctcc 128220
ttgtatctct ggtagaattc ggctgtgaat ccatctggtc ctggactctt tttggttggt 128280
aagctgttga ttattgccac aatttcagat cctgttattg gtctattcag agattcaact 128340
tcttcctggt ttagtcttgg gagagtgtat gtgtccagga atcccttatc catttcttct 128400
agattttcta gtttatttgc gtagaggatt ttgtagtatt ctctgatggt agtttgtatt 128460
tctgtgggat cggtgatgat atccccttta tcatttttta ttgcgtctat ttgattcttc 128520
tctcttttt tctttattag tcttgttagc ggtctatcaa ttttgttgat cctttcaaaa 128580
aaccagctcc tggattcatt aattttttga agggtttttt gtgtctctat ttccttcagt 128640
tctctgattt tagttatttc ttgccttctg ctagcttttg aatgtgtttg ctcttgcttt 128700
tctagttcct ttaattatga tgttagggtg tcaattttgg atctttcctg cttcctcttg 128760
tgggcattta gtgctataaa tttccctcta cacactgctt tgaatgtgtc ccagagattc 128820
tggtatgttg cgtctttgtt ctcgttggtt tcaaagaaca tctttatttc tgccttcatt 128880
tcattgtgta cccagtagtc attcaggagc aggttgttca gtttccatgt agttgagtgg 128940
ttttgagtga gattcttaat cctgagttct agtttgattg cactgtggtc tgagagacag 129000
tttgttataa tttctgttct tttacatttg ctgaggagag ctttacttcc aagtatgtgg 129060
tcaattttgg aataggtgtg gtgtggtgct gaaaaaaatg tatattctgt tgatttgggg 129120
tggagagttc tgtagatgtc tattaggtcc gcttggtgca gagctgagtt caattcctgg 129180
atatccttgt tgactttctg tcttgttgat ctgtctgatg ttgacagtgg ggtgttaaag 129240
tctcccttta ttaatgtgtg ggagtctaag tctctttgta ggtcactcag gacttgcttt 129300
atgaatctgg gtgctcctgt attgggtgca tatatattta ggatagttag ctcttcttgt 129360
tgaattgatc cctttaccat tatgtaatgg ccttctttgt ctcttttgat ctttgttggt 129420
ttaaagtctg ttttatcaga gactaggatt gcaacccctg cctttttttg ttttccattt 129480
gcttggtaga tcttcctcca tcctttttatt ttgagcctat atgcgtctct gcacgtgaga 129540
tgggtttcct gaacacagca cactgatggg tcttgactct ttacccaatg tgccagtctg 129600
tgtcttttaa ttggagcatt tagtccattt acatttaaag ttaatattgt tatgtgtgaa 129660
tttggtcctg tcattatgat gttagctggt tattttgctc gttaattgat gcagtttctt 129720
cctagtctcg atggtcttta cattttggca tgattttgca gtggctggta ccggttgttc 129780
ctttccatgt ttagcacttc cttcaggagc tcttttaggt caggcctggt ggtgacaaaa 129840
tctctcagca tttgcttgtc tgtaaagtat tttatttctc cttcacttat gaagcttagt 129900
ttggctggat atgaaattct gggttggaaa ttcttttctt aaagaatgtt gaatattggc 129960
ccccactctc ttctggcttg tagagtttct gctgagagat ccgctgttag tctgatgggc 130020
ttccctttga gggtaacccg acctttctct ctggctgccc ttaacatttt ttccttcatt 130080
tcaactttgg taaatctgac aattatgtgc cttggagttg ctcttctcaa ggagtatctt 130140
tgtggcgttc tctgtatttc ctgaatctga atgttggcct gccttgctag attggggaag 130200
ttctcctgga taatatcctg cagagtgttt tccaacttgg ttccattctc cccatcactt 130260
tcaggtacac caatcagacg tagatttggt cttttcacat agtcccatat ttcttggagg 130320
ctttgttcgt ttctttttat tctttttttct ctaaacttcc cttctcgctt cacttcattt 130380
atttcatctt ccatcgctga taccctttct tccagttgat ctcatcggct cctgaggctt 130440
ctgcattctt cacgtagttc tcgagccttg gttttcatct ccatcagctc ctttaagcac 130500
ttctctgtat tggttattct agttatacat tcttctaaat ttttttcaaa gttttcaact 130560
tctttgcctt tggtttgaat gtcctcccgt agctcagagt aatttgatca tctgaagcct 130620
tcttctctca gctcgtcaaa gtcattctcc atccagcttt gttccgttgc tggtgaggaa 130680
ctgtgtttct ttggaggagg agagttgctc tgctttttag agtttccagt ttttctgctc 130740
tgttttttcc ccatctttgt ggttttatcg acttttggtc tttgatgatg gtgatgtaca 130800
gatgggtttt tggtgtggat gtcctttctg tttgttagtt ttccttttaa cagacaggac 130860
cctcagctgc aggtctgttg gagtaccagg cagtgtgagg tgtcagtctg cccctgctgt 130920
ggggtgcctc ccagttaggc tgctggaggg tcaggggtca gggacccact tgaggaggca 130980
gtctgccctt tctcagatct ccagctgtgt gctgggagaa ccactgctct cttcaaagct 131040
gtcagacagg gacatttaag tctgcagagg ttactgctgt ctttttgttt gtctgtgccc 131100
tgcccccaga ggtggagcct acagaggcag gcaggcctcc ttgagctgtg gtgggctcca 131160
cccagttgga gcttcttggc tgctttgttt acctaagcaa gcctgggcaa tggcgggcgc 131220
ccctccccca gcctcgctgc cgccttgcag tttgatctca gactgctgtg ctagcaatca 131280
gcgagactcc atgagcgtag gaccctccga gtcaggtgca ggatataatc tcctggtgtg 131340
ccgtttttta agcccgtcag aaaagtgcag tattcaggtg ggagtgaccc gattttccag 131400
gtgccgtctg tcaccccttt ctttgactag gaaagggaac tccctgaccc cttgcgcttc 131460
ccgagtgagg caatgcctcg ccctgcttca gctcgcgcat ggtgcgcaca cccactgtcc 131520
tgctcccact gtctggcact ccctagtgag atgaacccgg tacctcagat ggaaatgcag 131580
aaatcacccg tcttctgtgt tgctcacgct gggagctgta gaccggagct gttcctattc 131640
agccatcttg cctcctcccc ccctacagta atactaaatt aataactcat taaaaaaatc 131700
aaaattctgt aagaagggaa gaaatgaaag gaaaattatt ttcaacaatt taccactgaa 131760

-continued

```
gaaagactat atctcagtcc tttctgtgga acttctggtg gcctagcaat accagtgcct 131820
ttttatgtgg ctactttctt atagccattt taatgacaga ggaggcacaa ctgtttaggg 131880
acattttgat gtagtatgta aacagacatc ttcaccccag gagtggagac cgggaggagt 131940
gagagatagt gttaggggag gattccatct ggtaggccaa ctaaaaatca ttgagagtca 132000
tatgttacca cacctattcg tatccaaaag ggccaacaaa ttatcctaaa caaagtatat 132060
gttcattctt tgaatattca ctaatagctt gaatgttctg cttctcaaat tacctgattt 132120
tgctctaaaa gtgaaagaga aaactatagt ttctgcctga atttcaatag caggcttcac 132180
aaaaaaatct cgattaaatg tcatctgttc aggaggtatt ttcttagttc tctcaataat 132240
atctaaaaat gatatcaata tgttaacact cttcttcata atgctggttt ccaaggacat 132300
tccccatgga ggcccaacca gaactgacaa acttaaagaa atatttgctt atttctggtt 132360
atagttggaa tacatgctaa aaaagcagat aatgtaagaa tgaataaagt aaaaatttaa 132420
agctcctata gttatatgga gtatagtgat agaataatga ttaggactct tgtagcacat 132480
atattttgat aataagaaaa atagtagttt ggctcatttc agtgcaactg ctttaaaatg 132540
gttattttag gatgtcttga ttcatcctca cgttagagaa gcaacctcaa tgtgttatgt 132600
agttctattt gacaatgtct aataagctca tcaggaggat attttttttt ctagctctaa 132660
gagatttttt cttttcggaa tagtgaacaa cgtagtggac cttatcttca aacactgtag 132720
tatatagaat tatggaggcc ttccatatat gttgttttta tattggccct atttttcttt 132780
ttcaaactca aattttacct cactcctcct attgtctgga aatgatcttg ccttttgtat 132840
tcaattatcc agtgagtggg ctaaggcctt tcaacagtag tcagtctttt tttttccttc 132900
ccttcacctc tctgtaatgt atgcatttgt taagcccttc tgtatttttt tgttttgttt 132960
tgttttcata cctgtagttt tttcttctat ctctttgtag gttcatcccc ttccacctgg 133020
ccactgaatg taggagttcc tcaaagaccc agccctaggc cctctttctt cacatattcg 133080
tatatgcatt ctcttttgag cccagagttt taatagccat cagcatacca taatccccaa 133140
atttgtatct ccaactcaga cttctttgat gcattttcat gtaaatatgt taaaggcaca 133200
tcagttatca gtcataatat ctcaactgaa ttcatgctct tccactgatc tctctctctc 133260
atgattagta ccatccacca tatgcttgat acataggccg gaaatctaga catttttctt 133320
gataggcctc ctatatctct ttcttctcca caaaaaagac ttttctacca ctaccctagg 133380
caaaggtatt tgtcttggac tagccaccta gatagtctct gtacatattc tttctatact 133440
ttctgtctcc attctctctc ttaccattcc tacttgagcc tactccagtc agatttttgc 133500
ccccaccact gacattgctc ttgtcaagga cactgatgac tttcatattg ctaaattcaa 133560
tagtcaagcc tcagctctca tcttccttaa ccagtcagct gaatttaacc caattgagct 133620
cttctttgaa atactttctt ctcttgtccc ccacgacact acacttcatt tttcttttgt 133680
cccactgact gttcttctta gtctcctgct ggttgctcat catcttcctg acttctaaat 133740
gttggagtgc caagaactca gtttttgaca tcttttaaaa gtattctctt cctcatagtg 133800
gtccagcctc atggacattt atctctgatg acttttaaat ttataaacct cttctctgac 133860
ctttaaacca atatgtacaa cagcctacgc tgtgtctcca cgtgactctc tgataggcat 133920
tttggaggta acatattcaa tactatgctt ctgatgatct gcctaaacct gctatcctca 133980
tgttcttccc catcccagtt aactgactca gcatggagtt aacttcattc ttctgtttcc 134040
tcaggccaaa aatcttggag tcatccttga ttctactctt tcttttacac acatccactt 134100
```

cgggagcaaa tattatcgtt tccactttca aaataaatcc cgtatctaac cacttctgaa 134160
aactgccact gctatcaggt tgggtcatgc cacagccatt ctcatttgta ttattacagt 134220
agcctcccaa cttgtgttct acgtctgtcc tcaccccatt tgttctgttc tgagtgtggc 134280
agtgattctc ttaaaatgta caacagattg catcattgtc tcttcagaat cctgtagtgt 134340
cttcctatgt gagaatgaga accaaaagcc ttagaaggac ctacaaagtc cccatcagaa 134400
ctggctgtca tcacctctct gaccttttgt tctactagtt gtttcactct aatccagtga 134460
cactggcctg cttattgttc ctcagacatt ccaggcacag tcaaatctca gtacctcttc 134520
acttgctgtt tcctcataac tacagctctc ttcacttcag cacctacata gcccacttcc 134580
ccatcacctt cagagcttca ttccctggta agcctactta aaactgtaaa ttcaattccc 134640
aaccatagac ttactcccaa tagcccccaa ttctttgatt gtattgtttg cccctttatg 134700
cccaatttct agaactgtgc ttggcataca gtatgtgttc aaaaatattg gttgaatgta 134760
aatacaggag tcagattggg gacaaattat taagaacctt catatcatgc tgtggaggag 134820
atgagaaacc aaggaataat tttagattaa gaaagtattc tgataagata tttttataag 134880
ggtactaagg gtcatgaaac aaatacaaaa atcctcaact ttgtggaata tgggttagaa 134940
gaaggagaga atggagataa gactaattag ttgttgaaat attccagcca gcaataggga 135000
atatggttga attgacaagc tttggtacca gtaagagaat agatacagta atggcagaga 135060
aatatggaaa aatgattatt tcggactatt ttttttaag agtctctttg gtagcccaca 135120
ctggagtgca gtgatgccat cttggctctc tgcagcctct gcctcctggg ttcaagcaat 135180
tcttctgcct cagcttcccg agtagctggg actacaggca tgtgccacca cgcccagcta 135240
atttttgtat ttttagtaga gacggggttt caccatgttg accaggctgg tgtcaaactc 135300
gtgacctcat atgatctgcc tgcctcagcc tcccaaagtg ctaggattac aggtgtgagc 135360
caccaggcct ggcctatttc agacttttta tctaagagat taggtgaatg aaagaccatt 135420
aaccagaaca gagaaggcag gaagaaggta tagaactagt aggacaaagg gaatccaatg 135480
actgttgaga ataagagctg agctggagaa agatttctaa gtcattagca tataatttaa 135540
aaatttagac acctagcaca gtacttgtcc agtaaatttt aatgcatttt aatctttatc 135600
tgcctctctt gcaattcacc ttccataatt atccagagga aaaaggtttt cttaaaaaaa 135660
aaaaggacat tttttaaaaa gacctcttct tcataattct tattttcact taatttcata 135720
accttttgt attggatatc ttttctgttt ttttcttacc cagaggatct tcccctcttt 135780
tttaagagcc atttgtttca tgcttttcat ctatcttttt ctcatgccat attactttga 135840
actatatttt gttacctatt gtttttaagg attcttatgt tgctcttctc tctctgtagc 135900
taatatttct ctaccctttt ttattgtttg ttttttaag aattctacag tattcactta 135960
ctttttaaaa gtactgtgag atgggaactg ttagtatcca cccacctttt atggatgagg 136020
aaactaggtc ccaggatctc agttagtaag tgatgaagca acattctacc tcatttagaa 136080
tgaggtagaa tctcacttag tgagagactc acttagttaa aattttttgt tggagttctc 136140
tcaccttttt cagatgcaca tattaggtac aaaacttgta tagaactatt tagagcattt 136200
gatgtaaata gatgaatata taaattagga aaacagagat taatgtagac cataaaacct 136260
tgtttcctaa tttaaataca tatgtttgtg tatttcacat agtaatgtta aaaaagcagg 136320
tactctgatt ttttacattt ggtatggtcc agcatacatt catcatgcac aaaattatga 136380
acacattgtt catcagatat gtatagctga tttatataaa tgattgtctt tctcctttcc 136440
ttagctgttt gaattgggtc ctgatggagg agatcatgaa actgatggtg accttcttgc 136500
agagactgat gtattggctt atgactgtgc tgctaggtaa ataatttgtg cattattcat 136560
tgtaactctt gcatacttaa tattaaaaat ttattataaa tgaataaaca tactttaaaa 136620
ggaagtttta aatctgctat gaatatcaaa tacttgagaa attaaattat atattaagca 136680
atataagtat tgctttcaaa aatgctgaat taaaactaat atacttcata aatttatttc 136740
ataagtcaac tgtttcaata ttgaagataa aaatggaaat atgcatatat tttatacacc 136800
tttactttca tgcatctctt acggaatacc tagtttgctg gtgttctagt aataatacag 136860
ttatttatta ctcctagcat tacaggtaat aaataattag cgtcaagtgg tcatgtttga 136920
ccataattca gattacccat gtactctgac atcatgctgc tagaatatat ttgataataa 136980
cacacttggg gaggtgacta gctttactga aaccttttgg gagtttataa aaattagtat 137040
gtttatttat gaaggttcat taagtaagag gatacttaca ctttatcagt cctctctacg 137100
taatcctaag aattatctca atattgtgtt atgatcagtg ttccctggtt tgaagcaggg 137160
aatattatta taagaaaaat tataaactga gcttcatagt agtaatagtg tgctatgttt 137220
cccaacaata actatgttag gaaaaccttg taggttttct tgctagtgaa aatgtatatt 137280
ttcagaaaca aggatgatcg taagatactg actttgcttg tacaagatat aaatactttt 137340
gaaaacaaaa gagtaaatct aaagaaaatt ttgactattt cttaggcatt aactaatatc 137400
gcaagatttt tttagtaacc tttagtgttt tatacaaatg aatattaggg aaaattttaa 137460
gaaagctaat tgattaattt tcagcaaagc cttaaggtgc cattgtcatt tgccgtattt 137520
atttatttct ttatttattc atttattaat ttttattttt gagacagagt ctcactccat 137580
cacctaggct ggagtgcagt ggtgtgatct caactcactg caacctctgc ctcccggatt 137640
taagcgattc tcatgcctca gcctcctgag tagttgggac tacagtcgca tgccaccagg 137700
cccggctaat gtttgtattt ttagtagaga tggggtttta ccatgctgac caggctggcc 137760
ttgaactcct gacctcaagt gatcctcctg ccttggcctc tgaaagtgct gggattacag 137820
gaatgagcca ctgtgcctgg ctgccatttg tttttgacca tatgagtttg agtcgaaaat 137880
ataaagcaca gtttcattta tagagaatcg tctaggattt cttcattagc ttatatacaa 137940
agcccagact cctaaggcat tgggagcatt gaaggatttc cataacatcc agcatctttt 138000
ttgactttct accactactc ttctacagct gtcttaatgc attaatgaaa ttaataatga 138060
acaccttgtc atttcctgac ctcttttgta cttccatacc tctacagatt ttttcatgac 138120
attctcctgc ttctttaaat gccctttatt cttctttcaa ttccagctac aaccaataaa 138180
cattccttcc actctgttac ctagtacttt gtaacttgtt tatatccttt agaagatgcc 138240
cttatttatt gtcttttttc ttcttctaaa ttaataatgt ttgtatagat attatgtgac 138300
agactccaaa cacctatctg acttaattca ttctaaagga caactctatg agcaggatat 138360
tattttcacc acagttttca ggtgaagaag ctaaggtact gagaggatag agtaacttgc 138420
cctgcgttgc cctgctagca ggtcacagag ctgggccttg aacccaggct gcctgactcc 138480
agggccattt tcttaatatg ctgcctttca aaactattta gctgaatgaa tgagctttaa 138540
aactaaagtt cagattttta ttttccagca aaatttgaat gtttttaat atcagtttaa 138600
aacattctaa ttttaatatg aaagttttat aacatttaag gatattgtag aattcaagaa 138660
gaggaggaag aaatgtaatt ctatcaccat aacataaata actatatttg cttgcattct 138720
tgtccagact tcttagagtg tttttaatgt tgtttgataa gaattttata atacagttag 138780
tttcatgttt ttgttcacaa gggattttga aaaaataaat atatgtgaca gagaagtaag 138840

-continued aaaatattgt ttttgactca ctaatttttt ctcagagaaa aatatgcaat gatgtttgat 138900
gagcctgttc tcctgcaagc tgggtggtgg tatgtggcat gggcccgagt gtcaggaccc 138960
agcagtgact gtggatctca tggacaggca tctattacca cagatgatgg gtaagtaaat 139020
gcccaagtgt tacttaagca atacttattt ttgttagagg aatattgttt tgaaaattca 139080
gagtactttc agcaggattc aaaagcttag gaagactaga gcataatata actgctaaaa 139140
attaaattca tgtaacctca tgccaaattg aggtctagac agaacaagga gataataaga 139200
ccactgtact ttgctcctgt cagatggtat ttgtatatat ttctgggtat tacattgttt 139260
acgagcttga ttaccaaatt agaaattata tagaggaagg tgacaaggaa aatgaggagt 139320
ttggaaccat aaaaaagaag tagatatgtg atattaaatt tgatagtgca tgagaaaaca 139380
gtttaaaatt tcaaagcttc agcaatgtgt gttattttaa taaaatatag ggaaaatttt 139440
gctgttttaa aataactttc acgtatagag tacttttcag ttcatattct tatattttat 139500
ctgatttgat gccctcaata gctttgtgaa gcagttatta gccccatttt atactccagg 139560
gactagagaa ataaaaaggt gaaattattt gctatttcct gagagtcatg tggttaaaac 139620
caaggtcaga cctgtaacct gttgactcta aatccaacat ttcaatattc tattactatg 139680
atttatgtat tctaaaggac tatcatttgt aagataaatt cagtttattc ttgattactc 139740
ctgagcataa actatttgaa atcagttgaa gttatataac agtatatatt ccagtgcagg 139800
tcaattcata acaaagctga ccaaaaaaag aaatagactt atttgtgagg tgaatttcct 139860
gttgctgaat attcaaggag actactgtag aaaaatcaca tctgttgtta tgtgcatcaa 139920
cttaagaatg tctttagaac taagtgacta ctttgaccct ggactgtatg attttcatag 139980
acagttcatt cagacttgga atgtcatggc acactgaggc taaagcttat catgcagcta 140040
gtcaagcaga tattatacta cttagttgta agtagaaatt ttagaagttt actgctgtgg 140100
ttaaagctga gttggagagc taggagggac aggacagcta ctcatttagg agtcctaatc 140160
acgttcagtt ctttcatttt actgactaac ccattcagag ctagaatgaa aatctagaaa 140220
ataccttttt gcttttcttt atgtaaaaga gtgaatcatt ttcattgaca taagatttga 140280
aaacatgttt cttaaatttc ttatttcctg taatgatcat gttgtttttg gtatcattgt 140340
tttctcttct tagggttgtt ttccagttca agagttcaaa gaaatcaaat aatggtacag 140400
atgttaatgc gggtcagata cctcagttat tatacaggta tttagcatat ttatactgaa 140460
ttagtatggt ttattatttt gctataatga agtagaatca ttacaaaacg tggcataata 140520
gggagaaatt atttgaagca ttcagcaaat tataatatgc tggtagaact ataaatatat 140580
ttaacaaaaa cagttaatat tttgtatatt tttaaacatt ttccatacag gcttaacttt 140640
aaactttgcc tgattactca gattatctgt attataccaa taacaatatt ttactgactt 140700
taaaaaaaat ctatccattg attttcttac taatttcaaa tgttgtaaaa gaataaaatt 140760
tgtcttggag aagtgagatt gcagggaaga tggggaggac tatagatgca ggcctggttg 140820
atatattgta gtctcataag actgataaaa tgagttggaa aattccctac tgttggtaaa 140880
ttttcacctt tagctaaaat accaaataat aacttgctca tataatattt actatatttt 140940
taacattatt gaaaaatttt aacttacaat aatttaagca tgtataaagg catatgcctg 141000
tgtttacctt atttatttct agactactgc aatactttta gaataaagaa ttcaaatgga 141060
tataaaccgt tactgaaaaa tgttgtcatt cgttaagcag taaaaaatca aaggaaatgg 141120
tctagaactg tgattctatc tccctatctt tctttctggt aatcactttg tggttacaaa 141180
cattattttt ccccaaaagg ttttttcgtt tgtttggttt ttatgcaccg tgcaatctgt 141240
tatagttact gtttgtaata tgtagctcta caaacataac gtgttgcatt ggactactcc 141300
caggtactca ctggttgaat aacttttaaa taacagcatt aatagtagca ttactagaga 141360
atataagtta tatgttatat acattatata tgttctctaa gaagaggaaa aagcctctac 141420
tactcggtct tgcgaaggta ggatttaaag gaagtgccca tatgctaaaa actttgttta 141480
gcttggaaaa atgtttcaaa aaagccctgt attggcatta cctggcaaaa aaatttaaat 141540
atataattta ttttcccatt caaaaatgta taatatactt taaaaagaaa aaatgacatt 141600
ggactttcta acataatttt atatgtgtct actgccttta gacttccaac cagtgatggc 141660
agtgcttcaa aaggcaaaca gcaaaccagt gaacctgtac acattttaaa gaggtctttt 141720
gcaagaactg tctcagtggt aagccatgtt ttaaaaaatt tcagcttttc tcttcagtcc 141780
tcagatacat tttgatgttt agagtttagc tgctcttgta agtttatctt agcctagatt 141840
tataaactca gatttggttt tgtattcaca tttatattct agaccacaga taaagtatac 141900
tttaaatcat agaaaaatgg aggtgttggc ctatgatttt aacatgacca gatgaattgg 141960
ccttgctgtt tttgaaacaa ataacgattt gcttttctag taaatcatat atgaatgcat 142020
atgctgaatg aattagaaaa tgaaggaaaa gttaaggatg gtgctggccc aaaaaagcgt 142080
gattactact tgaggaacta ggtggaagag ttgcatatct aactaggaag tttgttgaac 142140
cacttgccat ccccattgta cacatgaaga agcacagtgc cattgaggtt aacagtgcag 142200
aatggaaagt caacatgatg taaataaatg aaagtataaa ttaaggtctt gatctctcat 142260
gtattaattg aggattctta cgtatgttac ctaagtaaat tacatcatag cattttgaat 142320
ttctaatgag ataaggggtg taagatgttt ttggaactgt aaggcaccat ctgaatgtga 142380
tttattaata tagctagtag tctttcatat tagtaaaatg cataggaaga atgtttcttt 142440
cccttttaaa tttatttttc aacccaccaa gtgaatatat attcctggta ggaatgagat 142500
aaaagtatcc taaaagtata tgaaagattt ttctcccatt ctcatgatca ccatatatac 142560
ctactattta cattttggtg tgtatcttcc cagacctttt tttttttttt tttttggtga 142620
ggcagagtct cgctctgtcg cccaggctgg agtgcagtgg cacgatcttg gctcactgca 142680
acctccgcgt cctgagttca agcaattctc ctgcctcagc ctcctgagta gctgggatta 142740
caggcgcctg ccaccacgcc cagctaattt ttgtattttt agtagagagg gggtttcacc 142800
atgttggtgg tggtctcgaa cccctgacct cgaacaggct ggtctcgaac ccctgacctc 142860
atgacccacc cgcctcggcc tcccaaagtg ctgggattac aggtgtgagc caccgcaccc 142920
ggccttccca gaccattttt atatgcaaaa aaacttatta gtacgtatca aatacaggat 142980
gctctacaac atgcttgctt gtttcttacg atacttacag ttttcatctt ttttagaaaa 143040
tttcgtatta tatatcatgg acatccttcc ctggcagtac atttggctct gtcagtcttc 143100
tccgtttgcg taccattatt ctaatttatt caatctgata tctatcaaag aaccactttg 143160
attctcattt tttgttattt catcttgctt catgagcatc tatacacata catctttaaa 143220
tacttgtgta cttatgtgca tacttctact ggaaatatgc ccatttaaag tttggtatat 143280
cctctcaaag ttgaccttcc aaaagagcca tggcagtttg tagagcttgt gctttgaata 143340
aaagactatg agaactttgg cttcttggta actttgcatc ctattagtct taagttgagt 143400
ttggtatctt ttgattcaaa taaggatctt tgactctgtt atgctttctt tagtgatctc 143460
acttttctgt gcttggtaac ccctttgtat ttatgtttaa gtggttttgt ggccattagg 143520
taattgtaga ctttatatac aaaacttatt cagtcatttc tttaaaaggt aaactatagg 143580

-continued gcttagcaca ttggctcacg cctataatcc cagcactttt ggaggccgag gcaggaggat 143640
tgcttgagct caggagttca agaccagcca gggcaatata gtgaaacccc catctaaaaa 143700
aacttaaaaa ttagctgggt atggtggtgc gcacttgtag tcccagctgc ttgggaggct 143760
gagggggtgg tgagaggata gcttgagtcc aggaggttga ggttgcagtg acccgtgatc 143820
acaccattgc attccagtct gggtgataga ggaagactct atctcaaaaa aaaaaaaaaa 143880
aaaaaattga atctataaac tcgttttcag gagctctggg atttggtggg aatggggcag 143940
taagtgctct gctttgagat tcaggtggta tctgttgtca tttaaccatg ataaaaccag 144000
aagactagaa ctgcaaagaa aatctaccat cttaaactca tatgctagaa ttttaaataa 144060
tcaaaatagg aattttttag tattttctag tcaattttta tcttctatta atgtatttat 144120
caaaaattga ctgtagtttg tattgcaaat tttaatatat agacataaaa taagttattt 144180
gatactgtta ctgatatcta acactaaaac tctattttat tttttactac agtgactgta 144240
aaaagcttta tttttcttc aagtaaacat gcattgtttt ataagtgctt ctcatttttc 144300
ccttgtttat atgataagct agatagctgg gtagcaggaa cactgaaaaa tttattttta 144360
aataggtaaa tattgaagaa tgttgttttt agaaatgctt aactacttta cctttttgt 144420
aacaaacttc aaagttactg ttgagggtaa tttaataaat gaactataaa agtgtcttgg 144480
gctcagtaaa aaaaattcaa ttaaaaaact cagtaaaaaa attcaaaaga aagttttgaa 144540
gttgtctacc attgcctttc catttgattc cgtttatggt atcatttgaa ttaattgttg 144600
tctgtttttt catattctgg attaggaatg ttttgagtca ttgttgagta ttcttcactg 144660
gagctggacc accttagtct taggagttga agaacttaga ggattaaaag gattccagtt 144720
cacagctaca ctcctagatt tagagagact gcgctttgtg ggtacctgtt gtctgaggtt 144780
attgcgtgtc tatacctgtg aaatttaccc agtgtcaggt atgatgcatt tttttaaat 144840
gactataggg agaaaatatt agagacattg agaagattta ctttgagata actgagagtt 144900
tatgcccccc agctgcattt aagctgcttc taaaatgagg ggagaaagtc agcttgctat 144960
gatgcttatg tatttgctta taaagagtaa aatagattac atgtcattct gatacaaaaa 145020
gtaatagtgg gccaaagtta aataatctaa taaagtttaa ttttaaacaa attctgtcaa 145080
atagaaatat tttgaacaag caatttggac ttaaatgctg aaactaggtt tttattcccc 145140
cttccattta gattaaaaat tgggactaca cttaatctct aagttgtttc atttctaaga 145200
tattagtact tgtgatactt agctgtatag ggaattactg aattatattg attgttttca 145260
tgcatattta atattttgct taattaccaa tctgcttttt cccccctcaaa gctacaggaa 145320
aagcagttgt agaagaaact agcaaattag cagagtgtat tggaaaaacc agaactttgt 145380
taagaaaaat tttatcagaa ggagttgatc actgcatggt gaaattggat aatgatcctc 145440
aaggatatct cagtcaaccc ttgagtcttc tagaagctgt ccttcaggaa tgtcataata 145500
ctttcactgc ctgctttcat tctttctacc caactcctgc cttacagtgg gcttgccttt 145560
gtgatctgct gaattgtttg gatcaggtaa tttaagtttg taaaatgtta gttgaaaatc 145620
tgatatattg cttaatactc ttcaagaaaa taaattgcag ttgccatatc ttcttaactt 145680
gtataaaaga taaattagga aatcattcgg tgtacatgac ttatataagc aaagtttaaa 145740
attttttaaa tctgcttcat catcttttag ttacaaaatt ggtaggcaca ttgtgcagtt 145800
gctgattggt ttttgaattg gagtgagtga ttctgagaga gggagagagg aaaagaacca 145860
tagtgaccag gggagagcag ggatagcacc aggaggcccc cgccaccctc atctgtgaga 145920
acaggaagga gagagagctg agagaacagt catactagca ttgttcattc attcatgagg 145980
aagccacaac ctttgtaaac ctttatgcac caagtcacag agtttcacaa cacctgaggc 146040
aaaacactga cagaactaca gggagaaata gattcacatt gacagctggg gactttaaca 146100
ctcctctttc agtaattaat agaggaacta ggccaaaaac atcagcgatg cagatttgaa 146160
cagtactgtc aaccatcttg atctgacatt tacaaaacag gatatgaaac tgcaaaatac 146220
atattctttt caagtacaca tgatttttaa aagaaatatt tgggaccatt cactaaggta 146280
gatcatatgc tagaccataa aatgtcttaa taaatttcaa aagattaaaa tgtgaaagaa 146340
tatattttca gaccacagta gaattacagt aaaaatcaat agcaaaggat atccagaaaa 146400
agcaccaaac atttggaaaa tgacagcact tctaagtaag cagttgatca aagaagaagt 146460
tataaaggaa attttaaaat gtttcacata gaaagataaa aacataatat cagaatttgt 146520
gggatttagc taaagcattg cttaaaagag ctctttatac ccttaaatgc ttatatgaag 146580
aagaaaggtt taaaatcagt gacctaagct gctatgttaa gaatctagaa ggaaaagcaa 146640
atctaaccca aagttagaag gaaggaagga aataataaag ataagagcag aaatcaatga 146700
aatagaaagt agagaaaatt aacacagcta aaagttggtt ttttgaagaa aaaaagttgg 146760
taaactccta gcaaacctga ctgggagaga agagagaaag aaaaaacatg aaataccata 146820
atcaaaagtg aaataggggt tcaccgggca cggtggctca tgcctgtaat cccagcactt 146880
tgggaggctg aggtgggtgg atcacttgag gtcaggagtt cgagaccagc ctaacatggc 146940
aaaactcagt ctctaccaaa aatacaaaaa ttagccaggc atggtggtgc acagctgtaa 147000
tctcagctac tcgggaggct gaggcacgag aattgcttga aggcgggagg tgaaggttgc 147060
attgaggcaa gattgtgcca ctgcactcca gcctggtgac agaatgatac tccatctcaa 147120
aaaaaaaaaa aaaaaaaaaa aaaaaaagaa atagggacta tcactataaa caactttata 147180
ctggtgaatt tttcagcctt agaggaagtt gacaaattcc ttgaaaaata taattttatc 147240
aaaactaaca cattaagaaa tagaaaaatc tgaattgcct catatccatt taaaaattat 147300
caaaaacttt cccacaaaga aaatttcaag tccaaatatt gtcatttatg aattctgtta 147360
aacatttaag aaagaaataa tgtcaacctt ttacaaagtc ttttggaaaa tacaggaggc 147420
aacacttccc aactaatttt atgagtttag ctttatccta taccaaaacc taactaagat 147480
actacaagga aaaattacag atgaatatca ctcagaaaca tagatgctct taaaaatatt 147540
atcaaaccaa attgaacatg taaacaatat atcataacca agtgggattt atcttagaaa 147600
tacttagtta aataattgaa aatcgatgta atttaccatg ttaactgaaa aaagaaggca 147660
aattgatgat ttcctccata tagctacagg aacagtggtt gatgaaacta gcagttactc 147720
aatgatgaaa acctctcagg aaagtaggat ataaggaaac tcctaaatct gataaaaaga 147780
tatttacaaa aaaatcttca ctaacaacat cccacttact ggtgaaatct gaatatgccc 147840
ctaagtttgg aaacaagaca cgtggtatct acactcacca cttatattca gcagtgcact 147900
ggaagtccta ggcctccccg ccctccttcg tgaaaaaaat cattgtcatc actaatgcat 147960
cccaggcaac tttgcatcca tgtagcagag tagtatgttt taccactcaa tttccagggg 148020
caagattatt gcctggacta gtgcacaact taattactct ctcactctga accttcccag 148080
tctgatatgg ttcttttctt ctttgctaca gaacaggcta gatttagcaa atgttggttt 148140
aacatatgga atgttactct gcttttatgc ttaactttgt aacacagatg tttgaaggac 148200
taggtaatgt gtacacaatt ttgtgaatta ggatatcatg tgttggcttt aatgcttttt 148260
tatgaaattt tgtaagtatg ctactaattt ttcttggtaa attatggaat gtgataatat 148320

```
aattttgtga ccttagtgaa atgtgcttgt aatagcacag atttataatt tgcatcattt 148380
attatttgag aaaaatagtc tcagtcctta ttgaaaatac cttagataca ttctaattgg 148440
ggccttttg gcatctccct ttgaaacagt gctagagagt actgtgattg tgaggatatg 148500
aaaatataaa aatgctcatt tactagagga caggagcctg atttttcttg accagactta 148560
atttttcatc ttcattgaat agaaacttaa acaatttttt aaatatatag atgtagtatt 148620
attctataac aagacaattt aaatgacaga gtgacagaaa attttggtat aatttaaaag 148680
atggtttacc ttttatgtat tcagaaactt agattatact gatgctatat tttttggttg 148740
gggggccata tttttgtttt taaaaggata tccaagaagc aaacttcaag acatcaagta 148800
gccgactcct tgcagctgtt atgtcagctc tgtgtcacac gtctgttaag ctgacttcca 148860
tcttcccgat tgcgtatgat ggagaagtat tactacgatc aattgttaaa caagttagta 148920
cagagaacga ctcaacacta gttcatcgtt ttcccctttt ggtggcacat atggaaaaac 148980
tcagccaggt aggtctgtct ctgaaatctt ttatacagag gcactaaaac tctaaatggt 149040
tttatttatt gcctctttta tacagaggca ataaaactat aaacacacca agctaagcgt 149100
atttagcttg gtgcttattc ttctctattt ttaagtatat ttacaaaatg attattttaa 149160
atattttga aaaatgttca tatttaccta taaaatgaag ttttttgct ctaacggttt 149220
aatcacacac ctttaaaaaa atttgagagt tatacaatga atacctacat atttgttttt 149280
cctgaaccat ttgaaggtaa gttgcagata ctttacattc taatataata ttttagattt 149340
ctaagataga acaataagaa aataaaggat ttttaaaata tctacttaat aacactttgg 149400
tatattaaaa taagcactgt aaataatagg tataggaaac attcacataa atcattttca 149460
tgctggaaat cagctaaatt aatcatcttt tcccttttt ctgaaaaata aagtattttt 149520
cctttattga gactctgtga cttcttgaaa tttttctacc ggtaggggtt ggaattttct 149580
tatctccact taggaaaaca aatacagtag aaattataaa actacatagg aatcatatgt 149640
gtgtacaaaa agaattttgt taaaaaagtg atttacacag actacagttg cattacagct 149700
aaatatacta gaatttatta tctcagatta agaccttgtc ctatagaaaa agctttttat 149760
ttttgttttt taagactagc tcattctgtc acccagtcta cagtgcagtt gtgccatcgc 149820
agtttactgc aacctcaacc tcctggactc aaacgatctt cccacctcag cctcccaagt 149880
agctggggct gtaggcacat accaccacac ccagctaact ttttaaaaaa acattttgta 149940
gagacaaagt cttactatgt tgcccaagct ggtctcaaac tcctggcctc aagtgatcct 150000
cccatctcag cctcccaaag tgctggtatt gctgacacca cgcccagcca aaaaagcttt 150060
ttaaatggaa agaagtttc tgtctgtcat atagaattgt aaattgaaag ttaaataaga 150120
gaataaaata ggactcaaag ctaataaaaa catttcgtaa atgtatggta ctttgatacg 150180
cagagacaga taattcaaaa aagaacttct aagtgaaaag tggctccaca tataaccaga 150240
aagatttgta gaaattgacc ctgattcaag tctgaatttt aagagtatca gaaagacaag 150300
gttttcaaat tgagtactcc tatgaaggaa aataaaacaa taccttagaa ctttttctta 150360
tgtatcgcag agtgaagaga atatctcagg gatgacaagc ttccgtgaag ttctggagaa 150420
aatgctggtc attgttgtgc taccagtcag gaacagcctg aggagagaaa atgaactctt 150480
ctcctcccac ctcgtctcta acacctgtgg attactggcc agcattgtca gtgaactgac 150540
agcgtcagcc ctgggatctg aggtaataca ttatattttg acactggata aaaagcacat 150600
gtgtaagttt tttacacagt ttcttttttc aactattttg gctttgtgga agctaatttc 150660
agattggatt agcaacccca atgcattgtt tttcttttt gcctttctct ccacctccta 150720
```

ctttctctga tttgttactt ctctctcacc agtttaccca gcatccacag gaatataaag 150780
tatacatttt cctcatagag caggtcgtca tctgccccat tgcacaagcc caccaccatg 150840
ccccgtgaaa agcaaagata gttctcactg ctggaagatg agtaacattg ctgaagtcag 150900
gccctactca tagtgcacac atagtgtggg aaaggtaatg aggtttagac ttcagctctg 150960
cccactcaac cgaccctaga gaaatacata cttaaaattg gaataataat ttttatttca 151020
cctctatcac aggttttttg aaattatagt aaaatataca taatataaaa tttgccattc 151080
taatcatttt tacgtgtaca gttcagtggc attaaatgca ttcactttgt tgtacttagt 151140
tgtacattat cacaaagttt tcaaagtctc aaatattatg tttgagaaaa tcactttgaa 151200
agtgccttta cattttgtaa agtaacatta ttccatttca ctgccttact ctttcttata 151260
acttaactga atgttttgac tgaatttggg gaatgtttct gttttttcct cctaaaaaac 151320
agacagtaga ttggtttgga aaatcatgtc ctaatatgaa atatcttaca tcattcaaat 151380
gaatgtttaa taatcagcat atattcagtg gccctagctc ccaagttctt gtcaaggaac 151440
ttcttttctc tattttactt ttataattcc taatctttgc ttttttaaa aaatttattt 151500
taacacctat tctgaattaa cccatccaat atatacacat tattgattaa ttgtgacagt 151560
ttagccttta gaatttcatt gtatgaaatt catacgtaag aaattcgcat acatatggtt 151620
catcgcatac acttgagcta attttagtct ctcatcctgg gaagcacttt ctaagtttct 151680
tggttaactt tgagtttggc ctcagagacg attgaagccc ttgtcagaaa ttttttaact 151740
ttttacattt actcatttag tctataatac cttcctttga tagtatactc tgcaggatgc 151800
aggaaagtct ataatgtgta gatccccttc caaagtttac taaagagttc tcccctttaa 151860
acttaccttt ccaatgaaaa ggaataccaa aagttacagg gtgcctggta tacaactttg 151920
ggagttccca caggtcctgg cttagagatg aatatttctt tctcagagaa gtttgcaatt 151980
tttgttagaa tcataaactt ccatttttgt atctatttag tctcccaaaa ttctgtagcc 152040
aagttagatt agaagtaggc tttgtaaata aaaagagcga tttcaaccca aagtaagttc 152100
tctaattctc tctagtgaaa gtctataatt agtatagttg cacatgtgta tgtgtacgta 152160
ttcaaatact gaatgctgtt acaaaaatat cactgtatat attcgtagta ttcaatctta 152220
gggtatagac cattttcttc aaatgaagtt ttacttgcaa attcacaggt aagaggagag 152280
aggacatagt ctggttgaag aggggaacca taaatttacc tcttccttgc acacctatct 152340
ctgcagaatt tctagagctc tgtgttgcat agtttgaaaa ctgttgatct atagaatttc 152400
gatgaaattt ttagcatctc ttttcaaagt ctgatgattt attcatacat tatgactgat 152460
aagacaagct tgtacttctg acattataaa ttaagtggaa agtatagttt catatggcta 152520
aaggaagaaa atactgtcaa gtgacattga tttgtgaatt tagaatgata aaatctggtt 152580
ttattgtgag ttaatctctc agtagaacat acctttagga atgtttatat ccacttatta 152640
aataaaggtt attttattag acttcttaga aacctttgga tggttttgtt aaaggtatac 152700
caactactga tacaattgct tttattgttc acaggttgat ggacttaatt ctcttcactc 152760
tgtaaaagct agtgctaacc gatttacaaa aacaagtcag ggcagaagtt ggaacactgg 152820
gaacgggtcc cctgatgcaa tctgtttttc agtagacaaa cctggaatag ttgtggttgg 152880
tttctctgtc tatggaggag gtggaattca tgaatatgaa ttagaggtgt tggttgatga 152940
tgtaagtatc accctttttag tatttatcct gattagtggg ttgtgtatca ggatttacca 153000
ttgtcatagt atgttcaggg gtttactaga tcaatcactg atgaatgaca ctaaagaaat 153060

-continued tgaaaaagac tggccacagt ggctcacacc tgtaatctca gctctttgag aggctgaggc 153120
agttggatga cttgagcaca ggagttcaag gccagcctag gcaatatggc aaaaccctat 153180
ctctacgaaa aatacaacgc acgcctgtaa tcccagctac tctggaggct ggggtgggag 153240
gatcacttga gcccgggagg ttgaggctgc agtgagccat aatcatgcca ctgcactcaa 153300
gcctgggcag cagagtgaga cccgaccctg tctcaaaaaa aaaaaaaaaa aaaagaaaga 153360
aaagaaattg aaaaataatg attttacctg attgtttgtg ttccatcttt ccaccttggg 153420
tcactactgc ttcatatttt ttgtactttc agaaagagaa agatttaaag tagaattaaa 153480
gactaaaagt gtttagctaa gtccctgatg acaagtcttg agtagttttt tttttttttt 153540
atattgtcat ttttcaagaa acacaatgtt gagatggact atgtcataga gtactaatgg 153600
gtgattctta gtgaagacac tatttgttga ctgattgagc tatatctttc tatattctct 153660
aaaattaaag tacctgagtt ttattaaaat gggacagatg gggtagcatg taaatcattg 153720
cctattaaat agcaagtcta tctctatctc taacttgatt cctttcacta gttaatttga 153780
atttattccc tacttcatta ggctttataa atgtgaagaa gtagaaatag tttaagtcat 153840
cagatgagaa aagcttattt atgttgtagt cttctcaaga aatcacataa aaatgtatat 153900 agtacccccca actttttctt tcatatgtat gggaaaatac taatggctaa ttttatattc 153960
aagaaaataa attttaaaaa taataattat aaatcaaaat tgttcataca ataaaattaa 154020
gagtctgttg gaatttttgt gtttcatttt tttttttag agtgaacatg caggagattc 154080
aactcattcc cacagatgga catctctgga attagtgaaa ggaacgtaca caacggatga 154140
ctcacccagt gatatagctg agatcagact tgacaaagtg gttcctttaa aggtagtttc 154200
aactgaatgt ttctattgtg aataagaggt attattatgt agttaaaata gtgaagagta 154260
ttccatgaat tttgtttgtt acctatagct atttgtaagt tatcctttat atggtactta 154320
aatatttatg gagtacctac tacgtaccta atgttgtacc acattatatt atatttttgc 154380
ataatgtttc ttaaagtcag gagtagtagg aagttttgta gtcaaacaga cttagctttg 154440
gatacctgct gttccacatg ctgactttaa gacactggca gatcattatt taaccacttt 154500
gagacttatc tgtagattgg gaagaataat acctgcattg tagtagtatt gagattaaat 154560
aatggaaata aaacacctgc cttagtgtct agcacaatat gaaaaataaa tattagctcc 154620
tgtcttttct tctcttattg tgccctaact catttaaaaa aaaaaaaaag tgtttttgtt 154680
ttgttttgtt ttgtttcttt attttttttt aattattatt attatttttt tttagatgga 154740
gtctcactct gtcgcccagg ctggagtgca gtggtgtgat cttggctcac tgcaacctct 154800
gcctcccggg tttaaatgat tctcctgtgt cagcctcccg agtagctgga attacagcca 154860
cgtgccacta tgcccagcta attttgtatt tttagtagag ggtttcact gtgttgacca 154920 ggctggtctc gaactcctgc cctcaagtga tccactccgc ttggcctccc aaagttctgg 154980
gattacaagc gtgagccacc gcgcccagcc tatttcctaa caatatttgg caaaatagag 155040
aaattttacc acatcaaagt aattatagat gttaaaataa aattaaagta tttctgaatt 155100
caactgaaat aaatttcatt atagagcaga attttggata agatcggtac acgagaggtt 155160
tcatcaggaa gaatttagat actgaaaaac caaaaagctt ttattgtgaa atttatatca 155220
tgggtcataa agcattagtt tctatagctc acattttaaa agtacagtgc attatatttt 155280
ggacagcttt tttcctatgg gtttttttc tcatgtctgt ttgcctatat atttctatct 155340
ctgagttttt cttaaaaata taatagactc accatttttt tcctcacatc taaaattatt 155400
ttaaaagtta aactagtcaa ggaaaagtat cagcttatgc aattaaaatc ccttattgcc 155460
gggcacagta gcgcacacct gtaattccag tacttttgag acaccaggga gggaggatca 155520
cttgagcttg ggagtttgag gctaggctgg gcaatatagt cagaccttat ctctacagaa 155580
acaccctaaa aaattaactg agtgtgatgg aacacaccgg tgggaggatt gcttgagccc 155640
aggaagagga ggccacattg aaccaaaatt gcaccactgc actccaggct gggtgacaga 155700
gcaagatcct gtctcagaaa aaaatatata tatataatat ataaaatata tatatattat 155760
atatatataa tatatattat atatatatag tatggctaat attctagcag taaaattaag 155820
agcaggcact agttacattg gttgtgttca gacctagttc catcacttac tagctgcgtg 155880
actttgaaca agttacttaa cttctctgaa cctcagattc ctcatctgta aaatagggat 155940
agtaatgata cttaccttat gaggtcattt taaggattaa ttaaattcca taaagtagtt 156000
aggacagttg cttttatgca acaggtgttc agtaaatgtt agccgtcatc gtgtttgatt 156060
cattaaaaac ttatttaatt atatcatctg taaatatgac aaagaatttc agtatatttg 156120
cctattttac tgctagagtt ctttttatat atcctctgta cattgtgaat aaaagatgtt 156180
ttacatcttt ataatgaagg aaaatgttaa atatgctgtg cgcttgagga actatggaag 156240
ccgtacagcc aatggagatg gaggaatgac cacagttcag tgccctgatg gtgtgacatt 156300
cacattcagc acgtgcagct tgagcagtaa cggcacaaac caaaccagag gacagatccc 156360
acagatactc tactataggt gggtgaatgt atagagataa cggaaatact ttacagtggt 156420
agaacataca cagtctacta ccaggtaaaa ttgctaactg gatacttata attaaattgt 156480
acagtgtatc ttcttagcac atacttgtac aaattcatat aaagaaatct ctttttaata 156540
tataaattca atgtttgcta caaaagttaa tgctttaaaa tatttttgct gttatttctt 156600
caatatcatt gaaatgtttg tgtactgggc atatgtgctg ttgctgtcac tctataattt 156660
ctggtctgca atttcaaatt taaaggatat tcatttcttt ttataaaata cctcaaacta 156720
atgatcagat agactgtact cagatagtgg tgttgccttg atcttgttat ctagtcacag 156780
aatattttga tgtctgtgaa tcttggacct gccccctggg gccctagaat atataatagt 156840
gtgtttctta taatgttttt aacaaaaacc attccttatg taaaccttgg aaaataaaag 156900
aatgataaca acccttgggt taaaaaaatc ttttaaataa acatttctca ctgagtctga 156960
atttttcttg tagcggcaaa gctggcgtct taggtagtca tgagtaccat ttaccacatt 157020
tgtcctcagc ctgacttggc attaaatcac tgaatttcca tgtcactttc agaggcttgc 157080
tgcttcctct ctttccttca tgaagagtct agggatggtg cctacgtaga tagtataaaa 157140
taatttccct agatatagat tttctgcttc ctctttccat cagaaataga atagaaatag 157200
caggcagcaa atagctatgt agttcattgt tgctgctgaa atacaaaagc tgtctagtct 157260
tttgccccag tcaagaaaag ctttctgtta cataagcact acaataaata gtacattatt 157320
ctctttctta aactatggat taaaaactct gttatgcgta agagttacgt gtttcagaaa 157380
gctggagagc cactaagagc atctgccatc caaactttat atcttataca aaatacagtg 157440
ttttgagtat tttcatgttt tctattaagc tttaaatacc cttagcttta catttttat 157500 aaatgaaaaa tgttaaagtc ctttagtttt aaataccatc ctgctctgat agctcccaag 157560
tttacatccc tagccttcat gacctctgag ccctggactc cgggtctctc ttctgacatc 157620
ttcatttgga tgacactagt ggagatggtg ttagttactg tgtgccagga catgctttga 157680
gtatgttacc tgtgttattt caccttgtcc tcacagtaac cccaggaggt aggtactttc 157740
cttatccctg tttcacagat gatggaactg agacgctgaa ttgtctagag tcacacctct 157800

-continued gttaagttac gctactgcga cttgtaggca ggaagtcaga tttcaggtga tacaccctta 157860
accagaatgc tgcactttct ctttaaggat gttcgttata gttggctagt agacatctga 157920
ggtttcatgt ggctagaata ttcatctccc ttccacagtt acagccagac accttggagt 157980
cattctggac ttctctttcc ctcatacttt acacctagtt catcaagaag tcctgtcagc 158040
tgtacttcta aaatgtccta aatgtgacct tttcttctac ttccatattt aatagtctag 158100
accaagccac tgcaacctct acctgctaac tgtaataagc ctctaaacta gtctccctcc 158160
tttcactatt ggtctcctac aatcagttct ctacagcaca gccagagtga tctgataaaa 158220
atataaatca taccaagttc caccccttgct ccaaacccag cttcccattc tcataccagt 158280
ataaaatgta aagtcattat gtggcctaca aaccttacac aatttgactc ttgtttccct 158340
tcccacccat cacgcttcac tctttctcct tttcttccag ccatacatgt cttcattctg 158400
ttcctttaat tcaccagtat gttccttttg ccctgacagt tttccctcag ctcttcgcgt 158460
gggtctttaa aaaaaaaaaa aaattcaggt cagctgggtg cgcggctcac tcctataatc 158520
ccagcacttt gggagtccaa gatgggtgga tcacgaggtc aggagtttga gaccagcctg 158580
gccaacgtgg tgaaacccca tctctactaa aaacagaaaa attagctggg cgtggtggtg 158640
catgcctata atcccagcta tttgggaggc cgagggagga gaatcgcttg aacctgggag 158700
gcggaggttg cagtgagccg agatcatgcc actgcactcc agcctgggcg acagagcaag 158760
actctgtctc aaataagtaa ataatttaat taattaattc aggtctttgt taaatatgag 158820
ttcctcggag aactgatctt atttaaaata acacccttca ctttatgccc tatgctgctt 158880
tgtttttctt caaagccctt atcattccct attattgtat agttgcatgt ttactttttt 158940 aactttttaaa aagctataaa ttaaatgagg atctcagatc tagatatgat ttctggcact 159000
ggatcatgtt ttacttacca ttgtaaaata atctcatgtt tgctcatgct acaggagtga 159060
atttgatgga gatttacaat cccaacttct gagtaaagcc aatgaagaag ataaaaactg 159120
tagcagagca ttgtctgttg taagcactgt cgttcgagcc tctaaggacc tcctgcacag 159180
agctcttgct gtggatggta atattttttc tttctcagta gtcatatttt agattcttta 159240
ttcactaaat ttttgcatag aattattgaa gaggagcctt ctattataca attttataga 159300
atctaagtgt tatttataga tccacccatg gattaatttt ggataggtca cactctccat 159360
actgtaatgc agaattattt agaatgctca aaaggagtta ccatatattc ttattttctt 159420
agttaattta gtaaaagaaa aattgtattt gagttaaact gggtctttat tcttctttta 159480
gtaatcaaaa agctttttct tcctctctgt tctttttcca gtaatgtatc gctatccacc 159540
caaaactctg ggtaccccta accatctcct cagaggcact tgtctaaatt cagctctatg 159600
agtttttcca ttggaatctc tctagtttgt attctcctct ctttcacttc ttctcctgct 159660
gtcatttaga ctgccatggt gcaagtacat ttcatttttt aatatagggt taatatcccg 159720
ataatctcac tgctgccttt cccccattct ccatctagtt gtttagttat tcttcacact 159780
ggcagcagag ttatcattat gaaaacatgg ttatggccgg acatggtggc tcatgcctgt 159840
aatcccagca ctttgggagg ccgaggaagg cagatcatga ggtcaggagt ttgagacgag 159900
cctgagcaac atggtgaaag cccatctcta ctaaaaataa aaaaattagc caggcgtggt 159960
ggcaggtgcc tgtaatccta gctactcaga aggctgaggc aggagaatcg cttgaaccca 160020
ggaggcggag gctgcagtga gccgagatcg caccactgca ctccagcctg gatgtcagag 160080
tgacactcca tctcaaaaaa aaaaaaaaaa agttacctcc acctccttat tgtataacat 160140
taattcctaa acctagttta acatcagaac cacctggaaa gcttgctgaa aataaagact 160200

-continued attagattta tccccaggtc ctgaagctag gctaaaaaac tattttttaa ataagtgtgc 160260
agcctgtttt gatataacag cagacctagg aatcagtatt tgggagaata attggcttat 160320
aaaataaagg tcttcacagt ataggctcag cttatctttc cagcaccatg ttcatggata 160380
actgactaaa atgttaatca gcaaagtgct tttcttggaa aaacagaaag caatgtagct 160440
taataacagt aaacattttt ggagtgctga atatgtgtag gtgttgttct aagtgtttta 160500
catatattac ctcgtttaat cttcccaaca tccaaatgag aggaatactg ttgtgaacct 160560
aagttacaga gtaagtaatt tgcctaatgt cactgataca gccatgtttg gtgccagaat 160620
ggtaatttaa aataaagact ccattaccct aggttctgat tccagctcta ttattttaca 160680
ggtacatgta cttatgtatt aagtattttg ggtaagatac ttaaacccta tgtgccatgg 160740
ttttcctttc tgaaaattgg ggataataaa agtatcttat tgtgagtatt agttgagata 160800
aggcatgtat tctcaaaagc ctttagaata gtaccaggcc cttgacaagc acccaattgg 160860
tgtcaactat agtttcgctc aaaagagcag aatatagatt tagtacagca tgtatgcagt 160920
acaatgaaat taccttctga ctatagtttt aatgcctttt atgccttttt ttagctgatg 160980
acattccaga actgctgagt tcttccagtc tgttttccat gctgctcccc cttattatag 161040
cctacatagg accagtagct gctgctattc ccaaggtgtg taatttaatt ctataacttt 161100
gaatgttttt tttaaatatc ttttttaaaa aaagactttg tgtcttgtct ttacaaaaac 161160
ttgcatcttt gaggcatctg ggatataggt aacaagcaga gatagatctg ctaattatta 161220
aacttctctc ttcttagtat tgtttactgg attgctgtgc ttatttgttg gctttttttt 161280
tttttttttt tttgagacgg agtcttgttc tgtcacccag gcgggagtgc tgtggcgcga 161340
tctccgctca ctgcaagctc cgccttccgg gttcacgcca ttctcctgcc tcagcctccc 161400
gagttgctgg gactacaggc gcccgccact gcgcccggct aattttttgt atttttagta 161460
gagacggggt ttcaccgtgg tctcgatctc ctgacctcgt gatccgcccg cctcgccctc 161520
ccaaagtgct gggattacag gcgtgagcca ccgcgcccgg cctgttggct ttacatttga 161580
agaatctgtg aatgggaaat agatttagc aattttagga atatgatatg taaggaaaga 161640
ttatgttaac tgaggttttt cacatttatg aggttgatgc caaatggtct tcattaataa 161700
caatagcaat gttaaaggat aagagtgttt taaaatagtg acatattcaa gagatggaag 161760
aaatgataaa ctattgattc tttggcataa ttaagtaaaa cctgatttac ttcagatcat 161820
gaaaaaacaa gtttttaaaa atatagattt agatattgtc atgtaacatc taagataaat 161880
cttttttttaa tcaattgaaa gatttctctt tggacaaaaa cttaactagt ggaaaattta 161940
gatggaaatt gttattagag taaccaacaa ttattgtaat gcataatttt agaaccactt 162000
tcacgtgtat ctcatttaac catattttta tatgtgtact aggtggctgt agaagtcttt 162060
ggccttgtcc aacaattgct tccgtcagtt gccattttga atcagaagta tgcaccgcct 162120
gccttcaacc ctaatcagtc gacagatagc accacaggaa accagcctga acagggcctc 162180
tctgcttgta caacctccag tcactatgct gtcatagaga gtgagcaccc gtataaacct 162240
gcctgtgtga tgcattacaa ggtaggcacc ggttcttagt gtgattcgaa tgtaaaactt 162300
ggcatgaggt tctctgatga tatcttaaag aatgcctggc ctgtatttac aagtgtattt 162360
tcttttatag tatttacata tagagaatca gcaggtgatt aggcactgtt ggatatataa 162420
aataatttaa gatggaattt ttatctcaaa gatgataaaa ttttattggt ttatgagagt 162480
tgttcttaaa tcttcctaca agtatagtgt ggtatataat gctaaacttc atgctgtgat 162540

-continued

```
ttgcaatagt agtagatata agcattaaca attttaaatt gtatttttttg aactaacatt 162600
atttgtacca cagcctgagc tctgaaaatt tacaacccca atgtaagatt taaagtagtc 162660
tatacataat gttaaaaaaa ctatgtataa aatgtttata aatttaatgt tattagagag 162720
tattcaaaat ccgtattctt tgtttttttca ttgtatcatg caaattaagg aagagaagga 162780
taaacttgta ttttgtgtgc ttgtaaaata ttccactttt catggtagaa actattaagc 162840
atatagaagt aaacaagcta gtacagtgca cttgtttatc catcatccca gattcagcag 162900
tttcaactgt tagtcagacc tgtcttattt attcccaacc tacttcctaa cctcctatat 162960
tgttttaaag cacatttatg atatttattg atacaatgtc tccaaaatat aaagaccctt 163020
aaatataacc atagtattat cacattgaag aaaacaattt aatgtctgca aacatcatgt 163080
aaatttttaa taatttgagt tagaatccat ataaaatcca tatattgtga ttagtatgtc 163140
tcttaagtcc cctttaatct taagtccctt taaatctata agtctccctc tgtctctctc 163200
tctttttgtt cccttgagtt ctatttgttg aagaaactgg atcctatgta tttgttagat 163260
gggagcctct tcagcttacc tgctggttct ttcagacacc cctcttgcag tcattcctag 163320
cttccttgct ttctggtagg ataagatgtt ccaggctccc tttatatgtt tgatgcctca 163380
gacttggaac taaccatttt ttcaaagtgt cctgatttct gttatacata cacacacatg 163440
ttatatttat atatgtatat acataaatgt atatatgttt atgtacagat agatttatgt 163500
gtatagtttt ttaaagataa aatacctcat gagtttatac tgttgatact aattcaaaca 163560
aggaccacag acacacctca gtctcctttc tcttatatct aaaattccta ttagtgacac 163620
tgggaatatc agaattagaa aatcattaaa ttatttcatt tggtgtgtgt gtgtgtgtgt 163680
gtgtgtgtgt gtgtgtgtgt gtgtgtgtgt gtatgtgtgt gttttgtctt tgaagtatat 163740
cccatctaag tgtatgtcaa attactgtgt ttaaagtaag ttggaatgct ccctctgcat 163800
gattatgcat tcattggata tacacttaga gagtcattta ttttatctta gattttagga 163860
attgcttttt aaatttggat tttgttttat aattctttac ataattacat actttgaagt 163920
caaatttatg aaacaaatct agcttttatc tctgtcctct ttactctgtt cctccttctc 163980
tgtcataggt aacattttat tctattttaa ttttgtactt tatcctgttg tgtcatttaa 164040
taaaagcata gacacacaca cacatacaga tgcagatgtg tatgtttgtg tatatatata 164100
tctgtattca tgtcactttg cctgttgacc tcaggtgaca ttcccagaat gtgtgaggtg 164160
gatgacaatc gaatttgacc ctcagtgtgg tactgcacag tcagaagatg tccttcgttt 164220
gttgattcct gtcagaactg ttcagaattc aggatatgga ccaaaattga catctgttca 164280
tgaaaatctt aattcatgga tagaattaaa gaaattttca ggatcctctg ggtggcctac 164340
tatggttttg gtgttgccag gtaagttttt tttttcttct gttttatgtg gtaaaataag 164400
tgcatttatg tatatttagt aagggtgtat cattgaaaat gtttatctaa tttttagaga 164460
aatttattaa agacctacta tgtatctgga ttgcattcga ggaataaata aggtaccctg 164520
ggcaaggggc acagcctgat ctgagttttg gagaagacaa tgttttaagg attttgtgaa 164580
aaaaagatta gcttgagcaa agcagagtgt taacgttgag gagtagctag ctgtctgtgt 164640
agttgggtcc aaattataga aaacaatgga ttagatcttt tattttccca ggaagtgcta 164700
aattttcaga acttacctaa ggactgaagt ccttcattgt aagagaattc gtaaaccact 164760
ttcttgtgtg aagagaaact atgttttaaa acttatggtt tgttgcattc ttaaccagtt 164820
aaccaggact actcttgtga tccttcaaac taataggcaa tttcatttca gaaacttctt 164880
ctttccactc tgacctgcct atttgtttgt ttgtttggga aaagatcaga aaaagccaca 164940
```

ctccagggta gaggattgcc cactttgaaa aataaaaagg ctaacctcag tatttgacaa 165000
ataattgaaa aatgattgcc catgtaactg aagtacttta ttaagcaggg gagtttgatt 165060
atgaaaaaaa gtaacaattc atttgcgata gacctgttgt ttctagtgtt atttttggta 165120
cagtttcctc aagtagatat aggaacgctc cccgccgcaa gtctatttaa gttatgtagt 165180
atatgatttg tgtttttacc tatcttgtga taaaagagaa agtccattgg ataaaagaca 165240
gggaaatttt tataaaattg ttttagagtt tgaactcaat tctggcattt ttattaggaa 165300
atgaggccct tttttcattg gagactgcat cagattatgt gaaagatgac aaagcttctt 165360
tctatggttt taagtgtttt gcaattggat atgaatttag ccctggacct gatgaggtaa 165420
gaatgaatta tcttttcatt cttttaagga agattgtgtt tctaagggct agtgagttgt 165480
gcttctaact gacttaaatt gtactgttgc ctctattcga aaaattgggg cctggtgcag 165540
tggctcacac ctgtaattgc agcactttga gaggtgagag aatcccttga gacagtttga 165600
gaccagccta ggcaatatat cgaaatcctt tctctacaaa aaaaataaaa agaaattaat 165660
tttaacctag gggtgtgcaa ttctaaattt ttgtagttta tgtgcagtgg tctgttttgc 165720
tacttttaat acatgaagag gatggagttt gtgcaacatg acccagcctt tgaagtatag 165780
ttatacctgc cctgaacctg ctcagttggc tataccttc tgagtaaaca gtagaacctg 165840
ttttcaaaaa ggggctatca tcttgtctaa atgttttaaa tcatacaata agataaaacc 165900
aaggacaaag tgggccaaag tcatgaatga acagttattt gaacaatgaa cctttaaacc 165960
tgaaccttat aaccagcctg agccacaaca ttgagtactg aatctcatct actctcaatt 166020
taaccattag cttcacgtgc ttccttctca tttcaaaagt aatgcttgaa ttcaaatcac 166080
attttgttga taatccgtat tatcattcaa acatttttaa agcagcaaat tttatgcaat 166140
tccataggga gtcatccaat tggaaaaaga attagccaat cttggtgggg tttgtgcagc 166200
agctctgatg aagaaggacc tagcacttcc tattggtaag tgtggccaat actggatgtt 166260
ttttgatagg gttttgtttt gttttgtatg tattataaaa gggccaaaaa tagatttgca 166320
aaatgaattt tgtaatctca tatattcatg agcaataact gcttcatgta ctggtaattt 166380
gagtttgttt agagactgaa gggtatcctc tgaccttttt taatttacac acgcacatgg 166440
acaccctttt tatgcatata catgctttga gccaggcagt gggtatagtg tgtatattca 166500
gccaagcact gaatatatag tattaaacca aaagttctag atatttctta aatattctag 166560
tggaaatatc aagtagacaa ctgaatactc attgtctaga tcagagaaca ggtcgataga 166620
aatgtaattg aatatgatcg ttatttaaag acatgggact gtatgaaaga tattctacag 166680
caagtagata agaaagagaa gatagcttag gattaaagct gtgacttatc aaaatttcaa 166740
agatgcacag aacaggaaga ggaggctgca gatgagactg tgaaggaaca gtcagtgaag 166800
aggagagaaa ccaggagagg ggatgctcct gggatttttg catgctctga gaagtgaatt 166860
aaaatctatc attggacttg aagacttgtt ggttgcttgt atatgcaata agaaatatgt 166920
tagcaaaatg agagaactgt aagtactttc agagtagaga gggagaatgg aaagtaagga 166980
agggcggtcc atttgaatat aggtagctct ttagaagaat ttttcattga agcagaacag 167040
agatgaggca gtggcagaaa tggtactttt ttatatggag caaatttgta tgatatatag 167100
attaatctat aatcaaggga gtaaagttga aagtaaaaat gcttactgat tctctaatat 167160
ttatacatgg tttaaagttt tattttctta cccccccaaa atccatcttt actccttcat 167220
tgaagattac tcttcccact gttatttttt tcctcccttt tcttcctctg cctttccttc 167280

-continued tttattccct tttctcttcc tggtcccttt tattcttctc catccctttt ctcccactta 167340
atattggtat atatgtatgg aaatgagacc ttgtattcta gccacatgag gaaaattgct 167400
agcaacctat ttttgtcaat agctgttaaa ttttacatta tatatacttt ttgacataga 167460
aaatttttat acatacttgc acaaatactc aaaaagtgta tgttgaaggg tggattaata 167520
tagcagtgct tgtgattgta aaacctagaa acaaccaaaa tgtctttcag ttgggaactg 167580
gttaaataag taatggcata gccattcaat ggtagtatat gcagctcttt gaaaaagtag 167640
acctatacag cctaacaagg aaagctgtcc aaattatatt gagaaaagca agttgcagaa 167700
gaaggtccca tttttgcata cattactctg tatattacaa aaaagtatga tcatgcctgt 167760
aatcccagca ctttgtgagg ccaaggtggg tggatcacaa ggtcaggaaa ttgagaccat 167820
cctggctaac acagtgaaac cccgtctcta ctaaaaatac aaaaattagc cgggcatggt 167880
ggcacatgcc tgtagtccca gctactcggg aggctggggc aggagaatca cttaaaccca 167940
tgaggtggag gttgcagtga gccgagatcg caccactgca ctccagcctg ggcaacagag 168000
tgagactcca tctcaaaaga aaaaaaaaga gtatgtttat gtgtggttga aacacatata 168060 ccttttttggt ttgtttgcac accaagtttc tagaacaaca cataggctgt tgacactgga 168120
tagttttaag ggagcacggc actggttaga ggtttagaat tttttgttct acactcctat 168180
acaatttgag tatttcccat tgaacaagta ttactttatt agtaacattt aataattaaa 168240
ctatcaaaga aagatcaata aataaaatat gttctatatt aactaataaa ggagaaaatg 168300
gctaggggat gcagtcactg ccttatattt ttctgtgagt ccctgttgtt tactaaagtc 168360
atagctcttc tgtaaggcaa ccaaaatata aaggcccaga tctgaaataa tttgttccct 168420
ctttttttag acaaaacgaa tacactaagt tcagaaagta tacatttata ttcataaatg 168480
taggatatat ctttggcaaa tcacccatgg atgcttcttg agtattgcct tgagaattgt 168540
agtatattcc cactggaagt atcttatata ttaaactgta tgccactagg atttttttcca 168600 gaatcacaaa tcttttcaat ctggaatagc agaattattt ttttaaaaaa agtgtaatga 168660
atgcaaagga ctagaaaatt aaactaaact aaatattgac atattttagt aaaactcttt 168720
atttacacaa caggtaatga attagaagaa gaccttgaaa ttcttgagga ggctgcattg 168780
caggtattgt cccaaatgtt ttaaggataa actttgtaca ttaatttaaa aagtattgtc 168840
actcagatca gcctatttgt cttgaccatt gggttcattc attaagtact tcactttatt 168900
cattggcatt atagagataa ataacttatc attgctccct ttggtgggag aaacccatgt 168960
gagccctatg tatttggtgg gtaattgact ctggagttag acaaaaatcc ttcgggagaa 169020
aaaaacaaat caagtgccaa gggtgcggag gatggcttgc agaactgtgg ccatttaaat 169080
tgcatcttga aagaatttgt ttttcttttt ttgcctgcta gagaaagggg aaagacattt 169140
cacaaaggat gtatagttgt gttataagaa gcagcaaaag gtgaggttgg tacagttggt 169200
gagctcagtc tgtgacaaac cagtatgtca tattaagtgg ttagggctag ttgcctgtag 169260
acaattggga gccatcattt gttgttttta ttattgtttg ctttaccttt tttgctcgtt 169320
taggcattaa ctagcacatt tggcactgaa tggaaataca tgagtactat atttcagtgc 169380 aatacccccct ttggatctgt tacgtcaacc taatatttct caaaattgcc tagagatgac 169440
tacattgttt tcttacttca ttagtctgac ttcagctagc tagtaatctg taataggatg 169500
gaaatatcag aatctgtaga cagcatttgt caaattgtaa tacctactta ggccaaacca 169560
gagtttctga tgtactgcta agtgagcccc attggatacc acacactgag aacatcagtg 169620
atggggaaaa ttttgcatct agcaatggtg tgaagataga agaaaagttg agagtctctc 169680
aactggatca gtgttactca gaccctagga tgtgatagat ttgtaaaatt ttccaaaaat 169740
atttttcctg agaacttatt aagtaaaaac actctttaaa aatgtactac tttttatcag 169800
caatgtctta taaaataaaa gacattttaa tagccccaga tggaaaggtc ttagaatgga 169860
agactctgtt atagccttag tttttctaat tctgccatgg atcagagaac tttgggccca 169920
catttggaaa acaccaattt agatcatact tattttctat actaggtata tgtagttagt 169980
aatagtgatt taaataatat ctgtagagca cttcataggt ttcagcatct ttaatattat 170040
ctctctgttt ttataattac acttcgaaat cagtattagg tcttgcatct tacaattata 170100
ataactgaag ttcaaagaag ttttgtgact tcttgaagac tcagaaggga aacaaaggct 170160
ggtacccaga ccttgtaatt gtgaaggcta gtgctttaca ttttacttat ttcctgaggt 170220
gaattaatca aagcggtaat aatgaaaaca tttatttcat ctttgtcaag cactatttta 170280
aacattttgt gcatttttaa ctccccacag caacccaatg aattaaaaag ttttatctcc 170340
atttacaaat gaggcataga gcatttaggc agttcgccca cgatcataca gctagtgagc 170400
aactgcactg ggatttgttc gctggcagtt tggtgacaaa agaaaccccg tctcattagc 170460
tgggcgtggt ggcgcatgcc tgtaatccca gctactcagg aggctgaggc aggagaatcg 170520
cttgaacccg ggagtcggag gttgaggtga gccaagatca tgccattgta ctccagccca 170580
ggcaacaaga gtgaaacgcc gtctcaaaaa aaaaaaaaaa aaagtttgtg attttgaaca 170640
ctgtcttctg atcataggga gctgtagtgt tgtcaataat gttaagaaac gtctgagttt 170700
taaaaagcca ttggcatctt atgtgtattc ctttttaaa gttaaatctt tgtaccttaa 170760
gattcaaaat aaaaataaat tcaacagata tataataaac aatatgtgtc aggcaacatt 170820
ctaggtgaag gagaactatc aaagagtttc tattagtcca ttttcacact gctataaaga 170880
actacctgag gctgggtaat ttataaagaa aagaggttta attgactcac agttccctac 170940
atggctgagg aggcctcagg aaacttacaa tcatggcaga aggcaaaagg gaagcaaggc 171000
aagtcttaca tggcagcagg agagagagaa ggggaaaggc ctacacactt atcaaacaac 171060
cagatattgt aaggaaaaca gcaaggggga agtctgcccc catgattcag tcacctcccg 171120
ccaggtcact cccccaacat gtggagattt ataattcgag ttgagatttg ggtggggaca 171180
cagagccaaa ccatatcaga gttcatatat ggtttataat ttcagggatt attatggtat 171240
ataaggtgtc atctagacca gatatggaga gatctttatt atgttattgt tcaagaaaaa 171300
aaaaaatggt gtcccaaatt gcctcttttt ggcatgtaag gtagttattc tgataatcta 171360
acatgtatta aacacttact atttgttagg caatgtatta tatactttat atgcattatt 171420
tagtttgaat tttttaactg tgtaagagag attatttgat gaccagttta tacattttac 171480
agattcaggg atggtaactt tttagcttaa gagcacacag caaataattt gtccaaagcc 171540
aggatttgaa tttaagtcta tttgattcca aagatgatta tttttgaaac tgtataattt 171600
caaatttgat agtactagaa atgtaattat tttctatgaa aaaatcttac tggaatttat 171660
tttatagtca gtaaaaagtt ttcagagttc cagcatttaa aacaagtctc tccaaaaaca 171720
taagacttgc ttgtcagata ggtgaaacct aaaatttgtt ttatctgcct cttcttctta 171780
actttagtaa ggcttaggca ggctaatgag atgtgtgtgc tgccacaatc aggcttccac 171840
ccacttttta cccaagtcaa gaccttggtg cccacccacc caagagaaca gacacacctt 171900
actcatgata gctgcctgta agggggactg aaaaagaggg aagccggatg cagtggctca 171960
ggcttataat cccagcattt tgatagggca aggtgggagg attacttgag gccaggagtt 172020

-continued caagaccagc ctgggcaaca tagcaagacc ccatctctac aaaaagtttt aaaaaaaatt 172080
agccagccat ggtggcatac gcctgtaagt cccagctact tgggaggctg aggcagaagg 172140
atcgcttgag cccaggaggt tgaggctaca atgagctatg atggcaccac tgtactcctg 172200
ggtggcagag taaggccctg tctcaaaaag aaaaaagggg gagacatcca cagttgctga 172260
cagaagggag ctctggccct gaaaaatgag gacataacat atagaggact ggcatggaag 172320
gagatacacc attttatcca gcatgcagat ctctgacaag gcatttattt ttgagggagg 172380
aaagagactg gaaatattgt ctcatatttt tctctcctag gaatttccta ttctgtgggt 172440
taaaagaagg aacagtgggg tacgtggaga aaatgatttc tccgtaaagg cctatctgaa 172500
agtatctgca tgttgaaaaa ttttatgtaa ttaaagtttt atttttaaga atatataaat 172560
attctttttt acttaacagg tgtgcaaaac ccattctgga attcttggaa agggtctagc 172620
tctttctcat tcaccaacta tattagaagc acttgaggga aatttaccac tccaaatcca 172680
aagcaatgaa cagtcttttc tggatgattt tattgcctgt gtcccaggat caagtggtgg 172740
aaggcttgca aggtaaatgt actttaagtt acttacttta ttttagggct ttcatctttc 172800
ttcatttctg aaagagggga gtcattagaa tattaaaata ctactttaaa aaagtctggt 172860
ttatgtatgt ttaacttgct gaaatataaa atgatagtta atatttttgt ttggcggttg 172920
tttgtttgtt tgtttttgag agagagggtc tcactgtgtt gcccaggctg gagtgcagtg 172980
gcatgatctc agctcactgc aacctccact tcctggactc aagcgattct tgtgcctcag 173040
cctcccaggt agctgggatt acagatatgc caccacaccc ggctattttt cttttttgta 173100
tttttgtag aaacagagtt tccccatgtt gcccaggctg gaatagttat gatagtatat 173160
gataagacca ggtgcaatgg ctcatgcctg taatcccagc actttaggag gctgaggtaa 173220
gtggattgct agagcatagg agttgaagac aagtctggcc aacatggtga aatcctgtgt 173280
ctacaaaaaa tacaaaaatt agccaggcat ggtggcacac tcctgtagtc ccagctactt 173340
ggaggctgag gtggaaggat tgctcaaacc ctggaggcag aggttgcttt gattgtgcca 173400
gtgcaatcca tggtgaaacc ctgtctctgc aaaaaataca aaaattagcc aagcatggtg 173460
gcacacacct gtagtcccag cttcttggag gctgaggtgg gaggattgct caaaccctag 173520
aggcggaggt tgctgtgatt gtgccactgc aaccagcttg ggcaacagag caagacccta 173580
tctcaaaaaa aaattaacta attaaattaa atttattata gttgttaatt gattattttt 173640
gttgcttttt gtttttagga tgaaaaggga aaaaaatatg ctggcctgca tgattttact 173700
agtaaaaaaa aaatcccaac ttttttctgg ttttaatttt aaaattgcag agattactct 173760
ttagttttta aaaatcacaa aatagtgatt ggagaggaat gtcaaatcac ttaagtcagc 173820
ctcactacta tactatgcag acgtttttat gtaatgcatg gtagaattac ttattactca 173880
gctcacagga caacttgaat gtgtagatca cagaatgaat tcaggaatga acatcacaaa 173940
ttacacaaca ttgatgcatt ttaggtggaa agcaaggtaa tgaggaagat agttgagaaa 174000
ctgtgaaaaa aagatgggca gtacaccttg aacctggctg ctgtcaggca agtagagggc 174060
catttctacc cctgctttta cagagacact gctttttcca ggcttgcagg atggcagagt 174120
aaggtggagc tccttcagag agaatgagcc tgctcaggac ttcaaattat gcacaaccta 174180
cattcgtgtt cttggtgatt ttaaattagc catagttaaa atttcaagtt tcctggtttt 174240
aaaaagtatt tttatactgt atttaaatat cagaaatctc ctgtgcttag gcatgttttt 174300
taaatgaatt tgtccttaac agtttctgag ggagacactc atgattatca ctgagttgga 174360
aatgaagata atgttttagc attttgtttg atacaagttt tgttcatttg gcttaatttt 174420
atattaattg ttgaagatgc tgatcagtgt ttggggtttt gtttatttgt ttttcattac 174480
tgttaggtgg cttcagccag attcatatgc ggatcctcag aaaacatctt tgatcctgaa 174540
taaggatgat attcgttgtg gttggcctac caccataact gttcaaacaa aagaccagta 174600
tggggatgtg gtacatgttc ccaatatgaa ggtaattata actggattaa attagcagac 174660
atctatatac tggctgcaat gactgataaa attttagaaa tgccaagtgc tgagagtcca 174720
tttgttctac cctctttata taaagggtga tgctgaaagt ttgtttaaat gacttgttta 174780
tattaattag tccccaagtg tccaagttac acctgttttt tttgtgagtt tgttctttac 174840
attttgctac ctgttacggg gactcaaagg agggataaga aagtatccat ctaaagagtg 174900
ctagacacat acagtgaagc ccctcaatat gtattgattg aataaatgca tgaaagaata 174960
catttttaaa ttttgtgtat agttttgaaa gactcaagta cgttctgtgt ttggtattac 175020
tgaaaccaca ttttaaaaat aacactcatt aagttagaaa tatatgagtt tagattgtaa 175080
aagaatgagg aattgaaata gttgtatacc atattgatga atatagagtt tttaggatac 175140
ctcttacctg aaatattaat aataatgttt cagagcatat tatacataat tatttgtgat 175200
ttaatctgtt aatatgaata tctcatttaa aacttttatt tctgaaaaaa ttatattgaa 175260
taaaatttta tataggcagt ccccagccct ttcctccttc aaagttgtct tatagagtga 175320
ttggttgttt gaagcttaga gctgattaag ccacaaaatc ctttttgctc attgggtagc 175380
taattttgcc tcaatattat tttcagtaga actatttcaa ctacttcatg cattctttca 175440
tttatagcgt gaagaagtac aatgccaatg tagcatctta cctaagtaaa aaataagaac 175500
acattgctta catgacttaa gaccagtaaa taaaactgta tggaaaaggt ttcaaccctg 175560
atactaaatc aaaatcagtc ttttagcagt atctttcaaa tatttggcca tgatccatag 175620
tcagaatttt tattataacc caaagatata aatataatat atgatggaat agtgtctatg 175680
taatagcata tgttaagtac atataatata ctttatatat acatacacac atacatacat 175740
aatatgctat actctgatgc tttctctatc ttattttta aggcaagtca tacccttcac 175800
aaactgagtt catgcctact tggaattatt ctatacaatg caaaaagcat cacaaattat 175860
aagaaaaaaa gatttaaaaa taaagttatc ctgatagtga tatgaaaaaa attactactc 175920
aaggacagat ttttgatcac agtacaatac acgttaagat gttgaagggc ttgtatattg 175980
tgtattcact gatgaatttc tcaatgtagt gagttgttaa atccaatctt tgaaccctca 176040
agattaagtt ttttattcat gtgacaacat tctaatacca tgttcatact gttacgcttc 176100
tgatatttct ttagttgtat tttctttctt gtgttttctc ctttgcacct tttattatct 176160
cttttgatat ctggtatgtt tatatcttgc atttgaaagt cagacttcat cttttttttct 176220
tttcatctta gagttctttt ttttaaccata tgatggatct gctttttttt ttcctctctt 176280
cttccctctc ctctttccct ttcacctcct tctccttttt ccttcttttc ttcctcttct 176340
ttctcctcca tatatttgct tctcctacta tctttccttg acttaaacct cttactcagt 176400
gtgctctaaa ttcatgtcag atttatccaa tttagaaact ttctagaaaa ccactctaaa 176460
tactatctag aagaagtgat ttgtgctcct actgatgttt aatgtattaa tatcatatta 176520
tattagctgg aaacaaaatt aatttaacct attttacttt cagcctatta gtatatgaag 176580
tcttaggagc actttagact gttcataaat tgttaaaatc tttatgcagt aatagctaat 176640
tatttgaagc ataaaagttg atttgcagct aatatttcaa tgagttccaa aatgctttca 176700
aaagcaacaa gtgttattgt tataattttt tacttataaa atgactgttc cctacctgtg 176760
ataaaatgag ttagaactaa acacacatat tgtaccaatg tcaatttcct ggttttggtt 176820
cagtaccatc agtgtctgac agtgttggat aaaatgtagc cattggggga acctgagtga 176880
agggtacata ggacatttca tctatttttg aaacttcctg tgaattaaaa aaaaaagttt 176940
attttaagga aatcttattt attgacaaga gaaagtcaca taggaaatac aagaataact 177000
tttttttttaa gtaacacagt ttgtaaaaga aagcagaatg gttattctat aatgtctcag 177060
ttttcttaaa gtataaaatt attcagtgat ttacttcaag gttcatggtg catacacaca 177120
tagactctaa tgataattta ttaaatactt agggtaaata tagttgctta cagaaaggtt 177180
aaattgaaat agtatgtata aaaatagtgt ctgtaattta atatcaaata tgtttgagac 177240
aggagagttc ccttgacccc tttgtgggac ttgggacgtg ggtgtcgtgt ggctcattta 177300
cttgactgct gcactcaaac cccttgcagg atggcgagca ctgaggcaag caggtgccag 177360
ggcccaggca agcacctctg ggctccagcc ccacagcagc atctaggagt gtgtcacaat 177420
taatgctttt ttagctttgt tgtctgtgga tggctaagtg ttaaacagct cagtgaagaa 177480
tcagcatgac agccttttg ggttcctgca cccagtgtgt cctgaattct tgtctggcat 177540
tcaggaagaa tcaggtcata tgaatggttt gaaacgcgat gaatgcgtga atacagcaga 177600
tttttttttt tttttttttt ttttgagaca gagtctcgct ctgtcgccca ggctggagta 177660
cagtggcacg atttcagctc actgcaagct ccgcttcctg ggttcactcc attctcctgc 177720
ctcagcctcc cgagtagctg agactacagg cacccgccac cacgcctggc taattttttg 177780
tatttttagt agagacgggg tttcaccgtg ttagccagga tggtctcgat ctcctgacct 177840
tgtgattcgc ccgcctcaga ctccaaaagt gctgggatta caggcgtgag ccaccgcgcc 177900
cagccacggc ggattttatc aaacggtgga agtggctctc agcagaaggg gagctagaaa 177960
gggcatggtg tgagaagaag gtgatatttc cctgaagccc agccgtctcc agccatgctc 178020
ctctcctaag tggtgccatc tgaggttaag ccgcgcgtct catcagttgc tgcttctcct 178080
cttggtattc gccacttgtc tctttgctag ctgaagtctg ggatttatag gggcataggg 178140
taggggggca gggctggcca aaaaggcaac atttaggcgg aatacaagga taaactgttc 178200
tcatttaggg tcatggtttc caggcttgag agtggggcct ttgccaggga accaccttct 178260
cctatccagt atatccctga ctcctgtctg tatcatcttc agatttttta attgtttaaa 178320
gtttaaagct ttttatgctg gcacatgtgt ttgagttgaa attttaacca tatacctgta 178380
aactgccatt ttttaaatat aagaatgggt ttttaatatt tccaggggtt tgtgtcagtc 178440
caaatactga tctcttgtaa cctcacctga agatagtggt cacttaatgg aacatatttg 178500
tcacctgtgc ctaacattat ataaatagcg aaagtctcaa actactgatt ccatagaatc 178560
gcgttgttaa gaacaataaa cataaagaca gtctgtagtt ctgaggtagc tctcaattac 178620
ttaaaaatac tatcactttt atctctgcac tttttctatt tctgtgacaa ttctgttgaa 178680
ttacctgttc ttgccaacca caaaactatt gtctgtaggg agcagcagaa actttgagta 178740
aagctcagaa tggtgatacc tgctgaagaa ctaaagtggt attcaaattg tgtgtacatt 178800
tgtggttgcc taggggtcaa gtgtttttct gccaatgcat aaacaaataa aaacaatgtt 178860
ttcttataat ttctgggaaa tatttctaaa aagtattttt cagaaatagt agttagtaga 178920
tgaaatagta gagttagtag atcaaagata gtcccgtttt gttgaagaaa ttgagttgca 178980
aagttataat tcctggaaaa tatatctaaa aggtattttt ataagacaat ttgtattttc 179040
agtatattaa catccattaa cgaatctgtt ttttgcatct atactgtaga gttagtggac 179100
gaaagatagt cccattttat tcttaaagaa agtgagttgc aaagtttaat tatttaatag 179160
attgcttaaa tcaaatgttg atgttggtga tagggctgtc taataatatt ctttcttcac 179220
ccgagtaaag aaacatattt gggctttagg tataagattt gttttattaa gtgttaattt 179280
ttgaaacttc tataaataga gtacattttc ttctgtagaa cagtgcagct caaactgaca 179340
ttagtgcttt aaaatgtgct gagattgtgg gaaagcattt acacttgcat tacctgataa 179400
aataatttgt tagtccctgc aataacttaa tgtagattca ttccactatc ttttcctgta 179460
ctttattagt ggtgcatttg tttttatgtt ttgatatctc tgattatgta ttccaaaact 179520
atgaggcctt gtttttacac cgtgttcatg gttcatattg tcaacccatc ttgaggtcat 179580
ttgaactctt ttcaataagc ctttgaaggg aatgccagag acagaccaat gctaacataa 179640
agtatacata attatgagtt tataatagta agttgcttat tttgatgtca gtgacaatta 179700
aataataatg gtatttggtt tctataatac catgtttagg tggaagtgaa agctgtccct 179760
gtttctcaga aaaaaatgtc tttacaacaa gatcaagcaa agaaacctca aaggattcct 179820
ggcagtcctg cagtaacagc tgcatcttct aatactgaca tgacttatgg agggctggca 179880
tcaccaaagc tagatgtttc atatgaacca atgatagtga aggaagctcg atatattgcc 179940
ataacaatga tgaaggtaat ttattttact tatcagaaaa attttagttt tcagcatttg 180000
tttatttaac caacatttca gtgattcaga tgcagacatg aaattgtaag tccaaagagc 180060
atttgatgga tattaaattt gcagcaacac ttattaagat gatgttatcc tgtcttcaga 180120
gaggattttc attggttttt ggcagatgtc cagaggggat caccaattac agatcaagtt 180180
aatcgaatca gagatacaga tggattaggc tgagtttcag ttcctgtgaa agtacttgtc 180240
tacttctgac caggaacagt ggcccacacc tataatccca gggctttggg aggccaagga 180300
gggaacatca cttgaggcca agagttcgag accagcctca gtaatgtagt gagaccccat 180360
ctctacaaaa aaataaaaat aaaataaaat ttctaagtac ttgtctattt gcagtttact 180420
attcttgcta gaatgtatct cttcagggtt ttggggttta cctatgcccc cttcaatttt 180480
gggttctctc aaatgccaga tgtatctcct agaactcttt gggattttta gctctctaat 180540
acctttagac atttaaaaaa tatatatttt ggatgtttta gttatcttca gaggcaatgt 180600
taatccgaat tatcaaggta gtcattattt gaagctgaag tttgtaattt tggcattttc 180660
agagagcagt ggtgagccat tgaaggcttt tgggtagagg aatggcttga ttagatttgt 180720
gttttgtaac gattgtggtg gaatatggac agtgtaattg ggcagatgat caagaaacat 180780
gacttggttt tagtctcttt aggggactat tgacttaatt tggtgagata tgctgatcag 180840
ttggactagt gagttgtcaa tgaggataga ttcaatagaa tcagtagaac ctggtagcta 180900
gtggaggtgg agtaaagaag aaaggtagga aataaaagat gaaattcaca tattgagctt 180960
gtgtccaatt gataatggaa gaggggcagg ttttggttga gaaagatagc agattcagtt 181020
ttggatgagg tgagttttag atacttctga aatacctacg tgaagatgta taaaacaaag 181080
ttagatgtac agacctgagt gatcacagtc tgacctcaag aaaaggattc aggaatcatt 181140
agcacttaca ttacttatga agtcatggga atagatgata ccttctatgg tgaatgaaga 181200
cagaagttcc aggataggat cctaagaaac accaatatca ctgagtctca gactcttctc 181260
tacatcagaa gcatctggag cacttactta aaaaaaaaaa aagatttcca agcacccaga 181320
gatttagatt cagtgggttt ggagagaggt tcaggaattt acctgaaaca aatatgcagt 181380
gattcaaatt caaaacctaa actttgagaa atactgattt acaaggtaga taagagaaaa 181440
agaaaggaaa aggaaaaacg attcacattg gtaagaatac tagccaaaga agcaacacat 181500

-continued

```
aattaaggga atggctgaag tgagtgtaga taagcctttc aagatgtttg actatagaaa 181560
gaaccagagg aaatggaatt gagtgaaggc tttggagtat ggggtcttat taatagagat 181620
agagttacat atttgagtgc tgattaggag gtaattgaga gaaaaaacaa taaagatact 181680
ccgaatataa aaatagaatc tagagctcaa gtggtagcat tggccttaaa taggaggagg 181740
agtagtgctt gtttcattct accagaagaa ggaaaagaaa gcttaataca gatgctagta 181800
aatttgtagg ttttgcagcc aaaggaatta tttaaaacag taattatgtg ttttgggatg 181860
gaaatggaag tgatgaatct tagggtcaag gttttgaaac aaagcggata aaatgaaatt 181920
gttattctag agattaaaag aaagcaccga tcagaaaaga tttattagat gcctttgaat 181980
aatcagttga aattgaagat tatttgtgaa taacagtgtg agtcatatga gcatggataa 182040
aacaatcatt tggatggatc tagcattaaa attttgctag accagcaaaa gaacagtgga 182100
acaaggaagt taagtatatg gtagctaaag agaggacagt ggaacctaat ttagtttgga 182160
agggaagaaa tttcagagtc aaggaagtaa gagggactag acgtcaaagt agatataaga 182220
atagttattg aggtaaaaaa ctgaacaggc cattttattt tgatttcaga gacagaacaa 182280
ttctgagtaa tgtcacaggt ctgtgacttt tggtgtgagt ggctggaaaa aaagttgaag 182340
ttattgaggt taaagaaatc agggaatgag aaactagagt tctaggtgaa ttgtccactg 182400
gctgttaaag aattcctgga aaaaaagttg aagttattga ggttaaagaa atcagggaat 182460
gagaaactag agttctaggt gaattgtcca ctggctgtta aagaattctc ttctctcact 182520
ttttactcac caaattaata atctcattat gaattctata tccgaaataa atatttgtct 182580
catttttttaa aaaatccatc ttacacattt ggctatttta gtatcaaatt ttaaaattat 182640
ttctactatt aaaaaaaaaa gcaaggctaa aaattcttct ctattccaac acttgcttaa 182700
ggaatttagt ttctagtctc cttacctccc taatctttta gtttcctatg aacatgcttc 182760
agtttgtata atttcttttg caaattttgt taccacaacg gaatgcaata tttcaaacat 182820
gttctgagta gcctaggttt agagcaggta tggaatacca ttcccaaaca gtatctgtga 182880
aatgttaatt caggtcccag gaaaggaaat tttccttatc aaccattcac agatactatg 182940
tattcactca gtagtgagcc aagtattgta gaggatggaa agatgaaata tggtctcttc 183000
tttcattact aagtgtgtta ataatatgaa tttgagggag agtgatgaaa tagaaaatac 183060
attgtactga aagtctagaa acatggattt ccttttctca cctttgtatg gctaaagact 183120
cagccttaac ttgcgttttt ctcatgtgta acttttgagt aggtaaagtc agctagatca 183180
tttctaattc atttttatga aaacaaaaag ggtagagaga aggaaggggg ctttgagttt 183240
gcttcctttt actgtaagta caggaggagt tagaagtaga tgagcagttg gacatcttga 183300
cctgaacctt gaaagataat gatttctttg ctaatgttgc aggcatacag aagtattcag 183360
aataatgtgc caagtttcat gtacctacag cccatttttg tctttacatt ttaccataat 183420
tgtttcaggt cattttgtta ttttttttatt aagaaacaga ttgctacagg tacaattgaa 183480
gcctgcctaa acccttcctc agacccatta ccaccccttc cttagaggta accactgccc 183540
tgagtgtagt gattctcatt cctgtatata tttttaggct cttactgaat acaaatttat 183600
tcataagcag tatattttgg gttgttcaat acgttttcca gaagtttata aaataatatc 183660
gtattgtatg tatcattttg ccagattttt gcttaatgtt gtttttgagg ttcagccgtg 183720
tagctatagg tcattcattt taactgcttt aaagcattcc attggggatc tattccataa 183780
tctgtccatt ctcccattga tggacgctta ttataaactg tactgaaata aacattctgt 183840
atttgtctcc ttttgtacat gagcaagagt ttctgtaaga tacatactta gaagtggaat 183900
```

tgttaagttg tagggcatgc acaactacaa ctacattaag tattgccaaa actcacactc 183960
ccacgagcaa tgtatgaaag tagcaggtgc tgcatgttct cctctgcgct tggttcttac 184020
caacacaatt tgatgaccat gatgtgattt attttagttt tgttttaatt cgtattttcc 184080
tccaagttta gttaaataac ttttctagtc tttattgacc tttcagattt cttcttcaga 184140
gaattgtctt gactgtcttt ttttgttgtt gtttatctct tttgtatgga tttattctct 184200
atatgttatg gatgcatatc acctttgggt tatacgagtt acaaatctcc ttctccaagg 184260
tggaagcttt tcctttctgt atagtatttg ttttggaaaa ctttaaaatt ttaatgtact 184320
caaaagatgt tatctgtttt tttcttttgc tttttttttt taagttttgg tgtttacttt 184380
tggatcttca aaccttgtag aatttatctt taataaatgg tctaaagtag gtaatttttt 184440
ttctttttct cctatatgta taaccagttg tctcacaacc atttattgaa taatatatta 184500
ctctgttaat tgagaatgtt tttaaatgat tttacgattg ttcagactgg tctctttctt 184560
aaaggtttat gaaaattatt catttgaaga actacgtttt gcatcaccaa ctcctaagag 184620
gtaaggatcg ttttctcaaa gtataaccaa aacatgtgtt gtcagctgct tgcaactaaa 184680
atcatcctgc atttcaactt tattttctat aaataaatac tttatagcat ttttctaggt 184740
tgccgataga gatgtcatat aataatgtat agatttgcag aaagaatgtg tttacattca 184800
actgtaatac tgccaatata ttacataata ctacctacta gtgaaaatag gtatgtaaag 184860
tagatatcta gtatgtaaaa atgtttaaat tgacttgttt agggttgatt agtttgtttt 184920
ttgtttgttt gctatttaaa aattgttcct tttctccttc caatgaattg tggagagatt 184980
tcagcatgtg gtatacttgt atttgattgt actgtcttaa tttttcagcc cgtaagtaat 185040
tctgttaact tcagatttaa ggactttttt tgagttaata ttttatttgt taggaacagt 185100
actacttaaa atagaaactt ggaaaaaata attagatgca ttatactttg gagagatcac 185160
ctccatagaa tttagaaaaa tctctgaagt gaatctgaga tagcagaatt atgtataggc 185220
tggaaatacc agtttgaaac tcatggggaa aataaatttg ggaatcatct atattgagat 185280
ggcatttaaa actgaggaat ggttgtcacc tagatagatg gcataggtag aaaaaagatg 185340
acccagaccc aaatcctggg gcattcctta aattaaacgg tagtcagaaa agggaaagca 185400
acaaaacact gacaaagaat ggccagtgag ataagaaaaa agccaggaaa atgtcacaga 185460
agcaaaaaga aggaagtatt tcaagatagg aagagttgtc agctatcaga tgctactgag 185520
agattgctga ggatgaagtg accattgaac ttggggacgt ggtggtcatt ggtgactttg 185580
acatcagcag ttgtaaggaa atgttggaaa caaaagccta ataaggataa attgtggaaa 185640
ggaagtagaa gtgagagaat ggagtttgat ataaatcgga gaagagatgt aagaccttat 185700
tagagggggt tgtaatacca aagggaggtg ttagtgaaga ttctaaagtt tgtgtgctaa 185760
tcgaaatgat tcactaaatt gagagtaatt gatgatgcat gagagagaac aaggtgattg 185820
cagcataaaa atgttgaggg aataagattc acagcacaag gggagggact agctttggat 185880
cagatccagg acacttcctc cattctacca tgagagaagg caggggaaag taggtttatt 185940
aatcacattg caactttgag gttgtatctg attgcttatt gtctcacaga agaaagaggt 186000
gaggtcatga tcacctgaga gttaggaaga gaggtgatgc aggtttgagg taagaaagaa 186060
gtgaaattca agcattttgg agagtaggca agcgtactat ggcagggtgg taggattgcc 186120
aggaggtatg caaacaaatt aaatgtttgc tgaactatcg taatgatgtt gactgcttaa 186180
ccaaaagtaa aatttccaat atccatctta tttcttttca gacccagtga gaatatgctg 186240

-continued atccgtgtca ataatgatgg gacttattgt gcaaattgga ctccaggggc tattggactc 186300
tacactcttc atgttaccat tgatggcatt gaaatcggta ttttctttaa agccatgagc 186360
tactacttac ttcaaataac tagagtcaaa attattttta tcttctagtt ttgcccatta 186420
acttgcacta gacatatgga taggtttcat aacttatttg aggccttgtt ttctctttca 186480
taatgagtat ttaattagtg cattaacatt ttgtaataat ttctggtgtc cgcccaggca 186540
ctgtagccct catgactctc tccctccatt tcctgatgtt actagtcagg tgtgctctct 186600
tccacgctgc tgttaccctg tctctcccct gtgggtgtgt ctgtgcctct cctgactgtg 186660
agcagaaagc attcatgttt ggatcttcca gtgtagctca gtgcctggca cataatgaca 186720
gcaaatatgg atgaatgaat gcatttttaa atcgatcatt gtgttaatct gggttctcca 186780
gagagacaga accaatagga tatctataca gtcatgtacc tcatagcatt ttggtcagtg 186840
acgaacagcg tatataatgg tggtcctata agattttcct gtaccttttc tatgcttaga 186900
tatgtttaga tatgcaaatc cttaccattg tgttacagtt acctgcagta ttcagtaggg 186960
taacatgctg tacaggattg tagcctaaga ccaataggct gtaccatata acccaggtaa 187020
tctgtaccat ctaggtttgc ttaagtccac tctgatgttt gcacaatgat gaaattgcct 187080
ggtgattcat ttctcagaac atttccccat ccttaagcaa tgcatgtcta tattagatat 187140
atgagaggat ttattaggga aattggctcg cacaattatg gagtctgaaa agtcccatta 187200
tgggccacac ctgcaagctg gagatcctga gatgcaggta gcctcagaac cagggaagca 187260
gatgatgtaa ctctcagtct gaggccaaag gtctgagaat ccaggagggc cactaataat 187320
aagtcctgga gtctaaatgc tggggaccct ggagttcaaa tgtcaaggga cagtagagga 187380
agtgtttatc caagctccaa aaaatagaaa tacattcacc tctcctctgt ttttgtttgc 187440
tctgtgtccc cagctgattg gacagcgcct gtccacattg aaagcagatc ttctccacct 187500
actccactca cactcacacg ccagtcttgt ctggaaacac cctcacagac gcaaaagtaa 187560
tgccttacca ggtttctagg tattctttaa tccagtcaag tggacaccta gaagtaatca 187620
tcacaaccat taactttgaa aaacatattt cttttgtttt aggcattaat cttttcttta 187680
cttttaaact gtctgtataa taggataaca aggagaaaac tctagtactt atcagtgtga 187740
atttcttgta acattatttt tcctgatgct cctcaaggaa aggggtttct gtgatcagat 187800
aaatttcgaa aacctggttt gggatgagta tcttttatct gaaatgcttg gcaccagaag 187860
tattctagat tttggacttt ttctgatttt ggaatagttg tattacagtt accagttgag 187920
catccctaat tcaaaatttc aaaattcaga atgctccagt gagcactttt tttgagcatc 187980
atgtcagcac ccaaaggttt tagattttag atcattttgg atttggggtt ttcagattag 188040
agatgctcaa cttgtatatg gtagtctcac ttgagacatt cacacaatct acattaacat 188100
attagggatt ctgagaagtt ctgaaatcaa gaaacttgtc tgactatgtt taatccttat 188160
cgtgggaccc cttgcaagtg gagaagagag aaacagggtg gagatagtaa taataccaat 188220
taatatttca ccaaaatatt tgggaaaccc tgctttaagt agtttgcttt ggcagtggag 188280
gtaaagaggt actttacatt gatgtaattg tatgttctca tacattaatg taactatata 188340
gactcagata tatccagttc atctgtacca ttctagagac cttcaccagc agcctttgct 188400
gcactcttct ttatttcaat atattcataa agcctttagt tcagcaaatg ttttttggtt 188460
ctgagcatac attttcctgg gtaagacaat tcctgtcaag tgttaacact ttaatgagga 188520
ttgtgaaaat aaaacacgca aacaaaaatc ttatgaagta gaatataagt agtgacacac 188580
aagacataca aattacagta ggaattcgaa agtagaaata gccaagaatg acattgtgaa 188640

-continued aattttcttt tctctaaaaa ttctggtaaa atttcagtag atagagtttt tttcatcatc 188700
ttatctaata gtggggatga agaaaactga tacaaattag ataagaaaaa tccacttata 188760
tttgtttttt ggaatgaagc tgaacaaaaa tacttgctta cttagaatca tccattttct 188820
tccatactca acttccctgc tcttcttcct aagttttctc cgatgccatc aatgggctgc 188880
gaccttgctt gaccatagac aagcagagat aataattcac tagaatagtt ataataataa 188940
tagctagcat ttattgtgca tttaatatat atctaaattt tctctatgta tacttttttt 189000
tttttttttt tgagacagag tctcactctg ttgcacaggc tggaatgcag tggcgcgatc 189060
cctgcccact gcaacctcca cctcacaggt tcaagcaatt ctcatgcttc agcttcctga 189120
gtacctagaa ttacaggtgc gcgccaccag gcccggctaa tttttgtatt tttagtagag 189180
atggggtttc actatggtgg ccaggctgat cttgaactcc cgacctcagg tgatccgcct 189240
gccccggcct cccaaagtgc tgggattaca attgtgaacc actgcgcctg gccccttgta 189300
cattttacgt catttatttc ctacaacagc tcggtgagtt agatactgtt atttttccca 189360
ttttatagat gaagaaattg aggcacagag agtcaaacag ttagtgcgag atattggagt 189420
aaccaaagca gtctaacatg agaacctcag cttctcacaa ccatgctaca ttgtcataga 189480
gaggactggt agagatgatg agtggtattc tgattggata ttgtcagata agatttaatt 189540
ctcaagggtt cttttttta ttattttcca ttttttctgt atcatttcat atgttctagt 189600
taaagatagg gagccccttc ttttccttga catcctgaga cattccttta gaatctcagg 189660
gccattttta aaatatttct cttgtttagc ctattaaata tccatcacct taaaaggaca 189720
gaaatcagat atttgtgtta atttttaaaa atagcctgtg gatgtttata agattaggtt 189780
taaggatctt ccttctcttt ttttctcaaa tgttacagtt ctctgatttt tctgacagat 189840
gctggtctgg aagtaaaagt aaaagaccca ccaaaaggga tgataccacc aggaactcag 189900
ttggtcaaac caaagtctga acctcagcct aataaggtta gggcagaatg aattgagagc 189960
cggaatcatt caatttttac gtttgtcact gatgcttcaa aatggccagt aaacatctaa 190020
cattttactt gatttcagga cttgaattct aaatatccct aaataaattt agagagtagt 190080
tcatggtaat atttctaagt tgtagcatgt gtacttcttt atttggtaca tattgtattc 190140
ttcctgctgt ggaacattta caatgaacaa aagtctactg aaattaagtg taaagtttgc 190200
aaggtgaaaa tgtcctctac tgtcaaaaga aaagttaatt tctgaaatct aaagagtaag 190260
tacaggcatt ttggtaaact gcatgttaaa aaaatgaaat attggtaatt gaatttattt 190320
ttctaacaga aagaaatggt ttttatcctt cttaacacgt atcttcagta tttagaaatg 190380
agttaaaata tatataattg tctaagcttt attttcagta atacacattt cagtgcttaa 190440
aagttctgtt gttagtgttg ttatactgtt atttgcagag ggagcctctc tacaaataat 190500
tctggaacct tattaagaat tacgatactt tcaaacctgc ttaattttac ttcttgctac 190560
ttgtaagatc tctattctat gttcttccta cctcactgtt tatctttgcc tttctcaggt 190620
tcgaaaattt gtggccaagg acagtgcggg gcttcgcatc cgtagccacc cttcccttca 190680
gagtgagcag ataggcatag tgaaagtcaa tggaactatc acttttattg atgaggtaat 190740
tgataaagga gcttttggta gtaaattttg gacagaaagt ttttgcattg tttgcataat 190800
aataaggtta ctgagttttt tgtcagaata tgttttaagc agtttgggaa atattttaaa 190860
actattttat agaatgtgtt cattgagttt caaacatttc atttatttta tcattaaaaa 190920
atgactaaaa ttatattttg aacatgaaaa gaacaatgtt cgacatagta ttcagaacct 190980
gtacatgtat tcactgaaaa tgggtatagt tcttcatgac attttaaaat gttgtttgtt 191040
ttgaaatgtg tttcttactg ctttaacttt ggacagtata tttttctggt aatataacca 191100
agtaacttct gtttcttaaa atataaatat aagggaagga agactcatat tcctttggga 191160
aacatctgat tttactgttt atgtatctta aagtgtggtt tccttgtgtt tttattccta 191220
agtgaaattg tttttacagt cttgccacat gaattaccat attgtgttgg cactctttgc 191280
tgcttttttt ttccctggag ggtctctcag acttactttc tgcaaaaact agatgcttaa 191340
tctgcacatg caccatcatt tttctgcttt gcagactttc agaccttgct agcctcatag 191400
gacttacagg aaggcctggc ttgtttctgt tgctttttc tatagatcca taatgatgat 191460
ggtgtgtggc tgaggctgaa tgatgagaca ataaagaagt atgtccctaa catgaatggt 191520
tacactgaag cctggtgcct ctcttttaat caacatcttg gcaagagtct tctggtccct 191580
gttgacgtaa gtaaaaggtg gttttaaaaa gcattataga tacacgctgt ttgttttaca 191640
gagctttctt taattaaggc ttttcagttc tgaggtaacc cacaactaag taacctttac 191700
tttacaattt cttgaattct taagggcttc tgtgtaatga aagtgaagtt tggcaaggtt 191760
aaggccctta gtgcagatta tgatccatca cagataggca ggaagtagta aatttaatta 191820
attgctactt aattaaaact actgaattcc tttcaaagag gtagaaaatg agagtggtta 191880
catttttttc tttcttattt atacagctgt gtggaatgaa ttccaaacta aagtttatga 191940
actcagaatt atacattcaa aaacatgtat aaatgtatgt tatgttcaca ttttgcagat 192000
agttctgtgt gttctgtcta attttgactc tcttccttct cggcttataa tactattatt 192060
tagatttgtg gtgctccgtt gtattctagt tgaagttaaa tcctagtctt tgagagaatt 192120
cattgtacct ccttgttgag tatagtagaa tagagccagt gttcacaaga ttgctacttc 192180
atgaagtata ataataaccc acacttcgtt ttatatatta accaggaaag aatgattttt 192240
cctttttttca ttaccatcaa atgtgtgtgc tctttaggat agagctaata aatagcacgg 192300
gtaaaatttt atttaaaaac ttagtatttt aaacagttga atttcttaaa aatccgttta 192360
taaagttagc ttattgtatc aaaccattca gtatattcca tttgactttc tccttgattg 192420
tccataataa tgttctccaa agcagtagtt tatataatac aagacaattc tttggtgaag 192480
aaaacattgg aatttctatt tctatttatt gatctcattc tttttatat gcttttgtgt 192540
atgttttata atagcacagt ggagactgta tatagacaga gagcaagaaa gagaaggaag 192600
atatgtgatc aagaagattt agagtgttgg cttactgctt tacggaggtt aagttgaaca 192660
atgatacatc tataagtaaa atactaaatt ttaaattaaa aaattacatc aattacgtct 192720
tattaaattt tcctcagatt tatacctgca gttaaaaata aaaaggattt tgaccctcta 192780
tgaaagtgta ttttaaagag ataattatag caaccacttt tgtacagttt tttttccaa 192840
tatagacttt tttgttgggc aagggggagt tggtttttgt tttttataca gatgggagag 192900
ccaggcgagg tggctcacgc ctgtaatccc agcacttttg gaagccaagg ccagtggatc 192960
acctgaggtc aggagaccag cctggccaac atggtgaaac cccgtctcta ctaaaaatgc 193020
aaaaaattag ccaggtgtgg tggcgggcac ctgtaatcct agctactctg gaggctgaag 193080
cgggagaatc gctggaactc aggaggtgga ggttgcagtg attcaagatc acgccactgc 193140
actccagcct gggagacaga gcgaatctct gtctcaaaaa aaacacaaaa atatagagat 193200
ggggtctcac tatgttgccc aggctggtct caaactcctg agctcaagcg atcatcttac 193260
cttggcctca caaagtgctc atattacagg catgagctac cacacctggc cattgtgtgt 193320
tttatttaag aaaattttct taagtcccta ataaaatgtt attccagatt atattatctt 193380
ttctaccttc ctagtccaaa ttttctctga tttctttgct catttgagga gctgcttttg 193440
ggagagaaag atactcacac agataaagca agtcaataaa caaaagtaga aaggaagagc 193500
aagaagtacc atctgtcaca attctgaatc ccacgatttt attttaaagc attgtgttct 193560
gttacttgat gcttttgaac cccatccaag agacaatctg tagtagacag tctccttaag 193620
gtcagggaaa gaagggagta acaaaggtta gaggagcggt aaggagtgga gtgaggcata 193680
cagatacttg tgggtggttt tcactggaat gtgagtgcgg aggttgttaa tgtaaacagc 193740
tcaagagtgt ctggtattgt taggaagcta gggttttttt ggtttcttca ttttaagagt 193800
agtagtgact tgagagtttt ataagttaaa agaaagatac tagtagaaaa agggagaaat 193860
taaagatata gatgacaaga ctgaagactg agaaacagga ggaggaaatg gaattaaggg 193920
caccttagag agcttgcttc tgtaaaagag aggggaatat gcatggcagt agttatgttt 193980
tagaggaggg agggacgaag ggaagaggtt gagggagact acaagttccc ttaaaataga 194040
agataggaaa acgatcagtt cagaatcaaa agaatgagtt aagttagggg gttgagaaat 194100
gcaatgaata tttgaaatat tgtttgaagg attactgggc cactaaagac tcaatgagac 194160
cactgtatag acccaactgg aatcccctgc ctagtccttt attgccctaa gtgtctggaa 194220
ttaaaagagc caagaaagag ccaagaaagc aaattatagt actagttgct gagctgctgt 194280
gacagaaata gcaattaaga ttatcagttc tgggaatgtg gactcagacc taagttagaa 194340
atgtgaaagg acaaatggaa ggtccaaggg atttagaaga tttaataaaa tcctagaaca 194400
atatagtgaa tgcactatag ttaaagagtt ggaaaaatgc aggcaataaa gtagaatatt 194460
tgtatttgat atcataggta gggcacttta acaaatgaga tactctatta cattgccatg 194520
ggagggtggc tgaagtgcag tgcacgtgga agtcactaca agtgcctaag tctaggaact 194580
aagaagttag gcaggtggaa gatcatctgc atggacttga agacacacag atgatgtgac 194640
tcacaaagtt aaagataaaa acaggctggg cacggtggct cacgcctatt atgccagcac 194700
tttgggaggc caagacgggt ggatcacaag gttagcagtt caagatggtg aaatcctgtc 194760
tctactaaaa atacaaaaat tagccaggcg tggtggtgga cgcctatagt cccagctact 194820
caggaggctg aggcagagaa ttgcttgaac ccaggaggca gaggttgcag tgagctgaga 194880
tcacaccact gcactccagc ctgggtgaca gagtgagact ccgtctcaaa aaaaaaaaag 194940
aaaaaaaaga taaaaacaat gtgtttacca ttggaggaag gggtccataa gacacaattt 195000
aaagtcatgg ggggatggga atagtttgga tcaggaagaa acagagcagt ttggtataaa 195060
aatgaaagaa caggtagatg acataaggat ttatgttttg ggtggtgatc aaagatgaca 195120
gatggggtac agtatggcaa aattaattgg catagggctc taaacagatc tgggataaag 195180
ttacttcagt acaggtatta actgaggact catacagagt cagaggcctg gcataggcag 195240
ggacaggtat gattttctgt agggactagg gcagacccct tacgcagtca gtacattttt 195300
tttatgagta tctgactgtg cagggctaaa catggtagga catagaataa tgattccctc 195360
tcatcttctc aaggaaataa cacacctaaa tagttgcatc ttgctgcctc ttcttttgta 195420
tgtcttatac atttactgct ggaaaaacta tctttctccc ttcttacttc agttcgttta 195480
aagtaaatga actttaatca tggctgttaa ttgtaaaaca tgactcaata aaaaaatgaa 195540
agctgggaga tatgaaatca aattagaagt attcaaacac caatgctgct aacttaaaaa 195600
gaagtgaaag tactgaaaag ttgccttcag cactgtttgt gtctatctct tcaacctttt 195660
ctagttaaaa caattttgta ttgacatcaa tgtgtgcacg ttatttggat cccaactcaa 195720

-continued acaaactata gagagaggaa tgggggcaga gattggaagt ttgaacactg actgaatgtt 195780
ggatgaatta tttttaaaaa taagattact ataattaccc attttagata atccttaaag 195840
tgatcttgtc atgctgtctt gtttactcat gttttagaat tcgtgtattc atcgttaagt 195900
atgaacttta gctcaatttg gatctatcag tctttctatt taaacaccat atttgactga 195960
aaaatattca tatcctaatt tagttcaaag tgactttaac tgtttttagt aatgctctag 196020
ttgagagaca aaataacatt agacattcat attatgactg tatcgtttcc aaaataattt 196080
ttaagtcaat gggaaagata gagctaaata gatgaagggt tcagatcctc tgtgaggcat 196140
tcattatcaa ttatgtagaa ctttttgccc tttttagaac acttttcctt tttttttttg 196200
ttatttttgt tgttgttttt tgttttgttt tttgtttgtt tgtttgtttt tacagcacct 196260
tgccctgcca cccaagctgg agttcagtgg cacgatcttg gctcactgca acctccacct 196320
cccaggttca agcgattctt atgtctcagc ctcccaagta gctggtatta caggcataca 196380
ccaccacacc cagctaattt ttgtattttt agtagagacg ggcagggttt taccatgttg 196440
gccaggctgc tctcgaactc ctggcctcaa gtgatccacc taccttggct tcccacagtg 196500
ctgggattac agactgggat taaagacgtg agccactgca cccggctgag aacatgcttt 196560
ccagttttat gtcttaagag tctttgtttt gttgtctaat ttatctagaa tggtttcact 196620
tccatttttt tctaatctta agttgtccag actcaaaaat tggttggtga tcttctcttt 196680
attttccatt tttgctatag tcattaattc attaattgct catttagtaa atatttgagt 196740
tcttattcgt agaattctta tttgcattct tgttagtaat aaatactaag ctggaaagta 196800
ggcattgggt ggagatgcag aggggaggga tacagagtaa ataacatggg gtgaagttct 196860
gatccttgga gtactcacca tgtaatgtgg tagacatacc atattcacat aattaaattg 196920
cattgtgata agttgtggaa tggcttcact taagtgacat ttgaggagga cttgaagaaa 196980
agttgccagg aaacagtaaa ggaatttcta gacagagaat caaatgttca gagttatggg 197040
gacatgctat gtatgtgaac taatgaatag ttgatatagg taaagcagag aattgagggt 197100
ggaaaacaga tatgtactgg ggagaatagc tttctctctt ccttctcagg cagcacttaa 197160
tctgtagaag tagagaaggc ttacttcttt ctccagctac ccataatatt tgtttttctt 197220
gccttcagcc catttgtgtt tatgtacctc ttatttctgt ttttaagcta cttaaggata 197280
aggactcatt caggatccct tctcactcac atttgtttct tcctaagcat taaaaattac 197340
actttgctca tagtaggttt tcacagtttg ttgatgcttt acacatttgt ggatgcttaa 197400
ttttagttct ttgcatttga tatgatcatt ctgtttaaaa taatttctaa catatatatg 197460
ctccttgcct taattatctc atttaatcct cattgtgacc ctgtgatgtt aagcatatta 197520
taattctcat ttttgcaatg agtaaagata gccactcacc caggatcaca agtagaaagt 197580
agtggagctg gtattggaac accagttgat atgattccaa agcccatgca tttatgttcc 197640
gtatgcatta atctagtgga gagataagga taaatatagt tataaaagga tgaagcaact 197700
atagctgtaa taatcctgtt actttgacta gaactgccaa actacagaaa gataaatact 197760
tataacctta atggttgaat gaggatgaat accatatgta ttgaagatga catgagttat 197820
tctttgattg catacctggg gaacattgat tgattttaaa ttaaaattct gaagatgtgg 197880
aatctgcaaa atgtgagcta gtagaatgtt tcaaatatca gggacaatgc aagtaaaaag 197940
atgaagagag aatttattat gcacctacca aggaagacat tagactctgg aatcacaagc 198000
ttaatttttt ggaaaacaag tgtacttcta tgataggaga tgttaatggt ttcaaactta 198060
cacacccaat tctttgggta ctctgtcaaa aatgagatct tttaacattg tgaggggggt 198120
tgagtggaag agaaagttta tatcaaggga agtagatgat agacaaatgg aagtattctg 198180
aggtatcttt atagttccca tataatctga attcttacag aattgagttt ctgtatatct 198240
ccatgcattt atacagatta cttcttattt taggctgatg ggtgttcaca tatagaaagt 198300
atactgattt tccaaatttt ggaacctgaa agatttgaag tagagttgaa gagaaagtat 198360
catttgttaa tcttgtttgt atagcttcac ctgggttaat tgataaaatt ggcaaatgtt 198420
tcttgcattt taaatccaat ttcattcctt tttacctaat aacattaaat ccaatttcat 198480
tcctttttgc ctaataacac ttagcagtca cagctttaac ataccccaga tttcctgatt 198540
ttgttaatag ctttgtgtgt atgtgtatac ataacccgtg ttttaatctc aataatatta 198600
acttaataca acattagtaa atgtgctgtt cttatatggt taagaacagc tttatttcat 198660
tctttagctt agtgttaaag tttcgtaaac agaatgagat taaaacagtt aaattaagat 198720
tgtaataata tatatacgct attcttaatt ttcctgagtc atttcatcat tttgctttaa 198780
caatggcaat tcttagcttt gtgcttatct aacacaagga aagatttttt tcttttattt 198840
gcatgagcat ttggcatggt tggtcactta ttttcactgt gataattatt cacttgttgg 198900
tctcttttct acgccatgaa agattatcag cttagagttg caatttggtg ttcattaatt 198960
tagttagatt cccagtatgc tttaattttc taattttctt gacagaactt ttctgccttt 199020
aaaatagtat ttgagaatga aatgttattt tatatatatg tgtgttcgta tatacacatg 199080
cacacacaag ctgtgcttat aataatctgt gaaattatac tatatgaaag ctaacatatt 199140
ttaatagtga gaaattgggg ctttggaaaa attaacattt tcctgaatgt tcatatcttt 199200
agactaaaac atttctaaat ttccaaagaa cactattcaa gtgtgtgtgt gtgtgtgtgt 199260
gtgtttgttt gtgtgtgtgt gtgtgtgtgt gtgtttgaga tgaagtcttg ttgttgccca 199320
agctggactt gaacttctgg gctcaaggag tcctgccttc tcagcttccc acgtagctgt 199380
gactacaggc atgtactacc atgccgagct atatttttaa attattttgt agagacgagg 199440
tctctctgtc ttatccaggc tggtctcgaa ctcctggatt caagcaatcc tcctgtctca 199500
gccttctgaa tagctacgag tataggcatg cactactcac ccagctattc aagtatattt 199560
tatttttaaa ctccagcttt ctgttagtca aatttctgct tcttgataaa tgcagtttta 199620
ttaggacatt gcattttgaa aataatctta gggtaaacca gtgtgaatta agaattttct 199680
acaactgcag aacaaaagca aaaaagtata aagtttcaat ttacatggaa gcatatacag 199740
aattgatttt attggcaatt tattaccaca gttagcagtt aacatcattt taaaatatca 199800
ttgtacatgt tgttgactga gaaagcactt atgtttgcac attgacttaa aagagagaca 199860
taagctttaa atattgtcaa ccagtcatca cattgcttct ttatcactaa ctttacctgc 199920
attactttta acaattgcct ttcatgttac tttaatacta gaataattta tgctaaaaaa 199980
tagaatacgc taaaaaaaag tgatattgtt ttatgtcaaa aagtctgtcc cactatgctt 200040
tgtaagggag aaaaacccat tgaccaagta ctctacaaat tcttatatac gtggatgaac 200100
cagtatagac atttttcccc taaaacatag cacttcaaaa tgctctgcaa tatgtttttc 200160
actttaccta aagagaaagg acgtattccc tatccacttt taattagggg gcagttggct 200220
ttggttttgg tttacattta tttgtaggca tattattaga cactttgttt agagttttat 200280
atgtcttata tttatgaatt agtatatatt tatgtagatg ggtgtgtacc cacattcatc 200340
tgtacatata tatgtatata tccatatata tatatggata tggaaaatat agaactagaa 200400
aacagtaaat aaagtctcat tatctaaaat gagataatga gaaaagtttc attatctaaa 200460

-continued atgagataat gagaaaagtt tcattatcta aaatgactta taattgataa ggaattttga 200520
tgtttctttt ttgttgaagt cttagttgat ctttttttatt aatattttga atgtcctctt 200580
ttttggttca aaataaccgt ttatcataat atttacataa gcaataaaat tgtgcaattg 200640
ctactcacta gaaagatttt aatttcaaat cagataaata tagattgata gcatgagata 200700
actacgaaaa tgtatatcat ttaaattatc agtaaaacat tttgtgaaga tgttaatttt 200760
tctaggataa cgtttctgtg aattaattgt tccttaacaa aacattttta gacttaaact 200820
tagagatcct aaatgctctg catttcctaa actttgagat agagaaaagt aggcctgtct 200880
tttgataaaa ttgattacat ttttatcttt tgataaaaaa ttgattgtat gtattatgtt 200940
tttcttatca aatttgttag tagcattcag aaacatttcc aaatgaattt tttcctactt 201000
ataaagggaa ggaaaattga aaaaaatgac tcagactttt tattttttac ttttttagtt 201060
tttattttta tttttgtact tcaaaaagtg ataagttcac gtaaactaca tgccattatt 201120
attcataatg ataattgcat tttctataca atcgatatca tttccatttt tattataaaa 201180
cagcagactg gtttctgtca taaaacaaat ctggcttgta ttagaacaaa tacatcctca 201240
tttaaagaat tttaaggttt ctttcttgca ttgagtatct taagctttat aacaacgtct 201300
ggctcttaat tttagtaaat ggcatgacac actatatcca tggagagctt ctgacaaaaa 201360
cttacttatc agacagaatt tcttcggtgt gttgtttact cagatggctt cagtttctct 201420
ttagtaaaat aatatttcca tgttggtgct agagtacaga aaaatgttgt tactgtgcac 201480
gcatcttctg cagatgatat cctgttccct ttctttgttg atatttttct ttcttaaact 201540
ttgttgctca gaatatcttt aatgctagcc aaggagtcag ggatttggac gtattttcat 201600
ggacttccaa agcttttttc ccccaggtga gttaactgta aggaacaata atattttatt 201660
caggtatttc agcatgtata acaaattttg tgtctttaaa acctttgctt aagattaata 201720
aaacctttta accaaaaaaa gatctatatg aagtgctgca attgagtttt ctcactcctg 201780
ccaaaaagaa tgtattatta gtttaagtga tacttccaca tgacttcaaa tttgctatat 201840
ttagttttat gagtagcttt tccaatgact atatctaaga ttagtgtttt cacaactaac 201900
ttatttaggt gacagtgtcc tggccttatg gctcttttat tttttctgct gccaacactt 201960
tcacattccc tctttgaatg ttcatctgag aatgggatgg gaatggaggg agaaaataat 202020
aatattgaaa ttcatgaatt taatatgctg gtacctgggt cttacatttc tgtattgaat 202080
aaagcatgta ttttactatt gcttgagcat gataggcaca gttctatgac tttatgtctg 202140
tcagtgtttt atactgttta gcacaagaat tggataaact ttgttttata cttattaata 202200
tagttttatt accttttcaa taaaatatta ttttaaattt ttaacaagtt ttcataattg 202260
cctttcagtg actagtttgc aattataatt agttgtgcca aggcttaact cccagtgtta 202320
ccctgaatga tcaaaagtta gaattattgt tataattaat taaatgcact aggaatatta 202380
ttaaatacca gtgaagttgg gttttttttgc taaatctatg gatatttgct tttttatgtt 202440
gccatgtaat ttttaagaat cagttgtgag tgggattaaa acttgcccct tccaactatg 202500
aaatggcatg atgtatttat ttattaacca tttacaaaca gacattttaa aatgtttaca 202560
gaaaatcttg tgagtgtaat agcaagtact atgtaaagtt tagacctgtg ttactctcaa 202620
tttttatctt gagtgctctc tgtgtattca tgtaggtttg catatatata aattcttaca 202680
aatatatatg atgagtatat aaaatgcgta ttttacattt attttcggtt gtaaatctaa 202740
gttttttgag tgtttaaaat tctcatttcc gttaaatttc caatatgtaa ccaaagaata 202800
ttggtaaata aaatataatt acagtaaatg taaattaatt tttcttagta catatttgta 202860
taagtaaaaa ttggttattc atcactatag tgagattcac aaaatattat gtgaaagtta 202920
atggtgactt taacattttc cctgaccagt catgtatgga attaacaaag tagcaggtat 202980
acagaattct tgaatctaca tatttttaaa cctgaggatt ctatttttaa tattctactg 203040
tgttactgtg tgtatgaaca tgtatacata tctcttcatt atgaggctac tggtagggat 203100
agaactattt aatacaattc tatcttgcat aatgttagtt gttaaatttt tattctattt 203160
ataacattat taaatatcag ttttaaccta atgtttgcat gtgtgtctct ttatggttat 203220
ctattactct atctgaatat gaaataaatt atagagttca tattactgta tttaaaaatg 203280
cagttttaaa tctcttttaa aggagtaatg atgacaatga gaacacccag tgtggaccct 203340
ttatttacat ttagttggga aaaagagaaa atatggaaag gttattattt ctctttatta 203400
cattcacata ggaaacaatt ttatcacagc attacaattt aacagaaaat ttagggaagg 203460
ttctttcatt ttagaagtga ctcttttcaa taataaattt acgttatatt tacttaaatc 203520
catgtttaat ttctcctttc tactaaaaat atagtctgtt tttctgttac tagcattaat 203580
gtatcactgc atagtaatgg cttaacaaat ctagcaagac gtttttattt gtacaatatt 203640
agagagtata agttgttaaa atattgtaag catcaatatt tcattcataa ctaacaaata 203700
gcaagatata gctatatttt taatgcatat ttttcatcat ctctgcttat ggatcagttt 203760
tcagattctt catacctgtt ttctctattt ataaataatt atttcaacat gggaagaaat 203820
gaatatttag actttttttt acccataaca atatacagta atgcagtaat aatgattcaa 203880
aattattccc ttgtggttca catagtatag tatttttatt tttccaactt taaatattgc 203940
attaaagata aaagtaaaat caaggatgat tatatttctc aaattatggt gggcagaagc 204000
cagaggttga ctggtttcct gctatatttt cttgccttca actttatttt aaatagcatt 204060
gttgaaaaac tgagattctt taattagtgc taatgactaa ttcttcagtt atctttagtt 204120
atgtgttttt tttatattga cagtactgta gacttgctat aaaagctatt aataggaagg 204180
ctttgaaagt gataatagat tgtattttgt ttatttttct ttcctattca aattttcagg 204240
aatctaaaac taatactgat gactttttca aagacataaa ctcctgctgc ccacaggaag 204300
caacaatgca agaacaagat atgccattct tgcgaggagg gccaggcatg tacaaggtag 204360
tgaagacggg accttcaggt cacaacatca gaagctgccc taaccttaga ggtatcccaa 204420
ttggaatgtt agttctggga aacaaagtca aagcagtggg agaggtatgg attcttgtag 204480
cttcatgact tctaagatac tcatttttaa tgtaatacaa ccaaagcatc tcttctaaag 204540
gttgccattt ctaccacagg tttttcaatg ttaatgtatt ttatctttac ttgtattgca 204600
aatacataat ttttctgtgc ttctgtctaa tgatttgcat aattatcctt gtgtaaacaa 204660
tatattaaca aatgatttgt attgtatata taaatgtttg gtatttgcac atattttttc 204720
attattacaa atgtactata ccatcatgga ttatcatcac ttaaaatatt ctatgtgatc 204780
ggtatggaga tgtggtcata tgcaaaaggt ttcatttctt tgttcccatt catagtctc 204840
actgaagtcc tgagcaaata aaattactct ttaggctact gtggcatttg cctcagctga 204900
taagcttgaa gatgtagtgt gtcatgctat ttctcagtaa gggtcatttt caagttacac 204960
tatggatact ctcaacctaa ataatagcaa gtcggctgtg ttaggacatt ttagatgcag 205020
aaaaaagaaa atgagccatg tgttcttggg taattcttaa aattatttag gtgttatctt 205080
tgtgctttga aagttattat tttaaccaaa ttcataaata agcagtattt tacagaactt 205140
tttattgact tctgtcttac ctcaggctgt ggccttaatt tcagaaacta atttcttagt 205200

-continued

```
agaaatgtat tggaatgatt acactattca gacacgtaag atttttactg gttttcagac 205260
tgagttccct gaaagaatca agccaatcaa tcatgctttt tgttatgtac caggtaacca 205320
attctgaagg gacatgggtg caactggatc agaacagcat ggtagagttc tgtgagagtg 205380
atgaaggaga ggcatggtcc ttagctagag acagaggcgg aaaccagtac ctccgacatg 205440
aagatggcaa gttggcttaa atttgtgatt tattccaatt aagctttcaa atacagaagt 205500
ttaatgccta ttgtattgct tttgttttaa agagtttttt gtgtgtttgc tttttaacaa 205560
gcaaaactaa aagttaaaaa atcttgcaac tgttaaaatt ggtttgtaaa atacgtgagt 205620
acttaatgca cattaaagaa gaaaattaaa agaaaattcg aaacatatag actcatcttt 205680
ataaaacagg cttttaattt cattaatata aatttatata cctctttctt ctgtaccagt 205740
ccaggactga acgttctatc ccttctataa taaaatgaaa cttcggtatt ccaactacca 205800
atctcagtac ttctcccagg caacttcatt tgattgcatt ttgtcttagg gaaagagcat 205860
tgaataaatg catagtgtct ttagggtttc ctgttgttag attttcaact ttaaatttta 205920
ttttaccttt ttcaacatgg ctatcactta ataaaatata ttcctttttg tccccctctc 205980
tttgatatct tggtggcaaa aatttgttct tcgaagttga gaccacatta tcacttgtgt 206040
gatgctttaa ctgatcacaa cagagcaaag aatttcttgt gttcctaaag aattgtgctc 206100
accactagaa caatagtgtc atagtgaagt tcatgtttat ttcttcatac ccagttatga 206160
gtcccttgtg gacaggcaca tggtttttat ctttccattc ctagtactga aacagttttg 206220
acacatacta gttgctcatg aagttttgta atacaacttg aattataaaa ataatagcac 206280
atcaaaataa gtatgtaagc aaacatggac ttgtctgcca aatcccaaaa tttataggat 206340
gaagttaggt aaataagaga acatgcatct ttattcaaaa gataataaat ttataatact 206400
tattattcca agaggcaatt tggccataaa tatggattca gaaaaggttt gaaatttgca 206460
ataatgatgg agtatctttg gagatatctc cctttttccc cccacaacac acctttgagg 206520
taggtgatat aatcttaaat ttataggtag gaaactcaag ctctagaatt taaactaacg 206580
tgtctatggt tgtacagctg gtgacatagc agatgtaaga cttcagccag aatcttcatt 206640
cgtgttttaa atgctgtact cattacacca tgctgtacac attgagcaca acttgagaac 206700
ctacctcctc tccttgtttt tcccagatag actttttta gtctaagatg atatggtcat 206760
aaaataatgt cctgaaacag tagaactgtt catttgaaaa agataagggt tccgcttgat 206820
gtaaatcaga catttactaa atgacttttt cacttactat gtgcttatta tatattgctg 206880
tatatttact tcatattcat aaatttttaa acatttttct ttatatagga atattcagat 206940
ataaatgaaa atacctaagg ggagatcagc tttatttaag ataagttaaa tatgagaaca 207000
gcttaggtga cttctaaagg acttttctag cttaatcctt aataattttt taactggcag 207060
tacaaaaaat atgtaagagt ggattctgaa gcaggactgc cagggtactg atcccagctg 207120
tgcaactttt tactcatgtg accttgacca agttaaccta atatctctgt gcctcagttt 207180
tcccatttat aaaatgacct tataggtcat aaccacataa atttgatatg aagactaaat 207240
gagcaaataa cagataaagc taatggatgg taagttaggt cttattgtta aaatgcaaaa 207300
tgccttccat gctaaggatc aagttttaac ctgggaaatt ttattcttat aaacttagaa 207360
gatagaagct tctttcaaga taaaatgcct cttaaattag agtatcattt aagaaaagtt 207420
taaatttttc tctgtaatta gttaatcatc ttttactctt gatgtataga tacagacata 207480
aatatggata tttggtgatc atgtgaatct tactatttta atataaaacc tggagtgata 207540
aggaaagaaa tgatatgaag ttagtgcctt taaatcacta agattagttg atgtgctgcc 207600
```

caaatagtct gttcattggt gataatattt aatatggaag tacaaagatt tggcactatg 207660
gtaatttata tgaagtcatg tgagtaaaac aaaagctttc ctctttgtaa aaattctcta 207720
ttggtctttg aaatctgtag taggcaaagt tactgctgtg gtaaaaacag acttcactct 207780
gggtgctaga ccattcttag tctagagagg aagcagtgct atcttttccg ttcagtttac 207840
tgttcatggg tgtttttctg aagaaacatt ctactgctga aatattgcat gctgaagagt 207900
attgcctaag ggaagtgcta agattggttt tttaaatcaa gtctacaaat gctggtaaag 207960
ggatagatta tacagtacca ctggtttagc agaattgcaa tttacaggta ggaaggaaac 208020
actctaccac accctgtctg tagttccctg ttctgtttaa aggactattg actttttttt 208080
tttttttttt ttgagatgga gtctcgctct gtcacccagg ctggggtgca gtggcgcgat 208140
ctcggctcac tgcaagctcc gcctcccagg ttcatgccat tctcctgcct cagcctctct 208200
gagtagctgg gactacaggc gccggccacc acgcccggct aatttttgt atttttagta 208260 cagaaggggt ttcaccgtgg tctcgatctc ctgacctcgt gatccgcctg ccttggcctc 208320
ccaaagtgct gggattacaa gcgtaagcca ccgcgaccgg ccaaggacta ttgactttta 208380
aaaaagatat ttaagatact taaagatatt ttaaaaataa gatatttaaa aatatacttg 208440
agatatttta tttttcataa ggttatttta atggaataaa taccttttcc ccccaatttt 208500
acttgacaga ctttattttg cctttttgg ctggcattaa tatggatatt taactaaggt 208560
attgttttat atcagacaga gtcttggagc cagttgattg ttcatagggg attaatttag 208620
tttgcatatt ttataggtca catcttgcca tttgtaaatg gataaaacat ttgccatttt 208680
ctgcttgaaa taagaattct gatacattta tagactctga ttatgtaaca tggtttatta 208740
ttatccttct atttgggaaa aatatcttta tgtgataaaa taagttaaaa gttaagtttt 208800
ccataatttt cacattcata acttagaaca gttaacaaat gaaaattcct tttggtacta 208860
gatacttagt ttttttctct attctaatac taatatgcaa aatactttta tttctggttt 208920
ataggttatc cattttgttt tgcaaaatac tcttgtataa atttgttgca aatacaaaga 208980
gttcctggtc cagaaatatt agtatgcatt cagtaatgta tcctgccaca ataaaagtaa 209040
attggcttca taagagccta tctcatttct aaatttcact gtgtatttga taaataaaaa 209100
caaagatttg tcaggtgctt tgttaatgtt aagatgacct gactggtatt taaattgatc 209160
aaatctagat gtgagcttat tttaaaatct aaccatcata aaatcttttg caattttctc 209220
tctttgttgt atgaataggg aatagcacgt aagaaactaa tgttacagct atggctttta 209280
ttgtagaaca agctcttctg gatcagaatt ctcaaactcc tcctccaagc cctttctcag 209340
tgcaagcttt taataaaggg gcaagttgca gtgcccaagg atttgattat ggactcggaa 209400
atagcaaagg taggtattta aaagtaagtc ttttacttac ctaacttcaa tattttttat 209460
taccttctct tttatacact ttttatttgt gttcacccag aaatctttat taaattaaaa 209520
tttgttcatg gaaagctaat aaaaaatgtt tacaaaggtg ttcttttcat agtattgttt 209580
tttgctgttg ttttttgttt ttaaccagtt ttggcttaag tttatgagag tgcttgctta 209640
ttttttttct atttaaaaaa cactcatttt gatttcatat cctaaagatt ctatttcact 209700
aaatctagta aaatttgatt tttatcatcc acttattagg atggtaatgt taatgagaaa 209760
cagagaactt gctcaaatga tccatttaaa atcaaactat tacttctaaa taatattttt 209820
aagtaatatt acacatgagc tttataaaat ttatgtggtt ttgaatttct aacccagtaa 209880
tcttagttaa tttagaatta tgtgaaatga tctgtttggt tttaatatct ataataaaac 209940

-continued

```
cagaaagttg taaaaagaag aaaaccctaa gtcatatgaa tataatatat atacagctgt 210000
tttggctgca ttaatggaag agaccagcat catggactgt ccaaacaata gttaattttg 210060
aaacaattta tgctggaggt tcatcagaaa ttgcattttt atgtgaattc acacactctt 210120
gttctttcct atgtacctga tctagactcc ttcaaaatca gccctattgt ccacaggtaa 210180
catacagctg ggtcatgagt aaaagggagc agatagctta cgtggaaata attttacttt 210240
aattttattt aaattaattc acaggacttg attccaaggg acaaatacag tgtcattata 210300
cctgacttga agaacaagtg aaaaaataaa acagtgaaca aaatgtataa ggaatattct 210360
gtttaaaata aaactacttc tattgaatag cttcattact ttccacaaag tatttttatg 210420
aaggaaacct agccacaaga ttttttttta ctcccttgga ctagcctatc tcataggatt 210480
gggtatcatc tgctcgctta cttcgggtac ctgatttcca ttaacttaag ctagatcttt 210540
gtacttacat agtgtaaatg cttggtggtg ttttctttat gtccctttct ctttaccttt 210600
gtcaactctt aaaatctcag catttgctta ccgctactat atctctatat agtaatgttt 210660
taaagccttg tttaacacaa attgtatgct ttcagtcttt aaactgtctg tcattgtact 210720
aatagctatc acagtaaatc agtcattata atttattaaa atatcattaa aataaatata 210780
aatgtttgag acacaaacat tgccgagaaa atttgttatt atgtacaaat aataaagtat 210840
tactttttaa acatgagatt ttgtgaatat cgttcaaaaa tagcatgcac catgccaggc 210900
atagtggctc atgcctatag tcccagctac ctgggaagct gaggcaacag gatcacttga 210960
ggccaggagt ttaaggatgt agtctgctat agtcgtgcct gtgaatagcc acacgctcca 211020
tcctgggcaa cagagcagga tcctgtttcc ttaaaaaaat attaataata agcctactct 211080
tgttaacaag cttttaaaat atttagaagg agcaaagaaa taataagaaa cttaaacttg 211140
atgaaatata tctaacttta ttatctgtaa cagtagttcc cattttaact cttaatactg 211200
tccaagatcg aagagctgtt ttttgtaagt ttttttttct taaaacagta ttttagaaaa 211260
ttcttcatga tctctaaatt ttttcctata atctacagca tttatttatt atttcaaaaa 211320
aagatatatg gctcgtgtac acagttcttt ccacataaat ctatcccgtg taggtacttc 211380
agttgaaatt ttcacatatg aaactttatt atatttcaga aatatgacta gaaagatact 211440
attttccagt ttctgcatca cctagtctgg atgtagttcc ctctccccac ctccagcatc 211500
atttaaacta tttaatgtat actcacaaat aaggagttat tatccatcac ataatttcat 211560
tatcttaaaa aaaattttg taaaaccttt tggtacaagg aaaaatgtta gaatcgatat 211620
tttagatact attcaaatta ggtagctcat aatccttttt gtcatatagg acttacagat 211680
ttttaaatta ttcatctaag caaaatattt catgctttta aagtagaatt tctttggcag 211740
taacaactta aaaaagaaag tattaattta taactataat gtaaacacat tgctatgtta 211800
ataacatact ttgccccatt ctgcttttttg aagaaaaact gttaattgct tattttctgc 211860
atgaaatata ctgccgatga ggcagggtgg tattagtcat tgttgggaac tatggaaaag 211920
gcatcattta cttaaatctt catttatata tgttcaatat tgaagcaatt tatcactgat 211980
tcttcataga gtcttcgttc tcccatacat aatgagagat gttatatatg aatttaaatg 212040
gatttgtttt tataggtggg cttctatata agatttggtg gggcgcttcc attaaaaaaa 212100
aaagcttgca aaattcggtc cctaatctga ggatgattaa cagtcaccaa ttttcactca 212160
tttctgaatt ggcatggttt tatttagtgt tcaactctat ctgaatgtca taaagcacca 212220
tttactttgc cattttggat gttaatgaat aacgagttgt agttttgact gttttaccca 212280
ctgcaggtga ccaactgagt gccatattga attccattca gtcacgaccc aatctcccag 212340
```

ctccttccat ctttgatcaa gctgcaaaac ctccctcttc cctagtacac agcccatttg 212400
tgttcggaca gcccctttcc ttccagcagc ctcagcttca gagtaagtct gtcagcctta 212460
cctgcctcat caagcatttc tgaagctttg ttctgagttg cttatcagtt actaattagt 212520
tatcaactca cctgactggt ttttttaat taggatgtta tcccctccca catttttgaa 212580
atatctaagc tattctgagc taagacattc tgcagctaag acatttaaag ttgatttaaa 212640
gttcatatgc atgactatgg taagcatcac atacagggac aactttcagt ggatttttct 212700
tacttcaaga tgtcccaaaa ggataaagcc atttcactct tatcagtggg tagaagagag 212760
actgtacttg tttggacagg tttgtttgtt ttttctaagt gaatttggta tctatgaaat 212820
gtatgacaat ttagttttcc cggttttctc aaattgttgt ttcctgtctt tatttttatt 212880
tttttgttgt tgttcctaat atgttaaatt gatcatttga ttccagttct gtcttttagg 212940
attgctctag tccttcattc atgatagtaa ttcacattgg tttggaaaag atacccaaaa 213000
aaattatact taactgagtg ttcttttttc ttaataacct cctgaacctt ccacctaaac 213060
ttttcaaagc tctgtccagt atgacaacag tgtgttcttc ttggcattca gttctcatgt 213120
tggctataca atatataaac acattaattg aatgagctag tttatgaaag tttcagcttg 213180
tataccattt ttcggattca aatgcacaac ctctttgctt tggtaaagta cattcacact 213240
taggtctaag ttatttgttt acaaaaatac tttaataact gttattaggg tcatgtaaaa 213300
gaatgctagc tggtttagtt tttattaaaa actaggttag tatgtagcta gcaaatgata 213360
ttattcatta ctttatccac cttaggtaaa gggtacacaa gagtataaac ttttctgggt 213420
ttccactatc cattaggaaa gtttaattga tgaaattaat tagtttggaa atataagtac 213480
tatcaatttc tagcttatca tgttcgttca tgtataatat taatttgaat gtctattaag 213540
agaagaattt caaagaaaca aaatagtgtc acatgtgcga aatagttttt tccttctatg 213600
ataaatatta ttttagaaga atgaaacaga agtgaggagt tagtttatta attttgtgtt 213660
gcatcagact ttttacattt agaagtacta cttaggtttc aagaagtttt aaaggtaagg 213720
acaaagggaa aaacaaagga aaaatatcag gatcagtcag gtagaaaatt tatactagaa 213780
aatttaaatt cattcatatt caaattcagt tttaaatgaa aaattgcctg tgtcatagca 213840
gtagcagaca aaagaactaa ggagaaagga gaaccttttt gttctagcta aagaatcatt 213900
gcaagtcttt acaaaaacaa gcataattac cattttaatt ttaccaaatt taattaataa 213960
aatatttcaa aacaataaac agtaataaaa gttgatttgt ctcttccagg gaataacagt 214020
ttctaggtga cattgtgtca atataatttt atgcatatgt gttatcagta ccaccacttt 214080
atttaccact atcttgaagc aaatttgaaa tcatggctta gctatgtttc aattagcaat 214140
tttctgaatc attacttgcc tatagtccag caatggaaat tacttaggtc ttgttttaaa 214200
cttcttattc gcaacaggac gtctctaaat tttgacttcc aaattccaga aaatggaagt 214260
cttaatcttt agcatcacaa aaaaaagtat ggaatctgaa aatagtttta atttttttaaa 214320
ataattcaga attgtatttt ttataccgtg ttgggaaagg taaatgtggc aaagtgccaa 214380
catttaagac tccccaagca aggtattctt ccctgaacct cactaccatg tatcccacta 214440
gtatatcacc tatgctttag aagatggctt attcttagtg aacttcccta tgctatttag 214500
taaaatgaga tttatttttg ttttatacct ttgtgatact aaataaatca ttatgtagaa 214560
gaccatattt actcaacttt gtttatactg atagtcgcca ctatgtagta aacactgtac 214620
ttaagcactt tgatacagcc tcatttgaga tactgtctct tatgtctgtt ttacagagaa 214680
ggaaacatag gcttagagag gataaatgat ttgccccaga aacatacata gtaaaatggt 214740
agagccagaa cttgaggtca attctgttga ctacaaaggc tattttaaat attcagcctt 214800
acctcggtaa ataatgcaaa atctacttta atatatatat atttttaatt tatatttaaa 214860
ctaggtctgg catctagagt attagctttg ttcagattga ttattttttct ttttatagtt 214920
tgactttttt taatgtaaca gtagtttgaa tggaaaaaaa gatttcctga atgtcataac 214980
tcaagatcct ggttaactag aaaaattcta caaagacaca catcaaccgg tgcatggttt 215040
aacttcatct agcatttcta tgagcattat tatctgtaat tctttggttt ttttttccg 215100
aatcatagtt tttacaccta tctttggaaa tttgaaaata atctggcaca ttaagttaat 215160
ttttgatacc ttttctttag aatcaggcaa cattttattc cataaaatag aatatttggt 215220
aatttttaaa ttagcaaaat tatttgattt tatatacgta gaaattattt caagtgttat 215280
tctagtgaag tagaatgtta tagaagtaaa agttaacaaa tttcccttgt cttatgtgtg 215340
tgcacacaga gacatgaaaa agaaaagtat gtatatagaa ttttctttac tgttctacaa 215400
tttacttttt aatttaaaaa ctaattatat agtttttaga attggtaagc aatttggcaa 215460
aaaaatttta gtgaaccaaa gtggagaatg atatctgtat ctgctttctt taagaatatt 215520
acattcctta ttttcattat caccatttct cttgaaagct tcattttatg tcctgtacct 215580
tctgacagtg tcttacacat cacaggcatt caaggagtgt ttattgactg taggtattta 215640
agattaccat ttcatcaatt taagatcttg tgttttctat tatgatattc cattgtttac 215700
tcagagaaca tcttcaaaga agagaattta tttctttctc ttagtaatta aagccaacta 215760
tactgtgaca atatgatgta tgataattgt gggtttatac tgattgaatt ctaagcaaga 215820
ttatccaact gaaaaactat attgcaaatg gcttcattta acatagcatt ttatcacttt 215880
ctacctactg ttccagaggc tgaatagttc atttttcaac ttttatttat ttgtttgtgg 215940
tagaaaaatg gcaaataaaa ctgaagacaa tttgcttttc tcccagaaac tttttaatac 216000
ttttttattt ttataatgtt ttatttttaa ttttgatggg tacatagtag acatcttcca 216060
gcaatttcaa acatgaaata tatgatatat gtcaaaagac agtactttca agcacagata 216120
tcatagctct aggttacctt gcaacaagag tttttctatt atactcataa gtcacattct 216180
tatgtgggac aaaaaaaatt aaatgtgacc ccaaaattca tttggatatc tgcatgacta 216240
tttatttaca tttgagaata tgaacacact aaagtactat gtttacttag cttgtagaaa 216300
catagtcatg gaaagacttt cagctcagat ttcccttcca gctacttact agctctctaa 216360
gttatctgac aggtctgaat ttttgttacc tcattataaa atgggattcc caataaatgt 216420
tatcttttga tgttattatt gccttttgat gcaaatactt aatacctctc atgctttgag 216480
gaaaatatag aaaaagtcct tctctaaaag agagcaatct attcttggtg tggaatgagt 216540
tgcaggaagg aatttagaaa gggacaaatg agctttccta gttccttttg ggtctatttt 216600
tgcaatgtaa ttcagttacc tattttaaga ttcttaatgt atttagactg cattcagatg 216660
ttagtgtgaa tgttagcata aaagccaggt ttgtttgtaa ggcttagact gagtcatttc 216720
taccccggat tataatctca gcactgtatt tgtcagtttg ttgtttgcct gctttgaagg 216780
tatgtggatg aagcacttga tttaggaatg aggacctgtg ggatttaatc cctgttttag 216840
aagattagag tcagcattgg ttcacatatc aaagtttaat aaaacttttc cacttgactt 216900
tataacatct gtcacaacaa ccaacatatt tattttagtt ttggggctaa catctccagc 216960
atccctacaa atacaaatca ttttaggcat gggcttgaat ttatcttcac tgagctgagc 217020
catcttctca gtgacctaaa agctttgacc caggtatttt gttttgctgc ttcatcagtg 217080
atttattcat ccacccttta cttcatccta ggaattcaaa ccacaaagaa tgctgatgtt 217140
gcttacaaga cattttgtcc cagtgcattt gtttgctttc tcctggcttg atttgacctt 217200
ttatctctcc ctcttccccc acctctttgt ttgctactgt gtttatttca cccttcatta 217260
ccatctttct ttagatgact tattcattct tccatttatt cacctgcttt tgttaagtat 217320
ctactctgtg ctaggttatg gtgatgagca aggttaaaaa aaaaacaaaa aaccatgatc 217380
actgatcttg aaggcttcta gaatatttta agagatacaa cctagttaaa gaaaaaataa 217440
tggcatgttt taagtgcaac aagagcagta gtcacaggat gcaatggaaa cataggaaag 217500
cttctggctc agctaggaga ggttagagaa acattcaaaa aagaggcagg tcctactcag 217560
agtgttgaag gacttgtgag aatttatcag gcaaggagga gtggagatga ggaaggaggt 217620
taatggagca ttccaactat aaggataaca tgagttacat tacagagatc caatgaatca 217680
caaagtattt tattgagtcc acctacgtgt caggcagtgt actaagcact gttcatgcag 217740
agggccagtt tggagtaatg aaactccaaa gtttgattag aataggctta ggagaaaacg 217800
gggaaggaga aattggagac aatgagtata gagaagtgtg tcaagatttg atctaaagag 217860
aagatactaa gagagaagat acaagatctg gagaggtttt tgttctattt tgtttgttaa 217920
tggaaaaaaa agtatatcaa ggttgttttc taatgagagt aattcagttg aaagaaatat 217980
taataatgca ggagggtgag gagaattact ggcacaatat tcttttatag aagaggggat 218040
gcagaccagg cgtagtggct cacacctata ttcccagcat ttggcaaggc caaggtagaa 218100
ggatggcttg aggccaggag tttgagacca gccaagacaa catagcaagt ccttgtttct 218160
ataaaaatta agaaaaattt ttttaaagat cagctgggca tagtgatgca cacctgtaat 218220
cctagctact tgagaggctg aagcaggcaa atcacttaag cccaggagtt cgaggctgca 218280
gtcagccata attgcatgcc accccactct agcctgagca acagagtgag accttgtctc 218340
taatatgtat atatacagat ataatatata atatataaaa tacattctat ataaaatata 218400
tattatatat tatataaata aaatattata tataaaatat atattatata aataaaacat 218460
tatatataaa atatatattt tatatatata taatataaag aagaggggat acagtccagt 218520
gcaaagtgga aaggttggct aagtgggatc ataaatagtt atccatcata acaagcaaga 218580
aagaagtatg tatattattg ggagctcttt tttctaagta aaataggaag cacttatcag 218640
ctcggagtta ccatggagag actgcattga tagtttgagg aaagagaaga tatgagattt 218700
taaaagctaa catatgtcaa atatttatca catgccaggc accattcatg ggaatcaact 218760
tttatccctg tccaagaaca tggttcactt gagaaacttc atgcatgtgc agctttaagt 218820
gacctagtgt cagtgtctta gactagagag gttggggctg gatcatgaag ggtcttgtaa 218880
gccatactta gtttagactt tatgtgcagt gaataaatgg agggagcaca tggaggaaat 218940
tgttctgcag aattttaaat aaaaagagtg atatgatcag ttttacattt gggacagata 219000
actgaaaata ttatgaaaaa ggtcctggag aaagggagaa tgttggaggc aaagaatcca 219060
gagaaaagct gagtagggtt taagctaagg ttaattgcag ggagaatgta gaagaaatat 219120
ttaggcagta aaatgcttag gaccagtctg gacaacaaag cgagaccctg tctctactta 219180
aaagaaaaaa aaaaaaaatt agccaagcat tgagggctgc acctatattc ctggctactt 219240
gggaggctga agcaggagga ttccttgagc ccaggagttt gaggctgcag tgagcagcct 219300
gggcgaaaag agcaagaccc tgcctcttaa aaaaaaaaaa aaaaaggaag tgacatgctg 219360
attaaagtta ggagccagtc tcaaatgaca tctactttta tgctctgttt tgaaaggtaa 219420
tatcttatct agtaccaaga ataaaacaca aaaccacctt ttaaggaaaa atgagttcgg 219480
ttggatgact tagctccagt tggctataat ataacttgaa attgagaaat atatttagca 219540
ttctcataat taaagatggc attgttgact gacaagttga aaatagaaaa ttattcatat 219600
attacatttt attaaaaaat attattaaag cattctcatg attttgcact caatttagga 219660
aggattaggt ctgctatatc tcccactttg ttattctctc aaacttctgt acctgtagta 219720
tatctcatta cttaagctga acaaaacgtt catttttttgt aatcagactt ctcatcctta 219780
tcatcagatt gtctttcctc ctttggttta tttaagaagt gtgcatcagc agcagccgtt 219840
atgtcttatg atggcataat ttcaagtgtt ctaggggcct aagaagttat ccagctctca 219900
ttttgagatg agagaattct tgctgacttg cccaaagtca tagctggcaa atctaggact 219960
tgaacatgag agtctgtatt gggggaaccc gcccccaata tttcaacgta ggttctttct 220020
attttcccta agcattggcc agtctgagaa aaaaagagaa agagtacaaa gaggaatttt 220080
acagctgggc ctctggcggt gacatcacat attggtagga ccgtgatgtc ctctgagcca 220140
caaaaccagc aggtttttat taagcaggtt tttatcaaaa agggagggga tgcaagaaca 220200
gggagtaggt cacaaagatc acatgcctta aagggcaaaa agatcacaag gcaaagggca 220260
aagcaaagat cacaaggcag agggcaaaat taaaattact gatgagggtc tatgttcagc 220320
tgtgcacgta ttgtcttgat aaacatctta acagaaaaca gggttcaaga gcagagaacc 220380
gatctgacct caatttcacc agggtggggt tttttccccg ccttctgagc ctgagggtac 220440
tgcaggagac cagggcgtat ttcagtcctt atctcaaccg aataagacag acactcccag 220500
agcagccgtt tatagacctc cccccaggaa tgcaattctt ttcttagggt cttaatattt 220560
aatattcctt gctaggagaa gaatttagtg atatctctcc tacttgcaca tctgtttata 220620
ggctctctgt aagaagaaaa atgtggctct attctgccta accccgcagg cagtcagacc 220680
ttatggttgt cttcccttgt tccttgaaaa tcgctgttgt tctgttcatt ttcaaggtgc 220740
actgatttca tgttgttcaa acacacatgt tttacaatca atttgtacaa taatggtcct 220800
gaggtgacgt acattctcag cttacaaaga taacaggatt aagagattaa agtaaagaca 220860
ggcataagaa actgtaagag tattatttgg gaactgataa atgtccatga aatcttcaca 220920
atttatgttc agagattgca gtaaaaacag gtgtaagaaa ttataaaagt attaatttgg 220980
ggaactgata aatgtccatg aaatcttcac aatttatgtt cctctgccac ggttccagcc 221040
agtccctcca ttcaggatct ctgactttcc gcaacaagtc tgctaactca ttccagtggt 221100
tttttccaac tgcatctcag ttatcttaca tagactgcaa gaagtgagaa agacaagagg 221160
ttatctagtc cagccttgct attttatagt ttaaatccct caaccacatc cctgatgaac 221220
ttttgccagg ccggtaatta acaatatcac aaggctgttc tgattgtctg tatttctcag 221280
tgtttgttag agcagggatg tccaaccccc aggccacaga ccaatactgg tccaaggcct 221340
gttaggaacc cagctgtaca gcaggaggag agcattactg tctcagctct acttcctgtc 221400
agatcagctg cggcattaga ttctcataag agtgcaaacc ctagtatgaa ctgtgcatgc 221460
aagggatcta ggttgagagc tcctcatgag aatctaatgc ctgatgatct gaggtggagc 221520
agttccatct tgagactatt tccccaaccc cccatcatat ggaaaaattg tctcccaaga 221580
aaccagtccc tggtcccaga aagttagggg accattgtgt tagagaacta aggaaaccgt 221640
cctctacctg ccacataaga ataaaggaaa caatggaaca gtttccctac tttccctaat 221700
taacacgtat tcccattttg aggcagtgag ttgctggtac ctgctttctc cttctttctc 221760
caaatagtac tttaaaagta tcttatcctg gctgggcaca gtggctcatg cctgtaatcc 221820
cagcactttg ggaggatgag gcgggtgaat cacgaggtcg accatcctgg ctaacacagt 221880
gaaaccccgt ctctactaaa aatacaaaaa attagctggg tgtggtggca ggcacctgta 221940
gtcccagcta ctcaggaagc tgaggcggga gaatggtgta aacctgggag gcagagcttg 222000
cagtgagctg agatcgtgcc tctgcacttt agcctgggca acagagcaag actccatctc 222060
aaaaaaaaaa aaaaaataaa gtatcttatc ctaaaagcac ttctgttttt ggtttaggtt 222120
ttagctgtct ttgtgctgcg taagcgttgt ctctttctca ggatgtcact tctggaggca 222180
ggaaagggtt atggttaatg ctaatcactt tatcaaaatg tctgatttct ctgatgtata 222240
attaatattt ttcccttgca actaataagc aacttgtggg agtaagattt ttacttttaa 222300
aagcatatcc aaccttcttg tgtctcaagt taatgctcgg gaagcaatac ctgtctctta 222360
tattttgaag ttattctttc taaggcctaa gatatatacc catcaaatta tgctcagaat 222420
ttttgtctca gccatcacaa accctgaaat gatacgcttt tcctaagtgt tattttcctt 222480
aaccatattt actagagatt tggaatatat tcaataatat gctatgagta tgttttcttc 222540
aagttcaatt atgtgtagat gtcatttaga gaaacagtat attttggggg gaatccactt 222600
tatgtgtccc atcttctttc cacattcaga tcatgtggat taatgtcata gtctagtaaa 222660
aagcttgttt ctattttatc cttaagttta aaatgttgtt ctttcattct attagcatga 222720
ttcttttagt atactaacat ttatgtaaat aagtcttaca taaatacagt tatataaaca 222780
aatctttagt ctaattcttt tagtatacca acatttatgt aaataaatct tagtttctgt 222840
tccacgtcct aagctgcttt accattcaca taattccata ttcctcctaa gtttactaca 222900
aagaagaata ttagatgtat tgattatgca gtgatactgc atctaaagct gtcagtcaag 222960
aatggctgcc atagctaaga gtatatacaa atcatcactg ttactttatt ttattttttt 223020
aattttatgt atttatttat ttttttgaga caatttcact ctgtcgccca cactggagta 223080
cagtggtgca atctaggctc actgcaacct ccctctccca ggctctagtg atcctcccac 223140
ctctgcctcc tgagtagtga ggactggagg cgagtgtccc cacacctgcc taatttttgt 223200
atttttttgt ggaaatgggg tttcaccatg ttgcctaagc tggtctcaaa ctcctgggct 223260
caagcaattt gattgccttg gcctaccaaa gtgctaggat aacggacttg agccactgtg 223320
cctagtcctg tcactttctg aaaaatccta tgaagcatta atagaagtaa aatcacactt 223380
aattatgcct gtttttaaat ctgcatattg tttgattaat cacatctttt ggccaagttg 223440
aaggcataat ttatatattg tctataagaa tcaataaact agtttctaaa tatgttttaa 223500
ataaataatt taaaaattaa tttctcaaat atcctcaact ataaagttag acctatttac 223560
tgtttcttgt aggagcctat tgctgtcaaa aatatctgaa gttctattca gagaaaaata 223620
gaaatgcaca atgactggga cttaagctga ggaaagtcag caacactgtt cccatcattc 223680
taccataaat gtggcaaaat cttattgttt gtgacagatc tatagaatta gattttctta 223740
tatctaaaga aatatatata aatacataaa cgtaggtatg tatagcatga acagaataca 223800
gtgctatttg accattgtca caagacttat ttataaaacc tcctcaagct cttgccaata 223860
tcttagttaa gattgcatct aaggtgggag gaggatgaag attgaagaac tgtcaggtaa 223920
tgcttgatta cctgggtgac aaaattatgt ttacaccaaa cccccatgac acacagttta 223980
cccatgtaac aaacctacac atgtccccct tgaacctaaa ataaaagttg gaaagaaaaa 224040
aattggaaag aaaaaaaagg aacttaaaga gaagaaaaag attgtatcta gtagttttac 224100
taagactata aaatttctga cggctccact acctcctcaa gattgagaac taaacaacat 224160

-continued gagaagcaca attacatgcc aaagattctt tttgctgtct tcatttgtag catcccagtg 224220
gaatgtcttt gaaaaaaatt ttttttatct gtattatctc acctgctctg agtattggtg 224280
acagtgatat atgcattgtg attagacgcc tagcctcctg aatataatgt atttccagta 224340
tattgtcctt ctgaatagcc tgtttacaat tctttgaaca ttgcctgcca ataatttagc 224400
aaattgttat tgaatgtcac agcttgatta tagaacatag taagaaatca acaaattgaa 224460
caccaaactg aatttaatgc taaaaattat ccttttaaaa aataatgtat tactaatttt 224520
tactcatgaa atttaacatt tccaatcatt gcttagttgt tgactcaaca ctcaaaaata 224580
atatatgcta cttttaaaat cccaaaacct ccagatttgt gtactgccac caggtgttga 224640
caggtgcctt gattcttcta gtttgtggtt ccagagataa ggtcagggtc ctgatacagc 224700
aaaaccacca tttgtctttg ttaaactgaa atgagaatgc gttccttatt ggaaagaaaa 224760
gttacacggt tttattatta tcatcagtac ttagagaaga cttaaaaagt acaacttaaa 224820
atgaactcaa agtttctgtg actaggaaat gatatgactc agggaattta atacttggga 224880
tccaaaacaa agaaaacaaa atgacccata aagaaccatg ttgtttatga gggcaaacta 224940
tagtaagcaa acaatattaa cttcaaatga gcactggaga aaaatcctga ttctttaaaa 225000
ttgtttttaa tattattctc ttaaacttag tgatacccaa aaaagaatca aaattttgtg 225060
gagaggaata taataactgg ttgtcttatc tgtattaaca ggattttgta aaagcattat 225120
tatttctgtc aattgatttt taaaacatct atcaactttt tttcttttgt gtatagatat 225180
caatgtatct catagattgc ttcccttttt taaattaaaa agtataaatc tttataaaaa 225240
ttaactataa ctttatgaaa gtatgtttaa acttgagcag attttgtaaa aatttaatgt 225300
gtagaacatg tgttgttttc agcaacagct taatttcttt agtcacttaa cctttttttag 225360
acttttgttt ttaaaaatat ttcttttttt cactctgaat catacctagg aatcaagtct 225420
ctctagcctt tgtaatatat tgaaaagact tgaaggccat tttgccttca aactttttttc 225480
caggagtttg tccttaaacc tctaacatct tataagtttc ctcatagttt ttcacatttc 225540
tgttttatgt gtgcttccaa ttaagatggt attcttctga tttcctattc ctgtgtcttc 225600
ctgctatgtg gagtcttcac agatttttag cagccaggcc aggagattgt attccttcct 225660
atattggcag gttggattcc ccctgaatta actcttccat tcagaggctg ccaccgttct 225720
agttcgtgtc ttgaagaatt gtatcaccct cctaactgat attttaacaa tagctgcaaa 225780
ctccttatta tatgacactt aaatagcata agagctcctt ttgcagcacc tgacatcttt 225840
tgaggtttat agatttgttc aaaatgaagg atgtacaaaa atattaaaaa tttaactttt 225900
taaaacttag attaagatgg ctttatgcca tggtatgttg ctatctactc ctcccattgt 225960
ctcttgagcc cactgcattc cagctttagt ccctatcctc ggaaactgct gtagtcagtc 226020
tgtgactttt gtgttgccaa attcagttgt cggttctaag gtgtcagttt tacttaatct 226080
gtcagcagta tttgacagag ttggtctttc ttcctagaaa cacattcatt tgcctgccgg 226140
atatttcctg ccttactggc tgctgaattc tagtctcctt tctacatcct catctatttg 226200
gtcatctaga aatgtcctag ggctttggcc tcttctaggc gtcactccca aagtggtatt 226260
ctgcagtcat ggagaatgac acatctgtag gcatatgact cccaagtttc tcagcacctg 226320
atgtgatgta tacttatttg ttcattccct ctctcctttc tcctaaatat aaactctgtg 226380
agaataggga ctttgttcct gttcaccact gtgtctgcaa tgcatagaac agtatctaac 226440
acgtaatata tactcatact ttacattgaa tgatttctta atttatgggt cattcatcat 226500
taatcttgat cataataatg aatcagccga aaacagcact ttttttaaga aaagtgtgtg 226560

-continued

```
ttatgtctag tttatttcaa taatactaag acaactatct ccttactacc tgaatttatt 226620
tcagcacaac cgattaattt taattgctat gagttaaaaa ctttaaatac agtgagtttt 226680
tttaaattca gatagagatg ttttttagct tactgctttt aaaagactgc aatttaaagg 226740
ttctgttaat tcttcaaaaa aagataaatt aagtgcttca ttttcctgca tagtaaatca 226800
ttgacgttcc taacattttt tcaataactt ataaattttc tttgctttgt ttgtgttgtg 226860
acacgttgtg taaatgagat ttgatatcag aagtaggatc tacaaaacaa acactaaata 226920
ctggggttag tactaacgtt ttcactgaag atggacccag aaaagtagcc aaacacagtg 226980
tcaccccgag tccattctga gatacatact ggaaaattat agtaatcggt tcattcagga 227040
aaccaagtga caataggtta agccatgagt aatataagta atataagtaa catttcttta 227100
tcttccacta ttaaaaaaaa acttgtaaat ctttatttaa atgaacacca aattaaagaa 227160
aactgagcca aagaaatgta agtctaaaat gaaatgctca attttgattt atcagagata 227220
taagccttac taagttttaa gttaacaaat ttggacctta acacatatta atctaaatta 227280
attaattcga cctttgtttt cagttttaga gaaatgtaaa cttgttcaaa aatatagcag 227340
aatataaact atttaaaata acagtttata cttgcatacc atttgaaatg ctttgttttt 227400
gcttgtgttc tctgctaaat tttttttcca ttgaatctgt gctgcttctt tgccaatgtt 227460
ttccactgta gaatctccat ctcgcaacct tgcttctcgt gagcgcattt acaaaaatta 227520
tggtgtagct gggcctgcct ctgctctctc atctctgtct cacaaactga agggtgggta 227580
tacatgcatt catggatggg ccattcttaa tgaacataag gagtgtcatt aaagatgttt 227640
ccgttcgtct cagtcatgtt catgccattc catttttta attaaagttt atcattttat 227700
ttacatttat atatgtttga gtaatttatg atgctcctat tcagtattat aatatagatt 227760
atcccagtag ctatgcatgt ttattacatc tataggttaa acattactct tacttaattt 227820
taaaacttta tgagatcatt aaaattaaaa taggtataag gaaagaatta cctaattggg 227880
ggaattttg aaatcatttt tatcagaaaa agatgatata tgtgcaaggc ataaagcaca 227940
tttttagtc ttaaacttat tgttatataa tataaaaatc attttactat tttagtcttt 228000
tatgagaaac actgataatg aacttaaagt ttttaagttt aaattagtta ttaggactca 228060
tgtgtctatt tatatttata tgtaaaccta cctgtcctat ctggcataaa tttttctaat 228120
attgttttcc tagtgactaa gttttaatat tttaaactta gaaatgttta aactattgac 228180
aattgacaaa atttcagaca atttaaaaat atgtttttgg ttttttgaaa cactacagat 228240
gcctacttaa atattttgtc ttaaagtatt atttaattaa atttaaatct tgtaaatctt 228300
ttaaaatctt gtatttaaat aaaattttat caaaaagaac ttttacagca atgcctaaca 228360
tattgtataa gtttttcaac taattactga ttttcttttt ttcttagaaa tagataaaac 228420
agctatatgt ttctcattat acaattgaca gtataaacat ataaatagga aatataaaaa 228480
tatactaaat agtattgtac aacctgtgct atatagtata tagtattgtg tgtaatagca 228540
tatagtatca tgtaacctga tatatgctat atatcatgcc atgtgatata tgcatatagt 228600
attatgatat agtatgatcc tgataattta agatttgggc atgaaaaaat gtatgggtca 228660
tttagtgaat gaatgcttac catttaacat gtttagtaac atttaacttg cttgccctaa 228720
gtttctatcc tgtcattatt atttcttcag gtttccttta aagttagaaa aatgtttgca 228780
tattatcatt taaatgtaaa agtacagtca ttaaataaat taggagatga atgtgaaagt 228840
attacgtata gtctgaagat ttttagcaaa ctgtttatat ttgttggtat tttgagcagc 228900
```

cacaacatac aatttttagt aatatttaat aacatgctgc aaaacatttg aaacacaaat 228960
gaagcagata aacataaatt agcacagggg cttaccccac ttaacaagca tagttttttt 229020
taatatataa aatacgtttt ggaaaaataa atttttcaaa aagatttagt tatcatttga 229080
gaaatacatc tgaaaaagaa atatttctgc cattatttgt atgcctaaac ttcaacaggt 229140
atttagctgt caccacttac agatcttaag aaaatattca ccactattag agatataata 229200
agatatacaa atgcctattc tttctaacac tatgtaataa actttttgc tcacatatga 229260
caagtggtgt tcctggtatt tggcagattc catttttcag gcaaccacag aggttgtttt 229320
catgatgagt aaataaccta ccattgtaag ttcatatgca ttcctagaat agaggtagca 229380
tcagcaggta ttcaccattc ctttgcatgc agctgttgtg caggtcaacc actaagacac 229440
atctgacaca gggagtaggt aatctttgtc acgaaccctt cctatttgtt agaaatccta 229500
cacaagttgt cctttttat aaattagaga gaaaacctct ttcagtttac agatggattt 229560
tttggagaaa gggataccaa atataaaaga cttactaatt gtttgtctag attcccatta 229620
tgtgtggttc agtttctgaa ataaatgtga tgataaaggt gataaacatg tctccagctg 229680
tcagattaat aacaaaaaac aagtattcca aacatcacat actcaaaatt aatggccatg 229740
actactgatt taatctacca aatataattt gtttaccaaa tttgccatat gctgttacta 229800
ggtcagtaag attagatggg tagcaatttt ttgaactact tttgaacagt ttaagggtac 229860
ttattcatag atcacatctg tttatctgtg ctctcccaag acagcattga tagttagaat 229920
tctaaattgg gatttttta accctttttt caaaacttag ccccatctgt taatactgta 229980
tttataaaac agagcacata atatgataaa ggaggttaat gattgaataa tgaagctttg 230040
caagaaacta aaaagcatta tgttttagtt acttttattc atccaaagaa caggaaaaat 230100
tatcttaaat attggcatgt tgcaattaaa catttagttc atcagtgtgc cctgtataaa 230160
gtacttgcca tactctatta tttcaccatg taattactca gtttgcaagc atctaaccct 230220
tgcacatcaa taactaatgt cacctctgtc ctgtggcctt gggagcctta attgtaaaaa 230280
gtagacttct ggagaagctg aatacttggg agtagcagaa gaaaaaaatc aagaaaattg 230340
gaatatatta ctcattcaac acatatttat tgaataccta ctgtattcct ggattcattc 230400
ttggtattac atcagtgaag agtaacagac aaaaatacct gcccttgaca aagactgggg 230460
cagattctcc agcactactg tcctgagcca tagagaaata gagcgtgact atacacactt 230520
aacacatgca cggaagcata aaaaacattt tcctacatca tctgaatttg ttcacatcct 230580
tttttctttt aaaaaataat aacatgcagt tatagccagt taacaaatct accttaattt 230640
cctaggaact gtctttgaaa aaatataaat acttccagat aggtttatgg attttcagtt 230700
ttttatacca cttgaaaccc ttcagtcaga ttgcttttct cctaacaact aactggtatc 230760
acttgcacta agagtagaag tttttatttt aaggaggaaa ggtgatgttg aagtttgtac 230820
catttacttg ggtcacagac agcctggctc taatgcctca aagaaaagca taaaatagaa 230880
tgaaggagag acactgaatg aaggcagggt gctaaaaaca attaatgtcc atgcagaaac 230940
atctaatgct ttgccttaga aaagggaggt gattcttctt ttcatcctgt ttttctgtca 231000
ttctcctgac tccttgtttt gagggtccac agttcagact tttaccactc attctgagga 231060
tccaccgttt ctgtggtttc caagggaaca caggctctga gttctaagca gctaagcttc 231120
ctgaactttt ggagtgtaac ctgtttataa ataattaaat aacagcttca gggcattcat 231180
gtgctcattg taaactagtc taatctgatc ataaaacaga gtgcctctta agcaactctt 231240
tgttagccta attgtatgca tacacttaaa aattataatt gtgtctatgc ataaattcag 231300

-continued ttctctaatt caacaaaacc cataccgttg ccctaaggat gcgaggtatc actctgctgg 231360
aaatttagct ctactctaca tttaaaatac aagttttcac attaaataat ttcttattcc 231420
ccaaaagatt aatttctgtc tctttctagt ccctcactga atttaaattc taactagtta 231480
ttgcactagg gcagaggttg agatatcact gatagttcac actggatttg ttcaacctgt 231540
tgttttgcgt ccatgaaaat agtttttggt ggtaatgttg tgtaatgatg tgtagaaatt 231600
ttattagaaa tatttccccc ttctttcctt tattcttcaa gtattttagt atgtatgaca 231660
aacaatataa attttgtagc tatgtttttt tatttcagtg tttagtggct aaattatcag 231720
taagttataa ttttattaat aagtttcact gtaaaatgga ccatacaggt gatcgaggaa 231780
acatctcaac atcttctaaa ccagcctcta catcaggaaa atcagagctg tcctctaaac 231840
acagcagatc gcttaaacct gatggacgta tgagccggac tactgctgat cagaagaagc 231900
caaggggcac agaaagttta tctgctagtg aatccctcat cttaaaatct gatgctgcaa 231960
agttgaggtc agattcccac agtaggtcat tatcccccaa ccataacacc ttgcagacat 232020
tgaaatctga tgggaggatg ccttctagct ccagagctga atccccagga ccaggttctc 232080
ggttgtcatc tcctaagcca aagactctcc cagccaatag gtctagccca tcgggtgcta 232140
gttctccacg ctcctcctca ccacatgata aaaatctacc tcaaaaaagt actgctcctg 232200
ttaagacaaa gcttgatcct cctcgggaac gttctaaatc agactcttac acacttgatc 232260
cagataccct ccgcaagaag aaaatgcccc tcacagaacc tttgagagga cggtcaacgt 232320
caccaaaacc aaaatcagta ccaaaggatt ctacagattc ccctggatct gaaaatagag 232380
ctccctctcc ccatgtggta caggaaaacc tccacagtga ggtggtcgaa gtctgcacct 232440
caagtacttt aaaaacaaat agtctaacag acagcacctg cgatgacagc agtgaattta 232500
agagtgtgga tgaaggttca aataaagttc attttagcat tggaaaagca ccactgaaag 232560
atgaacagga aatgagagca tctcccaaaa taagtcgaaa atgtgctaat agacacacca 232620
ggcccaaaaa agaaaaatcg agttttcttt tcaaaggaga tggatccaag cctttagagc 232680
cagccaagca agccatgtct ccttctgtgg ccgaatgtgc cagagctgtg tttgcttcct 232740
tcctctggca tgaaggcata gtacatgatg caatggcttg ttcttctttc ctaaagtttc 232800
atcctgaact ttccaaagaa catgctccta taaggagtag tttaaatagc caacaaccta 232860
cagaggaaaa agaaaccaag ttaaaaaata gacattcatt agaaatatca tctgcactga 232920
atatgtttaa tattgcaccc catggaccag atatatctaa gatgggtagc atcaacaaaa 232980
acaaggtatt gtctatgctt aaggaaccac ctctgcatga aaaatgtgag gatgggaaaa 233040
ccgagaccac ttttgaaatg tccatgcata acacaatgaa gtctaagtct cctcttccct 233100
taactttaca acatttagtg gctttttggg aagacatctc tttggctact atcaaagctg 233160
cttcccagaa tatgattttt ccaagtcctg gttcctgtgc agttcttaaa aagaaagagt 233220
gtgagaaaga gaataagaag tccaaaaagg aaaaaaagaa aaaagaaaag gcagaagtta 233280
ggcccagggg taatttgttt ggagagatgg cccagctggc agtaggagga ccagagaaag 233340
ataccatctg tgaactgtgt ggggagtcac atccataccc ggtgacctat cacatgagac 233400
aagctcaccc aggtaaatga tactgttgaa tgtacgtata agtgcttttt tctttaatga 233460
accagatcac tttatttgag ctgttctatg aattttgtca aaggataggg aatttatagt 233520
atcttagaat gtcattttta aagtacatta tcagtacagg gttttgtgaa aaacagataa 233580
attctaatat tatgatggcc aggtcattta gtgctatttc actttcatgt agcatgtttt 233640

-continued aaaaaatatt atgtgttacc caaagggtgt gccattaatg tgtctgtctc acacagcaga 233700
aacagtggca tgcccataca cacagggcat ctcctttgat tttactattt tcctgttcag 233760
aattgcaaat taaattagat tagattgatt tctataggct ttttcctacg gaagtgatat 233820
tgttttatca gaagactgca ttttcagtaa atgtaatgat ttctgtaaca ttgactaata 233880
ttccaaattc acctaataca aatttggtta attttttttct ttgtctacat attatacctc 233940
aaatgtctta tgaatatgtg atttctgaaa atatatcatt gttatagaac ttttatactt 234000
gtattgtcta attttattga cataattaag tatatctaaa tatacctata ttctatctct 234060
cttttaatat gcctgattag aaactaagta tctctcatat ttggggcatc atttaattga 234120
ttgcttttttg atcaagtaag ctatttttct gatatagtta atagcctgaa aaataagata 234180
tctacttcag tattttgctt tctttgagaa ggtaaatctg tcattaatgt atgagtaata 234240
aggatcaaac tattaaggac acttggagtg ttaaatattt atttttggta ttgtttcaag 234300
gttgtggccg atatgctggt ggacaaggtt acaatagcat tgggcatttt tgtggaggat 234360
gggctggtaa ctgtggtgat ggtggcatag gaggaagcac ttggtatctg gtatgtgatc 234420
gctgtagaga aaaatacctc cgcgaaaaac aggctgctgc aagggagaag gtattttatt 234480
ccatttggag ctatactttt aatgatatgg atacactgta taaaaaatacc ttgttataat 234540
cttactacat cagataattc cacatagttg atattaaaag atcagctttt ataatggaaa 234600
tcatatacaa atttaatatt tgtactaagt caaatgcttt taattttaaa aattaactat 234660
atattggaat aacactagat aacctctgct acatatgcct tattgacaaa tatttgttgt 234720
gtaactcttt attattaatt gtctgttatt ctctctatgg agagctttcc ttttcacctt 234780
ctttctcttt tcctcttttt ttggctcctt tgtttcccta ttccatatct actctctctt 234840
ttctttattc actctagtgg cacctaacta aaaaatttca ctgaatacac gcactgaaat 234900
gatttacttt ttaaaaaaat gaattacatt tagatttaac tagttaggtg ttaaattttt 234960
ctgaagaagg aaaggaagta tagtttgtgt ttgatacaaa attgtcttgg tcagcccagg 235020
atgaatatga aatgaatgtt gttttttata atcttattat cttaaaatag ctttacaagt 235080
gtttaataat ttttattgga aactcaaaat acttagctta agaaactaag gattttaatg 235140
taagtcagaa aagattagtt tgattttttt cttcgccagg tcaaacaatc taggagaaaa 235200
ccaatgcaag tcaagacccc tcgtgccttg cccaccatgg aagctcacca ggtgattaaa 235260
gccaatgcac tcttcctgct gtccctgagc agtgcagcag aaccgagcat tctgtgttac 235320
catcctgcaa agccattcca atctcagttg cccagtgtaa aagaaggcat ttctgaggat 235380
cttcctgtga aaatgccttg tctctacctg cagacattag ctaggtaata aaattttgct 235440
gttgtttttt aatcaccttt ggattaacag cgattgttta ttgatatcta gggtagttcg 235500
gtatttgacc tacactttat tagctattgt gtactataaa caaacttcca ggcatttatt 235560
ttttgagttg ccttgactga cataatgact ttatggtaat aggtatttaa aaaactataa 235620
aaatgcttca tcaatttgca ttgtattaat acacaacatg tcttagaaaa taagactata 235680
gctatctttt actctttggt aggctgactt cactctgtta gtgcgaaatg ctgaagtgta 235740
aagaaagtgt gtttccttag cagtctttta tttcgtaaat tattcattct gttagcattt 235800
aaatgaatac caactgggca cctaccagcc ttgtgctagg ccctgaatgt atgaatataa 235860
caaaatcctg gcttctatgt actcatactc ggatgtcaag tcagacatgt tagtgaaaca 235920
tttgaaatgc catgtgagga gtgctacaat agaagtatgt atgtaagatg ctgttagagc 235980
ataaaagatg gagagtatct gaatcttccc caggaaatca gaaaaggctt cccagagggt 236040
ctgagccttt agtagagtct caaaggataa atagaaatct gtcaggcaag cgacaggaag 236100
aaagcgactc ttggaagaat aacccaggtg agtaaagaca caaatgaaat ctcattacac 236160
atttcaggaa tcacgggttg ttaaaggact ggctactgga ggaaatatgt gaaagcccgt 236220
tcaaagtgat tggttcaccc aagtaatgtc gggctctgta gcccaggtta agattgcatt 236280
ttatcccatg agcagaggaa acagtggaag aattttaaac agagaaatac atgaactggt 236340
ttgcaattaa aaaatcactg tggaatgtgg aagctaatgt ggagactaga taaaagtgca 236400
ttactggaga tagaaacctg ttagtattct gttttcatat attggacctc agtggtgcag 236460
cctgtacttt cacacatcat gcactgacac tccaaaagag cctttcatat accaaaacca 236520
aattttttc atcagctgac aaatgaaggt aatctagata ttgcccactg acatggcttg 236580
ccgaccaaca gttccatttt ggaaattgtc ctctttgtgt agcagagttg tatggttttt 236640
aaaattttgt gcttactatt acaataaaat gaataagcaa caaaaatgaa aatatcagac 236700
taagtacatt tgagactgag gtggaaatca tcagtatgcc aaaatacaat agatctttag 236760
tgtgaatcac accactcagt ggacttaggt tagcaactat ttgttcattt tgaaaaggaa 236820
agaatcaaat tgtaaaacgt gaaaaatgct aacacagcat aattatagat tttttctttt 236880
ttagctgtct ggggaatggg cacccccttcc accctgaacc acagaaaatt tcatatatct 236940
aatattttc aaatatgatc ttatgtatgt tcctacccaa aaaagtaact gcttgtattt 237000
cagtggtctg tgcaagaaat aataagcatg aaccaaggca gtgatgatag ggaatgagaa 237060
gagagaatgg ctctgagagg aaacctaata tcatgggctt gaaagatgat gatgatagag 237120
ggctaagcct actacaacac tggaaatatt ttagcttaag caactggatg gttggtgggc 237180
ttattcacca aaacactgga agatggaaaa gttctcaaaa ggaaagaaac tgagttcaat 237240
tttggatttg aaatgttcgt ggtacctgga atgttgatga ataaaattat cagactttta 237300
ttttcaccta cctacatcta cgattatttt aatgctttgc ctttaactat gatttacatg 237360
tgctgctttt cctgttatga aagagattaa aaatggagag gatctgtatt gccatcatgc 237420
tttaagttat tgggtttgat ttaatgcagg catcatcatg aaaattttgt gggctatcaa 237480
gatgacaatc tattccagga tgaaatgaga tatctacgtt caacatctgt acctgccccg 237540
tatatatcag taactcctga tgcaagtcct aatgtatttg aagagccaga gagcaatatg 237600
aagtctatgc caccaaggta ttttagttct ctcctgtctg ttgaatagct agtgtttggt 237660
ggaagaaaga ctttgaacta gaaaagagtc ctgtagaagt tctttaatac atctgtgagc 237720
cagttttgct aactgctgga gcagtaagaa aaagcataca tgtatgacta aggtaaggtc 237780
cttgatggga gaggcagact agttggagag aagagatcaa ctagtgaagg aattaaagat 237840
tacattatat gacattactt aatgctgtag taaatcagag tagggaaggg ttactttgag 237900
ttttcatggg agcagtggca ttgaaaataa atcttaaact tcttggatta ttgtttacag 237960
tgcctcctaa cttaggtatg gtagtatcag agtaaagagc ttctcggaaa gctgaataga 238020
aacttgttac aataatgtaa tacacaagaa aatagaggcc aggcgctgtg gctcacacct 238080
gtaatcccag cactttggga ggccaaggcg ggtggatcac ctgaggtcag gagtttgaga 238140
ccagcctgac caacatggtg aaaccctgtc tttactaaaa atacaaaaaa ttagccgagc 238200
atggtgacac acacctgtaa tcccagctac tcgggaggct gaggcaggag aattacttga 238260
acctgggagg cagaggttgc agtgagctga gattgcacca ctgaactcca gcttgaggaa 238320
aaaaaaaaat agagtaccac tgaaactttt ttagaggacg aatgatgtga taaaaatgca 238380

-continued

```
aaggtagtct cacagtgaca attgagaagc tgacatatgg attaaagaga tatattttgt 238440
aggaaaaata agtgtgactt gttgactaac tggataatga aaaagataag tttaagatga 238500
catgaagatt tcagtcacga ataactgtga acatggtatc attggaaagg aagacatttg 238560
ctgaatgaaa agagaatgtg cttattaaaa gagcatgcca ctgtgttact actatacaac 238620
tataattata aactaatata ataaatactt taatgagcgc aatgggacat atatatccaa 238680
atgaggtttt tttttttttt cattaaaaat acatgcaact tctcccctcc ccaactgtgt 238740
ggattactcg tcagaatttc tttgaagctg ctcttgacat tttctccaga gtgcagtgca 238800
acctttttata tctttaaaag tgataaagta tttctaaagg agatacactt tttaaaagag 238860
ttagaaactg ttttgaggct agtctgacaa gtgtgattct cattgggtta ctattacccc 238920
ttaggatcaa aatccaggag gctgaggcaa gaggatggct tcagcctagg attttgaggt 238980
tacagtgagc tacgattgtg tcactgcact tcagcctagg tgacagagca agaccccttc 239040
tatttaaaaa aaaaaagttg atgaataaat gaattcatta aatcagtggt tctcaattga 239100
gggtgatatt tgcctctctg ttgacatctg gaaatatttg gaaataactt tgtcacaact 239160
gggctagttg agtgggcatc ctagtgagtt gaggccaggg atgttgctaa ccatcctaca 239220
ggaggcaaga cagcctaaca aggaattacc tggctcaggg tagccattca attaaagatg 239280
tcatctttgc tttcttcttt ggattttctt gtgttgcttg aattctttca caagcaattt 239340
tttttttttt ttggtaaaaa gtcacttttt aaatttgtgt aatttttttt aagttagtag 239400
aaaacttcct ctgaaaacag aacaaatgtc tgtgctttat agtaacacca tatataaagt 239460
gaattaagtt aatgtttccc tgtattctag tcattctgga accaagcaac ctatactaac 239520
acccagggac atttactgcc aatcagttat gtacagtatt tatagtctat tcaaacaaga 239580
atgtacataa gcttagagaa gtggtgagta aagaaaacac ctaggcagtt agccgtctat 239640
tagaaaatag ataattttac caagggacac aggatttcaa acctggcttg aatgatggaa 239700
aaaactccag aaccaacggt gagcaaaaat attccaattt gaattcaggt gacagaaaaa 239760
ggagctcacg aaaagaatag tttctaaatt tgttttagag aaataagaaa gagaagggat 239820
ttctcttttt ttataaaatg tgtcaataaa ggaaattgta tagctctctt aataactttg 239880
taagtatttt taaatgttgc tttaataaat agaaaagctg ttagtttact taagcctgaa 239940
taaaaccatt aagttctttt atagagtgta aatacaacac tggtgccaaa aatcagtttg 240000
ttacctctca tgacaccttg atgcagccat cctccaaggg ctttgggcaa catttcccaa 240060
gagtgagaaa cctcacagaa cactgaagac accaaaagaa aactttggaa ccaaattttg 240120
cttcctgttt tattaggttt tcatgtgtac atatccattt tctttctatt tggtgcactt 240180
acgattatat ctgactgttt ttcctgaata ttatgataca tgaattccac cccagtgctt 240240
ttgattctaa aaggagcttg gaaacctttc ttctttttca tttaaaatac aaagtagatt 240300
taagaaaacc ataagtttta aggtacaatg ctgaaatcag tcaaaatgtt actgcatttg 240360
aaaagatcaa attatgattt aaagagagat tatcaatttg gctttgattt tgtttctcca 240420
catgaaatat tgagtcacat attttgcatc attataagta tagttacatt tcattcagct 240480
cttctgagtt tgtatctgtt gcattgttcc atgtacagtt tagaaaccag tcccataact 240540
gatactgatc ttgcaaagag aactgtcttc caaagatcat actcagttgt tgcttccgaa 240600
tatgataaac aacactccat tttacctgca cgagttaaag ctattcctag aagaagagtt 240660
aacagtggag acactggtaa gtatgaggat aaaaaagaat attgagtgat ctgactacta 240720
caaataaaaa aattgtttta tttgcatata atttttaaaa tttaattttt gaaggaaaag 240780
```

-continued gcatgggata atttctaatg tgtgattgac attccttcta tatgacatag ctataaatgt 240840
gcatctctaa attttgcatc ttagttgaag ggaaatctgg agatcattca gtgattgttc 240900
gagaataaat tgacctttac aatcttactt gttaggtatc taagccaaat gttacaacca 240960
ttatcccttc cactaaactt ttgtggacca ggagttccaa tgacgtacac attcacagtt 241020
atctctccac cccaactgaa gcttgataac tcttggagct gccatcattc taagtagata 241080
ataaaacttt ggggatataa atagccctta atcgatttaa aaaaaaaaaa aaaacagtta 241140
catgatctgg accagttggt atcaacagcc ccaaattgga gctggggatt ctacctcaag 241200
aataatttta aaaacccaag aagaacaggg taatatagtg atcaattatc agagagatca 241260
cttgctaaaa tgaagatttg gcctaaaaat tatagtcaga tgattaagtt atcttactga 241320
agacttttaa gaaaaacatt attgaagatt gtccagcaat ttataggttc attcaacaaa 241380
tatttttgac ctcctgttaa gaaatgtttc ttataaagcc atcttttaga aaatgatgca 241440
gatgagatgt agatttcatt tagagaaaat ataaatcact tagcttttag agtgttttag 241500
aaaaggtgaa ctttagattc agctctgatt caaaacccac ctctacaact taatagctat 241560
atgactttca gagagtaaca tatttaatct ttctgaacct tggtttcctc agtaaaagtt 241620
gaaattgtta tgatttgtgt catgttcaaa aaaccaatga caaaggcttt aagtgaatat 241680
attagatatt attatcttaa atatatatgc actgcctatg aaaattaata attttctttt 241740
tctttaatag aagttggttc ttccctttttg agacatccgt ctcctgagct ttctcggcta 241800
atctcagccc acagctctct ttctaaagga gaacgaaatt tccagtggcc agttttagct 241860
tttgttatac aacatcatga tctagaaggt cttgaaatag caatgaaaca ggccctaagg 241920
aaatctgctt gtcgagtttt tgctatggag gtatgaagac attaatgaaa ttactgattc 241980
attgattata caaatcatgt gatgattcta tttcacgatg ccactttttt accaacagaa 242040
attgtgtgaa attaaaaggc attagccaat taaaagtatt aagtgttcct ataaaaatca 242100
gactctaaag tttatgaata taaatgaatt tagaatttca tatttaagca ccctaaagaa 242160
atttatttct gtattgcttt actatttgaa tcttgagatt atcttttttt taaaagcttt 242220
ttatactcag aatgtcattt tattagaatg aaatgacaga gtaatcatgg aaagaagata 242280
aggagtaggg cttttgagtg gtaagttgac cagtaataac ttctctgggc ctttggtctc 242340
tggaaataat aggattactg tatattacag gcctatatat agtaaatctg tgtttttatc 242400
aaatgtgata aataacctac cacttcatgg atgggaatta tatgaatata tttaagtaaa 242460
tggttgcttg cctagagctt gagatacact ttgtgttcat ccagatgcaa gttggaaaaa 242520
atgtgcttga ataaattaat attaaaatga attttcaaag taaaatgtga tttgaaaaaa 242580
tattttggta ttgtatctta taaattattt ttcctgtttt ttttaaatta aaaccccaaa 242640
ttattaactg tttcaagttc cgtgtgcttt cagtgaaata aaggtcagat tttcaaggtg 242700
ccaagcatag tagcccatgc ttgtaatcct agcactttgg gaggcggagg agggaggatc 242760
acttgagcgc aagagtttga gaccagcgtg ggcaacatgt gagacctcat ttctacaaaa 242820
aaaaagtttt aaaatcagct gggtgtggtg gtacacacct gtagtcccag ctacttggga 242880
ggctgaggtg ggaggatcat ttgtgcctgg gtgcttgagg ctgcagtgag ccatgatcac 242940
accactgtac tccaacctgg gtgacagagc gagacactgt ctcttaaaaa gaaaaacaaa 243000
tagtaaaact ataaggcatt ttttttaatt aaaaaagatt ttctagtatc tttctttgaa 243060
gtcttaatcc atggaggtac tttatttctg agtactttt aaactcatgt attttattct 243120

-continued tgaactcatt taaccgtcat ttcttcaggc tttcaactgg cttctgtgta atgtcatcca 243180
aaccacttct ctccatgata ttctgtggca ttttgtggca tcactgactc ctgcaccagt 243240
ggaaccagag gaagaagagg atgaagaaaa taaaacaagc aaagaaaatt cagaacaagt 243300
aaatgaaatt tttgttttga ttgtgcatat ttttatagaa actggtagta taccttcaaa 243360
tagtccaata atttgcatga aatcattcgc agatctaact tgaaagcaaa aagaatattt 243420
tagtgctatg ggcaaagtat taataatgag acctggattt tatagaaggc agcctgtata 243480
atggagagag cattgaatta gggcactagg agcctgagtt cagcctcatt tctaccctat 243540
tgtagttgta tgacttgtag gcctcggttt ccatgtctgt aaaatgaaag taatctaggt 243600
gacatttatc ttattcccag tcactctgaa attatgtgaa tggcatttta ggttaatttc 243660
caaggatatc aagcaacatt atcatagtca aattcttaaa actcacaaac aagacaccat 243720
gagcaagaac taacaaaaac aatagacagt agaaatagac cctcaacaat ggttgtaatt 243780
atctatgtaa atgtagaata atgtgttaat atgcttaaag aaataaaaga gaaactttaa 243840
aatatgagaa gaaattgtaa gaagaaatat gaagtgatga atttgataaa gaactaaaga 243900
aaacataaat actaatctaa gtataattga tatttttagt tttgagattt tatagcatgt 243960
cagtgaaaaa attggctaaa tataagagaa tgatggattc gataaagaac taaagaaaat 244020
acgtaaaaat taatctaagt ataattgata tttaaaaaac aatcagttgg acattttata 244080
gcatgtcagc aaacaaattg gttaaatata agagacctgt agaaattatc tagacttcaa 244140
cacagaaaaa gtaaataaaa aatacaagtt gctaagagca atgaagggca aaatgatgta 244200
caacttacct acttggagtt tcagaaggag aagacagaat ggaagagaga cagtgtttaa 244260
gagttaatac ttgagaattt cccagaattg attacagata acaacccatt gagtcaagaa 244320
gcccagtaaa ccccaagcag aataaataca aatcatggtg gacaaattat agtgaatcac 244380
ctgaacacca aaaacaaaga aagagatctt ttaagcagcc acagaaaaaa atattagctt 244440
tcaaaagagg gacagtgaga ataattgctt aatttttggt agcaacatta caagttaaaa 244500
tactgagttt gtttaaaagg ctgtcagttg gttttttttca acgtgctgaa agaaaatact 244560
tgttaaccca gttgaagggt ctttgaagaa caagaccaaa gacatttcca gaataaaaac 244620
tgggagaaat ggccatggag tatcaatgaa gagaaaagaa agtgtaaata tgagggcata 244680
tcttaaaaaa cattgactat gtaaaaagta atgatatgtc atggtgatgt acaaaatgat 244740
aaaagatcaa tcctggatat gtatctacct aatactgtaa ccttaaaaaa agtaacaatt 244800
gacagactgc aaggaaaaat aggacagtct acagttacaa tgtgagattg tcatatacct 244860
gtaacagcta tctgttcctg cataactacc ccagaactca ctggactaaa acagttgttt 244920
atttgctgac agtctgtggg ttggcaattg cagcaaggct ccactgagag gaatgactct 244980
ttcctgtttt ggttacatag tgtgcttcaa gtggtacccc ctgagctctt ttatcctcca 245040
gaatgctggc ctaggtttgt tcagatgcca gaagcattca agaaagagag cacagaagct 245100
gcaaagccaa aatggcgaac actaaactca tatgccatgc ttctgccacc ttccattagc 245160
tagtataatt cacaaggccg gtcaaattca aagactgaga aataaactcc acctgttgat 245220
ggaaagagcg acagagaatt tgtggctgtt ttgtgtatag taccataaca ctctttttag 245280
tactggatag gtcaggcaga gaaaaagaat cagaaagtac acagatttga atgattgaca 245340
gtcttgatag aatatacaaa acattgcata tagttgttta cattcttttc agatacacac 245400
aaatgtctat ggaaattgac tgtttactgg acacataaag caagttttaa caaacttgaa 245460
ataattggtt ttcttcccac catgtcctca gtctttattg ctagtatata agaattagat 245520
aacaaaacaa taacaagaaa aatatttata gggaaattaa gtaacgcttc caaatgagtt 245580
gcatcaaaga agaattataa cagaaaatat tttaaatgga atggcaataa tagtacatct 245640
caaaacttgt tgtttggcag agttctagtt atagttacga tgaaacagcc agtgtcagca 245700
ttagttctta tagtaagtaa caaaaagctg ggcaaaatat ttaaaacaat tgttcatagg 245760
ctctgaggag tgaccagtac agggctgtaa tccttgagag aagaaaaggg catgaggtaa 245820
gccccacaat tgggaaaaga gcccaagcag agtacgtcag ttgtgttggc agagatcaaa 245880
gtttaggact gtaactttgg gatgtgggaa gcagggcact agtggtacag agctgcagaa 245940
agggagtcta aaatttttgc ataaaaatat ccctagggtc ctggccactc ttagactggg 246000
catgcaattt ctctggagga tctagcagtg gaaatgaatt gtaagctgag aactgaacag 246060
attcttagct tcagagctgg gttctgaagt tttagtccaa ccagaggtgg ggtgagcgtg 246120
atgaatactc ctggcatgcc cttgaaaccc cagaaagacc atactcaagg aatacagacc 246180
atgccttagg agtaagggca gtgcctaaaa tcaagggcaa aactgaaata accccagtct 246240
aacaaagtcg aatgccaagc cttgatggaa tctagatggc ctgctatctc cctgtaagaa 246300
caaaactaca ttctttagaa gacaatataa accagaactt ctatatcagt agaagataat 246360
ataaaccaga acttctatat cagtaatcaa tatatgcaca aagaaggagg caaaaagcaa 246420
ccatctttta cttagctcag tgacatagtt taaaaagttt gatgggctta cattggtagc 246480
aagatggaag aacaaacatt ctttgctgtg gagtagcagc ttcttagaga atggtttggt 246540
aagatctatc aaaattcaca ttaaaaatca ttcagtaatt ccacttttat gaagttctcc 246600
ttatcatata tgcatgtgtg aaaagacaga tatacaagtt gattcattgc agaatgttat 246660
ataaaaacaa aagattggaa acaacctaaa tgactgttct gaagtggact gatgaaataa 246720
actatggtat ttttattcat cagaatacta tgcagtggga taatatatgt tacatacata 246780
tctaataagt aataatctca aagataaatt attgttaaaa gaacacagat cagtttgttt 246840
ccagtgctgc catttgtgta aatgaacaat atttatagac agtccaagaa actggtaata 246900
gaaattgcca gtgggagggc atctaggtgg ctgggctgta gagacaggga gactttttat 246960
ggtatttttt tatacctctt gaatatttta ttatgatgtg tgttatctac tcaaaataat 247020
aaaaagttat tccatagtta atattattaa tggagccatc tgagggttgt aatgagaaat 247080
gaaattcaac ccctacttct ctttcctagc tgtggtccat ttgcgtagaa aggagctttt 247140
ttttctaatt cacataaaaa tgctgtatga gttagtgacc accccaactt ctaaacatat 247200
gttatttttt atacataaac atacacacaa aacataccta catatatgta tgtgtatata 247260
tccatacaca tacatatata tgcacacaca ctacacatac acatgcatac acatgtggat 247320
tcaccctaca ggtatctttg tgagtacact agaattgata catttattca tttgcatgct 247380
gattttgctt gtgactaaac ttacagcttt tttccctaaa ataatacaag cataattagt 247440
taaaattact gtatctttct gggtacaatt tggttttgtt gtttgtattt ctgttacatg 247500
accatttttt aagtatacat aatagtcttt tgtgaagagg attccttcca gcacacaaac 247560
tgataaactt gtttcaattt ctgccttagg agaaagatac aagagtatgt gaacatccac 247620
tctcagacat agtgattgcc ggggaagctg ctcatccttt accacacacc tttcaccgct 247680
tgctgcagac catctcagac cttatgatgt ctctccccag cggcagttca ttacagcaaa 247740
tggccctgag gtaattttgg tatccacata tcctaggtac attggacaag agagtttatg 247800
gaatattcaa agtatgaaat gctccaaaaa aagctcttta aatagtaaga tagaatccct 247860

-continued acattatata gatggtgcct ccctccttac agtcataatt tttagaatgg tccttcctct 247920
tagttaacat ttgtttgccc tcctgtaaaa tgtggctaat gtaattctta gtgccctaaa 247980
ttatcactgt agcaatctcc ctcactttcc ccagtctcct acctcaaatc acttaaatgt 248040
cccaaaaaga gagagggaaa atgaaatctc aaaaacaaaa accaaaatag agttttgact 248100
tgaaaagaat cttggggaaa acagagcctg gttgtatgca cccagtccta aaagcacctt 248160
aaggagcatc acagatgctc aacagattcc aatttcaatt tgaaatgtgt tgagaattta 248220
gcattgcttt tacactgtga accttgttac tagattcaca tactggactc acacttataa 248280
ataaattctc ctaattaatg tatacaagaa atagattgat ggaatgcttg ggcttcccat 248340
gttactaatg ataagaccag tggaagagag atttctcttt gtcctcctca caagattttt 248400
gaactacaag ataaactata ccctgatgaa ttagtatggc attgtaagag taataaattt 248460
gaggggttgt tgcagttggt gtaccacttg tttacacaat agattcatta cccttttttgc 248520
ttctgtagcc ttgatcttca tctgtctaat tcttttatat ttaaaatggg tcaactttcc 248580
ttagaattta ccttgttcca aagaagttac ctttatttct caaaaacaaa aacaatagga 248640
atgattttct tccctgaatt tttaaaatgt ctgttactag aacattaaaa tttcttgaga 248700
tattagctac agagtactca tctaagagtt ccttagatgt tcctggaaaa taattatttc 248760
gtatattgct tatatatcgc ctttttaggt gctggagtct caaattcaag caatctgatc 248820
accagttcct tcatcagagc aacgtctttc atcacattaa caatattttg tcaaagtcag 248880
atgatggcga tagtgaagag agttttagca tcagtataca gtctggcttt gaagctatga 248940
gtcaggtcag tcatttcagt tattatcctg gttgtcctgt tagttaataa tacatcaaag 249000
gagaaactgt aagttattca taatcaattt gatcctgtct tccattatgt tttatcttat 249060
acctgtttgt tttatcatca cgaaagattt gcttttaagt atcataagta cttatatttg 249120
tttctgatag gaattatgca tagtaatgtg cttaaaggac ttaaccagca ttgttgacat 249180
aaaaacttca agccgacctg ccatgattgg cagtttgaca gacggctcca cagaaacctt 249240
ttgggaatca ggagatgaag ataaaaacaa aactaagaac atcaccatca actgtgtaaa 249300
aggaatcaat gcccgctatg tgtctgttca cgtggacaat tcccgagatc ttggggtaag 249360
aaagcaaacg tgatttacgg ctctttagct cttttcagat cttagtattc atgcactttc 249420
atttctgaat ttagcaacaa gctttatcac ctggaatttc accaaccaaa catcattgct 249480
ataatcccca aataaatctt aagtctaaaa acaaattaat atgattggga gcactgtgga 249540
attccatttc tgaaaagagg tctgattaca aatataccat ggctacagct aagcaaaatg 249600
aaagtctgct ctacaatttt ctgctgccat tcccttggtt aagattttcc cgtgacctgg 249660
aagtcctccc cttaaactct gctgatcaat tcttccaggg tctctcaaac tcagcagaga 249720
aattctaagt aactcctcta aaaaattact ctttccctct gctgattctt tttgtattac 249780
tctggtggca cttaataata atctttgacc tatagtgtaa tcagcttttt ttttttttc 249840
tgagatggag tctccctctg tcacccaggc tggagtgcag tggcacaatc ttggctcact 249900
gcaaccttcg cctccaggtt caaacgattc tcctgcttca acctcctgag tagctgggat 249960
tacaagcaca cgccaccatg cttggctaat ttttgtattt ttagtagaga cagggtttca 250020
ccatgttgtc caggccggtc tcaaacccct ggcctcaagt gatctgccca cctcagcctc 250080
ccaaagtgct aggattacag acatgagcca ctgcacccag cctatcttca agtgtctact 250140
ttgccacagt cctcatgaaa taaaaaataa gtttcagact gtcccaaata atcataattt 250200
atattctctt cagcctagtt catccatgtg tttcaactga attaaatatt cttttataaa 250260
aggcactaaa caagaaaaaa gagtcctatt tgcttgagta ttaacaacca agaaagaaat 250320
agcactaact gccagactgc ctttcttcta cctcatttag aattttttttc ctcagaatgg 250380
atgtggcttg ctagcagata cagtattaat ggctctcctt gaaccattgc ctggcttctc 250440
ctgtgccatt tgcatatttc ctttctcagg aagagccaca gtggtaggat tgggtctcag 250500
ataacctgga tgcaggccag tctgcaatca gagcaacctc caactcctgt acatcagtgc 250560
aggttctatt cctccctggt attgagtaag taaaagaggc ttagctaata taatatgagc 250620
tatttcctcc tcagacctaa gaatttccac tggtgtaact actttatctt actggaaagt 250680
caagtgtaac aaagcaaaac atttttgtag ctagaactca ctgttcagtg caaagctatc 250740
tttggctcat ggtacatttt aagcaaggac atactctccc tcagaacaat gattgcaatc 250800
aatttaacac ttctgtcttt tctaagagga aataatcata acagtattca ttttcaaaat 250860
tcccaacatg taagctgaca tctactttcc ttttaacagg cttcctctat gttataggtt 250920
gagcattcca aatctgaaaa tccaaaatgc tacagaatct gaaacttttt gaacacagat 250980
atgacactta aaggaaatgc atattggagc atttctggtt ttagatattc agatttgggg 251040
tgcccagcca gtaaggataa tgcaaataga gtatttcaaa atcctaaaaa atccctaatc 251100
caaaacactt ctagtcccaa atatttctaa taaaggatac tcaacctgta tgtatgtttt 251160
ccttgagtta tgtacctcca tgttcctcaa cctgcctacc acagagcctt gtacacagca 251220
tttgttgatt tgagttgtat cagcctacag cactcatatt atgcagctct ccaaggaatt 251280
aatgttaatc tatttcttga tgtgctttgc gtaaaactta ttcagcctta agatatttga 251340
cactagtttg aacatgtatt gaacttgtac tgtttgacat ttattttgtg tattaatgtt 251400
gccttcccta gtttggcaag tatcttgggg gatagaacct cctctcatat atcctacttc 251460
aaatctgtaa ggaagtctgg gtacattgtg acactcataa gtatttgtta gttcagttac 251520
cttccctctt tatacttcca aaagtaatga aaatatagca acaagagtct gacataagtg 251580
acaagcagat ttgttgaaag gcttcatgag gaaggaatct gaatatttag actttgaata 251640
aggagaggga atgtcaagct gtgagagagc acctggagag aggctgaaat gtgcaattta 251700
agatggagtt tgtgagaatg agactaaagt tataggaacc gtggttagtt ggagggatgg 251760
ggtggggtca atcaggaagg accataagag acaggcagaa gagttgatgt ggtattagta 251820
ggtcatgaga aaccattgta agttctgaag caggaatata gcatattaac tattgtgaat 251880
tgtctatttc agaataaagt tacctcaatg accttcttaa ctggcaaagc agtagaagat 251940
ttgtgcagaa taaagcaggt aattgaaatt ttgtcattaa atgtttcgct acctagagag 252000
aaatttcttc ttctcagcct tcactattga attccacccct tggcacacaa ccaaagtatt 252060
atagggaatt atctatttac agaacactaa attgacaagt ggtccaaaac ataggaatag 252120
taaccaccat ccctgtgctg gacatctcac ctgttttcct aaatgttccc cagtcatgag 252180
caattatatt gtacctacag tctccctacc ctactcccca acaaagactc agggtatctt 252240
aaaatttatc acagatccca ttcacactta aaaccttact tcacctatac tttgagttaa 252300
tacaggttat tgtcctctgg cctgaaaaat ctgtctgtta taacacttat aacactgcag 252360
ctatatccag gttgcaagtc agtttaaacc aactttagaa acaagttaag ttttatctag 252420
gcatgtgtct gagactgtgc tcaagctccc ttacttgtat tcatgaaact ttgtcaaatc 252480
tgttcctcac tggctacttt atctcacaaa aagttggcca atcgcttgct tgcttgcttg 252540
ttttcaaatc acattgaagg aatcaattaa gattttggac taaacatata ataaattttg 252600
tttaaattgt tgaagaattt gggaaaataa tcctattcaa tgagattgtg tttgtttata 252660
cttaataccc ctttttgaaa attgacatta ttaattaaaa taatatcaac ttaatgtcta 252720
tttaaatcac atagaaatcg ccaggtcatt tcttggttat taaatgccat aagaacagtt 252780
tttattttat gaagggaata gtgtcaagaa ctatttcaca gtatattaac atttaatcct 252840
tgaaaaaaaa agtcatattc tcaatgaaaa ttagtgaaat aaggaatcac aagtgtgaag 252900
ttacatatta tgtaattttt gttcaaaagt aaaacatatt aagtaactgc actttaaagt 252960
cccttatctt taaatggtac tttaatgtga ggatgcacaa aaaaagaacc cttttctgat 253020
cttgtgaggt ttccacttac agatgatata gataaagtac agtcatataa attatttgta 253080
attatttcac tcatataatt ttgctcggaa gccatatcgt agtcaggcct ggattttaat 253140
tctcaattcc accatttact gaaaatccct taacctgtat taaccttagt ttcttcatct 253200
gtgtaatagc tactataaat aatattactt atcttcacct ggttgaaata agaaaatcag 253260
tgtgaaataa cctcataacc tttactctgt gcaattcttt gttatttgag cttgctggta 253320
tcaatgctaa gtccagcaca gtgataaaag tgatccagct gaatcaggtt cctgcctctt 253380
ttctactcaa ccaggttgat ctggattcca ggcacattgg ctgggtaaca agtgaacttc 253440
caggagggga taatcacatc ataaaaattg aattaaaagg cccagaaaat acactgagag 253500
ttcgacaagt caaagtcctg ggctggaaag atggtgaaag cacaaaaata gctggccaga 253560
tttcagccag tgtggcccag cagaggaact gtgaagctga gactctgcga gtattcagac 253620
tgattacgtc tcaagtgagt gtccttacaa catattctag cacaggataa ttgatgtaat 253680
atattttaag agtgtaacaa aatattttgt gaaacttatt acagaaattt ctggctataa 253740
atgttgccca ttttttcttt tcatagccct aaacacctga gttccatgtt gcatttgtaa 253800
ttaagaaaaa tagtggtgta tattagcaag agtagcatat tataaaacct gcggaatcag 253860
ctaatgagtc ctctggccaa tatagtgtta atgcctgtca ttaattcctt ctcacatgca 253920
tatcttcatc aggtatttgg aaagctcatc tctggagatg ctgaacctac accagaacaa 253980
gaggaaaaag cactattgtc atcacctgaa ggagaagaaa aagtatacaa tgtatttatt 254040
tgtattctaa agatatttat ttcccttttt tattcttttt ttcagtgaaa taattcattt 254100
attgctgtat attttgatgg atatgtaata acagttttat gcagttcata tttgttctta 254160
gaaagatgaa ggaactatct aaaagaaatt cattattcat gtataatcta gctagtattt 254220
taagtaacag caaatttgct ctataccttg ggtttttgca ttcatttgta atcatttctg 254280
tgctataccc catcagttat cttctccctc ctccattgtc cctgtccttc acagttcagc 254340
tcaaaagtac tgtcttcttc atgaaacttt tttacgattt atcctcttca tgaaatttgt 254400
ttatgatttc cccaaacaaa agcagttttc tctctgctgg agttcataat aatctgtatg 254460
tgtctcttct tcatttttct cttatgttta tctacatgga tgttttctct cttctactga 254520
accatagctt cttaaagacc aagtccatgt ctaatttgtc tttgtatcca tcatggtagc 254580
atcacacaca tgtttagtaa atttttatta gaataactac tctttgttac tgttcttgaa 254640
atttcttgca aaaatacagt tgctttactt tttcggtcct gactaaaaca ctatacctaa 254700
aacttttgta cttcatccat ttgcaaaaag agaagtcaac tctgactagt ctcaatattc 254760
tagtgtcttt aaatgctaca aataatcacc ttggcagccc tttgaaagat aaatttcaag 254820
gatttccctt gtctcaccct gtgtttctta atacagtagt atctaatcat tgtcctgttt 254880
ttgtttgagg tctgaaaaaa ataagatttc ttaaatgctg gtaacttctt tcaacatctt 254940
ttggagattt catttgaatg actacaagac tgtgtaacta cctgttaagt caattgaatt 255000
ttagcagatg tcaactctgt actaaacaat tgtgagaatg gcaagccctc aaaaagcttg 255060
cattctgttc ttggttatga accctctgca ttcccctcac cccccccaaa aagaaatcaa 255120
caaagatact atatagtata aaagcaagtt attaaatgtg tgaaaaaaat tggatcattg 255180
tgccctggag tggtcagaga aggcttctta ggggatattg gactggagtt agatctgaaa 255240
gagaatgaag ggattcaaat gagattagta gagagaatgg gagcaaggac tgatcagaga 255300
gactggccta agggtgggag agtgtatgct gaggagttaa ggttgagtag gaaaggttat 255360
actgtcatgt gtgtgcccat gaaataacat gatttttaag agaatctttt tttaagttag 255420
attattgaag cacaatttac atacagaaat tcctcatttt aaactgtatc attcaatgaa 255480
tttttacttg tgtacactag tgaaatcatt atcacaatca agtttgtttt gttttgtttt 255540
gcttgagacc gggtctctct ctgtcatcca ggatagagtg cagtggtatg atcacggctc 255600
actgcaacct caacctcccg ggctcaatgg atcctcctgt ctcagcctcc caagtagctg 255660
gaactacagg tgcacgtcac cgtgcccagc tgattttaat atatctgcag agatgtggtt 255720
ttgccatgtt gcccaggctg gtctcagact cctgggctca agcagtctgc cagcattggc 255780
ctcccaaagt gctgagatta cagatatgag ccaccatgcc cagcccacaa ccaagtttta 255840
aaacacatca ctccccaaat ttctctcatg ttcctttgca ggcaatcccc caacctcaca 255900
cttagagcct agcaactact gaactatatt ctgccagtgt tgtgttgcct tttcctggat 255960
gtcatataaa tggaaccact cagaatgtag cctttttgtc ttgtttcttt cactttagtg 256020
taatgctttt gagatttatc catgttgtag catgtagcca tggttcattc ttttggttgc 256080
tgagaagtgt tccattatat ggatttaccg taatttgttt atcctttcat tttttgatgg 256140
atatttgggt tgtttctgct gtttggctac tattagtaaa gctgctgtga acactcacat 256200
acagatcttt gcaggtcttt taccaattat gtgttttcaa atattttctc ctagtctgtg 256260
tcttatcttt cagagaacag aagtttttaa gtttgataaa gtccagtttt ttcttgtttt 256320
tttgattcat gatttttatg tatggtctag aacccaaggt cacacagata ttctcttctt 256380
ttcctttaga aatgttatag ttttagttct tttctttaga actgtataca ttttaatttt 256440
tatgtgcagt gtaagaattg aggcttatct tttgcatata gatgttcaat tgttctacta 256500
cgattcattg agaagactat catttatcaa tagtcaattt accataaatg gtaggtctgt 256560
ttctggactc tattctgctc cattgatcca tcaaagtgtc ttacttactg tagctttata 256620
aaaagtcttg atatcaggtt ctaactttgt tctttatcta agttattttg gctattctag 256680
atctcttgca tttccatata aagcttagaa tcagcttgac cgtttcttta aaaaaaaaag 256740
gggggggggc ggtggggatg gaattttgac tggaattaac accaaattga tagtttaggg 256800
agaatcgcca tgtcaataat attgagtctt cgtatctgtg aacatgatat gtatcagggg 256860
ttttcttaca tctgtttaaa atttctctca gcagtgtttt gtaattcatt gtacacatct 256920
tgtacatatt ttattaaatt tattcctaaa catttaacat ttgtaaagct attgtaaatg 256980
gtattttta tttcactttc caattgttca tttctagtgt ataaaaatag aattgacttt 257040
tgtatattag atttctaccc tgtgatctta aattcactta ctaatttcag aaacttttta 257100
tagactcttt ggggttttct tagataatca tgtagtcttc aataaatttg ggttttttcc 257160
tttctaaact atatgcctta aatttctttt cttatattat tgtgttattg cattgattaa 257220
gcccttaagc gccatgctga atagaagtaa tgagaacaga tagctctgac ttgttctgga 257280
tcttgaaaag aaagtataaa ccattcatta ttaagtgtga tgtgaactgt agattttttg 257340

-continued ggggtgaatc tttttaataa gattggagaa tgttttcttc tattcctagt ttgctgagaa 257400
tttctatcag aatggattct tttttaagag acctggtctt aactctgtca cccagacaag 257460
agcacagtgg tacctttata tgtttctctt tcttcatttc ttttattccg taagataatc 257520
catatattgc tatgcatttt agtcaacatg tgatactagc ttgtatacag ttcattttcc 257580
ttcagtgaaa aaaaaaacta ggggatggta gctacatgat atagtgcttc ttttagaagt 257640
aataaaaatg ctgtaatatt gactgacgac gatagttgca catatctgaa tgtactaaaa 257700
accattgaat tctatgcttt aaacagatga atagcatggt atgtgaacta tatctcaata 257760
aagatgtttt taaaaagcaa aaataaatga tgaaagaggt aaacaagatg aaagaactat 257820
ctaaaagaga ctcatatata atctaactag tacttaagta gcaaaataaa tgctctattc 257880
taaaaattca ctttctttaa tagataacag agctgtttca gttatctgtt tctttttggg 257940
taagctttag tagttctgac actcaagcaa tttgtccatt tcatctaagt ttctggattt 258000
attgccataa gttgttcata atataccctt atgtcttttt aatatctgta gaacctgtag 258060
tgatgtgtct tggtgatttg tgtcttcatt cttttttct gaaatagttt ctctaaagat 258120
tcatcagttt gatctcttca gagaactagc tttttgtttc attgattttc ctctattttt 258180
gcttctttta ataatcacaa ctttatttct ttccctatgt ttgccttgta ttcatttgtt 258240
catctttttc tgacttctta aggtccaaga tcagatcgta gactccaaga cctttctttt 258300
ctcatctaag tatttaatgc tattattttc ttctaagcac tacattagct gcatttcaca 258360
aatttggggt attctgtttt tattttcatt caattcacaa tgttttctta gttttcttat 258420
tcccatttga tttcttttt ttttttttt tcttttttt tgaaatggag tcttgccctg 258480
tcgcccaggc tggagtgcag tggtgcaatc tcggctcact gcaagctctg actcctgggt 258540
tcacgccatt ctcctgcctc agcctcccaa gtagctggga gtacaggcgc ccgccaccat 258600
gcccagctaa tttttgtat tttttttagt agagatgggg tttcaccacg ttagccagga 258660
tggtctcgat ctcctgacct cgtgatccac ccacctcggc ctcccaaagt gctgggatta 258720
caggcgtgag ccactgtatc cggccccatt ttgatttctt ctttgaccct tgggtaattt 258780
agaagcacct tgtttaattc ccaaatattt gggaattttc ctgttagctt tatattatta 258840
atttctggtt cagtttcatt gtggtcaaac tgtattgtat acttcgtata atttcagtcc 258900
ttttaaaatt gttaagattt ggattctggc ctataatata gtctgtttta gtgaatgtcc 258960
acgtgcactt caaaaaaatg tgaactctgc tgttcttctt tgaggggttc tataaatatc 259020
agttagttca agttgatcaa taatattcaa gtctttaaga gccttaatat tcaagtcttt 259080
aagagcctta ctggtttttg gttttttgct tgtttacttg ttctgttaag tactgaaaga 259140
agagttttga agtatccaac taactggatt tgtttatttg gaattcattc tacctggtag 259200
ctgatctcaa cattctaatg gactccaaaa aaaaagtttt ggttttgtag atgatcaggt 259260
ttttcctcat tgttagggcg aaagggacat tctcttctgg ctctctatct taagaaatgt 259320
aaaaccaagc atcatttttg attcttaaac aaaagagttt cttacctcag ttttcttacc 259380
tgtaaagtag gcaaaatatt acaatttacc ttctggggtt gttgcgaaga ttagataaga 259440
tttgtgtgtg tgtgtgtgtg tgtgtgtgtg tgtgtgtgtg cgtgtgcaca cacgtgcatg 259500
catatatata tatacacaca catatataca tatgtggcac ttagaagaac agcgtgcaca 259560
taataagctc tataaaattt tagcctttat atttttcctt atgatacatt tctttgatga 259620
cttggtgttc cgatagctta atttaagacc actatcatca cagaggtttg ttaggacact 259680
ttcctttttaa acaaatgtta ttttcctgga ttgttcttca aacaattaaa tgtgggatgt 259740
gaactaataa tgtttacaat ttagaaatag atttaatcaa agctactcaa attgactaca 259800
ttaaagaaat ttgtgaaagg agaatatact tctctgaatt tcctaagttc tgagattttg 259860
ttctttttat ttcaaacttt atcctttgtc ttagtattat aagcctcaat ttaaaataaa 259920
tttactttaa aaatatatac acaaaattat ttctcaagtt actttgaaat atcacatata 259980
caaattttat ttaaagagac cacttcattc tttttttttt ttttcttttt ctatgtaaag 260040
gcaacatcag atgctgacct gaaagaacat atggttggaa tcatattcag caggagtaag 260100
ctgactaact tacaaaaaca ggttggttaa cagctatttc attgtcttca ttagttttgt 260160
gtgtgtgtgt gtgtgtgttt gtttgtttgt ctgtttgttt gttattaggg tataaagcag 260220
ggatgtccaa tcttttggct tccctgggcc atatttgaag aaaaagaatt gtcttaggct 260280
acacataaaa tacactaagg ctaacaatag ctgatgaact aaaaaaaaaa ttgcaagaaa 260340
aaaaaatctc ctaatacttt aagaaagttt atgaatttgt gttgggccac attcaaagcc 260400
atcctgggcc acaggcagtc ccccggctgc aggttggatg agcttggtat aaagtatttt 260460
gaaaaattta tgaaggcttt tttatgctcg ccccttttata ggtcctgcag aatgtgcctg 260520
ccatttttta gagaggaatg agtattttgg catacttca tcattttaaa gattttactt 260580
atgaaaactt gcttaccttg ctgctatttg ttatgggtag atttttttatt tggtgtcaaa 260640
tacccagcta tatcagattt gatttgcatt tcccatattt cttttccccc attcttctgt 260700
gtgttggctg agcaattaac agtgttaact ataccagtgt taatattttt aaatataacc 260760
aggtgaggaa atagcgctat attgttcata taatggggtg ctacataaca taaaaatatc 260820
acttcaaaag tcaaataaaa tattgatttt aaattaacct attattctaa cttttttttt 260880
tttcgagagg gagtctcgct ctgttgccca ggctggagtg cagtggtgcg atctcggccc 260940
actgcaagct ccgcctcctg ggttcacacc attctcctgc ctcagcctcc tgagtagctg 261000
ggactacaga tgcctgccac cacggctggc taattttttt tttttttttt ttttttttta 261060
gtacagacgg ggtttcaccg tgttagccag gatggtctcg atctcctgac ctcgtgatcc 261120
acccgcctcg gcctcccaaa gtgctgggat tacaggcata atatttttgt atttttagta 261180
gagacggggt ttcaccgtgt tagccagaat ggtctcgatc tcctgacctc atgatccacc 261240
tgcctcggcc tcccaaactg ctgggattac aggtgtaatt tttttgtatt tttagtagag 261300
acgggatttc accatattag ccaggatggt ctcgatctcc tgatctcatg atccgcccgc 261360
ctcggcctcc caaattgctg ggattacagg cgtgagccac ggcacccagc cctattctaa 261420
ctttctacac tattattctt ttcaatgaac tacaacatga atttattttt gctttatctt 261480
tctagcagtg tttcattgaa tcttagatgc tttcaattgt aaaatgtcat gtataatttc 261540
agtattgtga atcttatcag ctataaagca ccttatgaac ataatggtaa accatgagaa 261600
aaagtgcctt cagtgataaa atatggtgat tggtttttga cgtgctaaac tgtaagcata 261660
ggcattaata acttgcatat aatcagtttg cacatagtag ttgatttaaa tatttccatt 261720
tttattgtgg ctcccttagc tttacttgtt tcttagatga gttaagagaa tgacatatga 261780
tggagaatta actgggagaa tagtattaaa ttgagtatca atttacattc ttgtcttatt 261840
cttttgtttg cttgttttgc taggagtagt aaatcaaact aaccctatat ttttacatgt 261900
tctgtgttaa ctttaaatag gtgtgtgctc atattgtcca agctattcgc atggaagcta 261960
ccagagtccg tgaagaatgg gaacatgcta tatcaagcaa agaaaatgcc aattctcagc 262020
caaatgatga agatgcctcc tctgatgcct actgctttga gctgctctct atggttttag 262080
cactgagtgg ctctaacgtt ggccggcaat atctggctca acagctaacc ctgcttcagg 262140
atctcttctc gctgcttcac acagcctctc ctagagtcca gagacaggtg actgatcaca 262200
ctacagcctt tccattgctt ttgttacttg aaacattgtt aaaagttgca atgcaaagag 262260
aattatctaa ggaccctaag tatagatttt tatttcgtat tttgttatat tttgtttggg 262320
gcctgtattt tactcccttt tttactgttt atagtgagag tatagaatag taaaatatgt 262380
tccattttat taatgtgttg tgataagaga gtattctggc tactgattac catattacca 262440
tgaaatatat aatgtcattt agccctgacc agaaagaaaa ggtatttttt ttcgtgctgc 262500
cttgggttag taattaccac tactattacc atttgaatag tatgtatatc atattttctt 262560
ccttcacaaa atgtaaaata gtgtttaaat catatttctt ttcttaaaga ttttgaagtt 262620
acagaatggt agttaggtac attaaaaaat gaagcctggg atggggtaca gtgacttatg 262680
cctgtaatcc cagcactttg ggaggcaaag ctgggaggat cccttgagcc taggagttca 262740
aggctgcagt gagctgtggt tgctccactg cactccaacc tgggcaacaa agcaagaccc 262800
tgtctttaaa aaaagaaaag agaaataaaa gaaaccttaa aacattagtc tttacatgga 262860
attctctcat tttattttc ttaccaggta acctctttac taagaagagt tttgcctgaa 262920
gtaaccccta gtcgtctggc cagcatcata ggagtgaaat ccctcccccc agcagatatc 262980
agtgatatca ttcactcaac agagaaagga gactggaata agctgggtat cttggacatg 263040
tttctaggat gcattgccaa agcactcact gtacagctaa aagccaaagg aaccaccatc 263100
actggaacag ctggtaccac tgtgggcaaa ggagttacaa cagttactct tccgatgatt 263160
ttcaattcca ggttagttat tgcctctatt ttagtaccaa aacagaatag agtgagctac 263220
tgttcagaaa tttaagacat aatttcagat tttaccttgt taggttactc accaaataaa 263280
atccataaac aactggctaa tatctaaaaa ggtcatgtat ataataaaag tgtcatttat 263340
aattagtggg gaatagaaag taggctgaat atgtgatgtc agaatatttg gatatccatg 263400
ttaaaaaaaa ttctagatac ctacctctca ccatatacaa aattaaactt cagttttagg 263460
taatatgttt ttttgccaca ataaaaagaa ataaatatgg gggaataaag taaagttcag 263520
gtcaactaaa gctttatgta catttctttt taaaactgta ctgggacaaa ttatagaaga 263580
atatttttgt aatcttcaat ttgataagac cttcttaaac aaaacacaga acccaaaatc 263640
atataggaag atatttatag atttgactat ataaaaatga aaattacttg ataggtgata 263700
atatttaaat gttttaaaat atagggaaat aacttagaaa aatacttaaa cctatataat 263760
agacaatgac ttgttagcat aatatagaag tatgactaca aatcaatttt aaaaaggcaa 263820
acaactgata agaataataa atgacaagaa cagtcagttc acagaaaaaa acttataaat 263880
gccagtagtc agttcacaga aaaaaactta taaatgccag taaacaaatg aaaacacctc 263940
actactaatc agagaaatgt agattaaaat aattgcaaaa tatctttgat gctttggcaa 264000
cattatgagg aaataggcat tttcatctca tataaattgc tgcagccttt ttggatatct 264060
gtttataata tctaactata ttttaaatat gcatatcttt tgacctacca attctacttc 264120
taaaactttc atgcatttgc accaaggtat atatgcaagg atgttctgta attgtgtgta 264180
acagtagaga attagagaca tctgaacagt gctacttgta gagccaatcc atgacaatat 264240
gcagataaca tcagaatgtt aatcattgta tcacttcttt cctgtagtct tgctaggaaa 264300
aaagtcagct gaactaaata gtagtgtgct tagtgataca gtgaatttat attccggtta 264360
agctccacat tatccgcatg tgccctagaa ataagtcgtg tgtggtccct ggactgtact 264420
tctaaaagat gcacacagaa ataatgtgca aacagagaaa tacttgaaag ggaactcaaa 264480

-continued taaccttaac tgctgtcttg ggatttgggg taatggtttg atgaattttc tttttaaatg 264540
ttttaattga ttcagtcact taaaaatcta aaatgctgca ttctgaaata acattttcat 264600
ctttttcatt tgttactact actgataatt tattggcttt ttaagtgcta atttttcttg 264660
tagttatctc cgacgaggtg aaagtcattg gtggatgaag ggctcaaccc ctacccagat 264720
ctcagagatc atcattaaac ttatcaagga tatggcagca gtaagttccc attcttctgt 264780
tttggcagtg aagtgcggca ggaagctgac acaaaacagc ttactctgct gaattgatag 264840
gagatgtaga ttagtgtaac tttacttaaa gactatttgt agtatgttaa ctatcatgct 264900
gtttgtcttt tcagtgagtg ataatttgtc atttatgtaa accatgttca tttcaaattt 264960
tccagttaat ttgtgtggga attgttacgt gactttaaaa tctaataaaa taaaatatgc 265020
tctttcagac cctaagaaag aacttgattc aaaaaaccta aaggaaaaaa agaggaagag 265080
agctctcgaa agtggaagtt tctcattctc ctcagtcctc atggttttta aacccttttat 265140
tcttctttat taatgtcata taccctctgt cttaagatgg tggcttccaa aggagatctg 265200
ggagtgtgga ggacagggag ttactttaca gaatgcctgg ctctgattag ttgctccttg 265260
tcattttcca cacattgtat tatttctagg agggcagcct gagaaggaca agatagtatg 265320
gaatgtagag tcagaaggaa tagaaggcag cttggagaag gaggaggaat tgaactgccc 265380
cttaaatcat gtggatatga gaagtgggag gattttctgg gggaaagatg aagttctatc 265440
acttttccca acagcgtgga tattttctca acctctgtgg caaacagact ttctcagggt 265500
gttcattgaa ttaaaatatt taggagtaat atttaggaac acctaaatta tatgatagtt 265560
aaatgtttgt tcattacaaa tcaaggtagc aaataaaggt agttgcagtt tgaacctgtt 265620
tatattttag gttcctgtaa tactcatcta aagcagttag cttcactgtg taaattttat 265680
gctaagtgac aaacttctca aacatagata accttagtat ttctgttatg tttttatcag 265740
atgtgagagt aattgccctt gatttccagg aaaagagtat tgagaactta atttttttatt 265800
tatttatttt taaatatcaa aatgatgatt agaagttgaa ttttccatag gatcacgaag 265860
aaattttagt tcaaaagttt gtgcccataa tctaaaattc catggtctca ctaaaaacaa 265920
atatttcctt tgataggaga tgttatttaa gaaaaaagag tttactatgg taatacattt 265980
ctggtcactt attaaaatac tctgttctgc tcaatagggt catctgtcag aagcttggtc 266040
ccgagtgaca aaaaatgcta ttgcagaaac catcattgcc ttgaccaaga tggaagaaga 266100
atttaggtct ccagtgagat gtattgcaac aactagagta ggttttgctt tgttttgttt 266160
tgttttaaat ttggtgtgta tcattgcgtg ttcttttta gtaatagatt taaacaaatt 266220
ttaatcacta agtcaacata attattttt aaccaaatac cgtatttatt gaaaaagtat 266280
aaagggcttt tatattatga actagtcgtt acttctcact gttatgtgtt ctgtgtcact 266340
tgtttttgtt attgtttagg aagccaaggg tacactggtt agaaaaggct aattacattg 266400
tacattgttt gcgtgttgtc tttctaatga tctgtttgct gtagtttacc acagtaagtt 266460
tagtgccagc attatgctgt gatagaccga aggtcctttg gagacaagac ccctgcctat 266520
gcctggttgt tcctaatgta gagccctgta acttacttac aggatttata ggtcttactt 266580
ctaaaaagca agaagtgctt gtccagggca gggtcagggt ggaaatcttt gaggaaatga 266640
gattgcattc ttcagatgac acatttatag taagttttaa cctgctagat ttcatgtccc 266700
atatacttcc agaagagatt tgagatttcc ttgaaggagg gcagtctgac aacgttagga 266760
agaagtgaat gctggtaaaa attgcttagg ttaatcctca gaaatctgaa gaagataaac 266820
tatatatccc tagggcggaa aaagtcaatt tatgctatct tgctattatt gactgtgaca 266880
cctgaaatag gtatttttga cagtaatcct ttcctaccac tcatgtgttg ctttctttca 266940
gtctgcattc cccttcctcc ttgcatgcat tatttctttt tctatttttc tgtccctatt 267000
ttaacatctc ttgctttctg tatccaataa cactcacatg cacttcttag agttgagcta 267060
gttaagtcat tttctattct tcattaatga ggggatatat cattctatat aaaactgaag 267120
cttacccttt aagcctcaga aatttttaac tatttctgaa aacagttgtc tttttttttt 267180
tttttttttt tttgagacag agtttcactc ttgatgccca ggctggagtg caatggtacg 267240
atcttggctc actgcagcct ccgcctgcag gtacaagcga ttctcctgtc tcagcctccc 267300
aagtagctcg gattacaggc atataccacc acacctggct aatttttttt gtatttagta 267360
aagactgggt ttcaccatgt tagtcaggct ggtcataacc ccctgacctc aggtgatcca 267420
cccaccttgg cctcccaaag tgctgggatt acaggcatgt gccactgtgc ccggccctat 267480
tttggagaac agttttctaa agcttttaga catgtatgta tttctgacaa agtgcaccaa 267540
gtatagtatt aggctttctg gggcaacaag gggcaacaaa gacttctgag gaacttttat 267600
tatctagaag gatttaatgt gtacctgact actcatggga ctgtacacaa tttagcagtt 267660
gctgtaccac cttctttggc atttaatgat actaaatgga aaaatattca gaagacatta 267720
gtagtaaata ttaaatatgc caattcattt attcatatgt tgtttacata gtagaccaat 267780
aaaggataat tttatttgtc agatagaaga cagggtggtt catcagagaa acagtcactt 267840
gttcagtaga tatctgagtg cctcctgtgt gcatggcaca taggacagtg atcgtgtatg 267900
cctgctacca catcaggaag acttgagtgc cactgagtat ctatgtattt tcaaaatcag 267960
ccagcattta ttgagctgtt gtgatgtgtc acagtcagca tttcataagt ctttcctaaa 268020
aattcagtgg tgtaacagcc ttccctttca acagctctgg cttgctctcg catccctatg 268080
tgttcttgat caggaccacg tagatcgtct ctcctcgggg agatggatgg gaaaggatgg 268140
acaacaaaaa caaatggtaa gatcagaatt ttgtaagaat ttatcttgct ttcctttaca 268200
gtaagcttta gcttagctta aaaacaaaca aacaaacaaa aaacacatca acataaacag 268260
ttagtggatc tcttgaaaga ttgtgtccct tcggccaagt tcatctcaca agtctatttc 268320
agagagtccc tacttcatag tatatggaaa ctttaggggc ttttatttaa gtatattaaa 268380
gagctttctt cttctctgag tcatgtttgc atcatatcaa aatttatttt tagccagagt 268440
ctgatttagt gactagatat tttactaaaa tgtaatcagt cttatggtag gaaggaaata 268500
aagcaataac acaggcaaca tgacacacca cctgttcaca tatatactta agtaggtttg 268560
atgggtatct ttaagttcac tagaaaggaa aactttatat aggccctttc accattttct 268620
tattaatgtt caagtttcaa aaataaacag tttcttcctt tggcatacag aatgtttaga 268680
tatataatgg ggcagacatt tcttaagtct ctaagtaaca aagtatacct gttcattgta 268740
ttaatcattg aacctgcaaa gcacattaat gattggattt ggagttttga gagattttta 268800
tagttaagta catttgcaat aattctgttt aatattcaga ttctaaattc ttaatagact 268860
tccgaataac ggtttatttt tgtaaataaa ttatattcaa tttgtatgag agtctgagac 268920
ttgcttgtta atctaagtaa cgtggaaatg tcttatttta gcctatgtgt gataaccatg 268980
atgatggtga aactgcagca atcattttat gcaatgtctg tggaaattta tgtacagact 269040
gtgacagatt ccttcacctt catcgaagaa ccaaaactca tcaaagacag gtgaagattt 269100
ttgtctctgg agcataaaat atgttcagtg aattttgaaa taaatgtgtg aaagaggctt 269160
tgtgtagtag ggggaaaaag tggactttgg aatcaaagac cttggttgag ttcacagctg 269220

```
tctcgcttac catctataaa tagcaagttg ttttatcctt agaaacactt aatttctcca 269280
tttataaaaa agggactgct gtgaagatta aagagaagat tggaaatatt caaaacttct 269340
tagagtgctt aaatgaaagc cattattatt attgaataat taaattttat actctccctt 269400
tcagagtgat aaataagcat atttttccct gttctttaat gaaataatag gtcttcaaag 269460
aagaagaaga agctataaag gttgaccttc atgaaggttg tggtagaacc aaattgttct 269520
ggttgatggc actggcagat tctaaaacaa tgaaggcaat ggtggaattc cgagaacaca 269580
caggtaaaag gtttaaagat tgagccatgc ctttaaaacc cacaaaaaaa gattaaaccg 269640
tgccaactga ttaaactgtg aataattttg agtgatattc tgatgtttaa ttatgacatc 269700
attgatctat atatttacta aatatataga gtgttctatg gtgaagagag cattagacca 269760
aaagtcaaga aacctgattt gccactaact agctgtgtgg tgtcgagcaa gtcacttaac 269820
ctctggaact cattgacttc atttataaag tgagaggatc acaactaatg gggctccata 269880
gataaaatac atttctattg ataattccct tctagttctg ctagttgttg ccccacaata 269940
aaaattgctg cactagatga tcactaagat ctctatttat tataaggttg tatgatttta 270000
tgatatttag aggtttttgt agacctaatg cttctgaagg tgttgtgaat ggtactgttt 270060
ccattgatag caataaaata attaacaaaa atgaatagac ataaaacaaa aggtaaccta 270120
tgtatgttaa atgtattttt atctctaaaa catagttttc attttgctgc ttttctaaag 270180
taaatcttgt atattcctag ttcaaagtta tgttgaatct tacaaattct cagttttcag 270240
cacatctgca gtctgccatt tgactgacac gaacttccag tgttggagtt aggtgtaaat 270300
ccgaatcaat ttaattctag ggtgactttg catgctgcaa gagcatgacc ttcttttctc 270360
atagttgatt tcttcctcct ataatctgtc agtgctgtat actgcattaa taaatgttct 270420
aatgtcaaac catccttgta aaccatcctt tttaaataga tttttctgta aatattgctg 270480
aattcaatat attgatatta attatagtta gatttttata tctgtgttta aaaatcagct 270540
tggtctgtaa ttttcaaatc ttcacgttct ttttcttatt gctctgttct tgttttattg 270600
attctgtttc ttctttaagt atttcaaaca tatttaaatt ccttttcaaa ttgcagagtt 270660
cctgaggtag gaattctgtt tttcaagttt catactctga tgataggctt tataccatgc 270720
cttataattt tgttatatat agttaaagat ttccctaact tctgtgtatt tttatttaat 270780
ttttggttat catatttttt atggtattgt gcatttggag tcaggggctt gtaacagctg 270840
ctcagtctgg taacttgact agaagtctag tctgtttctt tcactgaaaa aaaatattag 270900
tcgagagtgt atttggcttc agataggtct ttaatttctt tttttgtgtg tcattattta 270960
ctttataatt aggacaactt agaaaccttc cgttctaaaa ctgtcaggct gatttcccaa 271020
ggatagcaac ttatacaaac ctagtttgct ttttaaaatt tagttctgtt aacatatcta 271080
gaaaacatcc ataagaagga tttttatttt tctgcttgaa cctaggcaaa cccaccacga 271140
gtagctcaga agcatgtcgc ttctgtggtt ccaggagtgg aacagagtta tctgctgttg 271200
gcagtgtttg ttctgatgca gattgccagg tgagtatata gtgacacagg ccatcccatt 271260
gtccatgttc ccctgtgaca cctttacttc atacagaaaa gagttttagc tcagcgtcac 271320
tccagcttcc taaatgagtg tattacctat gtgaagcatc aaatgcctta ccaaagttga 271380
agaatgggtc aaataaggct ctcaagccca aaccacactc tttttgtatg tttctcagtt 271440
accatgatca tatgtattta atatctactt ttgtactaga aacagttaaa aatttatgaa 271500
ctgtatttcc tttatctctt acagacatta ttcacttatt tccttaaaat acattttcaa 271560
```

-continued catctaagag ttctttaatc ctgaacatat ataaacatat tctatgttgt ccaaatgttt 271620
ttggtttctc aattaataag aatgtggata tgctcagaga gtcaaaggta cctttttaaa 271680
aaaaaaaaaa atctgcattt tggtgatgcg gagagtggtg actgggaaat tatacattgg 271740
ggaacttttt ttattttta tttttttgag acggagtctg gctgtgtcgc ccaggctgga 271800
gtacagtggc acgatctcgg ctcactgcaa cctccgcctc ccgggttcaa gcgattctcc 271860
tgcctcagct tcctaagtag ctgggattac aggcgcgcgc caccatgcct ggttaatttt 271920
tgtattttta gtagagatgg ggtttcacca tattggtcag gctggtctca aactcctgat 271980
ctcgtgatct gcccacctca gcctcccaaa gtgctgggat tacaggtgta agccacgact 272040
cccagccagg aactttttgc tttatagctg tgcatgatga caaatatgaa attataattc 272100
acttatcagc attcccttta tagagagtgg catttttaa aaatcgcatc aaaaaaaaaa 272160
aactttgtta agaagcctaa tttatattca aacaaagatt agaaataact ttactttgtt 272220
gttacttggc ctgcatagat acttcctgtg ggaaagtaat ctttggaaat ttatataata 272280
aggaaaatta ccagaatgtg tgctttttta catacttgtg taacattgta attcatcttt 272340
aacaggaata cgctaagata gcctgtagta agacgcatcc ttgtggccat ccatgcgggg 272400
gtgttaaaaa cgaagagcac tgtctgccct gtctacacgg ctgtgacaaa agtgccacaa 272460
gcctgaagca agacgccgat gacatgtgca tgatatgttt caccgaagcg ctctcggcag 272520
caccagccat tcaggttgcc tcagctttta aagtattgaa tgtatccaga cattaagatg 272580
gggaatatat ttgtcaaata aacattgatt gaggccgggc gcagtggctc atgcctgtaa 272640
tcccagcact ttgggaggcc gaggcaggtg gatcacgagg tcaggagatc gagaccatcc 272700
tggctaacac agtgagaccc cgtctctact acaaaaatac aaaaaaatta gctgggcgtg 272760
gtggtgggtg cctgtagtcc cagctactca ggaggctgag tcaggagaat ggcatgaagc 272820
caggagacgg agcttgcagt gatctgagat ggcaccactg cactgcagcc tggtgacaga 272880
gcgagactct gtctcaaaaa aaaaaaaaaa aaaaaaagca gttgattgaa atcttttttt 272940
atatcactag gcagaagtgt tcttttaatc tatacatgta ccaggctaat gaggagcaaa 273000
ttctgcctct ttatgctgtg ctttctatgt tgcatgctca gctttaattt gtgatttgtg 273060
tgaacctctg taatcaacag aatgtataaa atattcagaa gccaggggga aataattaga 273120
ttatccccca gtagctaagg ctcttcttaa tttccaaaat ccagaatggt atttttacaa 273180
cattatataa ttgatctata cataatgata catacttcta tacatacaca agttactgtg 273240
cactaaatag gtttttttaa cttttgccca ttgcttatat tttcagttct catgattcca 273300
agataataat agtctccaaa agaaaatcat aagtcagtaa tttcttcttc tttctgtgag 273360
atacaaaatt gaataatttt acttttttc ctaacctagc ttactttata taagtggcat 273420
gaatgttaaa aagcaggaga agccaaaggc ctagttaata gtatcccaat ttactgtaat 273480
gaaatttagt aaataataat gtcccaattt cagtgtccca atgaattttc attatagtaa 273540
atttcttgat ttttctctta cctgctttaa gtagtgcctt gcattaaata atctcccagt 273600
cactcaactg tttatcatta ttatatttgc ttatgtcctt ttcttttgtt tatttaagct 273660
ggattgtagt cacatattcc acttacagtg ctgtcggcga gtattagaaa atcgatggct 273720
tggcccaagg ataacatttg gatttatatc ttgtcccatt tgcaaggtat ggaaagaatc 273780
tgaaatcatg tactttcttt ttcttttgtt ctttctttc acctttcaaa ataaacatat 273840
gtcagtatct cttggtttta cccaccagcc cctagcagtt tcttcccttc tcattcatgt 273900
ggaacctgag aatataatct ctctgttata atgcatctca aaacagtaat tgtccattta 273960
aaactgatta cattctgtta aacatattac atgagaaagt tcatttaaac atcgtgatgc 274020
attaaagggc atgcatctct actctcagac cactagagag ctcagttgac ataacatgac 274080
aacggctacc aaaaagaaga atgatcctct ggtgtttgta gaaactgata cctgccatta 274140
aagagtgaaa ttggaaccct cagtaccact agaacagatt cttttagagc ttagttaaaa 274200
caaggagaaa gttcttggca ttttgacaca tttgtacaaa ggtagtcagc aagtaggaag 274260
ttgttttggc aagctaataa tgattaacaa aaagctgttt ttgaagaatg tggcagtact 274320
ttccctatta attcatcgcc ccttttgtt ctattaagct ctccctattt tcttatcttc 274380
gtatttgcaa actaatataa agggtagaat gtggaaagac ttagcacaat cattgtctag 274440
atagactgag gaataatcaa aaagattgta gtattttgct ctcccctatc atatggtgct 274500
acaaatatta atagatacat gaaagtttta cagcaaatac tacctgttca cttctgtcac 274560
ctggcgttct gccttcccct caaggaagca aaacacacac acacacacac acacacacac 274620
acacacacac acacacacac acacacacac accaaacaca gagcgtgtct tatttgtggc 274680
aacaaggtaa ctttgtttcc acaatagcta gggcaacagg agatatattt cagacgcagg 274740
aaatataaag ctaataaaat ggaattttca tgctctgtgt cccatttgcc ccatttcccc 274800
tgctcttgga aaaatatggg cttctaaaga atttacagaa tgtttttcaa atgacatttt 274860
atttagaata tgtgtgctgt ctggttatct tctagcacaa tgcttggcac ttaggtgcat 274920
gctaagtgtt tgttgagttg gttaataaat gattctgcta aagagtgttc atttttattt 274980
gcagaacaaa attaatcaca tagtactaaa agacctactt gatccaataa aagaactcta 275040
tgaggatgtc agaagaaaag ccttaatgag attggaatat gaaggtctgc ataagagtga 275100
agctatcaca actcctggtg tgaggtttta taatgaccca gctggctatg caatgaatag 275160
atatgcatat tatgtgtgct acaaatgcag aaaggtatgc tataaattat actgagaagt 275220
tttaaaaact agagcttacc tatatgatta agaattcaaa ttgtacagtg atatctaatt 275280
attccatctt aagcctgaag ttaaaaataa gatagcttgg tacaatgttt cccaatgttt 275340
ccagtaaaac ttgtttactt aacttgtttg gggattcttt atttaacctg aacaaacttt 275400
tcgaaacatg cagtatttct gtatacaagc tgcttcccat cagtaataac ctgttggccc 275460
agggcaattc cttctcgaat aaacttctct cacttgactc tgctaaccat tccttcctta 275520
aaacccttaa ttccttggct tccaggacaa cacactcttt ttctgtcctc cttcctttct 275580
agtcatttat ctttaactac ttcttctttt ttttttttta acctacccct tacatatttg 275640
ttttcctaga gctccattct tgcctactta ataaatactt ccttaccttg ggtgacctct 275700
tttacatcta taccttcacc taccatgtat atgtttatga ccccccaaaa tttttgagat 275760
ttagttacaa ataaccaact gcgtaccaga catttggatc tctcacacat acttcagagt 275820
tcacatgtca ggtattatat tcatcaatct tggccgggca cagtggctca cacctgtaat 275880
cccagcactt tgggaggcca aggtgggcag atttcttgag ctctggagtt tgagaccacc 275940
cagggcaaga tggcaaaacc ccatctctac aagaaataca aaaattagac aggtaggttg 276000
gcatctgcct gtagtcccag ctacttgggg gactgaggca ggggaatcgc ttgagtccag 276060
ggggttgagg ctgcaatgag ctgtgtttgt gccactgcag tccagcctgg gtgacatagt 276120
gagaccctgt ctcaaaaaaa aaaaaaaaga ctttaccaat ctctgatctt tattgacaaa 276180
atcctatcaa ttctgtctcc agatctctct tgagtccttt tttctttcca ttacatctcc 276240
agcaaaccta atcattttcc ttggtaatta cagtagcctt cttcctgagc tcgggtgtag 276300

-continued aacccctaat tcctctgttg catcccttac actgctgcta attaatactt ctagatctaa 276360
aatctaactg gatcactctt ctacttataa tacggtagcc cagtctccct ctccagtctc 276420
atctcccaag atgctaccat ttgctctcca tttgctgcca cataccaaat aacttgcatt 276480
tcccaaactc agccctgtct gctcacccac tgacaccccc atgccattgc acaggccatt 276540
ggtgtttaaa ggatgctctt ctctacctcc ccctgcatat tttactctga cctgccaccc 276600
ccaaccccat acacacatgc tgtcatgcag agcctaatct gtcttgtcat acctcgggct 276660
tcagctcagg tttcacctcc tctgtaacat acccccatct cacttccatc aacaccacca 276720
ccacatgatt ttggtatctt gcaggcatct agcatagaac tccctattct gcattatgac 276780
tactggacca cttatctctc tgccctactt gataagttcc atgaggacaa agagtatgtt 276840
ttttcatttt tctatctcta gtactttgca cttactagat acaaagttaa gtggagaatg 276900
aataaatgag tgaaagaatg actacatgag aaaggtgcat agtctcccaa tgtagcaaaa 276960
agaaaataca gaggatgaat ggatgtctaa gtagagagat gatagccaga aaggcagata 277020
aatacatgca cacccaatag tgcacattta tgaagcttgt attgttacaa ataataaaat 277080
agtatttctg tgtgtttcat gtactaaaca ttataaatga atattgtgct attacagggt 277140
agcagtcaaa tgcttaggaa gccaagcaga ggatatagaa aagtgaaaca gctggagtaa 277200
gcagtcccca agacaaaccg aaatacttcc agggttaggt ttagctggtg aacgaccgtt 277260
tataacctct gcatcaatgg atcctgtctt tggacctgtt tttctagtat agataataga 277320
tttatattga ctcagtttgt ttattcccaa tccggacata gctttttgac tatgagacaa 277380
tcagtgcatg caaattgtcc cagttccttg gcctcactta atctctgccc agggcaaata 277440
cagataaatc acccatcatg atatttttat ttattcatga taattttatt tattcaaatt 277500
ctatttatgc aagtgtctgt attggaaact gttgagttcc tgcctactgc ataactttat 277560
aactatgagc agaattctga acagaattat caaatttgcc tttttttttt ttttgagacg 277620
gggtctcacc atatcaccca ggctggagtg cagtggcatg atctcagctt actgcagcct 277680
ccacctcctg ggctcaaaca agcctcccac ctcagccttc tcagtagctg ggaccacagg 277740
tcctcaccac cacgcctggc taatttctgt gtttgtttgt atttttgata gagatgggtt 277800
ttgccatgtt gcccaggctg gtcttgaact cctgagctca aggaatctgt ctgcctcacc 277860
ctcccaaagt gctgggatta caggtgtgag ccaccatgcc cagccggcct tttcttctta 277920
aaaaatgtgt gatcagagga tgcttaaaat tactttttttc tttcccatta gccttggaat 277980
tataattcta tactaattac tttatgtata ttttgttcta cagtattata aattgggaac 278040
tgctaagcat atttattaaa acagtagaag gggatatgta ttttaatatt tcaaaatgag 278100
aaaaatttct caaactttac cctgaaaaaa gcatagcttt tactacttaa tattctgttg 278160
atatttactt ggaatattat actttttgt tttgacagga caatgtaact gcctacttta 278220
agcttgaatc catttgagag tcgaaatagc tttaggccag gcatgtggct catgccaata 278280
atcccagcac tttgggaggc caaggcaaga ggatcacctg agcccaggag tttgagacca 278340
gcctgggcag catagggaga ctctgtctct acaaataatt aaacaattag ccgggtgtgg 278400
tggcgtgcac ctatgatcct agccactcag gaggctgagt tgggcggatc gcctgagccc 278460
aagaggttga ggctgtcggg agccatgatt gcgccactat gctccagcct gggcaacaga 278520
gtgagagccc gtctcaaaga aacagagaga gaggtggaag aggagaagag aagagaaggg 278580
aaggaaggga aggagggaag gaaggtagga ggggaagaaa gaaaaagaag aaatagcttt 278640
atttcttacc ctgatccacc ctacatacag tcagcaagca atatgggcat gcacttggca 278700

-continued tttcaaggga tggtctagta gataatggta ttttctaaaa cccctagatc ttactttcac 278760
tatgcccata ctgtatctcc catgccagag ttttcttttt tcctgctgta atctagatgt 278820
gttttctcca caggcatatt ttggtggtga agctcgctgc gatgctgagg ctggacgggg 278880
agatgattat gatcccagag agctcatttg tggtgcctgt tctgatgttt ccagggctca 278940
ggtaggcaga acattttatt agaaacaaca gtttagaaat gttaaatagt attatttttt 279000
aaacaataat atggtgggaa tgtaaatcag gcttttctcc tcagtatttt ctgatatttg 279060
ttcagtgttg tataattttt cacattattt catatatatt atttcctttg ggcgatattt 279120
ttattttata attttgtctt ccatgaaatg atcaccatag ttaaacaatg taataaattt 279180
tcttattttc ttagtttctt aaacgtgcag tgaaactttt aggttttccc ctcttcagtg 279240
aaatgttcac agtacatctg tgagattata agagaggtta atttcattaa ttttcagttt 279300
gaccagccat aaaacattca taaagaaatt aagtaccttg cttattaaat cagatagatt 279360
atgatggaaa tggaattaga acttggatct ttgtccagac cttttggaca ggccacatat 279420
ttatttgtta gttttcaaac atgtgtatca tcagtttttc aatcaatttt tagagttatg 279480
taggccctca aaatatgaat taaggagctg tctatgtata tgcctatctt aagtgtgatt 279540
gaaatagtct cactatgatc ttgtgtctgt ctcttctctt ttgctataga tgtgtcccaa 279600
acatggcaca gactttttgg aatataaatg tcgctactgc tgttcagtgg ctgttttttt 279660
ctgttttgga acaacacatt tttgtaatgc ttgtcatgat gattttcaaa gaatgactag 279720
cattcctaag gaagaactac cacactgtcc tgcaggtatg cttttaatat tttaaaatca 279780
cgattatgat ctatatacca tagttttatg taaacattat atgaaagctc tgtttcaagt 279840
gacagaaact caattcaaac tagcctaaag aagcaggagg aattccttga tccttgtaag 279900
cttatgactt tctgggtgaa ttaggaagca ggctcatcat catgagtgag aagttagctg 279960
tgacggagca gatctcatgg ggagtgagaa tgaagtctac taaggattgg tgaaaagatg 280020
gctgttcagc actaaaaagt catatgaagt tcaatattac agaaccattt aaaaggattc 280080
tgtgattttt tttttttttt aacgaagcct ggaaccgttg ccataaaatg aaccaagtga 280140
tttaatctag aatggctggg aatcagtagt gtagtgagca tcagaaagtc aagggaatta 280200
aagaaaccac tcagaataca ggagaaatta ttgtctatgg aaagcaggct gaggggaaag 280260
aagtatgaaa ccaaaaagaa gctgaaaata ctggaagagg acaggaggct agtggcaacg 280320
gtgaggtgga ataccaggct tcacggaagt gagagaagtg gaaggagagg tccgtgcaac 280380
cataggagag aattttacat aagatatatc tgaaattagt gaaaatacat gcacaagtac 280440
atacaacaca atataccgtg ttgtcaaagc tagaaaacac acactgccat ctgctgccta 280500
tcagagtgca agtgatagac ctctccggaa aacagcttaa tagtgcctct caaaattacc 280560
agcgtatcaa cccttcagca ctccctcttc agggatatag ctacaaatgt gaggacagta 280620
aaaaagggca aataaacaag gttattaact acagctttgc tatgataata aaaatgtata 280680
aacaatgcta gtgtccagta gggtagtggc taatattacg catcagttta aaaaaaaaaa 280740
agagtgagga tggtgtttct gtgtgctgat ttggaaagat cttcaggaga tagcatcaga 280800
tgaaaaaagt aaattaggcc aagtggtgtg actgacacct gtaatcccag cactatggga 280860
gaccgaagca ggtggatcac ttgaggtcag gagtacgaga ccagcctggc caacatggtg 280920
aaaccccatc tctactaaat gtacaaaaat tagccaggca tggtggcggg tacctgtaat 280980
ccgagctact cacgaggctg aggccagaga atcacttgag cctgagaggc ggaggttgca 281040
gtgagccaag attgcgccac tgcactccag cctgggcgac agagctgttt caaaaaaaaa 281100
aagcaaattg cagaacagag tatgcagtat gctgcctttt gtaagaggga aaatgagact 281160
atctagtcat atttgtttat atttacataa agaaacccct ggaaagatac tcaagaaact 281220
aatactattg attaactatt gggaaaagca agaaaaagat gagggtagag actagggaaa 281280
gttgcttcca attgtgttat catttttaac attttgattt taaaccatgt gaaacatata 281340
ctatccattt caaaataaag ataagtaggg ttttttcaag tatgactact ttttaccatt 281400
tgctcatgtc aaataaaaat tgttttactg tttctcctca aatactgttt ttttttaata 281460
gaagtagcag gctttgaaag aagcaaggcc agaatgatgt gaagccaggt tatggaggat 281520
aatggacaga acagagatgt gagccatgct tggagggagg gggtgatgtg ctggaggtca 281580
gcaagtgaag ggagtgtgga aagggcagta ttctagatga ctctagatga cttgagcttg 281640
gaggaagggc aattattgaa tgaaagttgt aggttgtggt ctggaaagaa ataggagcca 281700
agagaaaaat cagtcacacg ttgtagccat atgacctgga ggagcttggg agataaccag 281760
cctccagttg agaaagattt aaggcaagca gtatcttcag gggaaatcta gattttactt 281820
aaagtttcct ctatgttaaa aaacagaaat aagaatgcta aaaataagga agttaacaat 281880
gaaacacttt agagaactca gtggtgggta gtagctgaga gaggagggtc aggtttcctc 281940
acaggatcag ggcagccaac acaaaggaat cacaggaggg aggcggggga ggagccagag 282000
ttggcagaag gaaggaatga cctcggtcct gggcattttc acacatattt gctccatttt 282060
tacaatctgc gagtagatgg tattatccct atgttatcaa atggaaaatt gagggctagg 282120
gaggttaatg aactggccta agaacataca ctgagattga ggtatactct cccagcctca 282180
cacatccctc taactcatcc attcatttag agaactggaa tagaataaag gagatcccac 282240
agggatgtga gtagggaaga tggccatata cagtttactt agaaggacag aagaagcaat 282300
tctctaacca ctctcaaccc tgttaattct aatattttta gataatcagt cttcatccat 282360
tcaagctgct ataacaaaat actgtaaact gggtagctta taaacagtgg aaatttattc 282420
tcacagttct ggagaccagg aagtctaaga tctaggaatt agcagtcgag gtgtctggtg 282480
aggacccact ctcagcctca taggtggcac tttcttgctg tcgtggaagg gcagggggcc 282540
tctcctgggt ctcattgata ggaagagcac taatcccatt catggattcc accccatgac 282600
ctcatcacct cccacagctc cacctcctaa caccataaca ttggtgttaa tgttgtagtc 282660
tcagcagtgc accaagatat aacagtctct cattgtctga gataatgcca ggagttcttt 282720
gtcctacctc caagaagatt aaggagcaca gatacaaagg tgaggttaga gcgaaagttt 282780
aataagcaaa agaagaaagc tctctgccag cagagagggg ggcccaaaca ggatgctccc 282840
gtgaggctgg ggcccagggt ttttatggac tggaaagggg aaggaatgtg cttagtctgt 282900
gggctgtctt ggcccgcagc gtgactcagc ttggcccggg accctggccc aggaacccac 282960
tggagcccac tgtgcctatg cccacaaaag gagagagccc cctgactata caaaggacaa 283020
aggcatttct atcccaggtc ttgtccttta tctgattgaa ggtttttctg tctgtgcagc 283080
cgtgggcatg tctttaggca caatgccctg tgctagttcc ctcatcggtg cctgcagctt 283140
gactttttttt ccccaactgc tttttatgtt atatggggat gaggcactga cctgtggacc 283200
tggggctctc tggggaccct tcccttgcta tctacctaag gcaaactaac tcctttcatt 283260
aacacgtcag tatataaatt tggaggagca caaaaacatc cagaccatag cataatccct 283320
ctatccattt ctttctaaaa tatttattga ctaccttctc gtgccaggat acttaatctt 283380
cacagcaccc catgagttag gtattgctgt gtctatttta aagatgaggt atctaagaat 283440
cagaaaaaat aattttactt cagtttcata tctacaaaat gaggataatc gtttctgcct 283500
cctatgactg ttaaatggtt aagtagctga tatactagaa cagtgcctca gtagtaagca 283560
ctcagatgtt tgcaggtgtg ttttcactat ttttatttct caccaccatg ttggattgtg 283620
aacaccttga agatgggagc catgcacttt tcatctttaa tcccaagtac ctaagaatgc 283680
ccttcatata ttaggcatgc ggtaaatatt tgttgagtaa atgactcatt ttttccttga 283740
aaaaacccaa gggctgcagt ttgtgtcacc accattgata tgttgtgtat ctgaactaga 283800
tctgccattg agtgtcccca tcctgcgcac tctcccccac ccactggtgg ggtgggcacc 283860
aatctgcagt gtgatttgga gcaggagcta ctgaactact ttctaacagg aataattaac 283920
tttctagcaa acctctggca tcctcccatg ctgacccatc ctgaggtctg tgcctgcatt 283980
tgtctgaggt ggcactcatt gccactctca tgcctgttag ctctaacctg aagttgactt 284040
ctctgagatt agctgtcttc agtttgacac tctaatgtct tggtcttact cttgtacaga 284100
acttactttt tattcctcta gatcaggcct cagtttgtgg ttgttcagta atagtagtaa 284160
tagccaacat ttattgggta ttatactgtg cagtctaaga gctttataaa tgctagcctt 284220
ttatccatca tggtttcctt ctcttatgtc agaaatgttt ttaaacctag aaaaggtaaa 284280
gtaaatgaga cgtcattcct cattgatcag tgtaagctca ttccatccaa tctcgtgata 284340
tttttctctc aagcacaatc agaatttaga tttattattt tgaaaactag ctgtagaaaa 284400
ctaatgcaga gttcctattc cttcatctac tattaaatag ggactctgct ttcaagtata 284460
agcctagcgt gtttttctga caaagtaagc ctcctggttt ctaaaggaac taaaaatctt 284520
ttctaaatga tatgaaaccc atgacgtgaa gcacattaat ataataattt tcttttttaa 284580
aatactgttt ttggtacatt tgataggcct actttgatta ttatcaacaa attcatatct 284640
tccccaaagt gtttttttcca cattgtattt tataacattg ttcatgtttt taacctgata 284700
actttcattt tcctgctaat atccttcagg tacttttaaa aattacagga atcattggcc 284760
ttcccatttt accagtgtgg gctttttcat cagtaaaaat aaaagggaaa acatggcttc 284820
tttaaactta aatgttttta cttatagaaa aacattctac acaaaaatct ccctgttttc 284880
tattcagaaa aataatgttc tgccagacta aattgagggg ttttgtgacc tttttttgttc 284940
attactctgt tttaaaatga tatatctgat gcatttatta atagaaaaag atctgtagct 285000
cgaagtgatc ctctctaggc aggatatagt gagtaaggga ccccatcact tcttccattg 285060
tacatatctg tgttgaattt tttatagtga acattttttta cttttgtgat cagaagaaaa 285120
atttctaaat gttatatttg tataaccata gtcatgttat ttctttgaat aacctatcag 285180
tgatttatat ttctgtgagg tttatatgtg tgtattctta aaacattatt ttcctttgcc 285240
tccttcaaat tttatacaggt cccaaaggca agcagttaga aggaactgaa tgtccactcc 285300
atgttgttca tccacccact ggggaagagt ttgctctggg atgtggagtg tgcagaaatg 285360
cccacacttt ttagaacacg cagatccttt gtctacagag agaaaaattg ccttcatccc 285420
ccaagaggat gcggtgaagt ttaaactctg ctcaggataa ggacgggacc atttttacat 285480
ccatgaaaat gaaccattca cagtgcaaga aggataccaa ataccatgta cataattctt 285540
gctatgaaaa gtttccccat tattttggtt tatcttcttt tgaacaaatg acatcaaact 285600
tgtgaggtgt ttgcatgtgg ccattaccgt cattggcctg tgaagcattg gacatttata 285660
gataattgat ataaaagaat cgccatgccc atggactaag aacgatgctg gctttcaagc 285720
aaaaaagaaa aataatcatt gtttattgta tactgccttt ttgtaatcct gtacaattgc 285780
atcacgggtg gggataaaaa gaggaatatt ctggtttatt tcctagactg ttatttaaaa 285840
aaaaaaaaaa cattgtgtta ggacagcata taaatgtaat aagtatcaca ctgtatataa 285900
acatatcaat gtttgtcctg tataagaatt actaaattac aaatgcaatt tcatttaaac 285960
ttctaggtta agtttgagcc tgaaatttta atgaagtgca atactgagtg tgcctcatta 286020
tcttgcagct gtaaacatat tggaatgtac atgtcaataa aaccactgta catttttata 286080
cagtgataaa gtctaccact gtgggaggta ttgtttaaaa aacaaaattt gaacaccttt 286140
aaggtctaaa agtccagttt tcctcagaaa gaaatttact aacacaacac attcataatt 286200
ttcaaaactg ttagagaaaa taagaatagt aatgaagtgc aatgttggaa tcttaaaccc 286260
taagcagaag atcataaata tatatatata tattcgtagg taaatatatt cataccaaag 286320
acagaagaaa gcatttagga aattaacttc tattttaact agcagcattt ttaactttat 286380
ttatttattt atgagacagg gtcttacact gtcacccagg ctggagtaca gcggcgtgat 286440
ctcagctcac tgcagcctcc aactgggctc aagcgatcct ccagcctcag ccccctgagt 286500
agttgggact acaggcatgc accagcacca tgcccagcta attttgtaat ttttgtagag 286560
atggggtttt gccatgttgc cgaggctggt ctcaaactcc tagactcaag caatccccac 286620
tgctttggcc tcccaaagtg ctaggattac aggcgtgagc cattgcaccc agcccctttt 286680
tgaagttcat ataaagtaat aaaatcacta atttttttatt cattttctat agacaacggt 286740
gtgtttaggt acatcttttt gacactcgag tcatgaaatt gccaaattat tgattgttga 286800
ctcatcatac atcagattag caaaactttt gttgttgttg ttgtatttga gacagtctca 286860
ctctgctgcc cacactggag tgcagtggca ccatcttggc tcactgcaac ctccacctcc 286920
caggttcaag cgattctcct gcctcagcct cccaaggagc tgggactaca ggcgtgtgcc 286980
acctcaccca gctaattttt gtatttttag tagggatggg gtttcaccag gctggtcttg 287040
aactcctgac ctcaggtgat ccgctcgcct ccggcctccc aaaattccgg tattacaggc 287100
gtgagccacc gcgcctggcc aagactagca aaagttttaa tcacattttg ttctaaattc 287160
caactgtggg aaatatagaa cttaatttgt caatatagaa ttactgacaa atttaatgac 287220
atttgtgtta agcatttatg agaaatttaa aacaatcttt gccttgaagg aacttaaaaa 287280
ataaagatca gatctgagca caggtaacta ttttacagaa tgttctaata agtttcataa 287340
aaatatccaa gccaaatgct tcaggattta ggaaaaatca ttattgtttt gtcgttggga 287400
gtgtagctaa gaggccattt aagctgcctt ttgaagaata agtagcattt caaggagcag 287460
agatgtggag aaaggcatga gaaataccta agtaggaaaa tctagaatat gatcaaagaa 287520
cagtaagtat gagtgttcaa gcttaggatt gactgaaaat gtttccagaa aacacaaagt 287580
acgtagagag actaaagctg ttacaagaaa actggagggg agaatgcagt gaggacactg 287640
tcagtatatt tgacttgaca ctgtcagtat atttgactta aattcacagg ccacaggaat 287700
gaaactaacc ttgagaatgc cacacagata agagacttta tggacactta atagctgcga 287760
agaataccat cttgcgtcag ttaactttgc tggcaaactg gtcagctcag tttgtaaatc 287820
gtagaggaaa agaaacaaac tattgagatg gcttggctaa aaaagccatc tcaagttatg 287880
aaagggataa aatcaacaaa gctgtgtagt gaatactcac aatgacttca acttatcttc 287940
atttatgagg aagtcacttt tagtcaggat ctctagcacc tcaaaaccag agaacataaa 288000
catcttagca ataaattatg acaaagcaca ggaaggagtg gctttggcag gcatttttag 288060
ctcaagcatc ctacacacaa ggaccatcct tcaaacactg catgtaacat ccaaggcagg 288120
agacagaaag cagaatcaca gtggtagatg tcagtgaatc ttcctggaaa gaaattgttt 288180
ttccgttata ttttcaagcc taggaaaagc catttttctt agtattatgg ctagactgtt 288240
taggcctaaa atctccctat tttatcaata agcttatttg gttttggttt ttggtttttt 288300 gagtttttg ggttttttt tttttttta agaaagggtc tcactctgtc gccccagctg 288360
gagtgcagtg gcgttatctc ggctcgcagc aacctctgcc ttttgggctc aagtgatcct 288420
cccacctcag ccccaagtag ctgggagtac aggcacgagc caccatgccc agctaatttt 288480
tgtaattgaa acagggtttc accatgttgg ccaggctggt ctcaaactcc tgagctgaag 288540
cgatctacct gcctcagcta ggattacagg tgtgagccac cgcacccaac ctcaataagc 288600
ttatttgata aaatatatgc aatgctccct ttattcactt ttcattcaga atgtttagta 288660
atttgtattg tttttcagat tttcagccca atatatctcc ctgcccactg tgtcactgta 288720
ttctacctat acatcatcac gtgtttctgc tattggctgt atgatggaac actgcggctc 288780
attttcctga aaactgccga tagtgcatag agtgctggga tggaaaccag aagctttgaa 288840
ttcaagcctt ggttctgcct tgtttttgct tgggtggcct tgagtcagcc acataccttt 288900
taaaatctca atttattaga aattattcca aatcaaaatc aaatgagaag gtatatacaa 288960
aagtgcttta tcccacaata aactattcaa gagagagcaa aggagaggac atttactcaa 289020
cacctcctaa aaggcagcca gtgaaattag gcattttatt taatcctcct ggcaactctg 289080
agagtaaagc attattaatc ccattttggc tgtttaaaga aattatttgc actagattcc 289140
agctgtagtt tagcttcaga aaaaaaaatc ctgagatgtg aattcacagc tttctgggtt 289200
taaagcccaa gctctatcac atcatgctat tattgttaca ttactgctag ttctatgaaa 289260
agaaatacta atttatgaaa tacatcttat ccaaaatggt tgggaccaga agtgtttctg 289320
atttcgggtt ttttcaggtt tgggaatatt tgcattacca gttgagcatc ccaaatctga 289380
aatccaaaat gctccagtga gcattttatt tgggtatcag gcatgtcagt actcaaagtt 289440
ttaaatttca ggacacttat cgtatggcca aggttgcaca ggggacaaga cagcatatgc 289500
ctccaagagt gttcagtgtc gtcaggaggt acctccaccc agatttccct tcaggggagg 289560
ccccacctca aggagtccag ttagctgaca gcctccagct ttaatcaccc ccacatatga 289620
cccaatgtca cactcctcca gggcagcccc agcctgtgat agagttcaga tggggttctc 289680
gggcctggcc atttctgccc aagcggcact cctgcgtgcg cggtcttgcg taagaactca 289740
ggccgactga gactgtctta cagctgccct gcagtcggag gcttttccta cccaatcttt 289800
ccttctctct tctttcctag atgccagacc tgcatcacag tctaatggct ctccctgccc 289860
actcctgctc cctcatcact ttatctttca tagggattac ccccaacaga ttttctgcac 289920
ttctaactta atcttggcat ctgcttccta gaggacctgc ctgacacagg agggtaatac 289980
attttaaatg acttacttat ggcttcattt ctcaaatgtc ttagggtggc ttagaaaaaa 290040

<210> SEQ ID NO 4
<211> LENGTH: 739
<212> TYPE: DNA
<213> ORGANISM: Rattus norvegicus

<400> SEQUENCE: 4
gcttgccaaa cgattcaggt gccaacaata ctaaattcac tacagagaag tgtacaggca 60
gtgttggttg gaaagattca agtccaggac tggtttagca atggcattaa gaaagcagct 120
ttaatgcaca agtggccatt aaaggaaata tctgttgatg aagatgacca gtgtctgctt 180
cagaatgatg gattttttct ttatttgtta tgcaaggatg gattatacaa aataggctct 240

```
ggatacagtg gaacagttag gggtcatata tataattcta catctcgtat cagaaacaga    300

aaagaaaaga agtcttggtt aggatatgcc cagggttact tgttatatcg ggatgtgaat    360

aaccacagta tgacagccat aagaataagc cccgaaacgc tggagcaaga cggcactgta    420

atgttaccag cttgcagatg ttgcttgaca cattcctgaa gctgctgtct tataatgtca    480

tacacgggta aagagcggac acgggaagtt gtcagtgtga cgccgaagga agacccagcc    540

ctcagcccca gccctcaagc ctgaagaagc ctgctgtcat ttcatcactt ctttgacacg    600

gactacagtt tcttcaataa aatcatttgc tttttccctg acaagggata ctacttctct    660

gtagcttttc atcaagaaga gaagtagtaa actgtcagat ttataggtgg ttactgaata    720

ccatgtttaa aatgaacat                                                  739


<210> SEQ ID NO 5
<211> LENGTH: 473
<212> TYPE: DNA
<213> ORGANISM: Rattus norvegicus

<400> SEQUENCE: 5

gcagcttcag agtgacagag gaactgtctc aacatcttca agaccagtgt ctacatcagc     60

aaagtcagag ctgccctcca agaacagcag atcagttaaa cctgatgggc gtgtgagccg    120

gactactgct gaccagaaga agccacgggg cacagaaggc ttatctgcta gtgaatccct    180

catgttaaaa tctgatgctg caaagttgag gtcagactcc catagtaggt cactgtcccc    240

taaccataac actttgcaga cactgaagtc tgatggaagg gtatcttcta gcttcagggc    300

tgaatcccca ggaccaggct ctaggtcatc ctctcctaag cccaagactc tgccgactcc    360

caggtctagc ccatctggtg ctagctctcc acgctcctcc tcaccgcagg ataaaaatct    420

acctcagaaa agcacagctc ctgctaagac aaaacttgac ccacctcggg agc           473


<210> SEQ ID NO 6
<211> LENGTH: 708
<212> TYPE: DNA
<213> ORGANISM: Rattus norvegicus
<220> FEATURE:
<221> NAME/KEY: misc_feature
<222> LOCATION: (615)..(615)
<223> OTHER INFORMATION: n is a, c, g, or t

<400> SEQUENCE: 6

tttttttttt tttttttcc tttttcgttt ttttattctc tttctcacat tctttctttt     60

taaggactgc acaggaacct ggacttggaa aaatcatatt ctgggaagca gctttgattg    120

tagccaaaga gatgtcctcc cagaaggcca ctaagtgttg taatgttaag gggagcggag    180

acctagactt cactgagtga tgcatggaca tttcaaaagt ggcttccgat tttccgtctt    240

cacacttctc atgtagaggt ggctccttaa gcatagacag gaccttattt ttgttgatac    300

ttcccatctt ggatatgtct ggtccgtgag gtgaaatgtt gaacatattt agggcagatg    360

atatttccaa cgaatgtcta ttttttaact tgatttcctt ttcctctgtg ggtggctggc    420

tattcaaact acttcttatg ggagcatgtt ctttggaaag ttcaggatta aacttcagga    480

aggaagagca ggccattgca tcatgtacta tgccttcatg ccacagaaaa gaggcaaaga    540

cagctcgggc acactcagcc acggacgggg acatggcttg cttggctggc tctaaagatt    600

tggctccatc tcctnttgaa agaaagttag acttttcttt tttgggcctg gtgtgtctat    660

tagcacattt ccgacttatt ttggggtgat gctctcattt cctgttca                 708
```

-continued

<210> SEQ ID NO 7
<211> LENGTH: 529
<212> TYPE: DNA
<213> ORGANISM: Rattus norvegicus

<400> SEQUENCE: 7
taagcttgct ctgtccctgc cccgtacatc tcagtaactc ctgatgcaag tcccaatgtc 60
tttgaagagc cggagagcaa tatgaagtcg atgccaccaa gtttggaaac gagcccgata 120
actgacaccg acctggctaa gagaactgtc ttccagaggt catactcagt tgtcgcttcg 180
gaatatgata aacaacactc cattttacct gcacgagtta aagccatccc tagaaggaga 240
gtgaacagtg gagacacgga agttgggtct tctctcttgc gacatccgtc accggagctt 300
tcccggctta tatcagccca cagctctctc tccaaaggag agcgaaactt ccagtggcca 360
gtcttagctt tcgtcataca gcatcatgat ttagaagggc tggaaatcgc aatgaagcag 420
gccttaagga agtcggcttg ccgtgtgttt gctatggagg cattcaactg gcttctctgt 480
aatgtcatcc aaacaacgtc tctgcatgac attctctggc actttgtgg 529

<210> SEQ ID NO 8
<211> LENGTH: 667
<212> TYPE: DNA
<213> ORGANISM: Rattus norvegicus

<400> SEQUENCE: 8
acgaagggct gcataagagt gaagcgatca cgacgccggg cgtcaggttt tacaatgatc 60
cagccggcta tgccatgaac agatacgcat attatgtttg ctacaaatgc agaaaggcat 120
attttggtgg tgaagctcgc tgtgatgctg aggctggaca aggagacgac tacgacccca 180
gagagctcat ctgtggagcc tgttctgatg tgtctagggc tcagatgtgt cccaaacatg 240
gaacagactt tctagaatac aaatgtcgct actgctgttc agtggctgtc ttcttctgtt 300
ttggaacaac acatttctgc aatgcttgtc atgatgattt tcaaagaatg accagcattc 360
ctaaggaaga gctcccacac tgtcctgcag gtcccaaagg caaacagcta gaaggaactg 420
aatgtccact ccatgttgtt catccgccca cgggggaaga gtttgctctt ggttgtggag 480
tgtgcagaaa tgctcacacg ttttagaact ttcagatcct ttgtctacaa agaggatagt 540
tgccttcatc ccctgggagg atgcagtgaa actttaaact ctgctcaagg ataaggaacg 600
gggaccattt ttacattctg aaaacgaacc attttccagt gccaggaagt gatgccccaa 660
atacctg 667

<210> SEQ ID NO 9
<211> LENGTH: 652
<212> TYPE: DNA
<213> ORGANISM: Rattus norvegicus
<220> FEATURE:
<221> NAME/KEY: misc_feature
<222> LOCATION: (605)..(605)
<223> OTHER INFORMATION: n is a, c, g, or t

<400> SEQUENCE: 9
tttttttttt ttttttttga cgctctcact gtgtagagca cagtggttta ctgacgtaca 60
ttccaatatg ctgacagctg caaggtagtg aggcacaccc agtattgcac tgcattagag 120
cttcaggctc aaacgtaacc tacaggttta aatgagactg ctgtgtcatt tagtaattct 180
catacaggac aaacactgat agctttatat acagtctgat acttattaca attataggcc 240
ttactaacac aatttttttt tttaaataac agtctaggaa agaaaccaga atattcctct 300

-continued ttttataccc acccgtgatg caattgtaca ggattacaaa aaggcagtat acaataaaca 360
gtgattattt ttcttttttt gcttgaaagc cagcatcatt cttagtccat gagtatggag 420
atccttttat atcaattatc tataaatgtc caatgctcca caggccagtg acggtaatgg 480
ccacatgcaa acacctcaca agtttgatgt cttggttcaa agatgataaa ccaaaacaat 540
ggggaaacgt tcgtagcaag aattatgtac acagtatttg gcatcactcc tgcactggaa 600
atggntcgtt ttcagaatgt aaaatggtcc cgttcttatc ctgagcagag tt 652

<210> SEQ ID NO 10
<211> LENGTH: 18
<212> TYPE: DNA
<213> ORGANISM: Artificial
<220> FEATURE:
<223> OTHER INFORMATION: Oligonucleotide Primer (sense) used for amplification of rat GADPH

<400> SEQUENCE: 10
gaagggtggg gccaaaag 18

<210> SEQ ID NO 11
<211> LENGTH: 20
<212> TYPE: DNA
<213> ORGANISM: Artificial
<220> FEATURE:
<223> OTHER INFORMATION: Oligonucleotide Primer (antisense) used for amplification of rat GADPH

<400> SEQUENCE: 11
ggatgcaggg atgatgttct 20

<210> SEQ ID NO 12
<211> LENGTH: 24
<212> TYPE: DNA
<213> ORGANISM: Artificial
<220> FEATURE:
<223> OTHER INFORMATION: Oligonucleotide Primer (sense) used for amplification of rat PAM

<400> SEQUENCE: 12
ggtggtgaag ctcgctgtga tgct 24

<210> SEQ ID NO 13
<211> LENGTH: 24
<212> TYPE: DNA
<213> ORGANISM: Artificial
<220> FEATURE:
<223> OTHER INFORMATION: Oligonucleotide Primer (antisense) used for amplification of rat PAM

<400> SEQUENCE: 13
cgtgtgagca tttctgcaca ctcc 24

<210> SEQ ID NO 14
<211> LENGTH: 18
<212> TYPE: DNA
<213> ORGANISM: Artificial
<220> FEATURE:
<223> OTHER INFORMATION: ODNs primer (sense) from rat PAM

<400> SEQUENCE: 14
gactggttta gcaatggc 18

<210> SEQ ID NO 15
<211> LENGTH: 18

<212> TYPE: DNA
<213> ORGANISM: Artificial
<220> FEATURE:
<223> OTHER INFORMATION: ODN primer (antisense) from rat PAM

<400> SEQUENCE: 15
gccattgcta aaccagtc 18

<210> SEQ ID NO 16
<211> LENGTH: 18
<212> TYPE: DNA
<213> ORGANISM: Artificial
<220> FEATURE:
<223> OTHER INFORMATION: ODNs Antisense primer with 3 mutations from rat PAM

<400> SEQUENCE: 16
gcaattgcta aatcagta 18

<210> SEQ ID NO 17
<211> LENGTH: 1010
<212> TYPE: PRT
<213> ORGANISM: Homo sapiens

<400> SEQUENCE: 17

```
Asn Asn His Ser Met Thr Ala Ile Arg Ile Ser Pro Glu Thr Leu Glu
1               5                   10                  15

Gln Asp Gly Thr Val Met Leu Pro Asp Cys His Thr Glu Gly Gln Asn
            20                  25                  30

Ile Leu Phe Thr Asp Gly Glu Tyr Ile Asn Gln Ile Ala Ala Ser Arg
        35                  40                  45

Asp Asp Gly Phe Val Val Arg Ile Phe Ala Thr Ser Thr Glu Pro Val
    50                  55                  60

Leu Gln Gln Glu Leu Gln Leu Lys Leu Ala Arg Lys Cys Leu His Ala
65                  70                  75                  80

Cys Arg Ile Ser Leu Phe Asp Leu Glu Lys Asp Leu His Ile Ile Ser
                85                  90                  95

Thr Gly Phe Asp Glu Glu Ser Ala Ile Leu Gly Ala Gly Arg Glu Phe
            100                 105                 110

Ala Leu Met Lys Thr Ala Asn Gly Lys Ile Tyr Tyr Thr Gly Lys Tyr
        115                 120                 125

Gln Ser Leu Gly Ile Lys Gln Gly Gly Pro Ser Ala Gly Lys Trp Val
    130                 135                 140

Glu Leu Pro Ile Thr Lys Ser Pro Lys Ile Val His Phe Ser Val Gly
145                 150                 155                 160

His Asp Gly Ser His Ala Leu Leu Val Ala Glu Asp Gly Ser Ile Phe
                165                 170                 175

Phe Thr Gly Ser Ala Ser Lys Gly Glu Asp Gly Glu Ser Ile Lys Ser
            180                 185                 190

Arg Arg Gln Ser Lys Pro Tyr Lys Pro Lys Lys Ile Ile Lys Met Glu
        195                 200                 205

Gly Lys Ile Val Val Tyr Thr Ala Cys Asn Asn Gly Ser Ser Ser Val
    210                 215                 220

Ile Ser Lys Asp Gly Glu Leu Tyr Met Phe Gly Lys Asp Ala Ile Tyr
225                 230                 235                 240

Ser Asp Ser Ser Ser Leu Val Thr Asp Leu Lys Gly His Phe Val Thr
                245                 250                 255

Gln Val Ala Met Gly Lys Ala His Thr Cys Val Leu Met Lys Asn Gly
```

-continued

```
            260                 265                 270

Glu Val Trp Thr Phe Gly Val Asn Asn Lys Gly Gln Cys Gly Arg Asp
        275                 280                 285

Thr Gly Ala Met Asn Gln Gly Gly Lys Gly Phe Gly Val Glu Asn Met
    290                 295                 300

Ala Thr Ala Met Asp Glu Asp Leu Glu Glu Glu Leu Asp Glu Lys Asp
305                 310                 315                 320

Glu Lys Ser Met Met Cys Pro Pro Gly Met His Lys Trp Lys Leu Glu
                325                 330                 335

Gln Cys Met Val Cys Thr Val Cys Gly Asp Cys Thr Gly Tyr Gly Ala
            340                 345                 350

Ser Cys Val Ser Ser Gly Arg Pro Asp Arg Val Pro Gly Gly Ile Cys
        355                 360                 365

Gly Cys Gly Ser Gly Glu Ser Gly Cys Ala Val Cys Gly Cys Cys Lys
    370                 375                 380

Ala Cys Ala Arg Glu Leu Asp Gly Gln Glu Ala Arg Gln Arg Gly Ile
385                 390                 395                 400

Leu Asp Ala Val Lys Glu Met Ile Pro Leu Asp Leu Leu Leu Ala Val
                405                 410                 415

Pro Val Pro Gly Val Asn Ile Glu Glu His Leu Gln Leu Arg Gln Glu
            420                 425                 430

Glu Lys Arg Gln Arg Val Ile Arg Arg His Arg Leu Glu Glu Gly Arg
        435                 440                 445

Gly Pro Leu Val Phe Ala Gly Pro Ile Phe Met Asn His Arg Glu Gln
    450                 455                 460

Ala Leu Ala Arg Leu Arg Ser His Pro Ala His Val Lys His Lys Arg
465                 470                 475                 480

Asp Lys His Lys Asp Gly Ser Gly Glu Arg Gly Glu Lys Asp Ala Ser
                485                 490                 495

Lys Ile Thr Thr Tyr Pro Pro Gly Ser Val Arg Phe Asp Cys Glu Leu
            500                 505                 510

Arg Ala Val Gln Val Ser Cys Gly Phe His His Ser Val Val Leu Met
        515                 520                 525

Glu Asn Gly Asp Val Tyr Thr Phe Gly Tyr Gly Gln His Gly Gln Leu
    530                 535                 540

Gly His Gly Asp Val Asn Ser Arg Gly Cys Pro Thr Leu Val Gln Ala
545                 550                 555                 560

Leu Pro Gly Pro Ser Thr Gln Val Thr Ala Gly Ser Asn His Thr Ala
                565                 570                 575

Val Leu Leu Met Asp Gly Gln Val Phe Thr Phe Gly Ser Phe Ser Lys
            580                 585                 590

Gly Gln Leu Gly Arg Pro Ile Leu Asp Val Pro Tyr Trp Asn Ala Lys
        595                 600                 605

Pro Ala Pro Met Pro Asn Ile Gly Ser Lys Tyr Gly Arg Lys Ala Thr
    610                 615                 620

Trp Ile Gly Ala Ser Gly Asp Gln Thr Phe Leu Arg Ile Asp Glu Ala
625                 630                 635                 640

Leu Ile Asn Ser His Val Leu Ala Thr Ser Glu Ile Phe Ala Ser Lys
                645                 650                 655

His Ile Ile Gly Leu Val Pro Ala Ser Ile Ser Glu Pro Pro Pro Phe
            660                 665                 670

Lys Cys Leu Leu Ile Asn Lys Val Asp Gly Ser Cys Lys Thr Phe Asn
        675                 680                 685
```

Asp Ser Glu Gln Glu Asp Leu Gln Gly Phe Gly Val Cys Leu Asp Pro
    690                 695                 700

Val Tyr Asp Val Ile Trp Arg Phe Arg Pro Asn Thr Arg Glu Leu Trp
705                 710                 715                 720

Cys Tyr Asn Ala Val Val Ala Asp Ala Arg Leu Pro Ser Ala Ala Asp
                725                 730                 735

Met Gln Ser Arg Cys Ser Ile Leu Ser Pro Glu Leu Ala Leu Pro Thr
            740                 745                 750

Gly Ser Arg Ala Leu Thr Thr Arg Ser His Ala Ala Leu His Ile Leu
        755                 760                 765

Gly Cys Leu Asp Thr Leu Ala Ala Met Gln Asp Leu Lys Met Gly Val
    770                 775                 780

Ala Ser Thr Glu Glu Glu Thr Gln Ala Val Met Lys Val Tyr Ser Lys
785                 790                 795                 800

Glu Asp Tyr Ser Val Val Asn Arg Phe Glu Ser His Gly Gly Gly Trp
                805                 810                 815

Gly Tyr Ser Ala His Ser Val Glu Ala Ile Arg Phe Ser Ala Asp Thr
            820                 825                 830

Asp Ile Leu Leu Gly Gly Leu Gly Leu Phe Gly Gly Arg Gly Glu Tyr
        835                 840                 845

Thr Ala Lys Ile Lys Leu Phe Glu Leu Gly Pro Asp Gly Gly Asp His
    850                 855                 860

Glu Thr Asp Gly Asp Leu Leu Ala Glu Thr Asp Val Leu Ala Tyr Asp
865                 870                 875                 880

Cys Ala Ala Arg Glu Lys Tyr Ala Met Met Phe Asp Glu Pro Val Leu
                885                 890                 895

Leu Gln Ala Gly Trp Trp Tyr Val Ala Trp Ala Arg Val Ser Gly Pro
            900                 905                 910

Ser Ser Asp Cys Gly Ser His Gly Gln Ala Ser Ile Thr Thr Asp Asp
        915                 920                 925

Gly Val Val Phe Gln Phe Lys Ser Ser Lys Lys Ser Asn Asn Gly Thr
    930                 935                 940

Asp Val Asn Ala Gly Gln Ile Pro Gln Leu Leu Tyr Arg Leu Pro Thr
945                 950                 955                 960

Ser Asp Gly Ser Ala Ser Lys Gly Lys Gln Gln Thr Ser Glu Pro Val
                965                 970                 975

His Ile Leu Lys Arg Ser Phe Ala Arg Thr Val Ser Val Glu Cys Phe
            980                 985                 990

Glu Ser Leu Leu Ser Ile Leu His  Trp Ser Trp Thr Thr  Leu Val Leu
        995                 1000                1005

Gly Val
    1010

<210> SEQ ID NO 18
<211> LENGTH: 617
<212> TYPE: PRT
<213> ORGANISM: Homo sapiens

<400> SEQUENCE: 18

Ile Phe Ala Thr Ser Thr Glu Pro Val Leu Gln Gln Glu Leu Gln Leu
1               5                   10                  15

Lys Leu Ala Arg Lys Cys Leu His Ala Cys Arg Ile Ser Leu Phe Asp
            20                  25                  30

Leu Glu Lys Asp Leu His Ile Ile Ser Thr Gly Phe Asp Glu Glu Ser

-continued

```
        35                  40                  45

Ala Ile Leu Gly Ala Gly Arg Glu Phe Ala Leu Met Lys Thr Ala Asn
    50                  55                  60

Gly Lys Ile Tyr Tyr Thr Gly Lys Tyr Gln Ser Leu Gly Ile Lys Gln
65                  70                  75                  80

Gly Gly Pro Ser Ala Gly Lys Trp Val Glu Leu Pro Ile Thr Lys Ser
                85                  90                  95

Pro Lys Ile Val His Phe Ser Val Gly His Asp Gly Ser His Ala Leu
            100                 105                 110

Leu Val Ala Glu Asp Gly Ser Ile Phe Phe Thr Gly Ser Ala Ser Lys
        115                 120                 125

Gly Glu Asp Gly Glu Ser Ile Lys Ser Arg Arg Gln Ser Lys Pro Tyr
    130                 135                 140

Lys Pro Lys Lys Ile Ile Lys Met Glu Gly Lys Ile Val Val Tyr Thr
145                 150                 155                 160

Ala Cys Asn Asn Gly Ser Ser Ser Val Ile Ser Lys Asp Gly Glu Leu
                165                 170                 175

Tyr Met Phe Gly Lys Asp Ala Ile Tyr Ser Asp Ser Ser Ser Leu Val
            180                 185                 190

Thr Asp Leu Lys Gly His Phe Val Thr Gln Val Ala Met Gly Lys Ala
        195                 200                 205

His Thr Cys Val Leu Met Lys Asn Gly Glu Val Trp Thr Phe Gly Val
    210                 215                 220

Asn Asn Lys Gly Gln Cys Gly Arg Asp Thr Gly Ala Met Asn Gln Gly
225                 230                 235                 240

Gly Lys Gly Phe Gly Val Glu Asn Met Ala Thr Ala Met Asp Glu Asp
                245                 250                 255

Leu Glu Glu Glu Leu Asp Glu Lys Asp Glu Lys Ser Met Met Cys Pro
            260                 265                 270

Pro Gly Met His Lys Trp Lys Leu Glu Gln Cys Met Val Cys Thr Val
        275                 280                 285

Cys Gly Asp Cys Thr Gly Tyr Gly Ala Ser Cys Val Ser Ser Gly Arg
    290                 295                 300

Pro Asp Arg Val Pro Gly Gly Ile Cys Gly Cys Gly Ser Gly Glu Ser
305                 310                 315                 320

Gly Cys Ala Val Cys Gly Cys Cys Lys Ala Cys Ala Arg Glu Leu Asp
                325                 330                 335

Gly Gln Glu Ala Arg Gln Arg Gly Ile Leu Asp Ala Val Lys Glu Met
            340                 345                 350

Ile Pro Leu Asp Leu Leu Leu Ala Val Pro Val Pro Gly Val Asn Ile
        355                 360                 365

Glu Glu His Leu Gln Leu Arg Gln Glu Glu Lys Arg Gln Arg Val Ile
    370                 375                 380

Arg Arg His Arg Leu Glu Glu Gly Arg Gly Pro Leu Val Phe Ala Gly
385                 390                 395                 400

Pro Ile Phe Met Asn His Arg Glu Gln Ala Leu Ala Arg Leu Arg Ser
                405                 410                 415

His Pro Ala His Val Lys His Lys Arg Asp Lys His Lys Asp Gly Ser
            420                 425                 430

Gly Glu Arg Gly Glu Lys Asp Ala Ser Lys Ile Thr Thr Tyr Pro Pro
        435                 440                 445

Gly Ser Val Arg Phe Asp Cys Glu Leu Arg Ala Val Gln Val Ser Cys
    450                 455                 460
```

```
Gly Phe His His Ser Val Val Leu Met Glu Asn Gly Asp Val Tyr Thr
465                 470                 475                 480

Phe Gly Tyr Gly Gln His Gly Gln Leu Gly His Gly Asp Val Asn Ser
                485                 490                 495

Arg Gly Cys Pro Thr Leu Val Gln Ala Leu Pro Gly Pro Ser Thr Gln
            500                 505                 510

Val Thr Ala Gly Ser Asn His Thr Ala Val Leu Leu Met Asp Gly Gln
        515                 520                 525

Val Phe Thr Phe Gly Ser Phe Ser Lys Gly Gln Leu Gly Arg Pro Ile
    530                 535                 540

Leu Asp Val Pro Tyr Trp Asn Ala Lys Pro Ala Pro Met Pro Asn Ile
545                 550                 555                 560

Gly Ser Lys Tyr Gly Arg Lys Ala Thr Trp Ile Gly Ala Ser Gly Asp
                565                 570                 575

Gln Thr Phe Leu Arg Ile Asp Glu Ala Leu Ile Asn Ser His Val Leu
            580                 585                 590

Ala Thr Ser Glu Ile Phe Ala Ser Lys His Ile Ile Gly Leu Val Pro
        595                 600                 605

Ala Ser Ile Ser Glu Pro Pro Pro Phe
    610                 615


<210> SEQ ID NO 19
<211> LENGTH: 567
<212> TYPE: PRT
<213> ORGANISM: Homo sapiens

<400> SEQUENCE: 19

Gly Arg Glu Phe Ala Leu Met Lys Thr Ala Asn Gly Lys Ile Tyr Tyr
1               5                   10                  15

Thr Gly Lys Tyr Gln Ser Leu Gly Ile Lys Gln Gly Gly Pro Ser Ala
            20                  25                  30

Gly Lys Trp Val Glu Leu Pro Ile Thr Lys Ser Pro Lys Ile Val His
        35                  40                  45

Phe Ser Val Gly His Asp Gly Ser His Ala Leu Leu Val Ala Glu Asp
    50                  55                  60

Gly Ser Ile Phe Phe Thr Gly Ser Ala Ser Lys Gly Glu Asp Gly Glu
65                  70                  75                  80

Ser Ile Lys Ser Arg Arg Gln Ser Lys Pro Tyr Lys Pro Lys Lys Ile
                85                  90                  95

Ile Lys Met Glu Gly Lys Ile Val Val Tyr Thr Ala Cys Asn Asn Gly
            100                 105                 110

Ser Ser Ser Val Ile Ser Lys Asp Gly Glu Leu Tyr Met Phe Gly Lys
        115                 120                 125

Asp Ala Ile Tyr Ser Asp Ser Ser Ser Leu Val Thr Asp Leu Lys Gly
    130                 135                 140

His Phe Val Thr Gln Val Ala Met Gly Lys Ala His Thr Cys Val Leu
145                 150                 155                 160

Met Lys Asn Gly Glu Val Trp Thr Phe Gly Val Asn Asn Lys Gly Gln
                165                 170                 175

Cys Gly Arg Asp Thr Gly Ala Met Asn Gln Gly Gly Lys Gly Phe Gly
            180                 185                 190

Val Glu Asn Met Ala Thr Ala Met Asp Glu Asp Leu Glu Glu Glu Leu
        195                 200                 205

Asp Glu Lys Asp Glu Lys Ser Met Met Cys Pro Pro Gly Met His Lys
```

```
    210                 215                 220

Trp Lys Leu Glu Gln Cys Met Val Cys Thr Val Cys Gly Asp Cys Thr
225                 230                 235                 240

Gly Tyr Gly Ala Ser Cys Val Ser Ser Gly Arg Pro Asp Arg Val Pro
                245                 250                 255

Gly Gly Ile Cys Gly Cys Gly Ser Gly Glu Ser Gly Cys Ala Val Cys
            260                 265                 270

Gly Cys Cys Lys Ala Cys Ala Arg Glu Leu Asp Gly Gln Glu Ala Arg
        275                 280                 285

Gln Arg Gly Ile Leu Asp Ala Val Lys Glu Met Ile Pro Leu Asp Leu
    290                 295                 300

Leu Leu Ala Val Pro Val Pro Gly Val Asn Ile Glu Glu His Leu Gln
305                 310                 315                 320

Leu Arg Gln Glu Glu Lys Arg Gln Arg Val Ile Arg Arg His Arg Leu
                325                 330                 335

Glu Glu Gly Arg Gly Pro Leu Val Phe Ala Gly Pro Ile Phe Met Asn
            340                 345                 350

His Arg Glu Gln Ala Leu Ala Arg Leu Arg Ser His Pro Ala His Val
        355                 360                 365

Lys His Lys Arg Asp Lys His Lys Asp Gly Ser Gly Glu Arg Gly Glu
    370                 375                 380

Lys Asp Ala Ser Lys Ile Thr Thr Tyr Pro Pro Gly Ser Val Arg Phe
385                 390                 395                 400

Asp Cys Glu Leu Arg Ala Val Gln Val Ser Cys Gly Phe His His Ser
                405                 410                 415

Val Val Leu Met Glu Asn Gly Asp Val Tyr Thr Phe Gly Tyr Gly Gln
            420                 425                 430

His Gly Gln Leu Gly His Gly Asp Val Asn Ser Arg Gly Cys Pro Thr
        435                 440                 445

Leu Val Gln Ala Leu Pro Gly Pro Ser Thr Gln Val Thr Ala Gly Ser
    450                 455                 460

Asn His Thr Ala Val Leu Leu Met Asp Gly Gln Val Phe Thr Phe Gly
465                 470                 475                 480

Ser Phe Ser Lys Gly Gln Leu Gly Arg Pro Ile Leu Asp Val Pro Tyr
                485                 490                 495

Trp Asn Ala Lys Pro Ala Pro Met Pro Asn Ile Gly Ser Lys Tyr Gly
            500                 505                 510

Arg Lys Ala Thr Trp Ile Gly Ala Ser Gly Asp Gln Thr Phe Leu Arg
        515                 520                 525

Ile Asp Glu Ala Leu Ile Asn Ser His Val Leu Ala Thr Ser Glu Ile
    530                 535                 540

Phe Ala Ser Lys His Ile Ile Gly Leu Val Pro Ala Ser Ile Ser Glu
545                 550                 555                 560

Pro Pro Pro Phe Lys Cys Leu
                565


<210> SEQ ID NO 20
<211> LENGTH: 301
<212> TYPE: PRT
<213> ORGANISM: Homo sapiens

<400> SEQUENCE: 20

Ala Pro Met Pro Asn Ile Gly Ser Lys Tyr Gly Arg Lys Ala Thr Trp
1               5                   10                  15
```

```
Ile Gly Ala Ser Gly Asp Gln Thr Phe Leu Arg Ile Asp Glu Ala Leu
            20                  25                  30

Ile Asn Ser His Val Leu Ala Thr Ser Glu Ile Phe Ala Ser Lys His
        35                  40                  45

Ile Ile Gly Leu Val Pro Ala Ser Ile Ser Glu Pro Pro Pro Phe Lys
    50                  55                  60

Cys Leu Leu Ile Asn Lys Val Asp Gly Ser Cys Lys Thr Phe Asn Asp
65                  70                  75                  80

Ser Glu Gln Glu Asp Leu Gln Gly Phe Gly Val Cys Leu Asp Pro Val
                85                  90                  95

Tyr Asp Val Ile Trp Arg Phe Arg Pro Asn Thr Arg Glu Leu Trp Cys
            100                 105                 110

Tyr Asn Ala Val Val Ala Asp Ala Arg Leu Pro Ser Ala Ala Asp Met
        115                 120                 125

Gln Ser Arg Cys Ser Ile Leu Ser Pro Glu Leu Ala Leu Pro Thr Gly
    130                 135                 140

Ser Arg Ala Leu Thr Thr Arg Ser His Ala Ala Leu His Ile Leu Gly
145                 150                 155                 160

Cys Leu Asp Thr Leu Ala Ala Met Gln Asp Leu Lys Met Gly Val Ala
                165                 170                 175

Ser Thr Glu Glu Glu Thr Gln Ala Val Met Lys Val Tyr Ser Lys Glu
            180                 185                 190

Asp Tyr Ser Val Val Asn Arg Phe Glu Ser His Gly Gly Gly Trp Gly
        195                 200                 205

Tyr Ser Ala His Ser Val Glu Ala Ile Arg Phe Ser Ala Asp Thr Asp
    210                 215                 220

Ile Leu Leu Gly Gly Leu Gly Leu Phe Gly Gly Arg Gly Glu Tyr Thr
225                 230                 235                 240

Ala Lys Ile Lys Leu Phe Glu Leu Gly Pro Asp Gly Gly Asp His Glu
                245                 250                 255

Thr Asp Gly Asp Leu Leu Ala Glu Thr Asp Val Leu Ala Tyr Asp Cys
            260                 265                 270

Ala Ala Arg Glu Lys Tyr Ala Met Met Phe Asp Glu Pro Val Leu Leu
        275                 280                 285

Gln Ala Gly Trp Trp Tyr Val Ala Trp Ala Arg Val Ser
    290                 295                 300


<210> SEQ ID NO 21
<211> LENGTH: 101
<212> TYPE: PRT
<213> ORGANISM: Homo sapiens

<400> SEQUENCE: 21

Ala Pro Met Pro Asn Ile Gly Ser Lys Tyr Gly Arg Lys Ala Thr Trp
1               5                   10                  15

Ile Gly Ala Ser Gly Asp Gln Thr Phe Leu Arg Ile Asp Glu Ala Leu
            20                  25                  30

Ile Asn Ser His Val Leu Ala Thr Ser Glu Ile Phe Ala Ser Lys His
        35                  40                  45

Ile Ile Gly Leu Val Pro Ala Ser Ile Ser Glu Pro Pro Pro Phe Lys
    50                  55                  60

Cys Leu Leu Ile Asn Lys Val Asp Gly Ser Cys Lys Thr Phe Asn Asp
65                  70                  75                  80

Ser Glu Gln Glu Asp Leu Gln Gly Phe Gly Val Cys Leu Asp Pro Val
                85                  90                  95
```

Tyr Asp Val Ile Trp
100

<210> SEQ ID NO 22
<211> LENGTH: 204
<212> TYPE: PRT
<213> ORGANISM: Homo sapiens

<400> SEQUENCE: 22

Asp Glu Ala Leu Ile Asn Ser His Val Leu Ala Thr Ser Glu Ile Phe
1 5 10 15

Ala Ser Lys His Ile Ile Gly Leu Val Pro Ala Ser Ile Ser Glu Pro
20 25 30

Pro Pro Phe Lys Cys Leu Leu Ile Asn Lys Val Asp Gly Ser Cys Lys
35 40 45

Thr Phe Asn Asp Ser Glu Gln Glu Asp Leu Gln Gly Phe Gly Val Cys
50 55 60

Leu Asp Pro Val Tyr Asp Val Ile Trp Arg Phe Arg Pro Asn Thr Arg
65 70 75 80

Glu Leu Trp Cys Tyr Asn Ala Val Val Ala Asp Ala Arg Leu Pro Ser
85 90 95

Ala Ala Asp Met Gln Ser Arg Cys Ser Ile Leu Ser Pro Glu Leu Ala
100 105 110

Leu Pro Thr Gly Ser Arg Ala Leu Thr Thr Arg Ser His Ala Ala Leu
115 120 125

His Ile Leu Gly Cys Leu Asp Thr Leu Ala Ala Met Gln Asp Leu Lys
130 135 140

Met Gly Val Ala Ser Thr Glu Glu Glu Thr Gln Ala Val Met Lys Val
145 150 155 160

Tyr Ser Lys Glu Asp Tyr Ser Val Val Asn Arg Phe Glu Ser His Gly
165 170 175

Gly Gly Trp Gly Tyr Ser Ala His Ser Val Glu Ala Ile Arg Phe Ser
180 185 190

Ala Asp Thr Asp Ile Leu Leu Gly Gly Leu Gly Leu
195 200

<210> SEQ ID NO 23
<211> LENGTH: 38
<212> TYPE: PRT
<213> ORGANISM: Homo sapiens

<400> SEQUENCE: 23

Asp Glu Ala Leu Ile Asn Ser His Val Leu Ala Thr Ser Glu Ile Phe
1 5 10 15

Ala Ser Lys His Ile Ile Gly Leu Val Pro Ala Ser Ile Ser Glu Pro
20 25 30

Pro Pro Phe Lys Cys Leu
35

<210> SEQ ID NO 24
<211> LENGTH: 3030
<212> TYPE: DNA
<213> ORGANISM: Homo sapiens

<400> SEQUENCE: 24
aataaccaca gcatgacagc cataaggata agccctgaaa cactggagca agatggtact 60
gtgatgttac cagattgcca cactgaaggt caaaatattt tattcactga tggagaatat 120

-continued

```
attaatcaga tagctgcttc aagagatgat ggctttgttg tcagaatatt tgccacaagc    180
actgaacctg ttctacagca agaattgcaa cttaaactgg ctagaaaatg cttacatgcc    240
tgtcgtatct cattattcga tctggaaaag gacttgcata ttataagtac aggatttgat    300
gaggagtcag caattcttgg tgcaggacga gagtttgcgc taatgaaaac agcaaatgga    360
aagatatatt acactggcaa ataccagagt cttggaatca aacaaggtgg tccttcagca    420
ggaaaatggg ttgagctacc aattacaaaa tctccaaaga tagtacactt ctcagttgga    480
cacgatggct ctcacgccct tttagttgca gaagatggga gcatattctt tacaggatct    540
gctagtaaag gagaagatgg agaatcaatt aagagcagac ggcaatccaa accttataaa    600
cctaaaaaga taattaagat ggaaggaaag attgtggtat atacagcctg caataatgga    660
agtagttctg ttatttctaa agatggagaa ctctacatgt ttggaaaaga tgccatttac    720
tctgatagtt caagtttggt aactgatttg aagggccatt ttgtaactca ggtagctatg    780
ggcaaagctc acacttgtgt tttaatgaag aatggagagg tgtggacatt tggtgtaaat    840
aataaaggac agtgtggacg agatactggt gccatgaacc aaggtgggaa agggtttgga    900
gttgaaaata tggcaacagc aatggatgaa gacctggaag aagaactaga tgaaaaagat    960
gagaagtcta tgatgtgccc tccaggcatg cacaaatgga agctggagca gtgcatggtt   1020
tgcactgtct gtggagactg tacaggttat ggagccagct gtgtcagtag tggacggcca   1080
gacagagtcc ccggagggat ctgtggttgt ggttccggag aatctggttg tgctgtgtgt   1140
ggatgttgca aggcctgtgc aagagagtta gatggtcaag aggcaagaca aagaggaatt   1200
cttgatgcag tgaaagaaat gatacctta gatcttcttt tagctgtccc agtgcccggg    1260
gttaacattg aagaacacct tcagttacga caagaagaaa aacggcaacg tgtaatcaga   1320
aggcacagat tagaggaagg aagaggcccc cttgtatttg ctggtcctat ttttatgaac   1380
catcgagaac aggctctagc cagactcaga tcccatccag cacacgtaaa gcataaacgg   1440
gacaagcaca aagatggaag tggagaaaga ggcgaaaagg atgcaagcaa aatcacaaca   1500
taccctccag gctctgtgcg atttgactgt gagctccggg cagtccaagt cagctgtgga   1560
tttcaccatt cagtggtttt aatggaaaat ggagatgtct atacatttgg ttatgggcag   1620
catgggcagc taggacatgg agatgtcaac tccaggggat gtcccactct tgttcaagca   1680
ttgccaggcc ctagcacaca agtcactgca ggcagcaacc atacggcagt acttttaatg   1740
gatggacagg tcttcacatt tggaagtttt tctaaaggac aactgggcag accaattttg   1800
gatgtgccat attggaatgc aaagccagct cccatgccta acattggatc aaaatatgga   1860
agaaaagcta cttggatagg tgcaagtggg gaccaaactt ttttacgaat tgatgaagca   1920
cttattaatt ctcatgtact tgctacatca gaaatttttg ccagtaaaca cataataggc   1980
ttggtacctg cttctatatc agaacctcct ccatttaaat gccttctgat aaataaagtg   2040
gatgggagtt gtaaaacttt taatgactca gaacaagagg atctgcaagg atttggtgtg   2100
tgtcttgatc ctgtatatga tgtaatttgg aggtttcgac caaatactag agagctgtgg   2160
tgttacaatg cggtggttgc tgatgccagg cttccctctg cagcagacat gcagtccaga   2220
tgtagtatcc taagtcctga acttgcctta ccaacaggat caagggccct cactacccga   2280
tctcatgcag ctttgcacat tttaggttgt cttgatacct tggcagctat gcaggactta   2340
aaaatgggtg ttgcaagtac agaggaagag actcaagcag taatgaaggt ttattctaaa   2400
gaagattata gtgtggtaaa caggtttgaa agtcatggag gaggctgggg ttattctgcc   2460
```

-continued cattcagtag aagctatacg tttcagtgcc gacactgata ttttacttgg tggtcttggt 2520
ctgtttggag gtagaggaga atatactgct aaaattaagc tgtttgaatt gggtcctgat 2580
ggaggagatc atgaaactga tggtgacctt cttgcagaga ctgatgtatt ggcttatgac 2640
tgtgctgcta gagaaaaata tgcaatgatg tttgatgagc ctgttctcct gcaagctggg 2700
tggtggtatg tggcatgggc ccgagtgtca ggacccagca gtgactgtgg atctcatgga 2760
caggcatcta ttaccacaga tgatggggtt gttttccagt tcaagagttc aaagaaatca 2820
aataatggta cagatgttaa tgcgggtcag atacctcagt tattatacag acttccaacc 2880
agtgatggca gtgcttcaaa aggcaaacag caaaccagtg aacctgtaca cattttaaag 2940
aggtcttttg caagaactgt ctcagtggaa tgttttgagt cattgttgag tattcttcac 3000
tggagctgga ccaccttagt cttaggagtt 3030

<210> SEQ ID NO 25
<211> LENGTH: 1851
<212> TYPE: DNA
<213> ORGANISM: Homo sapiens

<400> SEQUENCE: 25
atatttgcca caagcactga acctgttcta cagcaagaat tgcaacttaa actggctaga 60
aaatgcttac atgcctgtcg tatctcatta ttcgatctgg aaaaggactt gcatattata 120
agtacaggat ttgatgagga gtcagcaatt cttggtgcag gacgagagtt tgcgctaatg 180
aaaacagcaa atggaaagat atattacact ggcaaatacc agagtcttgg aatcaaacaa 240
ggtggtcctt cagcaggaaa atgggttgag ctaccaatta caaaatctcc aaagatagta 300
cacttctcag ttggacacga tggctctcac gccctttttag ttgcagaaga tgggagcata 360
ttctttacag gatctgctag taaaggagaa gatggagaat caattaagag cagacggcaa 420
tccaaacctt ataaacctaa aaagataatt aagatggaag gaaagattgt ggtatataca 480
gcctgcaata atggaagtag ttctgttatt tctaaagatg gagaactcta catgtttgga 540
aaagatgcca tttactctga tagttcaagt ttggtaactg atttgaaggg ccattttgta 600
actcaggtag ctatgggcaa agctcacact tgtgttttaa tgaagaatgg agaggtgtgg 660
acatttggtg taaataataa aggacagtgt ggacgagata ctggtgccat gaaccaaggt 720
gggaaagggt ttggagttga aaatatggca acagcaatgg atgaagacct ggaagaagaa 780
ctagatgaaa aagatgagaa gtctatgatg tgccctccag gcatgcacaa atggaagctg 840
gagcagtgca tggtttgcac tgtctgtgga gactgtacag gttatggagc cagctgtgtc 900
agtagtggac ggccagacag agtccccgga gggatctgtg gttgtggttc cggagaatct 960
ggttgtgctg tgtgtggatg ttgcaaggcc tgtgcaagag agttagatgg tcaagaggca 1020
agacaaagag gaattcttga tgcagtgaaa gaaatgatac ctttagatct tcttttagct 1080
gtcccagtgc ccggggttaa cattgaagaa caccttcagt tacgacaaga agaaaaacgg 1140
caacgtgtaa tcagaaggca cagattagag gaaggaagag gccccccttgt atttgctggt 1200 cctattttta tgaaccatcg agaacaggct ctagccagac tcagatccca tccagcacac 1260
gtaaagcata aacgggacaa gcacaaagat ggaagtggag aaagaggcga aaaggatgca 1320
agcaaaatca caacataccc tccaggctct gtgcgatttg actgtgagct ccgggcagtc 1380
caagtcagct gtggatttca ccattcagtg gttttaatgg aaaatggaga tgtctataca 1440
tttggttatg ggcagcatgg gcagctagga catggagatg tcaactccag gggatgtccc 1500
actcttgttc aagcattgcc aggccctagc acacaagtca ctgcaggcag caaccatacg 1560

```
gcagtacttt taatggatgg acaggtcttc acatttggaa gtttttctaa aggacaactg   1620

ggcagaccaa ttttggatgt gccatattgg aatgcaaagc cagctcccat gcctaacatt   1680

ggatcaaaat atggaagaaa agctacttgg ataggtgcaa gtggggacca aacttttttta   1740

cgaattgatg aagcacttat taattctcat gtacttgcta catcagaaat tttgccagt   1800

aaacacataa taggcttggt acctgcttct atatcagaac ctcctccatt t            1851
```

<210> SEQ ID NO 26
<211> LENGTH: 1701
<212> TYPE: DNA
<213> ORGANISM: Homo sapiens

<400> SEQUENCE: 26

```
ggacgagagt ttgcgctaat gaaaacagca aatggaaaga tatattacac tggcaaatac     60

cagagtcttg gaatcaaaca aggtggtcct tcagcaggaa aatgggttga gctaccaatt    120

acaaaatctc caaagatagt acacttctca gttggacacg atggctctca cgccctttta    180

gttgcagaag atgggagcat attctttaca ggatctgcta gtaaaggaga agatggagaa    240

tcaattaaga gcagacggca atccaaacct tataaaccta aaaagataat taagatggaa    300

ggaaagattg tggtatatac agcctgcaat aatggaagta gttctgttat ttctaaagat    360

ggagaactct acatgtttgg aaaagatgcc atttactctg atagttcaag tttggtaact    420

gatttgaagg gccattttgt aactcaggta gctatgggca aagctcacac ttgtgtttta    480

atgaagaatg gagaggtgtg gacatttggt gtaaataata aaggacagtg tggacgagat    540

actggtgcca tgaaccaagg tgggaaaggg tttggagttg aaaatatggc aacagcaatg    600

gatgaagacc tggaagaaga actagatgaa aaagatgaga agtctatgat gtgccctcca    660

ggcatgcaca aatggaagct ggagcagtgc atggtttgca ctgtctgtgg agactgtaca    720

ggttatggag ccagctgtgt cagtagtgga cggccagaca gagtccccgg agggatctgt    780

ggttgtggtt ccggagaatc tggttgtgct gtgtgtggat gttgcaaggc ctgtgcaaga    840

gagttagatg gtcaagaggc aagacaaaga ggaattcttg atgcagtgaa agaaatgata    900

cctttagatc ttcttttagc tgtcccagtg cccggggtta acattgaaga acaccttcag    960

ttacgacaag aagaaaaacg gcaacgtgta atcagaaggc acagattaga ggaaggaaga   1020

ggccccccttg tatttgctgg tcctattttt atgaaccatc gagaacaggc tctagccaga   1080

ctcagatccc atccagcaca cgtaaagcat aaacgggaca agcacaaaga tggaagtgga   1140

gaaagaggcg aaaaggatgc aagcaaaatc acaacatacc ctccaggctc tgtgcgattt   1200

gactgtgagc tccgggcagt ccaagtcagc tgtggatttc accattcagt ggttttaatg   1260

gaaaatggag atgtctatac atttggttat gggcagcatg ggcagctagg acatggagat   1320

gtcaactcca ggggatgtcc cactcttgtt caagcattgc caggccctag cacacaagtc   1380

actgcaggca gcaaccatac ggcagtactt ttaatggatg gacaggtctt cacatttgga   1440

agtttttcta aaggacaact gggcagacca attttggatg tgccatattg gaatgcaaag   1500

ccagctccca tgcctaacat tggatcaaaa tatggaagaa aagctacttg gataggtgca   1560

agtggggacc aaactttttt acgaattgat gaagcactta ttaattctca tgtacttgct   1620

acatcagaaa tttttgccag taaacacata ataggcttgg tacctgcttc tatatcagaa   1680

cctcctccat ttaaatgcct t                                              1701
```

<210> SEQ ID NO 27

<211> LENGTH: 903
<212> TYPE: DNA
<213> ORGANISM: Homo sapiens

<400> SEQUENCE: 27
gctcccatgc ctaacattgg atcaaaatat ggaagaaaag ctacttggat aggtgcaagt 60
ggggaccaaa ctttttacg aattgatgaa gcacttatta attctcatgt acttgctaca 120
tcagaaattt ttgccagtaa acacataata ggcttggtac ctgcttctat atcagaacct 180
cctccattta aatgccttct gataaataaa gtggatggga gttgtaaaac ttttaatgac 240
tcagaacaag aggatctgca aggatttggt gtgtgtcttg atcctgtata tgatgtaatt 300
tggaggtttc gaccaaatac tagagagctg tggtgttaca atgcggtggt tgctgatgcc 360
aggcttccct ctgcagcaga catgcagtcc agatgtagta tcctaagtcc tgaacttgcc 420
ttaccaacag gatcaagggc cctcactacc cgatctcatg cagctttgca cattttaggt 480
tgtcttgata ccttggcagc tatgcaggac ttaaaaatgg gtgttgcaag tacagaggaa 540
gagactcaag cagtaatgaa ggtttattct aaagaagatt atagtgtggt aaacaggttt 600
gaaagtcatg gaggaggctg ggttattct gcccattcag tagaagctat acgtttcagt 660
gccgacactg atattttact tggtggtctt ggtctgtttg gaggtagagg agaatatact 720
gctaaaatta agctgtttga attgggtcct gatggaggag atcatgaaac tgatggtgac 780
cttcttgcag agactgatgt attggcttat gactgtgctg ctagagaaaa atatgcaatg 840
atgtttgatg agcctgttct cctgcaagct gggtggtggt atgtggcatg ggcccgagtg 900
tca 903

<210> SEQ ID NO 28
<211> LENGTH: 303
<212> TYPE: DNA
<213> ORGANISM: Homo sapiens

<400> SEQUENCE: 28
gctcccatgc ctaacattgg atcaaaatat ggaagaaaag ctacttggat aggtgcaagt 60
ggggaccaaa ctttttacg aattgatgaa gcacttatta attctcatgt acttgctaca 120
tcagaaattt ttgccagtaa acacataata ggcttggtac ctgcttctat atcagaacct 180
cctccattta aatgccttct gataaataaa gtggatggga gttgtaaaac ttttaatgac 240
tcagaacaag aggatctgca aggatttggt gtgtgtcttg atcctgtata tgatgtaatt 300
tgg 303

<210> SEQ ID NO 29
<211> LENGTH: 612
<212> TYPE: DNA
<213> ORGANISM: Homo sapiens

<400> SEQUENCE: 29
gatgaagcac ttattaattc tcatgtactt gctacatcag aaatttttgc cagtaaacac 60
ataataggct tggtacctgc ttctatatca gaacctcctc catttaaatg ccttctgata 120
aataaagtgg atgggagttg taaaactttt aatgactcag aacaagagga tctgcaagga 180
tttggtgtgt gtcttgatcc tgtatatgat gtaatttgga ggtttcgacc aaatactaga 240
gagctgtggt gttacaatgc ggtggttgct gatgccaggc ttccctctgc agcagacatg 300
cagtccagat gtagtatcct aagtcctgaa cttgccttac caacaggatc aagggccctc 360
actacccgat ctcatgcagc tttgcacatt ttaggttgtc ttgatacctt ggcagctatg 420
caggacttaa aaatgggtgt tgcaagtaca gaggaagaga ctcaagcagt aatgaaggtt 480
tattctaaag aagattatag tgtggtaaac aggtttgaaa gtcatggagg aggctggggt 540
tattctgccc attcagtaga agctatacgt ttcagtgccg acactgatat tttacttggt 600
ggtcttggtc tg 612

<210> SEQ ID NO 30
<211> LENGTH: 117
<212> TYPE: DNA
<213> ORGANISM: Homo sapiens

<400> SEQUENCE: 30
gatgaagcac ttattaattc tcatgtactt gctacatcag aaatttttgc cagtaaacac 60
ataataggct tggtacctgc ttctatatca gaacctcctc catttaaatg ccttctg 117

<210> SEQ ID NO 31
<211> LENGTH: 382
<212> TYPE: PRT
<213> ORGANISM: Homo sapiens

<400> SEQUENCE: 31

Met Gly Pro Thr Ser Val Pro Leu Val Lys Ala His Arg Ser Ser Val
1 5 10 15

Ser Asp Tyr Val Asn Tyr Asp Ile Ile Val Arg His Tyr Asn Tyr Thr
20 25 30

Gly Lys Leu Asn Ile Ser Ala Asp Lys Glu Asn Ser Ile Lys Leu Thr
35 40 45

Ser Val Val Phe Ile Leu Ile Cys Cys Phe Ile Ile Leu Glu Asn Ile
50 55 60

Phe Val Leu Leu Thr Ile Trp Lys Thr Lys Lys Phe His Arg Pro Met
65 70 75 80

Tyr Tyr Phe Ile Gly Asn Leu Ala Leu Ser Asp Leu Leu Ala Gly Val
85 90 95

Ala Tyr Thr Ala Asn Leu Leu Leu Ser Gly Ala Thr Thr Tyr Lys Leu
100 105 110

Thr Pro Ala Gln Trp Phe Leu Arg Glu Gly Ser Met Phe Val Ala Leu
115 120 125

Ser Ala Ser Val Phe Ser Leu Leu Ala Ile Ala Ile Glu Arg Tyr Ile
130 135 140

Thr Met Leu Lys Met Lys Leu His Asn Gly Ser Asn Asn Phe Arg Leu
145 150 155 160

Phe Leu Leu Ile Ser Ala Cys Trp Val Ile Ser Leu Ile Leu Gly Gly
165 170 175

Leu Pro Ile Met Gly Trp Asn Cys Ile Ser Ala Leu Ser Ser Cys Ser
180 185 190

Thr Val Leu Pro Leu Tyr His Lys His Tyr Ile Leu Phe Cys Thr Thr
195 200 205

Val Phe Thr Leu Leu Leu Leu Ser Ile Val Ile Leu Tyr Cys Arg Ile
210 215 220

Tyr Ser Leu Val Arg Thr Arg Ser Arg Arg Leu Thr Phe Arg Lys Asn
225 230 235 240

Ile Ser Lys Ala Ser Arg Ser Ser Glu Lys Ser Leu Ala Leu Leu Lys
245 250 255

Thr Val Ile Ile Val Leu Ser Val Phe Ile Ala Cys Trp Ala Pro Leu
260 265 270

```
Phe Ile Leu Leu Leu Leu Asp Val Gly Cys Lys Val Lys Thr Cys Asp
        275                 280                 285

Ile Leu Phe Arg Ala Glu Tyr Phe Leu Val Leu Ala Val Leu Asn Ser
    290                 295                 300

Gly Thr Asn Pro Ile Ile Tyr Thr Leu Thr Asn Lys Glu Met Arg Arg
305                 310                 315                 320

Ala Phe Ile Arg Ile Met Ser Cys Cys Lys Cys Pro Ser Gly Asp Ser
                325                 330                 335

Ala Gly Lys Phe Lys Arg Pro Ile Ile Ala Gly Met Glu Phe Ser Arg
            340                 345                 350

Ser Lys Ser Asp Asn Ser Ser His Pro Gln Lys Asp Glu Gly Asp Asn
        355                 360                 365

Pro Glu Thr Ile Met Ser Ser Gly Asn Val Asn Ser Ser Ser
    370                 375                 380


<210> SEQ ID NO 32
<211> LENGTH: 2753
<212> TYPE: DNA
<213> ORGANISM: Homo sapiens

<400> SEQUENCE: 32

gtcgggggca gcagcaagat gcgaagcgag ccgtacagat cccgggctct ccgaacgcaa      60

cttcgccctg cttgagcgag gctgcggttt ccgaggccct ctccagccaa ggaaaagcta     120

cacaaaaagc ctggatcact catcgaacca cccctgaagc cagtgaaggc tctctcgcct     180

cgccctctag cgttcgtctg gagtagcgcc accccggctt cctggggaca cagggttggc     240

accatggggc ccaccagcgt cccgctggtc aaggcccacc gcagctcggt ctctgactac     300

gtcaactatg atatcatcgt ccggcattac aactacacgg gaaagctgaa tatcagcgcg     360

gacaaggaga acagcattaa actgacctcg gtggtgttca ttctcatctg ctgctttatc     420

atcctggaga acatctttgt cttgctgacc atttggaaaa ccaagaaatt ccaccgaccc     480

atgtactatt ttattggcaa tctggccctc tcagacctgt tggcaggagt agcctacaca     540

gctaacctgc tcttgtctgg ggccaccacc tacaagctca ctcccgccca gtggtttctg     600

cgggaaggga gtatgtttgt ggccctgtca gcctccgtgt tcagtctcct cgccatcgcc     660

attgagcgct atatcacaat gctgaaaatg aaactccaca acgggagcaa taacttccgc     720

ctcttcctgc taatcagcgc ctgctgggtc atctccctca tcctgggtgg cctgcctatc     780

atgggctgga actgcatcag tgcgctgtcc agctgctcca ccgtgctgcc gctctaccac     840

aagcactata tcctcttctg caccacggtc ttcactctgc ttctgctctc catcgtcatt     900

ctgtactgca gaatctactc cttggtcagg actcggagcc gccgcctgac gttccgcaag     960

aacatttcca aggccagccg cagctctgag aagtcgctgg cgctgctcaa gaccgtaatt    1020

atcgtcctga gcgtcttcat cgcctgctgg gcaccgctct tcatcctgct cctgctggat    1080

gtgggctgca aggtgaagac ctgtgacatc ctcttcagag cggagtactt cctggtgtta    1140

gctgtgctca actccggcac caaccccatc atttacactc tgaccaacaa ggagatgcgt    1200

cgggccttca tccggatcat gtcctgctgc aagtgcccga gcggagactc tgctggcaaa    1260

ttcaagcgac ccatcatcgc cggcatggaa ttcagccgca gcaaatcgga caattcctcc    1320

cacccccaga aagacgaagg ggacaaccca gagaccatta tgtcttctgg aaacgtcaac    1380

tcttcttcct agaactggaa gctgtccacc caccggaagc gctctttact tggtcgctgg    1440

ccaccccagt gtttggaaaa aaatctctgg gcttcgactg ctgccaggga ggagctgctg    1500
```

```
caagccagag ggaggaaggg ggagaatacg aacagcctgg tggtgtcggg tgttggtggg   1560

tagagttagt tcctgtgaac aatgcactgg gaagggtgga gatcaggtcc cggcctggaa   1620

tatatattct acccccctgg agctttgatt ttgcactgag ccaaaggtct agcattgtca   1680

agctcctaaa gggttcattt ggcccctcct caaagactaa tgtccccatg tgaaagcgtc   1740

tctttgtctg gagctttgag gagatgtttt ccttcacttt agtttcaaac ccaagtgagt   1800

gtgtgcactt ctgcttcttt agggatgccc tgtacatccc acaccccacc ctcccttccc   1860

ttcatacccc tcctcaacgt tcttttactt tatactttaa ctacctgaga gttatcagag   1920

ctggggttgt ggaatgatcg atcatctata gcaaataggc tatgttgagt acgtaggctg   1980

tgggaagatg aagatggttt ggaggtgtaa aacaatgtcc ttcgctgagg ccaaagtttc   2040

catgtaagcg ggatccgttt tttggaattt ggttgaagtc actttgattt ctttaaaaaa   2100

catcttttca atgaaatgtg ttaccatttc atatccattg aagccgaaat ctgcataagg   2160

aagcccactt tatctaaatg atattagcca ggatccttgg tgtcctagga gaaacagaca   2220

agcaaaacaa agtgaaaacc gaatggatta acttttgcaa accaagggag atttcttagc   2280

aaatgagtct aacaaatatg acatccgtct ttcccacttt tgttgatgtt tatttcagaa   2340

tcttgtgtga ttcatttcaa gcaacaacat gttgtatttt gttgtgttaa aagtactttt   2400

cttgattttt gaatgtattt gtttcaggaa gaagtcattt tatggatttt tctaacccgt   2460

gttaactttt ctagaatcca ccctcttgtg cccttaagca ttactttaac tggtagggaa   2520

cgccagaact tttaagtcca gctattcatt agatagtaat tgaagatatg tataaatatt   2580

acaaagaata aaaatatatt actgtctctt tagtatggtt ttcagtgcaa ttaaaccgag   2640

agatgtcttg ttttttaaa aagaatagta tttaataggt ttctgacttt tgtggatcat   2700

tttgcacata gctttatcaa cttttaaaca ttaataaact gattttttta aag          2753
```

<210> SEQ ID NO 33
<211> LENGTH: 353
<212> TYPE: PRT
<213> ORGANISM: Homo sapiens

<400> SEQUENCE: 33

```
Met Gly Ser Leu Tyr Ser Glu Tyr Leu Asn Pro Asn Lys Val Gln Glu
1               5                   10                  15

His Tyr Asn Tyr Thr Lys Glu Thr Leu Glu Thr Gln Glu Thr Thr Ser
            20                  25                  30

Arg Gln Val Ala Ser Ala Phe Ile Val Ile Leu Cys Cys Ala Ile Val
        35                  40                  45

Val Glu Asn Leu Leu Val Leu Ile Ala Val Ala Arg Asn Ser Lys Phe
    50                  55                  60

His Ser Ala Met Tyr Leu Phe Leu Gly Asn Leu Ala Ala Ser Asp Leu
65                  70                  75                  80

Leu Ala Gly Val Ala Phe Val Ala Asn Thr Leu Leu Ser Gly Ser Val
                85                  90                  95

Thr Leu Arg Leu Thr Pro Val Gln Trp Phe Ala Arg Glu Gly Ser Ala
            100                 105                 110

Ser Ile Thr Leu Ser Ala Ser Val Phe Ser Leu Leu Ala Ile Ala Ile
        115                 120                 125

Glu Arg His Val Ala Ile Ala Lys Val Lys Leu Tyr Gly Ser Asp Lys
    130                 135                 140

Ser Cys Arg Met Leu Leu Leu Ile Gly Ala Ser Trp Leu Ile Ser Leu
```

```
145                 150                 155                 160

Val Leu Gly Gly Leu Pro Ile Leu Gly Trp Asn Cys Leu Gly His Leu
                165                 170                 175

Glu Ala Cys Ser Thr Val Leu Pro Leu Tyr Ala Lys His Tyr Val Leu
            180                 185                 190

Cys Val Val Thr Ile Phe Ser Ile Ile Leu Leu Ala Ile Val Ala Leu
        195                 200                 205

Tyr Val Arg Ile Tyr Cys Val Val Arg Ser Ser His Ala Asp Met Ala
    210                 215                 220

Ala Pro Gln Thr Leu Ala Leu Leu Lys Thr Val Thr Ile Val Leu Gly
225                 230                 235                 240

Val Phe Ile Val Cys Trp Leu Pro Ala Phe Ser Ile Leu Leu Leu Asp
                245                 250                 255

Tyr Ala Cys Pro Val His Ser Cys Pro Ile Leu Tyr Lys Ala His Tyr
            260                 265                 270

Phe Phe Ala Val Ser Thr Leu Asn Ser Leu Leu Asn Pro Val Ile Tyr
        275                 280                 285

Thr Trp Arg Ser Arg Asp Leu Arg Arg Glu Val Leu Arg Pro Leu Gln
    290                 295                 300

Cys Trp Arg Pro Gly Val Gly Val Gln Gly Arg Arg Arg Val Gly Thr
305                 310                 315                 320

Pro Gly His His Leu Leu Pro Leu Arg Ser Ser Ser Ser Leu Glu Arg
                325                 330                 335

Gly Met His Met Pro Thr Ser Pro Thr Phe Leu Glu Gly Asn Thr Val
            340                 345                 350

Val


<210> SEQ ID NO 34
<211> LENGTH: 1062
<212> TYPE: DNA
<213> ORGANISM: Homo sapiens

<400> SEQUENCE: 34

atgggcagct tgtactcgga gtacctgaac cccaacaagg tccaggaaca ctataattat     60

accaaggaga cgctggaaac gcaggagacg acctcccgcc aggtggcctc ggccttcatc    120

gtcatcctct gttgcgccat tgtggtggaa aaccttctgg tgctcattgc ggtggcccga    180

aacagcaagt tccactcggc aatgtacctg tttctgggca acctggccgc ctccgatcta    240

ctggcaggcg tggccttcgt agccaatacc ttgctctctg gctctgtcac gctgaggctg    300

acgcctgtgc agtggtttgc ccgggagggc tctgcctcca tcacgctctc ggcctctgtc    360

ttcagcctcc tggccatcgc cattgagcgc cacgtggcca ttgccaaggt caagctgtat    420

ggcagcgaca agagctgccg catgcttctg ctcatcgggg cctcgtggct catctcgctg    480

gtcctcggtg gcctgcccat ccttggctgg aactgcctgg gccacctcga ggcctgctcc    540

actgtcctgc ctctctacgc caagcattat gtgctgtgcg tggtgaccat cttctccatc    600

atcctgttgg ccatcgtggc cctgtacgtg cgcatctact gcgtggtccg ctcaagccac    660

gctgacatgg ccgccccgca gacgctagcc ctgctcaaga cggtcaccat cgtgctaggc    720

gtctttatcg tctgctggct gcccgccttc agcatcctcc ttctggacta tgcctgtccc    780

gtccactcct gcccgatcct ctacaaagcc cactactttt tcgccgtctc caccctgaat    840

tccctgctca accccgtcat ctacacgtgg cgcagccggg acctgcggcg ggaggtgctt    900

cggccgctgc agtgctggcg gccgggggtg gggtgcaag gacggaggcg ggtcgggacc    960
```

```
ccgggccacc acctcctgcc actccgcagc tccagctccc tggagagggg catgcacatg   1020

cccacgtcac ccacgtttct ggagggcaac acggtggtct ga                      1062


<210> SEQ ID NO 35
<211> LENGTH: 378
<212> TYPE: PRT
<213> ORGANISM: Homo sapiens

<400> SEQUENCE: 35

Met Ala Thr Ala Leu Pro Pro Arg Leu Gln Pro Val Arg Gly Asn Glu
1               5                   10                  15

Thr Leu Arg Glu His Tyr Gln Tyr Val Gly Lys Leu Ala Gly Arg Leu
            20                  25                  30

Lys Glu Ala Ser Glu Gly Ser Thr Leu Thr Thr Val Leu Phe Leu Val
        35                  40                  45

Ile Cys Ser Phe Ile Val Leu Glu Asn Leu Met Val Leu Ile Ala Ile
    50                  55                  60

Trp Lys Asn Asn Lys Phe His Asn Arg Met Tyr Phe Phe Ile Gly Asn
65                  70                  75                  80

Leu Ala Leu Cys Asp Leu Leu Ala Gly Ile Ala Tyr Lys Val Asn Ile
                85                  90                  95

Leu Met Ser Gly Lys Lys Thr Phe Ser Leu Ser Pro Thr Val Trp Phe
            100                 105                 110

Leu Arg Glu Gly Ser Met Phe Val Ala Leu Gly Ala Ser Thr Cys Ser
        115                 120                 125

Leu Leu Ala Ile Ala Ile Glu Arg His Leu Thr Met Ile Lys Met Arg
    130                 135                 140

Pro Tyr Asp Ala Asn Lys Arg His Arg Val Phe Leu Leu Ile Gly Met
145                 150                 155                 160

Cys Trp Leu Ile Ala Phe Thr Leu Gly Ala Leu Pro Ile Leu Gly Trp
                165                 170                 175

Asn Cys Leu His Asn Leu Pro Asp Cys Ser Thr Ile Leu Pro Leu Tyr
            180                 185                 190

Ser Lys Lys Tyr Ile Ala Phe Cys Ile Ser Ile Phe Thr Ala Ile Leu
        195                 200                 205

Val Thr Ile Val Ile Leu Tyr Ala Arg Ile Tyr Phe Leu Val Lys Ser
    210                 215                 220

Ser Ser Arg Lys Val Ala Asn His Asn Asn Ser Glu Arg Ser Met Ala
225                 230                 235                 240

Leu Leu Arg Thr Val Val Ile Val Val Ser Val Phe Ile Ala Cys Trp
                245                 250                 255

Ser Pro Leu Phe Ile Leu Phe Leu Ile Asp Val Ala Cys Arg Val Gln
            260                 265                 270

Ala Cys Pro Ile Leu Phe Lys Ala Gln Trp Phe Ile Val Leu Ala Val
        275                 280                 285

Leu Asn Ser Ala Met Asn Pro Val Ile Tyr Thr Leu Ala Ser Lys Glu
    290                 295                 300

Met Arg Arg Ala Phe Phe Arg Leu Val Cys Asn Cys Leu Val Arg Gly
305                 310                 315                 320

Arg Gly Ala Arg Ala Ser Pro Ile Gln Pro Ala Leu Asp Pro Ser Arg
                325                 330                 335

Ser Lys Ser Ser Ser Ser Asn Asn Ser Ser His Ser Pro Lys Val Lys
            340                 345                 350
```

-continued

```
Glu Asp Leu Pro His Thr Asp Pro Ser Ser Cys Ile Met Asp Lys Asn
        355                 360                 365

Ala Ala Leu Gln Asn Gly Ile Phe Cys Asn
    370                 375


<210> SEQ ID NO 36
<211> LENGTH: 1137
<212> TYPE: DNA
<213> ORGANISM: Homo sapiens

<400> SEQUENCE: 36

atggcaactg ccctcccgcc gcgtctccag ccggtgcggg ggaacgagac cctgcgggag      60

cattaccagt acgtggggaa gttggcgggc aggctgaagg aggcctccga gggcagcacg     120

ctcaccaccg tgctcttctt ggtcatctgc agcttcatcg tcttggagaa cctgatggtt     180

ttgattgcca tctggaaaaa caataaattt cacaaccgca tgtacttttt cattggcaac     240

ctggctctct gcgacctgct ggccggcatc gcttacaagg tcaacattct gatgtctggc     300

aagaagacgt tcagcctgtc tcccacggtc tggttcctca gggagggcag tatgttcgtg     360

gcccttgggg cgtccacctg cagcttactg gccatcgcca tcgagcggca cttgacaatg     420

atcaaaatga ggccttacga cgccaacaag aggcaccgcg tcttcctcct gatcgggatg     480

tgctggctca ttgccttcac gctgggcgcc ctgcccattc tgggctggaa ctgcctgcac     540

aatctccctg actgctctac catcctgccc ctctactcca agaagtacat tgccttctgc     600

atcagcatct tcacggccat cctggtgacc atcgtgatcc tctacgcacg catctacttc     660

ctggtgaagt ccagcagccg taaggtggcc aaccacaaca actcggagcg gtccatggca     720

ctgctgcgga ccgtggtgat tgtggtgagc gtgttcatcg cctgctggtc cccactcttc     780

atcctcttcc tcattgatgt ggcctgcagg gtgcaggcgt gccccatcct cttcaaggct     840

cagtggttca tcgtgttggc tgtgctcaac tccgccatga acccggtcat ctacacgctg     900

gccagcaagg agatgcggcg ggccttcttc cgtctggtct gcaactgcct ggtcagggga     960

cggggggccc gcgcctcacc catccagcct gcgctcgacc caagcagaag taaatcaagc    1020

agcagcaaca atagcagcca ctctccgaag gtcaaggaag acctgcccca cacagacccc    1080

tcatcctgca tcatggacaa gaacgcagca cttcagaatg ggatcttctg caactga       1137


<210> SEQ ID NO 37
<211> LENGTH: 384
<212> TYPE: PRT
<213> ORGANISM: Homo sapiens

<400> SEQUENCE: 37

Met Asn Ala Thr Gly Thr Pro Val Ala Pro Glu Ser Cys Gln Gln Leu
1               5                   10                  15

Ala Ala Gly Gly His Ser Arg Leu Ile Val Leu His Tyr Asn His Ser
            20                  25                  30

Gly Arg Leu Ala Gly Arg Gly Gly Pro Glu Asp Gly Gly Leu Gly Ala
        35                  40                  45

Leu Arg Gly Leu Ser Val Ala Ala Ser Cys Leu Val Val Leu Glu Asn
    50                  55                  60

Leu Leu Val Leu Ala Ala Ile Thr Ser His Met Arg Ser Arg Arg Trp
65                  70                  75                  80

Val Tyr Tyr Cys Leu Val Asn Ile Thr Leu Ser Asp Leu Leu Thr Gly
                85                  90                  95

Ala Ala Tyr Leu Ala Asn Val Leu Leu Ser Gly Ala Arg Thr Phe Arg
```

-continued

```
            100                 105                 110

Leu Ala Pro Ala Gln Trp Phe Leu Arg Glu Gly Leu Leu Phe Thr Ala
        115                 120                 125

Leu Ala Ala Ser Thr Phe Ser Leu Leu Phe Thr Ala Gly Glu Arg Phe
    130                 135                 140

Ala Thr Met Val Arg Pro Val Ala Glu Ser Gly Ala Thr Lys Thr Ser
145                 150                 155                 160

Arg Val Tyr Gly Phe Ile Gly Leu Cys Trp Leu Leu Ala Ala Leu Leu
                165                 170                 175

Gly Met Leu Pro Leu Leu Gly Trp Asn Cys Leu Cys Ala Phe Asp Arg
            180                 185                 190

Cys Ser Ser Leu Leu Pro Leu Tyr Ser Lys Arg Tyr Ile Leu Phe Cys
        195                 200                 205

Leu Val Ile Phe Ala Gly Val Leu Ala Thr Ile Met Gly Leu Tyr Gly
    210                 215                 220

Ala Ile Phe Arg Leu Val Gln Ala Ser Gly Gln Lys Ala Pro Arg Pro
225                 230                 235                 240

Ala Ala Arg Arg Lys Ala Arg Arg Leu Leu Lys Thr Val Leu Met Ile
                245                 250                 255

Leu Leu Ala Phe Leu Val Cys Trp Gly Pro Leu Phe Gly Leu Leu Leu
            260                 265                 270

Ala Asp Val Phe Gly Ser Asn Leu Trp Ala Gln Glu Tyr Leu Arg Gly
        275                 280                 285

Met Asp Trp Ile Leu Ala Leu Ala Val Leu Asn Ser Ala Val Asn Pro
    290                 295                 300

Ile Ile Tyr Ser Phe Arg Ser Arg Glu Val Cys Arg Ala Val Leu Ser
305                 310                 315                 320

Phe Leu Cys Cys Gly Cys Leu Arg Leu Gly Met Arg Gly Pro Gly Asp
                325                 330                 335

Cys Leu Ala Arg Ala Val Glu Ala His Ser Gly Ala Ser Thr Thr Asp
            340                 345                 350

Ser Ser Leu Arg Pro Arg Asp Ser Phe Arg Gly Ser Arg Ser Leu Ser
        355                 360                 365

Phe Arg Met Arg Glu Pro Leu Ser Ser Ile Ser Ser Val Arg Ser Ile
    370                 375                 380
```

<210> SEQ ID NO 38
<211> LENGTH: 1566
<212> TYPE: DNA
<213> ORGANISM: Homo sapiens

<400> SEQUENCE: 38

```
gagtcagccc ccgggggagg ccatgaacgc cacggggacc ccggtggccc ccgagtcctg     60

ccaacagctg gcggccggcg ggcacagccg gctcattgtt ctgcactaca accactcggg    120

ccggctggcc gggcgcgggg ggccggagga tggcggcctg ggggccctgc gggggctgtc    180

ggtggccgcc agctgcctgg tggtgctgga gaacttgctg gtgctggcgg ccatcaccag    240

ccacatgcgg tcgcgacgct gggtctacta ttgcctggtg aacatcacgc tgagtgacct    300

gctcacgggc gcggcctacc tggccaacgt gctgctgtcg gggggcccgca ccttccgtct    360

ggcgcccgcc cagtggttcc tacgggaggg cctgctcttc accgccctgg ccgcctccac    420

cttcagcctg ctcttcactg caggggagcg ctttgccacc atggtgcggc cggtggccga    480

gagcggggcc accaagacca gccgcgtcta cggcttcatc ggcctctgct ggctgctggc    540
```

```
cgcgctgctg gggatgctgc ctttgctggg ctggaactgc ctgtgcgcct ttgaccgctg    600

ctccagcctt ctgcccctct actccaagcg ctacatcctc ttctgcctgg tgatcttcgc    660

cggcgtcctg gccaccatca tgggcctcta tggggccatc ttccgcctgg tgcaggccag    720

cgggcagaag gccccacgcc cagcggcccg ccgcaaggcc cgccgcctgc tgaagacggt    780

gctgatgatc ctgctggcct tcctggtgtg ctggggccca ctcttcgggc tgctgctggc    840

cgacgtcttt ggctccaacc tctgggccca ggagtacctg cggggcatgg actggatcct    900

ggccctggcc gtcctcaact cggcggtcaa ccccatcatc tactccttcc gcagcaggga    960

ggtgtgcaga gccgtgctca gcttcctctg ctgcgggtgt ctccggctgg gcatgcgagg   1020

gcccggggac tgcctggccc gggccgtcga ggctcactcc ggagcttcca ccaccgacag   1080

ctctctgagg ccaagggaca gctttcgcgg ctcccgctcg ctcagctttc ggatgcggga   1140

gcccctgtcc agcatctcca gcgtgcggag catctgaagt tgcagtcttg cgtgtggatg   1200

gtgcagccac cgggtgcgtg ccaggcaggc cctcctgggg tacaggaagc tgtgtgcacg   1260

cagcctcgcc tgtatgggga gcagggaacg ggacaggccc ccatggtctt cccggtggcc   1320

tctcggggct tctgacgcca aatgggcttc ccatggtcac cctggacaag gaggtaacca   1380

ccccacctcc ccgtaggagc agagagcacc ctggtgtggg ggcgagtggt tccccacaac   1440

cccgcttctg tgtgattctg ggaagtcccg ggcccctctc tgggcctcag tagggctccc   1500

aggctgcaag ggtggactg tgggatgcat gccctggcaa cattgaagtt cgatcatggt   1560

aaaaaa                                                              1566


<210> SEQ ID NO 39
<211> LENGTH: 398
<212> TYPE: PRT
<213> ORGANISM: Homo sapiens

<400> SEQUENCE: 39

Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
            20                  25                  30

Gly Ala Gly Leu Arg Ala Asp Ala Val Val Cys Leu Ala Val Cys Ala
        35                  40                  45

Phe Ile Val Leu Glu Asn Leu Ala Val Leu Leu Val Leu Gly Arg His
    50                  55                  60

Pro Arg Phe His Ala Pro Met Phe Leu Leu Leu Gly Ser Leu Thr Leu
65                  70                  75                  80

Ser Asp Leu Leu Ala Gly Ala Ala Tyr Ala Ala Asn Ile Leu Leu Ser
                85                  90                  95

Gly Pro Leu Thr Leu Lys Leu Ser Pro Ala Leu Trp Phe Ala Arg Glu
            100                 105                 110

Gly Gly Val Phe Val Ala Leu Thr Ala Ser Val Leu Ser Leu Leu Ala
        115                 120                 125

Ile Ala Leu Glu Arg Ser Leu Thr Met Ala Arg Arg Gly Pro Ala Pro
    130                 135                 140

Val Ser Ser Arg Gly Arg Thr Leu Ala Met Ala Ala Ala Ala Trp Gly
145                 150                 155                 160

Val Ser Leu Leu Leu Gly Leu Leu Pro Ala Leu Gly Trp Asn Cys Leu
                165                 170                 175

Gly Arg Leu Asp Ala Cys Ser Thr Val Leu Pro Leu Tyr Ala Lys Ala
            180                 185                 190
```

-continued

```
Tyr Val Leu Phe Cys Val Leu Ala Phe Val Gly Ile Leu Ala Ala Ile
        195                 200                 205

Cys Ala Leu Tyr Ala Arg Ile Tyr Cys Gln Val Arg Ala Asn Ala Arg
    210                 215                 220

Arg Leu Pro Ala Arg Pro Gly Thr Ala Gly Thr Thr Ser Thr Arg Ala
225                 230                 235                 240

Arg Arg Lys Pro Arg Ser Leu Ala Leu Leu Arg Thr Leu Ser Val Val
                245                 250                 255

Leu Leu Ala Phe Val Ala Cys Trp Gly Pro Leu Phe Leu Leu Leu Leu
            260                 265                 270

Leu Asp Val Ala Cys Pro Ala Arg Thr Cys Pro Val Leu Leu Gln Ala
        275                 280                 285

Asp Pro Phe Leu Gly Leu Ala Met Ala Asn Ser Leu Leu Asn Pro Ile
    290                 295                 300

Ile Tyr Thr Leu Thr Asn Arg Asp Leu Arg His Ala Leu Leu Arg Leu
305                 310                 315                 320

Val Cys Cys Gly Arg His Ser Cys Gly Arg Asp Pro Ser Gly Ser Gln
                325                 330                 335

Gln Ser Ala Ser Ala Ala Glu Ala Ser Gly Gly Leu Arg Arg Cys Leu
            340                 345                 350

Pro Pro Gly Leu Asp Gly Ser Phe Ser Gly Ser Glu Arg Ser Ser Pro
        355                 360                 365

Gln Arg Asp Gly Leu Asp Thr Ser Gly Ser Thr Gly Ser Pro Gly Ala
    370                 375                 380

Pro Thr Ala Ala Arg Thr Leu Val Ser Glu Pro Ala Ala Asp
385                 390                 395
```

<210> SEQ ID NO 40
<211> LENGTH: 2306
<212> TYPE: DNA
<213> ORGANISM: Homo sapiens

<400> SEQUENCE: 40

```
gcgcggccca tggagtcggg gctgctgcgg ccggcgccgg tgagcgaggt catcgtcctg      60

cattacaact acaccggcaa gctccgcggt gcgcgctacc agccgggtgc cggcctgcgc     120

gccgacgccg tggtgtgcct ggcggtgtgc gccttcatcg tgctagagaa tctagccgtg     180

ttgttggtgc tcggacgcca cccgcgcttc cacgctccca tgttcctgct cctgggcagc     240

ctcacgttgt cggatctgct ggcaggcgcc gcctacgccg ccaacatcct actgtcgggg     300

ccgctcacgc tgaaactgtc ccccgcgctc tggttcgcac gggagggagg cgtcttcgtg     360

gcactcactg cgtccgtgct gagcctcctg gccatcgcgc tggagcgcag cctcaccatg     420

gcgcgcaggg ggcccgcgcc cgtctccagt cgggggcgca cgctggcgat ggcagccgcg     480

gcctggggcg tgtcgctgct cctcgggctc ctgccagcgc tgggctggaa ttgcctgggt     540

cgcctggacg cttgctccac tgtcttgccg ctctacgcca aggcctacgt gctcttctgc     600

gtgctcgcct tcgtgggcat cctggccgcg atctgtgcac tctacgcgcg catctactgc     660

caggtacgcg ccaacgcgcg gcgcctgccg gcacggcccg ggactgcggg gaccacctcg     720

acccgggcgc gtcgcaagcc gcgctcgctg gccttgctgc gcacgctcag cgtggtgctc     780

ctggcctttg tggcatgttg ggcccccctc ttcctgctgc tgttgctcga cgtggcgtgc     840

ccggcgcgca cctgtcctgt actcctgcag gccgatccct tcctgggact ggccatggcc     900

aactcacttc tgaaccccat catctacacg ctcaccaacc gcgacctgcg ccacgcgctc     960
```

-continued

```
ctgcgcctgg tctgctgcgg acgccactcc tgcggcagag acccgagtgg ctcccagcag   1020
tcggcgagcg cggctgaggc ttccgggggc ctgcgccgct gcctgccccc gggccttgat   1080
gggagcttca gcggctcgga gcgctcatcg ccccagcgcg acgggctgga caccagcggc   1140
tccacaggca gccccggtgc acccacagcc gcccggactc tggtatcaga accggctgca   1200
gactgacacc ctcggcccac gactgtcttc ccaagtttta cagacttgtt ctttttacat   1260
aaaggaattt gtaggaaatg cagccaaagg tgcagtcgga aaagatgcag ggaaatgta    1320
tttatgcagc gacaccccac aatgtgaaca aacagacaaa aaatctgtgc cctcgtggaa   1380
ttgacgttct gcttgggaac acagaaaaga actcggtgat gaaataatgg agatgattcc   1440
agtgacaaac gacagagatg gtgatggtgg tcagggaaga cctctctgca gaggtagtga   1500
cttgtgatgt gagctgagac ctctgtcctg ggaagaccaa aagaaaagca tttcaggatg   1560
agggaatggc atgcgcaaag gccctgaggc tgaaatgtgc ccatgtgttc taagaaatgc   1620
agcgatgctg gtgtgcctgg agcagggacg gagggggaga atgggaggag acaaggagct   1680
gaaggagtag ttcccgaagg accttgtggg tgatatagag gacttcgctt ttgctctgag   1740
tgaggtggga gccatagaag cttctaagca gaagagggac ttgccctaat tcaggtgatc   1800
acaggtgtct tgtggcctcc atgggaggtt gaaaaccaca gaaggtgaag gggggctgca   1860
ctgagccaca ggaacaatga tggagattcc agctaagccc agaccccgtg gattctagat   1920
agattttaga ggcagcagac agaattactg aggaattgag tgtaagagtg gaataaagtt   1980
atcaaggaca atgccaaggg tggggcaccc ccaaatttga ctttgggaga ctcagccaaa   2040
tcctatctgg taataaaatt tctttttat ttttctttc tttctttctt tctttctttc   2100
ttttttttt tttgagttgg gatcttgtgc tctgtcaccc aggctggagt gcaatgggca   2160
caattatagc tcactgcagc ctggaactcc tgggatcaag cctggagttc ctgcttcagc   2220
ctccctagta gctgggacta caggcatgca ccaccatgcc cagttaataa aatttcttca   2280
aatgcaaaaa aaaaaaaaaa aaaaaa                                        2306
```